US008883983B2

(12) United States Patent
Jackson et al.

(10) Patent No.: US 8,883,983 B2
(45) Date of Patent: *Nov. 11, 2014

(54) ANTIGEN BINDING PROTEINS TO PROPROTEIN CONVERTASE SUBTILISIN KEXIN TYPE 9 (PCSK9)

(71) Applicant: Amgen Inc., Thousand Oaks, CA (US)

(72) Inventors: Simon Mark Jackson, San Carlos, CA (US); Nigel Pelham Clinton Walker, Burlingame, CA (US); Derek Evan Piper, Santa Clara, CA (US); Wenyan Shen, Palo Alto, CA (US); Chadwick Terence King, North Vancouver (CA); Randal Robert Ketchem, Snohomish, WA (US); Christopher Mehlin, Seattle, WA (US); Teresa Arazas Carabeo, New York, NY (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/261,065

(22) Filed: Apr. 24, 2014

(65) Prior Publication Data

US 2014/0228547 A1    Aug. 14, 2014

Related U.S. Application Data

(60) Continuation of application No. 13/251,909, filed on Oct. 3, 2011, which is a division of application No. 12/197,093, filed on Aug. 22, 2008, now Pat. No. 8,030,457.

(60) Provisional application No. 60/957,668, filed on Aug. 23, 2007, provisional application No. 61/008,965, filed on Dec. 21, 2007, provisional application No. 61/010,630, filed on Jan. 9, 2008, provisional application No. 61/086,133, filed on Aug. 4, 2008.

(51) Int. Cl.
C07K 16/40    (2006.01)
C07K 16/00    (2006.01)

(52) U.S. Cl.
CPC ..................................... C07K 16/40 (2013.01)
USPC ............... 530/388.26; 530/388.1; 530/388.15

(58) Field of Classification Search
None
See application file for complete search history.

(56) References Cited

U.S. PATENT DOCUMENTS

| | | | |
|---|---|---|---|
| 5,545,807 A | 8/1996 | Surani et al. | |
| 5,766,886 A | 6/1998 | Studnicka et al. | |
| 5,869,619 A | 2/1999 | Studnicka | |
| 6,875,432 B2 | 4/2005 | Liu et al. | |
| 7,029,895 B2 | 4/2006 | Glucksmann et al. | |
| 7,261,893 B2 | 8/2007 | Veldman et al. | |
| 7,300,754 B2 | 11/2007 | Abi Fadel et al. | |
| 7,368,531 B2 | 5/2008 | Rosen et al. | |
| 7,411,051 B2 | 8/2008 | Rosen et al. | |
| 7,456,264 B2 | 11/2008 | Keler et al. | |
| 7,482,147 B2 | 1/2009 | Glucksmann et al. | |
| 7,572,618 B2 | 8/2009 | Mintier et al. | |
| 7,776,577 B2 | 8/2010 | Kapeller-Libermann et al. | |
| 7,968,689 B2 | 6/2011 | Rosen et al. | |
| 8,030,457 B2 | 10/2011 | Jackson et al. | |
| 8,062,640 B2 | 11/2011 | Sleeman et al. | |
| 8,080,243 B2 | 12/2011 | Liang et al. | |
| 8,168,762 B2 | 5/2012 | Jackson et al. | |
| 8,188,233 B2 | 5/2012 | Condra et al. | |
| 8,188,234 B2 | 5/2012 | Condra et al. | |
| 8,344,114 B2 | 1/2013 | Sparrow et al. | |
| 8,357,371 B2 | 1/2013 | Sleeman et al. | |
| 8,399,646 B2 | 3/2013 | Liang et al. | |
| 8,420,098 B2 | 4/2013 | Camphausen et al. | |
| 8,426,363 B2 | 4/2013 | Liang et al. | |
| 8,501,184 B2 | 8/2013 | Sleeman et al. | |
| 8,530,414 B2 | 9/2013 | Davies et al. | |
| 8,563,698 B2 | 10/2013 | Jackson et al. | |
| 8,598,320 B2 | 12/2013 | Hedrick et al. | |
| 8,697,070 B2 | 4/2014 | Condra et al. | |
| 8,748,583 | 6/2014 | Jackson et al. | |
| 2002/0045571 A1 | 4/2002 | Liu et al. | |
| 2002/0081679 A1 | 6/2002 | Chiang et al. | |
| 2003/0119038 A1 | 6/2003 | Bingham et al. | |
| 2004/0009553 A1 | 1/2004 | Glucksmann et al. | |
| 2004/0023243 A1 | 2/2004 | Henry et al. | |
| 2004/0038242 A1 | 2/2004 | Edmonds et al. | |
| 2004/0248177 A1 | 12/2004 | Abi Fadel et al. | |
| 2005/0101529 A1 | 5/2005 | Yue et al. | |
| 2005/0118625 A1 | 6/2005 | Mounts | |
| 2005/0147612 A1 | 7/2005 | Yayon et al. | |
| 2005/0197285 A1 | 9/2005 | Rosen et al. | |

(Continued)

FOREIGN PATENT DOCUMENTS

| | | |
|---|---|---|
| EP | 2481758 | 8/2012 |
| EP | 2650016 | 10/2013 |

(Continued)

OTHER PUBLICATIONS

U.S. Appl. No. 13/918,755, filed Dec. 26, 2013, Wu et al.
Office Action dated May 7, 2014 in Japanese Application No. 2013-195240 with English Translation.
U.S. Appl. No. 09/499,235, filed Feb. 7, 2000, Chiang et al.
U.S. Appl. No. 09/517,906, filed Mar. 3, 2000, Chiang et al.
U.S. Appl. No. 09/692,785, filed Oct. 20, 2000, Chiang et al.
U.S. Appl. No. 09/775,009, filed Feb. 1, 2001, Chiang et al.
U.S. Appl. No. 10/287,290, filed Nov. 1, 2002, Bingham et al.

(Continued)

Primary Examiner — Sharon Wen
(74) Attorney, Agent, or Firm — Knobbe, Martens, Olson & Bear, LLP

(57) ABSTRACT

Antigen binding proteins that interact with Proprotein Convertase Subtilisin Kexin Type 9 (PCSK9) are described. Methods of treating hypercholesterolemia and other disorders by administering a pharmaceutically effective amount of an antigen binding protein to PCSK9 are described. Methods of detecting the amount of PCSK9 in a sample using an antigen binding protein to PCSK9 are described.

30 Claims, 152 Drawing Sheets

(56) References Cited

U.S. PATENT DOCUMENTS

| | | |
|---|---|---|
| 2006/0116508 A1 | 6/2006 | Glucksmann et al. |
| 2006/0147945 A1 | 7/2006 | Edmonds et al. |
| 2006/0223088 A1 | 10/2006 | Rosen et al. |
| 2006/0223090 A1 | 10/2006 | Rosen et al. |
| 2006/0246483 A1 | 11/2006 | Rosen et al. |
| 2007/0015696 A1 | 1/2007 | Rosen et al. |
| 2007/0037206 A1 | 2/2007 | Rosen et al. |
| 2007/0041963 A1 | 2/2007 | Rosen |
| 2007/0055056 A1 | 3/2007 | Rosen et al. |
| 2007/0082345 A1 | 4/2007 | Ota et al. |
| 2007/0224663 A1 | 9/2007 | Rosen et al. |
| 2008/0008697 A1 | 1/2008 | Mintier et al. |
| 2008/0103090 A1 | 5/2008 | Rosen et al. |
| 2008/0113930 A1 | 5/2008 | Tan et al. |
| 2009/0142352 A1 | 6/2009 | Jackson et al. |
| 2009/0232795 A1 | 9/2009 | Condra et al. |
| 2009/0246192 A1 | 10/2009 | Condra et al. |
| 2009/0269350 A1 | 10/2009 | Glucksmann |
| 2009/0326202 A1 | 12/2009 | Jackson et al. |
| 2010/0040610 A1 | 2/2010 | Sitlani et al. |
| 2010/0040611 A1 | 2/2010 | Sparrow et al. |
| 2010/0041102 A1 | 2/2010 | Sitlani et al. |
| 2010/0068194 A1 | 3/2010 | Kim |
| 2010/0068199 A1 | 3/2010 | Liang et al. |
| 2010/0136028 A1 | 6/2010 | Sparrow et al. |
| 2010/0150937 A1 | 6/2010 | Sparrow et al. |
| 2010/0166768 A1 | 7/2010 | Sleeman et al. |
| 2010/0233177 A1 | 9/2010 | Yowe et al. |
| 2010/0291099 A1 | 11/2010 | Glucksmann |
| 2011/0027287 A1 | 2/2011 | Jackson et al. |
| 2011/0033465 A1 | 2/2011 | Hedrick |
| 2011/0065902 A1 | 3/2011 | Sleeman et al. |
| 2011/0105726 A1 | 5/2011 | Rosen et al. |
| 2011/0117011 A1 | 5/2011 | Jackson et al. |
| 2011/0142849 A1 | 6/2011 | Rue |
| 2011/0229489 A1 | 9/2011 | Pons et al. |
| 2011/0230392 A1 | 9/2011 | Chiang et al. |
| 2011/0256148 A1 | 10/2011 | Sleeman et al. |
| 2012/0014951 A1 | 1/2012 | Liang et al. |
| 2012/0015435 A1 | 1/2012 | Liang et al. |
| 2012/0020975 A1 | 1/2012 | Jackson et al. |
| 2012/0020976 A1 | 1/2012 | Jackson et al. |
| 2012/0027765 A1 | 2/2012 | Jackson et al. |
| 2012/0076799 A1 | 3/2012 | Sparrow et al. |
| 2012/0077964 A1 | 3/2012 | Sparrow et al. |
| 2012/0082679 A1 | 4/2012 | Sparrow et al. |
| 2012/0082680 A1 | 4/2012 | Sitlani et al. |
| 2012/0093818 A1 | 4/2012 | Jackson et al. |
| 2012/0195910 A1 | 8/2012 | Wu et al. |
| 2012/0208208 A1 | 8/2012 | Ni et al. |
| 2012/0208209 A1 | 8/2012 | Ichetovkin et al. |
| 2012/0213794 A1 | 8/2012 | Luo et al. |
| 2012/0213797 A1 | 8/2012 | Jackson et al. |
| 2012/0219558 A1 | 8/2012 | Ni et al. |
| 2012/0231005 A1 | 9/2012 | Luo et al. |
| 2012/0251544 A1 | 10/2012 | Jackson et al. |
| 2012/0301461 A1 | 11/2012 | Condra et al. |
| 2013/0052201 A1 | 2/2013 | Jackson et al. |
| 2013/0058944 A1 | 3/2013 | Jackson et al. |
| 2013/0064825 A1 | 3/2013 | Chan et al. |
| 2013/0064834 A1 | 3/2013 | Sleeman et al. |
| 2013/0071379 A1 | 3/2013 | Condra et al. |
| 2013/0071405 A1 | 3/2013 | Davies et al. |
| 2013/0072665 A1 | 3/2013 | Jackson et al. |
| 2013/0079501 A1 | 3/2013 | Jackson et al. |
| 2013/0079502 A1 | 3/2013 | Jackson et al. |
| 2013/0085265 A1 | 4/2013 | Jackson et al. |
| 2013/0085266 A1 | 4/2013 | Sleeman et al. |
| 2013/0115223 A1 | 5/2013 | Sparrow et al. |
| 2013/0189277 A1 | 7/2013 | Walsh et al. |
| 2013/0243784 A1 | 9/2013 | Swergold |
| 2013/0273069 A1 | 10/2013 | Liang et al. |
| 2013/0344085 A1 | 12/2013 | Wu et al. |
| 2014/0099312 A1 | 4/2014 | Sleeman et al. |
| 2014/0154262 A1 | 6/2014 | Hanotin et al. |
| 2014/0161808 A1 | 6/2014 | Mintier et al. |

FOREIGN PATENT DOCUMENTS

| | | |
|---|---|---|
| EP | 2703009 | 3/2014 |
| EP | 2706070 | 3/2014 |
| JP | 2005-130764 | 5/2005 |
| WO | WO 93/12227 | 6/1993 |
| WO | WO 98/24893 | 6/1998 |
| WO | WO 00/76310 | 12/2000 |
| WO | WO 01/31007 | 5/2001 |
| WO | WO 01/57081 | 8/2001 |
| WO | WO 01/98468 | 12/2001 |
| WO | WO 02/14358 | 2/2002 |
| WO | WO 02/46383 | 6/2002 |
| WO | WO 02/090526 | 11/2002 |
| WO | WO 02/102993 | 12/2002 |
| WO | WO 02/102994 | 12/2002 |
| WO | WO 2004/018649 | 3/2004 |
| WO | WO 2004/097047 | 11/2004 |
| WO | WO 2007/128121 | 11/2007 |
| WO | WO 2008/057457 | 5/2008 |
| WO | WO 2008/057457 A2 | 5/2008 |
| WO | WO 2008/057458 | 5/2008 |
| WO | WO 2008/057458 A2 | 5/2008 |
| WO | WO 2008/057459 | 5/2008 |
| WO | WO 2008/057459 A2 | 5/2008 |
| WO | WO 2008/063382 A2 | 5/2008 |
| WO | WO 2008/086395 | 5/2008 |
| WO | WO 2008/109871 A2 | 9/2008 |
| WO | WO 2008/125623 A2 | 10/2008 |
| WO | WO 2008/133647 A2 | 11/2008 |
| WO | WO 2008/109871 A3 | 2/2009 |
| WO | WO 2009/026558 A1 | 2/2009 |
| WO | WO 2009/055783 | 4/2009 |
| WO | WO 2008/109871 A8 | 7/2009 |
| WO | WO 2009/100297 A1 | 8/2009 |
| WO | WO 2009/100318 A1 | 8/2009 |
| WO | WO 2009/131740 A2 | 10/2009 |
| WO | WO 2010/029513 A2 | 3/2010 |
| WO | WO 2010/068526 | 6/2010 |
| WO | WO 2010/077854 | 7/2010 |
| WO | WO 2012/029513 A3 | 7/2010 |
| WO | WO 2011/037791 | 3/2011 |
| WO | WO 2011/053759 | 3/2011 |
| WO | WO 2011/053665 A1 | 5/2011 |
| WO | WO 2011/053743 A1 | 5/2011 |
| WO | WO 2011/053783 | 5/2011 |
| WO | WO 2011/072263 | 5/2011 |
| WO | WO 2011/111007 A2 | 9/2011 |
| WO | WO 2012/054438 | 4/2012 |
| WO | WO 2012/088313 | 6/2012 |
| WO | WO 2012/101251 | 8/2012 |
| WO | WO 2012/101252 | 8/2012 |
| WO | WO 2012/101253 | 8/2012 |
| WO | WO 2012/109530 | 8/2012 |
| WO | WO 2012/154999 | 11/2012 |
| WO | WO 2012/168491 | 12/2012 |
| WO | WO 2012/170607 | 12/2012 |
| WO | WO 2012/177741 | 12/2012 |
| WO | WO 2013/008185 | 1/2013 |
| WO | WO 2013/016648 | 1/2013 |
| WO | WO 2013/039958 | 3/2013 |
| WO | WO 2013/039969 | 3/2013 |
| WO | WO 2013/148284 | 10/2013 |
| WO | WO 2013/169886 | 11/2013 |
| WO | WO 2013/188855 | 12/2013 |

OTHER PUBLICATIONS

U.S. Appl. No. 10/426,776, filed Apr. 30, 2003, Glucksmann et al.
U.S. Appl. No. 11/313,836, filed Dec. 21, 2005, Glucksmann et al.
U.S. Appl. No. 12/198,817, filed Aug. 26, 2008, Rosen et al.
U.S. Appl. No. 12/312,383, filed May 7, 2009, Sitlani et al.
U.S. Appl. No. 12/312,397, filed May 7, 2009, Sparrow et al.
U.S. Appl. No. 12/312,398, filed May 7, 2009, Sparrow et al.
U.S. Appl. No. 12/312,399, filed May 7, 2009, Sparrow et al.
U.S. Appl. No. 12/312,401, filed May 7, 2009, Sitlani et al.

(56) References Cited

OTHER PUBLICATIONS

U.S. Appl. No. 12/316,681, filed Dec. 16, 2008, Kapeller-Libermann et al.
U.S. Appl. No. 12/316797, filed Dec. 16, 2008, Glucksmann et al.
U.S. Appl. No. 12/322,861, filed Feb. 6, 2009, Condra et al.
U.S. Appl. No. 12/322,867, filed Feb. 6, 2009, Condra et al.
U.S. Appl. No. 12/474,176, filed Dec. 31, 2009, Jackson et al.
U.S. Appl. No. 12/558,312, filed Sep. 11, 2009, Liang et al.
U.S. Appl. No. 12/595,538, filed Oct. 12, 2009, Yowe et al.
U.S. Appl. No. 12/637,942, filed Dec. 15, 2009, Sleeman et al.
U.S. Appl. No. 12/739,761, filed Oct. 6, 2010, Hedrick.
U.S. Appl. No. 12/817,236, filed Nov. 18, 2010, Glucksmann et al.
U.S. Appl. No. 12/903,084, filed Feb. 3, 2011, Jackson et al.
U.S. Appl. No. 12/949,846, filed Nov. 19, 2010, Sleeman et al.
U.S. Appl. No. 12/965,743, filed Dec. 10, 2010, Rue.
U.S. Appl. No. 13/045,345, filed Mar. 10, 2011, Pons et al.
U.S. Appl. No. 13/071,809, filed Sep. 22, 2011, Chiang et al.
U.S. Appl. No. 13/095,234, filed Apr. 27, 2011, Sleeman et al.
U.S. Appl. No. 13/174,423, filed Jun. 30, 2011, Jackson et al.
U.S. Appl. No. 13/225,265, filed Sep. 2, 2011, Liang et al.
U.S. Appl. No. 13/225,119, filed Sep. 2, 2011, Liang et al.
U.S. Appl. No. 13/242,744, filed Sep. 23, 2011, Sparrow et al.
U.S. Appl. No. 13/242,809, filed Sep. 23, 2011, Sparrow et al.
U.S. Appl. No. 13/242,831, filed Sep. 23, 2011, Sitlani et al.
U.S. Appl. No. 13/246,219, filed Sep. 27, 2011, Sparrow et al.
U.S. Appl. No. 13/251,909, filed Jan. 26, 2012, Jackson et al.
U.S. Appl. No. 13/251,955, filed Jan. 26, 2012, Jackson et al.
U.S. Appl. No. 13/252,016, filed Feb. 2, 2012, Jackson et al.
U.S. Appl. No. 13/333,315, filed Dec. 21, 2011, Wu et al.
U.S. Appl. No. 13/422,887, filed Mar. 16, 2012, Jackson et al.
U.S. Appl. No. 13/422,904, filed Mar. 16, 2012, Jackson et al.
U.S. Appl. No. 13/463,751, filed May 3, 2012, Jackson et al.
U.S. Appl. No. 13/466,433, filed May 8, 2012, Condra et al.
U.S. Appl. No. 13/466,439, filed May 8, 2012, Condra et al.
U.S. Appl. No. 13/469,032, filed Mar. 14, 2013, Chan et al.
U.S. Appl. No. 13/494,912, filed Jun. 12, 2012, Jackson et al.
U.S. Appl. No. 13/497,663, filed Sep. 15, 2010, Ni et al.
U.S. Appl. No. 13/503,708, filed Aug. 16, 2012, Ni et al.
U.S. Appl. No. 13/503,726, filed Apr. 24, 2012, Luo et al.
U.S. Appl. No. 13/503,729, filed Aug. 23, 2012, Luo et al.
U.S. Appl. No. 13/503,732, filed Aug. 16, 2012, Ichetovkin et al.
U.S. Appl. No. 13/611,196, filed Mar. 21, 2013, Davies et al.
U.S. Appl. No. 13/619,555, filed Mar. 21, 2013, Jackson et al.
U.S. Appl. No. 13/655,984, filed Mar. 7, 2013, Jackson et al.
U.S. Appl. No. 13/656,392, filed May 28, 2013, Jackson et al.
U.S. Appl. No. 13/672,792, filed Mar. 14, 2013, Sleeman, et al.
U.S. Appl. No. 13/682,698, filed Mar. 28, 2013, Jackson et al.
U.S. Appl. No. 13/690,585, filed Apr. 4, 2013, Sleeman, et al.
U.S. Appl. No. 13/724,447, filed May 9, 2013, Sparrow et al.
U.S. Appl. No. 13/742,205, filed Jan. 15, 2013, Merck.
U.S. Appl. No. 60/857,248, filed Nov. 7, 2006, Merck & Co., Inc.
U.S. Appl. No. 60/857,293, filed Nov. 7, 2006, Merck & Co., Inc.
U.S. Appl. No. 12/474,176, filed May 28, 2009, Jackson et al.
U.S. Appl. No. 13/174,423, filed Apr. 19, 2012, Jackson et al.
U.S. Appl. No. 13/463,751, filed Aug. 23, 2012, Jackson et al.
U.S. Appl. No. 13/494,912, filed Oct. 4, 2012, Jackson et al.
U.S. Appl. No. 13/619,555, filed Sep. 14, 2012, Jackson et al.
U.S. Appl. No. 13/655,984, filed Oct. 19, 2012, Jackson et al.
U.S. Appl. No. 13/656,392, filed Oct. 19, 2012, Jackson et al.
U.S. Appl. No. 13/682,698, filed Nov. 20, 2012, Jackson et al.
U.S. Appl. No. 13/860,016, filed Apr. 10, 2013, Jackson et al.
U.S. Appl. No. 14/261,087, filed Apr. 24, 2014, Jackson et al.
U.S. Appl. No. 14/260,975, filed Apr. 24, 2014, Jackson et al.
U.S. Appl. No. 14/261,063, filed Apr. 24, 2014, Jackson et al.
U.S. Appl. No. 14/260,985, filed Apr. 24, 2014, Jackson et al.
Abboud et al., "Proprotein Convertase Subtilisin/Kexin Type 9 (PCSK9) Gene is a Risk Factor of Large-Vessel Atherosclerosis Stroke," PLoS One, 2(10): e1043, Oct. 2007.
Abifadel et al., "Mutations in PCSK9 cause autosomal dominant hypercholesterolemia," Nature Genetics 34, 154-156 (2003).
Advisory Action received in U.S. Appl. No. 12/312,401, dated Nov. 2, 2012, filed on May 7, 2009 (Merck).
Akers et al., "Formulation Development of Protein Dosage Forms," Pharmaceutical Biotechnology, Kluwer, Dordrecht, NL, vol. 14, Jan. 1, 2002, pp. 47-127.
Alborn et al., "Serum proprotein convertase subtilisin kexin type 9 is correlated directly with serum LDL cholesterol," Clin Chem, 53(10): 1814-1819, (2007).
Allard et al., "Genetic heterogeneity of autosomal dominant hypercholesterolemia: PCSK9, a third genet involved in the disease," *Current Topics in Genetics*, 1, pp. 103-112, 2005.
Allard et al., "Novel mutations of the PCSK9 gene cause variable phenotype of autosomal dominant hypercholesterolemia," Human mutation, 26(5), pp. 497, Nov. 2005.
Allard et al., "PC9, a new actor in autosomal dominant hypercholesterolemia," Current Genomics, 6(7), pp. 535-543, Nov. 2005.
Amended Claims in 15 pages For European Application No. 09808999.8 filed Sep. 11, 2009 (WO 2010/029513).
Anderson et al., "Activation of the furin endoprotease is a multiple-step process: requirements for acidification and internal propeptide cleavage," EMBO J. 16, 1508-1518, 1997.
Attie et al., "Dual regulation of the LDL receptor—some clarity and new questions," Cell Metab., 1(5): 290-292, (2005).
Attie et al., "The mystery of PCSK9," Aterioscler Thromb Vasc Biol., 24(8): 1337-1339, (2004).
Austin et al., "Genetic causes of monogenic heterozygous familial hypercholesterolemia: a HuGE prevalence review," American Journal of Epidemiology, 160(5): 407-420, 2004.
Barrios et al., "Length of the Antibody Heavy Chain Complementarity Determining Region 3 as a Specificity-Determining Factor," J. Mol. Recognit., vol. 17, 2004, pp. 332-338.
Bansal et al., "Cord blood lipoproteins and prenatal influences," Current Opinion in Lipidology, 16(4): 400-408, Aug. 2005.
Basak, "Inhibitors of Proprotein Convertases," J Mol Med 83: pp. 844-855, 2005.
Bedi et al., "Inhibition of squalene synthase upregulates PCSK9 expression in rat liver," Arch Biochem Biophys., 470(2): 116-119, (2008).
Benjannet et al., "NARC-1/PCSK9 and its natural mutants: zymogen cleavage and effects on the low density lipoprotein (LDL) receptor and LDL cholesterol," J Biol Chem, 2004, 279(47): 48865-48875.
Benjannet et al., "The Proprotein Convertase (PC) PCSK9 Is Inactivated by Furin and/or PC5/6A," J Biol Chem, Oct. 13, 2006, 281(41): 30561-30572.
Berge et al., Missense mutations in the PCSK9 gene are associated with hypocholesterolemia and possibly increased response to statin therapy. Arterioscler. Thromb. Vasc. Biol. (2006) 26, 1094-1100.
Bingham et al., "Proapoptotic Effects of NARC 1 (= PCSK9), the Gene Encoding a Novel Serine Proteinase," Cytometry Part A, 2006, 69A: 1123-1131.
Bottomley et al., "Structural and biochemical characterization of the wild type PCSK9/EGF-AB complex and natural FH mutants," J Biol. Chem., Nov. 2008.
Brown et al., "Lowering LDL—not only how low, but how long?" Science 311, 1721-1723, (2006).
Brunger et al., "Crystallography & NMR System: A new software suite for macromolecular structure determination," Acta Crystallogr D Biol Crystallogr 54: 905-921 (1998).
Burnett et al., "New therapies for familial hypercholesterolemia," Expert Opin. Ther. Patents 16(3): 349-361, 2006.
Cameron et al., "Effect of mutations in the PCSK9 gene on the cell surface LDL receptors," Hum. Mol. Genet. 15: 1551-1558 (2006).
Cameron et al., "Berberine decreases PCSK9 expression in HepG2 cells," Atherosclerosis, 201(2): 266-273, (2008).
Cameron et al., "Characterization of novel mutations in the catalytic domain of the PCSK9 gene," J Intern Med., 263(4): 420-431, (2008).
Cameron et al., "Investigations on the evolutionary conservation of PCSK9 reveal a functionally important protrusion," The FEBS Journal, pp. 1-13, 2008.
Campbell, Chapter 1, Monoclonal Antibody Technology, 1984, pp. 1-32, Elsevier Science Publishers B.V., The Netherlands.

(56) References Cited

OTHER PUBLICATIONS

Careskey et al., "Atorvastatin increases human serum levels of proprotein convertase subtilisin/kexin type 9," J Lipid Res., 49(2): 394-398, (2008).
Casset et al., "A Peptide Mimetic of an Anti-CD4 Monoclonal Antibody by Rational Design," Biochemical and Biophysical Research Communications, 2003, vol. 307, pp. 198-205.
Cayman Chemical Company, "Material Safety Data Sheet PCSK9 (human) Polyclonal Antibody," Jul. 26, 2007, pp. 1-3.
Cayman Chemical Company, "Material Safety Data Sheet PCSK9 (murine) Polyclonal Antibody," Sep. 5, 2007, pp. 1-4.
Cayman Chemical Company, "Product information PCSK9 (murine) Polyclonal Antibody," Sep. 5, 2007, pp. 1-4.
Cayman Chemical Company, "Product information PCSK9 Polyclonal Antibody Catalog No. 10007185," Dec. 10, 2007, pp. 1-2.
"PCSK9 (mouse) Polyclonal Antibody Cayman Chemical"; Quartzy PCSK9 (mouse) Polyclonal Antibody; Website: https://www.quartzy.com/reagent-detail/1464130/1/PCSK9--mouse--Polyclonal-Antibody-Cayman; Cayman Chemical Company: "Product information Proprotein Convertase Subtilisin Kexin 9; NARC-1 antigen." The reference is a webpage, and no date of publication is immediately apparent in the document. Applicants note that the webpage was printed on Nov. 7, 2013, and has a copyright date of 2013 to Quartzy; however, the webpage may have been available, in some form, prior to this date. It is noted that the document includes an "introduction date" of Jan. 22, 2007. pp. 1-4.
CCP4. The CCP4 suite: programs for protein crystallography. Acta Crystallogr D. Biol Crystallogr 50, 760-763 (1994).
Chamov et al., TIBTECH 14: 52-60, 1996 (entitled "Antibody Engineering at the Millennium").
Chen et al., "Influence of histidine on the stability and physical properties of a fully human antibody in aqueous and solid forms" Pharmaceutical Research, Kluwer Academic Publishers, New York, NY vol. 20, No. 12, Dec. 1, 2003, pp. 1952-1960.
Chen et al., "A common PCSK9 haplotype, encompassing the E670G coding single nucleotide polymorphism, is a novel genetic marker for plasma low-density lipoprotein cholesterol levels and severity of coronary atherosclerosis," J Am Coll Cardiol. 45(10): 1611-1619, (2005).
Chen et al., "A common PCSK9 haplotype, encompassing the E670G cSNP, is associated with plasma low-density lipoprotein levels and severity of coronary atherosclerosis," Circulation 110 (17, Suppl. S), Oct. 26, 2004.
Chen et al., "Selection and Analysis of an Optimized Anti-VEGF Antibody: Crystal Structure of an Affinity Matured Fab in Complex with Antigen," J. Mol. Biol., 1999, vol. 293, pp. 865-881.
Cohen et al., "Sequence variations in PCSK9, low LDL, and protection against coronary heart disease," N. Engl. J. Med. 354, 1264-1272 (2006).
Cohen et al., "Erratum: Low LDL cholesterol in African Americans resulting from frequent nonsense mutations in PCSK9," Nature Genetics, 37(3), pp. 328, 2005.
Cohen et al., "Low LDL cholesterol in individuals of African descent resulting from frequent nonsense mutations in PCSK9," Nature Genetics, 37(2): 161-165, (2005).
Colman, "Effects of amino acid sequence changes on antibody-antigen interactions," Research in Immunology, vol. 145, pp. 33-36, 1994.
Comments to Communications filed Mar. 26, 2013 in European Patent Application No. 08798550.3.
Costet et al., "Hepatic PCSK9 Expression Is Regulated by Nutritional Status via Insulin and Sterol Regulatory Element-binding Protein 1c," Journal of Biological Chemistry, Mar. 2006, 281(10): pp. 6211-6218.
Costet et al., "PCSK9 and LDL cholesterol: unraveling the target to design the bullet," Trends Biochem Sci., 33(9): 426-434, (2008).
Costet et al., "Proprotein Convertase Subtilisin Kexin type 9 is repressed by the peroxisome proliferator activated receptor alpha ligand fenofibric acid," Circulation, 114, 18, Suppl. S., Oct. 31, 2006.

Cunningham et al., "Structural and biophysical studies of PCSK9 and its mutants linked to familiar hypercholesterolemia," Nature Structural & Molecular Biology, vol. 14, No. 5, pp. 413-419 (May 2007).
Damgaard et al., "No genetic linkage or molecular evidence for involvement of the PCSK9, ARH or CYP7A1 genes in the Familial Hypercholesterolemia phenotype in a sample of Danish families without pathogenic mutations in the LDL receptor and apoB genes," Atherosclerosis 177(2): 415-422, 2004.
Davignon et al., "Erratum to Narc-1: A potential new target for drug therapy of hypercholesterolemia," Atherosclerosis, 176, pp. 429, 2004.
Davignon et al., "Narc-1: A Potential New Target for Drug Therapy of Hypercholesterolemia," XIIIth International Symposium on Atherosclerosis, Sep. 28-Oct. 2, 2003, Kyoto, Japan, 182-183.
Dedoussis et al., "LDL-receptor mutations in Europe," *Human Mutation*, 24(6): 443-459, 2004.
De Pascalis et al., "Grafting of 'Abbreviated' Complementarity Determining Regions Containing Specificity Determining Residues Essential for Ligand Contact to Engineer a Less Immunogenic Humanized Monoclonal Antibody," J. Immunol, 2002, vol. 169, pp. 3076-3084.
Ding et al., "Molecular population genetics of PCSK9: a signature of recent positive selection," Pharmacogenet Genomics. 18(3): 169-179, (2008).
Dubuc et al., "Statins upregulate PCSK9, the gene encoding the proprotein convertase neural apoptosis-regulated convertase-1 implicated in familial hypercholesterolemia," Arterioscler. Thromb. Vase. Biol. 24: 1454-1459 (2004).
Duff et al., "Antibody-mediated disruption of the interaction between PCSK9 and the low-density lipoprotein receptor," Biochemical Journal, published online Feb. 5, 2009 as Manuscript BJ20082407.
EB 06682 Goat Anti-PCSK9 Antibody, Everest Biotech Online Catalogue, © 2007, auto-generated Sep. 7, 2007.
Ellis et al., "Engineered Anti-CD38 Monoclonal Antibodies for Immunotherapy of Multiple Myeloma," The Journal of Immunology 155: 925-937, 1995.
English Translation of Office Action dated Jul. 1, 2013 in Ukrainian Patent Application No. 201003346.
Evans et al., "The E670G SNP in the PCSK9 gene is associated with polygenic hypercholesterolemia in men but not in women," BMC Med Genet., 7: 66, (2006).
European Search Report and Opinion dated Jan. 8, 2014 in European Application No. 13151352.5.
*Ex Parte Quayle* action received in U.S. Appl. No. 13/095,234, dated Jul. 3, 2012 (Regeneron).
Extended European Search Report dated Oct. 14, 2013 in European Application No. 13151343.4.
Extended European Search Report dated Feb. 5, 2014 in European Application No. 13151381.4.
Fan et al., "Self-Association of Human PCSK9 Correlates with its LDLR-Degrading Activity," Biochemistry, 2008, 47: 1631-1639.
File History of European Appl. No. 07861680.2, filed Nov. 2, 2007. (WO 2008/057457 and EP 2083859).
File History of European Appl. No. 07861681.0, filed Nov. 2, 2007. (WO 2008/057458 and EP 2083860).
File History of European Appl. No. 07870839.3, filed Nov. 2, 2007. (WO 2008/063382 and EP 2083864).
File History of European Appl. No. 07874101.4, filed Nov. 2, 2007. (WO 2008/133647 and EP 2106261).
File History of European Appl. No. 08736129.1, filed Apr. 11, 2008. (WO 2008/125623 and EP 2137218).
File History of European Appl. No. 08841231.7, filed Oct. 27, 2008. (WO 2009/055783 and EP 2205639).
File History of European Appl. No. 09707156.7, filed Feb. 6, 2009. (WO 2009/100318 and EP 2245070).
File History of European Appl. No. 09808999.8, filed Sep. 11, 2009. (WO 2010/029513).
File History of PCT Appl. No. PCT/EP2008/054417, filed Apr. 11, 2008, 130 pages (Novartis).
File History of PCT Appl. No. PCT/IB2009/053990, filed Sep. 11, 2009, 362 pages.
File History of PCT Appl. No. PCT/US2007/023169, filed Nov. 2, 2007, 116 pages.

(56) References Cited

OTHER PUBLICATIONS

File History of PCT Appl. No. PCT/US2007/023212, filed Nov. 2, 2007, 114 pages.
File History of PCT Appl. No. PCT/US2007/023213, filed Nov. 2, 2007, 113 pages.
File History of PCT Appl. No. PCT/US2007/023214, filed Nov. 2, 2007, 114 pages.
File History of PCT Appl. No. PCT/US2007/023223, filed Nov. 2, 2007, 115 pages.
File History of PCT Appl. No. PCT/US2008/081311, filed Oct. 27, 2008, 154 pages.
File History of PCT Appl. No. PCT/US2009/033341, filed Feb. 6, 2009, 304 pages.
File History of PCT Appl. No. PCT/US2009/033369, filed Feb. 6, 2009, 310 pages.
File History of PCT Appl. No. PCT/US2009/068013, filed Dec. 15, 2009, 388 pages.
File History of U.S. Appl. No. 10/877,773, filed Jun. 25, 2004.
File History of U.S. Appl. No. 10/877,774, filed Jun. 25, 2004.
File History of U.S. Appl. No. 12/197,093, filed Aug. 22, 2008.
File History of U.S. Appl. No. 12/268,363, filed Nov. 10, 2008.
File History of U.S. Appl. No. 12/312,383, filed May 7, 2009.
File History of U.S. Appl. No. 12/312,397, filed May 7, 2009.
File History of U.S. Appl. No. 12/312,398, filed May 7, 2009.
File History of U.S. Appl. No. 12/312,399, filed May 7, 2009.
File History of U.S. Appl. No. 12/312,401, filed May 7, 2009.
File History of U.S. Appl. No. 12/322,861, filed Feb. 6, 2009.
File History of U.S. Appl. No. 12/322,867, filed Feb. 6, 2009.
File History of U.S. Appl. No. 12/396,313, filed Mar. 2, 2009.
File History of U.S. Appl. No. 12/474,176, filed May 28, 2009.
File History of U.S. Appl. No. 12/558,312, filed Sep. 11, 2009.
File History of U.S. Appl. No. 12/595,538, filed Oct. 12, 2009.
File History of U.S. Appl. No. 12/637,942, filed Dec. 15, 2009.
File History of U.S. Appl. No. 12/649,179, filed Dec. 29, 2009.
File History of U.S. Appl. No. 12/903,084, filed Oct. 12, 2010.
File History of U.S. Appl. No. 13/095,234, filed Apr. 27, 2011 (Regeneron).
File History of U.S. Appl. No. 13/225,265, filed Sep. 2, 2011 (Rinat/Pfizer).
File History of U.S. Appl. No. 13/242,809, filed Sep. 23, 2011 (Merck).
File History of U.S. Appl. No. 13/422,887, filed Mar. 16, 2012.
File History of U.S. Appl. No. 13/174,423, filed Jun. 30, 2011.
File History of U.S. Appl. No. 13/251,909, filed Oct. 3, 2011.
File History of U.S. Appl. No. 13/251,955, filed Oct. 3, 2011.
File History of U.S. Appl. No. 13/252,016, filed Oct. 3, 2011.
File History of U.S. Appl. No. 13/463,751, filed May 3, 2012.
File History of U.S. Appl. No. 13/422,904, filed Mar. 16, 2012.
File History of U.S. Appl. No. 13/494,912, filed Jun. 12, 2012.
File History of U.S. Appl. No. 13/619,555, filed Sep. 14, 2012.
File History of U.S. Appl. No. 13/655,984, filed Oct. 19, 2012.
File History of U.S. Appl. No. 13/656,392, filed Oct. 19, 2012.
File History of U.S. Appl. No. 13/682,698, filed Nov. 20, 2012.
File History of U.S. Appl. No. 13/860,016, filed Apr. 10, 2012.
File History of U.S. Appl. No. 14/261,087, Filed Apr. 24, 2014.
File History of U.S. Appl. No. 14/260,975, filed Apr. 24, 2014.
File History of U.S. Appl. No. 14/261,063, filed Apr. 24, 2014.
File History of U.S. Appl. No. 14/260,985, filed Apr. 24, 2014.
Fisher et al., "Effects of pH and low density lipoprotein (LDL) on PCSK9-dependent LDL receptor regulation," J Biol. Chem., 282(28): 20502-20512, (2007).
Folsom et al., "Variation in PCSK9, low LDL cholesterol, and risk of peripheral arterial disease," Atherosclerosis, 202(1): 211-215, (2009).
Fouchier et al., "PCSK9 mutations found in patients diagnosed with autosomal dominant hypercholesterolemia in the Netherlands," Circulation, 110 (17 Suppl. S) Oct. 26, 2004.
Fouchier et al., "Update of the molecular basis of familial hypercholesterolemia in the Netherlands," Human Mutation, 26(6), pp. 550-556, Dec. 2005.

Frank-Kamenetsky et al., "Therapeutic RNAi targeting PCSK9 acutely lowers plasma cholesterol in rodents and LDL cholesterol in nonhuman primates," Proc. Natl. Acad. Sci. USA, 105(33): 11915-11920, 2008.
Fu et al., "Folding pathway mediated by an intramolecular chaperone: The inhibitory and chaperone functions of the subtilisin propeptide are not obligatorily linked," J. Biol. Chem. 275: 16871-16878, 2000.
GenomeNet Database: PIR, Entry T1824D, Barrell et al., Nov. 1998.
GenomeNet Database: UniProt, Entry: A0E922, Parte, Aury et al., 2006.
Goldstein et al., "Familial hypercholesterolemia" in The Metabolic & Molecular Bases of Inherited Disease (eds. Scriver, C.S. et al.) 2863-2913 (McGraw-Hill, New York, 2001).
Goldstein et al., "The cholesterol quartet," Science 292, 1310-1312 (2001).
Graadt Van Roggen et al., "FH Afrikaner-3 LDL receptor mutation results in defective LDL receptors and causes a mild form of familial hypercholesterolemia," Arteriosclerosis, Thrombosis, and Vascular Biology, 15(6), pp. 765-772, Jun. 1995.
Graadt Van Roggen et al., "Low density lipoprotein receptor founder mutations in Afrikaner familial hypercholesterolaemic patients: A comparison of two geographical areas," Human Genetics, 88(2), pp. 204-208, 1991.
Graham et al., "Antisense inhibition of proprotein convertase subtilisin/kexin type 9 reduces serum LDL in hyperlipidemic mice," J Lipid Research, 48: 763-767, 2007.
Graham et al., "Genetic screening protocol for familial hypercholesterolemia which includes splicing defects gives an improved mutation detection rate," Atherosclerosis, 182(2), pp. 331-340, Oct. 2005.
Grefhorst et al., "Plasma PCSK9 preferentially reduces liver LDL receptors in mice," J Lipid Res., 49(6):1303-1311, (2008).
Grozdanov et al., "Expression and localization of PCSK9 in rat hepatic cells" Biochemistry and Cell Biology, Feb. 2006, 84(1): 80-92.
Grozdanov et al., "Expression of Pcsk9 in rat hepatic cells," FASEB Journal 19 (4 Suppl. S, Part 1, Mar. 4, 2005.
Hallman et al., "Relation of PCSK9 mutations to serum low-density lipoprotein cholesterol in childhood and adulthood (from the Bogalusa Heart Study)," Am J Cardiol., 100(1): 69-72, (2007).
Hampton et al., "The self-inhibited structure of full-length PCSK9 at 1.9 Å reveals structural homology with resistin within the C-terminal domain," Proc. Nat. Acad. Sci. USA, Sep. 2007, 104(37): 14604-14609.
Henrich et al., "The crystal structure of the proprotein processing proteinase furin explains its stringent specificity," Nat. Struct. Biol. 10: 520-526, 2003.
Henrich et al., "Proprotein convertase models based on the crystal structures of furin and kexin: Explanation of their specificity," J. Mol. Biol. 345: 211-227, 2005.
Holla et al., "Degradation of the LDL receptors by PCSK9 is not mediated by a secreted protein acted upon by PCSK9 extracelluarly," BMC Cell Biol., 8: 9, (2007).
Holla et al., "Low-density lipoprotein receptor activity in Epstein-Barr virus-transformed lymphocytes from heterozygotes for the D374Y mutation in the PCSK9 gene," Scand J Clin Lab., 66(4): 317-328, (2006).
Hooper et al., "The C679X mutation in PCSK9 is present and lowers blood cholesterol in a Southern African population," Atherosclerosis, 193(2): 445-448, (2007).
Horton et al., "Molecular biology of PCSK9: its role in LDL metabolism," Trends in Biochemical Sciences, 3(2): 71-77, 2006.
Houghten et al., "Relative Importance of Position and Individual Amino Acid Residues in Peptide Antigen-Antibody Interactions: Implications in the Mechanism of Antigenic Drift and Antigenic Shift," New Approaches to Immunization, Vaccines 86, Cold Spring Harbor Laboratory, p. 21-25, 1986.
Human Proprotein Convertase 9/PCSK9 Antibody, Antigen Affinity-purified Polyclonal Sheep IgG, Catalog No. AF3888. R & D Systems: Tools for Cell Biology Research™ Rev: Oct. 21, 2010 p. 1 of 1.
Human/Mouse Proprotein Convertase 9/PCSK9 Antibody, Monoclonal Rat IgG, Clone # 407119, Catalog No. MAB3888. R &

(56) References Cited

OTHER PUBLICATIONS

D Systems: Tools for Cell Biology Research™ Rev. Oct. 12, 2010 p. 1 of 1. Available for sale since Jun. 2007.
Human/Mouse Proprotein Convertase 9/PCSK9 Antibody, Monoclonal Rat IgG, Clone # 407119, Catalog No. MAB38881. R & D Systems: Tools for Cell Biology Research™ Rev. Oct. 12, 2010 p. 1 of 1. Available for sale since Apr. 2008.
Human/Mouse Proprotein Convertase 9/PCSK9 Antibody, Monoclonal Rat IgG, Clone # 407119, Catalog No. MAB38882. R & D Systems: Tools for Cell Biology Research™ Rev. Oct. 12, 2010 p. 1 of 1. Available for sale since Feb. 2009.
Ikemura et al., "Requirement of pro-sequence for the production of active subtilisin E in *Escherichia coli*," J. Biol. Chem. 262: 7859-7864, 1987.
International Preliminary Examination Report dated Mar. 4, 2010, received in Int'l Appl. No. PCT/US2008/074097 filed Aug. 22, 2008, 10 pages.
International Search Report and Written Opinion dated Dec. 19, 2008, received in Int'l Appl. No. PCT/US2008/073927.
International Search Report and Written Opinion dated Dec. 19, 2008, received in Int'l Appl. No. PCT/US2008/074097.
International Search Report dated Dec. 9, 2008, from Int'l Appl. No. PCT/EP2008/054417 (WO 2008/125623).
International Search Report dated Jan. 9, 2009, from Int'l Appl. No. PCT/US2007/023169 (WO 2008/133647).
International Search Report dated Jul. 31, 2009, from Int'l Appl. No. PCT/US2008/081311 (WO 2009/055783).
International Search Report dated Jun. 1, 2010, from Int'l Appl. No. PCT/IB2009/053990 (WO 2010/029513).
International Search Report dated Jun. 25, 2009, from Int'l Appl. No. PCT/US2009/033369 (WO 2009/100318).
International Search Report dated Oct. 1, 2008, from Int'l Appl. No. PCT/US2007/023213 (WO 2008/057458).
International Search Report dated Oct. 1, 2008, from Int'l Appl. No. PCT/US2007/023223 (WO 2008/063382).
International Search Report dated Oct. 15, 2008, from Int'l Appl. No. PCT/US2007/023212 (WO 2008/057457).
International Search Report published Feb. 5, 2009, in Int'l Appl. No. PCT/EP2008/054417.
International Search Report received in PCT Appl. No. PCT/US2008/074097, dated Dec. 5, 2008.
Issue Fee payment dated Aug. 12, 2011, in U.S. Appl. No. 12/197,093.
Jeon et al., "Structure and physiologic function of the low-density lipoprotein receptor," Annu. Rev. Biochem. 74: 535-562 (2005).
Jirholt et al., "How does mutant proprotein convertase neural apoptosis-regulated convertase 1 induce autosomal dominant hypercholersterolemia," *Arteriosclerosis, Thrombosis and Vascular Biology*, 24(8): 1334-1336, 2004.
Kala et al., "Phage Displayed Antibodies to Heat Stable Alkaline Phosphatase: Framework Region as a Determinant of Specificity," J. Biochem., vol. 132, 2002, pp. 535-541.
Kastelein et al., "What promise does PCSK9 hold?" J Am Coll Cardiol., 45(10): 1620-1621, (2005).
Kathiresan et al., "A PCSK9 missense variant associated with a reduced risk of early-onset myocardial infarction," N Engl J Med., 358(21): 2299-2300, (2008).
Kim et al., "Long-distance PCR-based screening for large rearrangements of the LDL receptor gene in Korean patients with familial hypercholesterolemia," Clinical Chemistry, 45(9), p. 1424-1430, 1999.
Knappik et al., "Fully Synthetic Human Combinatorial Antibody Libraries (HuCAL) Based on Modular Consensus Frameworks and CDRs Randomized with Trinucleotides." J Mol. Biol. 296 (2000): 57-86.
Kotowski et al., "A spectrum of PCSK9 alleles contributes to plasma levels of low-density lipoprotein cholesterol," Am. J. Hum. Genet. 78: 410-422, 2006.
Kotowski et al., "Multiple sequence variations in PCSK9 contribute to decreased plasma levels of LDL cholesterol," Circulation, 112 (17, Suppl. S), Oct. 25, 2005.
Kotze et al., "Familial hypercholesterolemia: Potential diagnostic value of mutation screening in a pediatric population of South Africa," Clinical Genetics, 54(1), pp. 74-78, Jul. 1998.
Kourimate et al., "Dual mechanisms for the fibrate-mediated repression of proprotein convertase subtilisin/kexin type 9," J Biol. Chem., 283(15): 9666-9673, (2008).
Kwon et al., "Molecular basis for LDL receptor recognition by PSK9," Proc. Natl. Acad. Sci. USA, Feb. 12, 2008, 105(6): 1820-1825.
Lagace et al., "Secreted PCSK9 decreases the number of LDL receptors in hepatocytes and in livers of parabiotic mice," The Journal of Clinical Investigation, 116(11): 2995-3005, Nov. 2006.
Lalanne et al., "Wild-type PCSK9 inhibits LDL clearance but does not affect apoB-containing lipoprotein production in mouse and cultured cells," J Lipid Res., 46(6): 1312-1319, (2005).
Lambert et al., "PCSK9: a promising therapeutic target for dyslipidemias?" Trends Endocrinol. Metab. 17, 79-81 (2006).
Lambert et al., "Fasting induces hyperlipidemia in mice overexpressing proprotein convertase subtilisin kexin type 9: lack of modulation of very-low density lipoprotein hepatic output by the low-density lipoprotein receptor," Endocrinology, 147(10): 4985-4995, (2006).
Lambert et al., "Molecular basis of PCSK9 function," Atherosclerosis, 203(1): 1-7, (2009).
Lambert et al., "Plasma PCSK9 concentrations correlate with LDL and total cholesterol in diabetic patients and are decreased by fenofibrate treatment," Clin Chem., 54(6): 1038-1045, (2008).
Lambert et al., "Unravelling the functional significance of PCSK9," Curr Opin Lipidol., 18(3): 304-309, (2007).
Lamminmaki et al., "Crystal Structure of a Recombinant Anti-estradiol Fab Fragment in Complex with 17β-Estradiol," The Journal of Biological Chemistry, 276(39): 36687-36694, Sep. 28, 2001.
Langhi et al., "Activation of the farnesoid X receptor represses PCSK9 expression in human hepatocytes," FEBS Lett., 582(6): 949-955, (2008).
Lederman et al., "A Single Amino Acid Substitution in a Common African Allele of the CD4 Molecule Ablates Binding of the Monoclonal Antibody, OKT4," Molecular Immunology 28: 1171-1181, 1991.
Leren et al., "Mutations in the PCSK9 gene in Norwegian subjects with autosomal dominant hypercholesterolemia," Clin. Genet., 65(5): 419-422, (2004).
Li et al., "β-Endorphin omission analogs: Dissociation of immunoreactivity from other biological activities," Proc. Natl. Acad. Sci. USA, 77(6): 3211-3214, Jun. 1980.
Li et al., "Secreted PCSK9 promotes LDL receptor degradation independently of proteolytic activity," Biochem J. 406, 203-207 (2007).
Lopez et al., "Inhibition of PCSK9 as a novel strategy for the treatment of hypercholesterolemia," Drug News Perspect., 21(6): 323-330, (2008).
Lopez et al., "PCSK9: an enigmatic process," Biochem Biophys Acta., 1781(4): 184-191, (2008).
Ma et al., "Functional Characterization of Novel Genes Regulated in a Cell Culture Model of Neuronal Apoptosis," Neuroscience 2002 Abstract, Nov. 5, 2002, p. 1.
MacCallum et al., "Antibody-antigen Interactions: Contact Analysis and Binding Site Topography," Journal of Molecular Biology, 1996, vol. 262, pp. 732-745.
Marais et al., "The diagnosis and management of familial hypercholesterolaemia," *European Review for Medical and Pharmacological Sciences*, 9(3), pp. 141-149, May 2005.
Maxwell et al., "Adenoviral-mediated expression of PCSK9 in mice results in a low-density lipoprotein receptor knockout phenotype," Proc Natl Acad Sci USA, May 2004, 101(18): 7100-7105.
Maxwell et al., "Novel putative SREBP and LXR target genes identified by microarray analysis in liver of cholesterol-fed mice," Journal of Lipid Research, vol. 14, 2109-2119, 2003.
Maxwell et al., "Overexpression of PCSK9 accelerates the degradation of the LDLR in a post-endoplasmic reticulum compartment," Proc. Natl. Acad. Sci. USA (2005) 102, 2069-2074.

(56) References Cited

OTHER PUBLICATIONS

Maxwell et al., "Overexpression of Pcsk9 leads to the formation of an LDLR-Pcsk9 complex and acceleration of LDLR degradation," Circulation, 110 (17 Suppl. S) Oct. 26, 2004.
Maxwell et al., "Proprotein convertase subtilisin kexin 9: The third locus implicated in autosomal dominant hypercholesterolemia," *Current Opinion in Lipidology*, 16(2), pp. 167-172, Apr. 2005.
Mayne et al., "Plasma PCSK9 levels are significantly modified by statins and fibrates in humans," Lipids Health Dis., 7: 22, (2008).
Mayne et al., "Plasma PCSK9 Levels Correlate with Cholesterol in Men but not in Women," Biochemical and Biophysical Research Communications (BBRC) 361: 451-456, 2007.
Mbikay et al., "Of PCSK9, cholesterol homeostasis and parasitic infections: possible survival benefits of loss-of-function PCSK9 genetic polymorphisms," Med Hypotheses, 69(5): 1010-1017, (2007).
McNutt et al., "Catalytic Activity Is Not Required for Secreted PCSK9 to Reduce Low Density Lipoprotein Receptors in HepG2 Cells," Journal of Biological Chemistry, 282(29): 20799-20803, Jul. 20, 2007.
McNutt et al., "Antagonism of secreted PCSK9 increases low density lipoprotein receptor expression in HepG2 cells," Journal of Biological Chemistry, 284(16): 10561-10570, Apr. 17, 2009.
Mendez et al., "Functional transplant of megabase human immunoglobulin loci recapitulates human antibody response in mice," Nature Genetics, 15: 146-156, Feb. 1997.
Naoumova et al., "Severe hypercholesterolemia in four British families with the D374Y mutation in the PCSK9 gene: Long-term follow-up and treatment response," *Arteriosclerosis, Thrombosis, and Vascular Biology*, 25(12): 2654-2660, Dec. 2005.
Nassoury et al., "The cellular trafficking of the secretory proprotein convertase PCSK9 and its dependence on the LDLR," Traffic, 8(6): 718-722, (2007).
Naureckiene et al., "Functional Characterization of Narc1, a Novel Proteinase Related to Proteinase K," Arch Biochem Biophys, Dec. 1, 2003; 420(1): 55-67.
New England Bio Labs, "Furin" Jan. 2006.
Ngo et al., "The Protein Folding Problem and Tertiary Structure Prediction," 1994, pp. 492-495.
Ni et al., "A PCSK9 C-terminal Domain Binding Fab Inhibits PCSK9 Internalization and Restores LDL-uptake," *Circulation*, vol. 120 No. 18 Suppl 2, Nov. 2009, p. S477.
Notice of Allowance dated Feb. 11, 2014, received in U.S. Appl. No. 13/860,0163.
Notice of Allowance dated Jun. 14, 2013, received in U.S. Appl. No. 13/252,016.
Notice of Allowance dated Jun. 17, 2013, received in U.S. Appl. No. 12/474,176.
Notice of Allowance dated Jun. 19, 2013, received in U.S. Appl. No. 12/474,176.
Notice of Allowance dated Jun. 27, 2011, received in U.S. Appl. No. 12/197,093.
Notice of Allowance dated Oct. 11, 2011, received in U.S. Appl. No. 12/322,861.
Notice of Allowance dated Oct. 13, 2011, received in U.S. Appl. No. 12/322,867.
Notice of Allowance dated Dec. 22, 2011, received in U.S. App. No. 13/251,955.
Notice of Allowance dated Mar. 5, 2012, received in U.S. Appl. No. 13/252,016.
Notice of Allowance dated Mar. 6, 2013, received in U.S. Appl. No. 13/252,016.
Notice of Allowance dated Mar. 25, 2014, received in U.S. Appl. No. 13/252,016.
Notice of Allowance dated Mar. 31, 2014 received in U.S. Appl. No. 13/174,423.
Notice of Allowance dated Jun. 21, 2012, received in U.S. Appl. No. 13/252,016.
Notice of Allowance dated Nov. 5, 2012, received in U.S. Appl. No. 13/252,016.
Notice of Allowance dated Oct. 9, 2013, received in U.S. Appl. No. 13/252,016.
Notice of Allowance dated Sep. 5, 2013 received in U.S. Appl. No. 13/174,423.
Notice of Allowance and Examiner Interview Summary dated Sep. 21, 2012, received in U.S. Appl. No. 13/095,234 (Regeneron).
Notice of Opposition received in Chilean Patent Application No. 2495-2008, dated Jul. 5, 2011.
Notice of Opposition received in Colombian Patent Application No. 10 033833, dated Jun. 24, 2011.
Notice of Publication received in U.S. Appl. No. 13/251,955, filed on Oct. 3, 2011.
Office Action and Search Report dated Jul. 4, 2013 for R.O.C. Taiwan Patent Application 097132236 (with English translation).
Office Action issued Jun. 27, 2013 for Chinese Patent Application 200880113475.4 (with English translation).
Office Action dated Apr. 9, 2013 received in Colombian Patent Appl. No. 10 033833 (with English translation).
Office Action dated Apr. 17, 2013 received in Philippines Patent Appl. No. 1/2010/500421.
Office Action dated May 21, 2013 received in Japanese Patent Appl. No. 2010-52208 (with English translation).
Office Action dated Aug. 8, 2013 received in U.S. Appl. No. 13/422,904.
Office Action dated Aug. 12, 2013, received in U.S. Appl. No. 13/494,912.
Office Action dated Aug. 16, 2013, received in U.S. Appl. No. 13/860,016.
Office Action dated Aug. 24, 2010, received in U.S. Appl. No. 12/322,867.
Office Action dated Aug. 25, 2010, received in U.S. Appl. No. 12/322,861.
Office Action dated Dec. 2, 2013 in Vietnamese Application No. 1-2010-00689 (with English Translation).
Office Action dated Dec. 16, 2013 in New Zealand Patent Application No. 618641.
Office Action dated Feb. 1, 2013, received in Australian Patent Application No. 2008288791.
Office Action dated Feb. 11, 2011, received in U.S. Appl. No. 12/322,867 (Merck).
Office Action dated Feb. 4, 2011, received in U.S. Appl. No. 12/558,312 (Pfizer).
Office Action dated Feb. 5, 2014 received in European Patent Appl. No. 08798550.3.
Office Action dated Mar. 27, 2012, received in U.S. Appl. No. 13/242,809 (Merck).
Office Action dated Nov. 6, 2013 in Israeli Patent Application No. 204013.
Office Action dated Jan. 18, 2011, received in U.S. Appl. No. 12/637,942 (Regeneron).
Office Action dated Jan. 20, 2012, received in U.S. Appl. No. 12/312,401 (Merck).
Office Action dated Jan. 26, 2011, received in U.S. Appl. No. 12/322,861 (Merck).
Office Action dated Jan. 5, 2011, received in European Application No. 08798550.3.
Office Action dated Jan. 15, 2014 in Malaysian Application No. PI2010000750.
Office Action dated Jan. 28, 2014 in U.S. Appl. No. 13/494,912.
Office Action dated Jan. 30, 2014 in U.S. Appl. No. 13/422,904.
Office Action dated Jul. 11, 2007, received in U.S. Appl. No. 11/439,325.
Office Action dated Jul. 13, 2012, received in New Zealand Patent Application No. 584101.
Office Action dated Jun. 12, 2012, received in New Zealand Patent Application No. 584101.
Office Action dated Jul. 31, 2012, received in Chinese Patent Application No. 200880113475.4 (with English Translation).
Office Action dated Oct. 15, 2013, received in Korean Patent Application No. 10-2010-7006252 (with English translation).
Office Action dated Oct. 21, 2013 in Columbian Application No. 13 202843 (with English Translation).

(56) References Cited

OTHER PUBLICATIONS

Office Action dated Oct. 29, 2012 in Peruvian Patent Application No. 001426-2008 (with English translation).
Office Action dated Sep. 24, 2012, received in U.S. Appl. No. 13/225,265 (Pfizer).
Office Action dated Sep. 26, 2011, received in U.S. Appl. No. 12/474,176.
Office Action received in Eurasian Patent Application No. 201000356, filed Aug. 22, 2008.
Office Action received in European Patent Application No. 08798550.3, dated Jan. 5, 2011.
Office Action received in European Patent Application No. 08798550.3, dated Jun. 15, 2012.
Office Action dated Feb. 13, 2012 in Israeli Patent Application No. 204013 (English Translation).
Office Action dated Feb. 13, 2012 in Israeli Patent Application No. 204013 (foreign language document).
Office Action received in Mexican Patent Application No. MX/a/2010/001921, dated Oct. 20, 2011.
Office Action received in New Zealand Patent Application No. 584101, dated Nov. 30, 2010.
Office Action received in U.S. Appl. No. 12/312,401, dated Jan. 20, 2012 (Merck).
Office Action received in U.S. Appl. No. 12/312,401, dated Jul. 17, 2012 (Merck).
Office Action received in U.S. Appl. No. 12/474,176, dated May 22, 2012.
Office Action received in U.S. Appl. No. 12/949,846, dated Jul. 11, 2012 (Regeneron).
Office Action received in U.S. Appl. No. 12/474,176, dated Jan. 10, 2013.
Otwinowski et al., "Multiparametric scaling of diffraction intensities," Acta Crystallogr A 59: 228-234 (2003).
Ouguerram et al., "Apolipoprotein B100 metabolism in autosomal-dominant hypercholesterolemia related to mutations in PCSK9," Arterioscler thromb Vasc Biol. 24: 1448-1453, 2004.
Padlan et al., "Structure of an Antibody-Antigen Complex: Crystal Structure of the HyHEL 10 Fab Lysozyme Complex," Proc. Natl. Acad. Sci., vol. 86, Aug. 1989, pp. 5938-5942.
Pandit et al., "Functional analysis of sites within PCSK9 responsible for hypercholesterolemia," J Lipid Res., 49(6): 1333-1343, (2008).
Parhofer et al., "What we have learned about VLDL and LDL metabolism from human kinetics studies," *Journal of Lipid Research*, 47(8), pp. 1620-1630, 2006.
Park et al., "Post-transcriptional regulation of low density lipoprotein receptor protein by proprotein convertase subtilisin/kexin type 9a in mouse liver," J. Biol. Chem. 279, pp. 50630-50638, 2004.
Paul, Fundamental Immunology, 3rd Edition, 1993, pp. 292-295, under the heading "Fv Structure and Diversity in Three Dimensions".
Peterson et al., "PCSK9 function and physiology," J Lipid Res., 49(7): 1595-1599, (2008).
Petition for Extension of Time to Respond dated Jan. 15, 2013 in U.S. Appl. No. 12/312,401 (Merck).
Piatesi et al., "Immunological Optimization of a Generic Hydrophobic Pocket for High Affinity Hapten Binding and Diels-Alder Activity," Chem Bio Chem, vol. 5(4), Apr. 2004, pp. 460-466.
Piper et al., "The Crystal Structure of PCSK9: A Regulator of Plasma LDL-Cholesterol," Structure, 15, 1-8, pp. 545-552 (May 2007).
Pisciotta et al., "Additive effect of mutations in LDLR and PCSK9 genes on the phenotype of familial hypercholesterolemia," *Atherosclerosis* 186(2), pp. 433-440, Jun. 2006.
Poirier et al., "Implication of the proprotein convertase NARC-1/PCSK9 in the development of the nervous system," J Neurochem, 98(3): 838-850, (2006).
Poirier et al., "The proprotein convertase PCSK9 induces the degradation of low density lipoprotein receptor (LDLR) and its closest family members VLDLR and ApoER2," J Biol Chem., 283(4): 2363-2372, (2008).
Polisecki et al., "Genetic variation a the PCSK9 locus moderately lowers low-density lipoprotein cholesterol levels, but does not significantly lower vascular disease risk in an elderly population," Atherosclerosis, 200(1): 95-101, (2008).
Preliminary Amendment for U.S. Appl. No. 13/422,887, filed Mar. 16, 2012.
Preliminary Amendment for U.S. Appl. No. 13/422,904, filed Mar. 16, 2012.
Preliminary Amendment for U.S. Appl. No. 13/463,751, filed May 3, 2012.
Preliminary Amendment for U.S. Appl. No. 13/494,912, filed Jun. 15, 2012.
Preliminary Amendment for U.S. Appl. No. 13/619,555, filed Sep. 14, 2012.
Preliminary Amendment dated Oct. 19, 2012 for U.S. Appl. No. 13/655,984, filed Oct. 19, 2012.
Preliminary Amendment dated Oct. 19, 2012 for U.S. Appl. No. 13/656,392, filed Oct. 19, 2012.
Preliminary Amendment dated Apr. 15, 2013 for U.S. Appl. No. 13/860,016.
Qian et al., "Secreted PCSK9 downregulates low density lipoprotein receptor through receptor-mediated endocytosis," J Lipid Res., 48(7): 1488-1498, (2007).
Rader et al., "Monogenic hypercholesterolemia: New insights in pathogenesis and treatment," *Journal of Clinical Investigation*, 111 (12), pp. 1795-1803, 2003.
Rashid et al., "Decreased plasma cholesterol and hypersensitivity to statins in mice lacking Pcsk9," PNAS, vol. 102, No. 15, 5374-5379 (Apr. 12, 2005).
Ratliff et al., "Transgenic Expression of CYP7A1 in LDL Receptor-Deficient Mice Blocks Diet-Induced Hypercholesterolemia," Journal of Lipid Research, 47, 2006, 1513-1520.
Rawlings et al., "MEROPS: the peptidase database," Nucleic Acids Res. 34, D270-D272, 2006.
RCSB Protein Data Bank: An Information Portal to Biological Macromolecular Structures. Search Results for keyword "pcsk9" search conducted Jan. 10, 2008. Website accessed at http://www.rcsb.org/pdb/home/home.do• Piper et al. "The Crystal Structure of Proprotein convertase subtilisin kexin type 9 (PCSK9)" (Released May 8, 2007)• Cunningham et al. "Crystal Structure of PCSK9" (Deposited Mar. 12, 2007, released Apr. 10, 2007)• Hampton et al. "The Crystal Structure of PCSK9 at 1.9 Angstroms Resolution Reveals Structure Homology to Resistin within the C-Terminal Domain" (Released Sep. 18, 2007)• Kwon, H.J. "PCSK9: EGF-A complex" (Deposited Dec. 19, 2007, released Feb. 12, 2008).
Response in 52 pages to EP Office Action received in EP Appl. No. 08736129.1, filed Apr. 11, 2008 (WO 2008/125623 and EP 2137218).
Response to Office Action dated Jan. 5, 2011 received in European Application No. 08798550.3.
Response to Office Action filed on Apr. 10, 2013 in U.S. Appl. No. 12/474,176.
Response to Office Action filed on Apr. 30, 2012 received in U.S. Appl. No. 12/312,401 (Merck).
Response to Office Action filed on Mar. 23, 2012 in U.S. Appl. No. 12/474,176.
Response to Final Office Action filed on Oct. 25, 2012 in U.S. Appl. No. 12/312,401 (Merck).
Response to Office Action filed on Nov. 20, 2012 in U.S. Appl. No. 12/474,176.
Response to Office Action filed on Aug. 23, 2013 in U.S. Appl. No. 12/989,404.
Response to Office Action filed on Dec. 21, 2012 in European Application No. 08798550.3.
Restriction Requirement dated Dec. 14, 2012 received in U.S. Appl. No. 13/494,912.
Restriction Requirement dated Feb. 24, 2014 received in U.S. Appl. No. 12/903,084.
Rudenko et al., "Structure of the LDL Receptor Extracellular Domain at Endosomal pH," Science 298, 2353-2358 (2002).
Rudikoff et al., "Single Amino Acid Substitution Altering Antigen Binding Specificity," Proc. Natl. Acad. Sci. 79: 1979-1983, 1982.
Saint-Jore et al., "Autosomal dominant type IIa hypercholesterolemia: Evaluation of the respective contributions of

(56) References Cited

OTHER PUBLICATIONS

LDLR and APOB gene defects as well as a third major group of defects," *European Journal of Human Genetics*, 8(8), pp. 621-630, 2000.
Sakai et al., "Molecular identification of the sterol-regulated luminal protease that cleaves SREBPs and controls lipid composition of animal cells," Mol. Cell 2: 505-514, 1998.
"Sanofi and Regeneron Report Positive Preliminary Phase 2 Program Results for Anti-PCSK9 Antibody in Hypercholesterolemia," http://www.prnewswire.com/news-releases/sanofi-and-regeneron-report-positive-preliminary-phase-2-program-results-for-anti-pcsk9-antibody-in-hypercholesterolemia-133590188.html, PR Newswire, Nov. 10, 2011, pp. 1-.
Schmidt et al., "A Novel Splicing Variant of Proprotein Convertase Subtilisin/Kexin Type 9," DNA Cell Biol, Apr. 2008, 27(4): 183-189.
Schmidt et al., "A 15-ketosterol is a liver X receptor ligand that suppresses sterol-responsive element binding protein-2 activity," *Journal of Lipid Research*, 47(5), May 2006, 1037-1044.
Schmidt et al., "Secreted proprotein convertase subtilisin/kexin type 9 reduces both hepatic and extrahepatic low-density lipoprotein receptors in vivo," Biochem Biophys Res Commun., 370(4): 634-640, (2008).
Search Report dated May 16, 2012 received in Chinese Patent Application No. 200880113475.4 (with English Translation).
Search Report dated Sep. 9, 2013 received in Korean Patent Application No. 10-2010-7006252 (with English Translation).
Search Report and Written Opinion received in Singaporean Patent Application No. 201001062-7 filed Aug. 22, 2008.
Seidah et al., "Mammalian subtilisin/kexin isozyme Ski-1: a widely expressed proprotein convertase with a unique cleavage specificity and cellular localization," Proc. Natl. Acad. Sci. USA 96: 1321-1326, 1999.
Seidah et al., "The proprotein convertases and their implication in sterol and/or lipid metabolism," Biological Chemistry, 387(7): 871-877, 2006.
Seidah et al., "The proprotein convertases in health and disease," Molecular & Cellular Proteomics, 2(9), Sep. 2003.
Seidah et al., "The secretory proprotein convertase neural apoptosis-regulated convertase 1 (NARC-1): Liver regeneration and neuronal differentiation," PNAS 100: 928-933, 2003.
Seidah et al., "The proprotein convertases are potential targets in the treatment of dyslipidemia," J. Mol. Med., 95: 685-696, Mar. 10, 2007.
Shan et al., "PCSK9 binds to multiple receptors and can be functionally inhibited by an EGF-A peptide," Biochem. Biophys. Res. Commun., pp. 1-5 (2008).
Shen et al., "The molecular genetics of coronary artery disease and myocardial infarction," *Acute Coronary Syndromes*, 6(4), pp. 129-141, 2004.
Shibata et al., "No genetic association between PCSK9 polymorphisms and Alzheimer's disease and plasma cholesterol level in Japanese patients," *Psychiatric Genetics*, 15(4), pp. 239, Dec. 2005.
Shioji et al., "Genetic variants in PCSK9 affect the cholesterol level in Japanese," Journal of Human Genetics, 49(2) pp. 109-114, 2004.
Stahl, "Regeneron: Investor Day Early Clinical Development #1 REGN727: anti-PCSK9," Jul. 15, 2010: pp. 1-21.
Sun et al., Evidence for effect of mutant PCSK9 on apoliprotein B secretion as the cause of unusually severe dominant hypercholesterolemia, Human Molecular Genetics 14: 1161-1169, 2005.
Tall, "Protease variants, LDL, and coronary heart disease," *New England Journal of Medicine*, 354(12), pp. 1310-1312, Mar. 23, 2006.
Tangrea et al., "Solution structure of the pro-hormone convertase 1 pro-domain from Mus musculus," J. Mol. Biol. 320: 801-812, 2002.
Third Party Observations for Application No. EP20080798550 dated Jan. 2013 by Anonymous.
Third Party Observations for Application No. EP20080798550 dated Jan. 2013 by Carpmaels & Ransford.
Third Party Observations for Application No. EP20080798550 submitted Dec. 22, 2012 by third party.
Timms et al., "A mutation in PCSK9 causing autosomal-dominant hypercholesterolemia in a Utah pedigree," Hum Genet., 114(4): 349-353, (2004).
Topol, "Cholesterol, racial variation and targeted medicines," Nature Medicine, 11(2), pp. 122-123, Feb. 2005.
Topol et al., "Genetic susceptibility to myocardial infarction and coronary artery disease," *Human Molecular Genetics*, 15 (Rev. Issue 2), R117-R123, 2006.
Transmittal page from Information Disclosure Statement dated May 28, 2009, in U.S. Appl. No. 12/474,176.
Tuakli-Wosornu et al., "Genetic deficiency of proprotein convertase Subtilisin/Kexin 9: identification of a compound heterozygote with no PCSK9," *Circulation*, 114 (18, Suppl. S). Oct. 31, 2006.
Vajdos et al., "Comprehensive Functional Maps of the Antigen Binding Site of an Anti ErbB2 Antibody Obtained with Shotgun Scanning Mutagenesis," J. Mol. Biol., 2002, vol. 320, pp. 415-428.
Van Regenmortel et al., "Mapping Epitope Structure and Activity: From One-Dimensional Prediction to Four-Dimensional Description of Antigenic Specificity," Methods: A Companion to Methods in Enzymology 9: 465-472, 1996.
Varret et al., "A Third Major Locus for Autosomal Dominant Hypercholesterolema Maps to 1p34.1-p32," *American Journal of Human Genetics*, 64: 1378-1387, 1999.
Varret et al., "ARCH and HCHOLA3: Two different genes at 1p both implicated in familial hypercholesterolemia," *American Journal of Human Genetics*, 71 (4 Supplement), Oct. 2002.
Varret et al., "Familial autosomal dominant hypercholesterolemia: Highly skewed contribution of mutations in the LDLR, APOB, FH3 and FH4 genes," *Circulation*, 106 (19 Supplement) Nov. 5, 2002.
Villeger et al., "Familial hypercholesterolemia: 30 years after Brown and Goldstein," *Recent Research Developments in Human Genetics*, 1(pt.1), pp. 35-51, 2002.
Wells, "Additivity of mutational effects in proteins," Biochemistry 29(37): 8509-8517, 1990.
Wu et al., "Humanization of a Murine Monoclonal Antibody by Simultaneous Optimization of Framework and CDR Residues," J. Mol. Biol., vol. 294: 151-162, 1999.
Yende et al., "Genetic polymorphisms that predict outcome and need for treatment in cardiovascular disease," *Current Opinion in Critical Care* 12(5), pp. 420-425, Oct. 2006.
Yue et al., "The c.43_44insCTG variation in PCSK9 is associated with low plasma LDL-cholesterol in a Caucasian population," *Human Mutation*, 27(5), pp. 460-466, May 2006.
Zaid et al., "Proprotein convertase subtilisin/kexin type 9 (PCSK9): hepatocyte-specific low-density lipoprotein receptor degradation and critical role in mouse liver regeneration," Hepatology, 48(2): 646-654, (2008).
Zhang et al., "Binding of PCSK9 to EGF-A Repeat of LDL Receptor Decreases Receptor Recycling and Increases Degradation," Journal of Biological Chemistry, Apr. 23, 2007.
Zhang et al., "Structural requirements for PCSK9-mediated degradation of the low-density lipoprotein receptor," PNAS, Sep. 2, 2008, 105(35): 13045-13050.
Zhang et al., "Binding of Proprotein Convertase Subtilisin/Kexin Type 9 to Epidermal Growth Factor-like Repeat A of Low Density Lipoprotein Receptor Decreases Receptor Recycling and Increases Degradation," Journal of Biological Chemistry, 282(25), pp. 18602-18612, Jun. 22, 2007.
Zhao et al., "Molecular characterization of loss-of-function mutations in PCSK9 and identification of a compound heterozygote," *American Journal of Human Genetics*, 79: 514-523, 2006.
Zhao et al., "Functional characterization of sequence variations in PCSK9," *Circulation*, 112 (17, Suppl. S.), Oct. 25, 2005.
Preliminary Amendment dated May 7, 2014 in U.S. Appl. No. 14/261,087.
Preliminary Amendment dated May 7, 2014 in U.S. Appl. No. 14/260,975.
Preliminary Amendment dated May 7, 2014 in U.S. Appl. No. 14/261,063.
Preliminary Amendment dated May 7, 2014 in U.S. Appl. No. 14/260,985.

(56) References Cited

OTHER PUBLICATIONS

Chan Joyce C Y et al. "A Proprotein convertase subtilisin/kexin type 9 neutralizing antibody reduces serum cholesterol in mice and non-human primates," Proc Nat Acad Sci, Jun. 16, 2009, vol. 106, No. 24, pp. 9820-9825.

Li Hai et al. "Recent patents on PCSK9: a new target for treating hypercholesterolemia," Recent Patents on DNA & Gene Sequences, Nov. 1, 2009, vol. 3, No. 3, pp. 201-212.

Ni Yan G et al. "A PCSK9-binding antibody that structurally mimics the EGF(A) domain of LDL-receptor reduces LDL cholesterol in vivo," J Lipid Research, Jan. 2011, vol. 52, No. 1, pp. 78-86.

Ni Yan G et al. "A proprotein convertase subtilisin-like/kexin type 9 (PCSK9) C-terminal domain antibody antigen-binding fragment inhibits PCSK9 internalization and restores low density lipoprotein uptake," J Biol Chem, Apr. 23, 2010, vol. 285, No. 17, Apr. 23, 2010, pp. 12882-12891.

Parhofer, Klaus. "Lipoprotein(a): Medical treatment options for an elusive molecule." Current Pharmaceutical Design, 2011, vol. 17, 871-876.

Soutar, Anne K. "Unexpected roles for PCSK9 in lipid metabolism," Current Opinion in Lipidology, Jun. 2011, vol. 22, No. 3, pp. 192-196.

European Patent Office communication dated Jul. 3, 2014 in European Patent Application No. 08798550.3.

Notice of Allowance dated Jun. 26, 2014 in U.S. Appl. No. 14/261,087.

Notice of Allowance dated Jun. 30, 2014 in U.S. Appl. No. 14/260,975.

Notice of Allowance dated Jun. 20, 2014 in U.S. Appl. No. 14/261,063.

Notice of Allowance dated Jun. 20, 2014 in U.S. Appl. No. 14/260,985.

European Patent Office Communication dated Jul. 24, 2014 in European Pat. App. No. 08798550.3.

Office Action dated May 28, 2014 in Korean Pat. App. No. 10-2010-7006252 (with English translation).

Office Action dated Jul. 17, 2014 in U.S. Appl. No. 12/903,084.

QEDEDGDYEELVLALRSEEDGLAEAPEHGTTATFHRCAKDPWRLPGTYVVVLKEETHL
SQSERTARRLQAQAARRGYLTKILHVFHGLLPGFLVKMSGDLLELALKLPHVDYIEEDS
SVFAQSIPWNLERITPPRYRADEYQPPDGGSLVEVYLLDTSIQSDHREIEGRVMVTDFEN
VPEEDGTRFHRQASKCDSHGTHLAGVVSGRDAGVAKGASMRSLRVLNCQGKGTVSGT
LIGLEFIRKSQLVQPVGPLVVLLPLAGGYSRVLNAACQRLARAGVVLVTAAGNFRDDAC
LYSPASAPEVITVGATNAQDQPVTLGTLGTNFGRCVDLFAPGEDIIGASSDCSTCFVSQS
GTSQAAAHVAGIAAMMLSAEPELTLAELRQRLIHFSAKDVINEAWFPEDQRVLTPNLVA
ALPPSTHGAGWQLFCRTVWSAHSGPTRMATAIARCAPDEELLSCSSFSRSGKRRGERME
AQGGKLVCRAHNAFGGEGVYAIARCCLLPQANCSVHTAPPAEASMGTRVHCHQQGHV
LTGCSSHWEVEDLGTHKPPVLRPRGQPNQCVGHREASIHASCCHAPGLECKVKEHGIPA
PQGQVTVACEEGWTLTGCSALPGTSHVLGAYAVDNTCVVRSRDVSTTGSTSEEAVTAV
AICCRSRHLAQASQELQ

SEQ ID NO:1

FIG. 1A

```
              10         20         30         40         50
         ----------|----------|----------|----------|----------|
Query  : atgggcaccgtcagctccaggcggtcctggtggccgctgccactgctgct    SEQ ID NO:2
Frame1 : M  G  T  V  S  S  R  R  S  W  W  P  L  P  L  L       SEQ ID NO:3

60         70         80         90        100
         ----------|----------|----------|----------|----------|
Query  : gctgctgctgctgctcctgggtcccgcgggcgcccgtgcgcaggaggacg
Frame1 : L  L  L  L  L  L  G  P  A  G  A  R  A  Q  E  D  E 110        120        130        140        150
         ----------|----------|----------|----------|----------|
Query  : aggacggcgactacgaggagctggtgctagccttgcgctccgaggaggac
Frame1 : D  G  D  Y  E  E  L  V  L  A  L  R  S  E  E  D 50       160        170        180        190        200
         ----------|----------|----------|----------|----------|
Query  : ggcctggccgaagcacccgagcacggaaccacagccaccttccaccgctg
Frame1 : G  L  A  E  A  P  E  H  G  T  T  A  T  F  H  R  C 210        220        230        240        250
         ----------|----------|----------|----------|----------|
Query  : cgccaaggatccgtggaggttgcctggcacctacgtggtggtgctgaagg
Frame1 : A  K  D  P  W  R  L  P  G  T  Y  V  V  L  K  E 50       260        270        280        290        300
         ----------|----------|----------|----------|----------|
Query  : aggagacccacctctcgcagtcagagcgcactgcccgccgcctgcaggcc
Frame1 : E  T  H  L  S  Q  S  E  R  T  A  R  R  L  Q  A 310        320        330        340        350
         ----------|----------|----------|----------|----------|
Query  : caggctgcccgccggggatacctcaccaagatcctgcatgtcttccatgg
Frame1 : Q  A  A  R  R  G  Y  L  T  K  I  L  H  V  F  H  G 50       360        370        380        390        400
         ----------|----------|----------|----------|----------|
Query  : ccttcttcctggcttcctggtgaagatgagtggcgacctgctggagctgg
Frame1 : L  L  P  G  F  L  V  K  M  S  G  D  L  L  E  L  A 410        420        430        440        450
         ----------|----------|----------|----------|----------|
Query  : ccttgaagttgccccatgtcgactacatcgaggaggactcctctgtcttt
Frame1 : L  K  L  P  H  V  D  Y  I  E  E  D  S  S  V  F 50       460        470        480        490        500
         ----------|----------|----------|----------|----------|
Query  : gcccagagcatccgtggaacctggagcggattacccctccgcggtaccg
Frame1 : A  Q  S  I  P  W  N  L  E  R  I  T  P  P  R  Y  R 510        520        530        540        550
         ----------|----------|----------|----------|----------|
Query  : ggcggatgaataccagcccccccgacggaggcagcctggtggaggtgtatc
Frame1 : A  D  E  Y  Q  P  P  D  G  G  S  L  V  E  V  Y  L
```

FIG. 1B$_1$

```
              50        560        570        580        590        600
         ---------|---------|---------|---------|---------|---------|
Query  : tcctagacaccagcatacagagtgaccaccgggaaatcgagggcagggtc
Frame1 :   L  D  T  S  I  Q  S  D  H  R  E  I  E  G  R  V 610        620        630        640        650
              ---------|---------|---------|---------|---------|
Query  : atggtcaccgacttcgagaatgtgcccgaggaggacgggacccgcttcca
Frame1 :   M  V  T  D  F  E  N  V  P  E  E  D  G  T  R  F  H 50        660        670        680        690        700
         ---------|---------|---------|---------|---------|---------|
Query  : cagacaggccagcaagtgtgacagtcatggcacccacctggcaggggtgg
Frame1 :   R  Q  A  S  K  C  D  S  H  G  T  H  L  A  G  V  V 710        720        730        740        750
              ---------|---------|---------|---------|---------|
Query  : tcagcggccgggatgccggcgtggccaagggtgccagcatgcgcagcctg
Frame1 :   S  G  R  D  A  G  V  A  K  G  A  S  M  R  S  L 50        760        770        780        790        800
         ---------|---------|---------|---------|---------|---------|
Query  : cgcgtgctcaactgccaagggaagggcacggttagcggcaccctcatagg
Frame1 :   R  V  L  N  C  Q  G  K  G  T  V  S  G  T  L  I  G 810        820        830        840        850
              ---------|---------|---------|---------|---------|
Query  : cctggagtttattcggaaaagccagctggtccagcctgtggggccactgg
Frame1 :   L  E  F  I  R  K  S  Q  L  V  Q  P  V  G  P  L  V 50        860        870        880        890        900
         ---------|---------|---------|---------|---------|---------|
Query  : tggtgctgctgcccctggcgggtgggtacagccgcgtcctcaacgccgcc
Frame1 :   V  L  L  P  L  A  G  G  Y  S  R  V  L  N  A  A 910        920        930        940        950
              ---------|---------|---------|---------|---------|
Query  : tgccagcgcctggcgagggctggggtcgtgctggtcaccgctgccggcaa
Frame1 :   C  Q  R  L  A  R  A  G  V  V  L  V  T  A  A  G  N 50        960        970        980        990       1000
         ---------|---------|---------|---------|---------|---------|
Query  : cttccgggacgatgcctgcctctactcccccagcctcagctcccgaggtca
Frame1 :   F  R  D  D  A  C  L  Y  S  P  A  S  A  P  E  V  I 1010       1020       1030       1040       1050
              ---------|---------|---------|---------|---------|
Query  : tcacagttggggccaccaatgcccaggaccagccggtgaccctggggact
Frame1 :   T  V  G  A  T  N  A  Q  D  Q  P  V  T  L  G  T 50       1060       1070       1080       1090       1100
         ---------|---------|---------|---------|---------|---------|
Query  : ttggggaccaactttggccgctgtgtggacctctttgccccaggggagga
Frame1 :   L  G  T  N  F  G  R  C  V  D  L  F  A  P  G  E  D
```

FIG. 1B$_2$

```
              100       1110      1120      1130      1140      1150
              ----------|---------|---------|---------|---------|
Query  : catcattggtgcctccagcgactgcagcacctgctttgtgtcacagagtg
Frame1 :  I  I  G  A  S  S  D  C  S  T  C  F  V  S  Q  S  G 150       1160      1170      1180      1190      1200
              ----------|---------|---------|---------|---------|
Query  : ggacatcacaggctgctgcccacgtggctggcattgcagccatgatgctg
Frame1 :  T  S  Q  A  A  A  H  V  A  G  I  A  A  M  M  L 200       1210      1220      1230      1240      1250
              ----------|---------|---------|---------|---------|
Query  : tctgccgagccggagctcaccctggccgagttgaggcagagactgatcca
Frame1 :  S  A  E  P  E  L  T  L  A  E  L  R  Q  R  L  I  H 250       1260      1270      1280      1290      1300
              ----------|---------|---------|---------|---------|
Query  : cttctctgccaaagatgtcatcaatgaggcctggttccctgaggaccagc
Frame1 :  F  S  A  K  D  V  I  N  E  A  W  F  P  E  D  Q  R 300       1310      1320      1330      1340      1350
              ----------|---------|---------|---------|---------|
Query  : gggtactgaccccccaacctggtggccgccctgccccccagcacccatggg
Frame1 :  V  L  T  P  N  L  V  A  A  L  P  P  S  T  H  G 350       1360      1370      1380      1390      1400
              ----------|---------|---------|---------|---------|
Query  : gcaggttggcagctgttttgcaggactgtgtggtcagcacactcggggcc
Frame1 :  A  G  W  Q  L  F  C  R  T  V  W  S  A  H  S  G  P 400       1410      1420      1430      1440      1450
              ----------|---------|---------|---------|---------|
Query  : tacacggatggccacagccatcgcccgctgcgccccagatgaggagctgc
Frame1 :  T  R  M  A  T  A  I  A  R  C  A  P  D  E  E  L  L 450       1460      1470      1480      1490      1500
              ----------|---------|---------|---------|---------|
Query  : tgagctgctccagtttctccaggagtgggaagcggcggggcgagcgcatg
Frame1 :  S  C  S  S  F  S  R  S  G  K  R  R  G  E  R  M 500       1510      1520      1530      1540      1550
              ----------|---------|---------|---------|---------|
Query  : gaggcccaaggggggcaagctggtctgccgggcccacaacgcttttgggggg
Frame1 :  E  A  Q  G  G  K  L  V  C  R  A  H  N  A  F  G  G 550       1560      1570      1580      1590      1600
              ----------|---------|---------|---------|---------|
Query  : tgagggtgtctacgccattgccaggtgctgcctgctaccccaggccaact
Frame1 :  E  G  V  Y  A  I  A  R  C  C  L  L  P  Q  A  N  C 600       1610      1620      1630      1640      1650
              ----------|---------|---------|---------|---------|
Query  : gcagcgtccacacagctccaccagctgaggccagcatggggacccgtgtc
Frame1 :  S  V  H  T  A  P  P  A  E  A  S  M  G  T  R  V
```

FIG. 1B₃

```
              650       1660      1670      1680      1690      1700
                ---------|---------|---------|---------|---------|
Query   : cactgccaccaacagggccacgtcctcacaggctgcagctcccactggga
Frame1  : H  C  H  Q  Q  G  H  V  L  T  G  C  S  S  H  W  E 700       1710      1720      1730      1740      1750
                ---------|---------|---------|---------|---------|
Query   : ggtggaggaccttggcacccacaagccgcctgtgctgaggccacgaggtc
Frame1  :  V  E  D  L  G  T  H  K  P  P  V  L  R  P  R  G  Q 750       1760      1770      1780      1790      1800
                ---------|---------|---------|---------|---------|
Query   : agcccaaccagtgcgtgggccacagggaggccagcatccacgcttcctgc
Frame1  :   P  N  Q  C  V  G  H  R  E  A  S  I  H  A  S  C 800       1810      1820      1830      1840      1850
                ---------|---------|---------|---------|---------|
Query   : tgccatgccccaggtctggaatgcaaagtcaaggagcatggaatcccggc
Frame1  :  C  H  A  P  G  L  E  C  K  V  K  E  H  G  I  P  A 850       1860      1870      1880      1890      1900
                ---------|---------|---------|---------|---------|
Query   : ccctcaggggcaggtgaccgtggcctgcgaggagggctggaccctgactg
Frame1  :   P  Q  G  Q  V  T  V  A  C  E  E  G  W  T  L  T  G 900       1910      1920      1930      1940      1950
                ---------|---------|---------|---------|---------|
Query   : gctgcagcgccctccctgggacctcccacgtcctgggggcctacgccgta
Frame1  :    C  S  A  L  P  G  T  S  H  V  L  G  A  Y  A  V 950       1960      1970      1980      1990      2000
                ---------|---------|---------|---------|---------|
Query   : gacaacacgtgtgtagtcaggagccgggacgtcagcactacaggcagcac
Frame1  :  D  N  T  C  V  V  R  S  R  D  V  S  T  T  G  S  T 2010      2020      2030      2040      2050
                ---------|---------|---------|---------|---------|
Query   : cagcgaagaggccgtgacagccgttgccatctgctgccggagccggcacc
Frame1  :   S  E  E  A  V  T  A  V  A  I  C  C  R  S  R  H  L 50       2060      2070      2080      2090      2100
                ---------|---------|---------|---------|---------|
Query   : tggcgcaggcctcccaggagctccag
Frame1  :  A  Q  A  S  Q  E  L  Q
```

FIG. 1B$_4$

| Seq ID No. | LINE | V | D | J | FR1 | CDR1 | FR2 |
|---|---|---|---|---|---|---|---|
| 4 | Germline | | | | DIVMTQSPLSLPVTPGEPASISC | RSSQSLLHSNGYNYLD | WYLQKPGQSPQLLIY |
| 5 | 30A4 | A3 | | JK3 | ---------------------- | -------F-N----- | --------------- |
| 6 | Germline | | | | DIQMTQSPSSLSASVGDRVTITC | RASQSISSYLN | WYQQKPGKAPKLLIY |
| 7 | 3C4 | O2 | | JK4 | ----S----P------------ | -----R-N-S | --L----I------- |
| 8 | Germline | | | | DIQMTQSPSSLSASVGDRVTITC | RASQSISSYLN | WYQQKPGKAPKLLIY |
| 9 | 23B5 | O2 | | JK5 | --L------------------- | ----------- | ---------V----- |
| 10 | 25G4 | O2 | | JK5 | ---------------------- | -------I--- | ------------Y-- |
| 11 | Germline | | | | QSVLTQPPSVSGAPGQRVTISC | TGSSSNIGAGYDVH | WYQQLPGTAPKLLIY |
| 12 | 31H4 | V1-13 | | JL2 | --------------------S | -------H----- | --V------------ |
| 13 | 27B2 | V1-13 | | JL2 | --------------------- | ------------- | ---------------S |
| 14 | Germline | | | | QSALTQPASVSGSPGQSITISC | TGTSSDVGGYNYVS | WYQQHPGKAPKLMIY |
| 15 | 25A7 | V1-4 | | JL2 | --------------------- | ----R-S------ | ------H-----V-- |
| 16 | 27H5 | V1-4 | | JL2 | --------------------- | ------S------ | ---------P----- |
| 17 | 26H5 | V1-4 | | JL2 | --------------------- | ------S------ | ---------P----- |
| 18 | 31D1 | V1-4 | | JL2 | --------------------- | ------S------ | ---------P----- |
| 19 | 20D10 | V1-4 | | JL2 | --------------------- | ------S------ | ---------P----- |
| 20 | 27E7 | V1-4 | | JL2 | --------------------- | ------S------ | ------Y--P--K-- |
| 21 | 30B9 | V1-4 | | JL2 | --------------------- | ---N--S------ | ---------P----- |
| 22 | 19H9 | V1-4 | | JL2 | --------------------- | ------S------ | ---------P----- |
| 23 | 26E10 | V1-4 | | JL2 | --------------------- | ------S------ | --------------- |
| 23 | 21B12 | V1-4 | | JL2 | --------------------- | ---A--S------ | --------------- |
| 24 | 17C2 | V1-4 | | JL2 | --------------------- | ------------- | ----------R---- |

FIG. 2A

| Seq ID No. | LINE | V | D | J | FR1 | CDR1 | FR2 |
|---|---|---|---|---|---|---|---|
| 25 | Germline | | | | QSALTQPASVSGSPGQSITISC | TGTSSDVGGYNYVS | WYQQHPGKAPKLMIY |
| 26 | 23G1 | V1-4 | | JL3 | ---------------------- | -------S----- | --------------- |
| 27 | Germline | | | | QSALTQPASVSGSPGQSITISC | TGTSSDVGSYNLVS | WYQQHPGKAPKLMIY |
| 28 | 13H1 | V1-7 | | JL3 | L--------------------- | --------N----- | ------YS------- |
| 29 | Germline | | | | QSVLTQPPSASGTPGQRVTISC | SGSSSNIGSNTVN | WYQQLPGTAPKLLIY |
| 30 | 9C9 | V1-16 | | JL3 | ---------------------- | -------K----- | --------------- |
| 31 | 9H6 | V1-16 | | JL3 | -----------P---------- | ------------- | -----V--------- |
| 32 | 31A4 | V1-16 | | JL3 | ---------------------- | ------------- | --------------- |
| 33 | 1A12 | V1-16 | | JL3 | ---------------------- | -------K----- | ------F-------- |
| 34 | Germline | | | | QSVLTQPPSVSVSAAPGQKVTISC | SGSSSNIGNNYVS | WYQQLPGTAPKLLIY |
| 35 | 16F12 | V1-19 | | JL1 | ---------------------- | ---------F---- | --------------- |
| 36 | 22E2 | V1-19 | | JL1 | ---------------------- | ---------F---- | --------------- |
| 37 | 27A6 | V1-19 | | JL1 | ---------------------- | ---------F---- | ------F-------- |
| 38 | 28B12 | V1-19 | | JL1 | ------T--------------- | ---------F---- | --------------- |
| 39 | 28D6 | V1-19 | | JL1 | ---------------------- | ---------F---- | --------------- |
| 40 | 31G11 | V1-19 | | JL1 | ---------------------- | ---------F---- | --------------- |
| 41 | Germline | | | | QSVLTQPPSVSAAPGQKVTISC | SGSSSNIGNNYVS | WYQQLPGTAPKLLIY |
| 42 | 13B5 | V1-19 | | JL2 | ---------------------- | ----N-------- | --------------- |
| 43 | Germline | | | | SYELTQPPSVSVSPGQTASITC | SGDKLGDKYAC | WYQQKPGQSPVLVIY |
| 44 | 31B12 | V2-1 | | JL2 | -------R------------- | ----------- | --------------- |
| 45 | Germline | | | | QPVLTQPPSASASLGASVTLTC | TLSSGYSNYKVD | WYQQRPGKGPRFVMR |
| 46 | 3B6 | V5-2 | | JL2 | ----LF--------------- | --------S-E-- | --------------- |

| Seq ID No. | LINE | CDR2 | FR3 | CDR3 | FR4 |
|---|---|---|---|---|---|
| 4 | | LGSNRAS | GVPDRFSGSGSGTDFTLKISRVEAEDVGVYYC | MQALQTPFT | FGPGTKVDIK |
| 5 | 30A4 | ----R--- | -------------------------------- | -V------- | ---------- |
| 6 | | AASSLQS | GVPSRFSGSGSGTDFTLTISSLQPEDFATYYC | QQSYSTPLT | FGGGTKVEIK |
| 7 | 3C4 | ------- | -----------------------------S-- | --------I | ---------- |
| 8 | | AASSLQS | GVPSRFSGSGSGTDFTLTISSLQPEDFATYYC | QQSYSTPIT | FGQGTSLEIK |
| 9 | 23B5 | ------- | --------------N----------------- | -----S--- | ---------- |
| 10 | 25G4 | ---A--- | -------------------------------- | ---A----- | ---------- |
| 11 | | GNSNRPS | GVPDRFSGSKSGTSASLAITGLQAEDEADYYC | QSVDSSLSGSV | FGGGTKLTVL |
| 12 | 31H4 | ------- | -------------------------------- | ----N---V- | ---------- |
| 13 | 27B2 | --TY--- | -------------------------------- | ------V--- | ---------- |
| 14 | | EVSNRPS | GVSNRFSGSKSGNTASLTISGLQAEDEADYYC | SSYTSSSVV | FGGGTKLTVL |
| 15 | 25A7 | ------- | ---T---------------------------- | ---------- | ---------- |
| 286 | 25A7v1 | ------- | ---T---------------------------- | ---T-M--- | ---------- |
| 16 | 27H5 | ------- | ---I---------------------------- | ---T-M--- | ---------- |
| 287 | 27H5v1 | ------- | ---I---------------------------- | ---T-M--- | ---------- |
| 17 | 26E5 | ------- | ---I---------------------------F- | ---T-M--- | ---------- |
| 18 | 31D1 | ------- | -------------------------------F- | ---T-M--- | ---------- |
| 19 | 20D10 | ------- | -------------------------------F- | ---T-M--- | ---------- |
| 20 | 27E7 | ------- | -------------------------------F- | ---T-M--- | ----A----- |
| 21 | 30B9 | ------- | ---I---------------------------F- | ---T-M--- | ---------- |
| 22 | 19H9 | ------- | ---I---------------------------F- | ---T-M--- | ---------- |
| 288 | 19H9v1 | ------- | ---I---------------------------F- | ---T-M--- | ---------- |
| 23 | 26E10 | ------- | -------------------------------- | N--T-M--- | ---------- |
| 23 | 21B12 | ------- | -------------------------------- | N--T-M--- | ---------- |
| 24 | 17C2 | ------- | -------------------------------- | ---TNM--- | ---------- |

| Seq ID No. | LINE | CDR2 | FR3 | CDR3 | FR4 |
|---|---|---|---|---|---|
| 25 | | EVSNRPS | GVSNRFSGSKSGNTASLTISGLQAEDEADYYC | SSYTSSS V | FGGGTKLTVL |
| 26 | 23G1 | --T---- | -------------------------------- | N---T-M- | ---------- |
| 27 | | EGSKRPS | GVSNRFSGSKSGNTASLTISGLQAEDEADYYC | CSYAGSST | FGGGTKLTVL |
| 28 | 13H1 | -V----- | -------------------------------- | -----IV | ---------- |
| 29 | | SNNQRPS | GVPDRFSGSKSGTSASLAISGLQSEDEADYYC | AAWDDSLN V | FGGGTKLTVL |
| 30 | 9C9 | R----L | -------------------------------- | ------W- | ---------- |
| 31 | 9H6 | ----R-- | -------------------------------- | ------W- | ---------- |
| 32 | 31A4 | ------- | -------------------------------- | -V----GWV | ---------- |
| 33 | 1A12 | ----R-- | -------------------------------- | ------W- | -----A---- |
| 34 | | DNNKRPS | GIPDRFSGSKSGTSATLGITGLQTGDEADYYC | GTWDSSLSAYV | FGTGTKVTVL |
| 35 | 16F12 | -Y----- | -------------------------------- | -----G--- | ------R--- |
| 36 | 22E2 | -Y----- | -------------------------------- | -----S--- | ------R--- |
| 37 | 27A6 | -Y----- | -------------------------------- | -----G--- | ------R--- |
| 38 | 28B12 | -Y----- | -------------------------------- | ---------- | ------R--- |
| 39 | 28D6 | -Y----- | -------------------------------- | -----G--- | ------R--- |
| 40 | 31G11 | -S----- | ------------D------------------- | ---------- | ---------- |
| 41 | | DNNKRPS | GIPDRFSGSKSGTSATLGITGLQTGDEADYYC | GTWDSSLSAVV | FGGGTKLTVL |
| 42 | 13B5 | ------- | ---------------N---------------- | ---------- | ---------- |
| 43 | | QDSKRPS | GIPERFSGSNSGNTATLTISGTQAMDEADYYC | QAWDSSTAVV | FGGGTKLTVL |
| 44 | 31B12 | -NT-W-L | -------K---V------------------- | -----V--- | ---------- |
| 45 | | VGTGGIVGSKGD | GIPDRFSVLGSGLNRYLTIKNIQEEDESDYHC | GADHGSGSNFVVV | FGGGTKLTVL |
| 46 | 3B6 | -D----E | -------------------------------- | ---T------- | ---------- |
| 45 | | VGTGGIV | GSKGDGIPDRFSVLGSGLNRYLTIKNIQEEDE | SDYHCGADHGSGSNFVVV | FGGGTKLTVL |
| 46 | 3B6v1 | -D----- | -----E------------------------- | --------T--------- | ---------- |

FIG. 2D

| Seq ID No. | LINE | V | D | J | FR1 | CDR1 | FR2 |
|---|---|---|---|---|---|---|---|
| 47 | Germline | | | | QVQLVQSGAEVKKPGASVKVSCKAS | GYTFTSYGIS | WVRQAPGQGLEWMG |
| 48 | 20D10 | VH1-18 | | JH6B | -I------------------------ | --PL------ | -------------- |
| 49 | 26E10 | VH1-18 | | JH6B | -------------------------- | ---L------ | -------------- |
| 49 | 21B12 | VH1-18 | | JH6B | -------------------------- | ---L------ | -------------- |
| 50 | 23G1 | VH1-18 | | JH6B | -------------------------- | ---L------ | -------------- |
| 51 | 26H5 | VH1-18 | | JH6B | -------------R------------ | ---L------ | -------------- |
| 52 | 27H5 | VH1-18 | | JH6B | -------------------------- | ---L------ | -------------- |
| 53 | 31D1 | VH1-18 | | JH6B | -I------------------------ | ---L------ | -------------- |
| 54 | 27E7 | VH1-18 | | JH6B | -------------------------- | --SL------ | -------------- |
| 55 | 30B9 | VH1-18 | | JH6B | ---------------L---------- | --PL------ | -------------- |
| 56 | 19H9 | VH1-18 | | JH6B | -------------------------- | --AL------ | -------------- |
| 57 | 17C2 | VH1-18 | | JH6B | -------------------------- | --S------- | -------------- |
| 58 | 25A7 | VH1-18 | | JH6B | -------------------------- | ----P----- | -------------- |
| 59 | Germline | | | | QVQLVQSGAEVKKPGASVKVSCKAS | GYTFTSYGIS | WVRQAPGQGLEWMG |
| 60 | 3B6 | VH1-18 | | JH4B | -------------------------- | ---------- | -------------- |
| 61 | Germline | | | | EVQLVESGGGLVQPGGSLRLSCAAS | GFTFSSYWMS | WVRQAPGKGLEWVA |
| 62 | 9H6 | VH3-7 | D7-27 | JH3A | -------------------------- | ----R----- | -------------- |
| 63 | Germline | | | | EVQLVESGGGLVQPGGSLRLSCAAS | GFTFSSYWMS | WVRQAPGKGLEWVA |
| 64 | 9C9 | VH3-7 | D7-27 | JH3B | -----------------------VV- | ---------- | -------------- |
| 65 | 1A12 | VH3-7 | D7-27 | JH3B | -------------------------- | -L---NF--- | -------------- |
| 66 | Germline | | | | EVQLVESGGGLVKPGGSLRLSCAAS | GFTFSSYSMN | WVRQAPGKGLEWVS |
| 67 | 31H4 | VH3-21 | D3-3 | JH3A | -------------------------- | ---------- | -------------- |
| 68 | Germline | | | | EVQLLESGGGLVQPGGSLRLSCAAS | GFTFSSYAMS | WVRQAPGKGLEWVS |
| 69 | 13B5 | VH3-23 | | JH4B | -------------------------- | ---------- | -------------- |

FIG. 3A

| Seq ID No. | LINE | V | D | J | FR1 | CDR1 | FR2 |
|---|---|---|---|---|---|---|---|
| 70 | | Germline | | | EVQLLESGGGLVQPGGSLRLSCAAS | GFTFSSYAMS | WVRQAPGKGLEWVS |
| 71 | 23B5 | VH3-23 | D2-8 | JH4B | ------------------------ | -----N-- | -------------- |
| 72 | 25G4 | VH3-23 | D2-8 | JH4B | ------------------------ | -----N-- | -------------- |
| 73 | | Germline | | | QVQLVESGGGVVQPGRSLRLSCAAS | GFTFSSYGMH | WVRQAPGKGLEWVA |
| 74 | 30A4 | VH3-33 | | JH6B | ------------------------ | ---------- | -------------- |
| 75 | | Germline | | | QVQLVESGGGVVQPGRSLRLSCAAS | GFTFSSYGMH | WVRQAPGKGLEWVA |
| 76 | 27A6 | VH3-33 | D6-6 | JH6B | --H--------------------- | ----N-F-- | -------------- |
| 77 | 28B12 | VH3-33 | D6-6 | JH6B | ------------------------ | ------F-- | -------------- |
| 289 | 28B12v1 | VH3-33 | D6-6 | JH6B | --H--------------------- | ------F-- | -------------- |
| 78 | 28D6 | VH3-33 | D6-6 | JH6B | ------------------------ | ------F-- | -------------- |
| 79 | 16F12 | VH3-33 | D6-6 | JH6B | --H--------------------- | ----N-F-- | -------------- |
| 80 | 22E2 | VH3-33 | D6-6 | JH6B | ------------------------ | ------F-- | -------------- |
| 81 | 31B12 | VH3-33 | D6-6 | JH6B | ------------------------ | ---------- | -------------- |
| 290 | 31B12v1 | VH3-33 | D6-6 | JH6B | ------------------------ | ---------- | ----------C--- |
| 82 | | Germline | | | QVQLVESGGGVVQPGRSLRLSCAAS | GFTFSSYGMH | WVRQAPGKGLEWVA |
| 83 | 31G11 | VH3-33 | D6-19 | JH6B | ------------------------ | ----R----- | -------------- |
| 84 | | Germline | | | QVQLQESGPGLVKPSQTLSLTCTVS | GGSISSGGYYWS | WIRHPGKGLEWIG |
| 85 | 3C4 | VH4-31 | | JH6B | ------------------------ | ---SD------ | -------------- |
| 86 | | Germline | | | QVQLQESGPGLVKPSQTLSLTCTVS | GGSISSGGYYWS | WIRHPGKGLEWIG |
| 87 | 27B2 | VH4-31 | D5-5 | JH4B | ------------------------ | ------------ | -------------- |
| 88 | | Germline | | | QVQLQQWGAGLLKPSETLSLTCAVY | GGSFSGYYWS | WIRQPPGKGLEWIG |
| 89 | 31A4 | VH4-34 | D6-6 | JH4B | ------------------------ | ---A---N- | -------------- |
| 90 | | Germline | | | QVQLQQSGPGLVKPSQTLSLTCAIS | GDSVSSNSAAWN | WIRQSPSRGLEWLG |
| 91 | 13H1 | VH6-1 | | JH4B | ------------------------ | ------------ | -------------- |

FIG. 3B

| Seq ID No. | LINE | CDR2 | FR3 | CDR3 | FR4 |
|---|---|---|---|---|---|
| 47 | 20D10 | WISAYNGNTNYAQKLQG | RVTMTTDTSTSTAYMELRSLRSDDTAVYYCAR | YGMDV | WGQGTTVTVSS |
| 48 | 26E10 | ---------------V- | S------------------------------- | G---- | ----------- |
| 49 | 21B12 | -V-F------------- | -G------------P----------------- | G---- | ----------- |
| 49 | 23G1 | -V-F------------- | -G------------P----------------- | G---- | ----------- |
| 50 | 26H5 | -V-F------------- | -G------------P----------------- | G---- | ----------- |
| 51 | 27H5 | ---F----------V-- | -------------------------------- | G---- | ----------- |
| 52 | 31D1 | ----F---------V-- | ------------------S------------- | G---- | ----------- |
| 53 | 27E7 | ---F------------- | -------------------------------- | G---- | ----------- |
| 54 | 30B9 | --------------V-- | -------------------------F------ | G---- | ----------- |
| 55 | 19H9 | ---F------------- | -------------------------------- | G---- | ----------- |
| 56 | 17C2 | -V----------F---- | -------------------------------- | G---- | ----------- |
| 57 | 25A7 | ----------------E | -----------------V-------------- | G-V-- | ----------- |
| 58 | 3B6 | WISAYNGNTNYAQKLQG | RVTMTTDTSTSTAYMELRSLRSDDTAVYYCAR | G-V-- | WGQGTLVTVSS |
| 59 | 9H6 | ---T------------- | -V-------------------F---------- | GY DY | ----------- |
| 60 | 61 | NIKQDGSEKYYVDSVKG | RFTISRDNAKNSLYLQMNSLRAEDTAVYYCAR | --TR- | WGQGTMVTVSS |
| 61 | 9H6 | -------H--------- | -------------------------------- | ES---F------ | ---H------- |
| 62 | 9C9 | NIKQDGSEKYYVDSVKG | RFTISRDNAKNSLYLQMNSLRAEDTAVYYCAR | NWG AFDI | WGQGTMVTVSS |
| 63 | 1A12 | ----------------- | --------------------S-T--------- | ES---F------ | ----------- |
| 64 | | SISSSSSYIYYADSVKG | RFTISRDNAKNSLYLQMNSLRAEDTAVYYCAR | ES---F------ | ----------- |
| 65 | | -------S--------- | --------------F----------------- | DYDFWSGYYTAFDV | WGQGTMVTVSS |
| 66 | 31H4 | AISGSGGSTYYADSVKG | RFTISRDNSKNTLYLQMNSLRAEDTAVYYCAK | --------A--D- | ----------- |
| 67 | 13B5 | T-----R--------- | -------------------------------- | FDY | WGQGTLVTVSS |
| 68 | | | | EVGSP--- | ----------- |

| Seq ID No. | LINE | CDR2 | FR3 | CDR3 | FR4 |
|---|---|---|---|---|---|
| 70 | | AISGSGGSTYYADSVKG | RFTISRDNSKNTLYLQMNSLRAEDTAVYYCAR | VLMVTA DY | WGQGTLVTVSS |
| 71 | 23B5 | T---DN--------- | ---------------------------- | KF-----ML- | ---------- |
| 72 | 25G4 | T---N---------- | ---------------------------- | KF-----ML- | --------H- |
| 73 | 30A4 | VIWYDGSNKYYADSVKG | RFTISRDMSKNTLYLQMNSLRAEDTAVYYCAR | YYYGMDV | WGQGTVTVTVSS |
| 74 | | -----D--------- | ---------------------------- | ETGPIKI | ---------- |
| 75 | 27A6 | VIWYDGSNKYYADSVKG | RFTISRDNSKNTLYLQMNSLRAEDTAVYYCAR | IAA GMDV | WGQGTLVTVSS |
| 76 | 28B12 | I---S---------- | ---------------------------- | AIAALYYY- | ---------- |
| 77 | 28D6 | L---N---------- | ---------------------------- | AIAALYYY- | ---------- |
| 78 | 16F12 | L---N---------- | ---------------------------- | AIAALYYY- | ---------- |
| 79 | 22E2 | L---S---DE----- | ---------------------------- | AIAALYYY- | ---------- |
| 80 | 22E2v1 | L---N---------- | ---------------------------- | AIAALYYY- | ---------- |
| 291 | 31B12 | I-------------- | ---------------------------- | RCGLAARPG | ---------- |
| 81 | 31B12v1 | I-------------- | ---------------------------- | RCGI---PG- | ---------- |
| 290 | 31G11 | VIWYDGSNKYYADSVKG | RFTISRDNSKNTLYLQMNSLRAEDTAVYYCAR | GIAVAYYYGMDV | WGQGTVTVTVSS |
| 82 | | L--E--T----V--- | -I---------L----------------- | YYYGMDV | ---------- |
| 83 | 3C4 | YIYYSGSTYYNPSLKS | RVTISVDTSKNQFSIKLSSVTAADTAVYYCAR | GGVTT----A- | WGQGTVTVTVSS |
| 84 | 27B2 | YIYYSGSTYYNPSLKS | RVTISVDTSKNQFSIKLSSVTAADTAVYYCAR | EDIAMV YFDY | WGQGTLVTVSS |
| 85 | | -----N--------- | ---------------------------- | ---P----- | ---------- |
| 86 | 31A4 | EINHSGSTNYNPSLKS | RVTISVDTSKNQFSLKLSSVTAADTAVYYCAR | GQLV FDY | WGQGTLVTVSS |
| 87 | | ------R-D------ | -------K---N---------------- | ---?------ | ---------- |
| 88 | 13H1 | RTYYRSKWYKDYAVSVKS | RITINPDPSKNQFSLQINSVFPEDTAVYYCAR | FDY | WGQGTLVTVSS |
| 89 | | --------KN-S--- | ---------------G------------- | GGPTAA---- | ---------- |

31H4

Nucleotide sequence of heavy chain variable region:
5'GAGGTGCAGCTGGTGGAGTCTGGGGGAGGCCTGGTCAAGCCTGGGGGGTCCCTGA
GACTCTCCTGTGCAGCCTCTGGATTCACCTTCAGTAGCTATAGCATGAACTGGGTCC
GCCAGGCTCCAGGGAAGGGGCTGGAGTGGGTCTCATCCATTAGTAGTAGTAGTAGT
TACATTTCCTACGCAGACTCAGTGAAGGGCCGATTCACCATCTCCAGAGACAACGCC
AAGAACTCACTGTATCTGCAAATGAACAGCCTGAGAGCCGAGGACACGGCTGTGTA
TTTCTGTGCGAGAGATTACGATTTTTGGAGTGCTTACTATGATGCTTTTGATGTCTGG
GGCCAAGGGACAATGGTCACCGTCTCTTCA3' (SEQ ID NO: 152)

Amino acid sequence of heavy chain variable region:
EVQLVESGGGLVKPGGSLRLSCAASGFTFSSYSMNWVRQAPGKGLEWVSSISSSSSYISY
ADSVKGRFTISRDNAKNSLYLQMNSLRAEDTAVYFCARDYDFWSAYYDAFDVWGQGT
MVTVSS (SEQ ID NO: 67)

Nucleotide sequence of light chain variable region:
5'CAGTCTGTGCTGACGCAGCCGCCCTCAGTGTCTGGGGCCCCAGGGCAGAGGGTCA
CCATCTCCTGCACTGGGAGCAGCTCCAACATCGGGGCAGGTTATGATGTACACTGGT
ACCAGCAGCTTCCAGGAACAGCCCCCAAACTCCTCATCTCTGGTAACAGCAATCGGC
CCTCAGGGGTCCCTGACCGATTCTCTGGCTCCAAGTCTGGCACCTCAGCCTCCCTGG
CCATCACTGGGCTCCAGGCTGAGGATGAGGCTGATTATTACTGCCAGTCCTATGACA
GCAGCCTGAGTGGTTCGGTATTCGGCGGAGGGACCAAGCTGACCGTCCTA3' (SEQ ID NO: 153)

Amino acid sequence of light chain variable region:
QSVLTQPPSVSGAPGQRVTISCTGSSSNIGAGYDVHWYQQLPGTAPKLLISGNSNRPSGV
PDRFSGSKSGTSASLAITGLQAEDEADYYCQSYDSSLSGSVFGGGTKLTVL (SEQ ID NO: 12)

Nucleotide sequence of heavy chain variable region:
5'CAGATTCAGCTGGTGCAGTCTGGAGCTGAGGTGAAGAAGCCTGGGGCCTCAGTGA
AGGTCTCCTGCAAGGCTTCTGGTTACCCCTTGACCAGCTATGGTATCAGCTGGGTGC
GACAGGCCCCTGGACAAGGGCTTGAGTGGATGGGATGGATCAGCGCTTACAATGGT
AACACAAACTATGCACAGAAGGTCCAGGGCAGCGTCACCATGACCACAGACACATC
CACGAGCACAGTCTACATGGAGCTGAGGAGCCTGAGATCTGACGACACGGCCGTGT
ATTACTGTGCGAGAGGCTACGGTATGGACGTCTGGGGCCAAGGGACCACGGTCACC
GTCTCCTCT3' (SEQ ID NO: 92)

Amino acid sequence of heavy chain variable region:
QIQLVQSGAEVKKPGASVKVSCKASGYPLTSYGISWVRQAPGQGLEWMGWISAYNGN
TNYAQKVQGSVTMTTDTSTSTVYMELRSLRSDDTAVYYCARGYGMDVWGQGTTVTV
SS (SEQ ID NO: 48)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGTACCCAGGCAAACCCCCCAAACTCAAGATTTATGAGGTCAGTAATCGGC
CCTCAGGGGTTTCTAATCGCTTCTCTGGCTCCAAGTCTGGCAACACGGCCTCCCTGA
CCATCTCTGGGCTCCAGGCTGAGGACGAGGCTGATTATTTCTGCAGCTCATATACAA
GCACCAGCATGGTCTTCGGCGGAGGGACCAAGCTGACCGTCCTA3' (SEQ ID NO: 93)

Amino acid sequence of light chain variable region:
QSALTQPASVSGSPGQSITISCTGTSSDVGGYNSVSWYQQYPGKPPKLKIYEVSNRPSGV
SNRFSGSKSGNTASLTISGLQAEDEADYFCSSYTSTSMVFGGGTKLTVL (SEQ ID NO: 19)

Nucleotide sequence of heavy chain variable region:
5'CAGGTTCAGCTGGTGCAGTCTGGAGCTGAGGTGAAGAAGCCTGGGGCCTCAGTGA
AGGTCTCCTGCAAGGCTTCTGGTTACACCTTAACCAGCTATGGTATCAGCTGGGTGC
GACAGGCCCCTGGACAAGGGCTTGAGTGGATGGGATGGGTCAGTTTTTATAATGGT
AACACAAACTATGCACAGAAGCTCCAGGGCAGAGGCACCATGACCACAGACCCATC
CACGAGCACAGCCTACATGGAGCTGAGGAGCCTGAGATCTGACGACACGGCCGTGT
ATTACTGTGCGAGAGGCTACGGTATGGACGTCTGGGGCCAAGGGACCACGGTCACC
GTCTCCTCT3' (SEQ ID NO: 94)

Amino acid sequence of heavy chain variable region:
QVQLVQSGAEVKKPGASVKVSCKASGYTLTSYGISWVRQAPGQGLEWMGWVSFYNG
NTNYAQKLQGRGTMTTDPSTSTAYMELRSLRSDDTAVYYCARGYGMDVWGQGTTVT
VSS (SEQ ID NO: 49)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGCACCCAGGCAAAGCCCCCAAACTCATGATTTATGAGGTCAGTAATCGGC
CCTCAGGGGTTTCTAATCGCTTCTCTGGCTCCAAGTCTGGCAACACGGCCTCCCTGA
CCATCTCTGGGCTCCAGGCTGAGGACGAGGCTGATTATTACTGCAATTCATATACAA
GCACCAGCATGGTATTCGGCGGAGGGACCAAGCTGACCGTCCTA3' (SEQ ID NO: 95)

Amino acid sequence of light chain variable region:
QSALTQPASVSGSPGQSITISCTGTSSDVGGYNSVSWYQQHPGKAPKLMIYEVSNRPSGV
SNRFSGSKSGNTASLTISGLQAEDEADYYCNSYTSTSMVFGGGTKLTVL (SEQ ID NO: 23)

Alternative Nucleotide sequence of light chain variable region (26E10v1):
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGCACCCAGGCAAAGCCCCCAAACTCATGATTTATGAGGTCAGTAATCGGC
CCTCAGGGGTTTCTAATCGCTTCTCTGGCTCCAAGTCTGGCAACACGGCCTCCCTGA
CCATCTCTGGGCTCCAGGCTGAGGACGAGGCTGATTATTACTGCAACTCATATACAA
GCACCAGCATGGTATTCGGCGGAGGGACCAAGCTGACCGTCCTA3' (SEQ ID NO: 293)

Nucleotide sequence of heavy chain variable region:
5'CAGGTTCAGCTGGTGCAGTCTGGAGCTGAAGTGAAGAAGCCTGGGGCCTCAGTGA
AGGTCTCCTGCAAGGCTTCTGGTTACACCTTGACCAGCTATGGTATCAGCTGGGTGC
GACAGGCCCCTGGACAAGGGCTTGAGTGGATGGGATGGATCAGCTTTTACAATGGT
AACACAAACTATGCACAGAAGGTCCAGGGCAGAGTCACCATGACCACAGACACATC
CACGAGCACAGTCTACATGGAGCTGAGGAGCCTGAGATCTGACGACACGGCCGTGT
ATTACTGTGCGAGAGGCTACGGTATGGACGTCTGGGGCCAAGGGACCACGGTCACC
GTCTCCTCT3' (SEQ ID NO: 96)

Amino acid sequence of heavy chain variable region:
QVQLVQSGAEVKKPGASVKVSCKASGYTLTSYGISWVRQAPGQGLEWMGWISFYNGN
TNYAQKVQGRVTMTTDTSTSTVYMELRSLRSDDTAVYYCARGYGMDVWGQGTTVTV
SS (SEQ ID NO: 51)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGCACCCAGGCAAACCCCCCAAACTCATGATTTATGAGGTCAGTAATCGGC
CCTCAGGGGTTTCTATTCGCTTCTCTGGCTCCAAGTCTGGCAACACGGCCTCCCTGAC
CATCTCTGGGCTCCAGGCTGAGGACGAGGCTGATTATTTCTGCAGCTCATATACAAG
CACCAGCATGGTCTTCGGCGGAGGGACCAAGCTGACCGTCCTA3' (SEQ ID NO: 97)

Amino acid sequence of light chain variable region:
QSALTQPASVSGSPGQSITISCTGTSSDVGGYNSVSWYQQHPGKPPKLMIYEVSNRPSGV
SIRFSGSKSGNTASLTISGLQAEDEADYFCSSYTSTSMVFGGGTKLTVL (SEQ ID NO: 17)

Nucleotide sequence of heavy chain variable region:
5'CAGATTCAGCTGGTGCAGTCTGGAGCTGAGGTGAAGAAGCCTGGGGCCTCAGTGA
AGGTCTCCTGCAAGGCTTCTGGTTACACCTTGACCAGCTATGGTATCAGCTGGGTGC
GACAGGCCCCTGGACAAGGGCTTGAGTGGATGGGATGGATCAGCTTTTACAATGGT
AACACAAACTATGCACAGAAGGTCCAGGGCAGAGTCACCATGACCACAGACACATC
CACGAGCACAGTCTACATGGAGCTGAGGAGCCTGAGATCTGACGACACGGCCGTGT
ATTTCTGTGCGAGAGGTTACGGTATGGACGTCTGGGGCCAAGGGACCACGGTCACC
GTCTCCTCA3' (SEQ ID NO: 98)

Amino acid sequence of heavy chain variable region:
QIQLVQSGAEVKKPGASVKVSCKASGYTLTSYGISWVRQAPGQGLEWMGWISFYNGNT
NYAQKVQGRVTMTTDTSTSTVYMELRSLRSDDTAVYFCARGYGMDVWGQGTTVTVS
S (SEQ ID NO: 53)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCGTGGTA
CCAACAGCACCCAGGCAAACCCCCCAAACTCATGATTTATGAGGTCAGTAATCGGC
CCTCAGGGGTTTCTAATCGCTTCTCTGGCTCCAAGTCTGGCAACACGGCCTCCCTGA
CCATCTCTGGGCTCCAGGCTGAGGACGAGGCTGATTATTTCTGCAGCTCATATACAA
GCACCAGCATGGTCTTCGGCGGAGGGACCAAGCTGGCCGTCCTA3' (SEQ ID NO: 99)

Amino acid sequence of light chain variable region:
QSALTQPASVSGSPGQSITISCTGTSSDVGGYNSVSWYQQHPGKPPKLMIYEVSNRPSGV
SNRFSGSKSGNTASLTISGLQAEDEADYFCSSYTSTSMVFGGGTKLAVL (SEQ ID NO: 18)

Nucleotide sequence of heavy chain variable region:
5'CAGGTTCAGCTGGTGCAGTCTGGAGCTGAGGTGAAGAAGCCTGGGGCCTCAGTGA
AGGTCTCCTGCAAGGCTTCTGGTTACACCTTAACCAGCTATGGTATCAGCTGGGTGC
GACAGGCCCCTGGACAAGGGCTTGAGTGGATGGGATGGGTCAGTTTTTATAATGGT
AACACAAACTATGCACAGAAGCTCCAGGGCAGAGGCACCATGACCACAGACCCATC
CACGAGCACAGCCTACATGGAGCTGAGGAGCCTGAGATCTGACGACACGGCCGTGT
ATTACTGTGCGAGAGGCTACGGTATGGACGTCTGGGGCCAAGGGACCACGGTCACC
GTCTCCTCA3' (SEQ ID NO: 100)

Amino acid sequence of heavy chain variable region:
QVQLVQSGAEVKKPGASVKVSCKASGYTLTSYGISWVRQAPGQGLEWMGWVSFYNG
NTNYAQKLQGRGTMTTDPSTSTAYMELRSLRSDDTAVYYCARGYGMDVWGQGTTVT
VSS (SEQ ID NO: 50)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGCACCCAGGCAAAGCCCCCAAACTCATGATTTATGAGGTCACTAATCGGC
CCTCAGGGGTTTCTAATCGCTTCTCTGGCTCCAAGTCTGGCAACACGGCCTCCCTGA
CCATCTCTGGGCTCCAGGCTGAGGACGAGGCTGATTATTACTGCAACTCATATACAA
GCACCAGCATGGTGTTCGGCGGAGGGACCAAGCTGACCGTCCTA3' (SEQ ID NO: 101)

Amino acid sequence of light chain variable region:
QSALTQPASVSGSPGQSITISCTGTSSDVGGYNSVSWYQQHPGKAPKLMIYEVTNRPSGV
SNRFSGSKSGNTASLTISGLQAEDEADYYCNSYTSTSMVFGGGTKLTVL (SEQ ID NO: 26)

Nucleotide sequence of heavy chain variable region:
5'CAGGTGCAGCTGCAGGAGTCGGGCCCAGGACTGGTGAAGCCTTCACAGACCCTGT
CCCTCACCTGCACTGTCTCTGGTGGCTCCATCAGCAGTGGTGGTTACTACTGGAGCT
GGATCCGCCAGCACCCAGGGAAGGGCCTGGAGTGGATTGGGTACATATATAACAGT
GGGAGCACCTACTACAACCCGTCCCTCAAGAGTCGAGTTACCATATCAGTAGACAC
GTCTAAGAACCAGTTCTCCCTGAAGCTGAGCTCTGTGACTGCCGCGGACACGGCCGT
GTATTACTGTGCGAGAGAGGATACAGCTATGGTTCCTTACTTTGACTACTGGGGCCA
GGGAACCCTGGTCACCGTCTCCTCA3' (SEQ ID NO: 102)

Amino acid sequence of heavy chain variable region:
QVQLQESGPGLVKPSQTLSLTCTVSGGSISSGGYYWSWIRQHPGKGLEWIGYIYNSGSTY
YNPSLKSRVTISVDTSKNQFSLKLSSVTAADTAVYYCAREDTAMVPYFDYWGQGTLVT
VSS (SEQ ID NO: 87)

Nucleotide sequence of light chain variable region:
5'CAGTCTGTACTGACGCAGCCGCCCTCAGTGTCTGGGGCCCCAGGGCAGAGGGTCA
CCATCTCCTGCACTGGGAGCAGCTCCAACATCGGGGCACATTATGATGTGCACTGGT
ACCAGCAGGTTCCAGGAACAGCCCCCAAACTCCTCATCTATGGTAACACCTATCGGC
CCTCAGGGGTCCCTGACCGATTCTCTGGCTCCAAGTCTGGCACCTCAGCCTCCCTGG
CCATCACTGGGCTCCAGGCTGAGGATGAGGCTGATTATTACTGCCAGTCCTATGACA
ACAGCCTGAGTGGTGTGGTATTCGGCGGAGGGACCAAGCTGACCGTCCTA3' (SEQ ID NO: 103)

Amino acid sequence of light chain variable region:
QSVLTQPPSVSGAPGQRVTISCTGSSSNIGAHYDVHWYQQVPGTAPKLLIYGNTYRPSG
VPDRFSGSKSGTSASLAITGLQAEDEADYYCQSYDNSLSGVVFGGGTKLTVL (SEQ ID NO: 13)

Nucleotide sequence of heavy chain variable region:
5'CAGGTGCACCTGGTGGAGTCTGGGGGAGGCGTGGTCCAGCCTGGGAGGTCCCTGA
GACTCTCCTGTGCAGCGTCTGGATTCACCTTCAACAGCTTTGGCATGCACTGGGTCC
GCCAGGCTCCAGGCAAGGGGCTGGAGTGGGTGGCACTTATCTGGTCTGATGGAAGT
GATGAATACTATGCAGACTCCGTGAAGGGCCGATTCACCATCTCCAGAGACAATTCC
AAGAACACGCTGTATCTGCAAATGAACAGCCTGAGAGCCGAGGACACGGCTGTGTA
TTACTGTGCGAGAGCCATAGCAGCCCTCTACTACTACTACGGTATGGACGTCTGGGG
CCAAGGGACCACGGTCACCGTCTCCTCA3' (SEQ ID NO: 104)

Amino acid sequence of heavy chain variable region:
QVHLVESGGGVVQPGRSLRLSCAASGFTFNSFGMHWVRQAPGKGLEWVALIWSDGSD
EYYADSVKGRFTISRDNSKNTLYLQMNSLRAEDTAVYYCARAIAALYYYYGMDVWGQ
GTTVTVSS (SEQ ID NO: 79)

Nucleotide sequence of light chain variable region:
5'CAGTCTGTGTTGACGCAGCCGCCCTCAGTGTCTGCGGCCCCAGGACAGAAGGTCA
CCATCTCCTGCTCTGGAAGCAGCTCCAACATTGGGAATAATTTTGTATCCTGGTACC
AGCAGCTCCCAGGAACAGCCCCCAAACTCCTCATTTATGACTATAATAAGCGACCCT
CAGGGATTCCTGACCGATTCTCTGGCTCCAAGTCTGGCACGTCAGCCACCCTGGGCA
TCACCGGACTCCAGACTGGGGACGAGGCCGATTATTACTGCGGAACATGGGATAGC
AGCCTGAGTGCTTATGTCTTCGGAACTGGGACCAGGGTCACCGTCCTA3' (SEQ ID NO: 105)

Amino acid sequence of light chain variable region:
QSVLTQPPSVSAAPGQKVTISCSGSSSNIGNNFVSWYQQLPGTAPKLLIYDYNKRPSGIPD
RFSGSKSGTSATLGITGLQTGDEADYYCGTWDSSLSAYVFGTGTRVTVL (SEQ ID NO: 35)

Nucleotide sequence of heavy chain variable region:

5'CAGGTGCAGCTGGTGGAGTCTGGGGGAGGCGTGGTCCAGCCTGGGAGGTCCCTGA
GACTCTCCTGTGCAGCGTCTGGATTCACCTTCAGCAGCTTTGGCATGCACTGGGTCC
GCCAGGCTCCAGGCAAGGGGCTGGAGTGGGTGGCACTTATATGGAATGATGGAAGT
AATAAATACTATGCAGACTCCGTGAAGGGCCGATTCACCATCTCCAGAGACAATTCC
AAGAACACGCTGTATCTGCAAATGAACAGCCTGAGAGCCGAGGACACGGCTGTGTA
TTACTGTGCGAGAGCCATAGCAGCCCTCTACTACTACTACGGTATGGACGTCTGGGG
CCAAGGGACCACGGTCACCGTCTCCTCA3' (SEQ ID NO: 106)

Amino acid sequence of heavy chain variable region:
QVQLVESGGGVVQPGRSLRLSCAASGFTFSSFGMHWVRQAPGKGLEWVALIWNDGSN
KYYADSVKGRFTISRDNSKNTLYLQMNSLRAEDTAVYYCARAIAALYYYYGMDVWGQ
GTTVTVSS (SEQ ID NO: 80)

Nucleotide sequence of light chain variable region:
5'CAGTCTGTGTTGACGCAGCCGCCCTCAGTGTCTGCGGCCCCAGGACAGAAGGTCA
CCATCTCCTGCTCTGGAAGCAGCTCCAACATTGGGAATAATTTTGTATCCTGGTACC
AGCAGCTCCCAGGAACAGCCCCCAAACTCCTCATTTATGACTATAATAAGCGACCCT
CAGGGATTCCTGACCGATTCTCTGGCTCCAAGTCTGGCACGTCAGCCACCCTGGGCA
TCACCGGACTCCAGACTGGGGACGAGGCCGATTATTACTGCGGAACATGGGATAGC
AGTCTGAGTGGTTATGTCTTCGGAACTGGGACCAGGGTCACCGTCCTA3' **(SEQ ID
NO: 107)**

Amino acid sequence of light chain variable region:
QSVLTQPPSVSAAPGQKVTISCSGSSSNIGNNFVSWYQQLPGTAPKLLIYDYNKRPSGIPD
RFSGSKSGTSATLGITGLQTGDEADYYCGTWDSSLSGYVFGTGTRVTVL (SEQ ID NO: 36)

Nucleotide sequence of heavy chain variable region:
5'CAGGTGCACCTGGTGGAGTCTGGGGGAGGCGTGGTCCAGCCTGGGAGGTCCCTGA
GACTCTCCTGTGCAGCGTCTGGATTCACCTTCAACAGCTTTGGCATGCACTGGGTCC
GCCAGGCTCCAGGCAAGGGGCTGGAGTGGGTGGCACTTATATGGTCTGATGGAAGT
GATAAATACTATGCAGACTCCGTGAAGGGCCGATTCACCATCTCCAGAGACAATTCC
AAGAACACGCTGTATCTGCAAATGAACAGCCTGAGAGCCGAGGACACGGCTGTGTA
TTACTGTGCGAGAGCCATAGCAGCCCTCTACTACTACTACGGTATGGACGTCTGGGG
CCAAGGGACCACGGTCACCGTCTCCTCA3' (SEQ ID NO: 108)

Amino acid sequence of heavy chain variable region:
QVHLVESGGGVVQPGRSLRLSCAASGFTFNSFGMHWVRQAPGKGLEWVALIWSDGSD
KYYADSVKGRFTISRDNSKNTLYLQMNSLRAEDTAVYYCARAIAALYYYYGMDVWGQ
GTTVTVSS (SEQ ID NO: 76)

Nucleotide sequence of light chain variable region:
5'CAGTCTGTGTTGACGCAGCCGCCCTCAGTGTCTGCGGCCCCAGGACAGAAGGTCA
CCATCTCCTGCTCTGGAAGCAGTTCCAACATTGGGAATAATTTTGTATCCTGGTACC
AGCAGTTCCCAGGAACAGCCCCCAAACTCCTCATTTATGACTATAATAAGCGACCCT
CAGGGATTCCTGACCGATTCTCTGGCTCCAAGTCTGGCACGTCAGCCACCCTGGGCA
TCACCGGACTCCAGACTGGGGACGAGGCCGATTATTACTGCGGAACATGGGATAGC
AGCCTGAGTTCTTATGTCTTCGGAACTGGGACCAGGGTCACCGTCCTA3' (SEQ ID NO: 109)

Amino acid sequence of light chain variable region:
QSVLTQPPSVSAAPGQKVTISCSGSSSNIGNNFVSWYQQFPGTAPKLLIYDYNKRPSGIPD
RFSGSKSGTSATLGITGLQTGDEADYYCGTWDSSLSSYVFGTGTRVTVL (SEQ ID NO: 37)

Nucleotide sequence of heavy chain variable region:
5'CAGGTGCAGCTGGTGGAGTCTGGGGGAGGCGTGGTCCAGCCTGGGAGGTCCCTGA
GACTCTCCTGTGCAGCGTCTGGATTCACCTTCAGCAGCTTTGGCATGCACTGGGTCC
GCCAGGCTCCAGGCAAGGGGCTGGAGTGGGTGGCACTTATATGGAATGATGGAAGT
AATAAATACTATGCAGACTCCGTGAAGGGCCGATTCACCATCTCCAGAGACAATTCC
AAGAACACGCTGTATCTGCAAATGAACAGCCTGAGAGCCGAGGACACGGCTGTGTA
TTACTGTGCGAGAGCCATAGCAGCCCTCTACTACTACTACGGTATGGACGTCTGGGG
CCACGGGACCACGGTCACCGTCTCCTCA3' (SEQ ID NO: 110)

Amino acid sequence of heavy chain variable region:
QVQLVESGGGVVQPGRSLRLSCAASGFTFSSFGMHWVRQAPGKGLEWVALIWNDGSN
KYYADSVKGRFTISRDNSKNTLYLQMNSLRAEDTAVYYCARAIAALYYYYGMDVWGH
GTTVTVSS (SEQ ID NO: 77)

Nucleotide sequence of light chain variable region:
5'CAGTCTGTGTTGACGCAGCCGCCCTCAGTGTCTGCGGCCCCAGGACAGAAGGTCA
CCATCTCCTGCTCTGGAAGCAGCTCCAACATTGGGAATAATTTTGTATCCTGGTACC
AGCAGCTCCCAGGAACAGCCCCCAAACTCCTCATTTATGACTATAATAAGCGACCCT
CAGGGATTCCTGACCGATTCTCTGGCTCCAAGTCTGGCACGTCAGCCACCCTGGGCA
TCACCGGACTCCAGACTGGGGACGAGGCCGATTATTACTGCGGAACATGGGATAGC
AGCCTGAGTGGTTATGTCTTCGGAACTGGGACCAGGGTCACCGTCCTA3' (SEQ ID
NO: 111)

Amino acid sequence of light chain variable region:
QSVLTQPPSVSAAPGQKVTISCSGSSSNIGNNFVSWYQQLPGTAPKLLIYDYNKRPSGIPD
RFSGSKSGTSATLGITGLQTGDEADYYCGTWDSSLSGYVFGTGTRVTVL (SEQ ID NO:
38)

Nucleotide sequence of heavy chain variable region:
5'CAGGTGCAGCTGGTGGAGTCTGGGGGAGGCGTGGTCCAGCCTGGGAGGTCCCTGA
GACTCTCCTGTGCAGCGTCTGGATTCACCTTCAGCAGCTTTGGCATGCACTGGGTCC
GCCAGGCTCCAGGCAAGGGGCTGGAGTGGGTGGCACTTATATGGAATGATGGAAGT
AATAAATACTATGCAGACTCCGTGAAGGGCCGATTCACCATCTCCAGAGACAATTCC
AAGAACACGCTGTATCTGCAAATGAACAGCCTGAGAGCCGAGGACACGGCTGTGTA
TTACTGTGCGAGAGCCATAGCAGCCCTCTACTACTACTACGGTATGGACGTCTGGGG
CCAAGGGACCACGGTCACCGTCTCCTCA3' (SEQ ID NO: 112)

Amino acid sequence of heavy chain variable region:
QVQLVESGGGVVQPGRSLRLSCAASGFTFSSFGMHWVRQAPGKGLEWVALIWNDGSN
KYYADSVKGRFTISRDNSKNTLYLQMNSLRAEDTAVYYCARAIAALYYYYGMDVWGQ
GTTVTVSS (SEQ ID NO: 78)

Nucleotide sequence of light chain variable region:
5'CAGTCTGTGTTGACGCAGCCGCCCACAGTGTCTGCGGCCCCAGGACAGAAGGTCA
CCATCTCCTGCTCTGGAAGCAGCTCCAACATTGGGAATAATTTTGTATCCTGGTACC
AGCAGCTCCCAGGAACAGCCCCCAAACTCCTCATTTATGACTATAATAAGCGACCCT
CAGGGATTCCTGACCGATTCTCTGGCTCCAAGTCTGGCACGTCAGCCACCCTGGGCA
TCACCGGACTCCAGACTGGGGACGAGGCCGATTACTACTGCGGAACATGGGATAGC
AGCCTGAGTGGTTATGTCTTCGGAACTGGGACCAGGGTCACCGTCCTA3' (SEQ ID NO: 113)

Amino acid sequence of light chain variable region:
QSVLTQPPTVSAAPGQKVTISCSGSSSNIGNNFVSWYQQLPGTAPKLLIYDYNKRPSGIPD
RFSGSKSGTSATLGITGLQTGDEADYYCGTWDSSLSGYVFGTGTRVTVL (SEQ ID NO: 39)

Nucleotide sequence of heavy chain variable region:
5'CAGGTGCAGCTGGTGGAGTCTGGGGGAGGCGTGGTCCAGCCTGGGAGGTCCCTGA
GACTCTCCTGTGCAGCGTCTGGATTCACCTTCAGGAGCTATGGCATGCACTGGGTCC
GCCAGGCTCCAGGCAAGGGGCTGGAGTGGGTGGCACTTATATGGCATGATGGAAGT
AATACATACTATGTAGACTCCGTGAAGGGCCGATTCACCATCTCCAGAGACAATTCC
AAGAACACGCTGTATCTGCAAATGAACAGCCTGAGAGCCGAGGACACGGCTGTGTA
TTACTGTGCGAGAGGTATAGCAGTGGCTTACTACTACTACGGTATGGACGTCTGGGG
CCAAGGGACCACGGTCACCGTCTCCTCA3' (SEQ ID NO: 114)

Amino acid sequence of heavy chain variable region:
QVQLVESGGGVVQPGRSLRLSCAASGFTFRSYGMHWVRQAPGKGLEWVALIWHDGSN
TYYVDSVKGRFTISRDNSKNTLYLQMNSLRAEDTAVYYCARGIAVAYYYYGMDVWGQ
GTTVTVSS (SEQ ID NO: 83)

Nucleotide sequence of light chain variable region:
5'CAGTCTGTGTTGACGCAGCCGCCCTCAGTGTCTGCGGCCCCAGGACAGAAGGTCA
CCATCTCCTGCTCTGGAAGCAGCTCCAACATTGGGAATAATTTTGTATCCTGGTACC
AGCAGCTCCCAGGAACAGCCCCCAAACTCCTCATTTATGACAGTAATAAGCGACCCT
CAGGGATTCCTGACCGATTCTCTGGCTCCAAGTCTGGCACGTCAGCCACCCTGGACA
TCACCGGACTCCAGACTGGGGACGAGGCCGATTATTACTGCGGAACATGGGATAGC
AGCCTGAGTGCTTATGTTTTCGGAACTGGGACCAAGGTCACCGTCCTA3' (SEQ ID
NO: 115)

Amino acid sequence of light chain variable region:
QSVLTQPPSVSAAPGQKVTISCSGSSSNIGNNFVSWYQQLPGTAPKLLIYDSNKRPSGIPD
RFSGSKSGTSATLDITGLQTGDEADYYCGTWDSSLSAYVFGTGTKVTVL (SEQ ID NO:
40)

Nucleotide sequence of heavy chain variable region:
5'GAGGTGCAGCTGTTGGAGTCTGGGGGAGGCTTGGTACAGCCTGGGGGGTCCCTGA
GACTCTCCTGTGCAGCCTCTGGATTCACCTTTAGCAGCTATGCCATGAACTGGGTCC
GCCAGGCTCCAGGGAAGGGGCTGGAGTGGGTCTCAACTATTAGTGGTAGTGGTGAT
AACACATACTACGCAGACTCCGTGAAGGGCCGGTTCACCATCTCCAGAGACAATTC
CAAGAACACGCTGTATCTGCAAATGAACAGCCTGAGAGCCGAGGACACGGCCGTAT
ATTACTGTGCGAAAAAGTTTGTACTAATGGTGTATGCTATGCTTGACTACTGGGGCC
AGGGAACCCTGGTCACCGTCTCCTCA3' (SEQ ID NO: 116)

Amino acid sequence of heavy chain variable region:
EVQLLESGGGLVQPGGSLRLSCAASGFTFSSYAMNWVRQAPGKGLEWVSTISGSGDNT
YYADSVKGRFTISRDNSKNTLYLQMNSLRAEDTAVYYCAKKFVLMVYAMLDYWGQG
TLVTVSS (SEQ ID NO: 71)

Nucleotide sequence of light chain variable region:
5'GACATCCTGATGACCCAGTCTCCATCCTCCCTGTCTGCATCTGTTGGAGACAGAGT
CACCATCACTTGCCGGGCAAGTCAGAGCATTAGCAGTTATTTAAATTGGTATCAGCA
GAAACCAGGGAAAGCCCCTAAGGTCCTGATCTATGCTGCCTCCAGTTTGCAAAGTGG
GGTCCCATCAAGGTTCAGTGGCAGTGGATCTGGGACAGATTTCACTCTCACCATCAA
CAGTCTGCAACCTGAAGATTTTGCAACTTACTACTGTCAACAGAGTTACAGTTCCCC
CATCACCTTCGGCCAAGGGACACGACTGGAGATTAAA3' (SEQ ID NO: 117)

Amino acid sequence of light chain variable region:
DILMTQSPSSLSASVGDRVTITCRASQSISSYLNWYQQKPGKAPKVLIYAASSLQSGVPSR
FSGSGSGTDFTLTINSLQPEDFATYYCQQSYSSPITFGQGTRLEIK (SEQ ID NO: 9)

Nucleotide sequence of heavy chain variable region:
5'GAGGTGCAGCTGTTGGAGTCTGGGGGAGGCTTGGTACAGCCGGGGGGGTCCCTGA
GACTCTCCTGTGCAGCCTCTGGATTCACCTTTAGCAGCTATGCCATGAACTGGGTCC
GCCAGGCTCCAGGGAAGGGGCTGGAGTGGGTCTCAACTATTAGTGGTAGTGGTGGT
AACACATACTACGCAGACTCCGTGAAGGGCCGGTTCACCATCTCCAGAGACAATTC
CAAGAACACGCTGTATCTGCAAATGAACAGCCTGAGAGCCGAGGACACGGCCGTAT
ATTACTGTGCGAAAAAGTTTGTACTAATGGTGTATGCTATGCTTGACTACTGGGGCC
AGGGAACCCTGGTCACCGTCTCCTCA3' (SEQ ID NO: 118)

Amino acid sequence of heavy chain variable region:
EVQLLESGGGLVQPGGSLRLSCAASGFTFSSYAMNWVRQAPGKGLEWVSTISGSGGNT
YYADSVKGRFTISRDNSKNTLYLQMNSLRAEDTAVYYCAKKFVLMVYAMLDYWGQG
TLVTVSS (SEQ ID NO: 72)

Nucleotide sequence of light chain variable region:
5'GACATCCAGATGACCCAGTCTCCATCCTCCCTATCTGCATCTGTAGGAGACAGAGT
CACCATCACTTGCCGGGCAAGTCAGAGCATTAGCATCTATTTAAATTGGTATCAGCA
GAAGCCAGGGAAAGCCCCTTACCTCCTGATCTATGCTGCAGCCAGTTTGCAAAGTGG
GGTCCCATCAAGGTTCAGTGGCAGTGGATCTGGGACAGATTTCACTCTCACCATCAG
CAGTCTGCAACCTGAAGATTTTGCAACTTACTACTGTCAACAGAGTTACAGTGCCCC
CATCACCTTCGGCCAAGGGACACGACTGGAGATTAAA3' (SEQ ID NO: 119)

Amino acid sequence of light chain variable region:
DIQMTQSPSSLSASVGDRVTITCRASQSISIYLNWYQQKPGKAPYLLIYAAASLQSGVPSR
FSGSGSGTDFTLTISSLQPEDFATYYCQQSYSAPITFGQGTRLEIK (SEQ ID NO: 10)

Nucleotide sequence of heavy chain variable region:
5'CAGGTTCAGCTGGTGCAGTCTGGAGCTGAGGTGAAGAAGCCTGGGGCCTCACTGA
AGGTCTCCTGCAAGGCTTCTGGTTACAGTTTGACCAGCTATGGTATCAGCTGGGTGC
GACAGGCCCCTGGACAAGGGCTTGAGTGGATGGGATGGATCAGCGCTTACAATGGT
AACACAAACTATGCACAGAAGGTCCAGGGCAGAGTCACCATGACCACAGACACATC
CACGAGCACAGTCTACATGGAGGTGAGGAGTCTGAGATCTGACGACACGGCCGTGT
ATTACTGTGCGAGAGGCTACGGTATGGACGTCTGGGGCCAAGGGACCACGGTCACC
GTCTCCTCA3' (SEQ ID NO: 120)

Amino acid sequence of heavy chain variable region:
QVQLVQSGAEVKKPGASLKVSCKASGYSLTSYGISWVRQAPGQGLEWMGWISAYNGN
TNYAQKVQGRVTMTTDTSTSTVYMEVRSLRSDDTAVYYCARGYGMDVWGQGTTVTV
SS (SEQ ID NO: 54)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGCACCCAGGCAAACCCCCCAAACTCATGATTTATGAGGTCAGTAATCGGC
CCTCAGGGGTTTCTAATCGCTTCTCTGGCTCCAAGTCTGGCAATACGGCCTCCCTGA
CCATCTCTGGGCTCCAGGCTGAGGACGAGGCTGATTATTTCTGCAGCTCATATACAA
GCACCAGCATGGTCTTCGGCGGAGGGACCAAGCTGACCGTCCTA3' (SEQ ID NO: 121)

Amino acid sequence of light chain variable region:
QSALTQPASVSGSPGQSITISCTGTSSDVGGYNSVSWYQQHPGKPPKLMIYEVSNRPSGV
SNRFSGSKSGNTASLTISGLQAEDEADYFCSSYTSTSMVFGGGTKLTVL (SEQ ID NO: 20)

Nucleotide sequence of heavy chain variable region:
5'CAGGTTCAGCTGGTGCAGTCTGGAGCTGAGGTGAAGAGGCCTGGGGCCTCAGTGA
AGGTCTCCTGCAAGGCTTCTGGTTACACCTTGACCAGCTATGGTATCAGCTGGGTGC
GACAGGCCCCTGGACAAGGGCTTGAGTGGATGGGATGGATCAGCGTTTACAATGGT
AACACAAACTATGCACAGAAGGTCCAGGGCAGAGTCACCATGACCACAGACACATC
CACGAGCACAGTCTACATGGAGCTGAGGAGCCTGAGCTCTGACGACACGGCCGTGT
ATTACTGTGCGAGAGGCTACGGTATGGACGTCTGGGGCCAAGGGACCACGGTCACC
GTCTCCTCA3' (SEQ ID NO: 122)

Amino acid sequence of heavy chain variable region:
QVQLVQSGAEVKRPGASVKVSCKASGYTLTSYGISWVRQAPGQGLEWMGWISVYNGN
TNYAQKVQGRVTMTTDTSTSTVYMELRSLSSDDTAVYYCARGYGMDVWGQGTTVTV
SS (SEQ ID NO: 52)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGCACCCAGGCAAACCCCCCAAACTCATGATTTATGAGGTCAGTAATCGGC
CCTCAGGGGTTTCTATTCGCTTCTCTGGCTCCAAGTCTGGCAACACGGCCTCCCTGAC
CATCTCTGGGCTCCAGGCTGAGGACGAGGCTGATTATTTCTGCAGCTCATATACAAG
CACCAGCATGGTCTTCGGCGGAGGGACCAAGCTGACCGTCCTA3' (SEQ ID NO: 123)

Amino acid sequence of light chain variable region:
QSALTQPASVSGSPGQSITISCTGTSSDVGGYNSVSWYQQHPGKPPKLMIYEVSNRPSGV
SIRFSGSKSGNTASLTISGLQAEDEADYFCSSYTSTSMVFGGGTKLTVL (SEQ ID NO: 16)

Nucleotide sequence of heavy chain variable region:
5'CAGGTTCAGCTGGTGCAGTCTGGAGCTGAGGTGAAGAAGCCTGGGGCCTCAGTGA
AGGTCTCCTGCAAGGCTTCTGGTTACCCCTTGACCAGCTATGGTATCAGCTGGGTGC
GACAGGCCCCTGGACAAGGGCTTGAGTGGATGGGATGGATCAGCGCTTACAATGGT
AACACAAACTATGCACAGAAGGTCCAGGGCAGAGTCACCATGACCACAGACACATC
CACGAGCACAGTCTACATGGAGTTGAGGAGCCTGAGATCTGACGACACGGCCGTGT
ATTACTGTGCGAGAGGCTACGGTATGGACGTCTGGGGCCAAGGGACCACGGTCACC
GTCTCCTCA3' (SEQ ID NO: 124)

Amino acid sequence of heavy chain variable region:
QVQLVQSGAEVKKPGASVKVSCKASGYPLTSYGISWVRQAPGQGLEWMGWISAYNGN
TNYAQKVQGRVTMTTDTSTSTVYMELRSLRSDDTAVYYCARGYGMDVWGQGTTVTV
SS (SEQ ID NO: 55)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGCACCCAGGCAAACCCCCCAAACTCATGATTTATGAGGTCAGTAATCGGC
CCTCAGGGGTTTCTAATCGCTTCTCTGGCTCCAAGTCTGGCAATACGGCCTCCCTGA
CCATCTCTGGGCTCCAGGCTGAGGACGAGGCTGATTATTTCTGCAGCTCATATACAA
GCACCAGCATGGTCTTCGGCGGAGGGACCAAGCTGACCGTCCTA3' (SEQ ID NO: 125)

Alternative Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGCACCCAGGCAAACCCCCCAAACTCATGATTTATGAGGTCAGTAATCGGC
CCTCAGGGGTTTCTAATCGCTTCTCTGGCTCCAAGTCTGGCAACACGGCCTCCCTGA
CCATCTCTGGGCTCCAGGCTGAGGACGAGGCTGATTATTTCTGCAGCTCATATACAA
GCACCAGCATGGTCTTCGGCGGAGGGACCAAGCTGACCGTCCTA3' (SEQ ID NO: 294)

Amino acid sequence of light chain variable region:
QSALTQPASVSGSPGQSITISCTGTSSDVGGYNSVSWYQQHPGKPPKLMIYEVSNRPSGV
SNRFSGSKSGNTASLTISGLQAEDEADYFCSSYTSTSMVFGGGTKLTVL (SEQ ID NO: 21)

Nucleotide sequence of heavy chain variable region:
5'CAGGTTCAGTTGGTGCAGTCTGGAGCTGAGGTGAAGAAGCCTGGGGCCTCAGTGA
AGGTCTCCTGCAAGGCTTCTGGTTACGCCTTGACCAGCTATGGTATCAGCTGGGTGC
GACAGGCCCCTGGACAAGGGCTTGAGTGGATGGGATGGATCAGCGCTTACAATGGT
AACACAAACTATGCACAGAAGGTCCAGGGCAGAGTCACCATGACCACAGACACATC
CACGAGCACAGTCTACATGGAGCTGAGGAGCCTGAGATCTGACGACACGGCCGTGT
ATTACTGTGCGAGAGGCTACGGTATGGACGTCTGGGGCCAAGGGACCACGGTCACC
GTCTCCTCA3' (SEQ ID NO: 126)

Amino acid sequence of heavy chain variable region:
QVQLVQSGAEVKKPGASVKVSCKASGYALTSYGISWVRQAPGQGLEWMGWISAYNGN
TNYAQKVQGRVTMTTDTSTSTVYMELRSLRSDDTAVYYCARGYGMDVWGQGTTVTV
SS (SEQ ID NO: 56)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAACAGTGACGTTGGTGGTTATAACTCTGTCTCCTGGTA
CCAACAGCACCCAGGCAAACCCCCCAAACTCATGATTTATGAGGTCAGTAATCGGC
CCTCAGGGATTTCTAATCGCTTCTCTGGCTCCAAGTCTGGCAACACGGCCTCCCTGA
CCATCTCTGGGCTCCAGGCTGAGGACGAGGCTGATTATTTCTGCAGCTCATATACAA
GCACCAGCATGGTCTTCGGCGGAGGGACCAAGCTGACCGTCCTA3' (SEQ ID NO: 127)

Amino acid sequence of light chain variable region:
QSALTQPASVSGSPGQSITISCTGTNSDVGGYNSVSWYQQHPGKPPKLMIYEVSNRPSGI
SNRFSGSKSGNTASLTISGLQAEDEADYFCSSYTSTSMVFGGGTKLTVL (SEQ ID NO: 22)

Nucleotide sequence of heavy chain variable region:
5'CAGGTTCAGCTGGTGCAGTCTGGAGCTGAGGTGAAGAAGCCTGGGGCCTCAGTGA
AGGTCTCCTGCAAGGCTTCTGGTTACAGCTTTACCAGCTATGGTATCAGCTGGGTGC
GACAGGCCCCTGGACAAGGGCTTGAGTGGATGGGATGGGTCAGCGCTTACAATGGT
AACACAAACTATGCACAGAAGTTCCAGGGCAGAGTCACCATGACCACAGACACATC
CACGAGCACAGCCTACATGGAACTGAGGAGCCTGAGATCTGACGACACGGCCGTGT
ATTACTGTGCGAGAGGCTACGTTATGGACGTCTGGGGCCAAGGGACCACGGTCACC
GTCTCCTCA3' (SEQ ID NO: 128)

Amino acid sequence of heavy chain variable region:
QVQLVQSGAEVKKPGASVKVSCKASGYSFTSYGISWVRQAPGQGLEWMGWVSAYNG
NTNYAQKFQGRVTMTTDTSTSTAYMELRSLRSDDTAVYYCARGYVMDVWGQGTTVT
VSS (SEQ ID NO: 57)

Nucleotide sequence of light chain variable region:
5'CAGTCTGCCCTGACTCAGCCTGCCTCCGTTTCTGGGTCTCCTGGACAGTCGATCAC
CATCTCCTGCACTGGAACCAGCAGTGACGTTGGTGCTTATAACTCTGTCTCCTGGTA
CCAACAGCACCCAGGCAAAGCCCCCAAACGCATGATTTATGAGGTCAGTAATCGGC
CCTCAGGGGTTTCTAATCGCTTCTCTGGCTCCAAGTCTGGCAACACGGCCTCCCTGA
CCATCTCTGGGCTCCAGGCTGAGGACGAGGCTGATTATTACTGCAGCTCATATACAA
GCACCAACATGGTATTCGGCGGAGGGACCAAGCTGACCGTCCTA3' (SEQ ID NO: 129)

Amino acid sequence of light chain variable region:
QSALTQPASVSGSPGQSITISCTGTSSDVGAYNSVSWYQQHPGKAPKRMIYEVSNRPSGV
SNRFSGSKSGNTASLTISGLQAEDEADYYCSSYTSTNMVFGGGTKLTVL (SEQ ID NO: 24)

Nucleotide sequence of heavy chain variable region:
5'CAGGTACAGTTGCAGCAGTCAGGTCCAGGACTGGTGAAGCCCTCGCAGACCCTCT
CACTCACCTGTGCCATCTCCGGGGACAGTGTCTCTAGCAACAGTGCTGCTTGGAACT
GGATCAGGCAGTCCCCATCGAGAGGCCTTGAGTGGCTGGGAAGGACATACTACAGG
TCCAAGTGGTATAAAAATTATTCAGTATCTGTGAAAAGTCGAATAACCATCAACCCA
GACACATCCAAGAACCAGTTCTCTCTGCAACTGAACTCTGTGACTCCCGGGGACACG
GCTGTGTATTACTGTGCAAGAGGGGGGCCAACTGCTGCTTTTGACTACTGGGGCCAG
GGAACCCTGGTCACCGTCTCCTCA3' (SEQ ID NO: 130)

Amino acid sequence of heavy chain variable region:
QVQLQQSGPGLVKPSQTLSLTCAISGDSVSSNSAAWNWIRQSPSRGLEWLGRTYYRSK
WYKNYSVSVKSRITINPDTSKNQFSLQLNSVTPGDTAVYYCARGGPTAAFDYWGQGTL
VTVSS (SEQ ID NO: 91)

Nucleotide sequence of light chain variable region:
5'CTTTCTGCCCTGACTCAGCCTGCCTCCGTGTCTGGGTCTCCTGGACAGTCGATCAC
CATCTCCTGCACTGGAACCAGCAGTGATGTTGGGAATTATAACCTTGTCTCCTGGTA
CCAACAGTATTCAGGCAAAGCCCCCAAACTCATGATTTATGAGGTCAGTAAGCGGC
CCTCAGGGGTTTCTAATCGCTTCTCTGGCTCCAAGTCTGGCAACACGGCCTCCCTGA
CAATCTCTGGGCTCCAGGCTGAGGACGAGGCTGATTATTACTGCTGCTCATATGCAG
GTAGTAGCACTTTGGTTTTCGGCGGAGGGACCAAGCTGACCGTCCTA3' (SEQ ID NO: 131)

Amino acid sequence of light chain variable region:
LSALTQPASVSGSPGQSITISCTGTSSDVGNYNLVSWYQQYSGKAPKLMIYEVSKRPSGV
SNRFSGSKSGNTASLTISGLQAEDEADYYCCSYAGSSTLVFGGGTKLTVL (SEQ ID NO: 28)

Nucleotide sequence of heavy chain variable region:
5'GAGGTGCAGTTGGTGGAGTCTGGGGGAGGCTTGGTCCAGCCTGGGGGGTCCCTGA
GACTCTCCTGTGTAGTCTCTGGATTCACCTTTAGTAGCTATTGGATGAGCTGGGTCCG
CCAGGCTCCAGGGAAGGGGCTGGAGTGGGTGGCCAACATAAAGCAAGATGGAAGT
GAGAAATACTATGTGGACTCTGTGAAGGGCCGATTCACCATCTCCAGAGACAACGC
CAAGAACTCACTGTATCTGCAAATGAACAGCCTGAGAGCCGAGGACACGGCTGTAT
ATTACTGTGCGAGAGAGTCAAACTGGGGATTTGCTTTTGATATCTGGGGCCAAGGGA
CAATGGTCACCGTCTCTTCA3' (SEQ ID NO: 132)

Amino acid sequence of heavy chain variable region:
EVQLVESGGGLVQPGGSLRLSCVVSGFTFSSYWMSWVRQAPGKGLEWVANIKQDGSE
KYYVDSVKGRFTISRDNAKNSLYLQMNSLRAEDTAVYYCARESNWGFAFDIWGQGTM
VTVSS (SEQ ID NO: 64)

Nucleotide sequence of light chain variable region:
5'CAGTCTGTGCTGACTCAGCCACCCTCAGCGTCTGGGACCCCCGGGCAGAGGGTCA
CCATCTCTTGTTCTGGAAGCAGCTCCAACATCGGAAGTAAGACTGTAAACTGGTACC
AACAGGTCCCAGGAACGGCCCCCAAACTCCTCATCTATAGGAATAATCAGCGGCCC
TTAGGGGTCCCTGACCGATTCTCTGGCTCCAAGTCTGGCACCTCAGCCTCCCTGGCC
ATCAGTGGGCTCCAGTCTGAGGATGAGGCTGATTATTATTGTGCAGCATGGGATGAC
AGCCTGAATTGGGTGTTCGGCGGAGGGACCAAGCTGACCGTCCTA3' (SEQ ID NO: 133)

Amino acid sequence of light chain variable region:
QSVLTQPPSASGTPGQRVTISCSGSSSNIGSKTVNWYQQVPGTAPKLLIYRNNQRPLGVP
DRFSGSKSGTSASLAISGLQSEDEADYYCAAWDDSLNWVFGGGTKLTVL (SEQ ID NO: 30)

Nucleotide sequence of heavy chain variable region:
5'GAGGTGCAGCTGGTGGAGTCTGGGGGAGGCTTGGTCCAGCCTGGGGGGTCCCTGA
GACTCTCCTGTGCAGCCTCTGGATTCACCTTTAGTCGCTATTGGATGAGCTGGGTCCG
CCAGGCTCCAGGGAAGGGGCTGGAGTGGGTGGCCAACATAAAGCATGATGGAAGTG
AGAAATACTATGTGGACTCTGTGAAGGGCCGATTCACCATTTCCAGAGACAACGCC
AAGAACTCACTGTATCTGCAAATGAACAGCCTGAGAGCCGAGGACACGGCTGTGTA
TTACTGTGCGAGAGAGTCAAACTGGGGATTTGCTTTTGATGTCTGGGGCCACGGGAC
AATGGTCACCGTCTCTTCA3' (SEQ ID NO: 134)

Amino acid sequence of heavy chain variable region:
EVQLVESGGGLVQPGGSLRLSCAASGFTFSRYWMSWVRQAPGKGLEWVANIKHDGSE
KYYVDSVKGRFTISRDNAKNSLYLQMNSLRAEDTAVYYCARESNWGFAFDVWGHGT
MVTVSS (SEQ ID NO: 62)

Nucleotide sequence of light chain variable region:
5'CAGTCTGTGCTGACTCAGCCACCCTCAGCGTCTGGGCCCCCCGGACAGAGGGTCA
CCATCTCTTGTTCTGGAAGCAGCTCCAACATCGGAAGTAATACTGTAAACTGGTACC
AGCAGCTCCCAGGAACGGCCCCCAAACTCCTCATCTATAGTAATAATCGGCGGCCCT
CAGGGGTCCCTGACCGATTCTCTGGCTCCAAGTCTGGCACCTCAGCCTCCCTGGCCA
TCAGTGGGCTCCAGTCTGAGGATGAGGCTGATTATTACTGTGCAGCATGGGATGACA
GCCTGAATTGGGTGTTCGGCGGAGGGACCAAGCTGACCGTCCTA3' (SEQ ID NO: 135)

Amino acid sequence of light chain variable region:
QSVLTQPPSASGPPGQRVTISCSGSSSNIGSNTVNWYQQLPGTAPKLLIYSNNRRPSGVPD
RFSGSKSGTSASLAISGLQSEDEADYYCAAWDDSLNWVFGGGTKLTVL (SEQ ID NO: 31)

Nucleotide sequence of heavy chain variable region:
5'GAGGTGCAGCTGTTGGAGTCTGGGGGAGGCTTGGTACAGCCTGGGGGGTCCCTGA
GACTCTCCTGTGCAGCCTCTGGATTCACCTTTAGCAGCTATGCCATGAGCTGGGTCC
GCCAGGCTCCAGGGAAGGGGCTGGAGTGGGTCTCAACTATTAGTGGTAGTGGTGGT
AGGACATATTACGCAGACTCCGTGAAGGGCCGGTTCACCATCTCCAGAGACAATTC
CAAGAACACGCTGTATCTGCAAATGAACAGCCTGAGAGCCGAGGACACGGCCGTAT
ATTACTGTGCGAAAGAAGTTGGCAGTCCCTTTGACTACTGGGGCCAGGGAACCCTGG
TCACCGTCTCCTCA3' (SEQ ID NO: 136)

Amino acid sequence of heavy chain variable region:
EVQLLESGGGLVQPGGSLRLSCAASGFTFSSYAMSWVRQAPGKGLEWVSTISGSGGRTY
YADSVKGRFTISRDNSKNTLYLQMNSLRAEDTAVYYCAKEVGSPFDYWGQGTLVTVSS
(SEQ ID NO: 69)

Nucleotide sequence of light chain variable region:
5'CAGTCTGTGTTGACGCAGCCGCCCTCAGTGTCTGCGGCCCCAGGACAGAAGGTCA
CCATCTCCTGCTCTGGAAGCAACTCCAACATTGGGAATAATTATGTATCCTGGTACC
AGCAGCTCCCAGGAACAGCCCCCAAACTCCTCATTTATGACAATAATAAGCGACCCT
CAGGGATTCCTGACCGATTCTCTGGCTCCAACTCTGGCACGTCAGCCACCCTGGGCA
TCACCGGACTCCAGACTGGGGACGAGGCCGATTATTACTGCGGAACATGGGATAGC
AGCCTGAGTGCTGTGGTATTCGGCGGAGGGACCAAGCTGACCGTCCTA3' (SEQ ID
NO: 137)

Amino acid sequence of light chain variable region:
QSVLTQPPSVSAAPGQKVTISCSGSNSNIGNNYVSWYQQLPGTAPKLLIYDNNKRPSGIP
DRFSGSNSGTSATLGITGLQTGDEADYYCGTWDSSLSAVVFGGGTKLTVL (SEQ ID
NO: 42)

Nucleotide sequence of heavy chain variable region:
5'CAGGTGCAGCTGGTGGAGTCTGGGGGAGGCGTGGTCCAGCCTGGGAGGTCCCTGA
GACTCTCCTGTGCAGCGTCTGGATTCACCTTCAGTAGCTATGGCATGCACTGGGTCC
GCCAGGCTCCAGGCAAGGGGCTGGAGTGGGTGGCAATTATATGGTATGATGGAAGT
AATAAATACTATGCAGACTCCGTGAAGGGCCGATTCACCATCTCCAGAGACAATTCC
AAGAACACACTGTATCTTCAAATGAACAGCCTGAGAGCCGAGGACACGGCTGTGTA
TTACTGTGCGAGGAGGGGGGGTCTGGCAGCTCGTCCGGGCGGTATGGACGTCTGGG
GCCAAGGGACCACGGTCACCGTCTCCTCA3' (SEQ ID NO: 138)

Amino acid sequence of heavy chain variable region:
QVQLVESGGGVVQPGRSLRLSCAASGFTFSSYGMHWVRQAPGKGLEWVAIIWYDGSN
KYYADSVKGRFTISRDNSKNTLYLQMNSLRAEDTAVYYCARRGGLAARPGGMDVWG
QGTTVTVSS (SEQ ID NO: 81)

Nucleotide sequence of light chain variable region:
5'TCCTATGAGCTGACTCAGCCACCCTCAGTGTCTGTGTCCCCAGGACAGACAGCCAG
AATCACCTGCTCTGGAGATAAATTGGGGGATAAATATGCTTGCTGGTATCAGCAGAA
ACCAGGCCAGTCCCCTGTGCTGGTCATCTATCAAAATACCAAGTGGCCCTTAGGGAT
CCCTGAGCGATTCTCTGGCTCCAAGTCTGGGAACACAGTCACTCTGACCATCAGCGG
GACCCAGGCTATGGATGAGGCTGACTATTACTGTCAGGCGTGGGACAGCAGCACTG
TGGTATTCGGCGGAGGGACCAAGCTGACCGTCCTA3' (SEQ ID NO: 139)

Amino acid sequence of light chain variable region:
SYELTQPPSVSVSPGQTARITCSGDKLGDKYACWYQQKPGQSPVLVIYQNTKWPLGIPE
RFSGSKSGNTVTLTISGTQAMDEADYYCQAWDSSTVVFGGGTKLTVL (SEQ ID NO: 44)

Alternative Nucleotide sequence of light chain variable region:
5'TCCTATGAGCTGACTCAGCCACCCTCAGTGTCCGTGTCCCCAGGACAGACAGCCA
GAATCACCTGCTCTGGAGATAAATTGGGGGATAAATATGCTTGCTGGTATCAGCAGA
AGCCAGGCCAGTCCCCTGTGCTGGTCATCTATCAAAATACCAAGTGGCCCTTAGGGA
TCCCTGAGCGATTCTCTGGCTCCAAGTCTGGGAACACAGTCACTCTGACCATCAGCG
GGACCCAGGCTATGGATGAGGCTGACTATTACTGTCAGGCGTGGGACAGCAGCACT
GTGGTATTCGGCGGAGGGACCAAGCTGACCGTCCTA3' (SEQ ID NO: 295)

Nucleotide sequence of heavy chain variable region:
5'CAGGTGCAGCTGCAGGAGTCGGGCCCAGGACTGGTGAAGCCTTCACAGACCCTGT
CCCTCACCTGCACTGTCTCTGGTGGCTCCATCAGCAGTAGTGATTACTACTGGAGCT
GGATCCGCCAGCACCCAGGGAAGGGCCTGGAGTGGATTGGGTACATCTATTACAGT
GGGAGCACCTACTACAACCCGTCCCTCAAGAGTCGAATTACCATATCAGTAGACAC
GTCTAAGAACCTGTTCTCCCTGAAGTTGAGCTCTGTGACTGCCGCGGACACGGCCGT
GTATTACTGTGCGAGAGGGGGGGTGACTACGTACTACTACGCTATGGACGTCTGGG
GCCAAGGGACCACGGTCACCGTCTCCTCA3' (SEQ ID NO: 140)

Amino acid sequence of heavy chain variable region:
QVQLQESGPGLVKPSQTLSLTCTVSGGSISSSDYYWSWIRQHPGKGLEWIGYIYYSGSTY
YNPSLKSRITISVDTSKNLFSLKLSSVTAADTAVYYCARGGVTTYYYAMDVWGQGTTV
TVSS (SEQ ID NO: 85)

Nucleotide sequence of light chain variable region:
5'GACATACAGATGACCCAGTCTCCATCCTCCCTGTCTGCATCTGTAGGAGACAGAGT
CACCATCACTTGCCGGGCAAGTCAGCGCATTAGCAACTATTTAAGTTGGTATCTGCA
GAAACCAGGGATTGCCCCTAAGCTCCTGATCTATGCTGCATCCAGTTTGCAGAGTGG
GGTCCCATCAAGGTTCAGTGGCAGTGGATCTGGGACAGATTTCACTCTCACCATCAG
CAGTCTGCAATCTGAAGATTTTGCAACTTACTACTGTCAACAGAGTTACAGTACCCC
GCTCATTTTCGGCGGAGGGACCAAGGTGGAGATCAAA3' (SEQ ID NO: 141)

Amino acid sequence of light chain variable region:
DIQMTQSPSSLSASVGDRVTITCRASQRISNYLSWYLQKPGIAPKLLIYAASSLQSGVPSR
FSGSGSGTDFTLTISSLQSEDFATYYCQQSYSTPLIFGGGTKVEIK (SEQ ID NO: 7)

Nucleotide sequence of heavy chain variable region:
5'CAGGTGCAGCTGGTGGAGTCTGGGGGAGGCGTGGTCCAGCCTGGGAGGTCCCTGA
GACTCTCCTGTGCAGCGTCTGGATTCACCTTCAGTAGCTATGGCATGCACTGGGTCC
GCCAGGCTCCAGGCAAGGGGCTGGAGTGGGTGGCAGTTATATGGTATGATGGAAGT
GATAAATACTATGCAGACTCCGTGAAGGGCCGATTCACCATCTCCAGAGACAATTCC
AAGAACACGCTGTATCTGCAAATGAACAGCCTGAGAGCCGAGGACACGGCTGTGTA
TTACTGTGCGAGAGAGACTGGTCCCTTGAAACTCTACTACTACGGTATGGACGTCTG
GGGCCAAGGGACCACGGTCACCGTCTCCTCA3' (SEQ ID NO: 142)

Amino acid sequence of heavy chain variable region:
QVQLVESGGGVVQPGRSLRLSCAASGFTFSSYGMHWVRQAPGKGLEWVAVIWYDGSD
KYYADSVKGRFTISRDNSKNTLYLQMNSLRAEDTAVYYCARETGPLKLYYYGMDVWG
QGTTVTVSS (SEQ ID NO: 74)

Nucleotide sequence of light chain variable region:
5'GATATTGTGATGACTCAGTCTCCACTCTCCCTGTCCGTCACCCCTGGAGAGCCGCC
CTCCATCTCCTGCAGGTCTAGTCAGAGCCTCCTGCATAGTAATGGATACAACTTTTTG
AATTGGTACCTGCAGAAGCCAGGGCAGTCTCCACAACTCCTGATCTATTTGGGTTCT
CATCGGGCCTCCGGGGTCCCTGACAGGTTCAGTGGCAGTGGATCAGGCACAGATTTT
ACACTGGAAATCAGCAGAGTGGAGGCTGAGGATGTTGGGGTTTATTACTGCATGCA
AGTTCTACAAACTCCATTCACTTTCGGCCCTGGGACCAAAGTGGATATCAAA3'
(SEQ ID NO: 143)

Amino acid sequence of light chain variable region:
DIVMTQSPLSLSVTPGEPPSISCRSSQSLLHSNGYNFLNWYLQKPGQSPQLLIYLGSHRAS
GVPDRFSGSGSGTDFTLEISRVEAEDVGVYYCMQVLQTPFTFGPGTKVDIK (SEQ ID NO: 5)

Nucleotide sequence of heavy chain variable region:
5'GAGGTGCAGCTGGTGGAGTCTGGGGGAGGCTTGGTCCAGCCTGGGGGGTCCCTGA
GACTCTCCTGTGCAGCCTCTGGACTCACCTTTAGTAACTTTTGGATGAGCTGGGTCCG
CCAGGCTCCAGGGAAGGGGCTGGAGTGGGTGGCCAACATAAAGCAAGATGGAAGT
GAGAAATACTATGTGGACTCTGTGAAGGGCCGATTCACCATCTCCAGAGACAACGC
CAAGAATTCACTGTATCTGCAAATGAACAGCCTGAGAGCCGAGGACACGGCTGTGT
ATTCCTGTACGAGAGAGTCAAACTGGGGATTTGCTTTTGATATCTGGGGCCAAGGGA
CAATGGTCACCGTCTCTTCA3' (SEQ ID NO: 144)

Amino acid sequence of heavy chain variable region:
EVQLVESGGGLVQPGGSLRLSCAASGLTFSNFWMSWVRQAPGKGLEWVANIKQDGSE
KYYVDSVKGRFTISRDNAKNSLYLQMNSLRAEDTAVYSCTRESNWGFAFDIWGQGTM
VTVSS (SEQ ID NO: 65)

Nucleotide sequence of light chain variable region:
5'CAGTCTGTGCTGACTCAGCCACCCTCAGCGTCTGGGACCCCCGGGCAGAGGGTCA
CCATCTCTTGTTCTGGAAGCAGCTCCAACATCGGAAGTAAAACTGTAAACTGGTACC
AGCAGTTCCCAGGAACGGCCCCCAAACTCCTCATCTATAGTAATAATCGGCGGCCCT
CAGGGGTCCCTGACCGATTCTCTGGCTCCAAGTCTGGCACCTCAGCCTCCCTGGCCA
TCAGTGGGCTCCAGTCTGAGGATGAGGCTGATTATTACTGTGCAGCATGGGATGACA
GCCTGAATTGGGTGTTCGGCGCAGGGACCAAGCTGACCGTCCTA3' (SEQ ID NO: 145)

Amino acid sequence of light chain variable region:
QSVLTQPPSASGTPGQRVTISCSGSSSNIGSKTVNWYQQFPGTAPKLLIYSNNRRPSGVPD
RFSGSKSGTSASLAISGLQSEDEADYYCAAWDDSLNWVFGAGTKLTVL (SEQ ID NO: 33)

Nucleotide sequence of heavy chain variable region:
5'CAGGTTCAGCTGGTGCAGTCTGGAGCTGAGGTGAAGAAGCCTGGGGCCTCAGTGA
AGGTCTCCTGCAAGGCTTCTGGTTACACCTTTACCAGCTATGGTATCAGCTGGGTGC
GACAGGCCCCTGGACAAGGGCTTGAGTGGATGGGATGGATCAGCACTTACAATGGT
AACACAAACTATGCACAGAAGGTCCAGGGCAGAGTCACCATGACCACAGACACATC
CACGAGCACAGCCTACATGGAGCTGAGGAGCCTGAGATCTGACGACACGGCCGTTT
ATTACTGTGCGAGAGGGTATACTCGGGACTACTGGGGCCAGGGAACCCTGGTCACC
GTCTCCTCA3' (SEQ ID NO: 146)

Amino acid sequence of heavy chain variable region:
QVQLVQSGAEVKKPGASVKVSCKASGYTFTSYGISWVRQAPGQGLEWMGWISTYNGN
TNYAQKVQGRVTMTTDTSTSTAYMELRSLRSDDTAVYYCARGYTRDYWGQGTLVTVS
S (SEQ ID NO: 60)

Nucleotide sequence of light chain variable region:
5'CAGCCTGTGCTGACTCAGCCACTTTTTGCATCAGCCTCCCTGGGAGCCTCGGTCAC
ACTCACCTGCACCCTGAGCAGCGGCTACAGTAGTTATGAAGTGGACTGGTATCAGCA
GAGACCAGGGAAGGGCCCCCGGTTTGTCATGCGAGTGGACACTGGTGGGATTGTGG
GATCCAAGGGGGAAGGCATCCCTGATCGCTTCTCAGTTTTGGGCTCAGGCCTGAATC
GGTATCTGACCATCAAGAACATCCAGGAAGAGGATGAGAGTGACTACCACTGTGGG
GCAGACCATGGCAGTGGGACCAACTTCGTGGTGGTATTCGGCGGAGGGACCAAGCT
GACCGTCCTA3' (SEQ ID NO: 147)

Amino acid sequence of light chain variable region:
QPVLTQPLFASASLGASVTLTCTLSSGYSSYEVDWYQQRPGKGPRFVMRVDTGGIVGSK
GEGIPDRFSVLGSGLNRYLTIKNIQEEDESDYHCGADHGSGTNFVVVFGGGTKLTVL
(SEQ ID NO: 46)

Nucleotide sequence of heavy chain variable region:
5'CAGGTGCAGCTACAGCAGTGGGGCGCAGGACTGTTGAAGCCTTCGGAGACCCTGT
CCCTCACCTGCGCTGTCTATGGTGGGTCCTTCAGTGCGTACTACTGGAACTGGATCC
GCCAGCCCCCAGGGAAGGGGCTGGAGTGGATTGGGGAAATCAATCATAGTGGAAGA
ACCGACTACAACCCGTCCCTCAAGAGTCGAGTCACCATATCAGTAGACACGTCCAA
GAAGCAGTTCTCCCTGAAGCTGAACTCTGTGACCGCCGCGGACACGGCTGTGTATTA
CTGTGCGAGAGGGCAGCTCGTCCCCTTTGACTACTGGGGCCAGGGAACCCTGGTCAC
CGTCTCTTCA3' (SEQ ID NO: 148)

Amino acid sequence of heavy chain variable region:
QVQLQQWGAGLLKPSETLSLTCAVYGGSFSAYYWNWIRQPPGKGLEWIGEINHSGRTD
YNPSLKSRVTISVDTSKKQFSLKLNSVTAADTAVYYCARGQLVPFDYWGQGTLVTVSS
(SEQ ID NO: 89)

Nucleotide sequence of light chain variable region:
5'CAGTCTGTGCTGACTCAGCCACCCTCAGCGTCTGGGACCCCCGGGCAGAGGGTCA
CCATCTCTTGTTCTGGAAGCAGCTCCAACATCGGAAGTAATACTGTAAATTGGTATC
AGCAACTCCCAGGAACGGCCCCCAAACTCCTCATCTATAGTAATAATCAGCGGCCCT
CAGGGGTCCCTGACCGATTCTCTGGCTCCAAGTCTGGCACCTCAGCCTCCCTGGCCA
TCAGTGGGCTCCAGTCTGAGGATGAGGCTGATTATTACTGTGCAGTATGGGATGACA
GCCTGAATGGTTGGGTGTTCGGCGGAGGGACCAAGCTGACCGTCCTA3' (SEQ ID NO: 149)

Amino acid sequence of light chain variable region:
QSVLTQPPSASGTPGQRVTISCSGSSSNIGSNTVNWYQQLPGTAPKLLIYSNNQRPSGVPD
RFSGSKSGTSASLAISGLQSEDEADYYCAVWDDSLNGWVFGGGTKLTVL (SEQ ID NO: 32)

Nucleotide sequence of heavy chain variable region:
5'CAGGTTCAGCTGGTGCAGTCTGGAGCTGAGGTGAAGAAGCCTGGGGCCTCAGTGA
AGGTCTCCTGCAAGGCTTCTGGTTACACCTTTCCCAGCTATGGTATCAGCTGGGTGC
GACAGGCCCCTGGACAAGGGCTTGAGTGGATGGGATGGATCAGCGCTTACAATGGT
AACACAAACTATGCAGAGAAGCTCCAGGGCAGAGTCACCATGACCACAGACACATC
CACGAGCACAGCCTACATGGAGGTGAGGAGCCTGAGATCTGACGACACGGCCGTGT
TTTACTGTGCGAGAGGCTACGTTATGGACGTCTGGGGCCAAGGGACCACGGTCACC
GTCTCCTCT3'   (SEQ ID NO: 150)

Amino acid sequence of heavy chain variable region:
QVQLVQSGAEVKKPGASVKVSCKASGYTFPSYGISWVRQAPGQGLEWMGWISAYNGN
TNYAEKLQGRVTMTTDTSTSTAYMEVRSLRSDDTAVFYCARGYVMDVWGQGTTVTVS
S (SEQ ID NO: 58)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTCGTTATAATTCTGTCTCCTGGTAC
CAACACCACCCAGGCAAAGCCCCCAAAGTCATGATTTATGAGGTCAGTAATCGGCC
CTCAGGGGTTTCTACTCGCTTCTCTGGCTCCAAGTCTGGCAACACGGCCTCCCTGAC
CATCTCTGGGCTCCAGGCTGAGGACGAGGCTGATTATTACTGCAGCTCATATACAAG
CAGCAGCGTTGTATTCGGCGGAGGGACCAAACTGACCGTCCTA3'   (SEQ ID NO: 151)

Amino acid sequence of light chain variable region:
QSALTQPASVSGSPGQSITISCTGTSSDVGRYNSVSWYQHHPGKAPKVMIYEVSNRPSGV
STRFSGSKSGNTASLTISGLQAEDEADYYCSSYTSSSVVFGGGTKLTVL (SEQ ID NO: 15)

Nucleotide sequence of heavy chain variable region:
5'CAGGTTCAGCTGGTGCAGTCTGGAGCTGAGGTGAAGAAGCCTGGGGCCTCAGTGA
AGGTCTCCTGCAAGGCTTCTGGTTACACCTTAACCAGCTATGGTATCAGCTGGGTGC
GACAGGCCCCTGGACAAGGGCTTGAGTGGATGGGATGGGTCAGTTTTTATAATGGT
AACACAAACTATGCACAGAAGCTCCAGGGCAGAGGCACCATGACCACAGACCCATC
CACGAGCACAGCCTACATGGAGCTGAGGAGCCTGAGATCTGACGACACGGCCGTGT
ATTACTGTGCGAGAGGCTACGGTATGGACGTCTGGGGCCAAGGGACCACGGTCACC
GTCTCCTCT3' (SEQ ID NO: 94)

Amino acid sequence of heavy chain variable region:
QVQLVQSGAEVKKPGASVKVSCKASGYTLTSYGISWVRQAPGQGLEWMGWVSFYNG
NTNYAQKLQGRGTMTTDPSTSTAYMELRSLRSDDTAVYYCARGYGMDVWGQGTTVT
VSS (SEQ ID NO: 49)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGCACCCAGGCAAAGCCCCCAAACTCATGATTTATGAGGTCAGTAATCGGC
CCTCAGGGGTTTCTAATCGCTTCTCTGGCTCCAAGTCTGGCAACACGGCCTCCCTGA
CCATCTCTGGGCTCCAGGCTGAGGACGAGGCTGATTATTACTGCAATTCATATACAA
GCACCAGCATGGTATTCGGCGGAGGGACCAAGCTGACCGTCCTA3' (SEQ ID NO: 296)

Amino acid sequence of light chain variable region:
QSALTQPASVSGSPGQSITISCTGTSSDVGGYNSVSWYQQHPGKAPKLMIYEVSNRPSGV
SNRFSGSKSGNTASLTISGLQAEDEADYYCNSYTSTSMVFGGGTKLTVL (SEQ ID NO: 23)

FIG. 3JJ

Constant Domains

Human IgG2:

ASTKGPSVFPLAPCSRSTSESTAALGCLVKDYFPEPVTVSWNSGALTSGVHTFPAVLQSSGLYSLSSVVT
VPSSNFGTQTYTCNVDHKPSNTKVDKTVERKCCVECPPCPAPPVAGPSVFLFPPKPKDTLMISRTPEVTC
VVVDVSHEDPEVQFNWYVDGVEVHNAKTKPREEQFNSTFRVVSVLTVVHQDWLNGKEYKCKVSNKGLP
APIEKTISKTKGQPREPQVYTLPPSREEMTKNQVSLTCLVKGFYPSDIAVEWESNGQPENNYKTTPPMLD
SDGSFFLYSKLTVDKSRWQQGNVFSCSVMHEALHNHYTQKSLSLSPGK (SEQ ID NO: 154)

Human IgG4:

ASTKGPSVFPLAPCSRSTSESTAALGCLVKDYFPEPVTVSWNSGALTSGVHTFPAVLQSSGLYSLSSVVT
VPSSSLGTKTYTCNVDHKPSNTKVDKRVESKYGPPCPSCPAPEFLGGPSVFLFPPKPKDTLMISRTPEVT
CVVVDVSQEDPEVQFNWYVDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIAVEWESNGQPENNYKTTPPVL
DSDGSFFLYSRLTVDKSRWQEGNVFSCSVMHEALHNHYTQKSLSLSLGK (SEQ ID NO: 155)

Human lambda:

QPKAAPSVTLFPPSSEELQANKATLVCLISDFYPGAVTVAWKADSSPVKAGVETTTPSKQSNNKYAASSY
LSLTPEQWKSHRSYSCQVTHEGSTVEKTVAPTECS (SEQ ID NO: 156)

Human kappa:

TVAAPSVFIFPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO: 157)

Nucleotide sequence of heavy chain variable region:

5'CAGGTGCAGGTGGTGCAGTCTGGGGCTGAGGTGAAGAAGCCTGGGGCCTC
AGTGAAGGTCTCCTGCAAGGCTTCTGGATACACCTTCACCGGCTACTATATAC
ACTGGGTGCGACAGGCCCCTGGACAAGGGCTTGAGTGGATGGGATGGATCAA
CCCTCACAGTGGTGGCGCAAACTATGCACAGAAGTTTCAGGGCAGGGTCACC
ATGACCAGGGACACGTCCATCAGCACAGCCTACATGGAGCTGAGCAGGCTGA
GATCTGACGACACGGCCGTGTATTACTGTGCGAGAGGCAACTGGAACTACGA
CTACTACGGTATGGACGTCTGGGGCCAAGGGACCACGGTCACCGTCTCCTCA
3' (SEQ ID NO:418)

Amino acid sequence of heavy chain variable region:

QVQVVQSGAEVKKPGASVKVSCKASGYTFTGYYIHWVRQAPGQGLEWMGWIN
PHSGGANYAQKFQGRVTMTRDTSISTAYMELSRLRSDDTAVYYCARGNWNYD
YYGMDVWGQGTTVTVSS (SEQ ID NO:419)

Nucleotide sequence of light chain variable region:

5'GACATCCAGATGACCCAGTCTCCATCCTCCCTGTCTGCATCTGTAGGAGAC
AGAGTCACCATCACTTGCCGGGCGAGTCAGGACATTAGCAATTATTTAGCCT
GGTATCAGCAGAAACCAGGGAAAGTTCCTAAGCTCCTGATCTATGCTGCATC
CACTTTGCAATCAGGGGTCCCATCTCGGTTCAGTGGCAGTGGATCTGGGACA
GATTTCACTCTCACCATCAGCAGCCTACAGCCTGAAGATGTTGCAACTTATTT
CTGTCAAAGGTATCAGATTGCCCCATTCACTTTCGGCCCTGGGACCAAGGTGG
ATATCAAA3' (SEQ ID NO:420)

Amino acid sequence of light chain variable region:

DIQMTQSPSSLSASVGDRVTITCRASQDISNYLAWYQQKPGKVPKLLIYAASTLQ
SGVPSRFSGSGSGTDFTLTISSLQPEDVATYFCQRYQIAPFTFGPGTKVDIK (SEQ
ID NO:421)

Nucleotide sequence of heavy chain variable region:

5'CAGGTGCAGCTGGTGGAGTCTGGGGGAGGCGTGGTCCAGCCTGGGAGGTC
CCTGAGACTCTCCTGTGCAGCGTCTGGATTCACCTTCAGTAGCTATGGCATGC
ACTGGGTCCGCCAGGCTCCAGGCAAGGGGCTGGAGTGGGTGGCAGTTATCTG
GTATGATGGAAGTACTAAATACTATGCAGACTCCGTGAAGGGCCGATCCACC
ATCTCCAGAGACAATTCCAAGAACACGCTGTATCTGCAAATGAACAGCCTGA
GAGCCGAGGACACGGCTGTGTATTACTGTGCGAGGTCAGTGGCTGGTTACCA
CTACTACTACGGTATGGACGTCTGGGGCCAAGGGACCACGGTCACCGTCTCC
TCA3' (SEQ ID NO:422)

Amino acid sequence of heavy chain variable region:

QVQLVESGGGVVQPGRSLRLSCAASGFTFSSYGMHWVRQAPGKGLEWVAVIW
YDGSTKYYADSVKGRSTISRDNSKNTLYLQMNSLRAEDTAVYYCARSVAGYHY
YYGMDVWGQGTTVTVSS (SEQ ID NO: 423)

Nucleotide sequence of light chain variable region:

5'TCTTCTGAGCTGACTCAGGACCCTGCTGTGTCTGTGGCCTTGGGACAGACA
GTCAGGATCACATGCCAAGGAGACAGCCTCAGAGGCTATTATGCAACCTGGT
ACCAGCAGAAGCCAAGACAGGCCCCTGTACTTGTCATCTATGGTAAAAACTA
CCGGCCCTCAGGGATCCCAGACCGATTCTCTGGCTCCACCTCAGGAAACACA
GCTTCCTTGACCATCACTGGGGCTCAGGCGGAAGATGAGGCTGACTATTACT
GTAACTCCCGGGACAGCATTGGTAACCATCTGGTGTTCGGCGGAGGGACCAA
GCTGACCGTCCTA3' (SEQ ID NO:424)

Amino acid sequence of light chain variable region:

SSELTQDPAVSVALGQTVRITCQGDSLRGYYATWYQQKPRQAPVLVIYGKNYRP
SGIPDRFSGSTSGNTASLTITGAQAEDEADYYCNSRDSIGNHLVFGGGTKLTVL
(SEQ ID NO:425)

Nucleotide sequence of heavy chain variable region:

5'CAGGTGCAGCTGGTGGAGTCTGGGGGAGGCGTGGTCCAGCCTGGGAGGTC
CCTGAGACTCTCCTGTGCAGCGTCTGGATTCACCTTCAGTAGCTATGGCTTGC
ACTGGGTCCGCCAGGCTCCAGGCAAGGGGCTGGAGTGGGTGGCAGTTATATG
GTTAGATGGAAGTAATAAATACTATGCAGACTCCGTGAAGGGCCGATCCACC
ATCTCCAGAGACAATTCCAAGAACACGCTGTATCTGCAAATGAACAGCCTGA
GAGCCGAGGACACGGCTGTGTATTACTGTGCGAGGTCAGTGGCTGGTTACCA
CTACTACTACGGTATGGACGTCTGGGGCCAAGGGACCACGGTCACCGTCTCC
TCA3' (SEQ ID NO:426)

Amino acid sequence of heavy chain variable region:

QVQLVESGGGVVQPGRSLRLSCAASGFTFSSYGLHWVRQAPGKGLEWVAVIWL
DGSNKYYADSVKGRSTISRDNSKNTLYLQMNSLRAEDTAVYYCARSVAGYHYY
YGMDVWGQGTTVTVSS (SEQ ID NO:427)

Nucleotide sequence of light chain variable region:
5'TCTTCTGAGCTGACTCAGGACCCTGCTGTGTCTGTGGCCTTGGGACAGACA
GTCAGGATCACATGCCAAGGAGACAGCCTCAGAAGTTATTATGGAAGCTGGT
ACCAGCAGAAGCCAAGACAGGCCCCTGTACTTGTCATCTTTGGTAAAAACAA
CCGGCCCTCAGGGATCCCAGACCGATTCTCTGGCTCCACCTCAGGAAACACA
GCTTCCTTGACCATCACTGGGGCTCAGGCGGAAGATGAGGCTGACTATTACT
GTAACTCACGGGACATCATTGGTGACCATCTGCTGTTCGGCGGAGGGACCAA
GCTGACCGTCCTA3' (SEQ ID NO:428)

Amino acid sequence of light chain variable region:

SSELTQDPAVSVALGQTVRITCQGDSLRSYYGSWYQQKPRQAPVLVIFGKNNRP
SGIPDRFSGSTSGNTASLTITGAQAEDEADYYCNSRDIIGDHLLFGGGTKLTVL
(SEQ ID NO:429)

Nucleotide sequence of heavy chain variable region:

5'CAGGTGCAGCTGGTGGAGTCTGGGGGAGGCGTGGTCCAGTCTGGGAGGTCC
CTGAGACTCTCCTGTGCAGCGTCTGGATTCACCTTCAGGAACTATGGCATGCA
CTGGGTCCGCCAGGCTCCAGGCAAGGGGCTGGAGTGGGTGGCAGTTATATGG
TTTGATGGAAGTAATAAATACTATGCAGACTCCGTGAAGGGCCGATCCACCA
TCTCCAGAGACAATTCCAAGAACACGCTGTATCTGCTAATGAACAGCCTGAG
AGCCGAGGACACGGCTGTGTATTACTGTGCGAGGTCAGTGGCTGGTTACCAC
TACTACTACGGTATGGACGTCTGGGGCCAAGGGACCACGGTCACCGTCTCCT
CA3'(SEQ ID NO:430)

Amino acid sequence of heavy chain variable region:

QVQLVESGGGVVQSGRSLRLSCAASGFTFRNYGMHWVRQAPGKGLEWVAVIW
FDGSNKYYADSVKGRSTISRDNSKNTLYLLMNSLRAEDTAVYYCARSVAGYHY
YYGMDVWGQGTTVTVSS (SEQ ID NO:431)

Nucleotide sequence of light chain variable region:

5'TCTTCTGAGCTGACTCAGGACCCTGCTGTGTCTGTGGCCTTGGGACAGACA
GTCAGGATCACATGCCAGGGAGACAGCCTCAGAAGCTATTATGCAAGCTGGT
ACCAGCAGAAGCCAAGACAGGCCCCTGTACTTGTCATCTATGGTAAAAACAA
CCGGCCCTCAGGGATCCCAGACCGAATCTCTGGCTCCACCTCAGGAAACACA
GCTTCCTTGACCATCACTGGGGCTCAGGCGGAAGATGAGGCTGACTATTACT
GTAAATCCCGGGACATCATTGGTGACCATCTGGTGTTCGGCGGAGGGACCAA
ACTGACCGTCCTA3' (SEQ ID NO:432)

Amino acid sequence of light chain variable region:

SSELTQDPAVSVALGQTVRITCQGDSLRSYYASWYQQKPRQAPVLVIYGKNNRP
SGIPDRISGSTSGNTASLTITGAQAEDEADYYCKSRDIIGDHLVFGGGTKLTVL
(SEQ ID NO:433)

Nucleotide sequence of heavy chain variable region:

5'CAGGTGCAGCTGGTGGAGTCTGGGGGAGGCGTGGTCCAGCCTGGGAGGTC
CCTGAGACTCTCCTGTGCAGCGTCTGGATTCACCTTCAGTAGCTATGGCATGC
ACTGGGTCCGCCAGGCTCCAGGCAAGGGGCTGGAGTGGGTGGCAGTTATATG
GTATGATGGAAGTAATAAATACTATGCAGACTCCGTGAAGGGCCGATTCACC
ATCTCCAGAGACAATTCCAAGAACACGCTGTATCTGCAAATGAACAGCCTGA
GAGCCGAGGACACGGCTGTGTATTACTGTGTGAGAGATCGGGGACTGGACTG
GGGCCAGGGAACCCTGGTCACCGTCTCCTCA3' (SEQ ID NO:434)

Amino acid sequence of heavy chain variable region:

QVQLVESGGGVVQPGRSLRLSCAASGFTFSSYGMHWVRQAPGKGLEWVAVIW
YDGSNKYYADSVKGRFTISRDNSKNTLYLQMNSLRAEDTAVYYCVRDRGLDW
GQGTLVTVSS (SEQ ID NO:435)

Nucleotide sequence of light chain variable region:

5'TCTTCTGAGCTGACTCAGGACCCTGCTGTGTCTGTGGCCTTGGGACAGACA
GTCAGGATCACATGCCAAGGAGACAGCCTCAGAGGCTATTATGCAAGCTGGT
ACCAGCAGAAGCCAAGACAGGCCCCTGTACTTGTCATCTATGGTAAAAACAA
CCGGCCCTCAGGGATCCCAGACCGATTCTCTGGCTCCACCTCAGGAAACACA
GCTTCCTTGACCATCACTGGGGCTCAGGCGGAAGATGAGGCTGACTATTACT
GTAAGTCCCGGGACAGCAGTGGTGACCATCTGGTGTTCGGCGGAGGGACCAA
GCTGACCGTCCTA3' (SEQ ID NO:436)

Amino acid sequence of light chain variable region:

SSELTQDPAVSVALGQTVRITCQGDSLRGYYASWYQQKPRQAPVLVIYGKNNRP
SGIPDRFSGSTSGNTASLTITGAQAEDEADYYCKSRDSSGDHLVFGGGTKLTVL
(SEQ ID NO:437)

Nucleotide sequence of heavy chain variable region:

5'CAGGTGCAGGTGGTGGAGTCTGGGGGAGGCGTGGTCCAGCCTGGGGGGTC
CCTGAGACTCTCCTGTGCAGCGTCTGGATTCACCTTCAGTAACTATGGCATGC
ACTGGGTCCGCCAGGCTCCAGGCAAGGGGCTGGAGTGGGTGGCAGTTATTTG
GTATGATGGAAGTAGTAAATACTATGCAGACTCCGTGAAGGGCCGATCCACC
ATCTCCAGAGACAATTCCAAGAACACGGTGTATCTGCAAATGAACAGCCTGA
GAGCCGAGGACACGGCTGTGTATTACTGTGCGAGGTCAGTGGCTGGTTACCA
CTACTACTACGGTATGGACGTCTGGGGCCAAGGGACCACGGTCACCGTCTCC
TCA3'(SEQ ID NO:438)

Amino acid sequence of heavy chain variable region:

QVQVVESGGGVVQPGGSLRLSCAASGFTFSNYGMHWVRQAPGKGLEWVAVIW
YDGSSKYYADSVKGRSTISRDNSKNTVYLQMNSLRAEDTAVYYCARSVAGYHY
YYGMDVWGQGTTVTVSS (SEQ ID NO:439)

Nucleotide sequence of light chain variable region:

5'TCTTCTGAGCTGACTCAGGACCCTGCTGTGTCTGTGGCCTTGGGACAGACA
GTCAGGATCACATGCCAAGGAGACAGCCTCAGAGGCTATTATGCAAGCTGGT
ACCAGCAGAAGCCAAGACAGGCCCCTGTACTTGTCATCTATGGTAAAAACAA
CCGGCCCTCAGGGATCCCAGACCGATTCTCTGGCTCCACCTCAGGAAACACA
GCTTCCTTGACCATCACTGGGGCTCAGGCGGAAGATGAGGCTGACTATTACT
GTAAGTCCCGGGACAGCAGTGGTGACCATCTGGTGTTCGGCGGAGGGACCAA
GCTGACCGTCCTA3' (SEQ ID NO:440)

Amino acid sequence of light chain variable region:

SSELTQDPAVSVALGQTVRITCQGDSLRGYYASWYQQKPRQAPVLVIYGKNNRP
SGIPDRFSGSTSGNTASLTITGAQAEDEADYYCKSRDSSGDHLVFGGGTKLTVL
(SEQ ID NO:441)

Nucleotide sequence of heavy chain variable region:

5'CAGGTGCAGCTGGTGGAGTCTGGGGGAGGCGTGGTCCAGCCTGGGAGGTC
CCTGAGTCTCTCCTGTGCAGCGTCTGGATTCACCTTCAGTAGCTATGGCATGC
ACTGGGTCCGCCAGGCTCCAGGCAAGGGGCTGGAGTGGGTGGCAGTTATATG
GTATGATGGAAGTTATAAAGACTATGCAGACTCCGTGAAGGGCCGATCCACC
ATCTCCAGAGACAACTCCAAGAACACGCTGTATCTGCAAATGAACAGCCTGA
GAGCCGAGGACACGGCTGTGTATTATTGTGCGAGGTCAGTGGCTGGTTACCA
CTACTACTACGGTATGGACGTCTGGGGCCAAGGGACCACGGTCACCGTCTCC
TCA3' (SEQ ID NO:442)

Amino acid sequence of heavy chain variable region:

QVQLVESGGGVVQPGRSLSLSCAASGFTFSSYGMHWVRQAPGKGLEWVAVIWY
DGSYKDYADSVKGRSTISRDNSKNTLYLQMNSLRAEDTAVYYCARSVAGYHYY
YGMDVWGQGTTVTVSS (SEQ ID NO:443)

Nucleotide sequence of light chain variable region:

5'TCTTCTGAGCTGACTCAGGACCCTGCTGTGTCTGTGGCCTTGGGACAGACA
GTCAGGATCACATGCCAAGGAGACAGCCTCAGAACCTATTATGCAAGCTGGT
ACCAGCAGAAGCCAAGACAGGCCCCTATTCTTGTCATCTATGGTAAAAACAA
CCGGCCCTCAGGGATCCCAGACCGATTCTCTGGCTCCACCTCAGGAATCACA
GCTTCCTTGACCATCACTGGGGCTCAGGCGGAAGATGAGGCTGACTATTACT
GTAAATCCCGGGACATCATTGGTAACCATCTGCTGTTCGGCGGAGGGACTAA
GCTGACCGTCCTA3' (SEQ ID NO:444)

Amino acid sequence of light chain variable region:

SSELTQDPAVSVALGQTVRITCQGDSLRTYYASWYQQKPRQAPILVIYGKNNRPS
GIPDRFSGSTSGITASLTITGAQAEDEADYYCKSRDIIGNHLLFGGGTKLTVL (SEQ
ID NO:445)

Nucleotide sequence of heavy chain variable region:

5'CAGGTGCAGCTGGTGGCGTCTGGGGGAGGCGTGGTCCAGCCTGGGAGGTCC
CTGAGACTCTCCTGTGCAGCGTCTGGATTCACCCTCAGTAGCTATGGCATGCA
CTGGGTCCGCCAGGCTCCAGGCCAGGGGCTGGAGTGGGTGGCAGTCATATGG
TATGATGGAAGTAACAAATACTATGCAGCCTCCGTGAAGGGCCGATTCACCA
TCTCCAGAGACAATTCCAAGAACACGCTGTATCTGCAAATGAACAGTCTGAG
AGCCGAGGACACGGCTGTGTATTACTGTGCGAGAGGGGGTGGTTCGGGGAGT
CATCGCTACTACTACTACGGTATGGACGTCTGGGGCCAAGGGACCACGGTCA
CCGTCTCCTCA3' (SEQ ID NO:446)

Amino acid sequence of heavy chain variable region:

QVQLVASGGGVVQPGRSLRLSCAASGFTLSSYGMHWVRQAPGQGLEWVAVIW
YDGSNKYYAASVKGRFTISRDNSKNTLYLQMNSLRAEDTAVYYCARGGGSGSH
RYYYYGMDVWGQGTTVTVSS (SEQ ID NO:447)

Nucleotide sequence of light chain variable region:

5'TCTTCTGAGCTGACTCAGGACCCTGCTGTGTCTGTGGCCTTGGGACAGACA
GTCAGGATCACATGCCAAGGAGACAGCCTCAGAACCTATTATGCAAGCTGGT
ACCAGCAGAAGCCAAGACAGGCCCCTATTCTTGTCATCTATGGTAAAAACAA
CCGGCCCTCAGGGATCCCAGACCGATTCTCTGGCTCCACCTCAGGAATCACA
GCTTCCTTGACCATCACTGGGGCTCAGGCGGAAGATGAGGCTGACTATTACT
GTAAATCCCGGGACATCATTGGTAACCATCTGCTGTTCGGCGGAGGGACTAA
GCTGACCGTCCTA3' (SEQ ID NO:448)

Amino acid sequence of light chain variable region:

SSELTQDPAVSVALGQTVRITCQGDSLRTYYASWYQQKPRQAPILVIYGKNNRPS
GIPDRFSGSTSGITASLTITGAQAEDEADYYCKSRDIIGNHLLFGGGTKLTVL (SEQ
ID NO:449)

FIG. 3SS

20E5.1 – version1 (v1)

Nucleotide sequence of heavy chain variable region:

5'CAGGTGCAAGTGGTGGAGTCTGGGGGAGGCGTGGTCCAGCCTGGGAGGTC
CCTGAGACTCTCCTGTGCAGCGTCTGGATTCACCTTCAGTAACTATGGCATGC
ACTGGGTCCGCCAGGCTCCAGGCAAGGGGCTGGAGTGGGTGGCAGTTATATG
GTATGATGGAGGTAATAAATACTATGCAGACTCCGTGAAGGGCCGATCCATC
ATCTCCAGAGACAATTCCAAGAGCACGCTGTATCTGCAAATGAACAGCCTGA
GAGCCGAGGACACGGCTGTTTATTATTGTGCGAGGTCAGTGGCTGGTTACCA
TTATTACTACGGTATGGACGTCTGGGGCCAAGGGACCACGGTCACCGTCGCC
TCA3' (SEQ ID NO:450)

Amino acid sequence of heavy chain variable region:

QVQVVESGGGVVQPGRSLRLSCAASGFTFSNYGMHWVRQAPGKGLEWVAVIW
YDGGNKYYADSVKGRSIISRDNSKSTLYLQMNSLRAEDTAVYYCARSVAGYHY
YYGMDVWGQGTTVTVAS (SEQ ID NO:451)

Nucleotide sequence of light chain variable region:

5'CAGTCTGCCCTGACTCAGCCTGCCTCCGTGTCTGGGTCTCCTGGACAGTCGA
TCACCATCTCCTGCACTGGAACCAGCAGTGACGTTGGTGGTTATAACTCTGTC
TCCTGGTACCAACAGCACCCAGGCAAACCCCCCAAACTCATGATTTATGAGG
TCAGTAATCGGCCCTCAGGGATTTCTAATCGCTTCTCTGGCTCCAAGTCTGGC
AACACGGCCTCCCTGACCATCTCTGGGCTCCAGGCTGAGGACGAGGCTGATT
ATTTCTGCAGCTCATATACAAGCACCAGCATGGTCTTCGGCGGAGGGACCAA
GCTGGCCGTCCTA3' (SEQ ID NO:452)

Amino acid sequence of light chain variable region:

QSALTQPASVSGSPGQSITISCTGTSSDVGGYNSVSWYQQHPGKPPKLMIYEVSN
RPSGISNRFSGSKSGNTASLTISGLQAEDEADYFCSSYTSTSMVFGGGTKLAVL
(SEQ ID NO:453)

FIG. 3TT

20E5.1 – version2 (v2)

Nucleotide sequence of heavy chain variable region:

5'CAGGTGCAAGTGGTGGAGTCTGGGGGAGGCGTGGTCCAGCCTGGGAGGTC
CCTGAGACTCTCCTGTGCAGCGTCTGGATTCACCTTCAGTAACTATGGCATGC
ACTGGGTCCGCCAGGCTCCAGGCAAGGGGCTGGAGTGGGTGGCAGTTATATG
GTATGATGGAGGTAATAAATACTATGCAGACTCCGTGAAGGGCCGATCCATC
ATCTCCAGAGACAATTCCAAGAGCACGCTGTATCTGCAAATGAACAGCCTGA
GAGCCGAGGACACGGCTGTTTATTATTGTGCGAGGTCAGTGGCTGGTTACCA
TTATTACTACGGTATGGACGTCTGGGGCCAAGGGACCACGGTCACCGTCGCC
TCA3' (SEQ ID NO:454)

Amino acid sequence of heavy chain variable region:

QVQVVESGGGVVQPGRSLRLSCAASGFTFSNYGMHWVRQAPGKGLEWVAVIW
YDGGNKYYADSVKGRSIISRDNSKSTLYLQMNSLRAEDTAVYYCARSVAGYHY
YYGMDVWGQGTTVTVAS (SEQ ID NO:455)

Nucleotide sequence of light chain variable region:

5'TCTTCTGAGCTGACTCAGGACCCTGCTGTGTCTGTGGCCTTGGGACAGACA
GTCAGGATCACATGCCAAGGAGACAGCCTCAGAGGCTATTATGCAAGCTGGT
ACCAGCAGAAGCCAAGACAGGCCCCTGTACTTGTCATCTATGGTAAAAACAA
CCGGCCCTCAGGGATCCCAGACCGATTCTCTGGCTCCACGTCAGGAAACACA
GCTTCCTTGACCATCACTGGGGCTCAGGCGGAAGATGAGGCTGACTATTACT
GTAACTCCCGGGACAACATTGGTGACCATCTGGTGTTCGGCGGAGGGACCAA
GCTGACCGTCCTA3' (SEQ ID NO:456)

Amino acid sequence of light chain variable region:

SSELTQDPAVSVALGQTVRITCQGDSLRGYYASWYQQKPRQAPVLVIYGKNNRP
SGIPDRFSGSTSGNTASLTITGAQAEDEADYYCNSRDNIGDHLVFGGGTKLTVL
(SEQ ID NO:457)

Nucleotide sequence of heavy chain variable region:

5'GAGGTGCAGCTGGTGGAGTCTGGGGGAGGCTTGGTCCAGCCTGGGGGGTCC
CTGAGACTCTCCTGTGCAGCCTCCGGATTCACCTTTAGTAGCTATTGGATGAG
CTGGGTCCGCCAGGCTCCAGGGAAGGGGCTGGAGTGGGTGGCCAGCATAAA
ACAAGATGGAAGTGAGAAATACTATGTGGACTCTGTGAAGGGCCGATTCACC
ATCTCCAGAGACAACGCCAGGAACTCACTGTATCTGCAAATGAACAGCCTGA
GAGCCGAGGACACGGCTGTGTATTACTGTGCGAGAGATCTTGTATTAATGGT
GTATGATATAGACTACTACTACTACGGTATGGACGTCTGGGGCCAAGGGACC
ACGGTCACCGTCTCCTCA3' (SEQ ID NO:458)

Amino acid sequence of heavy chain variable region:

EVQLVESGGGLVQPGGSLRLSCAASGFTFSSYWMSWVRQAPGKGLEWVASIKQ
DGSEKYYVDSVKGRFTISRDNARNSLYLQMNSLRAEDTAVYYCARDLVLMVYD
IDYYYYGMDVWGQGTTVTVSS (SEQ ID NO:459)

Nucleotide sequence of light chain variable region:

5'GATATTGTGATGACTCAGTCTCCACTCTCCCTGCCCGTCACCCCTGGAGAGC
CGGCCTCCATCTCCTGCAGGTCTAGTCAGAGCCTCCTGCATAGTAATGGATAC
AACTATTTGGATTGGTACCTGCAGAAGCCAGGGCAGTCTCCACAGCTCCTGA
TCTATTTGGGTTCTAATCGGGCCTCCGGGGTCCCTGACAGGTTCAGTGGCAGT
GGATCAGGCACAGATTTTACACTGAAAATCAGCAGAGTGGAGGCTGAGGATG
TTGGGGTTTATTACTGCATGCAAGCTCTACAAACTCCGCTCACTTTCGGCGGA
GGGACCAAGGTAGAGATCAAA3' (SEQ ID NO:460)

Amino acid sequence of light chain variable region:

DIVMTQSPLSLPVTPGEPASISCRSSQSLLHSNGYNYLDWYLQKPGQSPQLLIYLG
SNRASGVPDRFSGSGSGTDFTLKISRVEAEDVGVYYCMQALQTPLTFGGGTKVEI
K (SEQ ID NO:461)

Nucleotide sequence of heavy chain variable region:

5'GAGGTGCAGCTGGTGGAGTCTGGGGGAGGCTTGGTCCAGCCTGGGGGGTCC
CTGAGACTCTCCTGTGCAGCCTCCGGATTCACCTTTAGTAACTATTGGATGAG
CTGGGTCCGCCAGGCTCCAGGGAAGGGGCTGGAGTGGGTGGCCAGCATAAA
ACAAGATGGAAGTGAGAAATACTATGTGGACTCTGTGAAGGGCCGATTCGCC
ATCTCCAGAGACAACGCCAAGAACTCACTGTTTCTGCAAATGAACAGCCTGA
GAGCCGAGGACACGGCTGTGTATTACTGTGCGAGAGATCTTGTACTAATGGT
GTATGATATAGACTACTACTACTACGGTATGGACGTCTGGGGCCAAGGGACC
ACGGTCACCGTCTCCTCA3' (SEQ ID NO:462)

Amino acid sequence of heavy chain variable region:

EVQLVESGGGLVQPGGSLRLSCAASGFTFSNYWMSWVRQAPGKGLEWVASIKQ
DGSEKYYVDSVKGRFAISRDNAKNSLFLQMNSLRAEDTAVYYCARDLVLMVYD
IDYYYYGMDVWGQGTTVTVSS (SEQ ID NO:463)

Nucleotide sequence of light chain variable region:

5'GATATTGTGATGACTCAGTCTCCACTCTCCCTGCCTGTCACCCCTGGAGAGC
CGGCCTCCATCTCTTGCAGGTCTAGTCAGAGCCTCCTGCATAGTAATGGGTAC
AACTATTTGGATTGGTACCTGCAGAAGCCAGGGCAGTCTCCACAGCTCCTGA
TCTATTTGGGTTCTAATCGGGCCTCCGGGGTCCCTGACAGGTTCAGTGGCAGT
GGATCAGGCACACATCTTACACTGAAAATCAGCAGAGTGGAGGCTGAGGATG
TTGGAGTTTATTACTGCATGCAAACTCTACAAACTCCGCTCACTTTCGGCGGA
GGGACCAAGGTGGAGATCAAA3' (SEQ ID NO:464)

Amino acid sequence of light chain variable region:

DIVMTQSPLSLPVTPGEPASISCRSSQSLLHSNGYNYLDWYLQKPGQSPQLLIYLG
SNRASGVPDRFSGSGSGTHLTLKISRVEAEDVGVYYCMQTLQTPLTFGGGTKVEI
K (SEQ ID NO:465)

Nucleotide sequence of heavy chain variable region:

5'CAGGTGCAGCTGGTGGAGTCTGGGGGAGGCGTGGCCCAGCCTGGGAGGTC
CCTGAGACTCTCCTGTGCAGCGTCTGGATTCACCTTCAGTAGCTATGGCATGC
ACTGGGTCCGCCAGGCTCCAGGCAAGGGGCTGGAGTGGGTGGCAGTTATATA
CTATGATGGAATTAATAAACACTATGCAGACTCCGTGAAGGGCCGATTCACC
ATCTCCAGAGACAATTCCAAGAACACGCTGTATCTGCAAATGAACAGCCTGA
GAGCCGAGGACACGGCTGTGTATTACTGTGCGAGAGATCGGGGACTGGACTG
GGGCCAGGGAACCCTGGTCACCGTCTCCTCA3' (SEQ ID NO:466)

Amino acid sequence of heavy chain variable region:

QVQLVESGGGVAQPGRSLRLSCAASGFTFSSYGMHWVRQAPGKGLEWVAVIYY
DGINKHYADSVKGRFTISRDNSKNTLYLQMNSLRAEDTAVYYCARDRGLDWGQ
GTLVTVSS (SEQ ID NO:467)

Nucleotide sequence of light chain variable region:

5'GACATCGTGATGACCCAGTCTCCAGACTCCCTGGCTGTGTCTCTGGGCGAG
AGGGCCACCATCAACTGCAAGTCCAGCCAGAGTGTTTTATACAGCTCCAACA
GTAAGAACTACTTAGTTTGGTACCAGCAGAAACCAGGACAGCCTCCTAAGCT
GCTCATTTACTGGGCCTCTACCCGGGAATCCGGGGTCCCTGACCGATTCAGTG
GCAGCGGGTCTGGGACAGATTTCACTCTCACCATCAGCAGCCTGCAGGCTGA
AGATGTGGCAGTTTATTACTGTCAACAATATTATAGTACTCCGTGGACGTTCG
GCCAAGGGACCAAGGTGGAAATCAAA3' (SEQ ID NO:468)

Amino acid sequence of light chain variable region:

DIVMTQSPDSLAVSLGERATINCKSSQSVLYSSNSKNYLVWYQQKPGQPPKLLIY
WASTRESGVPDRFSGSGSGTDFTLTISSLQAEDVAVYYCQQYYSTPWTFGQGTK
VEIK (SEQ ID NO:469)

Nucleotide sequence of heavy chain variable region:

5'GAGGTGCAGCTGGTGGAGTCTGGGGGAGGCTTGGTCCAGCCTGGGGGGTCC
CTGAGACTCTCCTGTGCAGCCTCTGGACTCACCTTTAGTAACTTTTGGATGAG
CTGGGTCCGCCAGGCTCCAGGGAAGGGGCTGGAGTGGGTGGCCAACATAAA
GCAAGATGGAAATGATAAATACTATGTGGACTCTGTGAAGGGCCGATTCACC
ATCTCCAGAGACAACGCCAAGAATTCACTGTATCTGCAAATGAACAGCCTGA
GAGCCGAGGACACGGCTGTGTATTACTGTGCGAGAGAGTCAAACTGGGGATT
TGCTTTTGATATCTGGGGCCAAGGGACAATGGTCACCGTCTCTTCA3' (SEQ ID
NO:470)

Amino acid sequence of heavy chain variable region:

EVQLVESGGGLVQPGGSLRLSCAASGLTFSNFWMSWVRQAPGKGLEWVANIKQ
DGNDKYYVDSVKGRFTISRDNAKNSLYLQMNSLRAEDTAVYYCARESNWGFAF
DIWGQGTMVTVSS (SEQ ID NO:471)

Nucleotide sequence of light chain variable region:

5'CAGTCTGTGCTGACTCAGCCACCCTCAGCGTCTGGGACCCCCGGGCAGAGG
GTCACCATCTCTTGTTCTGGAAGCAGCTCCAACATCGGAAGTAAAACTGTAA
ACTGGTACCAGCAGTTCCCAGGAACGGCCCCCAAACTCCTCATCTATAGTAA
TAATCGGCGGCCCTCAGGGGTCCCTGACCGATTCTCTGGCTCCAAGTCTGGCA
CCTCAGCCTCCCTGGCCATCAGTGGGCTCCAGTCTGAGGATGAGGCTGATTAT
TACTGTGCAGCATGGGATGACAGCCTGAATTGGGTGTTCGGCGCAGGGACCA
AGCTGACCGTCCTA3' (SEQ ID NO:472)

Amino acid sequence of light chain variable region:

QSVLTQPPSASGTPGQRVTISCSGSSSNIGSKTVNWYQQFPGTAPKLLIYSNNRRP
SGVPDRFSGSKSGTSASLAISGLQSEDEADYYCAAWDDSLNWVFGAGTKLTVL
(SEQ ID NO:473)

Nucleotide sequence of heavy chain variable region:

5'GAGGTGCAGCTGGTGGAGTCTGGGGGAGGTTTGGTCCAGCCTGGGGGGTCC
CTGAGACTCTCCTGTGCAGCCTCTGGACTCACCTTTAGTAACTTTTGGATGAG
CTGGGTCCGCCAGGCTCCAGGGAAGGGGCTGGAGTGGGTGGCCAACATAAA
GCAAGATGGAAGTGAGAAATACTATGTGGACTCTGTGAAGGGCCGATTCACC
ATCTCCAGAGACAACGCCAAGAATTCACTGTATCTGCAAATGAACAGCCTGA
GAGCCGAGGACACGGCTGTGTATTACTGTGCGAGAGAGTCAAACTGGGGATT
TGCTTTTGATATCTGGGGCCAAGGGACAATGGTCACCGTCTCTTCA3' (SEQ ID
NO:474)

Amino acid sequence of heavy chain variable region:

EVQLVESGGGLVQPGGSLRLSCAASGLTFSNFWMSWVRQAPGKGLEWVANIKQ
DGSEKYYVDSVKGRFTISRDNAKNSLYLQMNSLRAEDTAVYYCARESNWGFAF
DIWGQGTMVTVSS (SEQ ID NO:475)

Nucleotide sequence of light chain variable region:

5'CAGTCTGTGCTGACTCAGCCACCCTCAGCGTCTGGGACCCCCGGGCAGAGG
GTCACCATCTCTTGTTCTGGAAGCAGCTCCAACATCGGAAGTAAAACTGTAA
ACTGGTACCAGCAGTTCCCAGGAACGGCCCCCAAACTCCTCATCTATAGTAA
TAATCGGCGGCCCTCAGGGGTCCCTGACCGATTCTCTGGCTCCAAGTCTGGCA
CCTCAGCCTCCCTGGCCATCAGTGGGCTCCAGTCTGAGGATGAGGCTGATTAT
TACTGTGCAACATGGGATGACAGACTGAATTGGGTGTTCGGCGCAGGGACCA
AGCTGACCGTCCTA3' (SEQ ID NO:476)

Amino acid sequence of light chain variable region:

QSVLTQPPSASGTPGQRVTISCSGSSSNIGSKTVNWYQQFPGTAPKLLIYSNNRRP
SGVPDRFSGSKSGTSASLAISGLQSEDEADYYCATWDDRLNWVFGAGTKLTVL
(SEQ ID NO:477)

Nucleotide sequence of heavy chain variable region:

5'CAGGTCACCTTGAAGGAGTCTGGTCCTGTGCTGGTGAAACCCACAGAGACC
CTCACGCTGACCTGCACCGTCTCTGGGTTCTCACTCAGCAATGTTAGAATGGG
TGTGAGCTGGATCCGTCAGCCCCAGGGAAGGCCCTGGAGTGGCTTGCACAC
ATTTTTTCGAATGACGAAAATTCCTACAGAACATCTCTGAAGAGCAGGCTCA
CCATCTCCAAGGACACCTCCAAAAGCCAGGTGGTCCTTACCATGACCAACAT
GGACCCTGTGGACACAGCCACATATTACTGTGCACGGATAGTGGGAGCTACA
ACGGATGATGCTTTTGATATCTGGGGCCAAGGGACAATGGTCACCGTCTCTTC
A3' (SEQ ID NO:478)

Amino acid sequence of heavy chain variable region:

QVTLKESGPVLVKPTETLTLTCTVSGFSLSNVRMGVSWIRQPPGKALEWLAHIFS
NDENSYRTSLKSRLTISKDTSKSQVVLTMTNMDPVDTATYYCARIVGATTDDAF
DIWGQGTMVTVSS (SEQ ID NO:479)

Nucleotide sequence of light chain variable region:

5'TCCTATGTGCTGACTCAGCCACCCTCGGTGTCAGTGGCCCCAGGACAGACG
GCCAGGATTACCTGTGGGGGAAACAACATTGGAAGTAAAAGTGTGCACTGGT
ACCAGCAGAAGCCAGGCCAGGCCCCTGTGCTGGTCGTCTATGATGATAGCGA
CCGGCCCTCAGGGATCCCTGAGCGATTCTCTGGCTCCAACTCTGGGAACACG
GCCACCCTGACCATCAGCAGGGTCGAAGCCGGGGATGAGGCCGACTTTTACT
GTCAGGTGTGGGATAGTAGTAGTGATCCTGTGGTATTCGGCGGAGGGACCAA
GCTGACCGTCCTA3' (SEQ ID NO:480)

Amino acid sequence of light chain variable region:

SYVLTQPPSVSVAPGQTARITCGGNNIGSKSVHWYQQKPGQAPVLVVYDDSDRP
SGIPERFSGSNSGNTATLTISRVEAGDEADFYCQVWDSSSDPVVFGGGTKLTVL
(SEQ ID NO:481)

Nucleotide sequence of heavy chain variable region:

5'GAGGTGCAGCTGGTGGAGTCTGGGGGAGGCTTGGTCCAGCCTGGGGGGTCC
CTGAGACTCTCCTGTGCAGCCTCTGGATTCACCTTTAGTAACTATTGGATGAC
CTGGGTCCGCCAGGCTCCAGGGAAGGGGCTGGAGTGGGTGGCCAGCATAAA
GCAAGATGGAAGTGAGAGATACTATGTGGACTCTGTGAAGGGCCGATTCACC
ATCTCCCGAGACACCGCCAAGAACTCTCTGTATCTCCAAATGAACAGCCTGC
GAGCCGAGGACACGGCTGTGTATTACTGTGCGAGACCTCTTGTACTAATGGT
GTATGCTCTACACTACTACTACTACGGTATGGACGTCTGGGGCCACGGGACC
ACGGTCACCGTCTCCTCA3' (SEQ ID NO:482)

Amino acid sequence of heavy chain variable region:

EVQLVESGGGLVQPGGSLRLSCAASGFTFSNYWMTWVRQAPGKGLEWVASIKQ
DGSERYYVDSVKGRFTISRDTAKNSLYLQMNSLRAEDTAVYYCARPLVLMVYA
LHYYYYGMDVWGHGTTVTVSS (SEQ ID NO:483)

Nucleotide sequence of light chain variable region:

5'GATATTGTGATGACTCAGTCTCCACTCTCCCTGCCCGTCACCCCTGGAGAGC
CGGCCTCCATCTCCTGCAGGTCTAGTCAGAGCCTCCTGCATAGTAATGGATAC
AACTATTTGGATTGGTACCTGCAGAAGCCAGGGCAGTCTCCACAGCTCCTGA
TCTATTTGGGTTCTAATCGGGCCTCCGGGGTCCCTGACAGGTTCAGTGGCAGT
GGATCAGGCACAGATTTTACACTGAAAATCAGCAGAGTGGAGGCTGAGGATG
TTGGGGTTTATTACTGCATGCAAGCTCTACAAACTCCGCTCACTTTCGGCGGA
GGGACCAAGGTGGAGATCAAA3' (SEQ ID NO:484)

Amino acid sequence of light chain variable region:

DIVMTQSPLSLPVTPGEPASISCRSSQSLLHSNGYNYLDWYLQKPGQSPQLLIYLG
SNRASGVPDRFSGSGSGTDFTLKISRVEAEDVGVYYCMQALQTPLTFGGGTKVEI
K (SEQ ID NO:485)

| Heavy variable | SEQ ID NO: | Germline | Germline | FR1 | CDR1 | FR2 |
|---|---|---|---|---|---|---|
| | | Germline | Germline | FR1 | CDR1 | FR2 |
| 5H5.1G | 493 | VH1\|1-02 | | QVQLVQSGAEVKKPGASVKVSCKAS | GYTFTGYYMH | WVRQAPGQGLEWMG |
| | 419 | VH1\|1-02 | JH6 | ---V-------------------- | ------I--- | -------------- |
| 24B9.1G | 494 | VH3\|3-33 | | QVQLVESGGGVVQPGRSLRLSCAAS | GFTFSSYGMH | WVRQAPGKGLEWVA |
| | 435 | VH3\|3-33 | JH4 | ------------------------- | ---------- | -------------- |
| | 495 | VH3\|3-33 | Germline | QVQLVESGGGVVQPGRSLRLSCAAS | GFTFSSYGMH | WVRQAPGKGLEWVA |
| 24F7.1G | 423 | VH3\|3-33 | JH6 | ------------------------- | ---------- | -------------- |
| 22B11.1G | 427 | VH3\|3-33 | JH6 | ------------------------- | -------L-- | -------------- |
| 20A5.1G | 443 | VH3\|3-33 | JH6 | --------S---------------- | ---------- | -------------- |
| 20A5.2G | 447 | VH3\|3-33 | JH6 | ----A------------------- | ------L--- | ---------Q---- |
| 30F1.1G | 431 | VH3\|3-33 | JH6 | --------S--------------- | -----RN--- | -------------- |
| 20E5.1GV1 | 451 | VH3\|3-33 | JH6 | ---V-------------------- | ------N--- | -------------- |
| 24B9.2G | 439 | VH3\|3-33 | JH6 | ---V---G---------------- | ------N--- | -------------- |

FIG. 3DDD

| Heavy variable | SEQ ID NO: | CDR2 | FR3 | CDR3 | FR4 |
|---|---|---|---|---|---|
| | 493 | WINPNSGGTNYAQKFQG | RVTMTRDTSISTAYMELSRLRSDDTAVYYCAR | | |
| 5H5.1G | 419 | ----H---A------- | -------------------------------- | GNWNYDYYGMDV | WGQGTTVTVSS |
| | 494 | VIWYDGSNKYYADSVKG | RFTISRDNSKNTLYLQMNSLRAEDTAVYYCAR | CDR3 | FR4 |
| 24B9.1G | 435 | ----------------- | -------------------V----------- | DRGLDWGQGTLVTVSS | |
| | 495 | VIWYDGSNKYYADSVKG | RFTISRDNSKNTLYLQMNSLRAEDTAVYYCAR | | FR4 |
| 24F7.1G | 423 | --------T-------- | -S------------------------------ | SVAGYHYYYGMDV | WGQGTTVTVSS |
| 22B11.1G | 427 | ----L------------ | -S------------------------------ | SVAGYHYYYGMDV | WGQGTTVTVSS |
| 20A5.1G | 443 | ------Y-D-------- | -S------------------------------ | SVAGYHYYYGMDV | WGQGTTVTVSS |
| 20A5.2G | 447 | ----------A------ | -------------------------------- | GGGSGSHRYYYYGMDV | WGQGTTVTVSS |
| 30F1.1G | 431 | ---F------------- | -S----------L------------------- | SVAGYHYYYGMDV | WGQGTTVTVSS |
| 20E5.1GV1 | 451 | ------G---------- | -SI--------S-------------------- | SVAGYHYYYGMDV | WGQGTTVTVAS |
| 24B9.2G | 439 | --------S-------- | -S-----------------V------------ | SVAGYHYYYGMDV | WGQGTTVTVSS |

| Kappa variable | SEQ ID NO: | | | | |
|---|---|---|---|---|---|
| | | Germline | FR1 | CDR1 | FR2 |
| | | Germline | DIQMTQSPSSLSASVGDRVTITC | RASQGISNYLA | WYQQKPGKVPKLLIY |
| 5H5.1K | 496 | VK1\|A20 | | | |
| | 421 | VK1\|A20 JK3 | --------------------- | ----D------ | --------------- |

| Lambda variable | | | | | |
|---|---|---|---|---|---|
| | | Germline | FR1 | CDR1 | FR2 |
| | | Germline | QSALTQPASVSGSPGQSITISC | TGTSSDVGGYNYVS | WYQQHPGKAPKLMIY |
| | 497 | VL2\|2a2 | | | |
| 20E5.1L v1 | 453 | VL2\|2a2 JL2 | --------------------- | ----------S-- | ------------P-- |

| | | Germline | FR1 | CDR1 | FR2 |
|---|---|---|---|---|---|
| | | Germline | SSELTQDPAVSVALGQTVRITC | QGDSLRSYYAS | WYQQKPGQAPVLVIY |
| | 498 | VL3\|3l | | | |
| 30F1.1L | 433 | VL3\|3l JL2 | --------------------- | ----------- | ------R-------- |
| 22B11.1L | 429 | VL3\|3l JL2 | --------------------- | -------G--- | ------R-------F |
| 24B9.1L | 437 | VL3\|3l JL2 | --------------------- | -------G--- | ------R-------- |
| 24B9.2L | 441 | VL3\|3l JL2 | --------------------- | -------G--- | ------R-------- |
| 20E5.1L v2 | 457 | VL3\|3l JL2 | --------------------- | -------G--- | ------R-------- |
| 24F7.1L | 425 | VL3\|3l JL2 | --------------------- | -------G---T | ------R-------- |
| 20A5.1L | 445 | VL3\|3l JL2 | --------------------- | -------T--- | ------R-----I-- |
| 20A5.2L | 449 | VL3\|3l JL2 | --------------------- | -------T--- | ------R-----I-- |

FIG. 3EEE

| Kappa variable | SEQ ID NO: | CDR2 | FR3 | CDR3 | FR4 |
|---|---|---|---|---|---|
| | 496 | AASTLQS | GVPSRFSGSGSGTDFTLTISSLQPEDVATYYC | QRYQIAPFT | FGPGTKVDIK |
| 5H5.1K | 421 | ------- | ------------------------------F- | | |

| Lambda_variable | SEQ ID NO: | CDR2 | FR3 | CDR3 | FR4 |
|---|---|---|---|---|---|
| | 497 | EVSNRPS | GVSNRFSGSKSGNTASLTISGLQAEDEADYYC | SSYTSTSMV | FGGGTKLAVL |
| 20E5.1L v1 | 453 | ------- | -I----------------------------F- | | |

| | SEQ ID NO: | CDR2 | FR3 | CDR3 | FR4 |
|---|---|---|---|---|---|
| | 498 | GKNNRPS | GIPDRFSGSSSGNTASLTITGAQAEDEADYYC | | |
| 30F1.1L | 433 | ------- | -----I----T-------------------- | KSRDIIGDHLV | FGGGTKLTVL |
| 22B11.1L | 429 | ------- | ----------T-------------------- | NSRDIIGDHLL | FGGGTKLTVL |
| 24B9.1L | 437 | ------- | ----------T-------------------- | KSRDSSGDHLV | FGGGTKLTVL |
| 24B9.2L | 441 | ------- | ----------T-------------------- | KSRDSSGDHLV | FGGGTKLTVL |
| 20E5.1L v2 | 457 | ------- | ----------T-------------------- | NSRDNIGDHLV | FGGGTKLTVL |
| 24F7.1L | 425 | ---Y--- | ----------T-------------------- | NSRDSIGNHLV | FGGGTKLTVL |
| 20A5.1L | 445 | ------- | ----------T----I--------------- | KSRDIIGNHLL | FGGGTKLTVL |
| 20A5.2L | 449 | ------- | ----------T----I--------------- | KSRDIIGNHLL | FGGGTKLTVL |

FIG. 3FFF

| | SEQ ID NO: | | Germline | Germline | FR1 | SEQ ID NO: | CDR1 | SEQ ID NO: | FR2 | SEQ ID NO: |
|---|---|---|---|---|---|---|---|---|---|---|
| | | | Germline | Germline | | | | | | |
| | | | VH2\|226 | | QVTLKESGPVLVKPTETLTLTCTVS | 506 | GFSLSNARMGVS | 507 | WIRQPPGKALEWLA | 509 |
| 11G1.5 | 479 | | VH2\|226 | JH3 | ------------------------ | 506 | -------V--- | 508 | -------------- | 509 |
| | | | Germline | Germline | | | | | | |
| | 487 | | VH3\|307 | | EVQLVESGGGLVQPGGSLRLSCAAS | 510 | GFTFSSYWMS | 511 | WVRQAPGKGLEWVA | 514 |
| 11H8.1 | 475 | | VH3\|307 | JH3 | ------------------------ | 510 | -L---NF--- | 512 | -------------- | 514 |
| 11H4.1 | 471 | | VH3\|307 | JH3 | ------------------------ | 510 | -L---NF--- | 512 | -------------- | 514 |
| 8A3.1 | 459 | | VH3\|307 | JH6 | ------------------------ | 510 | ---------- | 511 | -------------- | 514 |
| 11F1.1 | 463 | | VH3\|307 | JH6 | ------------------------ | 510 | ---N------ | 500 | -------------- | 514 |
| 8A1.2 | 483 | | VH3\|307 | JH6 | ------------------------ | 510 | ---N---T-- | 513 | -------------- | 514 |
| | | | Germline | Germline | | | | | | |
| | 488 | | VH3\|3-33 | | QVQLVESGGGVVQPGRSLRLSCAAS | 515 | GFTFSSYGMH | 517 | WVRQAPGKGLEWVA | 518 |
| 12H11.1 | 467 | | VH3\|3-33 | JH4 | ---------A-------------- | 516 | ---------- | 517 | -------------- | 518 |

FIG. 3GGG

|  | SEQ ID NO: | CDR2 | SEQ ID NO: | FR3 | SEQ ID NO: | CDR3 | SEQ ID NO: | FR4 |
|---|---|---|---|---|---|---|---|---|
|  |  |  |  |  |  |  |  |  |
|  | 486 | HIFSNDEKSYSTSLKS | 519 | RLTISKDTSKSQVVLTMTNMDPVDTATVYYCARI | 521 |  |  |  |
| 11G1.5 | 479 | ------N--R----- | 520 | -------------------------------- | 521 | VGATTDDAFDI | 522 | WGQGTMVTVSS | 523 |
|  |  | CDR2 |  | FR3 |  | CDR3 |  | FR4 |
|  | 487 | NIKQDGSEKYYVDSVKG | 526 | RFTISRDNAKNSLYLQMNSLRAEDTAVYYCAR | 529 |  |  |  |
| 11H8.1 | 475 | --------ND----- | 526 | -------------------------------- | 529 | ESNWGFAFDI | 533 | WGQGTMVTVSS | 523 |
| 11H4.1 | 471 | --------ND----- | 527 | -------------------------------- | 529 | ESNWGFAFDI | 533 | WGQGTMVTVSS | 523 |
| 8A3.1 | 459 | S--------------- | 501 | ------------R-------------------- | 530 | DLVLMVYDIDYYYGMDV | 502 | WGQGTTVTVSS | 524 |
| 11F1.1 | 463 | S--------------- | 501 | --A----------F------------------- | 531 | DLVLMVYDIDYYYGMDV | 502 | WGQGTTVTVSS | 524 |
| 8A1.2 | 483 | S-------R------- | 528 | --------T------------------------ | 532 | PLVLMVYALHYYYGMDV | 534 | WGHGTTVTVSS | 525 |
|  |  | CDR2 |  | FR3 |  | CDR3 |  | FR4 |
|  | 488 | VIWYDGSNKYYADSVKG | 535 | RFTISRDNSKNTLYLQMNSLRAEDTAVYYCAR | 537 |  |  |  |
| 12H11.1 | 467 | ---Y----I--H----- | 536 | -------------------------------- | 537 | DRGLD | 538 | WGQGTLVTVSS | 539 |

FIG. 3HHH

| | SEQ ID NO: | Germline | Germline | FR1 | SEQ ID NO: | CDR1 | SEQ ID NO: | FR2 | SEQ ID NO: |
|---|---|---|---|---|---|---|---|---|---|
| | 489 | VK2|A19 | | DIVMTQSPLSLPVTPGEPASISC | 540 | RSSQSLLHSNGYNYLD | 503 | WYLQKPGQSPQLLIY | 541 |
| 8A1.2 | 485 | VK2|A19 | JK4 | --------------------- | 540 | ---------------- | 503 | --------------- | 541 |
| 8A3.1 | 461 | VK2|A19 | JK4 | --------------------- | 540 | ---------------- | 503 | --------------- | 541 |
| 11F1.1 | 465 | VK2|A19 | JK4 | --------------------- | 540 | ---------------- | 503 | --------------- | 541 |
| | | Germline | Germline | FR1 | | CDR1 | | FR2 | |
| | 490 | VK4|B3 | | DIVMTQSPDSLAVSLGERATINC | 542 | KSSQSVLYSSNNKNYLA | 543 | WYQQKPGQPPKLLIY | 545 |
| 12H11.1 | 469 | VK4|B3 | JK1 | ---------------------- | 542 | --------S-----V | 544 | --------------- | 545 |
| | | Germline | Germline | FR1 | | CDR1 | | FR2 | |
| | 491 | VL1|1c | | QSVLTQPPSASGTPGQRVTISC | 546 | SGSSSNIGSNTVN | 547 | WYQQLPGTAPKLLIY | 549 |
| 11H4.1 | 473 | VL1|1c | JL3b | --------------------- | 546 | -------K---- | 548 | ----F---------- | 550 |
| 11H8.1 | 477 | VL1|1c | JL3b | --------------------- | 546 | -------K---- | 548 | ----F---------- | 550 |
| | | Germline | Germline | FR1 | | CDR1 | | FR2 | |
| | 492 | VL3|3h | | SYVLTQPPSVSVAPGKTARITC | 551 | GGNNIGSKSVH | 553 | WYQQKPGQAPVLVIY | 554 |
| 11G1.5 | 481 | VL3|3h | JL2 | -------------Q------- | 552 | ----------- | 553 | ------------V- | 555 |

FIG. 3III

| | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|
| | | CDR2 | | FR3 | | CDR3 | | FR4 | |
| 8A1.2 | 489 | LGSNRAS | 504 | GVPDRFSGSGSGTDFTLKISRVEAEDVGVYYC | 556 | | | | |
| 8A3.1 | 485 | ------- | 504 | -------------------------------- | 556 | MQALQTPLT | 558 | FGGGTKVEIK | 559 |
| | 461 | ------- | 504 | -------------------------------- | 556 | MQALQTPLT | 558 | FGGGTKVEIK | 559 |
| 11F1.1 | 465 | ------- | 504 | ------------HL------------------ | 557 | MQTLQTPLT | 505 | FGGGTKVEIK | 559 |
| | | CDR2 | | FR3 | | CDR3 | | FR4 | |
| | 490 | WASTRES | 560 | GVPDRFSGSGSGTDFTLTISSLQAEDVAVYYC | 561 | | | | |
| 12H11.1 | 469 | ------- | 560 | -------------------------------- | 561 | QQYYSTPWT | 562 | FGQGTKVEIK | 563 |
| | | CDR2 | | FR3 | | CDR3 | | FR4 | |
| | 491 | SNNQRPS | 564 | GVPDRFSGSKSGTSASLAISGLQSEDEADYYC | 566 | | | | |
| 11H4.1 | 473 | ---R--- | 565 | -------------------------------- | 566 | AAWDDSLNWV | 567 | FGAGTKLTVL | 569 |
| 11H8.1 | 477 | ---R--- | 565 | -------------------------------- | 566 | ATWDDRLNWV | 568 | FGAGTKLTVL | 569 |
| | | CDR2 | | FR3 | | CDR3 | | FR4 | |
| | 492 | YDSDRPS | 570 | GIPERFSGSNSGNTATLTISRVEAGDEADYYC | 572 | | | | |
| 11G1.5 | 481 | D------ | 571 | -------------------------------F | 573 | QVWDSSSDPVV | 574 | FGGGTKLTVL | 575 |

FIG. 3JJ

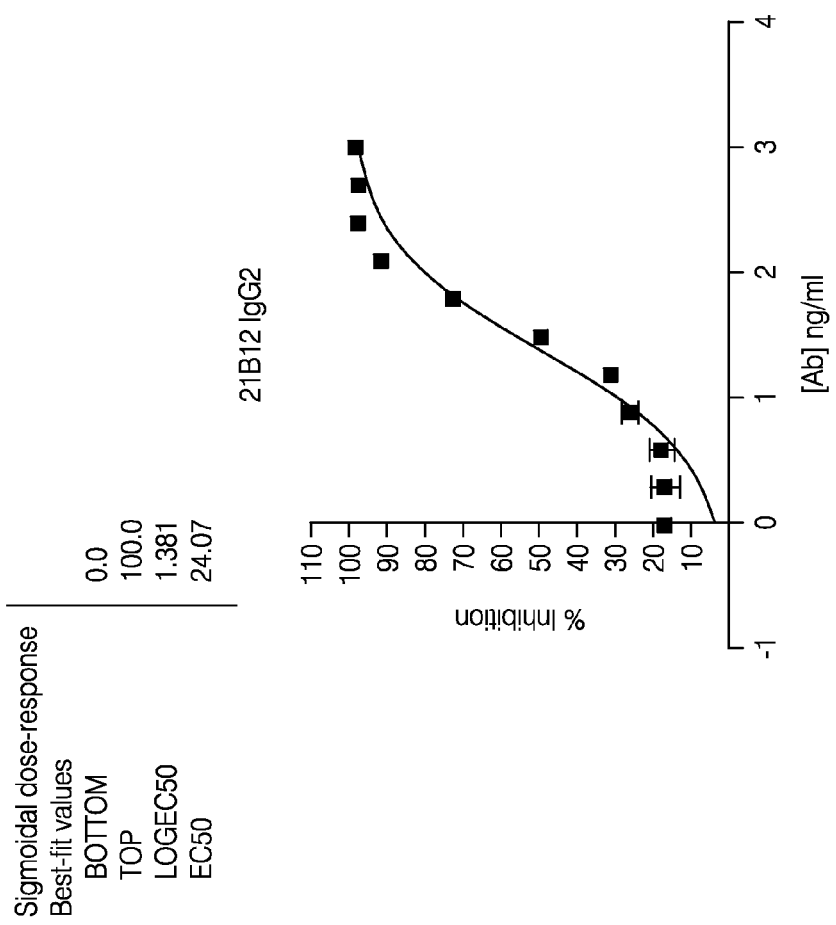

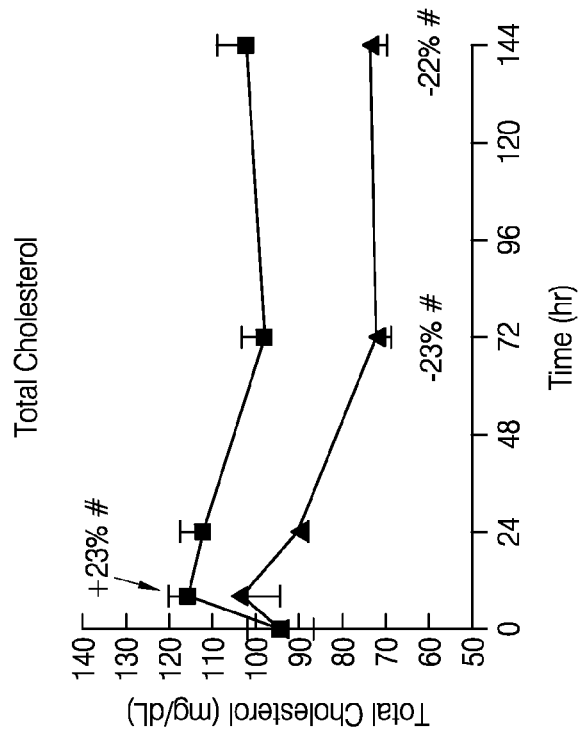
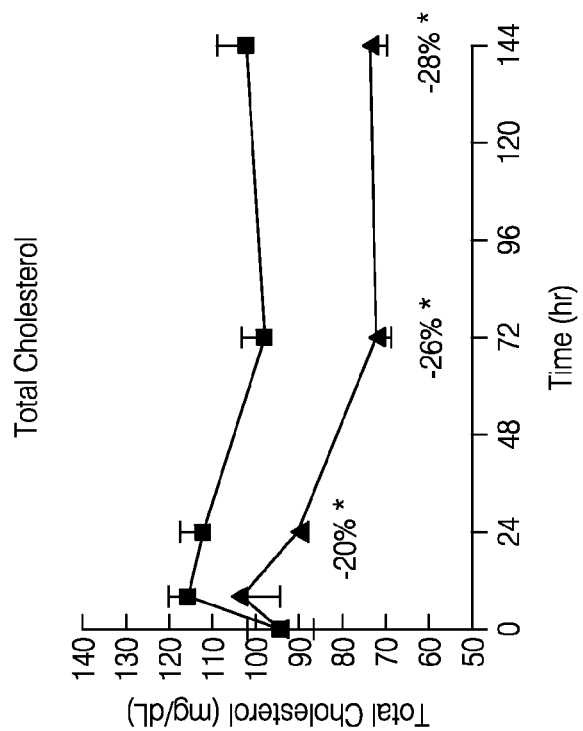
FIG. 8A
FIG. 8B

FIG. 13A

| | | | | |
|---|---|---|---|---|
| 23B5_light_cdr | RASQSI.....SSYLN | (SEQ ID NO:209) | AASSLQS | (SEQ ID NO:211) | QQSISSPIT~~~~~~~ | (SEQ ID NO:213) |
| 25G4_light_cdr | RASQSI.....SIYLN | (SEQ ID NO:308) | AAASLQS | (SEQ ID NO:393) | QQSYSAPIT~~~~~~~ | (SEQ ID NO:394) |
| 3C4_light_cdr | RASQRI.....SNYLS | (SEQ ID NO:219) | AASSLQS | (SEQ ID NO:211) | QQSYSTPLI~~~~~~~ | (SEQ ID NO:235) |
| 30A4_light_cdr | RSSQSLLHSNGYNYLN | (SEQ ID NO:220) | LGSHRAS | (SEQ ID NO:227) | MQVLQTFPT~~~~~~~ | (SEQ ID NO:236) |
| 21B12_light_cdr | ~~TGTSSDVAGYKNSVS | (SEQ ID NO:158) | EVTNKRPS | (SEQ ID NO:162) | NSYLSTSMV~~~~~~~ | (SEQ ID NO:395) |
| 23G1_light_cdr | ~~TGTSSDVGGYNNSVS | (SEQ ID NO:159) | EVSNRPS | (SEQ ID NO:163) | NSYLSTSMV~~~~~~~ | (SEQ ID NO:395) |
| 20D10_light_cdr | ~~TGTSSDVGGYNSVS | (SEQ ID NO:158) | EVSNRPS | (SEQ ID NO:162) | SSYTSTSMV~~~~~~~ | (SEQ ID NO:164) |
| 26B5_light_cdr | ~~TGTSSDVGGYNSVS | (SEQ ID NO:158) | EVSNRPS | (SEQ ID NO:162) | SSYTSTSMV~~~~~~~ | (SEQ ID NO:164) |
| 31D1_light_cdr | ~~TGTSSDVGGYNSVS | (SEQ ID NO:158) | EVSNRPS | (SEQ ID NO:162) | SSYTSTSMV~~~~~~~ | (SEQ ID NO:164) |
| 27E7_light_cdr | ~~TGTSSDVGGYNSVS | (SEQ ID NO:158) | EVSNRPS | (SEQ ID NO:162) | SSYTSTSMV~~~~~~~ | (SEQ ID NO:164) |
| 27B5_light_cdr | ~~TGTSSDVGGYNSVS | (SEQ ID NO:158) | EVSNRPS | (SEQ ID NO:162) | SSYTSTSMV~~~~~~~ | (SEQ ID NO:164) |
| 30B9_light_cdr | ~~TGTSSDVGGYNSVS | (SEQ ID NO:158) | EVSNRPS | (SEQ ID NO:162) | SSYTSTSMV~~~~~~~ | (SEQ ID NO:164) |
| 19B9_light_cdr | ~~TGTSSDVGAYNSVS | (SEQ ID NO:309) | EVSNRPL | (SEQ ID NO:162) | SSYTSTSMV~~~~~~~ | (SEQ ID NO:164) |
| 17C2_light_cdr | ~~TGTSSDVERYNSVS | (SEQ ID NO:390) | EVSNRPS | (SEQ ID NO:162) | SSYTSTSMV~~~~~~~ | (SEQ ID NO:164) |
| 25A7_light_cdr | ~~TGTSSDVERYNSVS | (SEQ ID NO:391) | EVSNRPS | (SEQ ID NO:162) | SSTYSSSVY~~~~~~~ | (SEQ ID NO:396) |
| 13H1_light_cdr | ~~TGTSSDVGNYNLVS | (SEQ ID NO:221) | EVSKRPS | (SEQ ID NO:228) | CSYAGSSTLV~~~~~~ | (SEQ ID NO:237) |
| 31H4_light_cdr | ~~TGSSSNIGAGYDVH | (SEQ ID NO:222) | GNSNRPS | (SEQ ID NO:229) | QSYDSSLSGSV~~~~~ | (SEQ ID NO:238) |
| 27B2_light_cdr | ~~TGSSSNIGAHYDVH | (SEQ ID NO:223) | GNTYRPS | (SEQ ID NO:230) | QSYDNSLSGWV~~~~~ | (SEQ ID NO:239) |
| 9H6_light_cdr | ~~SGSSSNIGSNT.VN | (SEQ ID NO:197) | SNNTRPS | (SEQ ID NO:199) | AAWDDSLN.WV~~~~~ | (SEQ ID NO:397) |
| 1A12_light_cdr | ~~SGSSSNIGSKT.VN | (SEQ ID NO:499) | SNNTRPS | (SEQ ID NO:199) | AAWDDSLN.WV~~~~~ | (SEQ ID NO:397) |
| 9C9_light_cdr | ~~SGSSSNIGSKT.VN | (SEQ ID NO:498) | RNNQRPL | (SEQ ID NO:392) | AAWDSLN.WV~~~~~~ | (SEQ ID NO:398) |
| 31A4_light_cdr | ~~SGSSSNIGSNT.VN | (SEQ ID NO:197) | SNNQRPS | (SEQ ID NO:231) | AVWDDSLNGWV~~~~~ | (SEQ ID NO:240) |
| 22B2_light_cdr | ~~SGSSSNIGNNF.VS | (SEQ ID NO:182) | DYNKRPS | (SEQ ID NO:183) | GTWDSSLSGYM~~~~~ | (SEQ ID NO:185) |
| 28B12_light_cdr | ~~SGSSSNIGNNF.VS | (SEQ ID NO:182) | DYNKRPS | (SEQ ID NO:183) | GTWDSSLSGYM~~~~~ | (SEQ ID NO:185) |
| 28D6_light_cdr | ~~SGSSSNIGNNF.VS | (SEQ ID NO:182) | DYNKRPS | (SEQ ID NO:183) | GTWDSSLSGYM~~~~~ | (SEQ ID NO:185) |
| 16F12_light_cdr | ~~SGSSSNIGNNF.VS | (SEQ ID NO:182) | DYNKRPS | (SEQ ID NO:183) | GTWDSSLSAVV~~~~~ | (SEQ ID NO:186) |
| 27A6_light_cdr | ~~SGSSSNIGNNT.VS | (SEQ ID NO:182) | DYNKRPS | (SEQ ID NO:183) | GTWDSSLSSV~~~~~~ | (SEQ ID NO:398) |
| 31G11_light_cdr | ~~SGSNSNIGNNY.VS | (SEQ ID NO:224) | DSMKRPS | (SEQ ID NO:194) | GTWDSSLSGYV~~~~~ | (SEQ ID NO:399) |
| 13B5_light_cdr | ~~~~~SGDKLGDKYAC | (SEQ ID NO:225) | QNTKWPL | (SEQ ID NO:232) | DNWDSLSAVV~~~~~~ | (SEQ ID NO:241) |
| 31B12_light_cdr | ~~~~~SGDKLGDKYAC | (SEQ ID NO:225) | QNTKWPL | (SEQ ID NO:233) | QAWDSSTVV~~~~~~~ | (SEQ ID NO:242) |
| 3B6_light_cdr | ~~~~TLSSGYSSYHVD | (SEQ ID NO:226) | VDTGGIV | (SEQ ID NO:234) | SDYKCGADRGSSTNFVVV | (SEQ ID NO:243) |

Consensus

FIG. 13C

Heavy Chain:

| Name | CDR1 | | CDR2 | | CDR3 | |
|---|---|---|---|---|---|---|
| 20D10_heavy_cdr | ~~GYPLTTSYGIS | (SEQ ID NO:168) | WISAYNG.NTNYAQKVQG | (SEQ ID NO:174) | GYGMDV~~~~~ | (SEQ ID NO:180) |
| 30B9_heavy_cdr | ~~GYPLTTSYGIS | (SEQ ID NO:168) | WISAYNG.NTNYAQKVQG | (SEQ ID NO:174) | GYGMDV~~~~~ | (SEQ ID NO:180) |
| 27E7_heavy_cdr | ~~GYSLTTSYGIS | (SEQ ID NO:366) | WISAYNG.NTNYAQKVQG | (SEQ ID NO:174) | GYGMDV~~~~~ | (SEQ ID NO:180) |
| 19H9_heavy_cdr | ~~GYALTTSYGIS | (SEQ ID NO:367) | WISAYNG.NTNYAQKVQG | (SEQ ID NO:174) | GYGMDV~~~~~ | (SEQ ID NO:180) |
| 21B12_heavy_cdr | ~~GYTLTTSYGIS | (SEQ ID NO:368) | WVSFYNG.NTNYAQKLQG | (SEQ ID NO:175) | GYGMDV~~~~~ | (SEQ ID NO:180) |
| 23G1_heavy_cdr | ~~GYTLTTSYGIS | (SEQ ID NO:368) | WVSFYNG.NTNYAQKLQG | (SEQ ID NO:175) | GYGMDV~~~~~ | (SEQ ID NO:180) |
| 26H5_heavy_cdr | ~~GYTLTTSYGIS | (SEQ ID NO:368) | WISFYNG.NTNYAQKVQG | (SEQ ID NO:176) | GYGMDV~~~~~ | (SEQ ID NO:180) |
| 31D1_heavy_cdr | ~~GYTLTTSYGIS | (SEQ ID NO:368) | WISFYNG.NTNYAQKVQG | (SEQ ID NO:176) | GYGMDV~~~~~ | (SEQ ID NO:180) |
| 27H5_heavy_cdr | ~~GYTLTTSYGIS | (SEQ ID NO:368) | WISVYNG.NTNYAQKFQG | (SEQ ID NO:177) | GYGMDV~~~~~ | (SEQ ID NO:180) |
| 17C2_heavy_cdr | ~~GYSFTTSYGIS | (SEQ ID NO:369) | WVSAYNG.NTNYAQKLQG | (SEQ ID NO:178) | GYGMDV~~~~~ | (SEQ ID NO:180) |
| 25A7_heavy_cdr | ~~GYTFPSYGIS | (SEQ ID NO:370) | WISAYNG.NTNYAEKLQG | (SEQ ID NO:179) | GYYMDV~~~~~ | (SEQ ID NO:387) |
| 3B6_heavy_cdr | ~~GYTFTTSYGIS | (SEQ ID NO:244) | WISTYNG.NTNYAQKVQG | (SEQ ID NO:252) | GYTRDY~~~~~ | (SEQ ID NO:261) |
| 9C9_heavy_cdr | ~~GFTFSSYWMS | (SEQ ID NO:371) | MIKQDGS.EKIYVDSVKG | (SEQ ID NO:343) | E....SNWGFAFDI | (SEQ ID NO:385) |
| 9H6_heavy_cdr | ~~GFTFSRNWMS | (SEQ ID NO:372) | MIKEDGS.EKIYVDSVKG | (SEQ ID NO:347) | E....SNWGFAFDV | (SEQ ID NO:386) |
| 1A12_heavy_cdr | ~~GLTFSNFWMS | (SEQ ID NO:373) | MIKQDGS.NTIYADSVKG | (SEQ ID NO:343) | E....SNWGFAFDI | (SEQ ID NO:385) |
| 23B5_heavy_cdr | ~~GFTFSSYAMN | (SEQ ID NO:374) | TISGSGD.NTIYADSVKG | (SEQ ID NO:365) | KFVLMVYAMLDY~~ | (SEQ ID NO:218) |
| 25G4_heavy_cdr | ~~GFTFSSYAMN | (SEQ ID NO:374) | TISGSGG.NTIYADSVKG | (SEQ ID NO:364) | KFVLMVYAMLDY~~ | (SEQ ID NO:218) |
| 13B5_heavy_cdr | ~~GFTFSSYAMS | (SEQ ID NO:245) | TISGSGG.RTIYADSVKG | (SEQ ID NO:253) | E....VGSPFDY~~ | (SEQ ID NO:262) |
| 22E2_heavy_cdr | ~~GFTFSSYGMH | (SEQ ID NO:188) | LIWNDGS.NKIYADSVKG | (SEQ ID NO:329) | AIAAL.YYYGMDV | (SEQ ID NO:195) |
| 28B12_heavy_cdr | ~~GFTFSSYGMH | (SEQ ID NO:188) | LIWNDGS.NKKYADSVKG | (SEQ ID NO:329) | AIAAL.YYYGMDV | (SEQ ID NO:195) |
| 28D6_heavy_cdr | ~~GFTFSSYGMH | (SEQ ID NO:188) | LIWNDGS.NKKYADSVKG | (SEQ ID NO:329) | AIAAL.YYYGMDV | (SEQ ID NO:195) |
| 16F12_heavy_cdr | ~~GFTFNSYGMH | (SEQ ID NO:375) | LIWSDGS.DEIYADSVKG | (SEQ ID NO:336) | AIAAL.YYYGMDV | (SEQ ID NO:195) |
| 27A6_heavy_cdr | ~~GFTFNSYGMH | (SEQ ID NO:375) | LIWSDGS.DKIYADSVKG | (SEQ ID NO:338) | AIAAL.YYYGMDV | (SEQ ID NO:195) |
| 31G11_heavy_cdr | ~~GFTFRSYGMH | (SEQ ID NO:376) | LIWBDGS.NTIYVDSVKG | (SEQ ID NO:334) | GIAVA.YYYGMDV | (SEQ ID NO:196) |
| 30A4_heavy_cdr | ~~GFTFSSYGMH | (SEQ ID NO:246) | VIWYDGS.DKIYADSVKG | (SEQ ID NO:254) | ETGPLKLYYGMDV | (SEQ ID NO:263) |
| 31B12_heavy_cdr | ~~GFTFSSYGMH | (SEQ ID NO:246) | IIWYDGS.NKIYADSVKG | (SEQ ID NO:255) | R..GGLAARPGGMDV | (SEQ ID NO:264) |
| 31H4_heavy_cdr | ~~GFTFSSYSMN | (SEQ ID NO:247) | SISSSSS.YISYADSVKG | (SEQ ID NO:256) | DYDFWSAYYDAFDV | (SEQ ID NO:265) |
| 27B2_heavy_cdr | GGSISSGGYYWS | (SEQ ID NO:248) | YIYNSGSTY..YNPSLKS | (SEQ ID NO:257) | ED.TAMVPY.FDY~ | (SEQ ID NO:266) |
| 3C4_heavy_cdr | GGSISSDYYWS | (SEQ ID NO:249) | YIYYSGSTY..YNPSLKS | (SEQ ID NO:258) | GG.VTTTYYAMDV~ | (SEQ ID NO:267) |
| 31A4_heavy_cdr | GGSFSA..YYWN | (SEQ ID NO:250) | EINHSGRTD..YNPSLKS | (SEQ ID NO:259) | GQ.LVPFDY~~~ | (SEQ ID NO:268) |
| 13H1_heavy_cdr | GDSVSSNSAAWN | (SEQ ID NO:251) | RTYYRSKWYKNYSVSVKS | (SEQ ID NO:260) | GGFTAAFDY~~~ | (SEQ ID NO:269) |
| Consensus | | | * | | | |

Consensus for Group 1:

```
                TGTSSDVGGYNSVS                        FVSNRPS                      SSYTSTSMV
20D10_light_heavy_cdr                 (SEQ ID NO:158)         (SEQ ID NO:162)                (SEQ ID NO:164)
30B9_light_heavy_cdr     S    G       (SEQ ID NO:158)    S    (SEQ ID NO:162)    TSM         (SEQ ID NO:164)
27E7_light_heavy_cdr     S    G       (SEQ ID NO:158)    S    (SEQ ID NO:162)    TSM         (SEQ ID NO:164)
19H9_light_heavy_cdr     N    G       (SEQ ID NO:159)    S    (SEQ ID NO:162)    S TSM       (SEQ ID NO:165)
21B12_light_heavy_cdr    S    G       (SEQ ID NO:158)    S    (SEQ ID NO:162)    TSM         (SEQ ID NO:164)
23G1_light_heavy_cdr     S    G       (SEQ ID NO:158)    E S  (SEQ ID NO:163)    TSM         (SEQ ID NO:164)
26H5_light_heavy_cdr     S    G       (SEQ ID NO:158)    S    (SEQ ID NO:162)    N TSM       (SEQ ID NO:165)
31D1_light_heavy_cdr     S    G       (SEQ ID NO:158)    S    (SEQ ID NO:162)    N TSM       (SEQ ID NO:164)
27H5_light_heavy_cdr     S    G       (SEQ ID NO:158)    S    (SEQ ID NO:162)    TSM         (SEQ ID NO:164)
17C2_light_heavy_cdr     S    A       (SEQ ID NO:160)    S    (SEQ ID NO:162)    TNM         (SEQ ID NO:166)
25A7_light_heavy_cdr     S    R       (SEQ ID NO:161)    S    (SEQ ID NO:162)    SSV         (SEQ ID NO:167)

CYPLTSYGIS                        WISAYNGNTNYAQKVQG                CYGMDV
20D10_light_heavy_cdr                 (SEQ ID NO:168)                (SEQ ID NO:174)    (SEQ ID NO:180)
30B9_light_heavy_cdr     PLT          (SEQ ID NO:168)    I A          (SEQ ID NO:174)   G (SEQ ID NO:180)
27E7_light_heavy_cdr     SLT          (SEQ ID NO:169)    I A          (SEQ ID NO:174)   G (SEQ ID NO:180)
19H9_light_heavy_cdr     ALT          (SEQ ID NO:170)    H A          (SEQ ID NO:174)   G (SEQ ID NO:180)
21B12_light_heavy_cdr    TLT          (SEQ ID NO:171)    M E          (SEQ ID NO:175)   G (SEQ ID NO:180)
23G1_light_heavy_cdr     TLT          (SEQ ID NO:171)    M E          (SEQ ID NO:175)   G (SEQ ID NO:180)
26H5_light_heavy_cdr     TLT          (SEQ ID NO:171)    H E          (SEQ ID NO:176)   G (SEQ ID NO:180)
31D1_light_heavy_cdr     TLT          (SEQ ID NO:171)    H E          (SEQ ID NO:176)   G (SEQ ID NO:180)
27H5_light_heavy_cdr     TLT          (SEQ ID NO:171)    H A          (SEQ ID NO:177)   G (SEQ ID NO:180)
17C2_light_heavy_cdr     SFT          (SEQ ID NO:172)    M A          (SEQ ID NO:178)   M (SEQ ID NO:181)
25A7_light_heavy_cdr     IFP          (SEQ ID NO:173)    H A          (SEQ ID NO:179)   V (SEQ ID NO:181)
```

Consensus for Group 2:

```
                SGSSSNIGNNFVS                    DYNKRPS                  GTWDSSLSGYV              ATAALYYYYGMDV
22E2_light_heavy_cdr                 (SEQ ID NO:182)            (SEQ ID NO:183)         (SEQ ID NO:185)            (SEQ ID NO:191)
28B12_light_heavy_cdr                (SEQ ID NO:182)    Y       (SEQ ID NO:183)    G    (SEQ ID NO:185)    A AL    (SEQ ID NO:191)
28D6_light_heavy_cdr                 (SEQ ID NO:182)    Y       (SEQ ID NO:183)    G    (SEQ ID NO:185)    A AL    (SEQ ID NO:191)
16F12_light_heavy_cdr                (SEQ ID NO:182)    Y       (SEQ ID NO:183)    A    (SEQ ID NO:186)    A AL    (SEQ ID NO:192)
27A6_light_heavy_cdr                 (SEQ ID NO:182)    Y       (SEQ ID NO:183)    S    (SEQ ID NO:187)    A AL    (SEQ ID NO:193)
31G11_light_heavy_cdr                (SEQ ID NO:182)    S       (SEQ ID NO:184)         (SEQ ID NO:186)      A     (SEQ ID NO:194)

GFTFSSFGME                        LIWNDGSNKYYADSVKG
22E2_light_heavy_cdr                 (SEQ ID NO:188)                (SEQ ID NO:191)    A TAALYYYGMDV (SEQ ID NO:195)
28B12_light_heavy_cdr    S F          (SEQ ID NO:188)    N NK       (SEQ ID NO:191)   A AL          (SEQ ID NO:195)
28D6_light_heavy_cdr     S F          (SEQ ID NO:188)    N NK       (SEQ ID NO:191)   A AL          (SEQ ID NO:195)
16F12_light_heavy_cdr    N F          (SEQ ID NO:189)    S DK       (SEQ ID NO:192)   A AL          (SEQ ID NO:195)
27A6_light_heavy_cdr     DE           (SEQ ID NO:188)    G DE       (SEQ ID NO:193)   A AL          (SEQ ID NO:195)
31G11_light_heavy_cdr    R N          (SEQ ID NO:190)    H NH       (SEQ ID NO:194)   G VA          (SEQ ID NO:196)
```

FIG. 13F

Consensus for Group 3:

```
9H6_light_heavy_cdr     SGSSSNIGSNTVN  (SEQ ID NO:197)              NNRRPS  (SEQ ID NO:199)       AAWDDSLNWV  (SEQ ID NO:201)
1A12_light_heavy_cdr           K       (SEQ ID NO:198)              S R S   (SEQ ID NO:199)       **********
9C9_light_heavy_cdr            K       (SEQ ID NO:198)              R Q L   (SEQ ID NO:200)
                        *********  ***                              **  **

9H6_light_heavy_cdr     GFTFSRYWMS  (SEQ ID NO:202)    NIKQDGSEKYVDSVKG  (SEQ ID NO:205)          ESNWGFAFLV  (SEQ ID NO:207)
1A12_light_heavy_cdr         NF     (SEQ ID NO:203)         Q              (SEQ ID NO:206)              I     (SEQ ID NO:208)
9C9_light_heavy_cdr        F SY     (SEQ ID NO:204)         Q              (SEQ ID NO:206)              I     (SEQ ID NO:208)
                        *   *  ***                     *** *************                            ********** 
```

Consensus for Group 4:

```
23B5_light_heavy_cdr    RASQSISSYLN  (SEQ ID NO:209)     AASSLQS  (SEQ ID NO:211)      QQSYSSPIT  (SEQ ID NO:213)
25G4_light_heavy_cdr           H     (SEQ ID NO:210)        A     (SEQ ID NO:212)           A     (SEQ ID NO:214)
                        *********                        ** ****                       ***** ***

23B5_light_heavy_cdr    GFTFSSYAMN  (SEQ ID NO:215)   TISGSGDNTYADSVKG  (SEQ ID NO:216)    KFVLMVYAMLDY  (SEQ ID NO:218)
25G4_light_heavy_cdr                                          G         (SEQ ID NO:217)    ************
                        **********                     ****** *********
```

FIG. 13G

Group 1 (11 members)

Light chain:

| | LV_CDR1 | SEQ ID NO: | LV_CDR2 | SEQ ID NO: | LV_CDR3 | SEQ ID NO: | H_CDR1 | SEQ ID NO: | H_CDR2 | SEQ ID NO: | H_CDR3 | SEQ ID NO: |
|---|---|---|---|---|---|---|---|---|---|---|---|---|
| | 1 | | | | | | | | 1 | | 58 | |
| CONSENSUS | TGTSSDVGGYNSVS | 305 | EVSNRPS | 306 | SSYTSTSMV | 307 | SYGIS | 308 | WISAYNGNTNYAQKVQG | 309 | GYGMDV | 310 |
| 25A7 | ..R........... | 311 | ....... | 312 | ...S.V... | 313 | ..... | 308 | ................. | 314 | .E.L.. | 315 |
| 17C2 | ..A........... | 316 | ....... | 312 | .....N... | 317 | ..V.. | 308 | ................. | 318 | ...V.. | 315 |
| 21B12 | .............. | 305 | ....... | 312 | .N....... | 319 | ..... | 308 | ..V.F............ | 320 | ....F. | 310 |
| 23G1 | .............. | 305 | ...T... | 321 | .N....... | 319 | ..... | 308 | ..V.F............ | 320 | ...L.. | 310 |
| 19H9 | .....N........ | 322 | ....... | 312 | ......... | 307 | ..... | 308 | .....V........... | 309 | ...... | 310 |
| 27H5 | .............. | 305 | ....... | 312 | ......... | 307 | ..... | 308 | .....V........... | 323 | ...... | 310 |
| 26H5 | .............. | 305 | ....... | 312 | ......... | 307 | ..... | 308 | .......F......... | 324 | ...... | 310 |
| 31D1 | .............. | 305 | ....... | 312 | ......... | 307 | ..... | 308 | .......F......... | 324 | ...... | 310 |
| 27E7 | .............. | 305 | ....... | 312 | ......... | 307 | ..... | 308 | ................. | 309 | ...... | 310 |
| 20D10 | .............. | 305 | ....... | 312 | ......... | 307 | ..... | 308 | ................. | 309 | ...... | 310 |
| 30B9 | .............. | 305 | ....... | 312 | ......... | 307 | ..... | 308 | ................. | 309 | ...... | 310 |

Group 2 (6 members)

Light chain:

| | LV_CDR1 | SEQ ID NO: | LV_CDR2 | SEQ ID NO: | LV_CDR3 | SEQ ID NO: |
|---|---|---|---|---|---|---|
| | 1 | | | | | |
| CONSENSUS | SGSSSNIGNNFVS | 325 | DYNKRPS | 326 | GTWDSSLSGYV | 327 |
| 31G11 | ............. | 325 | .S..... | 331 | ........A.. | 332 |
| 28D6 | ............. | 325 | ....... | 326 | ........... | 327 |
| 28B12 | ............. | 325 | ....... | 326 | ........... | 327 |
| 22E2 | ............. | 325 | ....... | 326 | ........... | 327 |
| 16F12 | ............. | 325 | ....... | 326 | ........A.. | 332 |
| 27A6 | ............. | 325 | ....... | 326 | ........S.. | 337 |

FIG. 13H

Group 2, continued
Heavy chain:

| | H_CDR1 | SEQ ID NO: | H_CDR2 | SEQ ID NO: | H_CDR3 | SEQ ID NO: |
|---|---|---|---|---|---|---|
| CONSENSUS | SFGMH | 328 | LIWNDGSNKYYADSVKG | 329 | AIAALYYYYGMDV | 330 |
| 31G11 | .Y... | 333 | ...H....T..V. | 334 | G..VA........ | 335 |
| 28D6 | ..... | 328 | ................. | 329 | ............. | 330 |
| 28B12 | ..... | 328 | ................. | 329 | ............. | 330 |
| 22E2 | ..... | 328 | ....S....DE..... | 336 | ............. | 330 |
| 16F12 | ..... | 328 | ....S....D...... | 338 | ............. | 330 |
| 27A6 | ..... | 328 | ................. | 329 | ............. | 330 |

Group 3 (3 members)

| | LV_CDR1 | SEQ ID NO: | LV_CDR2 | SEQ ID NO: | LV_CDR3 | SEQ ID NO: | H_CDR1 | SEQ ID NO: | H_CDR2 | SEQ ID NO: | H_CDR3 | SEQ ID NO: |
|---|---|---|---|---|---|---|---|---|---|---|---|---|
| CONSENSUS | SGSSSNIGSKTVN | 339 | SNNRRPS | 340 | AAWDDSLNWV | 341 | YWMS | 342 | NIKQDGSEKYYVDSVKG | 343 | ESNWGFAFDI | 344 |
| 9H6 | .........N... | 345 | ....... | 340 | .......... | 341 | R... | 346 | ....H............ | 347 | .......... | 348 |
| 9C9 | ............. | 339 | R..Q..L | 349 | .......... | 341 | S... | 350 | ................. | 343 | .........V | 344 |
| 1A12 | ............. | 339 | ....... | 340 | .......... | 341 | NF.. | 351 | ................. | 343 | .......... | 344 |

Group 4 (2 members)

| | KV_CDR1 | SEQ ID NO: | KV_CDR2 | SEQ ID NO: | KV_CDR3 | SEQ ID NO: |
|---|---|---|---|---|---|---|
| CONSENSUS | RASQSIS YLN | 352 | AA SLQS | 353 | QQSYS PIT | 354 |
| 25G4 | .......I.. | 355 | ..A.... | 356 | .....A... | 357 |
| 23B5 | .......S.. | 358 | ..S.... | 359 | .....S... | 360 |

| | H_CDR1 | SEQ ID NO: | H_CDR2 | SEQ ID NO: | H_CDR3 | SEQ ID NO: |
|---|---|---|---|---|---|---|
| CONSENSUS | SYAMN | 361 | TISGSSG NTYYADSVKG | 362 | KFVLMVYAMLDY | 363 |
| 25G4 | ..... | 361 | ...............G.. | 364 | ............ | 363 |
| 23B5 | ..... | 361 | ...............D.. | 365 | ............ | 363 |

FIG. 13J

| Chain Name | V | D | J | FR1 | CDR1 | FR2 | SEQ ID NO: |
|---|---|---|---|---|---|---|---|
| 26E10.1 | Germline | | | QSALTQPASVSGSPGQSITISC | TGTSSDVGGYNYVS | WYQQHPGKAPKLMIY | 14 |
| 26E10 | V1-4 | | JL2 | ---------------------- | -------------- | --------------- | 270 |
| 17C2.1 | V1-4 | | JL2 | ---------------------- | -----S-------- | --------------- | 23 |
| 17C2 | V1-4 | | JL2 | -----F---------------- | -----S-------- | ------------R-- | 271 |
| | V1-4 | | JL2 | ---------------------- | ---A--S------- | ------------R-- | 24 |
| 9C9.1 | Germline | | | QSVLTQPPSASGTPGQRVTISC | SGSSSNIGSNTVN | WYQQLPGTAPKLLIY | 29 |
| 9C9.2 | V1-16 | | JL3 | -------P-------------- | ------------- | --------------- | 272 |
| | V1-16 | | JL3 | -------P----------F--- | ------------- | --------------- | 273 |
| 31A4.2 | Germline | | | SYELTQPPSVSVSPGQTASITC | SGDKLGDKYAC | WYQQKPGQSPVLVIY | 274 |
| | V2-1 | | JL2 | ----------------R----- | ----------- | --------------- | 275 |
| 25A7.1 | Germline | | | SYELTQPPSVSVSPGQTASITC | SGDKLGDKYAC | WYQQKPGQSPVLVIY | 276 |
| | V2-1 | | JL2 | ----I----------------- | ----------- | ---R--------I-- | 277 |

FIG. 15A

| Chain Name | CDR2 | FR3 | CDR3 | FR4 | SEQ ID NO: |
|---|---|---|---|---|---|
| 26E10.1 | EVSNRPS | GVSNRFSGSKSGNTASLTISGLQAEDEADYYC | SSYTSSS#V | FGGGTKLTVL | 14 |
| 26E10 | ------- | --F----------------------------- | N----T-M- | ---------- | 270 |
| 17C2.1 | ------- | -------------------------------- | N----T-M- | ---------- | 23 |
| 17C2 | ------- | -------------------------------- | ----TNM-- | ---------- | 271 |
|  |  |  |  |  | 24 |
| 9C9.1 | SNNQRPS | GVPDRFSGSKSGTSASLAISGLQSEDEADYYC | AAWDDSLN#V | FGGGTKLTVL | 29 |
| 9C9.2 | --R---- | -------------------------------- | -------W- | ---------- | 272 |
|  | --R---- |  | -------W- |  | 273 |
| 31A4.2 | QDSKRPS | GIPERFSGSNSGNTATLTISGTQAMDEADYYC | QAWDSSTVV | FGGGTKLTVL | 274 |
|  | -NT-W-L | -----K----V-------------------- | ---------- |  | 275 |
| 25A7.1 | QDSKRPS | GIPERFSGSNSGNTATLTISGTQAMDEADYYC | QAWDSSTAVV | FGGGTKLTVL | 276 |
|  | --T---- | -------------------------------- | ---------- | ---------- | 277 |

FIG. 15B

| Chain Name | V | D | J | FR1 | CDR1 | FR2 | SEQ ID NO: |
|---|---|---|---|---|---|---|---|
| Germline | | | | QVQLVQSGAEVKKPGASVKVSCKAS | GYTFTSYGIS | WVRQAPGQGLEWMG | 47 |
| 26E10.1 | VH1-18 | | JH6B | ------------------------ | --L------- | -------------- | 49 |
| 26E10 | VH1-18 | | JH6B | ------------------------ | --L------- | -------------- | 49 |
| 17C2.1 | VH1-18 | | JH6B | ------------------------ | --S------- | -------------- | 57 |
| 17C2 | VH1-18 | | JH6B | ------------------------ | --S------- | -------------- | 57 |
| Germline | | | | EVQLVESGGGLVQPGGSLRLSCAAS | GFTFSSYWMS | WVRQAPGKGLEWVA | 63 |
| 9C9.1 | VH3-7 | D7-27 | JH3B | -----------------VV----- | ---------- | -------------- | 64 |
| 9C9.2 | VH3-7 | D7-27 | JH3B | -----------------VV----- | ---------- | -------------- | 401 |
| Germline | | | | QVQLQESGPGLVKPSETLSLTCTVS | GGSISSYYWS | WIRQPPGKGLEWIG | 400 |
| 25A7.1 | VH4-59 | D6-19 | JH4B | ------------------------ | ----T----- | -------------- | 278 |

FIG. 15C

| Chain Name | CDR2 | FR3 | CDR3 | FR4 | SEQ ID NO: |
|---|---|---|---|---|---|
| 26E10.1 | WISAYNGNTNYAQKLQG | RVTMTTDTSTSTAYMELRSLRSDDTAVYYCAR | #YGMDV | WGQGTTVTVSS | 47 |
| 26E10 | -V-F------------- | -G------P---------------------- | G----- | ----------- | 49 |
| 17C2.1 | -V-F------------- | -G------P---------------------- | G----- | ----------- | 49 |
| 17C2.2 | -V---------F----- | -------------------------------- | G-V--- | ----------- | 57 |
|  | -V---------F----- | -------------------------------- | G-V--- | ----------- | 57 |
| 9C9.1 | NIKQDGSEKYYVDSVKG | RETISRDNAKNSLYLQMNSLRAEDTAVYYCAR | ##NWG#AFDI | WGQGTMVTVSS | 63 |
| 9C9.2 | ----------------- | -------------------------------- | ES----F--- | ----------- | 64 |
|  | ----------------- | -------------------------------- | ES----F--- | ----------x | 401 |
| 25A7.1 | YIYYSGSTNYNPSLKS | RVTISVDTSKNQFSLKLSSVTAADTAVYYCAR | ##YSSGW##FDY | WGQGTLVTVSS | 400 |
|  | ---------------- | -------------------------------- | GS-----FE--- | ----------- | 278 |

FIG. 15D 1. 31H4
2. ProCat
3. VD
4. ProCat + 31H4
5. VD + 31H4
6. Std

1. Std
2. 21B12
3. ProCat
4. VD
5. ProCat + 21B12
6. VD + 21B12

21B12

Light Chain

ESALTQPASV SGSPGQSITI SCTGTSSDVG GYNSVSWYQQ HPGKAPKLMI YEVSNRPSGV SNRFSGSKSG
NTASLTISGL QAEDEADYYC NSYTSTSMVF GGGTKLTVLG QPKAAPSVTL FPPSSEELQA NKATLVCLIS
DFYPGAVTVA WKADSSPVKA GVETTTPSKQ SNNKYAASSY LSLTPEQWKS HRSYSCQVTH EGSTVEKTVA
PTECS    (SEQ ID NO:297)

Heavy Chain

EVQLVQSGAE VKKPGASVKV SCKASGYTLT SYGISWVRQA PGQGLEWMGW VSFYNGNTNY AQKLQGRGTM
TTDPSTSTAY MELRSLRSDD TAVYYCARGY GMDVWGQGTT VTVSSASTKG PSVFPLAPSS KSTSGGTAAL
GCLVKDYFPE PVTVSWNSGA LTSGVHTFPA VLQSSGLYSL SSVVTVPSSS LGTQTYICNV NHKPSNTKVD
KKVEPKSCAA DEVDHHHHHH (SEQ ID NO:298)

31H4

Light Chain

ESVLTQPPSV SGAPGQRVTI SCTGSSSNIG AGYDVHWYQQ LPGTAPKLLI SGNSNRPSGV PDRFSGSKSG
TSASLAITGL QAEDEADYYC QSYDSSLSGS VFGGGTKLTV LGQPKAAPSV TLFPPSSEEL QANKATLVCL
ISDFYPGAVT VAWKADSSPV KAGVETTTPS KQSNNKYAAS SYLSLTPEQW KSHRSYSCQV THEGSTVEKT
VAPTECS  (SEQ ID NO:299)

Heavy Chain

EVQLVESGGG LVKPGGSLRL SCAASGFTFS SYSMNWVRQA PGKGLEWVSS ISSSSSYISY ADSVKGRFTI
SRDNAKNSLY LQMNSLRAED TAVYFCARDY DFWSAYYDAF DVWGQGTMVT VSSASTKGPS VFPLAPSSKS
TSGGTAALGC LVKDYFPEPV TVSWNSGALT SGVHTFPAVL QSSGLYSLSS VVTVPSSSLG TQTYICNVNH
KPSNTKVDKK VEPKSCAADE VDHHHHHH (SEQ ID NO:300)

31A4

Light Chain

ALQSVLTQPP SASGTPGQRV TISCSGSSSN IGSNTVNWYQ QLPGTAPKLL IYSNNQRPSG
VPDRFSGSKS GTSASLAISG LQSEDEADYY CAVWDDSLNG WVFGGGTKLT VLGQPKAAPS
VTLFPPSSEE LQANKATLVC LISDFYPGAV TVAWKADSSP VKAGVETTTP SKQSNNKYAA
SSYLSLTPEQ WKSHRSYSCQ VTHEGSTVEK TVAPTECS (SEQ ID NO:301)

Heavy Chain

QVQLQQWGAG LLKPSETLSL TCAVYGGSFS AYYWNWIRQP PGKGLEWIGE INHSGRTDYN PSLKSRVTIS
VDTSKKQFSL KLNSVTAADT AVYYCARGQL VPFDYWGQGT LVTVSSASTK GPSVFPLAPS SKSTSGGTAA
LGCLVKDYFP EPVTVSWNSG ALTSGVHTFP AVLQSSGLYS HSSVVTVPSS SLGTQTYICN VNHKPSNTKV
DKKVEPKSCA ADEVDHHHHH H (SEQ ID NO:302)

| | | | | | | | BIN 1 | | | | | | | |
|---|---|---|---|---|---|---|---|---|---|---|---|---|---|---|
| | bead region | 9 | 12 | 21 | 38 | 45 | 60 | 74 | 84 | 20 | 23 | 42 | 92 | 96 |
| | clone | 01A12.2 | 03B6.1 | 09C9.1 | 17C2.1 | 21B12.2 | 23G1.1 | 25G4.1 | 26E10.1 | 11H4.1 | 11H8.1 | 19H9.2 | 26H5.1 | 27E7.1 |
| BIN 1 | 01A12.2 | 41 | 34 | 108 | 43 | 70 | 25 | 26 | 26 | 15 | 22 | -1 | 40 | -27 |
| | 03B6.1 | 60 | 69 | 107 | 44 | 73 | 49 | 53 | 49 | 60 | 69 | 5 | 41 | 17 |
| | 09C9.1 | 77 | 49 | 89 | 27 | 88 | 25 | 38 | 42 | 74 | 39 | -18 | 22 | 1 |
| | 17C2.1 | 43 | 34 | 135 | -2 | 50 | 14 | 47 | 12 | 53 | 75 | -4 | 22 | -20 |
| | 21B12.2 | 37 | 42 | 125 | 2 | 96 | 21 | 49 | 39 | 38 | 9 | -19 | 50 | -6 |
| | 23G1.1 | 29 | 41 | 114 | -4 | 62 | 26 | 35 | 46 | 39 | 37 | -13 | 34 | -26 |
| | 25G4.1 | 46 | 59 | 91 | 13 | 61 | 10 | 35 | 5 | 34 | 42 | 17 | 28 | 20 |
| | 26E10.1 | 30 | 50 | 73 | -5 | 61 | -10 | 22 | 26 | -5 | 17 | -36 | 9 | -33 |
| | 11H4.1 | 49 | 72 | 135 | 64 | 93 | 51 | 34 | 49 | 40 | 52 | 19 | 58 | -3 |
| | 11H8.1 | 37 | 49 | 118 | 27 | 72 | 39 | 33 | 30 | 34 | 46 | -27 | 41 | 4 |
| | 19H9.2 | 30 | 15 | 103 | 58 | 39 | 20 | 28 | 23 | 5 | 26 | -51 | 25 | 85 |
| | 26H5.1 | 39 | 48 | 133 | 1 | 84 | 46 | 33 | 41 | 34 | 24 | -36 | 59 | -50 |
| | 27E7.1 | 19 | 25 | 92 | 10 | 44 | 16 | 15 | 1 | 27 | 13 | 8 | 5 | -115 |
| | 27H5.1 | 29 | 49 | 170 | -12 | 153 | 11 | 49 | 73 | 69 | -13 | -26 | 68 | -47 |
| | 30B9.1 | 53 | 39 | 156 | 0 | 194 | 57 | 106 | 53 | 72 | 35 | -20 | 62 | 8 |
| | 02B5.1 | 42 | 67 | 130 | 64 | 126 | 85 | 39 | 83 | 47 | 62 | 15 | 80 | 23 |
| | 23B5.1 | 5 | 33 | 53 | -29 | 17 | -16 | -16 | -17 | 4 | 17 | -55 | -14 | -75 |
| BIN 1.1 | 27B2.6 | 48 | 38 | 133 | 36 | 75 | 11 | 54 | 34 | 21 | 21 | 5 | 37 | 35 |
| | 09H6.1 | 53 | 110 | 118 | | | 73 | | | 75 | 63 | 120 | | 121 |
| BIN 2 | 27B2.1 | 152 | 161 | 258 | 107 | 194 | | | | | 224 | 93 | 141 | 96 |
| | 27B2.5 | 130 | 115 | 197 | 85 | 153 | 97 | 92 | 94 | | 177 | 93 | 113 | 51 |
| | 12H11.1 | 30 | 46 | 89 | 35 | 70 | 26 | 36 | 26 | 41 | 42 | -4 | 57 | -11 |
| BIN 3 | 16F12.1 | | | | | | | | | | | | | |
| | 22H2.1 | | | | | | | | | | | | | |
| | 27A6.1 | | | | | | | | | | | | | |
| | 28B12.1 | | | | | | | | | | | | | |
| | 28D5.1 | | | | | | | | | | | | | |
| | 31G11.1 | | | | | | | | | | | | | |
| | 31H4.1 | | | | | | | | | | | | | |
| BIN 3.1 | 08A1.2 | 836 | 584 | 330 | | | | | | | | | | |
| | 08A3.1 | | | 398 | | | | | | | | | | |
| | 11F1.1 | | | 347 | | | | | | | | | | |
| BIN 4 non-comp | 11G1.5 | | | | | | | | | | | | | |
| | 03C4.1 | | | 378 | | | | | | | | | | |
| D | 30A4.1 | 75 | 62 | 125 | 60 | 107 | 38 | 48 | 42 | 70 | 59 | -17 | 45 | 8 |
| | 13B5.1 | | | | | | | | | | | | | |
| | 13H1.1 | | | | | | | | | | | | | |
| | 31A4.1 | | | | | | | | | | | | | |
| | 31B12.1 | | | | | | | | | | | | | |
| LOW SIGNAL | 05H5 | 65 | 93 | 103 | 102 | 135 | 107 | 57 | 114 | 65 | 87 | 63 | 110 | 45 |
| | 20A5 | 53 | 52 | 120 | 32 | 67 | 32 | 48 | 56 | 61 | 77 | 4 | 52 | -16 |
| | 20E5 | 56 | 54 | 129 | 44 | 63 | 19 | 39 | 24 | 71 | 64 | -4 | 37 | 3 |
| | 22B11 | 48 | 56 | 127 | 41 | 43 | 20 | 49 | 34 | 51 | 41 | -20 | 20 | -12 |
| | 24B9 | 62 | 59 | 116 | 34 | 63 | 32 | 73 | 37 | 60 | 65 | -22 | 42 | -34 |
| | 24F7 | 72 | 80 | 127 | 81 | 105 | 59 | 38 | 62 | 70 | 71 | 17 | 81 | 20 |
| | 30F1 | 34 | 56 | 102 | 30 | 78 | 24 | 35 | 35 | 77 | 50 | -6 | 45 | -5 |
| | huIgG | 94 | 155 | 163 | -46 | 57 | 22 | -5 | 18 | 31 | 87 | -57 | 8 | -71 |

|  | huIgG controls | | |
|---|---|---|---|
| 73 | 17 | 98 | 54 |
| 3CF1 | huIgG | huIgG | huIgG |
|  | -81 | -63 | -1 |
| 14 | 55 | -4 | -37 |
| 17 | 60 | 7 | 13 |
| 0 | -65 | -4 | 14 |
| 7 | 17 | 19 | 3 |
| 19 | -5 | -8 | -41 |
| 2 | 17 | 20 | 21 |
| -3 | -46 | -10 | 53 |
| 4 | -23 | -33 | -52 |
| 3 | 21 | 27 | 2 |
| -14 | -111 | -93 | -2 |
| 3 | -36 | 19 | -51 |
| -32 | -30 | -17 | -109 |
| -16 | 74 | 19 | -17 |
| 3 | 27 | 1 | 51 |
| 17 | 24 | -35 | -61 |
| -13 | -34 | -80 | -4 |
| 2 | -6 | -1 | 24 |
| 34 | 21 | 38 | 17 |
| 14 | -7 | 19 | -56 |
| 0 | 97 | 49 | -48 |
| 6 | -52 | -21 | -40 |
| -117 | -264 | -189 | -248 |
| 15 | 1 | -20 | 36 |
| 17 | -78 | -47 | -5 |
| 18 | -33 | -53 | -79 |
| 29 | 57 | 22 | 45 |
| 9 | 21 | -1 | 50 |
| 25 | 25 | 23 | 2 |
| 3 | -5 | -13 | 21 |
| 6 | -2 | 36 | 50 |
| 4 | 22 | -21 | 55 |
| 12 | 19 | 23 | 7 |
| 12 | 40 | 34 | 35 |
| 3 | 13 | -14 | 35 |
| -3 | 20 | 28 | -7 |
| -4 | -46 | -45 | -26 |
| 36 | -7 | 30 | -27 |
| 15 | 1 | 31 | 26 |
| 4 | -4 | -11 | -8 |
| 2 | -36 | -17 | 3 |
| -1 | -75 | -24 | 14 |
| -5 | -47 | -14 | -19 |
| -3 | -16 | -3 | 25 |
| 0 | 19 | 23 | 48 |
| -4 | -42 | -89 | -20 |
| 30 | 33 | 4 | 38 |

| FIG. 23A | FIG. 23B | FIG. 23C | FIG. 23D |

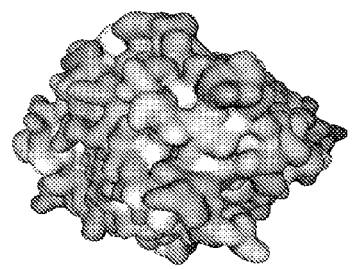
FIG. 25D
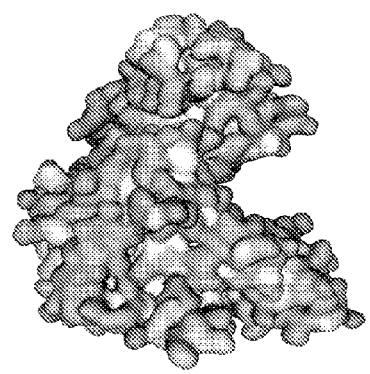
FIG. 25C
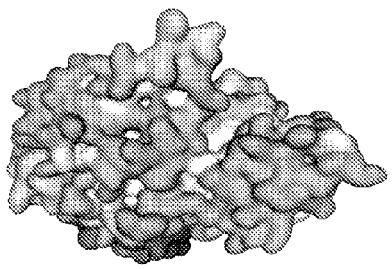
FIG. 25B
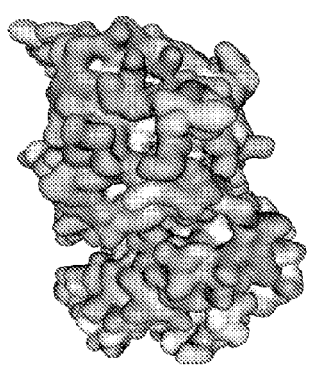
FIG. 25F
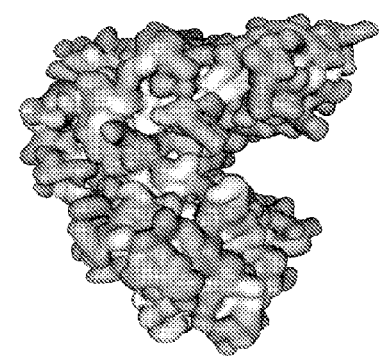
FIG. 25A
FIG. 25E

```
                  1------------------------------------------------50
PCSK9parent    (1) QEDEDGDYEELVLALRSEEDGLAEAPEHGTTATFHRCAKDPWRLPGTYVV
PCSK9mutants   (1) RRRRRRRRRRRRLRRRRRRRRRRRRRRHRRRRRRFRRCRRRPWRRPGRYVV
                  51--- pro domain ---------------------------------100
PCSK9parent   (51) VLKEETHLSQSERTARRLQAQAARRGYITKILHVFHGLLPGFLVKMSGDL
PCSK9mutants  (51) VLRRRRRRSRSRETAEELQRRAREEGRRTKIRRRFRGLLPGFLVRMRRRL
                  101------------------|===========================150
PCSK9parent  (101) LELALKLPHVDYIEEDSSVFAQSIEWNLERITPPRYRADEYQPEDGGSLV
PCSK9mutants (101) RRLARRLPRVRYIEEDSSVFRQRIFRNRREIRPPRYRARRRRPERGGRRV
                  151==============================================200
PCSK9parent  (151) EVYLLDTSIQSLHREIEGRVMVTDFENVHEEDGTRFHRQASKCDSHGTHL
PCSK9mutants (151) EVYLLDTRIRRRHEEIRGRVRRRRFRRRRRRRRREEERRRRCDRRGTHL
                  201==============================================250
PCSK9parent  (201) AGVVSGRDAGVAKGASMRSLRVLNCQGKGTVSGTLIGLEFIRKSQLVQPV
PCSK9mutants (201) AGVVSGERAGVARRARMRSLEVLNCRGRGRVSGTLIGLERIERRRRRRR
                  251================ catalytic domain ==========300
PCSK9parent  (251) GPLVVLLPLAGGYSRVLNAACQRLARAGVVLVTAAGNFRDDACLYSPASA
PCSK9mutants (251) RPLVVLLPLAGRYSEVLNRACRRLAERGVVLVTAAGNFRDDACRYSPARA
                  301==============================================350
PCSK9parent  (301) PEVITVGATNAQDQPVTLGTLGTNFGRCVDLFAPGEDIIGASSDCSTGFV
PCSK9mutants (301) PEVITVGATNRRRRPVRRGRRGTNFGRCVDLFAPGRRIIGASSRCSRGRR
                  351==============================================400
PCSK9parent  (351) SQSGTSQAAAHVAGIAAMMLSAEHELTLAELRQRLIHFSAKDVINEAWFP
PCSK9mutants (351) RRSGTSQAAAHVAGIAARMLRRRERLRRARLRQELRRRSRRRRIRRRRFP
                  401==============|-------------------------------450
PCSK9parent  (401) EDQRVLTPNLVAALPPSTHGAGWQLFCRTVWSAHSGHTRMATAIARCAHD
PCSK9mutants (401) RRRERLTPRLVARLPERRRRRGRRLFCRTVWSRRSGHRERARAIAECAHR
                  451----------------------------------------------500
PCSK9parent  (451) EELLSCSSFSRSGKRRGERMEAQGGKLVCRAHNAFGGEGVYAIARCCLLP
PCSK9mutants (451) EELLSCSSFSRSGKRRGERMERQGGKLVCRAHNARRGRGVYAIARCCLLP
                  501-------------- v domain ------------------550
PCSK9parent  (501) QANCSVHTAPPAEASMGTRVHCHQQGHVLTGCSSHWEVEDLGTHKPHVLR
PCSK9mutants (501) QARCSVHRAPPARRRGTEVRCRRRGHVLTGCSSHWRRRDRGTRKPERLR
                  551----------------------------------------------600
PCSK9parent  (551) PRGQPNQCVGHREASIHASCCHAPGLECKVKEHGIPAHQEQVTVACEEGW
PCSK9mutants (551) PEGRPRQCVGHREASIHASCCHAPGLECRRRRRRIPAHRERVTVRCRRGW
                  601------------------------------------------650
PCSK9parent  (601) TLTGCSALPGTSHVLGAYAVDNTCVVRSRDVSTTGSTSEEAVTAVAICCR
PCSK9mutants (601) TLTGCSALPGTSHVLGAYARDNTCVVRSEDRRRRRRRRERVTAVAICCE
                  651---------|            680
PCSK9parent  (651) SRHLAQASQELQGSSDYKDDDKHHHHHHHH   (SEQ ID NO:303)
PCSK9mutants (651) SEHLAQASQELQGSSDYKDDDKHHHHHHHH   (SEQ ID NO:304)
```

FIG. 26

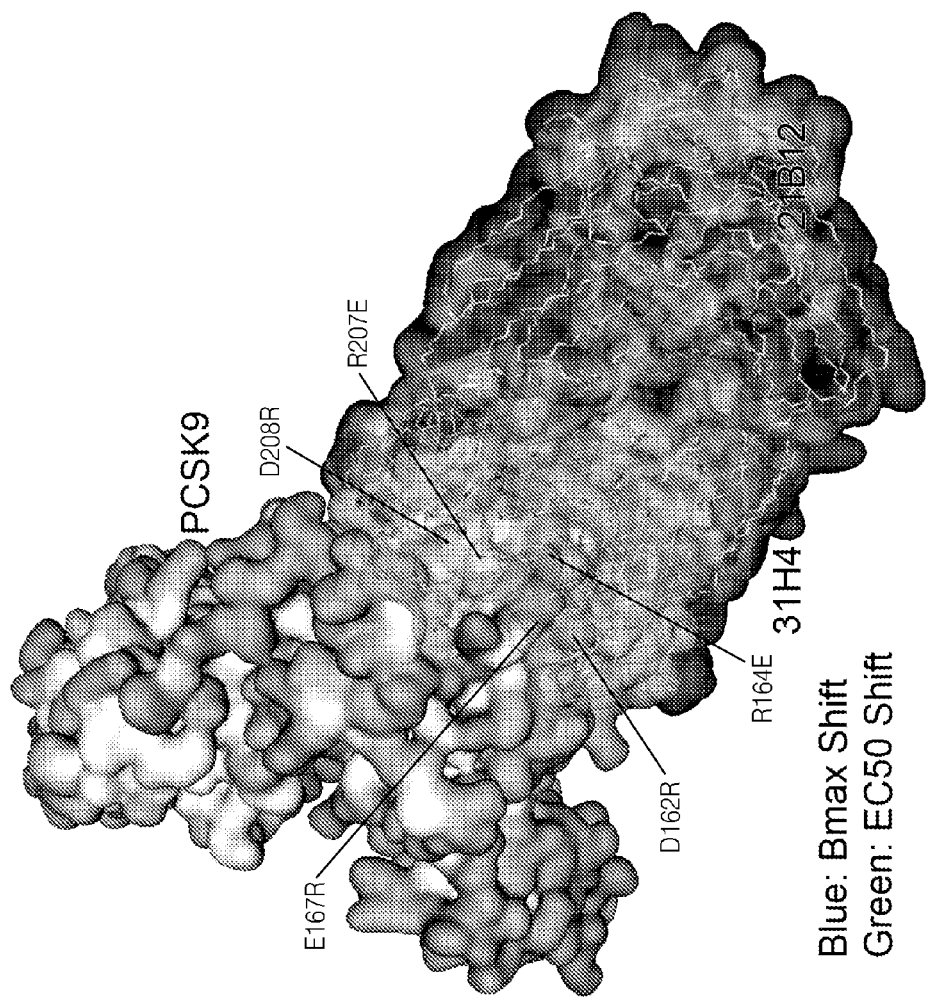

SEQUENCE LISTING

```
<160> NUMBER OF SEQ ID NOS: 575

<210> SEQ ID NO 1
<211> LENGTH: 662
<212> TYPE: PRT
<213> ORGANISM: Homo sapiens

<400> SEQUENCE: 1

Gln Glu Asp Glu Asp Gly Asp Tyr Glu Glu Leu Val Leu Ala Leu Arg
  1               5                  10                  15

Ser Glu Glu Asp Gly Leu Ala Glu Ala Pro Glu His Gly Thr Thr Ala
             20                  25                  30

Thr Phe His Arg Cys Ala Lys Asp Pro Trp Arg Leu Pro Gly Thr Tyr
         35                  40                  45

Val Val Val Leu Lys Glu Glu Thr His Leu Ser Gln Ser Glu Arg Thr
     50                  55                  60

Ala Arg Arg Leu Gln Ala Gln Ala Ala Arg Arg Gly Tyr Leu Thr Lys
 65                  70                  75                  80

Ile Leu His Val Phe His Gly Leu Leu Pro Gly Phe Leu Val Lys Met
                 85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
    130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
```

```
                195                 200                 205
Ala Gly Val Ala Lys Gly Ala Ser Met Arg Ser Leu Arg Val Leu Asn
    210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
                260                 265                 270

Arg Leu Ala Arg Ala Gly Val Val Leu Val Thr Ala Ala Gly Asn Phe
            275                 280                 285

Arg Asp Asp Ala Cys Leu Tyr Ser Pro Ala Ser Ala Pro Glu Val Ile
        290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
                340                 345                 350

Ser Gly Thr Ser Gln Ala Ala Ala His Val Ala Gly Ile Ala Ala Met
            355                 360                 365

Met Leu Ser Ala Glu Pro Glu Leu Thr Leu Ala Glu Leu Arg Gln Arg
        370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                405                 410                 415

Ser Thr His Gly Ala Gly Trp Gln Leu Phe Cys Arg Thr Val Trp Ser
                420                 425                 430

Ala His Ser Gly Pro Thr Arg Met Ala Thr Ala Ile Ala Arg Cys Ala
            435                 440                 445

Pro Asp Glu Glu Leu Leu Ser Cys Ser Ser Phe Ser Arg Ser Gly Lys
        450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
                500                 505                 510

Glu Ala Ser Met Gly Thr Arg Val His Cys His Gln Gln Gly His Val
            515                 520                 525

Leu Thr Gly Cys Ser Ser His Trp Glu Val Glu Asp Leu Gly Thr His
        530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                565                 570                 575

Glu Cys Lys Val Lys Glu His Gly Ile Pro Ala Pro Gln Gly Gln Val
                580                 585                 590

Thr Val Ala Cys Glu Glu Gly Trp Thr Leu Thr Gly Cys Ser Ala Leu
            595                 600                 605

Pro Gly Thr Ser His Val Leu Gly Ala Tyr Ala Val Asp Asn Thr Cys
        610                 615                 620
```

```
Val Val Arg Ser Arg Asp Val Ser Thr Thr Gly Ser Thr Ser Glu Glu
625                 630                 635                 640

Ala Val Thr Ala Val Ala Ile Cys Cys Arg Ser Arg His Leu Ala Gln
                645                 650                 655

Ala Ser Gln Glu Leu Gln
            660

<210> SEQ ID NO 2
<211> LENGTH: 2076
<212> TYPE: DNA
<213> ORGANISM: Homo sapiens

<400> SEQUENCE: 2
atgggcaccg tcagctccag gcggtcctgg tggccgctgc cactgctgct gctgctgctg      60
ctgctcctgg gtcccgcggg cgcccgtgcg caggaggacg aggacggcga ctacgaggag     120
ctggtgctag ccttgcgctc cgaggaggac ggcctggccg aagcacccga gcacggaacc     180
acagccacct ccaccgctg cgccaaggat ccgtggaggt tgcctggcac ctacgtggtg     240
gtgctgaagg aggagaccca cctctcgcag tcagagcgca ctgcccgccg cctgcaggcc     300
caggctgccc gccggggata cctcaccaag atcctgcatg tcttccatgg ccttcttcct     360
ggcttcctgg tgaagatgag tggcgacctg ctggagctgg ccttgaagtt gccccatgtc     420
gactacatcg aggaggactc ctctgtcttt gcccagagca tcccgtggaa cctggagcgg     480 attcccctc gcggtaccg gcggatgaa taccagcccc ccgacggagg cagcctggtg     540
gaggtgtatc tcctagacac cagcatacag agtgaccacc gggaaatcga gggcagggtc     600
atggtcaccg acttcgagaa tgtgcccgag gaggacggga cccgcttcca cagacaggcc     660
agcaagtgtg acagtcatgg caccccctg gcaggggtgg tcagcggccg ggatgccggc     720
gtggccaagg gtgccagcat cgcagcctg cgcgtgctca actgccaagg aagggcacg     780 gttagcggca ccctcatagg cctggagttt attcggaaaa gccagctggt ccagcctgtg     840
gggccactgg tggtgctgct gccctggcg ggtgggtaca gccgcgtcct caacgccgcc     900
tgccagcgcc tggcgaggc tggggtcgtg ctggtcaccg ctgccggcaa cttccgggac     960
gatgcctgcc tctactcccc agcctcagct cccgaggtca tcacagttgg ggccaccaat    1020
gcccaggacc agccggtgac cctggggact ttggggacca cttttggccg ctgtgtggac    1080
ctctttgccc aggggagga catcattggt gcctccagcg actgcagcac ctgctttgtg    1140
tcacagagtg ggacatcaca ggctgctgcc cacgtggctg gcattgcagc catgatgctg    1200
tctgccgagc cggagctcac cctggccgag ttgaggcaga gactgatcca cttctctgcc    1260
aaagatgtca tcaatgaggc ctggttccct gaggaccagc gggtactgac ccccaacctg    1320
gtggccgccc tgccccccag cacccatggg gcaggttggc agctgttttg caggactgtg    1380
tggtcagcac actcggggcc tacacggatg ccacagcca tcgcccgctg cgccccagat    1440
gaggagctgc tgagctgctc cagtttctcc aggagtggga gcggcggggg cgagcgcatg    1500
gaggcccaag ggggcaagct ggtctgccgg gcccacaacg cttttggggg tgagggtgtc    1560
tacgccattg ccaggtgctg cctgctaccc caggccaact gcagcgtcca cacagctcca    1620
ccagctgagg ccagcatggg gacccgtgtc cactgccacc aacagggcca cgtcctcaca    1680
ggctgcagct cccactggga ggtggaggac cttggcaccc acaagccgcc tgtgctgagg    1740
ccacgaggtc agcccaacca gtgcgtgggc acagggagg ccagcatcca cgcttcctgc    1800
tgccatgccc caggtctgga atgcaaagtc aaggagcatg gaatcccggc ccctcagggg    1860
```

```
caggtgaccg tggcctgcga ggagggctgg accctgactg gctgcagcgc cctccctggg    1920
acctcccacg tcctgggggc ctacgccgta gacaacacgt gtgtagtcag gagccgggac    1980
gtcagcacta caggcagcac cagcgaagag gccgtgacag ccgttgccat ctgctgccgg    2040
agccggcacc tggcgcaggc ctcccaggag ctccag                              2076
```

<210> SEQ ID NO 3
<211> LENGTH: 692
<212> TYPE: PRT
<213> ORGANISM: Homo sapiens

<400> SEQUENCE: 3

```
Met Gly Thr Val Ser Ser Arg Arg Ser Trp Trp Pro Leu Pro Leu Leu
 1               5                  10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335
```

Gly Ala Thr Asn Ala Gln Asp Gln Pro Val Thr Leu Gly Thr Leu Gly
                340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
                420                 425                 430

Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
    515                 520                 525

Leu Pro Gln Ala Asn Cys Ser Val His Thr Ala Pro Pro Ala Glu Ala
530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
    595                 600                 605

Lys Val Lys Glu His Gly Ile Pro Ala Pro Gln Gly Gln Val Thr Val
610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
    675                 680                 685

Gln Glu Leu Gln
    690

<210> SEQ ID NO 4
<211> LENGTH: 112
<212> TYPE: PRT
<213> ORGANISM: Homo sapiens

<400> SEQUENCE: 4

Asp Ile Val Met Thr Gln Ser Pro Leu Ser Leu Pro Val Thr Pro Gly

-continued

```
                1               5                   10                  15
        Glu Pro Ala Ser Ile Ser Cys Arg Ser Ser Gln Ser Leu Leu His Ser
                        20                  25                  30

Asn Gly Tyr Asn Tyr Leu Asp Trp Tyr Leu Gln Lys Pro Gly Gln Ser
                        35                  40                  45

Pro Gln Leu Leu Ile Tyr Leu Gly Ser Asn Arg Ala Ser Gly Val Pro
                50                  55                  60

Asp Arg Phe Ser Gly Ser Gly Ser Gly Thr Asp Phe Thr Leu Lys Ile
        65                  70                  75                  80

Ser Arg Val Glu Ala Glu Asp Val Gly Val Tyr Tyr Cys Met Gln Ala
                        85                  90                  95

Leu Gln Thr Pro Phe Thr Phe Gly Pro Gly Thr Lys Val Asp Ile Lys
                        100                 105                 110
```

<210> SEQ ID NO 5
<211> LENGTH: 112
<212> TYPE: PRT
<213> ORGANISM: Homo sapiens

<400> SEQUENCE: 5

```
        Asp Ile Val Met Thr Gln Ser Pro Leu Ser Leu Ser Val Thr Pro Gly
        1               5                   10                  15

Glu Pro Pro Ser Ile Ser Cys Arg Ser Ser Gln Ser Leu Leu His Ser
                        20                  25                  30

Asn Gly Tyr Asn Phe Leu Asn Trp Tyr Leu Gln Lys Pro Gly Gln Ser
                        35                  40                  45

Pro Gln Leu Leu Ile Tyr Leu Gly Ser His Arg Ala Ser Gly Val Pro
                50                  55                  60

Asp Arg Phe Ser Gly Ser Gly Ser Gly Thr Asp Phe Thr Leu Glu Ile
        65                  70                  75                  80

Ser Arg Val Glu Ala Glu Asp Val Gly Val Tyr Tyr Cys Met Gln Val
                        85                  90                  95

Leu Gln Thr Pro Phe Thr Phe Gly Pro Gly Thr Lys Val Asp Ile Lys
                        100                 105                 110
```

<210> SEQ ID NO 6
<211> LENGTH: 107
<212> TYPE: PRT
<213> ORGANISM: Homo sapiens

<400> SEQUENCE: 6

```
        Asp Ile Gln Met Thr Gln Ser Pro Ser Ser Leu Ser Ala Ser Val Gly
        1               5                   10                  15

Asp Arg Val Thr Ile Thr Cys Arg Ala Ser Gln Ser Ile Ser Ser Tyr
                        20                  25                  30

Leu Asn Trp Tyr Gln Gln Lys Pro Gly Lys Ala Pro Lys Leu Leu Ile
                        35                  40                  45

Tyr Ala Ala Ser Ser Leu Gln Ser Gly Val Pro Ser Arg Phe Ser Gly
                50                  55                  60

Ser Gly Ser Gly Thr Asp Phe Thr Leu Thr Ile Ser Ser Leu Gln Pro
        65                  70                  75                  80

Glu Asp Phe Ala Thr Tyr Tyr Cys Gln Gln Ser Tyr Ser Thr Pro Leu
                        85                  90                  95

Thr Phe Gly Gly Gly Thr Lys Val Glu Ile Lys
                        100                 105
```

```
<210> SEQ ID NO 7
<211> LENGTH: 107
<212> TYPE: PRT
<213> ORGANISM: Homo sapiens

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Ser Asn Tyr
            20                  25                  30

Leu Ser Trp Tyr Leu Gln Lys Pro Gly Ile Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Ser
65                  70                  75                  80

Glu Asp Phe Ala Thr Tyr Tyr Cys Gln Gln Ser Tyr Ser Thr Pro Leu
                85                  90                  95

Ile Phe Gly Gly Gly Thr Lys Val Glu Ile Lys
            100                 105

<210> SEQ ID NO 8
<211> LENGTH: 107
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105

<210> SEQ ID NO 9
<211> LENGTH: 107
<212> TYPE: PRT
<213> ORGANISM: Homo sapiens

<400> SEQUENCE: 9

Asp Ile Leu Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Val Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Asn Ser Leu Gln Pro
65                  70                  75                  80
```

```
Glu Asp Phe Ala Thr Tyr Tyr Cys Gln Gln Ser Tyr Ser Ser Pro Ile
                85                  90                  95

Thr Phe Gly Gln Gly Thr Arg Leu Glu Ile Lys
            100                 105

<210> SEQ ID NO 10
<211> LENGTH: 107
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ile Tyr
            20                  25                  30

Leu Asn Trp Tyr Gln Gln Lys Pro Gly Lys Ala Pro Tyr Leu Leu Ile
        35                  40                  45

Tyr Ala Ala Ala Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ala Pro Ile
                85                  90                  95

Thr Phe Gly Gln Gly Thr Arg Leu Glu Ile Lys
            100                 105

<210> SEQ ID NO 11
<211> LENGTH: 111
<212> TYPE: PRT
<213> ORGANISM: Homo sapiens

<400> SEQUENCE: 11

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu
            100                 105                 110

<210> SEQ ID NO 12
<211> LENGTH: 111
<212> TYPE: PRT
<213> ORGANISM: Homo sapiens

<400> SEQUENCE: 12

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30
```

Tyr Asp Val His Trp Tyr Gln Gln Leu Pro Gly Thr Ala Pro Lys Leu
            35                  40                  45

Leu Ile Ser Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu
                100                 105                 110

<210> SEQ ID NO 13
<211> LENGTH: 111
<212> TYPE: PRT
<213> ORGANISM: Homo sapiens

<400> SEQUENCE: 13

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala His
                20                  25                  30

Tyr Asp Val His Trp Tyr Gln Gln Val Pro Gly Thr Ala Pro Lys Leu
            35                  40                  45

Leu Ile Tyr Gly Asn Thr Tyr Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Asn Ser
                85                  90                  95

Leu Ser Gly Val Val Phe Gly Gly Gly Thr Lys Leu Thr Val Leu
                100                 105                 110

<210> SEQ ID NO 14
<211> LENGTH: 108
<212> TYPE: PRT
<213> ORGANISM: Homo sapiens

<400> SEQUENCE: 14

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                85                  90                  95

Ser Val Phe Gly Gly Gly Thr Lys Leu Thr Val Leu
                100                 105

<210> SEQ ID NO 15
<211> LENGTH: 109
<212> TYPE: PRT
<213> ORGANISM: Homo sapiens

<400> SEQUENCE: 15

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Arg Tyr
            20                  25                  30

Asn Ser Val Ser Trp Tyr Gln His Pro Gly Lys Ala Pro Lys Val
        35                  40                  45

Met Ile Tyr Glu Val Ser Asn Arg Pro Ser Gly Val Ser Thr Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Val Val Phe Gly Gly Gly Thr Lys Leu Thr Val Leu
            100                 105

<210> SEQ ID NO 16
<211> LENGTH: 109
<212> TYPE: PRT
<213> ORGANISM: Homo sapiens

<400> SEQUENCE: 16

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Pro Pro Lys Leu
        35                  40                  45

Met Ile Tyr Glu Val Ser Asn Arg Pro Ser Gly Val Ser Ile Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Thr Val Leu
            100                 105

<210> SEQ ID NO 17
<211> LENGTH: 109
<212> TYPE: PRT
<213> ORGANISM: Homo sapiens

<400> SEQUENCE: 17

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Pro Pro Lys Leu
        35                  40                  45

Met Ile Tyr Glu Val Ser Asn Arg Pro Ser Gly Val Ser Ile Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Thr Val Leu

<210> SEQ ID NO 18
<211> LENGTH: 109
<212> TYPE: PRT
<213> ORGANISM: Homo sapiens

<400> SEQUENCE: 18

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Pro Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Ala Val Leu
            100                 105

<210> SEQ ID NO 19
<211> LENGTH: 109
<212> TYPE: PRT
<213> ORGANISM: Homo sapiens

<400> SEQUENCE: 19

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln Tyr Pro Gly Lys Pro Pro Lys Leu
        35                  40                  45

Lys Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Thr Val Leu
            100                 105

<210> SEQ ID NO 20
<211> LENGTH: 109
<212> TYPE: PRT
<213> ORGANISM: Homo sapiens

<400> SEQUENCE: 20

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Pro Pro Lys Leu
        35                  40                  45

Met Ile Tyr Glu Val Ser Asn Arg Pro Ser Gly Val Ser Asn Arg Phe
    50                  55                  60

```
Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Thr Val Leu
            100                 105

<210> SEQ ID NO 21
<211> LENGTH: 109
<212> TYPE: PRT
<213> ORGANISM: Homo sapiens

<400> SEQUENCE: 21

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Pro Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Thr Val Leu
            100                 105

<210> SEQ ID NO 22
<211> LENGTH: 109
<212> TYPE: PRT
<213> ORGANISM: Homo sapiens

<400> SEQUENCE: 22

Gln Ser Ala Leu Thr Gln Pro Ala Ser Val Ser Gly Ser Pro Gly Gln
1               5                   10                  15

Ser Ile Thr Ile Ser Cys Thr Gly Thr Asn Ser Asp Val Gly Gly Tyr
            20                  25                  30

Asn Ser Val Ser Trp Tyr Gln Gln His Pro Gly Lys Pro Pro Lys Leu
        35                  40                  45

Met Ile Tyr Glu Val Ser Asn Arg Pro Ser Gly Ile Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Thr Val Leu
            100                 105

<210> SEQ ID NO 23
<211> LENGTH: 109
<212> TYPE: PRT
<213> ORGANISM: Homo sapiens

<400> SEQUENCE: 23

Gln Ser Ala Leu Thr Gln Pro Ala Ser Val Ser Gly Ser Pro Gly Gln
1               5                   10                  15
```

Ser Ile Thr Ile Ser Cys Thr Gly Thr Ser Ser Asp Val Gly Gly Tyr
                20                  25                  30

Asn Ser Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu
            100                 105

<210> SEQ ID NO 24
<211> LENGTH: 109
<212> TYPE: PRT
<213> ORGANISM: Homo sapiens

<400> SEQUENCE: 24

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
                20                  25                  30

Asn Ser Val Ser Trp Tyr Gln Gln His Pro Gly Lys Ala Pro Lys Arg
            35                  40                  45

Met Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Thr
                85                  90                  95

Asn Met Val Phe Gly Gly Gly Thr Lys Leu Thr Val Leu
            100                 105

<210> SEQ ID NO 25
<211> LENGTH: 108
<212> TYPE: PRT
<213> ORGANISM: Homo sapiens

<400> SEQUENCE: 25

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Val Phe Gly Gly Gly Thr Lys Leu Thr Val Leu
            100                 105

<210> SEQ ID NO 26
<211> LENGTH: 109

```
<212> TYPE: PRT
<213> ORGANISM: Homo sapiens

<400> SEQUENCE: 26

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
                 20                  25                  30

Asn Ser Val Ser Trp Tyr Gln Gln His Pro Gly Lys Ala Pro Lys Leu
             35                  40                  45

Met Ile Tyr Glu Val Thr Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Asn Ser Tyr Thr Ser Thr
                 85                  90                  95

Ser Met Val Phe Gly Gly Gly Thr Lys Leu Thr Val Leu
                100                 105

<210> SEQ ID NO 27
<211> LENGTH: 108
<212> TYPE: PRT
<213> ORGANISM: Homo sapiens

<400> SEQUENCE: 27

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Ser Tyr
                 20                  25                  30

Asn Leu Val Ser Trp Tyr Gln Gln His Pro Gly Lys Ala Pro Lys Leu
             35                  40                  45

Met Ile Tyr Glu Gly Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Ser Thr Phe Gly Gly Gly Thr Lys Leu Thr Val Leu
                100                 105

<210> SEQ ID NO 28
<211> LENGTH: 110
<212> TYPE: PRT
<213> ORGANISM: Homo sapiens

<400> SEQUENCE: 28

Leu Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Asn Tyr
                 20                  25                  30

Asn Leu Val Ser Trp Tyr Gln Gln Tyr Ser Gly Lys Ala Pro Lys Leu
             35                  40                  45

Met Ile Tyr Glu Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
```

```
                    85                  90                  95
Ser Thr Leu Val Phe Gly Gly Gly Thr Lys Leu Thr Val Leu
                100                 105                 110

<210> SEQ ID NO 29
<211> LENGTH: 108
<212> TYPE: PRT
<213> ORGANISM: Homo sapiens

<400> SEQUENCE: 29

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Val Phe Gly Gly Gly Thr Lys Leu Thr Val Leu
            100                 105

<210> SEQ ID NO 30
<211> LENGTH: 109
<212> TYPE: PRT
<213> ORGANISM: Homo sapiens

<400> SEQUENCE: 30

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Lys
            20                  25                  30

Thr Val Asn Trp Tyr Gln Gln Val Pro Gly Thr Ala Pro Lys Leu Leu
        35                  40                  45

Ile Tyr Arg Asn Asn Gln Arg Pro Leu Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Trp Val Phe Gly Gly Gly Thr Lys Leu Thr Val Leu
            100                 105

<210> SEQ ID NO 31
<211> LENGTH: 109
<212> TYPE: PRT
<213> ORGANISM: Homo sapiens

<400> SEQUENCE: 31

Gln Ser Val Leu Thr Gln Pro Pro Ser Ala Ser Gly Pro Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45
```

```
Ile Tyr Ser Asn Asn Arg Arg Pro Ser Gly Val Pro Asp Arg Phe Ser
    50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Trp Val Phe Gly Gly Gly Thr Lys Leu Thr Val Leu
                100                 105

<210> SEQ ID NO 32
<211> LENGTH: 110
<212> TYPE: PRT
<213> ORGANISM: Homo sapiens

<400> SEQUENCE: 32

Gln Ser Val Leu Thr Gln Pro Pro Ser Ala Ser Gly Thr Pro Gly Gln
  1               5                  10                  15

Arg Val Thr Ile Ser Cys Ser Gly Ser Ser Ser Asn Ile Gly Ser Asn
                 20                  25                  30

Thr Val Asn Trp Tyr Gln Gln Leu Pro Gly Thr Ala Pro Lys Leu Leu
             35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Val Trp Asp Asp Ser Leu
                 85                  90                  95

Asn Gly Trp Val Phe Gly Gly Gly Thr Lys Leu Thr Val Leu
                100                 105                 110

<210> SEQ ID NO 33
<211> LENGTH: 109
<212> TYPE: PRT
<213> ORGANISM: Homo sapiens

<400> SEQUENCE: 33

Gln Ser Val Leu Thr Gln Pro Pro Ser Ala Ser Gly Thr Pro Gly Gln
  1               5                  10                  15

Arg Val Thr Ile Ser Cys Ser Gly Ser Ser Ser Asn Ile Gly Ser Lys
                 20                  25                  30

Thr Val Asn Trp Tyr Gln Gln Phe Pro Gly Thr Ala Pro Lys Leu Leu
             35                  40                  45

Ile Tyr Ser Asn Asn Arg Arg Pro Ser Gly Val Pro Asp Arg Phe Ser
    50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Trp Val Phe Gly Ala Gly Thr Lys Leu Thr Val Leu
                100                 105

<210> SEQ ID NO 34
<211> LENGTH: 110
<212> TYPE: PRT
<213> ORGANISM: Homo sapiens

<400> SEQUENCE: 34
```

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Gly Thr Lys Val Thr Val Leu
            100                 105                 110

<210> SEQ ID NO 35
<211> LENGTH: 110
<212> TYPE: PRT
<213> ORGANISM: Homo sapiens

<400> SEQUENCE: 35

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Phe Val Ser Trp Tyr Gln Gln Leu Pro Gly Thr Ala Pro Lys Leu Leu
            35                  40                  45

Ile Tyr Asp Tyr Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Gly Thr Arg Val Thr Val Leu
            100                 105                 110

<210> SEQ ID NO 36
<211> LENGTH: 110
<212> TYPE: PRT
<213> ORGANISM: Homo sapiens

<400> SEQUENCE: 36

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Phe Val Ser Trp Tyr Gln Gln Leu Pro Gly Thr Ala Pro Lys Leu Leu
            35                  40                  45

Ile Tyr Asp Tyr Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Tyr Val Phe Gly Thr Gly Thr Arg Val Thr Val Leu
            100                 105                 110

<210> SEQ ID NO 37
<211> LENGTH: 110
<212> TYPE: PRT
<213> ORGANISM: Homo sapiens

<400> SEQUENCE: 37

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Phe Val Ser Trp Tyr Gln Gln Phe Pro Gly Thr Ala Pro Lys Leu Leu
        35                  40                  45

Ile Tyr Asp Tyr Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ser Tyr Val Phe Gly Thr Gly Thr Arg Val Thr Val Leu
            100                 105                 110

<210> SEQ ID NO 38
<211> LENGTH: 110
<212> TYPE: PRT
<213> ORGANISM: Homo sapiens

<400> SEQUENCE: 38

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Phe Val Ser Trp Tyr Gln Gln Leu Pro Gly Thr Ala Pro Lys Leu Leu
        35                  40                  45

Ile Tyr Asp Tyr Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Tyr Val Phe Gly Thr Gly Thr Arg Val Thr Val Leu
            100                 105                 110

<210> SEQ ID NO 39
<211> LENGTH: 110
<212> TYPE: PRT
<213> ORGANISM: Homo sapiens

<400> SEQUENCE: 39

Gln Ser Val Leu Thr Gln Pro Pro Thr Val Ser Ala Ala Pro Gly Gln
1               5                   10                  15

Lys Val Thr Ile Ser Cys Ser Gly Ser Ser Ser Asn Ile Gly Asn Asn
            20                  25                  30

Phe Val Ser Trp Tyr Gln Gln Leu Pro Gly Thr Ala Pro Lys Leu Leu
        35                  40                  45

Ile Tyr Asp Tyr Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln 65                    70                    75                    80

Thr Gly Asp Glu Ala Asp Tyr Tyr Cys Gly Thr Trp Asp Ser Ser Leu
                    85                          90                       95

Ser Gly Tyr Val Phe Gly Thr Gly Thr Arg Val Thr Val Leu
                 100                     105                    110

<210> SEQ ID NO 40
<211> LENGTH: 110
<212> TYPE: PRT
<213> ORGANISM: Homo sapiens

<400> SEQUENCE: 40

Gln Ser Val Leu Thr Gln Pro Pro Ser Val Ser Ala Ala Pro Gly Gln
1                    5                          10                    15

Lys Val Thr Ile Ser Cys Ser Gly Ser Ser Ser Asn Ile Gly Asn Asn
                    20                       25                     30

Phe Val Ser Trp Tyr Gln Gln Leu Pro Gly Thr Ala Pro Lys Leu Leu
                    35                       40                     45

Ile Tyr Asp Ser Asn Lys Arg Pro Ser Gly Ile Pro Asp Arg Phe Ser
     50                    55                       60

Gly Ser Lys Ser Gly Thr Ser Ala Thr Leu Asp Ile Thr Gly Leu Gln
65                  70                    75                    80

Thr Gly Asp Glu Ala Asp Tyr Tyr Cys Gly Thr Trp Asp Ser Ser Leu
                    85                       90                       95

Ser Ala Tyr Val Phe Gly Thr Gly Thr Lys Val Thr Val Leu
                 100                     105                    110

<210> SEQ ID NO 41
<211> LENGTH: 110
<212> TYPE: PRT
<213> ORGANISM: Homo sapiens

<400> SEQUENCE: 41

Gln Ser Val Leu Thr Gln Pro Pro Ser Val Ser Ala Ala Pro Gly Gln
1                    5                          10                    15

Lys Val Thr Ile Ser Cys Ser Gly Ser Ser Ser Asn Ile Gly Asn Asn
                    20                       25                     30

Tyr Val Ser Trp Tyr Gln Gln Leu Pro Gly Thr Ala Pro Lys Leu Leu
                    35                       40                     45

Ile Tyr Asp Asn Asn Lys Arg Pro Ser Gly Ile Pro Asp Arg Phe Ser
     50                    55                       60

Gly Ser Lys Ser Gly Thr Ser Ala Thr Leu Gly Ile Thr Gly Leu Gln
65                  70                    75                    80

Thr Gly Asp Glu Ala Asp Tyr Tyr Cys Gly Thr Trp Asp Ser Ser Leu
                    85                       90                       95

Ser Ala Val Val Phe Gly Gly Gly Thr Lys Leu Thr Val Leu
                 100                     105                    110

<210> SEQ ID NO 42
<211> LENGTH: 110
<212> TYPE: PRT
<213> ORGANISM: Homo sapiens

<400> SEQUENCE: 42

Gln Ser Val Leu Thr Gln Pro Pro Ser Val Ser Ala Ala Pro Gly Gln
1                    5                          10                    15

Lys Val Thr Ile Ser Cys Ser Gly Ser Asn Ser Asn Ile Gly Asn Asn
                    20                       25                     30

```
Tyr Val Ser Trp Tyr Gln Gln Leu Pro Gly Thr Ala Pro Lys Leu Leu
            35                  40                  45
Ile Tyr Asp Asn Asn Lys Arg Pro Ser Gly Ile Pro Asp Arg Phe Ser
 50                  55                  60
Gly Ser Asn Ser Gly Thr Ser Ala Thr Leu Gly Ile Thr Gly Leu Gln
 65                  70                  75                  80
Thr Gly Asp Glu Ala Asp Tyr Tyr Cys Gly Thr Trp Asp Ser Ser Leu
                 85                  90                  95
Ser Ala Val Val Phe Gly Gly Gly Thr Lys Leu Thr Val Leu
                100                 105                 110
```

<210> SEQ ID NO 43
<211> LENGTH: 107
<212> TYPE: PRT
<213> ORGANISM: Homo sapiens

<400> SEQUENCE: 43

```
Ser Tyr Glu Leu Thr Gln Pro Pro Ser Val Ser Val Ser Pro Gly Gln
  1               5                  10                  15
Thr Ala Ser Ile Thr Cys Ser Gly Asp Lys Leu Gly Asp Lys Tyr Ala
             20                  25                  30
Cys Trp Tyr Gln Gln Lys Pro Gly Gln Ser Pro Val Leu Val Ile Tyr
         35                  40                  45
Gln Asp Ser Lys Arg Pro Ser Gly Ile Pro Glu Arg Phe Ser Gly Ser
 50                  55                  60
Asn Ser Gly Asn Thr Ala Thr Leu Thr Ile Ser Gly Thr Gln Ala Met
 65                  70                  75                  80
Asp Glu Ala Asp Tyr Tyr Cys Gln Ala Trp Asp Ser Ser Thr Ala Val
                 85                  90                  95
Val Phe Gly Gly Gly Thr Lys Leu Thr Val Leu
                100                 105
```

<210> SEQ ID NO 44
<211> LENGTH: 106
<212> TYPE: PRT
<213> ORGANISM: Homo sapiens

<400> SEQUENCE: 44

```
Ser Tyr Glu Leu Thr Gln Pro Pro Ser Val Ser Val Ser Pro Gly Gln
  1               5                  10                  15
Thr Ala Arg Ile Thr Cys Ser Gly Asp Lys Leu Gly Asp Lys Tyr Ala
             20                  25                  30
Cys Trp Tyr Gln Gln Lys Pro Gly Gln Ser Pro Val Leu Val Ile Tyr
         35                  40                  45
Gln Asn Thr Lys Trp Pro Leu Gly Ile Pro Glu Arg Phe Ser Gly Ser
 50                  55                  60
Lys Ser Gly Asn Thr Val Thr Leu Thr Ile Ser Gly Thr Gln Ala Met
 65                  70                  75                  80
Asp Glu Ala Asp Tyr Tyr Cys Gln Ala Trp Asp Ser Ser Thr Val Val
                 85                  90                  95
Phe Gly Gly Gly Thr Lys Leu Thr Val Leu
                100                 105
```

<210> SEQ ID NO 45
<211> LENGTH: 116
<212> TYPE: PRT
<213> ORGANISM: Homo sapiens

<400> SEQUENCE: 45

Gln Pro Val Leu Thr Gln Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Gly Pro Arg Phe Val Met
        35                  40                  45

Arg Val Gly Thr Gly Gly Ile Val Gly Ser Lys Gly Asp Gly Ile Pro
    50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser Gly Ser Asn Phe Val Val Phe Gly Gly Thr Lys
            100                 105                 110

Leu Thr Val Leu
        115

<210> SEQ ID NO 46
<211> LENGTH: 116
<212> TYPE: PRT
<213> ORGANISM: Homo sapiens

<400> SEQUENCE: 46

Gln Pro Val Leu Thr Gln Pro Leu Phe Ala Ser Ala Ser Leu Gly Ala
1               5                   10                  15

Ser Val Thr Leu Thr Cys Thr Leu Ser Ser Gly Tyr Ser Ser Tyr Glu
            20                  25                  30

Val Asp Trp Tyr Gln Gln Arg Pro Gly Lys Gly Pro Arg Phe Val Met
        35                  40                  45

Arg Val Asp Thr Gly Gly Ile Val Gly Ser Lys Gly Glu Gly Ile Pro
    50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser Gly Thr Asn Phe Val Val Phe Gly Gly Thr Lys
            100                 105                 110

Leu Thr Val Leu
        115

<210> SEQ ID NO 47
<211> LENGTH: 114
<212> TYPE: PRT
<213> ORGANISM: Homo sapiens

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

```
Gln Gly Arg Val Thr Met Thr Thr Asp Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Gly Met Asp Val Trp Gly Gln Gly Thr Thr Val Thr Val
            100                 105                 110

Ser Ser
```

<210> SEQ ID NO 48
<211> LENGTH: 115
<212> TYPE: PRT
<213> ORGANISM: Homo sapiens

<400> SEQUENCE: 48

```
Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Pro Leu Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Val
50                  55                  60

Gln Gly Ser Val Thr Met Thr Thr Asp Thr Ser Thr Ser Thr Val Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115
```

<210> SEQ ID NO 49
<211> LENGTH: 115
<212> TYPE: PRT
<213> ORGANISM: Homo sapiens

<400> SEQUENCE: 49

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
                20                  25                  30

Gly Ile Ser Trp Val Arg Gln Ala Pro Gly Gln Gly Leu Glu Trp Met
            35                  40                  45

Gly Trp Val Ser Phe Tyr Asn Gly Asn Thr Asn Tyr Ala Gln Lys Leu
50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115
```

<210> SEQ ID NO 50
<211> LENGTH: 115
<212> TYPE: PRT

<213> ORGANISM: Homo sapiens

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115

<210> SEQ ID NO 51
<211> LENGTH: 115
<212> TYPE: PRT
<213> ORGANISM: Homo sapiens

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Ile Ser Phe Tyr Asn Gly Asn Thr Asn Tyr Ala Gln Lys Val
    50                  55                  60

Gln Gly Arg Val Thr Met Thr Thr Asp Thr Ser Thr Ser Thr Val Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115

<210> SEQ ID NO 52
<211> LENGTH: 115
<212> TYPE: PRT
<213> ORGANISM: Homo sapiens

<400> SEQUENCE: 52

Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Ile Ser Val Tyr Asn Gly Asn Thr Asn Tyr Ala Gln Lys Val
    50                  55                  60

```
Gln Gly Arg Val Thr Met Thr Thr Asp Thr Ser Ser Thr Val Tyr
 65                  70                  75                  80

Met Glu Leu Arg Ser Leu Ser Ser Asp Asp Thr Ala Val Tyr Tyr Cys
                 85                  90                  95

Ala Arg Gly Tyr Gly Met Asp Val Trp Gly Gln Gly Thr Thr Val Thr
            100                 105                 110

Val Ser Ser
        115

<210> SEQ ID NO 53
<211> LENGTH: 115
<212> TYPE: PRT
<213> ORGANISM: Homo sapiens

<400> SEQUENCE: 53

Gln Ile Gln Leu Val Gln Ser Gly Ala Glu Val Lys Lys Pro Gly Ala
  1               5                  10                  15

Ser Val Lys Val Ser Cys Lys Ala Ser Gly Tyr Thr Leu Thr Ser Tyr
             20                  25                  30

Gly Ile Ser Trp Val Arg Gln Ala Pro Gly Gln Gly Leu Glu Trp Met
         35                  40                  45

Gly Trp Ile Ser Phe Tyr Asn Gly Asn Thr Asn Tyr Ala Gln Lys Val
     50                  55                  60

Gln Gly Arg Val Thr Met Thr Thr Asp Thr Ser Ser Thr Val Tyr
 65                  70                  75                  80

Met Glu Leu Arg Ser Leu Arg Ser Asp Asp Thr Ala Val Tyr Phe Cys
                 85                  90                  95

Ala Arg Gly Tyr Gly Met Asp Val Trp Gly Gln Gly Thr Thr Val Thr
            100                 105                 110

Val Ser Ser
        115

<210> SEQ ID NO 54
<211> LENGTH: 115
<212> TYPE: PRT
<213> ORGANISM: Homo sapiens

<400> SEQUENCE: 54

Gln Val Gln Leu Val Gln Ser Gly Ala Glu Val Lys Lys Pro Gly Ala
  1               5                  10                  15

Ser Leu Lys Val Ser Cys Lys Ala Ser Gly Tyr Ser Leu Thr Ser Tyr
             20                  25                  30

Gly Ile Ser Trp Val Arg Gln Ala Pro Gly Gln Gly Leu Glu Trp Met
         35                  40                  45

Gly Trp Ile Ser Ala Tyr Asn Gly Asn Thr Asn Tyr Ala Gln Lys Val
     50                  55                  60

Gln Gly Arg Val Thr Met Thr Thr Asp Thr Ser Thr Ser Thr Val Tyr
 65                  70                  75                  80

Met Glu Val Arg Ser Leu Arg Ser Asp Asp Thr Ala Val Tyr Tyr Cys
                 85                  90                  95

Ala Arg Gly Tyr Gly Met Asp Val Trp Gly Gln Gly Thr Thr Val Thr
            100                 105                 110

Val Ser Ser
        115

<210> SEQ ID NO 55
```

```
<211> LENGTH: 115
<212> TYPE: PRT
<213> ORGANISM: Homo sapiens

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Leu Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Val
50                  55                  60

Gln Gly Arg Val Thr Met Thr Thr Asp Thr Ser Thr Ser Thr Val Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115

<210> SEQ ID NO 56
<211> LENGTH: 115
<212> TYPE: PRT
<213> ORGANISM: Homo sapiens

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Leu Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Val
50                  55                  60

Gln Gly Arg Val Thr Met Thr Thr Asp Thr Ser Thr Ser Thr Val Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115

<210> SEQ ID NO 57
<211> LENGTH: 115
<212> TYPE: PRT
<213> ORGANISM: Homo sapiens

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
                20                  25                  30

Gly Ile Ser Trp Val Arg Gln Ala Pro Gly Gln Gly Leu Glu Trp Met
            35                  40                  45
```

-continued

Gly Trp Val Ser Ala Tyr Asn Gly Asn Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Val Met Asp Val Trp Gly Gln Gly Thr Thr Val Thr
                100                 105                 110

Val Ser Ser
        115

<210> SEQ ID NO 58
<211> LENGTH: 115
<212> TYPE: PRT
<213> ORGANISM: Homo sapiens

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Glu Lys Leu
    50                  55                  60

Gln Gly Arg Val Thr Met Thr Thr Asp Thr Ser Thr Ser Thr Ala Tyr
65                  70                  75                  80

Met Glu Val Arg Ser Leu Arg Ser Asp Asp Thr Ala Val Phe Tyr Cys
                85                  90                  95

Ala Arg Gly Tyr Val Met Asp Val Trp Gly Gln Gly Thr Thr Val Thr
                100                 105                 110

Val Ser Ser
        115

<210> SEQ ID NO 59
<211> LENGTH: 113
<212> TYPE: PRT
<213> ORGANISM: Homo sapiens

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Asp Tyr Trp Gly Gln Gly Thr Leu Val Thr Val Ser
                100                 105                 110

Ser

```
<210> SEQ ID NO 60
<211> LENGTH: 115
<212> TYPE: PRT
<213> ORGANISM: Homo sapiens

<400> SEQUENCE: 60

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Thr Tyr Asn Gly Asn Thr Asn Tyr Ala Gln Lys Val
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Thr Arg Asp Tyr Trp Gly Gln Gly Thr Leu Val Thr
            100                 105                 110

Val Ser Ser
        115

<210> SEQ ID NO 61
<211> LENGTH: 116
<212> TYPE: PRT
<213> ORGANISM: Homo sapiens

<400> SEQUENCE: 61

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asn Trp Gly Ala Phe Asp Val Trp Gly Gln Gly Thr Met Val
            100                 105                 110

Thr Val Ser Ser
        115

<210> SEQ ID NO 62
<211> LENGTH: 119
<212> TYPE: PRT
<213> ORGANISM: Homo sapiens

<400> SEQUENCE: 62

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
                20                  25                  30

Trp Met Ser Trp Val Arg Gln Ala Pro Gly Lys Gly Leu Glu Trp Val
            35                  40                  45
```

Ala Asn Ile Lys His Asp Gly Ser Glu Lys Tyr Tyr Val Asp Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Glu Ser Asn Trp Gly Phe Ala Phe Asp Val Trp Gly His Gly
                100                 105                 110

Thr Met Val Thr Val Ser Ser
            115

<210> SEQ ID NO 63
<211> LENGTH: 116
<212> TYPE: PRT
<213> ORGANISM: Homo sapiens

<400> SEQUENCE: 63

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asn Trp Gly Ala Phe Asp Ile Trp Gly Gln Gly Thr Met Val
                100                 105                 110

Thr Val Ser Ser
            115

<210> SEQ ID NO 64
<211> LENGTH: 119
<212> TYPE: PRT
<213> ORGANISM: Homo sapiens

<400> SEQUENCE: 64

Glu Val Gln Leu Val Glu Ser Gly Gly Gly Leu Val Gln Pro Gly Gly
 1               5                   10                  15

Ser Leu Arg Leu Ser Cys Val Val Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Glu Ser Asn Trp Gly Phe Ala Phe Asp Ile Trp Gly Gln Gly
                100                 105                 110

Thr Met Val Thr Val Ser Ser
            115

<210> SEQ ID NO 65
<211> LENGTH: 119
<212> TYPE: PRT
<213> ORGANISM: Homo sapiens

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Asn Phe
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Glu Ser Asn Trp Gly Phe Ala Phe Asp Ile Trp Gly Gln Gly
            100                 105                 110

Thr Met Val Thr Val Ser Ser
        115

<210> SEQ ID NO 66
<211> LENGTH: 123
<212> TYPE: PRT
<213> ORGANISM: Homo sapiens

<400> SEQUENCE: 66

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Asp Phe Trp Ser Gly Tyr Tyr Thr Ala Phe Asp Val
            100                 105                 110

Trp Gly Gln Gly Thr Met Val Thr Val Ser Ser
        115                 120

<210> SEQ ID NO 67
<211> LENGTH: 123
<212> TYPE: PRT
<213> ORGANISM: Homo sapiens

<400> SEQUENCE: 67

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
    35                  40                  45

Ser Ser Ile Ser Ser Ser Ser Tyr Ile Ser Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
            85                  90                  95

Ala Arg Asp Tyr Asp Phe Trp Ser Ala Tyr Tyr Asp Ala Phe Asp Val
            100                 105                 110

Trp Gly Gln Gly Thr Met Val Thr Val Ser Ser
            115                 120

<210> SEQ ID NO 68
<211> LENGTH: 112
<212> TYPE: PRT
<213> ORGANISM: Homo sapiens

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Phe Asp Tyr Trp Gly Gln Gly Thr Leu Val Thr Val Ser Ser
            100                 105                 110

<210> SEQ ID NO 69
<211> LENGTH: 117
<212> TYPE: PRT
<213> ORGANISM: Homo sapiens

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Arg Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Glu Val Gly Ser Pro Phe Asp Tyr Trp Gly Gln Gly Thr Leu
            100                 105                 110

Val Thr Val Ser Ser
            115

<210> SEQ ID NO 70
<211> LENGTH: 117
<212> TYPE: PRT
<213> ORGANISM: Homo sapiens

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Met Val Tyr Ala Asp Tyr Trp Gly Gln Gly Thr Leu
            100                 105                 110

Val Thr Val Ser Ser
        115

<210> SEQ ID NO 71
<211> LENGTH: 121
<212> TYPE: PRT
<213> ORGANISM: Homo sapiens

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Gly Ser Gly Asp Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Phe Val Leu Met Val Tyr Ala Met Leu Asp Tyr Trp Gly
            100                 105                 110

Gln Gly Thr Leu Val Thr Val Ser Ser
        115                 120

<210> SEQ ID NO 72
<211> LENGTH: 121
<212> TYPE: PRT
<213> ORGANISM: Homo sapiens

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val

```
                35                  40                  45
Ser Thr Ile Ser Gly Ser Gly Asn Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Lys Phe Val Leu Met Val Tyr Ala Met Leu Asp Tyr Trp Gly
             100                 105                 110
Gln Gly Thr Leu Val Thr Val Ser Ser
             115                 120

<210> SEQ ID NO 73
<211> LENGTH: 116
<212> TYPE: PRT
<213> ORGANISM: Homo sapiens

<400> SEQUENCE: 73

Gln Val Gln Leu Val Glu Ser Gly Gly Gly Val Val Gln Pro Gly Arg
 1               5                   10                  15
Ser Leu Arg Leu Ser Cys Ala Ala Ser Gly Phe Thr Phe Ser Ser Tyr
             20                  25                  30
Gly Met His Trp Val Arg Gln Ala Pro Gly Lys Gly Leu Glu Trp Val
             35                  40                  45
Ala Val Ile Trp Tyr Asp Gly Ser Asn Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Tyr Tyr Tyr Gly Met Asp Val Trp Gly Gln Gly Thr Thr Val
             100                 105                 110
Thr Val Ser Ser
             115

<210> SEQ ID NO 74
<211> LENGTH: 123
<212> TYPE: PRT
<213> ORGANISM: Homo sapiens

<400> SEQUENCE: 74

Gln Val Gln Leu Val Glu Ser Gly Gly Gly Val Val Gln Pro Gly Arg
 1               5                   10                  15
Ser Leu Arg Leu Ser Cys Ala Ala Ser Gly Phe Thr Phe Ser Ser Tyr
             20                  25                  30
Gly Met His Trp Val Arg Gln Ala Pro Gly Lys Gly Leu Glu Trp Val
             35                  40                  45
Ala Val Ile Trp Tyr Asp Gly Ser Asp Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Glu Thr Gly Pro Leu Lys Leu Tyr Tyr Tyr Gly Met Asp Val
             100                 105                 110
Trp Gly Gln Gly Thr Thr Val Thr Val Ser Ser
```

115          120

<210> SEQ ID NO 75
<211> LENGTH: 116
<212> TYPE: PRT
<213> ORGANISM: Homo sapiens

<400> SEQUENCE: 75

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Ala Ala Gly Met Asp Val Trp Gly Gln Gly Thr Thr Val
            100                 105                 110

Thr Val Ser Ser
        115

<210> SEQ ID NO 76
<211> LENGTH: 122
<212> TYPE: PRT
<213> ORGANISM: Homo sapiens

<400> SEQUENCE: 76

Gln Val His Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Ser Phe
            20                  25                  30

Gly Met His Trp Val Arg Gln Ala Pro Gly Lys Gly Leu Glu Trp Val
        35                  40                  45

Ala Leu Ile Trp Ser Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ile Ala Ala Leu Tyr Tyr Tyr Tyr Gly Met Asp Val Trp
            100                 105                 110

Gly Gln Gly Thr Thr Val Thr Val Ser Ser
        115                 120

<210> SEQ ID NO 77
<211> LENGTH: 122
<212> TYPE: PRT
<213> ORGANISM: Homo sapiens

<400> SEQUENCE: 77

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

```
Gly Met His Trp Val Arg Gln Ala Pro Gly Lys Gly Leu Glu Trp Val
            35                  40                  45

Ala Leu Ile Trp Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ala Ile Ala Ala Leu Tyr Tyr Tyr Tyr Gly Met Asp Val Trp
               100                 105                 110

Gly His Gly Thr Thr Val Thr Val Ser Ser
            115                 120

<210> SEQ ID NO 78
<211> LENGTH: 122
<212> TYPE: PRT
<213> ORGANISM: Homo sapiens

<400> SEQUENCE: 78

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Phe
                20                  25                  30

Gly Met His Trp Val Arg Gln Ala Pro Gly Lys Gly Leu Glu Trp Val
            35                  40                  45

Ala Leu Ile Trp Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ala Ile Ala Ala Leu Tyr Tyr Tyr Tyr Gly Met Asp Val Trp
               100                 105                 110

Gly Gln Gly Thr Thr Val Thr Val Ser Ser
            115                 120

<210> SEQ ID NO 79
<211> LENGTH: 122
<212> TYPE: PRT
<213> ORGANISM: Homo sapiens

<400> SEQUENCE: 79

Gln Val His Leu Val Glu Ser Gly Gly Gly Val Val Gln Pro Gly Arg
  1               5                  10                  15

Ser Leu Arg Leu Ser Cys Ala Ala Ser Gly Phe Thr Phe Asn Ser Phe
                20                  25                  30

Gly Met His Trp Val Arg Gln Ala Pro Gly Lys Gly Leu Glu Trp Val
            35                  40                  45

Ala Leu Ile Trp Ser Asp Gly Ser Asp Glu Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ala Ile Ala Ala Leu Tyr Tyr Tyr Tyr Gly Met Asp Val Trp
               100                 105                 110
```

Gly Gln Gly Thr Thr Val Thr Val Ser Ser
        115                 120

<210> SEQ ID NO 80
<211> LENGTH: 122
<212> TYPE: PRT
<213> ORGANISM: Homo sapiens

<400> SEQUENCE: 80

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Phe
                20                  25                  30

Gly Met His Trp Val Arg Gln Ala Pro Gly Lys Gly Leu Glu Trp Val
            35                  40                  45

Ala Leu Ile Trp Asn Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ile Ala Ala Leu Tyr Tyr Tyr Gly Met Asp Val Trp
            100                 105                 110

Gly Gln Gly Thr Thr Val Thr Val Ser Ser
        115                 120

<210> SEQ ID NO 81
<211> LENGTH: 122
<212> TYPE: PRT
<213> ORGANISM: Homo sapiens

<400> SEQUENCE: 81

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Ile Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gly Leu Ala Ala Arg Pro Gly Gly Met Asp Val Trp
            100                 105                 110

Gly Gln Gly Thr Thr Val Thr Val Ser Ser
        115                 120

<210> SEQ ID NO 82
<211> LENGTH: 122
<212> TYPE: PRT
<213> ORGANISM: Homo sapiens

<400> SEQUENCE: 82

Gln Val Gln Leu Val Glu Ser Gly Gly Gly Val Val Gln Pro Gly Arg
 1               5                  10                  15

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Ile Ala Val Ala Tyr Tyr Tyr Tyr Gly Met Asp Val Trp
            100                 105                 110

Gly Gln Gly Thr Thr Val Thr Val Ser Ser
            115                 120
```

<210> SEQ ID NO 83
<211> LENGTH: 122
<212> TYPE: PRT
<213> ORGANISM: Homo sapiens

<400> SEQUENCE: 83

```
Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Leu Ile Trp His Asp Gly Ser Asn Thr Tyr Tyr Val Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Ile Ala Val Ala Tyr Tyr Tyr Tyr Gly Met Asp Val Trp
            100                 105                 110

Gly Gln Gly Thr Thr Val Thr Val Ser Ser
            115                 120
```

<210> SEQ ID NO 84
<211> LENGTH: 117
<212> TYPE: PRT
<213> ORGANISM: Homo sapiens

<400> SEQUENCE: 84

```
Gln Val Gln Leu Gln Glu Ser Gly Pro Gly Leu Val Lys Pro Ser Gln
 1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95
```

Cys Ala Arg Tyr Tyr Gly Met Asp Val Trp Gly Gln Gly Thr Thr
            100                 105                 110

Val Thr Val Ser Ser
            115

<210> SEQ ID NO 85
<211> LENGTH: 122
<212> TYPE: PRT
<213> ORGANISM: Homo sapiens

<400> SEQUENCE: 85

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Ser
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Ile Thr Ile Ser Val Asp Thr Ser Lys Asn Leu Phe
65                  70                  75                  80

Ser Leu Lys Leu Ser Ser Val Thr Ala Ala Asp Thr Ala Val Tyr Tyr
                85                  90                  95

Cys Ala Arg Gly Gly Val Thr Thr Tyr Tyr Tyr Ala Met Asp Val Trp
            100                 105                 110

Gly Gln Gly Thr Thr Val Thr Val Ser Ser
            115                 120

<210> SEQ ID NO 86
<211> LENGTH: 120
<212> TYPE: PRT
<213> ORGANISM: Homo sapiens

<400> SEQUENCE: 86

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Thr Ala Met Val Tyr Phe Asp Tyr Trp Gly Gln
            100                 105                 110

Gly Thr Leu Val Thr Val Ser Ser
            115                 120

<210> SEQ ID NO 87
<211> LENGTH: 121
<212> TYPE: PRT
<213> ORGANISM: Homo sapiens

<400> SEQUENCE: 87

Gln Val Gln Leu Gln Glu Ser Gly Pro Gly Leu Val Lys Pro Ser Gln

```
            1               5                  10                 15
        Thr Leu Ser Leu Thr Cys Thr Val Ser Gly Gly Ser Ile Ser Ser Gly
                    20                  25                  30

Gly Tyr Tyr Trp Ser Trp Ile Arg Gln His Pro Gly Lys Gly Leu Glu
                    35                  40                  45

Trp Ile Gly Tyr Ile Tyr Asn Ser Gly Ser Thr Tyr Tyr Asn Pro Ser
            50                  55                  60

Leu Lys Ser Arg Val Thr Ile Ser Val Asp Thr Ser Lys Asn Gln Phe
        65                  70                  75                  80

Ser Leu Lys Leu Ser Ser Val Thr Ala Ala Asp Thr Ala Val Tyr Tyr
                        85                  90                  95

Cys Ala Arg Glu Asp Thr Ala Met Val Pro Tyr Phe Asp Tyr Trp Gly
                        100                 105                 110

Gln Gly Thr Leu Val Thr Val Ser Ser
                    115                 120

<210> SEQ ID NO 88
<211> LENGTH: 115
<212> TYPE: PRT
<213> ORGANISM: Homo sapiens

<400> SEQUENCE: 88

Gln Val Gln Leu Gln Gln Trp Gly Ala Gly Leu Leu Lys Pro Ser Glu
        1               5                   10                  15

Thr Leu Ser Leu Thr Cys Ala Val Tyr Gly Gly Ser Phe Ser Gly Tyr
                    20                  25                  30

Tyr Trp Ser Trp Ile Arg Gln Pro Pro Gly Lys Gly Leu Glu Trp Ile
                    35                  40                  45

Gly Glu Ile Asn His Ser Gly Ser Thr Asn Tyr Asn Pro Ser Leu Lys
            50                  55                  60

Ser Arg Val Thr Ile Ser Val Asp Thr Ser Lys Asn Gln Phe Ser Leu
        65                  70                  75                  80

Lys Leu Ser Ser Val Thr Ala Ala Asp Thr Ala Val Tyr Tyr Cys Ala
                        85                  90                  95

Arg Gly Gln Leu Val Phe Asp Tyr Trp Gly Gln Gly Thr Leu Val Thr
                        100                 105                 110

Val Ser Ser
                115

<210> SEQ ID NO 89
<211> LENGTH: 116
<212> TYPE: PRT
<213> ORGANISM: Homo sapiens

<400> SEQUENCE: 89

Gln Val Gln Leu Gln Gln Trp Gly Ala Gly Leu Leu Lys Pro Ser Glu
        1               5                   10                  15

Thr Leu Ser Leu Thr Cys Ala Val Tyr Gly Gly Ser Phe Ser Ala Tyr
                    20                  25                  30

Tyr Trp Asn Trp Ile Arg Gln Pro Pro Gly Lys Gly Leu Glu Trp Ile
                    35                  40                  45

Gly Glu Ile Asn His Ser Gly Arg Thr Asp Tyr Asn Pro Ser Leu Lys
            50                  55                  60

Ser Arg Val Thr Ile Ser Val Asp Thr Ser Lys Lys Gln Phe Ser Leu
        65                  70                  75                  80

Lys Leu Asn Ser Val Thr Ala Ala Asp Thr Ala Val Tyr Tyr Cys Ala
```

```
                85                  90                  95
Arg Gly Gln Leu Val Pro Phe Asp Tyr Trp Gly Gln Gly Thr Leu Val
            100                 105                 110

Thr Val Ser Ser
        115

<210> SEQ ID NO 90
<211> LENGTH: 115
<212> TYPE: PRT
<213> ORGANISM: Homo sapiens

<400> SEQUENCE: 90

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Pro Ser Arg Gly Leu Glu
         35                  40                  45

Trp Leu Gly Arg Thr Tyr Tyr Arg Ser Lys Trp Tyr Asn Asp Tyr Ala
     50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Phe Asp Tyr Trp Gly Gln Gly Thr Leu Val Thr
            100                 105                 110

Val Ser Ser
        115

<210> SEQ ID NO 91
<211> LENGTH: 121
<212> TYPE: PRT
<213> ORGANISM: Homo sapiens

<400> SEQUENCE: 91

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Pro Ser Arg Gly Leu Glu
         35                  40                  45

Trp Leu Gly Arg Thr Tyr Tyr Arg Ser Lys Trp Tyr Lys Asn Tyr Ser
     50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Gly Asp Thr Ala Val
                 85                  90                  95

Tyr Tyr Cys Ala Arg Gly Gly Pro Thr Ala Ala Phe Asp Tyr Trp Gly
            100                 105                 110

Gln Gly Thr Leu Val Thr Val Ser Ser
            115                 120

<210> SEQ ID NO 92
<211> LENGTH: 345
<212> TYPE: DNA
<213> ORGANISM: Homo sapiens

<400> SEQUENCE: 92
```

```
cagattcagc tggtgcagtc tggagctgag gtgaagaagc ctggggcctc agtgaaggtc      60
tcctgcaagg cttctggtta ccccttgacc agctatggta tcagctgggt gcgacaggcc     120
cctggacaag ggcttgagtg gatgggatgg atcagcgctt acaatggtaa cacaaactat     180
gcacagaagg tccagggcag cgtcaccatg accacagaca catccacgag cacagtctac     240
atggagctga ggagcctgag atctgacgac acggccgtgt attactgtgc gagaggctac     300
ggtatggacg tctggggcca agggaccacg gtcaccgtct cctct                    345
```

<210> SEQ ID NO 93
<211> LENGTH: 327
<212> TYPE: DNA
<213> ORGANISM: Homo sapiens

<400> SEQUENCE: 93

```
cagtctgccc tgactcagcc tgcctccgtg tctgggtctc ctggacagtc gatcaccatc      60
tcctgcactg gaaccagcag tgacgttggt ggttataact ctgtctcctg gtaccaacag     120
tacccaggca accccccaa actcaagatt tatgaggtca gtaatcggcc ctcagggg tt    180 tctaatcgct tctctggctc caagtctggc aacacggcct ccctgaccat ctctgggctc    240
caggctgagg acgaggctga ttatttctgc agctcatata caagcaccag catggtcttc    300
ggcggaggga ccaagctgac cgtccta                                        327
```

<210> SEQ ID NO 94
<211> LENGTH: 345
<212> TYPE: DNA
<213> ORGANISM: Homo sapiens

<400> SEQUENCE: 94

```
caggttcagc tggtgcagtc tggagctgag gtgaagaagc ctggggcctc agtgaaggtc      60
tcctgcaagg cttctggtta caccttaacc agctatggta tcagctgggt gcgacaggcc     120
cctggacaag ggcttgagtg gatgggatgg gtcagttttt ataatggtaa cacaaactat     180
gcacagaagc tccagggcag aggcaccatg accacagacc catccacgag cacagcctac     240
atggagctga ggagcctgag atctgacgac acggccgtgt attactgtgc gagaggctac     300
ggtatggacg tctggggcca agggaccacg gtcaccgtct cctct                    345
```

<210> SEQ ID NO 95
<211> LENGTH: 327
<212> TYPE: DNA
<213> ORGANISM: Homo sapiens

<400> SEQUENCE: 95

```
cagtctgccc tgactcagcc tgcctccgtg tctgggtctc ctggacagtc gatcaccatc      60
tcctgcactg gaaccagcag tgacgttggt ggttataact ctgtctcctg gtaccaacag     120
cacccaggca aagccccca actcatgatt tatgaggtca gtaatcggcc ctcagggg tt     180 tctaatcgct tctctggctc caagtctggc aacacggcct ccctgaccat ctctgggctc    240
caggctgagg acgaggctga ttattactgc aattcatata caagcaccag catggtattc    300
ggcggaggga ccaagctgac cgtccta                                        327
```

<210> SEQ ID NO 96
<211> LENGTH: 345
<212> TYPE: DNA
<213> ORGANISM: Homo sapiens

<400> SEQUENCE: 96

```
caggttcagc tggtgcagtc tggagctgaa gtgaagaagc ctggggcctc agtgaaggtc        60
tcctgcaagg cttctggtta caccttgacc agctatggta tcagctgggt gcgacaggcc       120
cctggacaag ggcttgagtg gatgggatgg atcagctttt acaatggtaa cacaaactat       180
gcacagaagg tccagggcag agtcaccatg accacagaca catccacgag cacagtctac       240
atggagctga ggagcctgag atctgacgac acggccgtgt attactgtgc gagaggctac       300
ggtatggacg tctggggcca aggaccacg gtcaccgtct cctct                        345
```

<210> SEQ ID NO 97
<211> LENGTH: 327
<212> TYPE: DNA
<213> ORGANISM: Homo sapiens

<400> SEQUENCE: 97

```
cagtctgccc tgactcagcc tgcctccgtg tctgggtctc ctggacagtc gatcaccatc        60
tcctgcactg gaaccagcag tgacgttggt ggttataact ctgtctcctg gtaccaacag       120
cacccaggca aacccccaa actcatgatt tatgaggtca gtaatcggcc ctcaggggtt        180
tctattcgct tctctggctc caagtctggc aacacggcct ccctgaccat ctctgggctc       240
caggctgagg acgaggctga ttatttctgc agctcatata caagcaccag catggtcttc       300
ggcggaggga ccaagctgac cgtccta                                            327
```

<210> SEQ ID NO 98
<211> LENGTH: 345
<212> TYPE: DNA
<213> ORGANISM: Homo sapiens

<400> SEQUENCE: 98

```
cagattcagc tggtgcagtc tggagctgag gtgaagaagc ctggggcctc agtgaaggtc        60
tcctgcaagg cttctggtta caccttgacc agctatggta tcagctgggt gcgacaggcc       120
cctggacaag ggcttgagtg gatgggatgg atcagctttt acaatggtaa cacaaactat       180
gcacagaagg tccagggcag agtcaccatg accacagaca catccacgag cacagtctac       240
atggagctga ggagcctgag atctgacgac acggccgtgt atttctgtgc gagaggttac       300
ggtatggacg tctggggcca aggaccacg gtcaccgtct cctca                        345
```

<210> SEQ ID NO 99
<211> LENGTH: 327
<212> TYPE: DNA
<213> ORGANISM: Homo sapiens

<400> SEQUENCE: 99

```
cagtctgccc tgactcagcc tgcctccgtg tctgggtctc ctggacagtc gatcaccatc        60
tcctgcactg gaaccagcag tgacgttggt ggttataact ctgtctcgtg gtaccaacag       120
cacccaggca aacccccaa actcatgatt tatgaggtca gtaatcggcc ctcaggggtt        180
tctaatcgct tctctggctc caagtctggc aacacggcct ccctgaccat ctctgggctc       240
caggctgagg acgaggctga ttatttctgc agctcatata caagcaccag catggtcttc       300
ggcggaggga ccaagctggc cgtccta                                            327
```

<210> SEQ ID NO 100
<211> LENGTH: 345
<212> TYPE: DNA
<213> ORGANISM: Homo sapiens

<400> SEQUENCE: 100

| caggttcagc tggtgcagtc tggagctgag gtgaagaagc ctggggcctc agtgaaggtc | 60 |
| tcctgcaagg cttctggtta caccttaacc agctatggta tcagctgggt gcgacaggcc | 120 |
| cctggacaag gcttgagtg gatgggatgg gtcagttttt ataatggtaa cacaaactat | 180 |
| gcacagaagc tccagggcag aggcaccatg accacagacc catccacgag cacagcctac | 240 |
| atggagctga ggagcctgag atctgacgac acggccgtgt attactgtgc gagaggctac | 300 |
| ggtatggacg tctggggcca agggaccacg gtcaccgtct cctca | 345 |

<210> SEQ ID NO 101
<211> LENGTH: 327
<212> TYPE: DNA
<213> ORGANISM: Homo sapiens

<400> SEQUENCE: 101

| cagtctgccc tgactcagcc tgcctccgtg tctgggtctc ctggacagtc gatcaccatc | 60 |
| tcctgcactg gaaccagcag tgacgttggt ggttataact ctgtctcctg gtaccaacag | 120 |
| cacccaggca aagcccccaa actcatgatt tatgaggtca ctaatcggcc ctcagggggtt | 180 |
| tctaatcgct tctctggctc caagtctggc aacacggcct ccctgaccat ctctgggctc | 240 |
| caggctgagg acgaggctga ttattactgc aactcatata caagcaccag catggtgttc | 300 |
| ggcggaggga ccaagctgac cgtccta | 327 |

<210> SEQ ID NO 102
<211> LENGTH: 363
<212> TYPE: DNA
<213> ORGANISM: Homo sapiens

<400> SEQUENCE: 102

| caggtgcagc tgcaggagtc gggcccagga ctggtgaagc cttcacagac cctgtccctc | 60 |
| acctgcactg tctctggtgg ctccatcagc agtggtggtt actactggag ctggatccgc | 120 |
| cagcacccag ggaagggcct ggagtggatt gggtacatat ataacagtgg gagcacctac | 180 |
| tacaacccgt ccctcaagag tcgagttacc atatcagtag acacgtctaa gaaccagttc | 240 |
| tccctgaagc tgagctctgt gactgccgcg gacacggccg tgtattactg tgcgagagag | 300 |
| gatacagcta tggttcctta ctttgactac tggggccagg gaaccctggt caccgtctcc | 360 |
| tca | 363 |

<210> SEQ ID NO 103
<211> LENGTH: 333
<212> TYPE: DNA
<213> ORGANISM: Homo sapiens

<400> SEQUENCE: 103

| cagtctgtac tgacgcagcc gccctcagtg tctggggccc cagggcagag ggtcaccatc | 60 |
| tcctgcactg ggagcagctc caacatcggg gcacattatg atgtgcactg gtaccagcag | 120 |
| gttccaggaa cagcccccaa actcctcatc tatggtaaca cctatcggcc ctcaggggtc | 180 |
| cctgaccgat tctctggctc caagtctggc acctcagcct ccctggccat cactgggctc | 240 |
| caggctgagg atgaggctga ttattactgc cagtcctatg acaacagcct gagtggtgtg | 300 |
| gtattcggcg gagggaccaa gctgaccgtc cta | 333 |

<210> SEQ ID NO 104

<211> LENGTH: 366
<212> TYPE: DNA
<213> ORGANISM: Homo sapiens

<400> SEQUENCE: 104

```
caggtgcacc tggtggagtc tgggggaggc gtggtccagc ctgggaggtc cctgagactc    60
tcctgtgcag cgtctggatt caccttcaac agctttggca tgcactgggt ccgccaggct   120
ccaggcaagg ggctggagtg ggtggcactt atctggtctg atggaagtga tgaatactat   180
gcagactccg tgaagggccg attcaccatc tccagagaca attccaagaa cacgctgtat   240
ctgcaaatga acagcctgag agccgaggac acggctgtgt attactgtgc gagagccata   300
gcagccctct actactacta cggtatggac gtctggggcc aagggaccac ggtcaccgtc   360
tcctca                                                              366
```

<210> SEQ ID NO 105
<211> LENGTH: 330
<212> TYPE: DNA
<213> ORGANISM: Homo sapiens

<400> SEQUENCE: 105

```
cagtctgtgt tgacgcagcc gccctcagtg tctgcggccc caggacagaa ggtcaccatc    60
tcctgctctg gaagcagctc caacattggg aataattttg tatcctggta ccagcagctc   120
ccaggaacag cccccaaact cctcatttat gactataata gcgaccctc agggattcct    180
gaccgattct ctggctccaa gtctggcacg tcagccaccc tgggcatcac cggactccag   240
actggggacg aggccgatta ttactgcgga acatgggata gcagcctgag tgcttatgtc   300
ttcggaactg ggaccagggt caccgtccta                                    330
```

<210> SEQ ID NO 106
<211> LENGTH: 366
<212> TYPE: DNA
<213> ORGANISM: Homo sapiens

<400> SEQUENCE: 106

```
caggtgcagc tggtggagtc tgggggaggc gtggtccagc ctgggaggtc cctgagactc    60
tcctgtgcag cgtctggatt caccttcagc agctttggca tgcactgggt ccgccaggct   120
ccaggcaagg ggctggagtg ggtggcactt atatggaatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagagccata   300
gcagccctct actactacta cggtatggac gtctggggcc aagggaccac ggtcaccgtc   360
tcctca                                                              366
```

<210> SEQ ID NO 107
<211> LENGTH: 330
<212> TYPE: DNA
<213> ORGANISM: Homo sapiens

<400> SEQUENCE: 107

```
cagtctgtgt tgacgcagcc gccctcagtg tctgcggccc caggacagaa ggtcaccatc    60
tcctgctctg gaagcagctc caacattggg aataattttg tatcctggta ccagcagctc   120
ccaggaacag cccccaaact cctcatttat gactataata gcgaccctc agggattcct    180
gaccgattct ctggctccaa gtctggcacg tcagccaccc tgggcatcac cggactccag   240
actggggacg aggccgatta ttactgcgga acatgggata gcagtctgag tggttatgtc   300
```

```
ttcggaactg ggaccagggt caccgtccta                                      330
```

<210> SEQ ID NO 108
<211> LENGTH: 366
<212> TYPE: DNA
<213> ORGANISM: Homo sapiens

<400> SEQUENCE: 108

```
caggtgcacc tggtggagtc tggggggaggc gtggtccagc ctgggaggtc cctgagactc    60
tcctgtgcag cgtctggatt caccttcaac agctttggca tgcactgggt ccgccaggct   120
ccaggcaagg ggctggagtg ggtggcactt atatggtctg atggaagtga taaatactat   180
gcagactccg tgaagggccg attcaccatc tccagagaca attccaagaa cacgctgtat   240
ctgcaaatga acagcctgag agccgaggac acggctgtgt attactgtgc gagagccata   300
gcagccctct actactacta cggtatggac gtctggggcc aagggaccac ggtcaccgtc   360
tcctca                                                              366
```

<210> SEQ ID NO 109
<211> LENGTH: 330
<212> TYPE: DNA
<213> ORGANISM: Homo sapiens

<400> SEQUENCE: 109

```
cagtctgtgt tgacgcagcc gccctcagtg tctgcggccc caggacagaa ggtcaccatc    60
tcctgctctg gaagcagttc caacattggg aataattttg tatcctggta ccagcagttc   120
ccaggaacag cccccaaact cctcatttat gactataata gcgaccctc agggattcct    180
gaccgattct ctggctccaa gtctggcacg tcagccaccc tgggcatcac cggactccag   240
actggggacg aggccgatta ttactgcgga acatgggata gcagcctgag ttcttatgtc   300
ttcggaactg ggaccagggt caccgtccta                                    330
```

<210> SEQ ID NO 110
<211> LENGTH: 366
<212> TYPE: DNA
<213> ORGANISM: Homo sapiens

<400> SEQUENCE: 110

```
caggtgcagc tggtggagtc tggggggaggc gtggtccagc ctgggaggtc cctgagactc    60
tcctgtgcag cgtctggatt caccttcagc agctttggca tgcactgggt ccgccaggct   120
ccaggcaagg ggctggagtg ggtggcactt atatggaatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagagccata   300
gcagccctct actactacta cggtatggac gtctggggcc acgggaccac ggtcaccgtc   360
tcctca                                                              366
```

<210> SEQ ID NO 111
<211> LENGTH: 330
<212> TYPE: DNA
<213> ORGANISM: Homo sapiens

<400> SEQUENCE: 111

```
cagtctgtgt tgacgcagcc gccctcagtg tctgcggccc caggacagaa ggtcaccatc    60
tcctgctctg gaagcagctc caacattggg aataattttg tatcctggta ccagcagctc   120
```

```
ccaggaacag ccccaaaact cctcatttat gactataata agcgaccctc agggattcct    180
gaccgattct ctggctccaa gtctggcacg tcagccaccc tgggcatcac cggactccag    240
actggggacg aggccgatta ttactgcgga acatgggata gcagcctgag tggttatgtc    300
ttcggaactg ggaccagggt caccgtccta                                     330
```

<210> SEQ ID NO 112
<211> LENGTH: 366
<212> TYPE: DNA
<213> ORGANISM: Homo sapiens

<400> SEQUENCE: 112

```
caggtgcagc tggtggagtc tgggggaggc gtggtccagc ctgggaggtc cctgagactc     60
tcctgtgcag cgtctggatt caccttcagc agctttggca tgcactgggt ccgccaggct    120
ccaggcaagg ggctggagtg ggtggcactt atatggaatg atggaagtaa taaatactat    180
gcagactccg tgaagggccg attcaccatc tccagagaca attccaagaa cacgctgtat    240
ctgcaaatga acagcctgag agccgaggac acggctgtgt attactgtgc gagagccata    300
gcagccctct actactacta cggtatggac gtctggggcc aagggaccac ggtcaccgtc    360
tcctca                                                               366
```

<210> SEQ ID NO 113
<211> LENGTH: 330
<212> TYPE: DNA
<213> ORGANISM: Homo sapiens

<400> SEQUENCE: 113

```
cagtctgtgt tgacgcagcc gcccacagtg tctgcggccc caggacagaa ggtcaccatc     60
tcctgctctg gaagcagctc caacattggg aataattttg tatcctggta ccagcagctc    120
ccaggaacag cccccaaaact cctcatttat gactataata agcgaccctc agggattcct    180
gaccgattct ctggctccaa gtctggcacg tcagccaccc tgggcatcac cggactccag    240
actggggacg aggccgatta ctactgcgga acatgggata gcagcctgag tggttatgtc    300
ttcggaactg ggaccagggt caccgtccta                                     330
```

<210> SEQ ID NO 114
<211> LENGTH: 366
<212> TYPE: DNA
<213> ORGANISM: Homo sapiens

<400> SEQUENCE: 114

```
caggtgcagc tggtggagtc tgggggaggc gtggtccagc ctgggaggtc cctgagactc     60
tcctgtgcag cgtctggatt caccttcagg agctatggca tgcactgggt ccgccaggct    120
ccaggcaagg ggctggagtg ggtggcactt atatggcatg atggaagtaa tacatactat    180
gtagactccg tgaagggccg attcaccatc tccagagaca attccaagaa cacgctgtat    240
ctgcaaatga acagcctgag agccgaggac acggctgtgt attactgtgc gagaggtata    300
gcagtggctt actactacta cggtatggac gtctggggcc aagggaccac ggtcaccgtc    360
tcctca                                                               366
```

<210> SEQ ID NO 115
<211> LENGTH: 330
<212> TYPE: DNA
<213> ORGANISM: Homo sapiens

<400> SEQUENCE: 115

-continued

```
cagtctgtgt tgacgcagcc gccctcagtg tctgcggccc caggacagaa ggtcaccatc    60
tcctgctctg gaagcagctc caacattggg aataattttg tatcctggta ccagcagctc   120
ccaggaacag ccccaaaact cctcatttat gacagtaata gcgaccctc agggattcct   180 gaccgattct ctggctccaa gtctggcacg tcagccaccc tggacatcac cggactccag   240
actggggacg aggccgatta ttactgcgga acatgggata gcagcctgag tgcttatgtt   300
ttcggaactg ggaccaaggt caccgtccta                                    330
```

<210> SEQ ID NO 116
<211> LENGTH: 363
<212> TYPE: DNA
<213> ORGANISM: Homo sapiens

<400> SEQUENCE: 116

```
gaggtgcagc tgttggagtc tgggggaggc ttggtacagc ctggggggtc cctgagactc    60
tcctgtgcag cctctggatt cacctttagc agctatgcca tgaactgggt ccgccaggct   120
ccagggaagg ggctggagtg ggtctcaact attagtggta gtggtgataa cacatactac   180
gcagactccg tgaagggccg gttcaccatc tccagagaca attccaagaa cacgctgtat   240
ctgcaaatga acagcctgag agccgaggac acggccgtat attactgtgc gaaaaagttt   300
gtactaatgg tgtatgctat gcttgactac tggggccagg gaaccctggt caccgtctcc   360
tca                                                                 363
```

<210> SEQ ID NO 117
<211> LENGTH: 321
<212> TYPE: DNA
<213> ORGANISM: Homo sapiens

<400> SEQUENCE: 117

```
gacatcctga tgacccagtc tccatcctcc ctgtctgcat ctgttggaga cagagtcacc    60
atcacttgcc gggcaagtca gagcattagc agttatttaa attggtatca gcagaaacca   120
gggaaagccc ctaaggtcct gatctatgct gcctccagtt tgcaaagtgg ggtcccatca   180
aggttcagtg gcagtggatc tgggacagat ttcactctca ccatcaacag tctgcaacct   240
gaagattttg caacttacta ctgtcaacag agttacagtt cccccatcac cttcggccaa   300
gggacacgac tggagattaa a                                             321
```

<210> SEQ ID NO 118
<211> LENGTH: 363
<212> TYPE: DNA
<213> ORGANISM: Homo sapiens

<400> SEQUENCE: 118

```
gaggtgcagc tgttggagtc tgggggaggc ttggtacagc cggggggtc cctgagactc    60 tcctgtgcag cctctggatt cacctttagc agctatgcca tgaactgggt ccgccaggct   120
ccagggaagg ggctggagtg ggtctcaact attagtggta gtggtggtaa cacatactac   180
gcagactccg tgaagggccg gttcaccatc tccagagaca attccaagaa cacgctgtat   240
ctgcaaatga acagcctgag agccgaggac acggccgtat attactgtgc gaaaaagttt   300
gtactaatgg tgtatgctat gcttgactac tggggccagg gaaccctggt caccgtctcc   360
tca                                                                 363
```

<210> SEQ ID NO 119

<211> LENGTH: 321
<212> TYPE: DNA
<213> ORGANISM: Homo sapiens

<400> SEQUENCE: 119

| gacatccaga tgacccagtc tccatcctcc ctatctgcat ctgtaggaga cagagtcacc | 60 |
| atcacttgcc gggcaagtca gagcattagc atctatttaa attggtatca gcagaagcca | 120 |
| gggaaagccc cttacctcct gatctatgct gcagccagtt tgcaaagtgg ggtcccatca | 180 |
| aggttcagtg gcagtggatc tgggacagat ttcactctca ccatcagcag tctgcaacct | 240 |
| gaagattttg caacttacta ctgtcaacag agttacagtg cccccatcac cttcggccaa | 300 |
| gggacacgac tggagattaa a | 321 |

<210> SEQ ID NO 120
<211> LENGTH: 345
<212> TYPE: DNA
<213> ORGANISM: Homo sapiens

<400> SEQUENCE: 120

| caggttcagc tggtgcagtc tggagctgag gtgaagaagc ctggggcctc actgaaggtc | 60 |
| tcctgcaagg cttctggtta cagtttgacc agctatggta tcagctgggt gcgacaggcc | 120 |
| cctggacaag gcttgagtg gatgggatgg atcagcgctt acaatggtaa cacaaactat | 180 |
| gcacagaagg tccagggcag agtcaccatg accacagaca catccacgag cacagtctac | 240 |
| atggaggtga ggagtctgag atctgacgac acggccgtgt attactgtgc gagaggctac | 300 |
| ggtatggacg tctggggcca agggaccacg gtcaccgtct cctca | 345 |

<210> SEQ ID NO 121
<211> LENGTH: 327
<212> TYPE: DNA
<213> ORGANISM: Homo sapiens

<400> SEQUENCE: 121

| cagtctgccc tgactcagcc tgcctccgtg tctgggtctc ctggacagtc gatcaccatc | 60 |
| tcctgcactg gaaccagcag tgacgttggt ggttataact ctgtctcctg gtaccaacag | 120 |
| cacccaggca aaccccccaa actcatgatt tatgaggtca gtaatcggcc ctcaggggtt | 180 |
| tctaatcgct tctctggctc caagtctggc aatacggcct ccctgaccat ctctgggctc | 240 |
| caggctgagg acgaggctga ttatttctgc agctcatata aagcaccag catggtcttc | 300 |
| ggcggaggga ccaagctgac cgtccta | 327 |

<210> SEQ ID NO 122
<211> LENGTH: 345
<212> TYPE: DNA
<213> ORGANISM: Homo sapiens

<400> SEQUENCE: 122

| caggttcagc tggtgcagtc tggagctgag gtgaagaggc ctggggcctc agtgaaggtc | 60 |
| tcctgcaagg cttctggtta caccttgacc agctatggta tcagctgggt gcgacaggcc | 120 |
| cctggacaag gcttgagtg gatgggatgg atcagcgttt acaatggtaa cacaaactat | 180 |
| gcacagaagg tccagggcag agtcaccatg accacagaca catccacgag cacagtctac | 240 |
| atggagctga ggagcctgag ctctgacgac acggccgtgt attactgtgc gagaggctac | 300 |
| ggtatggacg tctggggcca agggaccacg gtcaccgtct cctca | 345 |

<210> SEQ ID NO 123
<211> LENGTH: 327
<212> TYPE: DNA
<213> ORGANISM: Homo sapiens

<400> SEQUENCE: 123

```
cagtctgccc tgactcagcc tgcctccgtg tctgggtctc ctggacagtc gatcaccatc    60
tcctgcactg gaaccagcag tgacgttggt ggttataact ctgtctcctg gtaccaacag   120
cacccaggca aacccccaa actcatgatt tatgaggtca gtaatcggcc ctcagggggtt   180
tctattcgct ctctggctc caagtctggc aacacggcct ccctgaccat ctctgggctc   240
caggctgagg acgaggctga ttatttctgc agctcatata caagcaccag catggtcttc   300
ggcggaggga ccaagctgac cgtccta                                       327
```

<210> SEQ ID NO 124
<211> LENGTH: 345
<212> TYPE: DNA
<213> ORGANISM: Homo sapiens

<400> SEQUENCE: 124

```
caggttcagc tggtgcagtc tggagctgag gtgaagaagc ctggggcctc agtgaaggtc    60
tcctgcaagg cttctggtta ccccttgacc agctatggta tcagctgggt gcgacaggcc   120
cctggacaag gcttgagtg gatgggatgg atcagcgctt acaatggtaa cacaaactat   180
gcacagaagg tccagggcag agtcaccatg accacagaca catccacgag cacagtctac   240
atggagttga ggagcctgag atctgacgac acggccgtgt attactgtgc gagaggctac   300
ggtatggacg tctggggcca aggaccacg gtcaccgtct cctca                    345
```

<210> SEQ ID NO 125
<211> LENGTH: 327
<212> TYPE: DNA
<213> ORGANISM: Homo sapiens

<400> SEQUENCE: 125

```
cagtctgccc tgactcagcc tgcctccgtg tctgggtctc ctggacagtc gatcaccatc    60
tcctgcactg gaaccagcag tgacgttggt ggttataact ctgtctcctg gtaccaacag   120
cacccaggca aacccccaa actcatgatt tatgaggtca gtaatcggcc ctcagggggtt   180
tctaatcgct ctctggctc caagtctggc aatacggcct ccctgaccat ctctgggctc   240
caggctgagg acgaggctga ttatttctgc agctcatata caagcaccag catggtcttc   300
ggcggaggga ccaagctgac cgtccta                                       327
```

<210> SEQ ID NO 126
<211> LENGTH: 345
<212> TYPE: DNA
<213> ORGANISM: Homo sapiens

<400> SEQUENCE: 126

```
caggttcagt tggtgcagtc tggagctgag gtgaagaagc ctggggcctc agtgaaggtc    60
tcctgcaagg cttctggtta cgccttgacc agctatggta tcagctgggt gcgacaggcc   120
cctggacaag gcttgagtg gatgggatgg atcagcgctt acaatggtaa cacaaactat   180
gcacagaagg tccagggcag agtcaccatg accacagaca catccacgag cacagtctac   240
atggagctga ggagcctgag atctgacgac acggccgtgt attactgtgc gagaggctac   300
ggtatggacg tctggggcca aggaccacg gtcaccgtct cctca                    345
```

<210> SEQ ID NO 127
<211> LENGTH: 327
<212> TYPE: DNA
<213> ORGANISM: Homo sapiens

<400> SEQUENCE: 127

```
cagtctgccc tgactcagcc tgcctccgtg tctgggtctc ctggacagtc gatcaccatc        60
tcctgcactg gaaccaacag tgacgttggt ggttataact ctgtctcctg gtaccaacag       120
cacccaggca aacccccaa actcatgatt tatgaggtca gtaatcggcc ctcagggatt        180
tctaatcgct tctctggctc caagtctggc aacacggcct ccctgaccat ctctgggctc       240
caggctgagg acgaggctga ttatttctgc agctcatata caagcaccag catggtcttc       300
ggcggaggga ccaagctgac cgtccta                                            327
```

<210> SEQ ID NO 128
<211> LENGTH: 345
<212> TYPE: DNA
<213> ORGANISM: Homo sapiens

<400> SEQUENCE: 128

```
caggttcagc tggtgcagtc tggagctgag gtgaagaagc ctggggcctc agtgaaggtc        60
tcctgcaagg cttctggtta cagctttacc agctatggta tcagctgggt gcgacaggcc       120
cctggacaag gcttgagtg gatgggatgg gtcagcgctt acaatggtaa cacaaactat        180
gcacagaagt tccagggcag agtcaccatg accacagaca catccacgag cacagcctac       240
atggaactga ggagcctgag atctgacgac acggccgtgt attactgtgc gagaggctac       300
gttatggacg tctggggcca agggaccacg gtcaccgtct cctca                       345
```

<210> SEQ ID NO 129
<211> LENGTH: 327
<212> TYPE: DNA
<213> ORGANISM: Homo sapiens

<400> SEQUENCE: 129

```
cagtctgccc tgactcagcc tgcctccgtt tctgggtctc ctggacagtc gatcaccatc        60
tcctgcactg gaaccagcag tgacgttggt gcttataact ctgtctcctg gtaccaacag       120
cacccaggca aagcccccaa acgcatgatt tatgaggtca gtaatcggcc ctcaggggtt       180
tctaatcgct tctctggctc caagtctggc aacacggcct ccctgaccat ctctgggctc       240
caggctgagg acgaggctga ttattactgc agctcatata caagcaccaa catggtattc       300
ggcggaggga ccaagctgac cgtccta                                            327
```

<210> SEQ ID NO 130
<211> LENGTH: 363
<212> TYPE: DNA
<213> ORGANISM: Homo sapiens

<400> SEQUENCE: 130

```
caggtacagt tgcagcagtc aggtccagga ctggtgaagc cctcgcagac cctctcactc        60
acctgtgcca tctccgggga cagtgtctct agcaacagtg ctgcttggaa ctggatcagg       120
cagtccccat cgagaggcct tgagtggctg ggaaggacat actacaggtc caagtggtat        180
aaaaattatt cagtatctgt gaaaagtcga ataaccatca acccagacac atccaagaac       240
cagttctctc tgcaactgaa ctctgtgact cccggggaca cggctgtgta ttactgtgca       300
agaggggggc caactgctgc ttttgactac tggggccagg gaaccctggt caccgtctcc       360
```

```
tca                                                                 363

<210> SEQ ID NO 131
<211> LENGTH: 330
<212> TYPE: DNA
<213> ORGANISM: Homo sapiens

<400> SEQUENCE: 131
ctttctgccc tgactcagcc tgcctccgtg tctgggtctc ctggacagtc gatcaccatc    60
tcctgcactg gaaccagcag tgatgttggg aattataacc ttgtctcctg gtaccaacag   120
tattcaggca aagcccccaa actcatgatt tatgaggtca gtaagcggcc ctcagggggtt   180 tctaatcgct ctctggctc caagtctggc aacacggcct ccctgacaat ctctgggctc    240
caggctgagg acgaggctga ttattactgc tgctcatatg caggtagtag cactttggtt   300
ttcggcggag ggaccaagct gaccgtccta                                    330

<210> SEQ ID NO 132
<211> LENGTH: 357
<212> TYPE: DNA
<213> ORGANISM: Homo sapiens

<400> SEQUENCE: 132
gaggtgcagt tggtggagtc tgggggaggc ttggtccagc ctgggggggtc cctgagactc    60 tcctgtgtag tctctggatt cacctttagt agctattgga tgagctgggt ccgccaggct   120
ccagggaagg ggctggagtg ggtggccaac ataaagcaag atggaagtga aaatactat    180 gtggactctg tgaagggccg attcaccatc tccagagaca acgccaagaa ctcactgtat   240
ctgcaaatga acagcctgag agccgaggac acggctgtat attactgtgc gagagagtca   300
aactggggat ttgcttttga tatctggggc caagggacaa tggtcaccgt ctcttca     357

<210> SEQ ID NO 133
<211> LENGTH: 327
<212> TYPE: DNA
<213> ORGANISM: Homo sapiens

<400> SEQUENCE: 133
cagtctgtgc tgactcagcc accctcagcg tctgggaccc ccgggcagag ggtcaccatc    60
tcttgttctg gaagcagctc caacatcgga agtaagacta taaactggta ccaacaggtc   120
ccaggaacgg cccccaaact cctcatctat aggaataatc agcggccctt agggtccct    180 gaccgattct ctggctccaa gtctggcacc tcagcctccc tggccatcag tgggctccag   240
tctgaggatg aggctgatta ttattgtgca gcatgggatg acagcctgaa ttgggtgttc   300
ggcggaggga ccaagctgac cgtccta                                      327

<210> SEQ ID NO 134
<211> LENGTH: 357
<212> TYPE: DNA
<213> ORGANISM: Homo sapiens

<400> SEQUENCE: 134
gaggtgcagc tggtggagtc tgggggaggc ttggtccagc ctgggggggtc cctgagactc    60 tcctgtgcag cctctggatt cacctttagt cgctattgga tgagctgggt ccgccaggct   120
ccagggaagg ggctggagtg ggtggccaac ataaagcatg atggaagtga aaatactat    180 gtggactctg tgaagggccg attcaccatt tccagagaca acgccaagaa ctcactgtat   240
```

```
ctgcaaatga acagcctgag agccgaggac acggctgtgt attactgtgc gagagagtca      300
aactggggat tgcttttga tgtctggggc cacgggacaa tggtcaccgt ctcttca          357
```

<210> SEQ ID NO 135
<211> LENGTH: 327
<212> TYPE: DNA
<213> ORGANISM: Homo sapiens

<400> SEQUENCE: 135

```
cagtctgtgc tgactcagcc accctcagcg tctgggcccc ccggacagag ggtcaccatc      60
tcttgttctg gaagcagctc caacatcgga agtaatactg taaactggta ccagcagctc     120
ccaggaacgg cccccaaact cctcatctat agtaataatc ggcggccctc aggggtccct     180
gaccgattct ctggctccaa gtctggcacc tcagcctccc tggccatcag tgggctccag     240
tctgaggatg aggctgatta ttactgtgca gcatgggatg acagcctgaa ttgggtgttc     300
ggcggaggga ccaagctgac cgtccta                                         327
```

<210> SEQ ID NO 136
<211> LENGTH: 351
<212> TYPE: DNA
<213> ORGANISM: Homo sapiens

<400> SEQUENCE: 136

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg gtctcaact attagtggta gtggtggtag gacatattac     180
gcagactccg tgaagggccg gttcaccatc tccagagaca attccaagaa cacgctgtat     240
ctgcaaatga acagcctgag agccgaggac acggccgtat attactgtgc gaaagaagtt     300
ggcagtccct ttgactactg ggccaggga accctggtca ccgtctcctc a               351
```

<210> SEQ ID NO 137
<211> LENGTH: 330
<212> TYPE: DNA
<213> ORGANISM: Homo sapiens

<400> SEQUENCE: 137

```
cagtctgtgt tgacgcagcc gccctcagtg tctgcggccc caggacagaa ggtcaccatc      60
tcctgctctg gaagcaactc caacattggg aataattatg tatcctggta ccagcagctc     120
ccaggaacag cccccaaact cctcatttat gacaataata gcgaccctc aggattcct      180 gaccgattct ctggctccaa ctctggcacg tcagccaccc tgggcatcac cggactccag     240
actggggacg aggccgatta ttactgcgga acatgggata gcagcctgag tgctgtggta     300
ttcggcggag ggaccaagct gaccgtccta                                      330
```

<210> SEQ ID NO 138
<211> LENGTH: 366
<212> TYPE: DNA
<213> ORGANISM: Homo sapiens

<400> SEQUENCE: 138

```
caggtgcagc tggtggagtc tgggggaggc gtggtccagc ctggggaggtc cctgagactc      60 tcctgtgcag cgtctggatt caccttcagt agctatggca tgcactgggt ccgccaggct     120
ccaggcaagg ggctggagtg ggtggcaatt atatggtatg atggaagtaa taatactat     180 gcagactccg tgaagggccg attcaccatc tccagagaca attccaagaa cacactgtat     240
```
cttcaaatga acagcctgag agccgaggac acggctgtgt attactgtgc gaggaggggg   300
ggtctggcag ctcgtccggg cggtatggac gtctggggcc aagggaccac ggtcaccgtc   360
tcctca                                                              366

<210> SEQ ID NO 139
<211> LENGTH: 318
<212> TYPE: DNA
<213> ORGANISM: Homo sapiens

<400> SEQUENCE: 139
tcctatgagc tgactcagcc accctcagtg tctgtgtccc caggacagac agccagaatc    60
acctgctctg gagataaatt gggggataaa tatgcttgct ggtatcagca gaaaccaggc   120
cagtcccctg tgctggtcat ctatcaaaat accaagtggc ccttaggat ccctgagcga   180 ttctctggct ccaagtctgg gaacacagtc actctgacca tcagcgggac ccaggctatg   240
gatgaggctg actattactg tcaggcgtgg gacagcagca ctgtggtatt cggcggaggg   300
accaagctga ccgtcccta                                                318

<210> SEQ ID NO 140
<211> LENGTH: 366
<212> TYPE: DNA
<213> ORGANISM: Homo sapiens

<400> SEQUENCE: 140
caggtgcagc tgcaggagtc gggcccagga ctggtgaagc cttcacagac cctgtccctc    60
acctgcactg tctctggtgg ctccatcagc agtagtgatt actactggag ctggatccgc   120
cagcacccag ggaagggcct ggagtggatt gggtacatct attacagtgg gagcacctac   180
tacaacccgt ccctcaagag tcgaattacc atatcagtag acacgtctaa gaacctgttc   240
tccctgaagt tgagctctgt gactgccgcg gacacggccg tgtattactg tgcgagaggg   300
ggggtgacta cgtactacta cgctatggac gtctggggcc aagggaccac ggtcaccgtc   360
tcctca                                                              366

<210> SEQ ID NO 141
<211> LENGTH: 321
<212> TYPE: DNA
<213> ORGANISM: Homo sapiens

<400> SEQUENCE: 141
gacatacaga tgacccagtc tccatcctcc ctgtctgcat ctgtaggaga cagagtcacc    60
atcacttgcc gggcaagtca gcgcattagc aactatttaa gttggtatct gcagaaacca   120
gggattgccc ctaagctcct gatctatgct gcatccagtt tgcagagtgg ggtcccatca   180
aggttcagtg gcagtggatc tgggacagat ttcactctca ccatcagcag tctgcaatct   240
gaagattttg caacttacta ctgtcaacag agttacagta ccccgctcat tttcggcgga   300
gggaccaagg tggagatcaa a                                             321

<210> SEQ ID NO 142
<211> LENGTH: 369
<212> TYPE: DNA
<213> ORGANISM: Homo sapiens

<400> SEQUENCE: 142
caggtgcagc tggtggagtc tggggaggc gtggtccagc ctgggaggtc cctgagactc    60

```
tcctgtgcag cgtctggatt caccttcagt agctatggca tgcactgggt ccgccaggct    120
ccaggcaagg ggctggagtg ggtggcagtt atatggtatg atggaagtga taaatactat    180
gcagactccg tgaagggccg attcaccatc tccagagaca attccaagaa cacgctgtat    240
ctgcaaatga acagcctgag agccgaggac acggctgtgt attactgtgc gagagagact    300
ggtcccttga aactctacta ctacggtatg gacgtctggg gccaagggac cacggtcacc    360
gtctcctca                                                            369
```

<210> SEQ ID NO 143
<211> LENGTH: 336
<212> TYPE: DNA
<213> ORGANISM: Homo sapiens

<400> SEQUENCE: 143

```
gatattgtga tgactcagtc tccactctcc ctgtccgtca cccctggaga gccgcctcc     60 atctcctgca ggtctagtca gagcctcctg catagtaatg gatacaactt tttgaattgg   120
tacctgcaga agccagggca gtctccacaa ctcctgatct atttgggttc tcatcggcc    180 tccggggtcc ctgacaggtt cagtggcagt ggatcaggca cagattttac actggaaatc   240
agcagagtgg aggctgagga tgttggggtt tattactgca tgcaagttct acaaactcca   300
ttcactttcg gccctgggac caaagtggat atcaaa                              336
```

<210> SEQ ID NO 144
<211> LENGTH: 357
<212> TYPE: DNA
<213> ORGANISM: Homo sapiens

<400> SEQUENCE: 144

```
gaggtgcagc tggtggagtc tgggggaggc ttggtccagc ctgggggtc cctgagactc      60 tcctgtgcag cctctggact cacctttagt aacttttgga tgagctgggt ccgccaggct    120
ccagggaagg ggctggagtg ggtggccaac ataaaagcaag atggaagtga gaaatactat   180
gtggactctg tgaagggccg attcaccatc tccagagaca acgccaagaa ttcactgtat    240
ctgcaaatga acagcctgag agccgaggac acggctgtgt attcctgtac gagagagtca    300
aactggggat ttgcttttga tatctggggc caagggacaa tggtcaccgt ctcttca       357
```

<210> SEQ ID NO 145
<211> LENGTH: 327
<212> TYPE: DNA
<213> ORGANISM: Homo sapiens

<400> SEQUENCE: 145

```
cagtctgtgc tgactcagcc accctcagcg tctgggaccc ccgggcagag ggtcaccatc     60
tcttgttctg gaagcagctc caacatcgga agtaaaactg taaactggta ccagcagttc    120
ccaggaacgg cccccaaact cctcatctat agtaataatc ggcggccctc aggggtccct    180
gaccgattct ctggctccaa gtctggcacc tcagcctccc tggccatcag tgggctccag   240
tctgaggatg aggctgatta ttactgtgca gcatgggatg acagcctgaa tgggtgttc    300 ggcgcaggga ccaagctgac cgtccta                                       327
```

<210> SEQ ID NO 146
<211> LENGTH: 345
<212> TYPE: DNA
<213> ORGANISM: Homo sapiens

<400> SEQUENCE: 146

```
caggttcagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag ggcttgagtg gatgggatgg atcagcactt acaatggtaa cacaaactat     180
gcacagaagt tccagggcag agtcaccatg accacagaca catccacgag cacagcctac     240
atggagctga ggagcctgag atctgacgac acggccgttt attactgtgc gagagggtat     300
actcgggact actggggcca gggaaccctg gtcaccgtct cctca                     345

<210> SEQ ID NO 147
<211> LENGTH: 348
<212> TYPE: DNA
<213> ORGANISM: Homo sapiens

<400> SEQUENCE: 147
cagcctgtgc tgactcagcc acttttgca tcagcctccc tgggagcctc ggtcacactc       60
acctgcaccc tgagcagcgg ctacagtagt tatgaagtgg actggtatca gcagagacca    120
gggaagggcc cccggtttgt catgcgagtg acactggtg ggattgtggg atccaagggg     180
gaaggcatcc ctgatcgctt ctcagttttg ggctcaggcc tgaatcggta tctgaccatc     240
aagaacatcc aggaagagga tgagagtgac taccactgtg gggcagacca tggcagtggg    300
accaacttcg tggtggtatt cggcggaggg accaagctga ccgtccta                 348

<210> SEQ ID NO 148
<211> LENGTH: 348
<212> TYPE: DNA
<213> ORGANISM: Homo sapiens

<400> SEQUENCE: 148
caggtgcagc tacagcagtg gggcgcagga ctgttgaagc cttcggagac cctgtccctc       60
acctgcgctg tctatggtgg gtccttcagt gcgtactact ggaactggat ccgccagccc    120
ccagggaagg ggctggagtg gattgggaa atcaatcata gtggaagaac cgactacaac     180
ccgtccctca agagtcgagt caccatatca gtagacacgt ccaagaagca gttctccctg    240
aagctgaact ctgtgaccgc cgcggacacg gctgtgtatt actgtgcgag agggcagctc    300 gtccccttg actactgggg ccagggaacc ctggtcaccg tctcttca                  348

<210> SEQ ID NO 149
<211> LENGTH: 330
<212> TYPE: DNA
<213> ORGANISM: Homo sapiens

<400> SEQUENCE: 149
cagtctgtgc tgactcagcc accctcagcg tctgggaccc ccgggcagag ggtcaccatc       60
tcttgttctg gaagcagctc caacatcgga agtaatactg taaattggta tcagcaactc    120
ccaggaacgg cccccaaact cctcatctat agtaataatc agcggccctc aggggtccct    180
gaccgattct ctggctccaa gtctggcacc tcagcctccc tggccatcag tgggctccag    240
tctgaggatg aggctgatta ttactgtgca gtatgggatg acagcctgaa tggttgggtg    300
ttcggcggag ggaccaagct gaccgtccta                                     330

<210> SEQ ID NO 150
<211> LENGTH: 345
<212> TYPE: DNA
<213> ORGANISM: Homo sapiens
```

<400> SEQUENCE: 150

```
caggttcagc tggtgcagtc tggagctgag gtgaagaagc ctggggcctc agtgaaggtc    60
tcctgcaagg cttctggtta cacctttccc agctatggta tcagctgggt gcgacaggcc   120
cctggacaag gcttgagtg gatgggatgg atcagcgctt acaatggtaa cacaaactat   180
gcagagaagc tccagggcag agtcaccatg accacagaca catccacgag cacagcctac   240
atggaggtga ggagcctgag atctgacgac acggccgtgt tttactgtgc gagaggctac   300
gttatggacg tctggggcca aggaccacg gtcaccgtct cctct                    345
```

<210> SEQ ID NO 151
<211> LENGTH: 327
<212> TYPE: DNA
<213> ORGANISM: Homo sapiens

<400> SEQUENCE: 151

```
cagtctgccc tgactcagcc tgcctccgtg tctgggtctc ctggacagtc gatcaccatc    60
tcctgcactg gaaccagcag tgacgttggt cgttataatt ctgtctcctg gtaccaacac   120
cacccaggca aagcccccaa agtcatgatt tatgaggtca gtaatcggcc ctcaggggtt   180
tctactcgct tctctggctc caagtctggc aacacggcct ccctgaccat ctctgggctc   240
caggctgagg acgaggctga ttattactgc agctcatata caagcagcag cgttgtattc   300
ggcggaggga ccaaactgac cgtccta                                       327
```

<210> SEQ ID NO 152
<211> LENGTH: 369
<212> TYPE: DNA
<213> ORGANISM: Homo sapiens

<400> SEQUENCE: 152

```
gaggtgcagc tggtggagtc tgggggaggc ctggtcaagc ctgggggtc cctgagactc     60
tcctgtgcag cctctggatt caccttcagt agctatagca tgaactgggt ccgccaggct   120
ccagggaagg gctggagtg gtctcatcc attagtagta gtagtagtta catttcctac   180
gcagactcag tgaagggccg attcaccatc tccagagaca cgccaagaa ctcactgtat   240
ctgcaaatga acagcctgag agccgaggac acggctgtgt atttctgtgc gagagattac   300
gattttggaa gtgcttacta tgatgctttt gatgtctggg gccaagggac aatggtcacc   360
gtctcttca                                                          369
```

<210> SEQ ID NO 153
<211> LENGTH: 333
<212> TYPE: DNA
<213> ORGANISM: Homo sapiens

<400> SEQUENCE: 153

```
cagtctgtgc tgacgcagcc gccctcagtg tctggggccc cagggcagag ggtcaccatc    60
tcctgcactg ggagcagctc caacatcggg gcaggttatg atgtacactg gtaccagcag   120
cttccaggaa cagcccccaa actcctcatc tctggtaaca gcaatcggcc ctcaggggtc   180
cctgaccgat tctctggctc caagtctggc acctcagcct ccctggccat cactgggctc   240
caggctgagg atgaggctga ttattactgc cagtcctatg acagcagcct gagtggttcg   300
gtattcggcg gagggaccaa gctgaccgtc cta                                333
```

<210> SEQ ID NO 154
<211> LENGTH: 326

```
<212> TYPE: PRT
<213> ORGANISM: Homo sapiens

<400> SEQUENCE: 154

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 155
<211> LENGTH: 327
<212> TYPE: PRT
<213> ORGANISM: Homo sapiens

<400> SEQUENCE: 155

Ala Ser Thr Lys Gly Pro Ser Val Phe Pro Leu Ala Pro Cys Ser Arg
 1               5                  10                  15
```

```
Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 156
<211> LENGTH: 105
<212> TYPE: PRT
<213> ORGANISM: Homo sapiens

<400> SEQUENCE: 156

Gln Pro Lys Ala Ala Pro Ser Val Thr Leu Phe Pro Pro Ser Ser Glu
  1               5                  10                  15

Glu Leu Gln Ala Asn Lys Ala Thr Leu Val Cys Leu Ile Ser Asp Phe
             20                  25                  30

Tyr Pro Gly Ala Val Thr Val Ala Trp Lys Ala Asp Ser Ser Pro Val
         35                  40                  45

Lys Ala Gly Val Glu Thr Thr Thr Pro Ser Lys Gln Ser Asn Asn Lys
     50                  55                  60
```

```
Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Cys Ser
            100                 105
```

<210> SEQ ID NO 157
<211> LENGTH: 106
<212> TYPE: PRT
<213> ORGANISM: Homo sapiens

<400> SEQUENCE: 157

```
Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
         35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105
```

<210> SEQ ID NO 158
<211> LENGTH: 14
<212> TYPE: PRT
<213> ORGANISM: Homo sapiens

<400> SEQUENCE: 158

```
Thr Gly Thr Ser Ser Asp Val Gly Gly Tyr Asn Ser Val Ser
 1               5                  10
```

<210> SEQ ID NO 159
<211> LENGTH: 14
<212> TYPE: PRT
<213> ORGANISM: Homo sapiens

<400> SEQUENCE: 159

```
Thr Gly Thr Asn Ser Asp Val Gly Gly Tyr Asn Ser Val Ser
 1               5                  10
```

<210> SEQ ID NO 160
<211> LENGTH: 14
<212> TYPE: PRT
<213> ORGANISM: Homo sapiens

<400> SEQUENCE: 160

```
Thr Gly Thr Ser Ser Asp Val Gly Ala Tyr Asn Ser Val Ser
 1               5                  10
```

<210> SEQ ID NO 161
<211> LENGTH: 14
<212> TYPE: PRT
<213> ORGANISM: Homo sapiens

<400> SEQUENCE: 161

Thr Gly Thr Ser Ser Asp Val Gly Arg Tyr Asn Ser Val Ser
1               5                   10

<210> SEQ ID NO 162
<211> LENGTH: 7
<212> TYPE: PRT
<213> ORGANISM: Homo sapiens

<400> SEQUENCE: 162

Glu Val Ser Asn Arg Pro Ser
1               5

<210> SEQ ID NO 163
<211> LENGTH: 7
<212> TYPE: PRT
<213> ORGANISM: Homo sapiens

<400> SEQUENCE: 163

Glu Val Thr Asn Arg Pro Ser
1               5

<210> SEQ ID NO 164
<211> LENGTH: 9
<212> TYPE: PRT
<213> ORGANISM: Homo sapiens

<400> SEQUENCE: 164

Ser Ser Tyr Thr Ser Thr Ser Met Val
1               5

<210> SEQ ID NO 165
<211> LENGTH: 9
<212> TYPE: PRT
<213> ORGANISM: Homo sapiens

<400> SEQUENCE: 165

Asn Ser Tyr Thr Ser Thr Ser Met Val
1               5

<210> SEQ ID NO 166
<211> LENGTH: 9
<212> TYPE: PRT
<213> ORGANISM: Homo sapiens

<400> SEQUENCE: 166

Ser Ser Tyr Thr Ser Thr Asn Met Val
1               5

<210> SEQ ID NO 167
<211> LENGTH: 9
<212> TYPE: PRT
<213> ORGANISM: Homo sapiens

<400> SEQUENCE: 167

Ser Ser Tyr Thr Ser Ser Ser Val Val
1               5

<210> SEQ ID NO 168
<211> LENGTH: 10
<212> TYPE: PRT
<213> ORGANISM: Homo sapiens

<400> SEQUENCE: 168

Gly Tyr Pro Leu Thr Ser Tyr Gly Ile Ser

```
                1               5                   10
```

<210> SEQ ID NO 169
<211> LENGTH: 10
<212> TYPE: PRT
<213> ORGANISM: Homo sapiens

<400> SEQUENCE: 169

```
Gly Tyr Ser Leu Thr Ser Tyr Gly Ile Ser
 1               5                   10
```

<210> SEQ ID NO 170
<211> LENGTH: 10
<212> TYPE: PRT
<213> ORGANISM: Homo sapiens

<400> SEQUENCE: 170

```
Gly Tyr Ala Leu Thr Ser Tyr Gly Ile Ser
 1               5                   10
```

<210> SEQ ID NO 171
<211> LENGTH: 10
<212> TYPE: PRT
<213> ORGANISM: Homo sapiens

<400> SEQUENCE: 171

```
Gly Tyr Thr Leu Thr Ser Tyr Gly Ile Ser
 1               5                   10
```

<210> SEQ ID NO 172
<211> LENGTH: 10
<212> TYPE: PRT
<213> ORGANISM: Homo sapiens

<400> SEQUENCE: 172

```
Gly Tyr Ser Phe Thr Ser Tyr Gly Ile Ser
 1               5                   10
```

<210> SEQ ID NO 173
<211> LENGTH: 10
<212> TYPE: PRT
<213> ORGANISM: Homo sapiens

<400> SEQUENCE: 173

```
Gly Tyr Thr Phe Pro Ser Tyr Gly Ile Ser
 1               5                   10
```

<210> SEQ ID NO 174
<211> LENGTH: 17
<212> TYPE: PRT
<213> ORGANISM: Homo sapiens

<400> SEQUENCE: 174

```
Trp Ile Ser Ala Tyr Asn Gly Asn Thr Asn Tyr Ala Gln Lys Val Gln
 1               5                   10                  15

Gly
```

<210> SEQ ID NO 175
<211> LENGTH: 17
<212> TYPE: PRT
<213> ORGANISM: Homo sapiens

<400> SEQUENCE: 175

```
Trp Val Ser Phe Tyr Asn Gly Asn Thr Asn Tyr Ala Gln Lys Leu Gln
```

-continued

```
                1               5                  10                  15
Gly

<210> SEQ ID NO 176
<211> LENGTH: 17
<212> TYPE: PRT
<213> ORGANISM: Homo sapiens

<400> SEQUENCE: 176

Trp Ile Ser Phe Tyr Asn Gly Asn Thr Asn Tyr Ala Gln Lys Val Gln
 1               5                  10                  15
Gly

<210> SEQ ID NO 177
<211> LENGTH: 17
<212> TYPE: PRT
<213> ORGANISM: Homo sapiens

<400> SEQUENCE: 177

Trp Ile Ser Val Tyr Asn Gly Asn Thr Asn Tyr Ala Gln Lys Val Gln
 1               5                  10                  15
Gly

<210> SEQ ID NO 178
<211> LENGTH: 17
<212> TYPE: PRT
<213> ORGANISM: Homo sapiens

<400> SEQUENCE: 178

Trp Val Ser Ala Tyr Asn Gly Asn Thr Asn Tyr Ala Gln Lys Phe Gln
 1               5                  10                  15
Gly

<210> SEQ ID NO 179
<211> LENGTH: 17
<212> TYPE: PRT
<213> ORGANISM: Homo sapiens

<400> SEQUENCE: 179

Trp Ile Ser Ala Tyr Asn Gly Asn Thr Asn Tyr Ala Glu Lys Leu Gln
 1               5                  10                  15
Gly

<210> SEQ ID NO 180
<211> LENGTH: 6
<212> TYPE: PRT
<213> ORGANISM: Homo sapiens

<400> SEQUENCE: 180

Gly Tyr Gly Met Asp Val
 1               5

<210> SEQ ID NO 181
<211> LENGTH: 6
<212> TYPE: PRT
<213> ORGANISM: Homo sapiens

<400> SEQUENCE: 181

Gly Tyr Val Met Asp Val
 1               5
```

```
<210> SEQ ID NO 182
<211> LENGTH: 13
<212> TYPE: PRT
<213> ORGANISM: Homo sapiens

<400> SEQUENCE: 182

Ser Gly Ser Ser Ser Asn Ile Gly Asn Asn Phe Val Ser
1               5                   10

<210> SEQ ID NO 183
<211> LENGTH: 7
<212> TYPE: PRT
<213> ORGANISM: Homo sapiens

<400> SEQUENCE: 183

Asp Tyr Asn Lys Arg Pro Ser
1               5

<210> SEQ ID NO 184
<211> LENGTH: 7
<212> TYPE: PRT
<213> ORGANISM: Homo sapiens

<400> SEQUENCE: 184

Asp Ser Asn Lys Arg Pro Ser
1               5

<210> SEQ ID NO 185
<211> LENGTH: 11
<212> TYPE: PRT
<213> ORGANISM: Homo sapiens

<400> SEQUENCE: 185

Gly Thr Trp Asp Ser Ser Leu Ser Gly Tyr Val
1               5                   10

<210> SEQ ID NO 186
<211> LENGTH: 11
<212> TYPE: PRT
<213> ORGANISM: Homo sapiens

<400> SEQUENCE: 186

Gly Thr Trp Asp Ser Ser Leu Ser Ala Tyr Val
1               5                   10

<210> SEQ ID NO 187
<211> LENGTH: 11
<212> TYPE: PRT
<213> ORGANISM: Homo sapiens

<400> SEQUENCE: 187

Gly Thr Trp Asp Ser Ser Leu Ser Ser Tyr Val
1               5                   10

<210> SEQ ID NO 188
<211> LENGTH: 10
<212> TYPE: PRT
<213> ORGANISM: Homo sapiens

<400> SEQUENCE: 188

Gly Phe Thr Phe Ser Ser Phe Gly Met His
1               5                   10

<210> SEQ ID NO 189
<211> LENGTH: 10
```

<212> TYPE: PRT
<213> ORGANISM: Homo sapiens

<400> SEQUENCE: 189

Gly Phe Thr Phe Asn Ser Phe Gly Met His
1               5                   10

<210> SEQ ID NO 190
<211> LENGTH: 10
<212> TYPE: PRT
<213> ORGANISM: Homo sapiens

<400> SEQUENCE: 190

Gly Phe Thr Phe Arg Ser Tyr Gly Met His
1               5                   10

<210> SEQ ID NO 191
<211> LENGTH: 17
<212> TYPE: PRT
<213> ORGANISM: Homo sapiens

<400> SEQUENCE: 191

Leu Ile Trp Asn Asp Gly Ser Asn Lys Tyr Tyr Ala Asp Ser Val Lys
1               5                   10                  15

Gly

<210> SEQ ID NO 192
<211> LENGTH: 17
<212> TYPE: PRT
<213> ORGANISM: Homo sapiens

<400> SEQUENCE: 192

Leu Ile Trp Ser Asp Gly Ser Asp Glu Tyr Tyr Ala Asp Ser Val Lys
1               5                   10                  15

Gly

<210> SEQ ID NO 193
<211> LENGTH: 17
<212> TYPE: PRT
<213> ORGANISM: Homo sapiens

<400> SEQUENCE: 193

Leu Ile Trp Ser Asp Gly Ser Asp Lys Tyr Tyr Ala Asp Ser Val Lys
1               5                   10                  15

Gly

<210> SEQ ID NO 194
<211> LENGTH: 17
<212> TYPE: PRT
<213> ORGANISM: Homo sapiens

<400> SEQUENCE: 194

Leu Ile Trp His Asp Gly Ser Asn Thr Tyr Tyr Val Asp Ser Val Lys
1               5                   10                  15

Gly

<210> SEQ ID NO 195
<211> LENGTH: 13
<212> TYPE: PRT
<213> ORGANISM: Homo sapiens

<400> SEQUENCE: 195

```
Ala Ile Ala Ala Leu Tyr Tyr Tyr Tyr Gly Met Asp Val
 1               5                  10
```

<210> SEQ ID NO 196
<211> LENGTH: 13
<212> TYPE: PRT
<213> ORGANISM: Homo sapiens

<400> SEQUENCE: 196

```
Gly Ile Ala Val Ala Tyr Tyr Tyr Tyr Gly Met Asp Val
 1               5                  10
```

<210> SEQ ID NO 197
<211> LENGTH: 13
<212> TYPE: PRT
<213> ORGANISM: Homo sapiens

<400> SEQUENCE: 197

```
Ser Gly Ser Ser Ser Asn Ile Gly Ser Asn Thr Val Asn
 1               5                  10
```

<210> SEQ ID NO 198
<211> LENGTH: 13
<212> TYPE: PRT
<213> ORGANISM: Homo sapiens

<400> SEQUENCE: 198

```
Ser Gly Ser Ser Ser Asn Ile Gly Ser Lys Thr Val Asn
 1               5                  10
```

<210> SEQ ID NO 199
<211> LENGTH: 7
<212> TYPE: PRT
<213> ORGANISM: Homo sapiens

<400> SEQUENCE: 199

```
Ser Asn Asn Arg Arg Pro Ser
 1               5
```

<210> SEQ ID NO 200
<211> LENGTH: 7
<212> TYPE: PRT
<213> ORGANISM: Homo sapiens

<400> SEQUENCE: 200

```
Arg Asn Asn Gln Arg Pro Leu
 1               5
```

<210> SEQ ID NO 201
<211> LENGTH: 10
<212> TYPE: PRT
<213> ORGANISM: Homo sapiens

<400> SEQUENCE: 201

```
Ala Ala Trp Asp Asp Ser Leu Asn Trp Val
 1               5                  10
```

<210> SEQ ID NO 202
<211> LENGTH: 10
<212> TYPE: PRT
<213> ORGANISM: Homo sapiens

<400> SEQUENCE: 202

```
Gly Phe Thr Phe Ser Arg Tyr Trp Met Ser
 1               5                  10
```

<210> SEQ ID NO 203
<211> LENGTH: 10
<212> TYPE: PRT
<213> ORGANISM: Homo sapiens

<400> SEQUENCE: 203

Gly Leu Thr Phe Ser Asn Phe Trp Met Ser
1               5                   10

<210> SEQ ID NO 204
<211> LENGTH: 10
<212> TYPE: PRT
<213> ORGANISM: Homo sapiens

<400> SEQUENCE: 204

Gly Phe Thr Phe Ser Ser Tyr Trp Met Ser
1               5                   10

<210> SEQ ID NO 205
<211> LENGTH: 17
<212> TYPE: PRT
<213> ORGANISM: Homo sapiens

<400> SEQUENCE: 205

Asn Ile Lys His Asp Gly Ser Glu Lys Tyr Tyr Val Asp Ser Val Lys
1               5                   10                  15

Gly

<210> SEQ ID NO 206
<211> LENGTH: 17
<212> TYPE: PRT
<213> ORGANISM: Homo sapiens

<400> SEQUENCE: 206

Asn Ile Lys Gln Asp Gly Ser Glu Lys Tyr Tyr Val Asp Ser Val Lys
1               5                   10                  15

Gly

<210> SEQ ID NO 207
<211> LENGTH: 10
<212> TYPE: PRT
<213> ORGANISM: Homo sapiens

<400> SEQUENCE: 207

Glu Ser Asn Trp Gly Phe Ala Phe Asp Val
1               5                   10

<210> SEQ ID NO 208
<211> LENGTH: 10
<212> TYPE: PRT
<213> ORGANISM: Homo sapiens

<400> SEQUENCE: 208

Glu Ser Asn Trp Gly Phe Ala Phe Asp Ile
1               5                   10

<210> SEQ ID NO 209
<211> LENGTH: 11
<212> TYPE: PRT
<213> ORGANISM: Homo sapiens

<400> SEQUENCE: 209

```
Arg Ala Ser Gln Ser Ile Ser Ser Tyr Leu Asn
 1               5                   10
```

<210> SEQ ID NO 210
<211> LENGTH: 11
<212> TYPE: PRT
<213> ORGANISM: Homo sapiens

<400> SEQUENCE: 210

```
Arg Ala Ser Gln Ser Ile Ser Ile Tyr Leu Asn
 1               5                   10
```

<210> SEQ ID NO 211
<211> LENGTH: 7
<212> TYPE: PRT
<213> ORGANISM: Homo sapiens

<400> SEQUENCE: 211

```
Ala Ala Ser Ser Leu Gln Ser
 1               5
```

<210> SEQ ID NO 212
<211> LENGTH: 7
<212> TYPE: PRT
<213> ORGANISM: Homo sapiens

<400> SEQUENCE: 212

```
Ala Ala Ala Ser Leu Gln Ser
 1               5
```

<210> SEQ ID NO 213
<211> LENGTH: 9
<212> TYPE: PRT
<213> ORGANISM: Homo sapiens

<400> SEQUENCE: 213

```
Gln Gln Ser Tyr Ser Ser Pro Ile Thr
 1               5
```

<210> SEQ ID NO 214
<211> LENGTH: 9
<212> TYPE: PRT
<213> ORGANISM: Homo sapiens

<400> SEQUENCE: 214

```
Gln Gln Ser Tyr Ser Ala Pro Ile Thr
 1               5
```

<210> SEQ ID NO 215
<211> LENGTH: 10
<212> TYPE: PRT
<213> ORGANISM: Homo sapiens

<400> SEQUENCE: 215

```
Gly Phe Thr Phe Ser Ser Tyr Ala Met Asn
 1               5                   10
```

<210> SEQ ID NO 216
<211> LENGTH: 17
<212> TYPE: PRT
<213> ORGANISM: Homo sapiens

<400> SEQUENCE: 216

```
Thr Ile Ser Gly Ser Gly Asp Asn Thr Tyr Tyr Ala Asp Ser Val Lys
 1               5                   10                  15
```

Gly

<210> SEQ ID NO 217
<211> LENGTH: 17
<212> TYPE: PRT
<213> ORGANISM: Homo sapiens

<400> SEQUENCE: 217

Thr Ile Ser Gly Ser Gly Gly Asn Thr Tyr Tyr Ala Asp Ser Val Lys
1               5                   10                  15
Gly

<210> SEQ ID NO 218
<211> LENGTH: 12
<212> TYPE: PRT
<213> ORGANISM: Homo sapiens

<400> SEQUENCE: 218

Lys Phe Val Leu Met Val Tyr Ala Met Leu Asp Tyr
1               5                   10

<210> SEQ ID NO 219
<211> LENGTH: 11
<212> TYPE: PRT
<213> ORGANISM: Homo sapiens

<400> SEQUENCE: 219

Arg Ala Ser Gln Arg Ile Ser Asn Tyr Leu Ser
1               5                   10

<210> SEQ ID NO 220
<211> LENGTH: 16
<212> TYPE: PRT
<213> ORGANISM: Homo sapiens

<400> SEQUENCE: 220

Arg Ser Ser Gln Ser Leu Leu His Ser Asn Gly Tyr Asn Phe Leu Asn
1               5                   10                  15

<210> SEQ ID NO 221
<211> LENGTH: 14
<212> TYPE: PRT
<213> ORGANISM: Homo sapiens

<400> SEQUENCE: 221

Thr Gly Thr Ser Ser Asp Val Gly Asn Tyr Asn Leu Val Ser
1               5                   10

<210> SEQ ID NO 222
<211> LENGTH: 14
<212> TYPE: PRT
<213> ORGANISM: Homo sapiens

<400> SEQUENCE: 222

Thr Gly Ser Ser Ser Asn Ile Gly Ala Gly Tyr Asp Val His
1               5                   10

<210> SEQ ID NO 223
<211> LENGTH: 14
<212> TYPE: PRT
<213> ORGANISM: Homo sapiens

<400> SEQUENCE: 223

```
Thr Gly Ser Ser Ser Asn Ile Gly Ala His Tyr Asp Val His
1               5                   10
```

<210> SEQ ID NO 224
<211> LENGTH: 13
<212> TYPE: PRT
<213> ORGANISM: Homo sapiens

<400> SEQUENCE: 224

```
Ser Gly Ser Asn Ser Asn Ile Gly Asn Asn Tyr Val Ser
1               5                   10
```

<210> SEQ ID NO 225
<211> LENGTH: 11
<212> TYPE: PRT
<213> ORGANISM: Homo sapiens

<400> SEQUENCE: 225

```
Ser Gly Asp Lys Leu Gly Asp Lys Tyr Ala Cys
1               5                   10
```

<210> SEQ ID NO 226
<211> LENGTH: 12
<212> TYPE: PRT
<213> ORGANISM: Homo sapiens

<400> SEQUENCE: 226

```
Thr Leu Ser Ser Gly Tyr Ser Ser Tyr Glu Val Asp
1               5                   10
```

<210> SEQ ID NO 227
<211> LENGTH: 7
<212> TYPE: PRT
<213> ORGANISM: Homo sapiens

<400> SEQUENCE: 227

```
Leu Gly Ser His Arg Ala Ser
1               5
```

<210> SEQ ID NO 228
<211> LENGTH: 7
<212> TYPE: PRT
<213> ORGANISM: Homo sapiens

<400> SEQUENCE: 228

```
Glu Val Ser Lys Arg Pro Ser
1               5
```

<210> SEQ ID NO 229
<211> LENGTH: 7
<212> TYPE: PRT
<213> ORGANISM: Homo sapiens

<400> SEQUENCE: 229

```
Gly Asn Ser Asn Arg Pro Ser
1               5
```

<210> SEQ ID NO 230
<211> LENGTH: 7
<212> TYPE: PRT
<213> ORGANISM: Homo sapiens

<400> SEQUENCE: 230

```
Gly Asn Thr Tyr Arg Pro Ser
1               5
```

<210> SEQ ID NO 231
<211> LENGTH: 7
<212> TYPE: PRT
<213> ORGANISM: Homo sapiens

<400> SEQUENCE: 231

Ser Asn Asn Gln Arg Pro Ser
1               5

<210> SEQ ID NO 232
<211> LENGTH: 7
<212> TYPE: PRT
<213> ORGANISM: Homo sapiens

<400> SEQUENCE: 232

Asp Asn Asn Lys Arg Pro Ser
1               5

<210> SEQ ID NO 233
<211> LENGTH: 7
<212> TYPE: PRT
<213> ORGANISM: Homo sapiens

<400> SEQUENCE: 233

Gln Asn Thr Lys Trp Pro Leu
1               5

<210> SEQ ID NO 234
<211> LENGTH: 7
<212> TYPE: PRT
<213> ORGANISM: Homo sapiens

<400> SEQUENCE: 234

Val Asp Thr Gly Gly Ile Val
1               5

<210> SEQ ID NO 235
<211> LENGTH: 9
<212> TYPE: PRT
<213> ORGANISM: Homo sapiens

<400> SEQUENCE: 235

Gln Gln Ser Tyr Ser Thr Pro Leu Ile
1               5

<210> SEQ ID NO 236
<211> LENGTH: 9
<212> TYPE: PRT
<213> ORGANISM: Homo sapiens

<400> SEQUENCE: 236

Met Gln Val Leu Gln Thr Pro Phe Thr
1               5

<210> SEQ ID NO 237
<211> LENGTH: 10
<212> TYPE: PRT
<213> ORGANISM: Homo sapiens

<400> SEQUENCE: 237

Cys Ser Tyr Ala Gly Ser Ser Thr Leu Val
1               5                   10

```
<210> SEQ ID NO 238
<211> LENGTH: 11
<212> TYPE: PRT
<213> ORGANISM: Homo sapiens

<400> SEQUENCE: 238

Gln Ser Tyr Asp Ser Ser Leu Ser Gly Ser Val
 1               5                  10

<210> SEQ ID NO 239
<211> LENGTH: 11
<212> TYPE: PRT
<213> ORGANISM: Homo sapiens

<400> SEQUENCE: 239

Gln Ser Tyr Asp Asn Ser Leu Ser Gly Val Val
 1               5                  10

<210> SEQ ID NO 240
<211> LENGTH: 11
<212> TYPE: PRT
<213> ORGANISM: Homo sapiens

<400> SEQUENCE: 240

Ala Val Trp Asp Asp Ser Leu Asn Gly Trp Val
 1               5                  10

<210> SEQ ID NO 241
<211> LENGTH: 11
<212> TYPE: PRT
<213> ORGANISM: Homo sapiens

<400> SEQUENCE: 241

Gly Thr Trp Asp Ser Ser Leu Ser Ala Val Val
 1               5                  10

<210> SEQ ID NO 242
<211> LENGTH: 9
<212> TYPE: PRT
<213> ORGANISM: Homo sapiens

<400> SEQUENCE: 242

Gln Ala Trp Asp Ser Ser Thr Val Val
 1               5

<210> SEQ ID NO 243
<211> LENGTH: 18
<212> TYPE: PRT
<213> ORGANISM: Homo sapiens

<400> SEQUENCE: 243

Ser Asp Tyr His Cys Gly Ala Asp His Gly Ser Gly Thr Asn Phe Val
 1               5                  10                  15

Val Val

<210> SEQ ID NO 244
<211> LENGTH: 10
<212> TYPE: PRT
<213> ORGANISM: Homo sapiens

<400> SEQUENCE: 244

Gly Tyr Thr Phe Thr Ser Tyr Gly Ile Ser
 1               5                  10
```

```
<210> SEQ ID NO 245
<211> LENGTH: 10
<212> TYPE: PRT
<213> ORGANISM: Homo sapiens

<400> SEQUENCE: 245

Gly Phe Thr Phe Ser Ser Tyr Ala Met Ser
1               5                   10

<210> SEQ ID NO 246
<211> LENGTH: 10
<212> TYPE: PRT
<213> ORGANISM: Homo sapiens

<400> SEQUENCE: 246

Gly Phe Thr Phe Ser Ser Tyr Gly Met His
1               5                   10

<210> SEQ ID NO 247
<211> LENGTH: 10
<212> TYPE: PRT
<213> ORGANISM: Homo sapiens

<400> SEQUENCE: 247

Gly Phe Thr Phe Ser Ser Tyr Ser Met Asn
1               5                   10

<210> SEQ ID NO 248
<211> LENGTH: 12
<212> TYPE: PRT
<213> ORGANISM: Homo sapiens

<400> SEQUENCE: 248

Gly Gly Ser Ile Ser Ser Gly Gly Tyr Tyr Trp Ser
1               5                   10

<210> SEQ ID NO 249
<211> LENGTH: 12
<212> TYPE: PRT
<213> ORGANISM: Homo sapiens

<400> SEQUENCE: 249

Gly Gly Ser Ile Ser Ser Ser Asp Tyr Tyr Trp Ser
1               5                   10

<210> SEQ ID NO 250
<211> LENGTH: 10
<212> TYPE: PRT
<213> ORGANISM: Homo sapiens

<400> SEQUENCE: 250

Gly Gly Ser Phe Ser Ala Tyr Tyr Trp Asn
1               5                   10

<210> SEQ ID NO 251
<211> LENGTH: 12
<212> TYPE: PRT
<213> ORGANISM: Homo sapiens

<400> SEQUENCE: 251

Gly Asp Ser Val Ser Ser Asn Ser Ala Ala Trp Asn
1               5                   10

<210> SEQ ID NO 252
<211> LENGTH: 17
```

```
<212> TYPE: PRT
<213> ORGANISM: Homo sapiens

<400> SEQUENCE: 252

Trp Ile Ser Thr Tyr Asn Gly Asn Thr Asn Tyr Ala Gln Lys Val Gln
1               5                   10                  15
Gly

<210> SEQ ID NO 253
<211> LENGTH: 17
<212> TYPE: PRT
<213> ORGANISM: Homo sapiens

<400> SEQUENCE: 253

Thr Ile Ser Gly Ser Gly Gly Arg Thr Tyr Tyr Ala Asp Ser Val Lys
1               5                   10                  15
Gly

<210> SEQ ID NO 254
<211> LENGTH: 17
<212> TYPE: PRT
<213> ORGANISM: Homo sapiens

<400> SEQUENCE: 254

Val Ile Trp Tyr Asp Gly Ser Asp Lys Tyr Tyr Ala Asp Ser Val Lys
1               5                   10                  15
Gly

<210> SEQ ID NO 255
<211> LENGTH: 17
<212> TYPE: PRT
<213> ORGANISM: Homo sapiens

<400> SEQUENCE: 255

Ile Ile Trp Tyr Asp Gly Ser Asn Lys Tyr Tyr Ala Asp Ser Val Lys
1               5                   10                  15
Gly

<210> SEQ ID NO 256
<211> LENGTH: 17
<212> TYPE: PRT
<213> ORGANISM: Homo sapiens

<400> SEQUENCE: 256

Ser Ile Ser Ser Ser Ser Ser Tyr Ile Ser Tyr Ala Asp Ser Val Lys
1               5                   10                  15
Gly

<210> SEQ ID NO 257
<211> LENGTH: 16
<212> TYPE: PRT
<213> ORGANISM: Homo sapiens

<400> SEQUENCE: 257

Tyr Ile Tyr Asn Ser Gly Ser Thr Tyr Tyr Asn Pro Ser Leu Lys Ser
1               5                   10                  15

<210> SEQ ID NO 258
<211> LENGTH: 16
<212> TYPE: PRT
<213> ORGANISM: Homo sapiens
```

<400> SEQUENCE: 258

Tyr Ile Tyr Tyr Ser Gly Ser Thr Tyr Tyr Asn Pro Ser Leu Lys Ser
 1               5                  10                  15

<210> SEQ ID NO 259
<211> LENGTH: 16
<212> TYPE: PRT
<213> ORGANISM: Homo sapiens

<400> SEQUENCE: 259

Glu Ile Asn His Ser Gly Arg Thr Asp Tyr Asn Pro Ser Leu Lys Ser
 1               5                  10                  15

<210> SEQ ID NO 260
<211> LENGTH: 18
<212> TYPE: PRT
<213> ORGANISM: Homo sapiens

<400> SEQUENCE: 260

Arg Thr Tyr Tyr Arg Ser Lys Trp Tyr Lys Asn Tyr Ser Val Ser Val
 1               5                  10                  15

Lys Ser

<210> SEQ ID NO 261
<211> LENGTH: 6
<212> TYPE: PRT
<213> ORGANISM: Homo sapiens

<400> SEQUENCE: 261

Gly Tyr Thr Arg Asp Tyr
 1               5

<210> SEQ ID NO 262
<211> LENGTH: 8
<212> TYPE: PRT
<213> ORGANISM: Homo sapiens

<400> SEQUENCE: 262

Glu Val Gly Ser Pro Phe Asp Tyr
 1               5

<210> SEQ ID NO 263
<211> LENGTH: 14
<212> TYPE: PRT
<213> ORGANISM: Homo sapiens

<400> SEQUENCE: 263

Glu Thr Gly Pro Leu Lys Leu Tyr Tyr Tyr Gly Met Asp Val
 1               5                  10

<210> SEQ ID NO 264
<211> LENGTH: 13
<212> TYPE: PRT
<213> ORGANISM: Homo sapiens

<400> SEQUENCE: 264

Arg Gly Gly Leu Ala Ala Arg Pro Gly Gly Met Asp Val
 1               5                  10

<210> SEQ ID NO 265
<211> LENGTH: 14
<212> TYPE: PRT
<213> ORGANISM: Homo sapiens

<400> SEQUENCE: 265

Asp Tyr Asp Phe Trp Ser Ala Tyr Tyr Asp Ala Phe Asp Val
1               5                   10

<210> SEQ ID NO 266
<211> LENGTH: 11
<212> TYPE: PRT
<213> ORGANISM: Homo sapiens

<400> SEQUENCE: 266

Glu Asp Thr Ala Met Val Pro Tyr Phe Asp Tyr
1               5                   10

<210> SEQ ID NO 267
<211> LENGTH: 12
<212> TYPE: PRT
<213> ORGANISM: Homo sapiens

<400> SEQUENCE: 267

Gly Gly Val Thr Thr Tyr Tyr Tyr Ala Met Asp Val
1               5                   10

<210> SEQ ID NO 268
<211> LENGTH: 8
<212> TYPE: PRT
<213> ORGANISM: Homo sapiens

<400> SEQUENCE: 268

Gly Gln Leu Val Pro Phe Asp Tyr
1               5

<210> SEQ ID NO 269
<211> LENGTH: 9
<212> TYPE: PRT
<213> ORGANISM: Homo sapiens

<400> SEQUENCE: 269

Gly Gly Pro Thr Ala Ala Phe Asp Tyr
1               5

<210> SEQ ID NO 270
<211> LENGTH: 109
<212> TYPE: PRT
<213> ORGANISM: Homo sapiens

<400> SEQUENCE: 270

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Glu Val Ser Asn Arg Pro Ser Gly Val Phe Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu
            100                 105

```
<210> SEQ ID NO 271
<211> LENGTH: 109
<212> TYPE: PRT
<213> ORGANISM: Homo sapiens

<400> SEQUENCE: 271

Gln Ser Ala Leu Thr Gln Pro Ala Ser Val Phe Gly Ser Pro Gly Gln
  1               5                  10                  15

Ser Ile Thr Ile Ser Cys Thr Gly Thr Ser Ser Asp Val Gly Ala Tyr
             20                  25                  30

Asn Ser Val Ser Trp Tyr Gln Gln His Pro Gly Lys Ala Pro Lys Arg
         35                  40                  45

Met Ile Tyr Glu Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Thr
             85                  90                  95

Asn Met Val Phe Gly Gly Gly Thr Lys Leu Thr Val Leu
            100                 105

<210> SEQ ID NO 272
<211> LENGTH: 109
<212> TYPE: PRT
<213> ORGANISM: Homo sapiens

<400> SEQUENCE: 272

Gln Ser Val Leu Thr Gln Pro Pro Ser Ala Ser Gly Pro Pro Gly Gln
  1               5                  10                  15

Arg Val Thr Ile Ser Cys Ser Gly Ser Ser Ser Asn Ile Gly Ser Asn
             20                  25                  30

Thr Val Asn Trp Tyr Gln Gln Leu Pro Gly Thr Ala Pro Lys Leu Leu
         35                  40                  45

Ile Tyr Ser Asn Asn Arg Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
             85                  90                  95

Asn Trp Val Phe Gly Gly Gly Thr Lys Leu Thr Val Leu
            100                 105

<210> SEQ ID NO 273
<211> LENGTH: 109
<212> TYPE: PRT
<213> ORGANISM: Homo sapiens

<400> SEQUENCE: 273

Gln Ser Val Leu Thr Gln Pro Pro Ser Ala Ser Gly Pro Pro Gly Gln
  1               5                  10                  15

Arg Val Thr Ile Phe Cys Ser Gly Ser Ser Ser Asn Ile Gly Ser Asn
             20                  25                  30

Thr Val Asn Trp Tyr Gln Gln Leu Pro Gly Thr Ala Pro Lys Leu Leu
         35                  40                  45

Ile Tyr Ser Asn Asn Arg Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80
```

```
Ser Glu Asp Glu Ala Asp Tyr Tyr Cys Ala Ala Trp Asp Asp Ser Leu
                85                  90                  95

Asn Trp Val Phe Gly Gly Gly Thr Lys Leu Thr Val Leu
            100                 105
```

<210> SEQ ID NO 274
<211> LENGTH: 106
<212> TYPE: PRT
<213> ORGANISM: Homo sapiens

<400> SEQUENCE: 274

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
            35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105
```

<210> SEQ ID NO 275
<211> LENGTH: 106
<212> TYPE: PRT
<213> ORGANISM: Homo sapiens

<400> SEQUENCE: 275

```
Ser Tyr Glu Leu Thr Gln Pro Pro Ser Val Ser Val Ser Pro Gly Gln
1               5                   10                  15

Thr Ala Arg Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
            35                  40                  45

Gln Asn Thr Lys Trp Pro Leu Gly Ile Pro Glu Arg Phe Ser Gly Ser
    50                  55                  60

Lys Ser Gly Asn Thr Val Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105
```

<210> SEQ ID NO 276
<211> LENGTH: 107
<212> TYPE: PRT
<213> ORGANISM: Homo sapiens

<400> SEQUENCE: 276

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30
```

```
Cys Trp Tyr Gln Gln Lys Pro Gly Gln Ser Pro Val Leu Val Ile Tyr
            35                  40                  45

Gln Asp Ser Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Ala Val
                 85                  90                  95

Val Phe Gly Gly Gly Thr Lys Leu Thr Val Leu
            100                 105
```

<210> SEQ ID NO 277
<211> LENGTH: 107
<212> TYPE: PRT
<213> ORGANISM: Homo sapiens

<400> SEQUENCE: 277

```
Ser Tyr Glu Leu Ile Gln Pro Pro Ser Val Ser Val Ser Pro Gly Gln
 1               5                  10                  15

Thr Ala Ser Ile Thr Cys Ser Gly Asp Lys Leu Gly Asp Lys Tyr Ala
            20                  25                  30

Cys Trp Tyr Gln Arg Lys Pro Gly Gln Ser Pro Ile Leu Val Ile Tyr
            35                  40                  45

Gln Asp Thr Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Ala Val
                 85                  90                  95

Val Phe Gly Gly Gly Thr Lys Leu Thr Val Leu
            100                 105
```

<210> SEQ ID NO 278
<211> LENGTH: 120
<212> TYPE: PRT
<213> ORGANISM: Homo sapiens

<400> SEQUENCE: 278

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Thr Tyr
            20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Ser Tyr Ser Ser Gly Trp Phe Glu Phe Asp Tyr Trp Gly Gln
            100                 105                 110

Gly Thr Leu Val Thr Val Ser Ser
            115                 120
```

<210> SEQ ID NO 279
<211> LENGTH: 12

```
<212> TYPE: PRT
<213> ORGANISM: Homo sapiens

<400> SEQUENCE: 279

Thr Leu Ser Ser Gly Tyr Ser Ser Tyr Glu Val Asp
1               5                   10

<210> SEQ ID NO 280
<211> LENGTH: 12
<212> TYPE: PRT
<213> ORGANISM: Homo sapiens

<400> SEQUENCE: 280

Val Asp Thr Gly Gly Ile Val Gly Ser Lys Gly Glu
1               5                   10

<210> SEQ ID NO 281
<211> LENGTH: 13
<212> TYPE: PRT
<213> ORGANISM: Homo sapiens

<400> SEQUENCE: 281

Gly Ala Asp His Gly Ser Gly Thr Asn Phe Val Val Val
1               5                   10

<210> SEQ ID NO 282
<211> LENGTH: 22
<212> TYPE: PRT
<213> ORGANISM: Homo sapiens

<400> SEQUENCE: 282

Gln Pro Val Leu Thr Gln Pro Leu Phe Ala Ser Ala Ser Leu Gly Ala
1               5                   10                  15

Ser Val Thr Leu Thr Cys
            20

<210> SEQ ID NO 283
<211> LENGTH: 15
<212> TYPE: PRT
<213> ORGANISM: Homo sapiens

<400> SEQUENCE: 283

Trp Tyr Gln Gln Arg Pro Gly Lys Gly Pro Arg Phe Val Met Arg
1               5                   10                  15

<210> SEQ ID NO 284
<211> LENGTH: 32
<212> TYPE: PRT
<213> ORGANISM: Homo sapiens

<400> SEQUENCE: 284

Gly Ile Pro Asp Arg Phe Ser Val Leu Gly Ser Gly Leu Asn Arg Tyr
1               5                   10                  15

Leu Thr Ile Lys Asn Ile Gln Glu Glu Asp Glu Ser Asp Tyr His Cys
            20                  25                  30

<210> SEQ ID NO 285
<211> LENGTH: 10
<212> TYPE: PRT
<213> ORGANISM: Homo sapiens

<400> SEQUENCE: 285

Phe Gly Gly Gly Thr Lys Leu Thr Val Leu
1               5                   10
```

<210> SEQ ID NO 286
<211> LENGTH: 108
<212> TYPE: PRT
<213> ORGANISM: Homo sapiens

<400> SEQUENCE: 286

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Arg Tyr
            20                  25                  30

Asn Ser Val Ser Trp Tyr Gln His Pro Gly Lys Ala Pro Lys Val
        35                  40                  45

Met Ile Tyr Glu Val Ser Asn Arg Pro Ser Gly Val Ser Thr Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Val Val Phe Gly Gly Gly Thr Lys Leu Thr Val
            100                 105

<210> SEQ ID NO 287
<211> LENGTH: 108
<212> TYPE: PRT
<213> ORGANISM: Homo sapiens

<400> SEQUENCE: 287

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Pro Pro Lys Leu
        35                  40                  45

Met Ile Tyr Glu Val Ser Asn Arg Pro Ser Gly Val Ser Ile Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Thr Val
            100                 105

<210> SEQ ID NO 288
<211> LENGTH: 108
<212> TYPE: PRT
<213> ORGANISM: Homo sapiens

<400> SEQUENCE: 288

Gln Ser Ala Leu Thr Gln Pro Ala Ser Val Ser Gly Ser Pro Gly Gln
1               5                   10                  15

Ser Ile Thr Ile Ser Cys Thr Gly Thr Asn Ser Asp Val Gly Gly Tyr
            20                  25                  30

Asn Ser Val Ser Trp Tyr Gln Gln His Pro Gly Lys Pro Pro Lys Leu
        35                  40                  45

Met Ile Tyr Glu Val Ser Asn Arg Pro Ser Gly Ile Ser Asn Arg Phe
    50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Phe Cys Ser Ser Tyr Thr Ser Thr
                 85                  90                  95

Ser Met Val Phe Gly Gly Gly Thr Lys Leu Thr Val
            100                 105

<210> SEQ ID NO 289
<211> LENGTH: 122
<212> TYPE: PRT
<213> ORGANISM: Homo sapiens

<400> SEQUENCE: 289

Gln Val His Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Phe
                 20                  25                  30

Gly Met His Trp Val Arg Gln Ala Pro Gly Lys Gly Leu Glu Trp Val
            35                  40                  45

Ala Leu Ile Trp Asn Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Ile Ala Ala Leu Tyr Tyr Tyr Tyr Gly Met Asp Val Trp
            100                 105                 110

Gly His Gly Thr Thr Val Thr Val Ser Ser
            115                 120

<210> SEQ ID NO 290
<211> LENGTH: 122
<212> TYPE: PRT
<213> ORGANISM: Homo sapiens

<400> SEQUENCE: 290

Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Cys Val
            35                  40                  45

Ala Ile Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Gly Gly Leu Ala Ala Arg Pro Gly Gly Met Asp Val Trp
            100                 105                 110

Gly Gln Gly Thr Thr Val Thr Val Ser Ser
            115                 120

<210> SEQ ID NO 291
<211> LENGTH: 121
<212> TYPE: PRT
<213> ORGANISM: Homo sapiens

```
<400> SEQUENCE: 291

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Leu Ile Trp Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ile Ala Ala Leu Tyr Tyr Tyr Gly Met Asp Val Trp
            100                 105                 110

Gly Gln Gly Thr Thr Val Thr Val Ser
        115                 120

<210> SEQ ID NO 292
<211> LENGTH: 119
<212> TYPE: PRT
<213> ORGANISM: Homo sapiens

<400> SEQUENCE: 292

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gly Leu Pro Gly Gly Met Asp Val Trp Gly Gln Gly
            100                 105                 110

Thr Thr Val Thr Val Ser Ser
        115

<210> SEQ ID NO 293
<211> LENGTH: 327
<212> TYPE: DNA
<213> ORGANISM: Homo sapiens

<400> SEQUENCE: 293
cagtctgccc tgactcagcc tgcctccgtg tctgggtctc ctggacagtc gatcaccatc      60
tcctgcactg gaaccagcag tgacgttggt ggttataact ctgtctcctg gtaccaacag     120
cacccaggca agcccccaa actcatgatt tatgaggtca gtaatcggcc ctcaggggtt      180
tctaatcgct tctctggctc caagtctggc aacacggcct ccctgaccat ctctgggctc     240
caggctgagg acgaggctga ttattactgc aactcatata agcaccagca tggtattc      300 ggcggaggga ccaagctgac cgtccta                                         327
```

```
<210> SEQ ID NO 294
<211> LENGTH: 327
<212> TYPE: DNA
<213> ORGANISM: Homo sapiens

<400> SEQUENCE: 294
cagtctgccc tgactcagcc tgcctccgtg tctgggtctc ctggacagtc gatcaccatc      60
tcctgcactg gaaccagcag tgacgttggt ggttataact ctgtctcctg gtaccaacag     120
cacccaggca acccccccaa actcatgatt tatgaggtca gtaatcggcc ctcagggggtt    180 tctaatcgct ctctggctc caagtctggc aacacggcct ccctgaccat ctctgggctc      240
caggctgagg acgaggctga ttatttctgc agctcatata caagcaccag catggtcttc    300
ggcggaggga ccaagctgac cgtccta                                         327

<210> SEQ ID NO 295
<211> LENGTH: 318
<212> TYPE: DNA
<213> ORGANISM: Homo sapiens

<400> SEQUENCE: 295
tcctatgagc tgactcagcc accctcagtg tccgtgtccc caggacagac agccagaatc      60
acctgctctg gagataaaatt gggggataaa tatgcttgct ggtatcagca gaagccaggc    120
cagtcccctg tgctggtcat ctatcaaaat accaagtggc ccttagggat ccctgagcga    180
ttctctggct ccaagtctgg gaacacagtc actctgacca tcagcgggac ccaggctatg    240
gatgaggctg actattactg tcaggcgtgg gacagcagca ctgtggtatt cggcggaggg    300
accaagctga ccgtccta                                                   318

<210> SEQ ID NO 296
<211> LENGTH: 327
<212> TYPE: DNA
<213> ORGANISM: Homo sapiens

<400> SEQUENCE: 296
cagtctgccc tgactcagcc tgcctccgtg tctgggtctc ctggacagtc gatcaccatc      60
tcctgcactg gaaccagcag tgacgttggt ggttataact ctgtctcctg gtaccaacag     120
cacccaggca aagccccccaa actcatgatt tatgaggtca gtaatcggcc ctcagggggtt    180 tctaatcgct ctctggctc caagtctggc aacacggcct ccctgaccat ctctgggctc      240
caggctgagg acgaggctga ttattactgc aattcatata caagcaccag catggtattc    300
ggcggaggga ccaagctgac cgtccta                                         327

<210> SEQ ID NO 297
<211> LENGTH: 215
<212> TYPE: PRT
<213> ORGANISM: Homo sapiens

<400> SEQUENCE: 297

Glu Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60
```

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Asn Ser Tyr Thr Ser Thr
                 85                  90                  95

Ser Met Val Phe Gly Gly Gly Thr Lys Leu Thr Val Leu Gly Gln Pro
                100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
210                 215

<210> SEQ ID NO 298
<211> LENGTH: 230
<212> TYPE: PRT
<213> ORGANISM: Homo sapiens

<400> SEQUENCE: 298

Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Leu Thr Ser Tyr
             20                  25                  30

Gly Ile Ser Trp Val Arg Gln Ala Pro Gly Gln Gly Leu Glu Trp Met
         35                  40                  45

Gly Trp Val Ser Phe Tyr Asn Gly Asn Thr Asn Tyr Ala Gln Lys Leu
 50                  55                  60

Gln Gly Arg Gly Thr Met Thr Thr Asp Pro Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Tyr Gly Met Asp Val Trp Gly Gln Gly Thr Thr Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Ala Ala Asp Glu Val Asp
210                 215                 220
```

His His His His His His
225                 230

<210> SEQ ID NO 299
<211> LENGTH: 217
<212> TYPE: PRT
<213> ORGANISM: Homo sapiens

<400> SEQUENCE: 299

Glu Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Ser Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 300
<211> LENGTH: 238
<212> TYPE: PRT
<213> ORGANISM: Homo sapiens

<400> SEQUENCE: 300

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
                85                  90                  95

```
Ala Arg Asp Tyr Asp Phe Trp Ser Ala Tyr Tyr Asp Ala Phe Asp Val
                100                 105                 110

Trp Gly Gln Gly Thr Met Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Ala Ala Asp Glu Val Asp His His His His His His
225                 230                 235
```

<210> SEQ ID NO 301
<211> LENGTH: 218
<212> TYPE: PRT
<213> ORGANISM: Homo sapiens

<400> SEQUENCE: 301

```
Ala Leu Gln Ser Val Leu Thr Gln Pro Pro Ser Ala Ser Gly Thr Pro
1               5                   10                  15

Gly Gln Arg Val Thr Ile Ser Cys Ser Gly Ser Ser Ser Asn Ile Gly
            20                  25                  30

Ser Asn Thr Val Asn Trp Tyr Gln Gln Leu Pro Gly Thr Ala Pro Lys
        35                  40                  45

Leu Leu Ile Tyr Ser Asn Asn Gln Arg Pro Ser Gly Val Pro Asp Arg
    50                  55                  60

Phe Ser Gly Ser Lys Ser Gly Thr Ser Ala Ser Leu Ala Ile Ser Gly
65                  70                  75                  80

Leu Gln Ser Glu Asp Glu Ala Asp Tyr Tyr Cys Ala Val Trp Asp Asp
                85                  90                  95

Ser Leu Asn Gly Trp Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

```
<210> SEQ ID NO 302
<211> LENGTH: 231
<212> TYPE: PRT
<213> ORGANISM: Homo sapiens

<400> SEQUENCE: 302

Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Ala Tyr
             20                  25                  30

Tyr Trp Asn Trp Ile Arg Gln Pro Pro Gly Lys Gly Leu Glu Trp Ile
         35                  40                  45

Gly Glu Ile Asn His Ser Gly Arg Thr Asp Tyr Asn Pro Ser Leu Lys
 50                  55                  60

Ser Arg Val Thr Ile Ser Val Asp Thr Ser Lys Lys Gln Phe Ser Leu
 65                  70                  75                  80

Lys Leu Asn Ser Val Thr Ala Ala Asp Thr Ala Val Tyr Tyr Cys Ala
             85                  90                  95

Arg Gly Gln Leu Val Pro Phe Asp Tyr Trp Gly Gln Gly Thr Leu Val
        100                 105                 110

Thr Val Ser Ser Ala Ser Thr Lys Gly Pro Ser Val Phe Pro Leu Ala
    115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser His Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Ala Ala Asp Glu Val
    210                 215                 220

Asp His His His His His His
225                 230

<210> SEQ ID NO 303
<211> LENGTH: 680
<212> TYPE: PRT
<213> ORGANISM: Homo sapiens

<400> SEQUENCE: 303

Gln Glu Asp Glu Asp Gly Asp Tyr Glu Glu Leu Val Leu Ala Leu Arg
  1               5                  10                  15

Ser Glu Glu Asp Gly Leu Ala Glu Ala Pro Glu His Gly Thr Thr Ala
             20                  25                  30

Thr Phe His Arg Cys Ala Lys Asp Pro Trp Arg Leu Pro Gly Thr Tyr
         35                  40                  45

Val Val Val Leu Lys Glu Glu Thr His Leu Ser Gln Ser Glu Arg Thr
 50                  55                  60

Ala Arg Arg Leu Gln Ala Gln Ala Ala Arg Arg Gly Tyr Leu Thr Lys
 65                  70                  75                  80

Ile Leu His Val Phe His Gly Leu Leu Pro Gly Phe Leu Val Lys Met
             85                  90                  95

Ser Gly Asp Leu Leu Glu Leu Ala Leu Lys Leu Pro His Val Asp Tyr
```

```
                100                 105                 110
Ile Glu Glu Asp Ser Ser Val Phe Ala Gln Ser Ile Pro Trp Asn Leu
            115                 120                 125

Glu Arg Ile Thr Pro Pro Arg Tyr Arg Ala Asp Glu Tyr Gln Pro Pro
        130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
        210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
        275                 280                 285

Arg Asp Asp Ala Cys Leu Tyr Ser Pro Ala Ser Ala Pro Glu Val Ile
        290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
            340                 345                 350

Ser Gly Thr Ser Gln Ala Ala Ala His Val Ala Gly Ile Ala Ala Met
        355                 360                 365

Met Leu Ser Ala Glu Pro Glu Leu Thr Leu Ala Glu Leu Arg Gln Arg
        370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                405                 410                 415

Ser Thr His Gly Ala Gly Trp Gln Leu Phe Cys Arg Thr Val Trp Ser
            420                 425                 430

Ala His Ser Gly Pro Thr Arg Met Ala Thr Ala Ile Ala Arg Cys Ala
        435                 440                 445

Pro Asp Glu Glu Leu Leu Ser Cys Ser Ser Phe Ser Arg Ser Gly Lys
        450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
            500                 505                 510

Glu Ala Ser Met Gly Thr Arg Val His Cys His Gln Gln Gly His Val
        515                 520                 525
```

```
Leu Thr Gly Cys Ser Ser His Trp Glu Val Glu Asp Leu Gly Thr His
            530                 535                 540
Lys Pro Pro Val Leu Arg Pro Arg Gly Gln Pro Asn Gln Cys Val Gly
545                 550                 555                 560
His Arg Glu Ala Ser Ile His Ala Ser Cys Cys His Ala Pro Gly Leu
                565                 570                 575
Glu Cys Lys Val Lys Glu His Gly Ile Pro Ala Pro Gln Glu Gln Val
            580                 585                 590
Thr Val Ala Cys Glu Glu Gly Trp Thr Leu Thr Gly Cys Ser Ala Leu
        595                 600                 605
Pro Gly Thr Ser His Val Leu Gly Ala Tyr Ala Val Asp Asn Thr Cys
    610                 615                 620
Val Val Arg Ser Arg Asp Val Ser Thr Thr Gly Ser Thr Ser Glu Glu
625                 630                 635                 640
Ala Val Thr Ala Val Ala Ile Cys Cys Arg Ser Arg His Leu Ala Gln
                645                 650                 655
Ala Ser Gln Glu Leu Gln Gly Ser Ser Asp Tyr Lys Asp Asp Asp Lys
            660                 665                 670
His His His His His His His His
            675                 680

<210> SEQ ID NO 304
<211> LENGTH: 680
<212> TYPE: PRT
<213> ORGANISM: Homo sapiens

<400> SEQUENCE: 304

Arg Arg Arg Arg Arg Arg Arg Arg Arg Arg Arg Leu Arg Arg Arg Arg
1               5                   10                  15
Arg Arg Arg Arg Arg Arg Arg Arg Arg His Arg Arg Arg Arg
            20                  25                  30
Arg Phe Arg Arg Cys Arg Arg Arg Pro Trp Arg Arg Pro Gly Arg Tyr
            35                  40                  45
Val Val Val Leu Arg Arg Arg Arg Ser Arg Ser Arg Glu Thr
    50                  55                  60
Ala Glu Glu Leu Gln Arg Arg Ala Arg Glu Glu Gly Arg Arg Thr Lys
65                  70                  75                  80
Ile Arg Arg Arg Phe Arg Gly Leu Leu Pro Gly Phe Leu Val Arg Met
                85                  90                  95
Arg Arg Arg Leu Arg Arg Leu Ala Arg Arg Leu Pro Arg Val Arg Tyr
            100                 105                 110
Ile Glu Glu Asp Ser Ser Val Phe Arg Gln Arg Ile Pro Arg Asn Arg
            115                 120                 125
Arg Glu Ile Arg Pro Pro Arg Tyr Arg Ala Arg Arg Arg Pro Pro
            130                 135                 140
Arg Gly Gly Arg Arg Val Glu Val Tyr Leu Leu Asp Thr Arg Ile Arg
145                 150                 155                 160
Arg Arg His Glu Glu Ile Arg Gly Arg Val Arg Arg Arg Phe Arg
                165                 170                 175
Arg Arg Pro Arg Arg Arg Arg Glu Arg Glu Arg Arg Arg
            180                 185                 190
Cys Asp Arg Arg Gly Thr His Leu Ala Gly Val Val Ser Gly Glu Arg
                195                 200                 205
Ala Gly Val Ala Arg Arg Ala Arg Met Arg Ser Leu Glu Val Leu Asn
```

```
              210                 215                 220
Cys Arg Gly Arg Gly Arg Val Ser Gly Thr Leu Ile Gly Leu Glu Arg
225                 230                 235                 240

Ile Glu Arg Arg Arg Arg Arg Pro Arg Pro Leu Val Val Leu
                245                 250                 255

Leu Pro Leu Ala Gly Arg Tyr Ser Glu Val Leu Asn Arg Ala Cys Arg
                260                 265                 270

Arg Leu Ala Glu Arg Gly Val Val Leu Val Thr Ala Ala Gly Asn Phe
                275                 280                 285

Glu Asp Asp Ala Cys Arg Tyr Ser Pro Ala Arg Ala Pro Glu Val Ile
                290                 295                 300

Thr Val Gly Ala Thr Asn Arg Arg Arg Pro Val Arg Arg Gly Arg
305                 310                 315                 320

Arg Gly Thr Asn Phe Gly Arg Cys Val Asp Leu Phe Ala Pro Gly Arg
                325                 330                 335

Arg Ile Ile Gly Ala Ser Ser Arg Cys Ser Arg Cys Arg Arg Arg
                340                 345                 350

Ser Gly Thr Ser Gln Ala Ala His Val Ala Gly Ile Ala Ala Arg
                355                 360                 365

Met Leu Arg Arg Pro Arg Leu Arg Arg Ala Arg Leu Arg Gln Glu
370                 375                 380

Leu Arg Arg Arg Ser Arg Arg Arg Ile Arg Arg Arg Phe Pro
385                 390                 395                 400

Arg Arg Arg Glu Arg Leu Thr Pro Arg Leu Val Ala Arg Leu Pro Pro
                405                 410                 415

Arg Arg Arg Arg Arg Gly Arg Arg Leu Phe Cys Arg Thr Val Trp Ser
                420                 425                 430

Arg Arg Ser Gly Pro Arg Glu Arg Ala Arg Ala Ile Ala Glu Cys Ala
                435                 440                 445

Pro Arg Glu Glu Leu Leu Ser Cys Ser Ser Phe Ser Arg Ser Gly Lys
450                 455                 460

Arg Arg Gly Glu Arg Met Glu Arg Gln Gly Gly Lys Leu Val Cys Arg
465                 470                 475                 480

Ala His Asn Ala Arg Arg Gly Arg Gly Val Tyr Ala Ile Ala Arg Cys
                485                 490                 495

Cys Leu Leu Pro Gln Ala Arg Cys Ser Val His Arg Ala Pro Pro Ala
                500                 505                 510

Arg Arg Arg Arg Gly Thr Glu Val Arg Cys Arg Arg Gly His Val
                515                 520                 525

Leu Thr Gly Cys Ser Ser His Trp Arg Arg Asp Arg Gly Thr Arg
530                 535                 540

Lys Pro Pro Arg Leu Pro Glu Gly Arg Pro Arg Gln Cys Val Gly
545                 550                 555                 560

His Arg Glu Ala Ser Ile His Ala Ser Cys His Ala Pro Gly Leu
                565                 570                 575

Glu Cys Arg Arg Arg Arg Arg Ile Pro Ala Pro Arg Glu Arg Val
                580                 585                 590

Thr Val Arg Cys Arg Arg Gly Trp Thr Leu Thr Gly Cys Ser Ala Leu
                595                 600                 605

Pro Gly Thr Ser His Val Leu Gly Ala Tyr Ala Arg Asp Asn Thr Cys
                610                 615                 620

Val Val Arg Ser Glu Asp Arg Arg Arg Arg Arg Arg Arg Glu
625                 630                 635                 640
```

```
Arg Val Thr Ala Val Ala Ile Cys Cys Glu Ser Glu His Leu Ala Gln
                645                 650                 655

Ala Ser Gln Glu Leu Gln Gly Ser Ser Asp Tyr Lys Asp Asp Asp Lys
            660                 665                 670

His His His His His His His
        675             680

<210> SEQ ID NO 305
<211> LENGTH: 14
<212> TYPE: PRT
<213> ORGANISM: Homo sapiens

<400> SEQUENCE: 305

Thr Gly Thr Ser Ser Asp Val Gly Gly Tyr Asn Ser Val Ser
1               5                   10

<210> SEQ ID NO 306
<211> LENGTH: 7
<212> TYPE: PRT
<213> ORGANISM: Homo sapiens

<400> SEQUENCE: 306

Glu Val Ser Asn Arg Pro Ser
1               5

<210> SEQ ID NO 307
<211> LENGTH: 9
<212> TYPE: PRT
<213> ORGANISM: Homo sapiens

<400> SEQUENCE: 307

Ser Ser Tyr Thr Ser Thr Ser Met Val
1               5

<210> SEQ ID NO 308
<211> LENGTH: 5
<212> TYPE: PRT
<213> ORGANISM: Homo sapiens

<400> SEQUENCE: 308

Ser Tyr Gly Ile Ser
1               5

<210> SEQ ID NO 309
<211> LENGTH: 17
<212> TYPE: PRT
<213> ORGANISM: Homo sapiens

<400> SEQUENCE: 309

Trp Ile Ser Ala Tyr Asn Gly Asn Thr Asn Tyr Ala Gln Lys Val Gln
1               5                   10                  15

Gly

<210> SEQ ID NO 310
<211> LENGTH: 6
<212> TYPE: PRT
<213> ORGANISM: Homo sapiens

<400> SEQUENCE: 310

Gly Tyr Gly Met Asp Val
1               5
```

```
<210> SEQ ID NO 311
<211> LENGTH: 14
<212> TYPE: PRT
<213> ORGANISM: Homo sapiens

<400> SEQUENCE: 311

Thr Gly Thr Ser Ser Asp Val Gly Arg Tyr Asn Ser Val Ser
1               5                   10

<210> SEQ ID NO 312
<211> LENGTH: 7
<212> TYPE: PRT
<213> ORGANISM: Homo sapiens

<400> SEQUENCE: 312

Glu Val Ser Asn Arg Pro Ser
1               5

<210> SEQ ID NO 313
<211> LENGTH: 9
<212> TYPE: PRT
<213> ORGANISM: Homo sapiens

<400> SEQUENCE: 313

Ser Ser Tyr Thr Ser Ser Ser Val Val
1               5

<210> SEQ ID NO 314
<211> LENGTH: 17
<212> TYPE: PRT
<213> ORGANISM: Homo sapiens

<400> SEQUENCE: 314

Trp Ile Ser Ala Tyr Asn Gly Asn Thr Asn Tyr Ala Glu Lys Leu Gln
1               5                   10                  15

Gly

<210> SEQ ID NO 315
<211> LENGTH: 6
<212> TYPE: PRT
<213> ORGANISM: Homo sapiens

<400> SEQUENCE: 315

Gly Tyr Val Met Asp Val
1               5

<210> SEQ ID NO 316
<211> LENGTH: 14
<212> TYPE: PRT
<213> ORGANISM: Homo sapiens

<400> SEQUENCE: 316

Thr Gly Thr Ser Ser Asp Val Gly Ala Tyr Asn Ser Val Ser
1               5                   10

<210> SEQ ID NO 317
<211> LENGTH: 9
<212> TYPE: PRT
<213> ORGANISM: Homo sapiens

<400> SEQUENCE: 317

Ser Ser Tyr Thr Ser Thr Asn Met Val
1               5
```

<210> SEQ ID NO 318
<211> LENGTH: 17
<212> TYPE: PRT
<213> ORGANISM: Homo sapiens

<400> SEQUENCE: 318

Trp Val Ser Ala Tyr Asn Gly Asn Thr Asn Tyr Ala Gln Lys Phe Gln
1               5                   10                  15
Gly

<210> SEQ ID NO 319
<211> LENGTH: 9
<212> TYPE: PRT
<213> ORGANISM: Homo sapiens

<400> SEQUENCE: 319

Asn Ser Tyr Thr Ser Thr Ser Met Val
1               5

<210> SEQ ID NO 320
<211> LENGTH: 17
<212> TYPE: PRT
<213> ORGANISM: Homo sapiens

<400> SEQUENCE: 320

Trp Val Ser Phe Tyr Asn Gly Asn Thr Asn Tyr Ala Gln Lys Leu Gln
1               5                   10                  15
Gly

<210> SEQ ID NO 321
<211> LENGTH: 7
<212> TYPE: PRT
<213> ORGANISM: Homo sapiens

<400> SEQUENCE: 321

Glu Val Thr Asn Arg Pro Ser
1               5

<210> SEQ ID NO 322
<211> LENGTH: 14
<212> TYPE: PRT
<213> ORGANISM: Homo sapiens

<400> SEQUENCE: 322

Thr Gly Thr Asn Ser Asp Val Gly Gly Tyr Asn Ser Val Ser
1               5                   10

<210> SEQ ID NO 323
<211> LENGTH: 17
<212> TYPE: PRT
<213> ORGANISM: Homo sapiens

<400> SEQUENCE: 323

Trp Ile Ser Val Tyr Asn Gly Asn Thr Asn Tyr Ala Gln Lys Val Gln
1               5                   10                  15
Gly

<210> SEQ ID NO 324
<211> LENGTH: 17
<212> TYPE: PRT
<213> ORGANISM: Homo sapiens

<400> SEQUENCE: 324

```
Trp Ile Ser Phe Tyr Asn Gly Asn Thr Asn Tyr Ala Gln Lys Val Gln
1               5                   10                  15

Gly

<210> SEQ ID NO 325
<211> LENGTH: 13
<212> TYPE: PRT
<213> ORGANISM: Homo sapiens

<400> SEQUENCE: 325

Ser Gly Ser Ser Ser Asn Ile Gly Asn Asn Phe Val Ser
1               5                   10

<210> SEQ ID NO 326
<211> LENGTH: 7
<212> TYPE: PRT
<213> ORGANISM: Homo sapiens

<400> SEQUENCE: 326

Asp Tyr Asn Lys Arg Pro Ser
1               5

<210> SEQ ID NO 327
<211> LENGTH: 11
<212> TYPE: PRT
<213> ORGANISM: Homo sapiens

<400> SEQUENCE: 327

Gly Thr Trp Asp Ser Ser Leu Ser Gly Tyr Val
1               5                   10

<210> SEQ ID NO 328
<211> LENGTH: 5
<212> TYPE: PRT
<213> ORGANISM: Homo sapiens

<400> SEQUENCE: 328

Ser Phe Gly Met His
1               5

<210> SEQ ID NO 329
<211> LENGTH: 17
<212> TYPE: PRT
<213> ORGANISM: Homo sapiens

<400> SEQUENCE: 329

Leu Ile Trp Asn Asp Gly Ser Asn Lys Tyr Tyr Ala Asp Ser Val Lys
1               5                   10                  15

Gly

<210> SEQ ID NO 330
<211> LENGTH: 13
<212> TYPE: PRT
<213> ORGANISM: Homo sapiens

<400> SEQUENCE: 330

Ala Ile Ala Ala Leu Tyr Tyr Tyr Tyr Gly Met Asp Val
1               5                   10

<210> SEQ ID NO 331
<211> LENGTH: 7
<212> TYPE: PRT
<213> ORGANISM: Homo sapiens
```

<400> SEQUENCE: 331

Asp Ser Asn Lys Arg Pro Ser
1               5

<210> SEQ ID NO 332
<211> LENGTH: 11
<212> TYPE: PRT
<213> ORGANISM: Homo sapiens

<400> SEQUENCE: 332

Gly Thr Trp Asp Ser Ser Leu Ser Ala Tyr Val
1               5                   10

<210> SEQ ID NO 333
<211> LENGTH: 5
<212> TYPE: PRT
<213> ORGANISM: Homo sapiens

<400> SEQUENCE: 333

Ser Tyr Gly Met His
1               5

<210> SEQ ID NO 334
<211> LENGTH: 17
<212> TYPE: PRT
<213> ORGANISM: Homo sapiens

<400> SEQUENCE: 334

Leu Ile Trp His Asp Gly Ser Asn Thr Tyr Tyr Val Asp Ser Val Lys
1               5                   10                  15

Gly

<210> SEQ ID NO 335
<211> LENGTH: 13
<212> TYPE: PRT
<213> ORGANISM: Homo sapiens

<400> SEQUENCE: 335

Gly Ile Ala Val Ala Tyr Tyr Tyr Tyr Gly Met Asp Val
1               5                   10

<210> SEQ ID NO 336
<211> LENGTH: 17
<212> TYPE: PRT
<213> ORGANISM: Homo sapiens

<400> SEQUENCE: 336

Leu Ile Trp Ser Asp Gly Ser Asp Glu Tyr Tyr Ala Asp Ser Val Lys
1               5                   10                  15

Gly

<210> SEQ ID NO 337
<211> LENGTH: 11
<212> TYPE: PRT
<213> ORGANISM: Homo sapiens

<400> SEQUENCE: 337

Gly Thr Trp Asp Ser Ser Leu Ser Ser Tyr Val
1               5                   10

<210> SEQ ID NO 338
<211> LENGTH: 17
<212> TYPE: PRT

-continued

```
<213> ORGANISM: Homo sapiens

<400> SEQUENCE: 338

Leu Ile Trp Ser Asp Gly Ser Asp Lys Tyr Tyr Ala Asp Ser Val Lys
1               5                   10                  15
Gly

<210> SEQ ID NO 339
<211> LENGTH: 13
<212> TYPE: PRT
<213> ORGANISM: Homo sapiens

<400> SEQUENCE: 339

Ser Gly Ser Ser Ser Asn Ile Gly Ser Lys Thr Val Asn
1               5                   10

<210> SEQ ID NO 340
<211> LENGTH: 7
<212> TYPE: PRT
<213> ORGANISM: Homo sapiens

<400> SEQUENCE: 340

Ser Asn Asn Arg Arg Pro Ser
1               5

<210> SEQ ID NO 341
<211> LENGTH: 10
<212> TYPE: PRT
<213> ORGANISM: Homo sapiens

<400> SEQUENCE: 341

Ala Ala Trp Asp Asp Ser Leu Asn Trp Val
1               5                   10

<210> SEQ ID NO 342
<211> LENGTH: 4
<212> TYPE: PRT
<213> ORGANISM: Homo sapiens

<400> SEQUENCE: 342

Tyr Trp Met Ser
1

<210> SEQ ID NO 343
<211> LENGTH: 17
<212> TYPE: PRT
<213> ORGANISM: Homo sapiens

<400> SEQUENCE: 343

Asn Ile Lys Gln Asp Gly Ser Glu Lys Tyr Tyr Val Asp Ser Val Lys
1               5                   10                  15
Gly

<210> SEQ ID NO 344
<211> LENGTH: 10
<212> TYPE: PRT
<213> ORGANISM: Homo sapiens

<400> SEQUENCE: 344

Glu Ser Asn Trp Gly Phe Ala Phe Asp Ile
1               5                   10

<210> SEQ ID NO 345
```

```
<211> LENGTH: 13
<212> TYPE: PRT
<213> ORGANISM: Homo sapiens

<400> SEQUENCE: 345

Ser Gly Ser Ser Ser Asn Ile Gly Ser Asn Thr Val Asn
1               5                   10

<210> SEQ ID NO 346
<211> LENGTH: 5
<212> TYPE: PRT
<213> ORGANISM: Homo sapiens

<400> SEQUENCE: 346

Arg Tyr Trp Met Ser
1               5

<210> SEQ ID NO 347
<211> LENGTH: 17
<212> TYPE: PRT
<213> ORGANISM: Homo sapiens

<400> SEQUENCE: 347

Asn Ile Lys His Asp Gly Ser Glu Lys Tyr Tyr Val Asp Ser Val Lys
1               5                   10                  15

Gly

<210> SEQ ID NO 348
<211> LENGTH: 10
<212> TYPE: PRT
<213> ORGANISM: Homo sapiens

<400> SEQUENCE: 348

Glu Ser Asn Trp Gly Phe Ala Phe Asp Val
1               5                   10

<210> SEQ ID NO 349
<211> LENGTH: 7
<212> TYPE: PRT
<213> ORGANISM: Homo sapiens

<400> SEQUENCE: 349

Arg Asn Asn Gln Arg Pro Leu
1               5

<210> SEQ ID NO 350
<211> LENGTH: 5
<212> TYPE: PRT
<213> ORGANISM: Homo sapiens

<400> SEQUENCE: 350

Ser Tyr Trp Met Ser
1               5

<210> SEQ ID NO 351
<211> LENGTH: 5
<212> TYPE: PRT
<213> ORGANISM: Homo sapiens

<400> SEQUENCE: 351

Asn Phe Trp Met Ser
1               5

<210> SEQ ID NO 352
```

```
<211> LENGTH: 10
<212> TYPE: PRT
<213> ORGANISM: Homo sapiens

<400> SEQUENCE: 352

Arg Ala Ser Gln Ser Ile Ser Tyr Leu Asn
1               5                   10

<210> SEQ ID NO 353
<211> LENGTH: 6
<212> TYPE: PRT
<213> ORGANISM: Homo sapiens

<400> SEQUENCE: 353

Ala Ala Ser Leu Gln Ser
1               5

<210> SEQ ID NO 354
<211> LENGTH: 8
<212> TYPE: PRT
<213> ORGANISM: Homo sapiens

<400> SEQUENCE: 354

Gln Gln Ser Tyr Ser Pro Ile Thr
1               5

<210> SEQ ID NO 355
<211> LENGTH: 11
<212> TYPE: PRT
<213> ORGANISM: Homo sapiens

<400> SEQUENCE: 355

Arg Ala Ser Gln Ser Ile Ser Ile Tyr Leu Asn
1               5                   10

<210> SEQ ID NO 356
<211> LENGTH: 7
<212> TYPE: PRT
<213> ORGANISM: Homo sapiens

<400> SEQUENCE: 356

Ala Ala Ala Ser Leu Gln Ser
1               5

<210> SEQ ID NO 357
<211> LENGTH: 9
<212> TYPE: PRT
<213> ORGANISM: Homo sapiens

<400> SEQUENCE: 357

Gln Gln Ser Tyr Ser Ala Pro Ile Thr
1               5

<210> SEQ ID NO 358
<211> LENGTH: 11
<212> TYPE: PRT
<213> ORGANISM: Homo sapiens

<400> SEQUENCE: 358

Arg Ala Ser Gln Ser Ile Ser Ser Tyr Leu Asn
1               5                   10

<210> SEQ ID NO 359
<211> LENGTH: 7
<212> TYPE: PRT
```

<213> ORGANISM: Homo sapiens

<400> SEQUENCE: 359

Ala Ala Ser Ser Leu Gln Ser
1               5

<210> SEQ ID NO 360
<211> LENGTH: 9
<212> TYPE: PRT
<213> ORGANISM: Homo sapiens

<400> SEQUENCE: 360

Gln Gln Ser Tyr Ser Ser Pro Ile Thr
1               5

<210> SEQ ID NO 361
<211> LENGTH: 5
<212> TYPE: PRT
<213> ORGANISM: Homo sapiens

<400> SEQUENCE: 361

Ser Tyr Ala Met Asn
1               5

<210> SEQ ID NO 362
<211> LENGTH: 16
<212> TYPE: PRT
<213> ORGANISM: Homo sapiens

<400> SEQUENCE: 362

Thr Ile Ser Gly Ser Gly Asn Thr Tyr Tyr Ala Asp Ser Val Lys Gly
1               5                   10                  15

<210> SEQ ID NO 363
<211> LENGTH: 12
<212> TYPE: PRT
<213> ORGANISM: Homo sapiens

<400> SEQUENCE: 363

Lys Phe Val Leu Met Val Tyr Ala Met Leu Asp Tyr
1               5                   10

<210> SEQ ID NO 364
<211> LENGTH: 17
<212> TYPE: PRT
<213> ORGANISM: Homo sapiens

<400> SEQUENCE: 364

Thr Ile Ser Gly Ser Gly Gly Asn Thr Tyr Tyr Ala Asp Ser Val Lys
1               5                   10                  15

Gly

<210> SEQ ID NO 365
<211> LENGTH: 17
<212> TYPE: PRT
<213> ORGANISM: Homo sapiens

<400> SEQUENCE: 365

Thr Ile Ser Gly Ser Gly Asp Asn Thr Tyr Tyr Ala Asp Ser Val Lys
1               5                   10                  15

Gly

<210> SEQ ID NO 366

```
<211> LENGTH: 10
<212> TYPE: PRT
<213> ORGANISM: Homo sapiens

<400> SEQUENCE: 366

Gly Tyr Ser Leu Thr Ser Tyr Gly Ile Ser
1               5                   10

<210> SEQ ID NO 367
<211> LENGTH: 10
<212> TYPE: PRT
<213> ORGANISM: Homo sapiens

<400> SEQUENCE: 367

Gly Tyr Ala Leu Thr Ser Tyr Gly Ile Ser
1               5                   10

<210> SEQ ID NO 368
<211> LENGTH: 10
<212> TYPE: PRT
<213> ORGANISM: Homo sapiens

<400> SEQUENCE: 368

Gly Tyr Thr Leu Thr Ser Tyr Gly Ile Ser
1               5                   10

<210> SEQ ID NO 369
<211> LENGTH: 10
<212> TYPE: PRT
<213> ORGANISM: Homo sapiens

<400> SEQUENCE: 369

Gly Tyr Ser Phe Thr Ser Tyr Gly Ile Ser
1               5                   10

<210> SEQ ID NO 370
<211> LENGTH: 10
<212> TYPE: PRT
<213> ORGANISM: Homo sapiens

<400> SEQUENCE: 370

Gly Tyr Thr Phe Pro Ser Tyr Gly Ile Ser
1               5                   10

<210> SEQ ID NO 371
<211> LENGTH: 10
<212> TYPE: PRT
<213> ORGANISM: Homo sapiens

<400> SEQUENCE: 371

Gly Phe Thr Phe Ser Ser Tyr Trp Met Ser
1               5                   10

<210> SEQ ID NO 372
<211> LENGTH: 10
<212> TYPE: PRT
<213> ORGANISM: Homo sapiens

<400> SEQUENCE: 372

Gly Phe Thr Phe Ser Arg Tyr Trp Met Ser
1               5                   10

<210> SEQ ID NO 373
<211> LENGTH: 10
<212> TYPE: PRT
```

<213> ORGANISM: Homo sapiens

<400> SEQUENCE: 373

Gly Leu Thr Phe Ser Asn Phe Trp Met Ser
1               5                   10

<210> SEQ ID NO 374
<211> LENGTH: 10
<212> TYPE: PRT
<213> ORGANISM: Homo sapiens

<400> SEQUENCE: 374

Gly Phe Thr Phe Ser Ser Tyr Ala Met Asn
1               5                   10

<210> SEQ ID NO 375
<211> LENGTH: 10
<212> TYPE: PRT
<213> ORGANISM: Homo sapiens

<400> SEQUENCE: 375

Gly Phe Thr Phe Asn Ser Phe Gly Met His
1               5                   10

<210> SEQ ID NO 376
<211> LENGTH: 10
<212> TYPE: PRT
<213> ORGANISM: Homo sapiens

<400> SEQUENCE: 376

Gly Phe Thr Phe Arg Ser Tyr Gly Met His
1               5                   10

<210> SEQ ID NO 377
<211> LENGTH: 16
<212> TYPE: PRT
<213> ORGANISM: Homo sapiens

<400> SEQUENCE: 377

Asn Ile Lys Gln Asp Gly Ser Glu Lys Tyr Val Asp Ser Val Lys Gly
1               5                   10                  15

<210> SEQ ID NO 378
<211> LENGTH: 16
<212> TYPE: PRT
<213> ORGANISM: Homo sapiens

<400> SEQUENCE: 378

Asn Ile Lys His Asp Gly Ser Glu Lys Tyr Val Asp Ser Val Lys Gly
1               5                   10                  15

<210> SEQ ID NO 379
<211> LENGTH: 16
<212> TYPE: PRT
<213> ORGANISM: Homo sapiens

<400> SEQUENCE: 379

Thr Ile Ser Gly Ser Gly Asp Asn Thr Tyr Ala Asp Ser Val Lys Gly
1               5                   10                  15

<210> SEQ ID NO 380
<211> LENGTH: 16
<212> TYPE: PRT
<213> ORGANISM: Homo sapiens

<400> SEQUENCE: 380

Thr Ile Ser Gly Ser Gly Gly Asn Thr Tyr Ala Asp Ser Val Lys Gly
1               5                   10                  15

<210> SEQ ID NO 381
<211> LENGTH: 16
<212> TYPE: PRT
<213> ORGANISM: Homo sapiens

<400> SEQUENCE: 381

Leu Ile Trp Asn Asp Gly Ser Asn Lys Tyr Ala Asp Ser Val Lys Gly
1               5                   10                  15

<210> SEQ ID NO 382
<211> LENGTH: 16
<212> TYPE: PRT
<213> ORGANISM: Homo sapiens

<400> SEQUENCE: 382

Leu Ile Trp Ser Asp Gly Ser Asp Glu Tyr Ala Asp Ser Val Lys Gly
1               5                   10                  15

<210> SEQ ID NO 383
<211> LENGTH: 16
<212> TYPE: PRT
<213> ORGANISM: Homo sapiens

<400> SEQUENCE: 383

Leu Ile Trp Ser Asp Gly Ser Asp Lys Tyr Ala Asp Ser Val Lys Gly
1               5                   10                  15

<210> SEQ ID NO 384
<211> LENGTH: 16
<212> TYPE: PRT
<213> ORGANISM: Homo sapiens

<400> SEQUENCE: 384

Leu Ile Trp His Asp Gly Ser Asn Thr Tyr Val Asp Ser Val Lys Gly
1               5                   10                  15

<210> SEQ ID NO 385
<211> LENGTH: 10
<212> TYPE: PRT
<213> ORGANISM: Homo sapiens

<400> SEQUENCE: 385

Glu Ser Asn Trp Gly Phe Ala Phe Asp Ile
1               5                   10

<210> SEQ ID NO 386
<211> LENGTH: 10
<212> TYPE: PRT
<213> ORGANISM: Homo sapiens

<400> SEQUENCE: 386

Glu Ser Asn Trp Gly Phe Ala Phe Asp Val
1               5                   10

<210> SEQ ID NO 387
<211> LENGTH: 6
<212> TYPE: PRT
<213> ORGANISM: Homo sapiens

<400> SEQUENCE: 387

Gly Tyr Val Met Asp Val
1               5

<210> SEQ ID NO 388
<211> LENGTH: 11
<212> TYPE: PRT
<213> ORGANISM: Homo sapiens

<400> SEQUENCE: 388

Arg Ala Ser Gln Ser Ile Ser Ile Tyr Leu Asn
1               5                   10

<210> SEQ ID NO 389
<211> LENGTH: 14
<212> TYPE: PRT
<213> ORGANISM: Homo sapiens

<400> SEQUENCE: 389

Thr Gly Thr Asn Ser Asp Val Gly Gly Tyr Asn Ser Val Ser
1               5                   10

<210> SEQ ID NO 390
<211> LENGTH: 14
<212> TYPE: PRT
<213> ORGANISM: Homo sapiens

<400> SEQUENCE: 390

Thr Gly Thr Ser Ser Asp Val Gly Ala Tyr Asn Ser Val Ser
1               5                   10

<210> SEQ ID NO 391
<211> LENGTH: 14
<212> TYPE: PRT
<213> ORGANISM: Homo sapiens

<400> SEQUENCE: 391

Thr Gly Thr Ser Ser Asp Val Gly Arg Tyr Asn Ser Val Ser
1               5                   10

<210> SEQ ID NO 392
<211> LENGTH: 7
<212> TYPE: PRT
<213> ORGANISM: Homo sapiens

<400> SEQUENCE: 392

Arg Asn Asn Gln Arg Pro Leu
1               5

<210> SEQ ID NO 393
<211> LENGTH: 7
<212> TYPE: PRT
<213> ORGANISM: Homo sapiens

<400> SEQUENCE: 393

Ala Ala Ala Ser Leu Gln Ser
1               5

<210> SEQ ID NO 394
<211> LENGTH: 9
<212> TYPE: PRT
<213> ORGANISM: Homo sapiens

<400> SEQUENCE: 394

Gln Gln Ser Tyr Ser Ala Pro Ile Thr
1               5

<210> SEQ ID NO 395
<211> LENGTH: 9
<212> TYPE: PRT
<213> ORGANISM: Homo sapiens

<400> SEQUENCE: 395

Asn Ser Tyr Thr Ser Thr Ser Met Val
 1               5

<210> SEQ ID NO 396
<211> LENGTH: 9
<212> TYPE: PRT
<213> ORGANISM: Homo sapiens

<400> SEQUENCE: 396

Ser Ser Tyr Thr Ser Ser Ser Val Val
 1               5

<210> SEQ ID NO 397
<211> LENGTH: 10
<212> TYPE: PRT
<213> ORGANISM: Homo sapiens

<400> SEQUENCE: 397

Ala Ala Trp Asp Asp Ser Leu Asn Trp Val
 1               5                  10

<210> SEQ ID NO 398
<211> LENGTH: 11
<212> TYPE: PRT
<213> ORGANISM: Homo sapiens

<400> SEQUENCE: 398

Gly Thr Trp Asp Ser Ser Leu Ser Ser Tyr Val
 1               5                  10

<210> SEQ ID NO 399
<211> LENGTH: 11
<212> TYPE: PRT
<213> ORGANISM: Homo sapiens

<400> SEQUENCE: 399

Gly Thr Trp Asp Ser Ser Leu Ser Ala Tyr Val
 1               5                  10

<210> SEQ ID NO 400
<211> LENGTH: 116
<212> TYPE: PRT
<213> ORGANISM: Homo sapiens

<400> SEQUENCE: 400

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

-continued

Lys Leu Ser Ser Val Thr Ala Ala Asp Thr Ala Val Tyr Tyr Cys Ala
                85                  90                  95

Arg Tyr Ser Ser Gly Trp Phe Asp Tyr Trp Gly Gln Gly Thr Leu Val
            100                 105                 110

Thr Val Ser Ser
        115

<210> SEQ ID NO 401
<211> LENGTH: 118
<212> TYPE: PRT
<213> ORGANISM: Homo sapiens

<400> SEQUENCE: 401

Glu Val Gln Leu Val Glu Ser Gly Gly Gly Leu Val Gln Pro Gly Gly
1               5                   10                  15

Ser Leu Arg Leu Ser Cys Val Val Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Asn Trp Gly Phe Ala Phe Asp Ile Trp Gly Gln Gly
            100                 105                 110

Thr Met Val Thr Val Ser
        115

<210> SEQ ID NO 402
<211> LENGTH: 115
<212> TYPE: PRT
<213> ORGANISM: Homo sapiens

<400> SEQUENCE: 402

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asn Trp Gly Ala Phe Asp Ile Trp Gly Gln Gly Thr Met Val
            100                 105                 110

Thr Val Ser
        115

<210> SEQ ID NO 403
<211> LENGTH: 6
<212> TYPE: PRT
<213> ORGANISM: Homo sapiens

<400> SEQUENCE: 403

Glu Asn Leu Tyr Phe Gln
1               5

<210> SEQ ID NO 404
<211> LENGTH: 14
<212> TYPE: PRT
<213> ORGANISM: Homo sapiens
<220> FEATURE:
<221> NAME/KEY: VARIANT
<222> LOCATION: 1
<223> OTHER INFORMATION: Xaa= D, A, R or no amino acid
<220> FEATURE:
<221> NAME/KEY: VARIANT
<222> LOCATION: 2
<223> OTHER INFORMATION: Xaa=Y, I, G or no amino acid
<220> FEATURE:
<221> NAME/KEY: VARIANT
<222> LOCATION: 3
<223> OTHER INFORMATION: Xaa=D, A, G or no amino acid
<220> FEATURE:
<221> NAME/KEY: VARIANT
<222> LOCATION: 4
<223> OTHER INFORMATION: Xaa=F, A, L or no amino acid
<220> FEATURE:
<221> NAME/KEY: VARIANT
<222> LOCATION: 5
<223> OTHER INFORMATION: Xaa=W, L, A or no amino acid
<220> FEATURE:
<221> NAME/KEY: VARIANT
<222> LOCATION: 6
<223> OTHER INFORMATION: Xaa=S, Y, A or no amino acid
<220> FEATURE:
<221> NAME/KEY: VARIANT
<222> LOCATION: (7)...(7)
<223> OTHER INFORMATION: Xaa=A, Y, R or no amino acid
<220> FEATURE:
<221> NAME/KEY: VARIANT
<222> LOCATION: (8)...(8)
<223> OTHER INFORMATION: Xaa=Y,  P or no amino acid
<220> FEATURE:
<221> NAME/KEY: VARIANT
<222> LOCATION: (9)...(9)
<223> OTHER INFORMATION: Xaa=Y, G or no amino acid
<220> FEATURE:
<221> NAME/KEY: VARIANT
<222> LOCATION: (10)...(10)
<223> OTHER INFORMATION: Xaa=D, G or no amino acid
<220> FEATURE:
<221> NAME/KEY: VARIANT
<222> LOCATION: (11)...(11)
<223> OTHER INFORMATION: Xaa=A, M or no amino acid
<220> FEATURE:
<221> NAME/KEY: VARIANT
<222> LOCATION: (12)...(12)
<223> OTHER INFORMATION: Xaa=F,D  or no amino acid
<220> FEATURE:
<221> NAME/KEY: VARIANT
<222> LOCATION: (13)...(13)
<223> OTHER INFORMATION: Xaa=D, V or no amino acid
<220> FEATURE:
<221> NAME/KEY: VARIANT
<222> LOCATION: (14)...(14)
<223> OTHER INFORMATION: Xaa=V or no amino acid

<400> SEQUENCE: 404

Xaa Xaa Xaa Xaa Xaa Xaa Xaa Xaa Xaa Xaa Xaa Xaa Xaa Xaa
1               5                   10

<210> SEQ ID NO 405
<211> LENGTH: 11
<212> TYPE: PRT
<213> ORGANISM: Homo sapiens
<220> FEATURE:
<221> NAME/KEY: VARIANT

```
<222> LOCATION: 1
<223> OTHER INFORMATION: Xaa=Q or G
<220> FEATURE:
<221> NAME/KEY: VARIANT
<222> LOCATION: 2
<223> OTHER INFORMATION: Xaa=S, T, A or no amino acid
<220> FEATURE:
<221> NAME/KEY: VARIANT
<222> LOCATION: 3
<223> OTHER INFORMATION: Xaa=Y, W or no amino acid
<220> FEATURE:
<221> NAME/KEY: VARIANT
<222> LOCATION: 4
<223> OTHER INFORMATION: Xaa=D or no amino acid
<220> FEATURE:
<221> NAME/KEY: VARIANT
<222> LOCATION: 5
<223> OTHER INFORMATION: Xaa=S or no amino acid
<220> FEATURE:
<221> NAME/KEY: VARIANT
<222> LOCATION: 6
<223> OTHER INFORMATION: Xaa=S or no amino acid
<220> FEATURE:
<221> NAME/KEY: VARIANT
<222> LOCATION: (7)...(7)
<223> OTHER INFORMATION: Xaa=L, T or no amino acid
<220> FEATURE:
<221> NAME/KEY: VARIANT
<222> LOCATION: (8)...(8)
<223> OTHER INFORMATION: Xaa=A, S or no amino acid
<220> FEATURE:
<221> NAME/KEY: VARIANT
<222> LOCATION: (9)...(9)
<223> OTHER INFORMATION: Xaa=G, A, V or no amino acid
<220> FEATURE:
<221> NAME/KEY: VARIANT
<222> LOCATION: (10)...(10)
<223> OTHER INFORMATION: Xaa=S, Y, V or no amino acid
<220> FEATURE:
<221> NAME/KEY: VARIANT
<222> LOCATION: (11)...(11)
<223> OTHER INFORMATION: Xaa=V or no amino acid

<400> SEQUENCE: 405

Xaa Xaa Xaa Xaa Xaa Xaa Xaa Xaa Xaa Xaa Xaa
 1               5                  10

<210> SEQ ID NO 406
<211> LENGTH: 10
<212> TYPE: PRT
<213> ORGANISM: Homo sapiens
<220> FEATURE:
<221> NAME/KEY: VARIANT
<222> LOCATION: 1
<223> OTHER INFORMATION: Xaa=G
<220> FEATURE:
<221> NAME/KEY: VARIANT
<222> LOCATION: 2
<223> OTHER INFORMATION: Xaa=Y, F or G
<220> FEATURE:
<221> NAME/KEY: VARIANT
<222> LOCATION: 3
<223> OTHER INFORMATION: Xaa=T or S
<220> FEATURE:
<221> NAME/KEY: VARIANT
<222> LOCATION: 4
<223> OTHER INFORMATION: Xaa=L or F
<220> FEATURE:
<221> NAME/KEY: VARIANT
<222> LOCATION: 5
<223> OTHER INFORMATION: Xaa=T, S or N
<220> FEATURE:
<221> NAME/KEY: VARIANT
<222> LOCATION: 6
<223> OTHER INFORMATION: Xaa=S or A
<220> FEATURE:
<221> NAME/KEY: VARIANT
```

```
<222> LOCATION: (7)...(7)
<223> OTHER INFORMATION: Xaa=Y or F
<220> FEATURE:
<221> NAME/KEY: VARIANT
<222> LOCATION: (8)...(8)
<223> OTHER INFORMATION: Xaa=G, S or Y
<220> FEATURE:
<221> NAME/KEY: VARIANT
<222> LOCATION: (9)...(9)
<223> OTHER INFORMATION: Xaa=I, M or W
<220> FEATURE:
<221> NAME/KEY: VARIANT
<222> LOCATION: (10)...(10)
<223> OTHER INFORMATION: Xaa=S, N or H

<400> SEQUENCE: 406

Xaa Xaa Xaa Xaa Xaa Xaa Xaa Xaa Xaa Xaa
 1               5                  10

<210> SEQ ID NO 407
<211> LENGTH: 14
<212> TYPE: PRT
<213> ORGANISM: Homo sapiens
<220> FEATURE:
<221> NAME/KEY: VARIANT
<222> LOCATION: 1
<223> OTHER INFORMATION: Xaa=T or no amino acid
<220> FEATURE:
<221> NAME/KEY: VARIANT
<222> LOCATION: 2
<223> OTHER INFORMATION: Xaa=G or S
<220> FEATURE:
<221> NAME/KEY: VARIANT
<222> LOCATION: 3
<223> OTHER INFORMATION: Xaa=S, T or G
<220> FEATURE:
<221> NAME/KEY: VARIANT
<222> LOCATION: 4
<223> OTHER INFORMATION: Xaa=S
<220> FEATURE:
<221> NAME/KEY: VARIANT
<222> LOCATION: 5
<223> OTHER INFORMATION: Xaa=S
<220> FEATURE:
<221> NAME/KEY: VARIANT
<222> LOCATION: 6
<223> OTHER INFORMATION: Xaa=N, D or S
<220> FEATURE:
<221> NAME/KEY: VARIANT
<222> LOCATION: (7)...(7)
<223> OTHER INFORMATION: Xaa=I, V or N
<220> FEATURE:
<221> NAME/KEY: VARIANT
<222> LOCATION: (8)...(8)
<223> OTHER INFORMATION: Xaa=G or I
<220> FEATURE:
<221> NAME/KEY: VARIANT
<222> LOCATION: (9)...(9)
<223> OTHER INFORMATION: Xaa=A or G
<220> FEATURE:
<221> NAME/KEY: VARIANT
<222> LOCATION: (10)...(10)
<223> OTHER INFORMATION: Xaa=G, Y, S or N
<220> FEATURE:
<221> NAME/KEY: VARIANT
<222> LOCATION: (11)...(11)
<223> OTHER INFORMATION: Xaa=Y or N
<220> FEATURE:
<221> NAME/KEY: VARIANT
<222> LOCATION: (12)...(12)
<223> OTHER INFORMATION: Xaa=D, S, T or F
<220> FEATURE:
<221> NAME/KEY: VARIANT
<222> LOCATION: (13)...(13)
<223> OTHER INFORMATION: Xaa=V
<220> FEATURE:
<221> NAME/KEY: VARIANT
```

-continued

```
<222> LOCATION: (14)...(14)
<223> OTHER INFORMATION: Xaa=S, N or H

<400> SEQUENCE: 407

Xaa Xaa Xaa Xaa Xaa Xaa Xaa Xaa Xaa Xaa Xaa Xaa Xaa Xaa
 1               5                   10

<210> SEQ ID NO 408
<211> LENGTH: 17
<212> TYPE: PRT
<213> ORGANISM: Homo sapiens
<220> FEATURE:
<221> NAME/KEY: VARIANT
<222> LOCATION: 1
<223> OTHER INFORMATION: Xaa=W, S, L or no amino acid
<220> FEATURE:
<221> NAME/KEY: VARIANT
<222> LOCATION: 2
<223> OTHER INFORMATION: Xaa=V, I or E
<220> FEATURE:
<221> NAME/KEY: VARIANT
<222> LOCATION: 3
<223> OTHER INFORMATION: Xaa=S, W or I
<220> FEATURE:
<221> NAME/KEY: VARIANT
<222> LOCATION: 4
<223> OTHER INFORMATION: Xaa=F, S or N
<220> FEATURE:
<221> NAME/KEY: VARIANT
<222> LOCATION: 5
<223> OTHER INFORMATION: Xaa=Y, S, D or H
<220> FEATURE:
<221> NAME/KEY: VARIANT
<222> LOCATION: 6
<223> OTHER INFORMATION: Xaa=N, S or G
<220> FEATURE:
<221> NAME/KEY: VARIANT
<222> LOCATION: (7)...(7)
<223> OTHER INFORMATION: Xaa=S or G
<220> FEATURE:
<221> NAME/KEY: VARIANT
<222> LOCATION: (8)...(8)
<223> OTHER INFORMATION: Xaa=N, Y, D or R
<220> FEATURE:
<221> NAME/KEY: VARIANT
<222> LOCATION: (9)...(9)
<223> OTHER INFORMATION: Xaa=T, I or E
<220> FEATURE:
<221> NAME/KEY: VARIANT
<222> LOCATION: (10)...(10)
<223> OTHER INFORMATION: Xaa=N, S, Y or D
<220> FEATURE:
<221> NAME/KEY: VARIANT
<222> LOCATION: (11)...(11)
<223> OTHER INFORMATION: Xaa=Y
<220> FEATURE:
<221> NAME/KEY: VARIANT
<222> LOCATION: (12)...(12)
<223> OTHER INFORMATION: Xaa=A and N
<220> FEATURE:
<221> NAME/KEY: VARIANT
<222> LOCATION: (13)...(13)
<223> OTHER INFORMATION: Xaa=Q, D or P
<220> FEATURE:
<221> NAME/KEY: VARIANT
<222> LOCATION: (14)...(14)
<223> OTHER INFORMATION: Xaa=K or S
<220> FEATURE:
<221> NAME/KEY: VARIANT
<222> LOCATION: (15)...(15)
<223> OTHER INFORMATION: Xaa=L or V
<220> FEATURE:
<221> NAME/KEY: VARIANT
<222> LOCATION: (16)...(16)
<223> OTHER INFORMATION: Xaa=Q or K
<220> FEATURE:
<221> NAME/KEY: VARIANT
```

```
<222> LOCATION: (17)...(17)
<223> OTHER INFORMATION: Xaa=G or S

<400> SEQUENCE: 408

Xaa Xaa Xaa Xaa Xaa Xaa Xaa Xaa Xaa Xaa Xaa Xaa Xaa Xaa Xaa
 1               5                   10                  15

Xaa

<210> SEQ ID NO 409
<211> LENGTH: 7
<212> TYPE: PRT
<213> ORGANISM: Homo sapiens
<220> FEATURE:
<221> NAME/KEY: VARIANT
<222> LOCATION: 1
<223> OTHER INFORMATION: Xaa=G, E, S or D
<220> FEATURE:
<221> NAME/KEY: VARIANT
<222> LOCATION: 2
<223> OTHER INFORMATION: Xaa=N, V or Y
<220> FEATURE:
<221> NAME/KEY: VARIANT
<222> LOCATION: 3
<223> OTHER INFORMATION: Xaa=S or N
<220> FEATURE:
<221> NAME/KEY: VARIANT
<222> LOCATION: 4
<223> OTHER INFORMATION: Xaa=N, Q or K
<220> FEATURE:
<221> NAME/KEY: VARIANT
<222> LOCATION: 5
<223> OTHER INFORMATION: Xaa=R
<220> FEATURE:
<221> NAME/KEY: VARIANT
<222> LOCATION: 6
<223> OTHER INFORMATION: Xaa=P
<220> FEATURE:
<221> NAME/KEY: VARIANT
<222> LOCATION: (7)...(7)
<223> OTHER INFORMATION: Xaa=S

<400> SEQUENCE: 409

Xaa Xaa Xaa Xaa Xaa Xaa Xaa
 1               5

<210> SEQ ID NO 410
<211> LENGTH: 14
<212> TYPE: PRT
<213> ORGANISM: Homo sapiens
<220> FEATURE:
<221> NAME/KEY: VARIANT
<222> LOCATION: 1
<223> OTHER INFORMATION: Xaa=D or no amino acid
<220> FEATURE:
<221> NAME/KEY: VARIANT
<222> LOCATION: 2
<223> OTHER INFORMATION: Xaa=Y, A or no amino acid
<220> FEATURE:
<221> NAME/KEY: VARIANT
<222> LOCATION: 3
<223> OTHER INFORMATION: Xaa=D, I or no amino acid
<220> FEATURE:
<221> NAME/KEY: VARIANT
<222> LOCATION: 4
<223> OTHER INFORMATION: Xaa=F, A or no amino acid
<220> FEATURE:
<221> NAME/KEY: VARIANT
<222> LOCATION: 5
<223> OTHER INFORMATION: Xaa=W, A or no amino acid
<220> FEATURE:
<221> NAME/KEY: VARIANT
<222> LOCATION: 6
<223> OTHER INFORMATION: Xaa=S, L or no amino acid
<220> FEATURE:
```

```
<221> NAME/KEY: VARIANT
<222> LOCATION: (7)...(7)
<223> OTHER INFORMATION: Xaa=A, Y, G or no amino acid
<220> FEATURE:
<221> NAME/KEY: VARIANT
<222> LOCATION: (8)...(8)
<223> OTHER INFORMATION: Xaa=Y, Q or no amino acid
<220> FEATURE:
<221> NAME/KEY: VARIANT
<222> LOCATION: (9)...(9)
<223> OTHER INFORMATION: Xaa=G, Y or L
<220> FEATURE:
<221> NAME/KEY: VARIANT
<222> LOCATION: (10)...(10)
<223> OTHER INFORMATION: Xaa=Y, D or V
<220> FEATURE:
<221> NAME/KEY: VARIANT
<222> LOCATION: (11)...(11)
<223> OTHER INFORMATION: Xaa=G, A or P
<220> FEATURE:
<221> NAME/KEY: VARIANT
<222> LOCATION: (12)...(12)
<223> OTHER INFORMATION: Xaa=M or F
<220> FEATURE:
<221> NAME/KEY: VARIANT
<222> LOCATION: (13)...(13)
<223> OTHER INFORMATION: Xaa=D
<220> FEATURE:
<221> NAME/KEY: VARIANT
<222> LOCATION: (14)...(14)
<223> OTHER INFORMATION: Xaa=V or Y

<400> SEQUENCE: 410

Xaa Xaa Xaa Xaa Xaa Xaa Xaa Xaa Xaa Xaa Xaa Xaa Xaa
 1               5                   10

<210> SEQ ID NO 411
<211> LENGTH: 11
<212> TYPE: PRT
<213> ORGANISM: Homo sapiens
<220> FEATURE:
<221> NAME/KEY: VARIANT
<222> LOCATION: 1
<223> OTHER INFORMATION: Xaa=Q, A, G or no amino acid
<220> FEATURE:
<221> NAME/KEY: VARIANT
<222> LOCATION: 2
<223> OTHER INFORMATION: Xaa=S, V, T or no amino acid
<220> FEATURE:
<221> NAME/KEY: VARIANT
<222> LOCATION: 3
<223> OTHER INFORMATION: Xaa=Y, N or W
<220> FEATURE:
<221> NAME/KEY: VARIANT
<222> LOCATION: 4
<223> OTHER INFORMATION: Xaa=S or D
<220> FEATURE:
<221> NAME/KEY: VARIANT
<222> LOCATION: 5
<223> OTHER INFORMATION: Xaa=S, Y or D
<220> FEATURE:
<221> NAME/KEY: VARIANT
<222> LOCATION: 6
<223> OTHER INFORMATION: Xaa=S or T
<220> FEATURE:
<221> NAME/KEY: VARIANT
<222> LOCATION: (7)...(7)
<223> OTHER INFORMATION: Xaa=L or S
<220> FEATURE:
<221> NAME/KEY: VARIANT
<222> LOCATION: (8)...(8)
<223> OTHER INFORMATION: Xaa=S, T or N
<220> FEATURE:
<221> NAME/KEY: VARIANT
<222> LOCATION: (9)...(9)
<223> OTHER INFORMATION: Xaa=G, S or A
<220> FEATURE:
```

```
<221> NAME/KEY: VARIANT
<222> LOCATION: (10)...(10)
<223> OTHER INFORMATION: Xaa=S, M, W or Y
<220> FEATURE:
<221> NAME/KEY: VARIANT
<222> LOCATION: (11)...(11)
<223> OTHER INFORMATION: Xaa=V

<400> SEQUENCE: 411

Xaa Xaa Xaa Xaa Xaa Xaa Xaa Xaa Xaa Xaa Xaa
 1               5                  10

<210> SEQ ID NO 412
<211> LENGTH: 10
<212> TYPE: PRT
<213> ORGANISM: Homo sapiens
<220> FEATURE:
<221> NAME/KEY: VARIANT
<222> LOCATION: 1
<223> OTHER INFORMATION: Xaa=G, P or A
<220> FEATURE:
<221> NAME/KEY: VARIANT
<222> LOCATION: 2
<223> OTHER INFORMATION: Xaa=Y, W, F, T or S
<220> FEATURE:
<221> NAME/KEY: VARIANT
<222> LOCATION: 3
<223> OTHER INFORMATION: Xaa=T, P, S, A, C, V, L or I
<220> FEATURE:
<221> NAME/KEY: VARIANT
<222> LOCATION: 4
<223> OTHER INFORMATION: Xaa=L, F, I, V, M, A or Y
<220> FEATURE:
<221> NAME/KEY: VARIANT
<222> LOCATION: 5
<223> OTHER INFORMATION: Xaa=T, P, S or A
<220> FEATURE:
<221> NAME/KEY: VARIANT
<222> LOCATION: 6
<223> OTHER INFORMATION: Xaa=S, T, A or C
<220> FEATURE:
<221> NAME/KEY: VARIANT
<222> LOCATION: (7)...(7)
<223> OTHER INFORMATION: Xaa=Y, W, F, T or S
<220> FEATURE:
<221> NAME/KEY: VARIANT
<222> LOCATION: (8)...(8)
<223> OTHER INFORMATION: Xaa=G, P or A
<220> FEATURE:
<221> NAME/KEY: VARIANT
<222> LOCATION: (9)...(9)
<223> OTHER INFORMATION: Xaa=I, L, V, M, A or F
<220> FEATURE:
<221> NAME/KEY: VARIANT
<222> LOCATION: (10)...(10)
<223> OTHER INFORMATION: Xaa=S, T, A or C

<400> SEQUENCE: 412

Xaa Xaa Xaa Xaa Xaa Xaa Xaa Xaa Xaa Xaa
 1               5                  10

<210> SEQ ID NO 413
<211> LENGTH: 14
<212> TYPE: PRT
<213> ORGANISM: Homo sapiens
<220> FEATURE:
<221> NAME/KEY: VARIANT
<222> LOCATION: 1
<223> OTHER INFORMATION: Xaa=T or S
<220> FEATURE:
<221> NAME/KEY: VARIANT
<222> LOCATION: 2
<223> OTHER INFORMATION: Xaa=G, P or A
<220> FEATURE:
<221> NAME/KEY: VARIANT
```

```
<222> LOCATION: 3
<223> OTHER INFORMATION: Xaa=T or S
<220> FEATURE:
<221> NAME/KEY: VARIANT
<222> LOCATION: 4
<223> OTHER INFORMATION: Xaa=S, N, T, A, C or Q
<220> FEATURE:
<221> NAME/KEY: VARIANT
<222> LOCATION: 5
<223> OTHER INFORMATION: Xaa=S, T, A or C
<220> FEATURE:
<221> NAME/KEY: VARIANT
<222> LOCATION: 6
<223> OTHER INFORMATION: Xaa=D or E
<220> FEATURE:
<221> NAME/KEY: VARIANT
<222> LOCATION: (7)...(7)
<223> OTHER INFORMATION: Xaa=V, I, M, L, F or A
<220> FEATURE:
<221> NAME/KEY: VARIANT
<222> LOCATION: (8)...(8)
<223> OTHER INFORMATION: Xaa=G, P or A
<220> FEATURE:
<221> NAME/KEY: VARIANT
<222> LOCATION: (9)...(9)
<223> OTHER INFORMATION: Xaa=G, A, R, P, V, L, I, K, Q or N
<220> FEATURE:
<221> NAME/KEY: VARIANT
<222> LOCATION: (10)...(10)
<223> OTHER INFORMATION: Xaa=Y, W, F, T or S
<220> FEATURE:
<221> NAME/KEY: VARIANT
<222> LOCATION: (11)...(11)
<223> OTHER INFORMATION: Xaa=N or Q
<220> FEATURE:
<221> NAME/KEY: VARIANT
<222> LOCATION: (12)...(12)
<223> OTHER INFORMATION: Xaa=Y, S, W, F, T, S, T, A or C
<220> FEATURE:
<221> NAME/KEY: VARIANT
<222> LOCATION: (13)...(13)
<223> OTHER INFORMATION: Xaa=V, I, M, L, F, or A
<220> FEATURE:
<221> NAME/KEY: VARIANT
<222> LOCATION: (14)...(14)
<223> OTHER INFORMATION: Xaa=S, T, A or C

<400> SEQUENCE: 413

Xaa Xaa Xaa Xaa Xaa Xaa Xaa Xaa Xaa Xaa Xaa Xaa Xaa Xaa
 1               5                  10

<210> SEQ ID NO 414
<211> LENGTH: 17
<212> TYPE: PRT
<213> ORGANISM: Homo sapiens
<220> FEATURE:
<221> NAME/KEY: VARIANT
<222> LOCATION: 1
<223> OTHER INFORMATION: Xaa=W, Y or F
<220> FEATURE:
<221> NAME/KEY: VARIANT
<222> LOCATION: 2
<223> OTHER INFORMATION: Xaa=V, I, M, L, F or A
<220> FEATURE:
<221> NAME/KEY: VARIANT
<222> LOCATION: 3
<223> OTHER INFORMATION: Xaa=S, T, A or C
<220> FEATURE:
<221> NAME/KEY: VARIANT
<222> LOCATION: 4
<223> OTHER INFORMATION: Xaa=A, F, V, L, I, Y or M
<220> FEATURE:
<221> NAME/KEY: VARIANT
<222> LOCATION: 5
<223> OTHER INFORMATION: Xaa=Y, W, F, T or S
<220> FEATURE:
<221> NAME/KEY: VARIANT
```

```
<222> LOCATION: 6
<223> OTHER INFORMATION: Xaa=N or Q
<220> FEATURE:
<221> NAME/KEY: VARIANT
<222> LOCATION: (7)...(7)
<223> OTHER INFORMATION: Xaa=G, P or A
<220> FEATURE:
<221> NAME/KEY: VARIANT
<222> LOCATION: (8)...(8)
<223> OTHER INFORMATION: Xaa=N or Q
<220> FEATURE:
<221> NAME/KEY: VARIANT
<222> LOCATION: (9)...(9)
<223> OTHER INFORMATION: Xaa=T or S
<220> FEATURE:
<221> NAME/KEY: VARIANT
<222> LOCATION: (10)...(10)
<223> OTHER INFORMATION: Xaa=N or Q
<220> FEATURE:
<221> NAME/KEY: VARIANT
<222> LOCATION: (11)...(11)
<223> OTHER INFORMATION: Xaa=Y, W, F, T or S
<220> FEATURE:
<221> NAME/KEY: VARIANT
<222> LOCATION: (12)...(12)
<223> OTHER INFORMATION: Xaa=A, V, L or I
<220> FEATURE:
<221> NAME/KEY: VARIANT
<222> LOCATION: (13)...(13)
<223> OTHER INFORMATION: Xaa=Q, E, N or D
<220> FEATURE:
<221> NAME/KEY: VARIANT
<222> LOCATION: (14)...(14)
<223> OTHER INFORMATION: Xaa=K, R, Q or N
<220> FEATURE:
<221> NAME/KEY: VARIANT
<222> LOCATION: (15)...(15)
<223> OTHER INFORMATION: Xaa=L, F, V, I, M, A or Y
<220> FEATURE:
<221> NAME/KEY: VARIANT
<222> LOCATION: (16)...(16)
<223> OTHER INFORMATION: Xaa=Q or N
<220> FEATURE:
<221> NAME/KEY: VARIANT
<222> LOCATION: (17)...(17)
<223> OTHER INFORMATION: Xaa=G, P or A

<400> SEQUENCE: 414

Xaa Xaa Xaa Xaa Xaa Xaa Xaa Xaa Xaa Xaa Xaa Xaa Xaa Xaa Xaa Xaa
 1               5                   10                  15

Xaa

<210> SEQ ID NO 415
<211> LENGTH: 7
<212> TYPE: PRT
<213> ORGANISM: Homo sapiens
<220> FEATURE:
<221> NAME/KEY: VARIANT
<222> LOCATION: 1
<223> OTHER INFORMATION: Xaa=E or D
<220> FEATURE:
<221> NAME/KEY: VARIANT
<222> LOCATION: 2
<223> OTHER INFORMATION: Xaa=V, I, M, L, F or A
<220> FEATURE:
<221> NAME/KEY: VARIANT
<222> LOCATION: 3
<223> OTHER INFORMATION: Xaa=S, T, A or C
<220> FEATURE:
<221> NAME/KEY: VARIANT
<222> LOCATION: 4
<223> OTHER INFORMATION: Xaa=N or Q
<220> FEATURE:
<221> NAME/KEY: VARIANT
<222> LOCATION: 5
<223> OTHER INFORMATION: Xaa=R, K, Q or N
```

```
<220> FEATURE:
<221> NAME/KEY: VARIANT
<222> LOCATION: 6
<223> OTHER INFORMATION: Xaa=P or A
<220> FEATURE:
<221> NAME/KEY: VARIANT
<222> LOCATION: (7)...(7)
<223> OTHER INFORMATION: Xaa=S, T, A or C

<400> SEQUENCE: 415

Xaa Xaa Xaa Xaa Xaa Xaa Xaa
 1               5

<210> SEQ ID NO 416
<211> LENGTH: 6
<212> TYPE: PRT
<213> ORGANISM: Homo sapiens
<220> FEATURE:
<221> NAME/KEY: VARIANT
<222> LOCATION: 1
<223> OTHER INFORMATION: Xaa=G, P, A or no amino acid
<220> FEATURE:
<221> NAME/KEY: VARIANT
<222> LOCATION: 2
<223> OTHER INFORMATION: Xaa=Y, W, F, T or S
<220> FEATURE:
<221> NAME/KEY: VARIANT
<222> LOCATION: 3
<223> OTHER INFORMATION: Xaa=G, V, P, A, I, M, L or F
<220> FEATURE:
<221> NAME/KEY: VARIANT
<222> LOCATION: 4
<223> OTHER INFORMATION: Xaa=M, L, F or I
<220> FEATURE:
<221> NAME/KEY: VARIANT
<222> LOCATION: 5
<223> OTHER INFORMATION: Xaa=D or E
<220> FEATURE:
<221> NAME/KEY: VARIANT
<222> LOCATION: 6
<223> OTHER INFORMATION: Xaa=V, I, M, L, F or A

<400> SEQUENCE: 416

Xaa Xaa Xaa Xaa Xaa Xaa
 1               5

<210> SEQ ID NO 417
<211> LENGTH: 9
<212> TYPE: PRT
<213> ORGANISM: Homo sapiens
<220> FEATURE:
<221> NAME/KEY: VARIANT
<222> LOCATION: 1
<223> OTHER INFORMATION: Xaa=S, N, T, A, C or Q
<220> FEATURE:
<221> NAME/KEY: VARIANT
<222> LOCATION: 2
<223> OTHER INFORMATION: Xaa=S, T, A or C
<220> FEATURE:
<221> NAME/KEY: VARIANT
<222> LOCATION: 3
<223> OTHER INFORMATION: Xaa=Y, W, F, T or S
<220> FEATURE:
<221> NAME/KEY: VARIANT
<222> LOCATION: 4
<223> OTHER INFORMATION: Xaa=T or S
<220> FEATURE:
<221> NAME/KEY: VARIANT
<222> LOCATION: 5
<223> OTHER INFORMATION: Xaa=S, T, A or C
<220> FEATURE:
<221> NAME/KEY: VARIANT
<222> LOCATION: 6
<223> OTHER INFORMATION: Xaa=S, T, A or C
<220> FEATURE:
```

```
<221> NAME/KEY: VARIANT
<222> LOCATION: (7)...(7)
<223> OTHER INFORMATION: Xaa=N, S, Q, T, A or C
<220> FEATURE:
<221> NAME/KEY: VARIANT
<222> LOCATION: (8)...(8)
<223> OTHER INFORMATION: Xaa=M, V, L, F, I or A
<220> FEATURE:
<221> NAME/KEY: VARIANT
<222> LOCATION: (9)...(9)
<223> OTHER INFORMATION: Xaa=V, I, M, L, F or A

<400> SEQUENCE: 417

Xaa Xaa Xaa Xaa Xaa Xaa Xaa Xaa Xaa
  1               5

<210> SEQ ID NO 418
<211> LENGTH: 363
<212> TYPE: DNA
<213> ORGANISM: Homo sapiens

<400> SEQUENCE: 418
caggtgcagg tggtgcagtc tggggctgag gtgaagaagc ctggggcctc agtgaaggtc      60
tcctgcaagg cttctggata caccttcacc ggctactata tacactgggt gcgacaggcc     120
cctggacaag gcttgagtg gatgggatgg atcaaccctc acagtggtgg cgcaaactat      180
gcacagaagt tcagggcag gtcaccatg accaggaca cgtccatcag cacagcctac        240
atggagctga gcaggctgag atctgacgac acggccgtgt attactgtgc gagaggcaac     300
tggaactacg actactacgg tatggacgtc tggggccaag ggaccacggt caccgtctcc     360
tca                                                                   363

<210> SEQ ID NO 419
<211> LENGTH: 121
<212> TYPE: PRT
<213> ORGANISM: Homo sapiens

<400> SEQUENCE: 419

Gln Val Gln Val Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
                 20                  25                  30

Tyr Ile His Trp Val Arg Gln Ala Pro Gly Gln Gly Leu Glu Trp Met
             35                  40                  45

Gly Trp Ile Asn Pro His Ser Gly Gly Ala Asn Tyr Ala Gln Lys Phe
         50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Asn Trp Asn Tyr Asp Tyr Tyr Gly Met Asp Val Trp Gly
                100                 105                 110

Gln Gly Thr Thr Val Thr Val Ser Ser
            115                 120

<210> SEQ ID NO 420
<211> LENGTH: 321
<212> TYPE: DNA
<213> ORGANISM: Homo sapiens

<400> SEQUENCE: 420
```

```
gacatccaga tgacccagtc tccatcctcc ctgtctgcat ctgtaggaga cagagtcacc      60
atcacttgcc gggcgagtca ggacattagc aattatttag cctggtatca gcagaaacca     120
gggaaagttc ctaagctcct gatctatgct gcatccactt tgcaatcagg ggtcccatct     180
cggttcagtg gcagtggatc tgggacagat ttcactctca ccatcagcag cctacagcct     240
gaagatgttg caacttattt ctgtcaaagg tatcagattg ccccattcac tttcggccct     300
gggaccaagg tggatatcaa a                                                321
```

<210> SEQ ID NO 421
<211> LENGTH: 107
<212> TYPE: PRT
<213> ORGANISM: Homo sapiens

<400> SEQUENCE: 421

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Arg Tyr Gln Ile Ala Pro Phe
                85                  90                  95

Thr Phe Gly Pro Gly Thr Lys Val Asp Ile Lys
            100                 105

<210> SEQ ID NO 422
<211> LENGTH: 366
<212> TYPE: DNA
<213> ORGANISM: Homo sapiens

<400> SEQUENCE: 422

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atctggtatg atggaagtac taaatactat     180
gcagactccg tgaagggccg atccaccatc tccagagaca attccaagaa cacgctgtat     240
ctgcaaatga acagcctgag agccgaggac acggctgtgt attactgtgc gaggtcagtg     300
gctggttacc actactacta cggtatggac gtctggggcc aagggaccac ggtcaccgtc     360
tcctca                                                                 366
```

<210> SEQ ID NO 423
<211> LENGTH: 122
<212> TYPE: PRT
<213> ORGANISM: Homo sapiens

<400> SEQUENCE: 423

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

```
Ala Val Ile Trp Tyr Asp Gly Ser Thr Lys Tyr Tyr Ala Asp Ser Val
     50                  55                  60

Lys Gly Arg Ser Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Val Ala Gly Tyr His Tyr Tyr Tyr Gly Met Asp Val Trp
            100                 105                 110

Gly Gln Gly Thr Thr Val Thr Val Ser Ser
            115                 120
```

<210> SEQ ID NO 424
<211> LENGTH: 324
<212> TYPE: DNA
<213> ORGANISM: Homo sapiens

<400> SEQUENCE: 424

```
tcttctgagc tgactcagga ccctgctgtg tctgtggcct tgggacagac agtcaggatc      60
acatgccaag agacagcct cagaggctat tatgcaacct ggtaccagca gaagccaaga     120
caggcccctg tacttgtcat ctatggtaaa aactaccggc cctcagggat cccagaccga     180
ttctctggct ccacctcagg aaacacagct tccttgacca tcactggggc tcaggcggaa     240
gatgaggctg actattactg taactcccgg gacagcattg gtaaccatct ggtgttcggc     300
ggagggacca agctgaccgt ccta                                            324
```

<210> SEQ ID NO 425
<211> LENGTH: 108
<212> TYPE: PRT
<213> ORGANISM: Homo sapiens

<400> SEQUENCE: 425

```
Ser Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg Gly Tyr Tyr Ala
             20                  25                  30

Thr Trp Tyr Gln Gln Lys Pro Arg Gln Ala Pro Val Leu Val Ile Tyr
         35                  40                  45

Gly Lys Asn Tyr Arg Pro Ser Gly Ile Pro Asp Arg Phe Ser Gly Ser
     50                  55                  60

Thr Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ile Gly Asn His
                 85                  90                  95

Leu Val Phe Gly Gly Thr Lys Leu Thr Val Leu
            100                 105
```

<210> SEQ ID NO 426
<211> LENGTH: 366
<212> TYPE: DNA
<213> ORGANISM: Homo sapiens

<400> SEQUENCE: 426

```
caggtgcagc tggtggagtc tgggggaggc gtggtccagc ctggagggtc cctgagactc      60
tcctgtgcag cgtctggatt caccttcagt agctatggct tgcactgggt ccgccaggct     120
ccaggcaagg ggctggagtg ggtggcagtt atatggttag atggaagtaa taaatactat     180
```

```
gcagactccg tgaagggccg atccaccatc tccagagaca attccaagaa cacgctgtat   240
ctgcaaatga acagcctgag agccgaggac acggctgtgt attactgtgc gaggtcagtg   300
gctggttacc actactacta cggtatggac gtctggggcc aagggaccac ggtcaccgtc   360
tcctca                                                              366
```

```
<210> SEQ ID NO 427
<211> LENGTH: 122
<212> TYPE: PRT
<213> ORGANISM: Homo sapiens

<400> SEQUENCE: 427

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Leu His Trp Val Arg Gln Ala Pro Gly Lys Gly Leu Glu Trp Val
             35                  40                  45

Ala Val Ile Trp Leu Asp Gly Ser Asn Lys Tyr Tyr Ala Asp Ser Val
         50                  55                  60

Lys Gly Arg Ser Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Val Ala Gly Tyr His Tyr Tyr Tyr Gly Met Asp Val Trp
                100                 105                 110

Gly Gln Gly Thr Thr Val Thr Val Ser Ser
            115                 120
```

```
<210> SEQ ID NO 428
<211> LENGTH: 324
<212> TYPE: DNA
<213> ORGANISM: Homo sapiens

<400> SEQUENCE: 428
tcttctgagc tgactcagga ccctgctgtg tctgtggcct tgggacagac agtcaggatc    60
acatgccaag agacagcct cagaagttat tatggaagct ggtaccagca gaagccaaga   120
caggcccctg tacttgtcat ctttggtaaa acaaccggc cctcaggat cccagaccga   180 ttctctggct ccacctcagg aaacacagct tccttgacca tcactggggc tcaggcggaa   240
gatgaggctg actattactg taactcacgg gacatcattg gtgaccatct gctgttcggc   300
ggagggacca gctgaccgt ccta                                           324
```

```
<210> SEQ ID NO 429
<211> LENGTH: 108
<212> TYPE: PRT
<213> ORGANISM: Homo sapiens

<400> SEQUENCE: 429

Ser Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg Ser Tyr Tyr Gly
                 20                  25                  30

Ser Trp Tyr Gln Gln Lys Pro Arg Gln Ala Pro Val Leu Val Ile Phe
             35                  40                  45

Gly Lys Asn Asn Arg Pro Ser Gly Ile Pro Asp Arg Phe Ser Gly Ser
         50                  55                  60
```

```
Thr Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ile Ile Gly Asp His
                 85                  90                  95

Leu Leu Phe Gly Gly Gly Thr Lys Leu Thr Val Leu
            100                 105
```

<210> SEQ ID NO 430
<211> LENGTH: 366
<212> TYPE: DNA
<213> ORGANISM: Homo sapiens

<400> SEQUENCE: 430

```
caggtgcagc tggtggagtc tgggggaggc gtggtccagt ctggaggtc cctgagactc    60 tcctgtgcag cgtctggatt caccttcagg aactatggca tgcactgggt ccgccaggct   120
ccaggcaagg gctggagtg gtggcagtt atatggtttg atggaagtaa taaatactat    180
gcagactccg tgaagggccg atccaccatc tccagagaca attccaagaa cacgctgtat   240
ctgctaatga acagcctgag agccgaggac acggctgtgt attactgtgc gaggtcagtg   300
gctggttacc actactacta cggtatggac gtctggggcc aagggaccac ggtcaccgtc   360
tcctca                                                              366
```

<210> SEQ ID NO 431
<211> LENGTH: 122
<212> TYPE: PRT
<213> ORGANISM: Homo sapiens

<400> SEQUENCE: 431

```
Gln Val Gln Leu Val Glu Ser Gly Gly Gly Val Val Gln Ser Gly Arg
 1               5                  10                  15

Ser Leu Arg Leu Ser Cys Ala Ala Ser Gly Phe Thr Phe Arg Asn Tyr
                20                  25                  30

Gly Met His Trp Val Arg Gln Ala Pro Gly Lys Gly Leu Glu Trp Val
            35                  40                  45

Ala Val Ile Trp Phe Asp Gly Ser Asn Lys Tyr Tyr Ala Asp Ser Val
        50                  55                  60

Lys Gly Arg Ser Thr Ile Ser Arg Asp Asn Ser Lys Asn Thr Leu Tyr
 65                  70                  75                  80

Leu Leu Met Asn Ser Leu Arg Ala Glu Asp Thr Ala Val Tyr Tyr Cys
                85                  90                  95

Ala Arg Ser Val Ala Gly Tyr His Tyr Tyr Tyr Gly Met Asp Val Trp
                100                 105                 110

Gly Gln Gly Thr Thr Val Thr Val Ser Ser
            115                 120
```

<210> SEQ ID NO 432
<211> LENGTH: 324
<212> TYPE: DNA
<213> ORGANISM: Homo sapiens

<400> SEQUENCE: 432

```
tcttctgagc tgactcagga ccctgctgtg tctgtggcct gggacagac agtcaggatc    60 acatgccagg gagacagcct cagaagctat tatgcaagct ggtaccagca gaagccaaga   120
caggcccctg tacttgtcat ctatggtaaa acaaccggc cctcagggat ccagaccga    180 atctctggct ccacctcagg aaacacagct tccttgacca tcactggggc tcaggcggaa   240
```

```
gatgaggctg actattactg taaatcccgg acatcattg gtgaccatct ggtgttcggc    300
ggagggacca aactgaccgt ccta                                          324
```

<210> SEQ ID NO 433
<211> LENGTH: 108
<212> TYPE: PRT
<213> ORGANISM: Homo sapiens

<400> SEQUENCE: 433

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Arg Gln Ala Pro Val Leu Val Ile Tyr
        35                  40                  45

Gly Lys Asn Asn Arg Pro Ser Gly Ile Pro Asp Arg Ile Ser Gly Ser
    50                  55                  60

Thr Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Ile Ile Gly Asp His
                85                  90                  95

Leu Val Phe Gly Gly Gly Thr Lys Leu Thr Val Leu
            100                 105
```

<210> SEQ ID NO 434
<211> LENGTH: 342
<212> TYPE: DNA
<213> ORGANISM: Homo sapiens

<400> SEQUENCE: 434

```
caggtgcagc tggtggagtc tgggggaggc gtggtccagc ctggggaggtc cctgagactc    60 tcctgtgcag cgtctggatt caccttcagt agctatggca tgcactgggt ccgccaggct   120
ccaggcaagg ggctggagtg ggtggcagtt atatggtatg atggaagtaa taatactat    180 gcagactccg tgaagggccg attcaccatc tccagagaca attccaagaa cacgctgtat   240
ctgcaaatga acagcctgag agccgaggac acggctgtgt attactgtgt gagagatcgg   300
ggactggact ggggccaggg aaccctggtc accgtctcct ca                       342
```

<210> SEQ ID NO 435
<211> LENGTH: 114
<212> TYPE: PRT
<213> ORGANISM: Homo sapiens

<400> SEQUENCE: 435

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Val Arg Asp Arg Gly Leu Asp Trp Gly Gln Gly Thr Leu Val Thr Val
            100                 105                 110
Ser Ser

<210> SEQ ID NO 436
<211> LENGTH: 324
<212> TYPE: DNA
<213> ORGANISM: Homo sapiens

<400> SEQUENCE: 436
tcttctgagc tgactcagga ccctgctgtg tctgtggcct tgggacagac agtcaggatc      60
acatgccaag agacagcct cagaggctat atgcaagct ggtaccagca gaagccaaga      120 caggccctg tacttgtcat ctatggtaaa acaaccggc cctcagggat cccagaccga       180
ttctctggct ccacctcagg aaacacagct tccttgacca tcactggggc tcaggcggaa      240
gatgaggctg actattactg taagtcccgg gacagcagtg gtgaccatct ggtgttcggc      300
ggagggacca agctgaccgt ccta                                             324

<210> SEQ ID NO 437
<211> LENGTH: 108
<212> TYPE: PRT
<213> ORGANISM: Homo sapiens

<400> SEQUENCE: 437

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Gly Tyr Tyr Ala
            20                  25                  30

Ser Trp Tyr Gln Gln Lys Pro Arg Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Thr Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Ser Ser Gly Asp His
                85                  90                  95

Leu Val Phe Gly Gly Gly Thr Lys Leu Thr Val Leu
            100                 105

<210> SEQ ID NO 438
<211> LENGTH: 366
<212> TYPE: DNA
<213> ORGANISM: Homo sapiens

<400> SEQUENCE: 438
caggtgcagg tggtggagtc tgggggaggc gtggtccagc ctgggggtc cctgagactc       60 tcctgtgcag cgtctggatt caccttcagt aactatggca tgcactgggt ccgccaggct      120
ccaggcaagg ggctggagtg ggtggcagtt atttggtatg atggaagtag taaatactat      180
gcagactccg tgaagggccg attccaccat tccagagaca attccaagaa cacggtgtat      240
ctgcaaatga acagcctgag agccgaggac acggctgtgt attactgtgc gaggtcagtg      300
gctggttacc actactacta cggtatggac gtctggggcc aagggaccac ggtcaccgtc      360
tcctca                                                                 366

<210> SEQ ID NO 439
```

```
<211> LENGTH: 122
<212> TYPE: PRT
<213> ORGANISM: Homo sapiens

<400> SEQUENCE: 439

Gln Val Gln Val Val Glu Ser Gly Gly Val Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Ser Lys Tyr Tyr Ala Asp Ser Val
50                  55                  60

Lys Gly Arg Ser Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Ser Val Ala Gly Tyr His Tyr Tyr Tyr Gly Met Asp Val Trp
            100                 105                 110

Gly Gln Gly Thr Thr Val Thr Val Ser Ser
        115                 120

<210> SEQ ID NO 440
<211> LENGTH: 324
<212> TYPE: DNA
<213> ORGANISM: Homo sapiens

<400> SEQUENCE: 440
tcttctgagc tgactcagga ccctgctgtg tctgtggcct tgggacagac agtcaggatc      60
acatgccaag agacagcct cagaggctat tatgcaagct ggtaccagca gaagccaaga     120
caggcccctg tacttgtcat ctatggtaaa aacaaccggc cctcagggat cccagaccga    180
ttctctggct ccacctcagg aaacacagct tccttgacca tcactggggc tcaggcggaa    240
gatgaggctg actattactg taagtcccgg gacagcagtg gtgaccatct ggtgttcggc    300
ggagggacca gctgaccgt ccta                                            324

<210> SEQ ID NO 441
<211> LENGTH: 108
<212> TYPE: PRT
<213> ORGANISM: Homo sapiens

<400> SEQUENCE: 441

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Tyr Tyr Ala
            20                  25                  30

Ser Trp Tyr Gln Gln Lys Pro Arg Gln Ala Pro Val Leu Val Ile Tyr
        35                  40                  45

Gly Lys Asn Asn Arg Pro Ser Gly Ile Pro Asp Arg Phe Ser Gly Ser
50                  55                  60

Thr Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Ser Ser Gly Asp His
                85                  90                  95

Leu Val Phe Gly Gly Gly Thr Lys Leu Thr Val Leu
            100                 105
```

<210> SEQ ID NO 442
<211> LENGTH: 366
<212> TYPE: DNA
<213> ORGANISM: Homo sapiens

<400> SEQUENCE: 442
caggtgcagc tggtggagtc tgggggaggc gtggtccagc ctggagggtc cctgagtctc    60
tcctgtgcag cgtctggatt caccttcagt agctatggca tgcactgggt ccgccaggct   120
ccaggcaagg ggctggagtg ggtggcagtt atatggtatg atggaagtta taaagactat   180
gcagactccg tgaagggccg atccaccatc tccagagaca actccaagaa cacgctgtat   240
ctgcaaatga acagcctgag agccgaggac acggctgtgt attattgtgc gaggtcagtg   300
gctggttacc actactacta cggtatggac gtctggggcc aagggaccac ggtcaccgtc   360
tcctca                                                              366

<210> SEQ ID NO 443
<211> LENGTH: 122
<212> TYPE: PRT
<213> ORGANISM: Homo sapiens

<400> SEQUENCE: 443

Gln Val Gln Leu Val Glu Ser Gly Gly Gly Val Val Gln Pro Gly Arg
1               5                   10                  15

Ser Leu Ser Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Tyr Lys Asp Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Val Ala Gly Tyr His Tyr Tyr Tyr Gly Met Asp Val Trp
            100                 105                 110

Gly Gln Gly Thr Thr Val Thr Val Ser Ser
        115                 120

<210> SEQ ID NO 444
<211> LENGTH: 324
<212> TYPE: DNA
<213> ORGANISM: Homo sapiens

<400> SEQUENCE: 444
tcttctgagc tgactcagga ccctgctgtg tctgtggcct tgggacagac agtcaggatc    60
acatgccaag agacagcct cagaacctat tatgcaagct ggtaccagca gaagccaaga   120
caggccccta ttcttgtcat ctatggtaaa aacaaccggc cctcagggat cccagaccga   180
ttctctggct ccacctcagg aatcacagct tccttgacca tcactggggc tcaggcggaa   240
gatgaggctg actattactg taaatcccgg gacatcattg gtaaccatct gctgttcggc   300
ggagggacta agctgaccgt ccta                                          324

<210> SEQ ID NO 445
<211> LENGTH: 108
<212> TYPE: PRT
<213> ORGANISM: Homo sapiens

<400> SEQUENCE: 445

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Arg Gln Ala Pro Ile Leu Val Ile Tyr
        35                  40                  45

Gly Lys Asn Asn Arg Pro Ser Gly Ile Pro Asp Arg Phe Ser Gly Ser
    50                  55                  60

Thr Ser Gly Ile Thr Ala Ser Leu Thr Ile Thr Gly Ala Gln Ala Glu
65                  70                  75                  80

Asp Glu Ala Asp Tyr Tyr Cys Lys Ser Arg Asp Ile Ile Gly Asn His
                85                  90                  95

Leu Leu Phe Gly Gly Gly Thr Lys Leu Thr Val Leu
            100                 105

<210> SEQ ID NO 446
<211> LENGTH: 375
<212> TYPE: DNA
<213> ORGANISM: Homo sapiens

<400> SEQUENCE: 446
caggtgcagc tggtggcgtc tgggggaggc gtggtccagc ctggggaggtc cctgagactc      60
tcctgtgcag cgtctggatt caccctcagt agctatggca tgcactgggt ccgccaggct     120
ccaggccagg gctggagtg gtggcagtc atatggtatg atggaagtaa caaatactat       180
gcagcctccg tgaagggccg attcaccatc tccagagaca attccaagaa cacgctgtat    240
ctgcaaatga acagtctgag agccgaggac acggctgtgt attactgtgc gagggggt      300
ggttcgggga gtcatcgcta ctactactac ggtatggacg tctggggcca agggaccacg    360
gtcaccgtct cctca                                                      375

<210> SEQ ID NO 447
<211> LENGTH: 125
<212> TYPE: PRT
<213> ORGANISM: Homo sapiens

<400> SEQUENCE: 447

Gln Val Gln Leu Val Ala Ser Gly Gly Gly Val Val Gln Pro Gly Arg
1               5                   10                  15

Ser Leu Arg Leu Ser Cys Ala Ala Ser Gly Phe Thr Leu Ser Ser Tyr
            20                  25                  30

Gly Met His Trp Val Arg Gln Ala Pro Gly Gln Gly Leu Glu Trp Val
        35                  40                  45

Ala Val Ile Trp Tyr Asp Gly Ser Asn Lys Tyr Tyr Ala Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Ser Gly Ser His Arg Tyr Tyr Tyr Gly Met
            100                 105                 110

Asp Val Trp Gly Gln Gly Thr Thr Val Thr Val Ser Ser
        115                 120                 125

<210> SEQ ID NO 448
<211> LENGTH: 324
<212> TYPE: DNA
<213> ORGANISM: Homo sapiens

<400> SEQUENCE: 448

```
tcttctgagc tgactcagga ccctgctgtg tctgtggcct tgggacagac agtcaggatc      60
acatgccaag agacagcct cagaacctat tatgcaagct ggtaccagca gaagccaaga     120
caggccccta ttcttgtcat ctatggtaaa acaaccggc cctcaggat cccagaccga     180
ttctctggct ccacctcagg aatcacagct tccttgacca tcactggggc tcaggcggaa     240
gatgaggctg actattactg taaatcccgg gacatcattg gtaaccatct gctgttcggc     300
ggagggacta agctgaccgt ccta                                            324
```

<210> SEQ ID NO 449
<211> LENGTH: 108
<212> TYPE: PRT
<213> ORGANISM: Homo sapiens

<400> SEQUENCE: 449

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Arg Gln Ala Pro Ile Leu Val Ile Tyr
        35                  40                  45

Gly Lys Asn Asn Arg Pro Ser Gly Ile Pro Asp Arg Phe Ser Gly Ser
    50                  55                  60

Thr Ser Gly Ile Thr Ala Ser Leu Thr Ile Thr Gly Ala Gln Ala Glu
65                  70                  75                  80

Asp Glu Ala Asp Tyr Tyr Cys Lys Ser Arg Asp Ile Ile Gly Asn His
                85                  90                  95

Leu Leu Phe Gly Gly Gly Thr Lys Leu Thr Val Leu
            100                 105

<210> SEQ ID NO 450
<211> LENGTH: 366
<212> TYPE: DNA
<213> ORGANISM: Homo sapiens

<400> SEQUENCE: 450

```
caggtgcaag tggtggagtc tgggggaggc gtggtccagc ctgggaggtc cctgagactc      60
tcctgtgcag cgtctggatt caccttcagt aactatggca tgcactgggt ccgccaggct     120
ccaggcaagg ggctggagtg gtggcagtt atatggtatg atggaggtaa taaatactat     180
gcagactccg tgaagggccg atccatcatc tccagagaca attccaagag cacgctgtat     240
ctgcaaatga acagcctgag agccgaggac acggctgttt attattgtgc gaggtcagtg     300
gctggttacc attattacta cggtatggac gtctggggcc aagggaccac ggtcaccgtc     360
gcctca                                                                366
```

<210> SEQ ID NO 451
<211> LENGTH: 122
<212> TYPE: PRT
<213> ORGANISM: Homo sapiens

<400> SEQUENCE: 451

Gln Val Gln Val Val Glu Ser Gly Gly Gly Val Val Gln Pro Gly Arg

```
            1               5                  10                 15
Ser Leu Arg Leu Ser Cys Ala Ala Ser Gly Phe Thr Phe Ser Asn Tyr
                20                  25                 30

Gly Met His Trp Val Arg Gln Ala Pro Gly Lys Gly Leu Glu Trp Val
            35                  40                 45

Ala Val Ile Trp Tyr Asp Gly Asn Lys Tyr Tyr Ala Asp Ser Val
    50                  55                 60

Lys Gly Arg Ser Ile Ile Ser Arg Asp Asn Ser Lys Ser Thr Leu Tyr
65                  70                  75                 80

Leu Gln Met Asn Ser Leu Arg Ala Glu Asp Thr Ala Val Tyr Tyr Cys
                85                  90                 95

Ala Arg Ser Val Ala Gly Tyr His Tyr Tyr Gly Met Asp Val Trp
                100                 105                110

Gly Gln Gly Thr Thr Val Thr Val Ala Ser
            115                 120
```

<210> SEQ ID NO 452
<211> LENGTH: 327
<212> TYPE: DNA
<213> ORGANISM: Homo sapiens

<400> SEQUENCE: 452

```
cagtctgccc tgactcagcc tgcctccgtg tctgggtctc ctggacagtc gatcaccatc    60
tcctgcactg gaaccagcag tgacgttggt ggttataact ctgtctcctg gtaccaacag   120
cacccaggca aacccccaa actcatgatt tatgaggtca gtaatcggcc ctcaggggatt   180
tctaatcgct tctctggctc caagtctggc aacacggcct ccctgaccat ctctggctc    240
caggctgagg acgaggctga ttatttctgc agctcatata caagcaccag catggtcttc   300
ggcggaggga ccaagctggc cgtccta                                      327
```

<210> SEQ ID NO 453
<211> LENGTH: 109
<212> TYPE: PRT
<213> ORGANISM: Homo sapiens

<400> SEQUENCE: 453

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Ser Val Ser Trp Tyr Gln Gln His Pro Gly Lys Pro Pro Lys Leu
            35                  40                  45

Met Ile Tyr Glu Val Ser Asn Arg Pro Ser Gly Ile Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Ala Val Leu
            100                 105
```

<210> SEQ ID NO 454
<211> LENGTH: 366
<212> TYPE: DNA
<213> ORGANISM: Homo sapiens

<400> SEQUENCE: 454

```
caggtgcaag tggtggagtc tgggggaggc gtggtccagc ctgggaggtc cctgagactc      60
tcctgtgcag cgtctggatt caccttcagt aactatggca tgcactgggt ccgccaggct     120
ccaggcaagg ggctggagtg ggtggcagtt atatggtatg atggaggtaa taaatactat     180
gcagactccg tgaagggccg atccatcatc tccagagaca attccaagag cacgctgtat     240
ctgcaaatga acagcctgag agccgaggac acggctgttt attattgtgc gaggtcagtg     300
gctggttacc attattacta cggtatggac gtctggggcc aagggaccac ggtcaccgtc     360
gcctca                                                                 366
```

<210> SEQ ID NO 455
<211> LENGTH: 122
<212> TYPE: PRT
<213> ORGANISM: Homo sapiens

<400> SEQUENCE: 455

```
Gln Val Gln Val Val Glu Ser Gly Gly Gly Val Val Gln Pro Gly Arg
  1               5                  10                  15

Ser Leu Arg Leu Ser Cys Ala Ala Ser Gly Phe Thr Phe Ser Asn Tyr
             20                  25                  30

Gly Met His Trp Val Arg Gln Ala Pro Gly Lys Gly Leu Glu Trp Val
         35                  40                  45

Ala Val Ile Trp Tyr Asp Gly Asn Lys Tyr Tyr Ala Asp Ser Val
     50                  55                  60

Lys Gly Arg Ser Ile Ile Ser Arg Asp Asn Ser Lys Ser Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Val Ala Gly Tyr His Tyr Tyr Tyr Gly Met Asp Val Trp
            100                 105                 110

Gly Gln Gly Thr Thr Val Thr Val Ala Ser
        115                 120
```

<210> SEQ ID NO 456
<211> LENGTH: 324
<212> TYPE: DNA
<213> ORGANISM: Homo sapiens

<400> SEQUENCE: 456

```
tcttctgagc tgactcagga ccctgctgtg tctgtggcct tgggacagac agtcaggatc      60
acatgccaag agacagcct cagaggctat tatgcaagct ggtaccagca gaagccaaga     120
caggcccctg tacttgtcat ctatggtaaa aacaaccggc cctcagggat cccagaccga     180
ttctctggct ccacgtcagg aaacacagct tccttgacca tcactggggc tcaggcggaa     240
gatgaggctg actattactg taactcccgg gacaacattg gtgaccatct ggtgttcggc     300
ggagggacca gctgaccgt ccta                                             324
```

<210> SEQ ID NO 457
<211> LENGTH: 108
<212> TYPE: PRT
<213> ORGANISM: Homo sapiens

<400> SEQUENCE: 457

```
Ser Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg Gly Tyr Tyr Ala
```

```
            20                  25                  30
Ser Trp Tyr Gln Gln Lys Pro Arg Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Thr Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Asn Ile Gly Asp His
                85                  90                  95

Leu Val Phe Gly Gly Gly Thr Lys Leu Thr Val Leu
            100                 105
```

<210> SEQ ID NO 458
<211> LENGTH: 381
<212> TYPE: DNA
<213> ORGANISM: Homo sapiens

<400> SEQUENCE: 458

```
gaggtgcagc tggtggagtc tgggggaggc ttggtccagc ctggggggtc cctgagactc    60
tcctgtgcag cctccggatt cacctttagt agctattgga tgagctgggt ccgccaggct   120
ccagggaagg ggctggagtg ggtggccagc ataaaacaag atggaagtga aaaatactat   180
gtggactctg tgaagggccg attcaccatc tccagagaca acgccaggaa ctcactgtat   240
ctgcaaatga acagcctgag agccgaggac acggctgtgt attactgtgc gagagatctt   300
gtattaatgg tgtatgatat agactactac tactacggta tggacgtctg gggccaaggg   360
accacggtca ccgtctcctc a                                             381
```

<210> SEQ ID NO 459
<211> LENGTH: 127
<212> TYPE: PRT
<213> ORGANISM: Homo sapiens

<400> SEQUENCE: 459

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Ser Ile Lys Gln Asp Gly Ser Glu Lys Tyr Tyr Val Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Val Leu Met Val Tyr Asp Ile Asp Tyr Tyr Tyr Tyr
            100                 105                 110

Gly Met Asp Val Trp Gly Gln Gly Thr Thr Val Thr Val Ser Ser
        115                 120                 125
```

<210> SEQ ID NO 460
<211> LENGTH: 336
<212> TYPE: DNA
<213> ORGANISM: Homo sapiens

<400> SEQUENCE: 460

```
gatattgtga tgactcagtc tccactctcc ctgcccgtca cccctggaga gccggcctcc      60
atctcctgca ggtctagtca gagcctcctg catagtaatg gatacaacta tttggattgg     120
tacctgcaga agccagggca gtctccacag ctcctgatct atttgggttc taatcgggcc     180
tccggggtcc ctgacaggtt cagtggcagt ggatcaggca cagattttac actgaaaatc     240
agcagagtgg aggctgagga tgttggggtt tattactgca tgcaagctct acaaactccg     300
ctcactttcg gcggagggac caaggtagag atcaaa                                336
```

<210> SEQ ID NO 461
<211> LENGTH: 112
<212> TYPE: PRT
<213> ORGANISM: Homo sapiens

<400> SEQUENCE: 461

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 462
<211> LENGTH: 381
<212> TYPE: DNA
<213> ORGANISM: Homo sapiens

<400> SEQUENCE: 462

```
gaggtgcagc tggtggagtc tgggggaggc ttggtccagc ctggggggtc cctgagactc      60
tcctgtgcag cctccggatt caccttagt aactattgga tgagctgggt ccgccaggct      120
ccagggaagg ggctggagtg gtggccagc ataaaacaag atggaagtga aaatactat       180 gtggactctg tgaagggccg attcgccatc tccagagaca acgccaagaa ctcactgttt      240
ctgcaaatga acagcctgag agccgaggac acggctgtgt attactgtgc gagagatctt      300
gtactaatgg tgtatgatat agactactac tactacggta tggacgtctg gggccaaggg      360
accacggtca ccgtctcctc a                                                 381
```

<210> SEQ ID NO 463
<211> LENGTH: 127
<212> TYPE: PRT
<213> ORGANISM: Homo sapiens

<400> SEQUENCE: 463

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Ser Ile Lys Gln Asp Gly Ser Glu Lys Tyr Tyr Val Asp Ser Val
            50                  55                  60

Lys Gly Arg Phe Ala Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                 85                  90                  95

Ala Arg Asp Leu Val Leu Met Val Tyr Asp Ile Asp Tyr Tyr Tyr Tyr
            100                 105                 110

Gly Met Asp Val Trp Gly Gln Gly Thr Thr Val Thr Val Ser Ser
            115                 120                 125

<210> SEQ ID NO 464
<211> LENGTH: 336
<212> TYPE: DNA
<213> ORGANISM: Homo sapiens

<400> SEQUENCE: 464
gatattgtga tgactcagtc tccactctcc ctgcctgtca cccctggaga gccggcctcc    60
atctcttgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cacatcttac actgaaaatc   240
agcagagtgg aggctgagga tgttggagtt tattactgca tgcaaactct acaaactccg   300
ctcactttcg gcggagggac caaggtggag atcaaa                              336

<210> SEQ ID NO 465
<211> LENGTH: 112
<212> TYPE: PRT
<213> ORGANISM: Homo sapiens

<400> SEQUENCE: 465

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr His Leu Thr Leu Lys Ile
 65                  70                  75                  80

Ser Arg Val Glu Ala Glu Asp Val Gly Val Tyr Tyr Cys Met Gln Thr
                 85                  90                  95

Leu Gln Thr Pro Leu Thr Phe Gly Gly Gly Thr Lys Val Glu Ile Lys
            100                 105                 110

<210> SEQ ID NO 466
<211> LENGTH: 342
<212> TYPE: DNA
<213> ORGANISM: Homo sapiens

<400> SEQUENCE: 466
caggtgcagc tggtggagtc tgggggaggc gtggcccagc ctggaggtc cctgagactc     60 tcctgtgcag cgtctggatt caccttcagt agctatggca tgcactgggt ccgccaggct   120
ccaggcaagg ggctggagtg ggtggcagtt atatactatg atggaattaa taaacactat   180

```
gcagactccg tgaagggccg attcaccatc tccagagaca attccaagaa cacgctgtat    240
ctgcaaatga acagcctgag agccgaggac acggctgtgt attactgtgc gagagatcgg    300
ggactggact ggggccaggg aaccctggtc accgtctcct ca                      342
```

<210> SEQ ID NO 467
<211> LENGTH: 114
<212> TYPE: PRT
<213> ORGANISM: Homo sapiens

<400> SEQUENCE: 467

```
Gln Val Gln Leu Val Glu Ser Gly Gly Gly Val Ala Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Tyr Tyr Asp Gly Ile Asn Lys His Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Gly Leu Asp Trp Gly Gln Gly Thr Leu Val Thr Val
            100                 105                 110

Ser Ser
```

<210> SEQ ID NO 468
<211> LENGTH: 339
<212> TYPE: DNA
<213> ORGANISM: Homo sapiens

<400> SEQUENCE: 468

```
gacatcgtga tgacccagtc tccagactcc ctggctgtgt ctctgggcga gagggccacc     60
atcaactgca gtccagcca gagtgtttta tacagctcca acagtaagaa ctacttagtt    120
tggtaccagc agaaaccagg acagcctcct aagctgctca tttactgggc ctctacccgg    180
gaatccgggg tccctgaccg attcagtggc agcgggtctg ggacagattt cactctcacc    240
atcagcagcc tgcaggctga agatgtggca gtttattact gtcaacaata ttatagtact    300
ccgtggacgt tcggccaagg gaccaaggtg gaaatcaaa                           339
```

<210> SEQ ID NO 469
<211> LENGTH: 113
<212> TYPE: PRT
<213> ORGANISM: Homo sapiens

<400> SEQUENCE: 469

```
Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Val Leu Tyr Ser
             20                  25                  30

Ser Asn Ser Lys Asn Tyr Leu Val Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80
```

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
            100                 105                 110

Lys

<210> SEQ ID NO 470
<211> LENGTH: 357
<212> TYPE: DNA
<213> ORGANISM: Homo sapiens

<400> SEQUENCE: 470
gaggtgcagc tggtggagtc tgggggaggc ttggtccagc ctgggggtc cctgagactc      60 tcctgtgcag cctctggact caccttagt aactttttgga tgagctgggt ccgccaggct    120
ccagggaagg gctggagtg gtggccaac ataaagcaag atggaaatga taaatactat     180
gtggactctg tgaagggccg attcaccatc tccagagaca acgccaagaa ttcactgtat    240
ctgcaaatga acagcctgag agccgaggac acggctgtgt attactgtgc gagagagtca    300
aactggggat tgcttttga tatctggggc caaggggacaa tggtcaccgt ctcttca       357

<210> SEQ ID NO 471
<211> LENGTH: 119
<212> TYPE: PRT
<213> ORGANISM: Homo sapiens

<400> SEQUENCE: 471

Glu Val Gln Leu Val Glu Ser Gly Gly Gly Leu Val Gln Pro Gly Gly
  1               5                  10                  15

Ser Leu Arg Leu Ser Cys Ala Ala Ser Gly Leu Thr Phe Ser Asn Phe
             20                  25                  30

Trp Met Ser Trp Val Arg Gln Ala Pro Gly Lys Gly Leu Glu Trp Val
         35                  40                  45

Ala Asn Ile Lys Gln Asp Gly Asn Asp Lys Tyr Tyr Val Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Glu Ser Asn Trp Gly Phe Ala Phe Asp Ile Trp Gly Gln Gly
            100                 105                 110

Thr Met Val Thr Val Ser Ser
        115

<210> SEQ ID NO 472
<211> LENGTH: 327
<212> TYPE: DNA
<213> ORGANISM: Homo sapiens

<400> SEQUENCE: 472
cagtctgtgc tgactcagcc accctcagcg tctgggaccc ccgggcagag ggtcaccatc      60
tcttgttctg gaagcagctc caacatcgga agtaaaactg taaactggta ccagcagttc    120
ccaggaacgg cccccaaact cctcatctat agtaataatc ggcggccctc aggggtccct    180
gaccgattct ctggctccaa gtctggcacc tcagcctccc tggccatcag tgggctccag    240
tctgaggatg aggctgatta ttactgtgca gcatgggatg acagcctgaa ttgggtgttc    300
ggcgcaggga ccaagctgac cgtccta 327

<210> SEQ ID NO 473
<211> LENGTH: 109
<212> TYPE: PRT
<213> ORGANISM: Homo sapiens

<400> SEQUENCE: 473

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Lys
            20                  25                  30

Thr Val Asn Trp Tyr Gln Gln Phe Pro Gly Thr Ala Pro Lys Leu Leu
        35                  40                  45

Ile Tyr Ser Asn Asn Arg Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Trp Val Phe Gly Ala Gly Thr Lys Leu Thr Val Leu
            100                 105

<210> SEQ ID NO 474
<211> LENGTH: 357
<212> TYPE: DNA
<213> ORGANISM: Homo sapiens

<400> SEQUENCE: 474
gaggtgcagc tggtggagtc tgggggaggt ttggtccagc ctgggggtc cctgagactc      60 tcctgtgcag cctctggact cacctttagt aacttttgga tgagctgggt ccgccaggct     120
ccagggaagg gctggagtg gtggccaac ataaagcaag atggaagtga aaatactat        180 gtggactctg tgaagggccg attcaccatc tccagagaca cgccaagaa ttcactgtat      240 ctgcaaatga acagcctgag agccgaggac acggctgtgt attactgtgc gagagagtca    300
aactggggat ttgcttttga tatctggggc caagggacaa tggtcaccgt ctcttca       357

<210> SEQ ID NO 475
<211> LENGTH: 119
<212> TYPE: PRT
<213> ORGANISM: Homo sapiens

<400> SEQUENCE: 475

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Asn Phe
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Asn Trp Gly Phe Ala Phe Asp Ile Trp Gly Gln Gly
            100                 105                 110

```
Thr Met Val Thr Val Ser Ser
        115

<210> SEQ ID NO 476
<211> LENGTH: 327
<212> TYPE: DNA
<213> ORGANISM: Homo sapiens

<400> SEQUENCE: 476
cagtctgtgc tgactcagcc accctcagcg tctgggaccc ccgggcagag ggtcaccatc     60
tcttgttctg gaagcagctc caacatcgga agtaaaactg taaactggta ccagcagttc    120
ccaggaacgg ccccccaaact cctcatctat agtaataatc ggcggccctc aggggtccct   180
gaccgattct ctggctccaa gtctggcacc tcagcctccc tggccatcag tgggctccag    240
tctgaggatg aggctgatta ttactgtgca acatgggatg acagactgaa ttgggtgttc    300
ggcgcaggga ccaagctgac cgtccta                                         327

<210> SEQ ID NO 477
<211> LENGTH: 109
<212> TYPE: PRT
<213> ORGANISM: Homo sapiens

<400> SEQUENCE: 477

Gln Ser Val Leu Thr Gln Pro Pro Ser Ala Ser Gly Thr Pro Gly Gln
  1               5                  10                  15

Arg Val Thr Ile Ser Cys Ser Gly Ser Ser Ser Asn Ile Gly Ser Lys
             20                  25                  30

Thr Val Asn Trp Tyr Gln Gln Phe Pro Gly Thr Ala Pro Lys Leu Leu
         35                  40                  45

Ile Tyr Ser Asn Asn Arg Arg Pro Ser Gly Val Pro Asp Arg Phe Ser
     50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Thr Trp Asp Asp Arg Leu
                 85                  90                  95

Asn Trp Val Phe Gly Ala Gly Thr Lys Leu Thr Val Leu
            100                 105

<210> SEQ ID NO 478
<211> LENGTH: 366
<212> TYPE: DNA
<213> ORGANISM: Homo sapiens

<400> SEQUENCE: 478
caggtcacct tgaaggagtc tggtcctgtg ctggtgaaac ccacagagac cctcacgctg     60
acctgcaccg tctctgggtt ctcactcagc aatgttagaa tgggtgtgag ctggatccgt    120
cagcccccag ggaaggccct ggagtggctt gcacacattt tttcgaatga cgaaaattcc    180
tacagaacat ctctgaagag caggctcacc atctccaagg acacctccaa aagccaggtg    240
gtccttacca tgaccaacat ggaccctgtg gacacagcca catattactg tgcacggata    300
gtgggagcta caacgatga tgcttttgat atctggggcc aagggacaat ggtcaccgtc    360
tcttca                                                                366

<210> SEQ ID NO 479
<211> LENGTH: 122
<212> TYPE: PRT
```

<213> ORGANISM: Homo sapiens

<400> SEQUENCE: 479

Gln Val Thr Leu Lys Glu Ser Gly Pro Val Leu Val Lys Pro Thr Glu
1               5                   10                  15
Thr Leu Thr Leu Thr Cys Thr Val Ser Gly Phe Ser Leu Ser Asn Val
            20                  25                  30
Arg Met Gly Val Ser Trp Ile Arg Gln Pro Pro Gly Lys Ala Leu Glu
        35                  40                  45
Trp Leu Ala His Ile Phe Ser Asn Asp Glu Asn Ser Tyr Arg Thr Ser
    50                  55                  60
Leu Lys Ser Arg Leu Thr Ile Ser Lys Asp Thr Ser Lys Ser Gln Val
65                  70                  75                  80
Val Leu Thr Met Thr Asn Met Asp Pro Val Asp Thr Ala Thr Tyr Tyr
                85                  90                  95
Cys Ala Arg Ile Val Gly Ala Thr Thr Asp Asp Ala Phe Asp Ile Trp
            100                 105                 110
Gly Gln Gly Thr Met Val Thr Val Ser Ser
        115                 120

<210> SEQ ID NO 480
<211> LENGTH: 324
<212> TYPE: DNA
<213> ORGANISM: Homo sapiens

<400> SEQUENCE: 480
tcctatgtgc tgactcagcc accctcggtg tcagtggccc caggacagac ggccaggatt      60
acctgtgggg gaaacaacat tggaagtaaa agtgtgcact ggtaccagca gaagccaggc     120
caggcccctg tgctggtcgt ctatgatgat agcgaccggc cctcaggat ccctgagcga      180
ttctctggct ccaactctgg gaacacggcc accctgacca tcagcagggt cgaagccggg     240
gatgaggccg acttttactg tcaggtgtgg atagtagta gtgatcctgt ggtattcggc     300
ggagggacca agctgaccgt ccta                                            324

<210> SEQ ID NO 481
<211> LENGTH: 108
<212> TYPE: PRT
<213> ORGANISM: Homo sapiens

<400> SEQUENCE: 481

Ser Tyr Val Leu Thr Gln Pro Pro Ser Val Ser Val Ala Pro Gly Gln
1               5                   10                  15
Thr Ala Arg Ile Thr Cys Gly Gly Asn Asn Ile Gly Ser Lys Ser Val
            20                  25                  30
His Trp Tyr Gln Gln Lys Pro Gly Gln Ala Pro Val Leu Val Val Tyr
        35                  40                  45
Asp Asp Ser Asp Arg Pro Ser Gly Ile Pro Glu Arg Phe Ser Gly Ser
    50                  55                  60
Asn Ser Gly Asn Thr Ala Thr Leu Thr Ile Ser Arg Val Glu Ala Gly
65                  70                  75                  80
Asp Glu Ala Asp Phe Tyr Cys Gln Val Trp Asp Ser Ser Ser Asp Pro
                85                  90                  95
Val Val Phe Gly Gly Gly Thr Lys Leu Thr Val Leu
            100                 105

<210> SEQ ID NO 482

-continued

```
<211> LENGTH: 381
<212> TYPE: DNA
<213> ORGANISM: Homo sapiens

<400> SEQUENCE: 482
gaggtgcagc tggtggagtc tgggggaggc ttggtccagc ctgggggtc cctgagactc      60 tcctgtgcag cctctggatt cacctttagt aactattgga tgacctgggt ccgccaggct    120
ccagggaagg ggctggagtg ggtggccagc ataaagcaag atggaagtga gagatactat    180
gtggactctg tgaagggccg attcaccatc tcccgagaca ccgccaagaa ctctctgtat    240
ctccaaatga acagcctgcg agccgaggac acggctgtgt attactgtgc gagacctctt    300
gtactaatgg tgtatgctct acactactac tactacggta tggacgtctg gggccacggg    360
accacggtca ccgtctcctc a                                              381

<210> SEQ ID NO 483
<211> LENGTH: 127
<212> TYPE: PRT
<213> ORGANISM: Homo sapiens

<400> SEQUENCE: 483

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Trp Met Thr Trp Val Arg Gln Ala Pro Gly Lys Gly Leu Glu Trp Val
        35                  40                  45

Ala Ser Ile Lys Gln Asp Gly Ser Glu Arg Tyr Tyr Val Asp Ser Val
    50                  55                  60

Lys Gly Arg Phe Thr Ile Ser Arg Asp Thr Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Leu Val Leu Met Val Tyr Ala Leu His Tyr Tyr Tyr Tyr
            100                 105                 110

Gly Met Asp Val Trp Gly His Gly Thr Thr Val Thr Val Ser Ser
        115                 120                 125

<210> SEQ ID NO 484
<211> LENGTH: 336
<212> TYPE: DNA
<213> ORGANISM: Homo sapiens

<400> SEQUENCE: 484
gatattgtga tgactcagtc tccactctcc ctgcccgtca cccctggaga gccggcctcc      60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactccg    300
ctcactttcg gcggagggac caaggtggag atcaaa                              336

<210> SEQ ID NO 485
<211> LENGTH: 112
<212> TYPE: PRT
<213> ORGANISM: Homo sapiens

<400> SEQUENCE: 485
```

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110
```

<210> SEQ ID NO 486
<211> LENGTH: 100
<212> TYPE: PRT
<213> ORGANISM: Homo sapiens

<400> SEQUENCE: 486

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile
            100
```

<210> SEQ ID NO 487
<211> LENGTH: 98
<212> TYPE: PRT
<213> ORGANISM: Homo sapiens

<400> SEQUENCE: 487

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg
```

```
<210> SEQ ID NO 488
<211> LENGTH: 98
<212> TYPE: PRT
<213> ORGANISM: Homo sapiens

<400> SEQUENCE: 488

Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 489
<211> LENGTH: 93
<212> TYPE: PRT
<213> ORGANISM: Homo sapiens

<400> SEQUENCE: 489

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys
                 85                  90

<210> SEQ ID NO 490
<211> LENGTH: 94
<212> TYPE: PRT
<213> ORGANISM: Homo sapiens

<400> SEQUENCE: 490

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
         50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys
                 85                  90
```

<210> SEQ ID NO 491
<211> LENGTH: 89
<212> TYPE: PRT
<213> ORGANISM: Homo sapiens

<400> SEQUENCE: 491

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys
                85

<210> SEQ ID NO 492
<211> LENGTH: 87
<212> TYPE: PRT
<213> ORGANISM: Homo sapiens

<400> SEQUENCE: 492

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys
                85

<210> SEQ ID NO 493
<211> LENGTH: 49
<212> TYPE: PRT
<213> ORGANISM: Homo sapiens

<400> SEQUENCE: 493

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly

<210> SEQ ID NO 494
<211> LENGTH: 98
<212> TYPE: PRT
<213> ORGANISM: Homo sapiens

<400> SEQUENCE: 494

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg
```

<210> SEQ ID NO 495
<211> LENGTH: 98
<212> TYPE: PRT
<213> ORGANISM: Homo sapiens

<400> SEQUENCE: 495

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg
```

<210> SEQ ID NO 496
<211> LENGTH: 88
<212> TYPE: PRT
<213> ORGANISM: Homo sapiens

<400> SEQUENCE: 496

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Asn Tyr
             20                  25                  30

Leu Ala Trp Tyr Gln Gln Lys Pro Gly Lys Val Pro Lys Leu Leu Ile
             35                  40                  45

Tyr Ala Ala Ser Thr Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys
                 85
```

<210> SEQ ID NO 497
<211> LENGTH: 90
<212> TYPE: PRT

<213> ORGANISM: Homo sapiens

<400> SEQUENCE: 497

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys
                85                  90

<210> SEQ ID NO 498
<211> LENGTH: 87
<212> TYPE: PRT
<213> ORGANISM: Homo sapiens

<400> SEQUENCE: 498

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys
                85

<210> SEQ ID NO 499
<211> LENGTH: 13
<212> TYPE: PRT
<213> ORGANISM: Homo sapiens

<400> SEQUENCE: 499

Ser Gly Ser Ser Ser Asn Ile Gly Ser Lys Thr Val Asn
1               5                   10

<210> SEQ ID NO 500
<211> LENGTH: 10
<212> TYPE: PRT
<213> ORGANISM: Homo sapiens

<400> SEQUENCE: 500

Gly Phe Thr Phe Ser Asn Tyr Trp Met Ser
1               5                   10

<210> SEQ ID NO 501
<211> LENGTH: 17
<212> TYPE: PRT
<213> ORGANISM: Homo sapiens

<400> SEQUENCE: 501

Ser Ile Lys Gln Asp Gly Ser Glu Lys Tyr Tyr Val Asp Ser Val Lys

-continued

```
                1               5                  10                 15
Gly

<210> SEQ ID NO 502
<211> LENGTH: 18
<212> TYPE: PRT
<213> ORGANISM: Homo sapiens

<400> SEQUENCE: 502

Asp Leu Val Leu Met Val Tyr Asp Ile Asp Tyr Tyr Tyr Gly Met
1               5                  10                 15

Asp Val

<210> SEQ ID NO 503
<211> LENGTH: 16
<212> TYPE: PRT
<213> ORGANISM: Homo sapiens

<400> SEQUENCE: 503

Arg Ser Ser Gln Ser Leu Leu His Ser Asn Gly Tyr Asn Tyr Leu Asp
1               5                  10                 15

<210> SEQ ID NO 504
<211> LENGTH: 7
<212> TYPE: PRT
<213> ORGANISM: Homo sapiens

<400> SEQUENCE: 504

Leu Gly Ser Asn Arg Ala Ser
1               5

<210> SEQ ID NO 505
<211> LENGTH: 9
<212> TYPE: PRT
<213> ORGANISM: Homo sapiens

<400> SEQUENCE: 505

Met Gln Thr Leu Gln Thr Pro Leu Thr
1               5

<210> SEQ ID NO 506
<211> LENGTH: 25
<212> TYPE: PRT
<213> ORGANISM: Homo sapiens

<400> SEQUENCE: 506

Gln Val Thr Leu Lys Glu Ser Gly Pro Val Leu Val Lys Pro Thr Glu
1               5                  10                 15

Thr Leu Thr Leu Thr Cys Thr Val Ser
            20                  25

<210> SEQ ID NO 507
<211> LENGTH: 12
<212> TYPE: PRT
<213> ORGANISM: Homo sapiens

<400> SEQUENCE: 507

Gly Phe Ser Leu Ser Asn Ala Arg Met Gly Val Ser
1               5                  10

<210> SEQ ID NO 508
<211> LENGTH: 12
<212> TYPE: PRT
```

<213> ORGANISM: Homo sapiens

<400> SEQUENCE: 508

Gly Phe Ser Leu Ser Asn Val Arg Met Gly Val Ser
1               5                   10

<210> SEQ ID NO 509
<211> LENGTH: 14
<212> TYPE: PRT
<213> ORGANISM: Homo sapiens

<400> SEQUENCE: 509

Trp Ile Arg Gln Pro Pro Gly Lys Ala Leu Glu Trp Leu Ala
1               5                   10

<210> SEQ ID NO 510
<211> LENGTH: 25
<212> TYPE: PRT
<213> ORGANISM: Homo sapiens

<400> SEQUENCE: 510

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 511
<211> LENGTH: 10
<212> TYPE: PRT
<213> ORGANISM: Homo sapiens

<400> SEQUENCE: 511

Gly Phe Thr Phe Ser Ser Tyr Trp Met Ser
1               5                   10

<210> SEQ ID NO 512
<211> LENGTH: 10
<212> TYPE: PRT
<213> ORGANISM: Homo sapiens

<400> SEQUENCE: 512

Gly Leu Thr Phe Ser Asn Phe Trp Met Ser
1               5                   10

<210> SEQ ID NO 513
<211> LENGTH: 10
<212> TYPE: PRT
<213> ORGANISM: Homo sapiens

<400> SEQUENCE: 513

Gly Phe Thr Phe Ser Asn Tyr Trp Met Thr
1               5                   10

<210> SEQ ID NO 514
<211> LENGTH: 14
<212> TYPE: PRT
<213> ORGANISM: Homo sapiens

<400> SEQUENCE: 514

Trp Val Arg Gln Ala Pro Gly Lys Gly Leu Glu Trp Val Ala
1               5                   10

<210> SEQ ID NO 515
<211> LENGTH: 25

```
<212> TYPE: PRT
<213> ORGANISM: Homo sapiens

<400> SEQUENCE: 515

Gln Val Gln Leu Val Glu Ser Gly Gly Gly Val Val Gln Pro Gly Arg
  1               5                  10                  15

Ser Leu Arg Leu Ser Cys Ala Ala Ser
            20                  25

<210> SEQ ID NO 516
<211> LENGTH: 25
<212> TYPE: PRT
<213> ORGANISM: Homo sapiens

<400> SEQUENCE: 516

Gln Val Gln Leu Val Glu Ser Gly Gly Gly Val Ala Gln Pro Gly Arg
  1               5                  10                  15

Ser Leu Arg Leu Ser Cys Ala Ala Ser
            20                  25

<210> SEQ ID NO 517
<211> LENGTH: 10
<212> TYPE: PRT
<213> ORGANISM: Homo sapiens

<400> SEQUENCE: 517

Gly Phe Thr Phe Ser Ser Tyr Gly Met His
  1               5                  10

<210> SEQ ID NO 518
<211> LENGTH: 14
<212> TYPE: PRT
<213> ORGANISM: Homo sapiens

<400> SEQUENCE: 518

Trp Val Arg Gln Ala Pro Gly Lys Gly Leu Glu Trp Val Ala
  1               5                  10

<210> SEQ ID NO 519
<211> LENGTH: 16
<212> TYPE: PRT
<213> ORGANISM: Homo sapiens

<400> SEQUENCE: 519

His Ile Phe Ser Asn Asp Glu Lys Ser Tyr Ser Thr Ser Leu Lys Ser
  1               5                  10                  15

<210> SEQ ID NO 520
<211> LENGTH: 16
<212> TYPE: PRT
<213> ORGANISM: Homo sapiens

<400> SEQUENCE: 520

His Ile Phe Ser Asn Asp Glu Asn Ser Tyr Arg Thr Ser Leu Lys Ser
  1               5                  10                  15

<210> SEQ ID NO 521
<211> LENGTH: 33
<212> TYPE: PRT
<213> ORGANISM: Homo sapiens

<400> SEQUENCE: 521

Arg Leu Thr Ile Ser Lys Asp Thr Ser Lys Ser Gln Val Val Leu Thr
  1               5                  10                  15
```

Met Thr Asn Met Asp Pro Val Asp Thr Ala Thr Tyr Tyr Cys Ala Arg
            20                  25                  30

Ile

<210> SEQ ID NO 522
<211> LENGTH: 11
<212> TYPE: PRT
<213> ORGANISM: Homo sapiens

<400> SEQUENCE: 522

Val Gly Ala Thr Thr Asp Asp Ala Phe Asp Ile
1               5                   10

<210> SEQ ID NO 523
<211> LENGTH: 11
<212> TYPE: PRT
<213> ORGANISM: Homo sapiens

<400> SEQUENCE: 523

Trp Gly Gln Gly Thr Met Val Thr Val Ser Ser
1               5                   10

<210> SEQ ID NO 524
<211> LENGTH: 11
<212> TYPE: PRT
<213> ORGANISM: Homo sapiens

<400> SEQUENCE: 524

Trp Gly Gln Gly Thr Thr Val Thr Val Ser Ser
1               5                   10

<210> SEQ ID NO 525
<211> LENGTH: 11
<212> TYPE: PRT
<213> ORGANISM: Homo sapiens

<400> SEQUENCE: 525

Trp Gly His Gly Thr Thr Val Thr Val Ser Ser
1               5                   10

<210> SEQ ID NO 526
<211> LENGTH: 17
<212> TYPE: PRT
<213> ORGANISM: Homo sapiens

<400> SEQUENCE: 526

Asn Ile Lys Gln Asp Gly Ser Glu Lys Tyr Tyr Val Asp Ser Val Lys
1               5                   10                  15

Gly

<210> SEQ ID NO 527
<211> LENGTH: 17
<212> TYPE: PRT
<213> ORGANISM: Homo sapiens

<400> SEQUENCE: 527

Asn Ile Lys Gln Asp Gly Asn Asp Lys Tyr Tyr Val Asp Ser Val Lys
1               5                   10                  15

Gly

<210> SEQ ID NO 528
<211> LENGTH: 17

```
<212> TYPE: PRT
<213> ORGANISM: Homo sapiens

<400> SEQUENCE: 528

Ser Ile Lys Gln Asp Gly Ser Glu Arg Tyr Tyr Val Asp Ser Val Lys
1               5                   10                  15

Gly

<210> SEQ ID NO 529
<211> LENGTH: 32
<212> TYPE: PRT
<213> ORGANISM: Homo sapiens

<400> SEQUENCE: 529

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 530
<211> LENGTH: 32
<212> TYPE: PRT
<213> ORGANISM: Homo sapiens

<400> SEQUENCE: 530

Arg Phe Thr Ile Ser Arg Asp Asn Ala Arg Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 531
<211> LENGTH: 32
<212> TYPE: PRT
<213> ORGANISM: Homo sapiens

<400> SEQUENCE: 531

Arg Phe Ala Ile Ser Arg Asp Asn Ala Lys Asn Ser Leu Phe Leu Gln
1               5                   10                  15

Met Asn Ser Leu Arg Ala Glu Asp Thr Ala Val Tyr Tyr Cys Ala Arg
            20                  25                  30

<210> SEQ ID NO 532
<211> LENGTH: 32
<212> TYPE: PRT
<213> ORGANISM: Homo sapiens

<400> SEQUENCE: 532

Arg Phe Thr Ile Ser Arg Asp Thr Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 533
<211> LENGTH: 10
<212> TYPE: PRT
<213> ORGANISM: Homo sapiens

<400> SEQUENCE: 533

Glu Ser Asn Trp Gly Phe Ala Phe Asp Ile
1               5                   10

<210> SEQ ID NO 534
```

```
<211> LENGTH: 18
<212> TYPE: PRT
<213> ORGANISM: Homo sapiens

<400> SEQUENCE: 534

Pro Leu Val Leu Met Val Tyr Ala Leu His Tyr Tyr Tyr Tyr Gly Met
 1               5                  10                  15

Asp Val

<210> SEQ ID NO 535
<211> LENGTH: 17
<212> TYPE: PRT
<213> ORGANISM: Homo sapiens

<400> SEQUENCE: 535

Val Ile Trp Tyr Asp Gly Ser Asn Lys Tyr Tyr Ala Asp Ser Val Lys
 1               5                  10                  15

Gly

<210> SEQ ID NO 536
<211> LENGTH: 17
<212> TYPE: PRT
<213> ORGANISM: Homo sapiens

<400> SEQUENCE: 536

Val Ile Tyr Tyr Asp Gly Ile Asn Lys His Tyr Ala Asp Ser Val Lys
 1               5                  10                  15

Gly

<210> SEQ ID NO 537
<211> LENGTH: 32
<212> TYPE: PRT
<213> ORGANISM: Homo sapiens

<400> SEQUENCE: 537

Arg Phe Thr Ile Ser Arg Asp Asn Ser Lys Asn Thr Leu Tyr Leu Gln
 1               5                  10                  15

Met Asn Ser Leu Arg Ala Glu Asp Thr Ala Val Tyr Tyr Cys Ala Arg
            20                  25                  30

<210> SEQ ID NO 538
<211> LENGTH: 5
<212> TYPE: PRT
<213> ORGANISM: Homo sapiens

<400> SEQUENCE: 538

Asp Arg Gly Leu Asp
 1               5

<210> SEQ ID NO 539
<211> LENGTH: 11
<212> TYPE: PRT
<213> ORGANISM: Homo sapiens

<400> SEQUENCE: 539

Trp Gly Gln Gly Thr Leu Val Thr Val Ser Ser
 1               5                  10

<210> SEQ ID NO 540
<211> LENGTH: 23
<212> TYPE: PRT
<213> ORGANISM: Homo sapiens
```

```
<400> SEQUENCE: 540

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 541
<211> LENGTH: 15
<212> TYPE: PRT
<213> ORGANISM: Homo sapiens

<400> SEQUENCE: 541

Trp Tyr Leu Gln Lys Pro Gly Gln Ser Pro Gln Leu Leu Ile Tyr
1               5                   10                  15

<210> SEQ ID NO 542
<211> LENGTH: 23
<212> TYPE: PRT
<213> ORGANISM: Homo sapiens

<400> SEQUENCE: 542

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 543
<211> LENGTH: 17
<212> TYPE: PRT
<213> ORGANISM: Homo sapiens

<400> SEQUENCE: 543

Lys Ser Ser Gln Ser Val Leu Tyr Ser Ser Asn Asn Lys Asn Tyr Leu
1               5                   10                  15

Ala

<210> SEQ ID NO 544
<211> LENGTH: 17
<212> TYPE: PRT
<213> ORGANISM: Homo sapiens

<400> SEQUENCE: 544

Lys Ser Ser Gln Ser Val Leu Tyr Ser Ser Asn Ser Lys Asn Tyr Leu
1               5                   10                  15

Val

<210> SEQ ID NO 545
<211> LENGTH: 15
<212> TYPE: PRT
<213> ORGANISM: Homo sapiens

<400> SEQUENCE: 545

Trp Tyr Gln Gln Lys Pro Gly Gln Pro Pro Lys Leu Leu Ile Tyr
1               5                   10                  15

<210> SEQ ID NO 546
<211> LENGTH: 22
<212> TYPE: PRT
<213> ORGANISM: Homo sapiens

<400> SEQUENCE: 546

Gln Ser Val Leu Thr Gln Pro Pro Ser Ala Ser Gly Thr Pro Gly Gln
```

-continued

```
                1               5                   10                  15
Arg Val Thr Ile Ser Cys
            20

<210> SEQ ID NO 547
<211> LENGTH: 13
<212> TYPE: PRT
<213> ORGANISM: Homo sapiens

<400> SEQUENCE: 547

Ser Gly Ser Ser Ser Asn Ile Gly Ser Asn Thr Val Asn
1               5                   10

<210> SEQ ID NO 548
<211> LENGTH: 13
<212> TYPE: PRT
<213> ORGANISM: Homo sapiens

<400> SEQUENCE: 548

Ser Gly Ser Ser Ser Asn Ile Gly Ser Lys Thr Val Asn
1               5                   10

<210> SEQ ID NO 549
<211> LENGTH: 15
<212> TYPE: PRT
<213> ORGANISM: Homo sapiens

<400> SEQUENCE: 549

Trp Tyr Gln Gln Leu Pro Gly Thr Ala Pro Lys Leu Leu Ile Tyr
1               5                   10                  15

<210> SEQ ID NO 550
<211> LENGTH: 15
<212> TYPE: PRT
<213> ORGANISM: Homo sapiens

<400> SEQUENCE: 550

Trp Tyr Gln Gln Phe Pro Gly Thr Ala Pro Lys Leu Leu Ile Tyr
1               5                   10                  15

<210> SEQ ID NO 551
<211> LENGTH: 22
<212> TYPE: PRT
<213> ORGANISM: Homo sapiens

<400> SEQUENCE: 551

Ser Tyr Val Leu Thr Gln Pro Pro Ser Val Ser Val Ala Pro Gly Lys
1               5                   10                  15

Thr Ala Arg Ile Thr Cys
            20

<210> SEQ ID NO 552
<211> LENGTH: 22
<212> TYPE: PRT
<213> ORGANISM: Homo sapiens

<400> SEQUENCE: 552

Ser Tyr Val Leu Thr Gln Pro Pro Ser Val Ser Val Ala Pro Gly Gln
1               5                   10                  15

Thr Ala Arg Ile Thr Cys
            20

<210> SEQ ID NO 553
```

```
<211> LENGTH: 11
<212> TYPE: PRT
<213> ORGANISM: Homo sapiens

<400> SEQUENCE: 553

Gly Gly Asn Asn Ile Gly Ser Lys Ser Val His
1               5                   10

<210> SEQ ID NO 554
<211> LENGTH: 15
<212> TYPE: PRT
<213> ORGANISM: Homo sapiens

<400> SEQUENCE: 554

Trp Tyr Gln Gln Lys Pro Gly Gln Ala Pro Val Leu Val Ile Tyr
1               5                   10                  15

<210> SEQ ID NO 555
<211> LENGTH: 15
<212> TYPE: PRT
<213> ORGANISM: Homo sapiens

<400> SEQUENCE: 555

Trp Tyr Gln Gln Lys Pro Gly Gln Ala Pro Val Leu Val Val Tyr
1               5                   10                  15

<210> SEQ ID NO 556
<211> LENGTH: 32
<212> TYPE: PRT
<213> ORGANISM: Homo sapiens

<400> SEQUENCE: 556

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 557
<211> LENGTH: 32
<212> TYPE: PRT
<213> ORGANISM: Homo sapiens

<400> SEQUENCE: 557

Gly Val Pro Asp Arg Phe Ser Gly Ser Gly Ser Gly Thr His Leu Thr
1               5                   10                  15

Leu Lys Ile Ser Arg Val Glu Ala Glu Asp Val Gly Val Tyr Tyr Cys
            20                  25                  30

<210> SEQ ID NO 558
<211> LENGTH: 9
<212> TYPE: PRT
<213> ORGANISM: Homo sapiens

<400> SEQUENCE: 558

Met Gln Ala Leu Gln Thr Pro Leu Thr
1               5

<210> SEQ ID NO 559
<211> LENGTH: 10
<212> TYPE: PRT
<213> ORGANISM: Homo sapiens

<400> SEQUENCE: 559

Phe Gly Gly Gly Thr Lys Val Glu Ile Lys
```

<210> SEQ ID NO 560
<211> LENGTH: 7
<212> TYPE: PRT
<213> ORGANISM: Homo sapiens

<400> SEQUENCE: 560

Trp Ala Ser Thr Arg Glu Ser
1               5

<210> SEQ ID NO 561
<211> LENGTH: 32
<212> TYPE: PRT
<213> ORGANISM: Homo sapiens

<400> SEQUENCE: 561

Gly Val Pro Asp Arg Phe Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 562
<211> LENGTH: 9
<212> TYPE: PRT
<213> ORGANISM: Homo sapiens

<400> SEQUENCE: 562

Gln Gln Tyr Tyr Ser Thr Pro Trp Thr
1               5

<210> SEQ ID NO 563
<211> LENGTH: 10
<212> TYPE: PRT
<213> ORGANISM: Homo sapiens

<400> SEQUENCE: 563

Phe Gly Gln Gly Thr Lys Val Glu Ile Lys
1               5                   10

<210> SEQ ID NO 564
<211> LENGTH: 7
<212> TYPE: PRT
<213> ORGANISM: Homo sapiens

<400> SEQUENCE: 564

Ser Asn Asn Gln Arg Pro Ser
1               5

<210> SEQ ID NO 565
<211> LENGTH: 7
<212> TYPE: PRT
<213> ORGANISM: Homo sapiens

<400> SEQUENCE: 565

Ser Asn Asn Arg Arg Pro Ser
1               5

<210> SEQ ID NO 566
<211> LENGTH: 32
<212> TYPE: PRT
<213> ORGANISM: Homo sapiens

<400> SEQUENCE: 566

```
Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Tyr Tyr Cys
            20                  25                  30
```

<210> SEQ ID NO 567
<211> LENGTH: 10
<212> TYPE: PRT
<213> ORGANISM: Homo sapiens

<400> SEQUENCE: 567

```
Ala Ala Trp Asp Asp Ser Leu Asn Trp Val
1               5                   10
```

<210> SEQ ID NO 568
<211> LENGTH: 10
<212> TYPE: PRT
<213> ORGANISM: Homo sapiens

<400> SEQUENCE: 568

```
Ala Thr Trp Asp Asp Arg Leu Asn Trp Val
1               5                   10
```

<210> SEQ ID NO 569
<211> LENGTH: 10
<212> TYPE: PRT
<213> ORGANISM: Homo sapiens

<400> SEQUENCE: 569

```
Phe Gly Ala Gly Thr Lys Leu Thr Val Leu
1               5                   10
```

<210> SEQ ID NO 570
<211> LENGTH: 7
<212> TYPE: PRT
<213> ORGANISM: Homo sapiens

<400> SEQUENCE: 570

```
Tyr Asp Ser Asp Arg Pro Ser
1               5
```

<210> SEQ ID NO 571
<211> LENGTH: 7
<212> TYPE: PRT
<213> ORGANISM: Homo sapiens

<400> SEQUENCE: 571

```
Asp Asp Ser Asp Arg Pro Ser
1               5
```

<210> SEQ ID NO 572
<211> LENGTH: 32
<212> TYPE: PRT
<213> ORGANISM: Homo sapiens

<400> SEQUENCE: 572

```
Gly Ile Pro Glu Arg Phe Ser Gly Ser Asn Ser Gly Asn Thr Ala Thr
1               5                   10                  15

Leu Thr Ile Ser Arg Val Glu Ala Gly Asp Glu Ala Asp Tyr Tyr Cys
            20                  25                  30
```

<210> SEQ ID NO 573
<211> LENGTH: 32
<212> TYPE: PRT

```
<213> ORGANISM: Homo sapiens

<400> SEQUENCE: 573

Gly Ile Pro Glu Arg Phe Ser Gly Ser Asn Ser Gly Asn Thr Ala Thr
1               5                   10                  15

Leu Thr Ile Ser Arg Val Glu Ala Gly Asp Glu Ala Asp Phe Tyr Cys
            20                  25                  30

<210> SEQ ID NO 574
<211> LENGTH: 11
<212> TYPE: PRT
<213> ORGANISM: Homo sapiens

<400> SEQUENCE: 574

Gln Val Trp Asp Ser Ser Ser Asp Pro Val Val
1               5                   10

<210> SEQ ID NO 575
<211> LENGTH: 10
<212> TYPE: PRT
<213> ORGANISM: Homo sapiens

<400> SEQUENCE: 575

Phe Gly Gly Gly Thr Lys Leu Thr Val Leu
1               5                   10
```

ANTIGEN BINDING PROTEINS TO PROPROTEIN CONVERTASE SUBTILISIN KEXIN TYPE 9 (PCSK9)

RELATED APPLICATIONS

This application is continuation of U.S. Non-Provisional application Ser. No. 13/251,909 filed Oct. 3, 2011, which is a divisional of U.S. Non-Provisional application Ser. No. 12/197,093, filed Aug. 22, 2008, which claims priority to U.S. Provisional Applications Ser. No. 61/086,133, filed Aug. 4, 2008, Ser. No. 60/957,668, filed Aug. 23, 2007, Ser No. 61/008,965, filed Dec. 21, 2007, and Ser. No. 61/010,630, filed Jan. 9, 2008, each of which is hereby incorporated by reference in its entirety.

SEQUENCE LISTING AND TABLES IN ELECTRONIC FORMAT

The present application is being filed along with a Sequence Listing in electronic format. The Sequence Listing is provided as a file entitled Sequence_Listing_APMOL-003D2.txt, created and last saved Sep. 30, 2011 which is 296,708 bytes in size, and replaced by a file entitled APMOL003C14REPLACEMENT.TXT created Sep. 29, 2014, which is 313,027 bytes in size. The information in the electronic format of the Sequence Listing is incorporated herein by reference in its entirety. The present application is being filed along with a collection of Tables in electronic format. The collection of Tables is provided as a file entitled Table__35-1-4_APMOL-003D2.txt, created and last saved on Sep. 30, 2011, which is 2,024,359 bytes in size. The information in the electronic format of the collection of Tables is incorporated herein by reference in its entirety.

human PCSK9 mutations that result in either increased or decreased levels of plasma LDL have been identified (Kotowski et al., 2006; Zhao et al, 2006). PCSK9 has been shown to directly interact with the LDLR protein, be endocytosed along with the LDLR, and co-immunofluoresce with the LDLR throughout the endosomal pathway (Lagace et al., 2006). Degradation of the LDLR by PCSK9 has not been observed and the mechanism through which it lowers extracellular LDLR protein levels is uncertain.

PCSK9 is a prohormone-proprotein convertase in the subtilisin (S8) family of serine proteases (Seidah et al., 2003). Humans have nine prohormone-proprotein convertases that can be divided between the S8A and S8B subfamilies (Rawlings et al., 2006). Furin, PC1/PC3, PC2, PACE4, PC4, PC5/PC6 and PC7/PC8/LPC/SPC7 are classified in subfamily S8B. Crystal and NMR structures of different domains from mouse furin and PC1 reveal subtilisin-like pro- and catalytic domains, and a P domain directly C-terminal to the catalytic domain (Henrich et al., 2003; Tangrea et al., 2002). Based on the amino acid sequence similarity within this subfamily, all seven members are predicted to have similar structures (Henrich et al., 2005). SKI-1/S1P and PCSK9 are classified in subfamily S8A Sequence comparisons with these proteins also suggest the presence of subtilisin-like pro- and catalytic domains (Sakai et al., 1998; Seidah et al., 2003; Seidah et al., 1999). In these proteins the amino acid sequence C-terminal to the catalytic domain is more variable and does not suggest the presence of a P domain.

Prohormone-proprotein convertases are expressed as zymogens and they mature through a multi step process. The function of the pro-domain in this process is two-fold. The pro-domain first acts as a chaperone and is required for proper folding of the catalytic domain (Ikemura et al., 1987). Once

LENGTHY TABLES

The patent contains a lengthy table section. A copy of the table is available in electronic form from the USPTO web site (http://seqdata.uspto.gov/?pageRequest=docDetail&DocID=US08883983B2). An electronic copy of the table will also be available from the USPTO upon request and payment of the fee set forth in 37 CFR 1.19(b)(3).

FIELD OF THE INVENTION

The present invention relates to antigen binding proteins that bind to proprotein convertase subtilisin kexin type 9 (PCSK9) and methods of using and making the antigen binding proteins.

BACKGROUND OF VARIOUS EMBODIMENTS

Proprotein convertase subtilisin kexin type 9 (PCSK9) is a serine protease involved in regulating the levels of the low density lipoprotein receptor (LDLR) protein (Horton et al., 2007; Seidah and Prat, 2007). In vitro experiments have shown that adding PCSK9 to HepG2 cells lowers the levels of cell surface LDLR (Benjannet et al., 2004; Lagace et al., 2006; Maxwell et al., 2005; Park et al., 2004). Experiments with mice have shown that increasing PCSK9 protein levels decreases levels of LDLR protein in the liver (Benjannet et al., 2004; Lagace et al., 2006; Maxwell et al., 2005; Park et al., 2004), while PCSK9 knockout mice have increased levels of LDLR in the liver (Rashid et al., 2005). Additionally, various the catalytic domain is folded, autocatalysis occurs between the pro-domain and catalytic domain. Following this initial cleavage reaction, the pro-domain remains bound to the catalytic domain where it then acts as an inhibitor of catalytic activity (Fu et al., 2000). When conditions are correct, maturation proceeds with a second autocatalytic event at a site within the pro-domain (Anderson et al., 1997). After this second cleavage event occurs the pro-domain and catalytic domain dissociate, giving rise to an active protease.

Autocatalysis of the PCSK9 zymogen occurs between Gln152 and Ser153 (VFAQ|SIP) (Naureckiene et al., 2003), and has been shown to be required for its secretion from cells (Seidah et al., 2003). A second autocatalytic event at a site within PCSK9's pro-domain has not been observed. Purified PCSK9 is made up of two species that can be separated by non-reducing SDS-PAGE; the pro-domain at 17 Kd, and the catalytic plus C-terminal domains at 65 Kd. PCSK9 has not been isolated without its inhibitory pro-domain, and measurements of PCSK9's catalytic activity have been variable (Naureckiene et al., 2003; Seidah et al., 2003).

SUMMARY OF VARIOUS EMBODIMENTS

In some embodiments, the invention comprises an antigen binding protein to PCSK9.

In some aspects, the invention comprises an isolated antigen binding protein that binds PCSK9 comprising: A) one or more heavy chain complementary determining regions (CDRHs) selected from the group consisting of: (i) a CDRH1 from a CDRH1 in a sequence selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60; (ii) a CDRH2 from a CDRH2 in a sequence selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60; (iii) a CDRH3 from a CDRH3 in a sequence selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60; and (iv) a CDRH of (i), (ii), and (iii) that contains one or more amino acid substitutions, deletions or insertions of no more than 4 amino acids; B) one or more light chain complementary determining regions (CDRLs) selected from the group consisting of: (i) a CDRL1 from a CDRL1 in a sequence selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46; (ii) a CDRL2 from a CDRL2 in a sequence selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46; (iii) a CDRL3 from a CDRL3 in a sequence selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46; and (iv) a CDRL of (i), (ii) and (iii) that contains one or more amino acid substitutions, deletions or insertions of no more than 4 amino acids; or C) one or more heavy chain CDRHs of A) and one or more light chain CDRLs of B). In some embodiments, the isolated antigen binding protein comprises at least one CDRH of A) and at least one CDRL of B). In some embodiments, the isolated antigen binding protein comprises at least two CDRH of A) and at least two CDRL of B). In some embodiments, the isolated antigen binding protein comprises said CDRH1, CDRH2, CDRH3, CDRL1, CDRL2 and CDRL3. In some embodiments, the CDRH of A) is selected from at least one of the group consisting of: (i) a CDRH1 amino acid sequence selected from the CDRH1 in a sequence selected from the group consisting of SEQ ID NO: 67, 79, 89, and 49; (ii) a CDRH2 amino acid sequence selected from the CDRH2 in a sequence selected from the group consisting of SEQ ID NO: 67, 79, 89, and 49; (iii) a CDRH3 amino acid sequence selected from the CDRH3 in a sequence selected from the group consisting of SEQ ID NO: 67, 79, 89, and 49; and (iv) a CDRH of (i), (ii) and (iii) that contains one or more amino acid substitutions, deletions or insertions of no more than 2 amino acids. In addition, the CDRL of B) is selected from at least one of the group consisting of: (i) a CDRL1 amino acid sequence selected from the CDRL1 in a sequence selected from the group consisting of SEQ ID NO: 12, 35, 32, and 23; (ii) a CDRL2 amino acid sequence selected from the CDRL2 in a sequence selected from the group consisting of SEQ ID NO: 12, 35, 32, and 23; (iii) a CDRL3 amino acid sequence selected from the CDRL3 in a sequence selected from the group consisting of SEQ ID NO: 12, 35, 32, and 23; and (iv) a CDRL of (i), (ii) and (iii) that contains one or more amino acid substitutions, deletions or insertions of no more than 2 amino acids; or C) one or more heavy chain CDRHs of A) and one or more light chain CDRLs of B. In some embodiments, the CDRH of A) is selected from at least one of the group consisting of: (i) a CDRH1 amino acid sequence of the CDRH1 amino acid sequence in SEQ ID NO: 67; (ii) a CDRH2 amino acid sequence of the CDRH2 amino acid sequence in SEQ ID NO: 67; (iii) a CDRH3 amino acid sequence of the CDRH3 amino acid sequence in SEQ ID NO: 67; and (iv) a CDRH of (i), (ii) and (iii) that contains one or more amino acid substitutions, deletions or insertions of no more than 2 amino acids; said CDRL of B) is selected from at least one of the group consisting of: (i) a CDRL1 amino acid sequence of the CDRL1 amino acid sequence in SEQ ID NO: 12; (ii) a CDRL2 amino acid sequence of the CDRL2 amino acid sequence in SEQ ID NO: 12; (iii) a CDRL3 amino acid sequence of the CDRL3 amino acid sequence in SEQ ID NO: 12; and (iv) a CDRL of (i), (ii) and (iii) that contains one or more amino acid substitutions, deletions or insertions of no more than 2 amino acids; or C) one or more heavy chain CDRHs of A) and one or more light chain CDRLs of B). In some embodiments, the antigen binding protein comprises A) a CDRH1 of the CDRH1 sequence in SEQ ID NO: 67, a CDRH2 of the CDRH2 sequence in SEQ ID NO: 67, and a CDRH3 of the CDRH3 sequence in SEQ ID NO: 67, and B) a CDRL1 of the CDRL1 sequence in SEQ ID NO: 12, a CDRL2 of the CDRL2 sequence in SEQ ID NO: 12, and a CDRL3 of the CDRL3 sequence in SEQ ID NO: 12. In some embodiments, the antigen binding protein comprises a heavy chain variable region (VH) having at least 80% sequence identity with an amino acid sequence selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60, and/or a light chain variable region (VL) having at least 80% sequence identity with an amino acid sequence selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46. In some embodiments, the VH has at least 90% sequence identity with an amino acid sequence selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60, and/or the VL has at least 90% sequence identity with an amino acid sequence selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46. In some embodiments, the VH is selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60, and/or the VL is selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46.

In some aspects, the invention comprises an isolated antigen binding protein that specifically binds to an epitope that is bound by any of the ABPs disclosed herein.

In some aspects, the invention comprises an isolated antigen binding protein that binds PCSK9, wherein the antigen binding protein comprises: A) one or more heavy chain CDRs (CDRHs) selected from at least one of the group consisting of: (i) a CDRH1 with at least 80% sequence identity to a CDRH1 in one of the sequences selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60; (ii) a CDRH2 with at least 80% sequence identity to a CDRH2 in one of the sequences selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60; and (iii) a CDRH3 with at least 80% sequence identity to a CDRH3 in one of the sequences selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60; B) one or more light chain CDRs (CDRLs) selected from at least one of the group consisting of (i) a CDRL1 with at least 80% sequence identity to a CDRL1 in one of the sequences selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46; (ii) a CDRL2 with at least 80% sequence identity to a CDRL2 in one of the sequences selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46; and (iii) a CDRL3 with at least 80% sequence identity to a CDRL3 in one of the sequences selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46; or C) one or more heavy chain CDRHs of A) and one or more light chain CDRLs of B). In some embodiments, the antigen binding protein comprises: A) one or more CDRHs selected from at least one of the group consisting of: (i) a CDRH1 with at least 90% sequence identity to a CDRH1 in one of the sequences selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60; (ii) a CDRH2 with at least 90% sequence identity to a CDRH2 in one of the sequences selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60; and (iii) a CDRH3 with at least 90% sequence identity to a CDRH3 in one of the sequences selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60; B) one or more CDRLs selected from at least one of the group consisting of: (i) a CDRL1 with at least 90% sequence identity to a CDRL1 in one of the sequences selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46; (ii) a CDRL2 with at least 90% sequence identity to a CDRL2 in one of the sequences selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46; and (iii) a CDRL3 with at least 90% sequence identity to a CDRL3 in one of the sequences selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46; or C) one or more heavy chain CDRHs of A) and one or more light chain CDRLs of B).

In some aspects, the invention comprises an isolated antigen binding protein that binds PCSK9, the antigen binding protein comprises: A) a heavy chain complementary determining region (CDRH) selected from at least one of the group consisting of: (i) a CDRH3 selected from the CDRH3 within the sequences selected from the group consisting of SEQ ID NOs: 67, 79, and 49, (ii) a CDRH3 that differs in amino acid sequence from the CDRH3 of (i) by an amino acid addition, deletion or substitution of not more than two amino acids; and (iii) $X_1X_2X_3X_4X_5X_6X_7X_8X_9X_{10}X_{11}X_{12}X_{13}X_{14}$ (SEQ ID NO: 404), wherein $X_1$ is selected from the group consisting of D, A, R, and not amino acid, $X_2$ is selected from the group consisting of Y, I, G, and no amino acid, $X_3$ is selected from the group consisting of D, A, G, and no amino acid, $X_4$ is selected from the group consisting of F, A, L, and no amino acid, $X_5$ is selected from the group consisting of W, L, A, and no amino acid, $X_6$ is selected from the group consisting of S, Y, A, and no amino acid, $X_7$ is selected from the group consisting of A, Y, R, and no amino acid, $X_8$ is selected from the group consisting of Y, P, and no amino acid, $X_9$ is selected from the group consisting of Y, G, and no amino acid, $X_{10}$ is selected from the group consisting of D, G, and no amino acid, $X_{11}$ is selected from the group consisting of A, M, and no amino acid, $X_{12}$ is selected from the group consisting of F, D, and no amino acid, $X_{13}$ is selected from the group consisting of D, V, and no amino acid, $X_{14}$ is selected from the group consisting of V and no amino acid; B) a light chain complementary determining region (CDRL) selected from at least one of the group consisting of: (i) a CDRL3 selected from the CDRL3 within the sequences selected from the group consisting of SEQ ID NOs: 12, 35, and 23, (ii) a CDRL3 that differs in amino acid sequence from the CDRL3 of (i) by an amino acid addition, deletion or substitution of not more than two amino acids; and (iii) a CDRL3 amino acid sequence selected from the group consisting of: $X_1X_2X_3X_4X_5X_6X_7X_8X_9X_{10}X_{11}$ (SEQ ID NO: 405), wherein $X_1$ is selected from the group consisting of Q and G, $X_2$ is selected from the group consisting of S, T, A, and no amino acid, $X_3$ is selected from the group consisting of Y, no amino acid, and W, $X_4$ is selected from the group consisting of D and no amino acid, $X_5$ is selected from the group consisting of S and no amino acid, $X_6$ is selected from the group consisting of S and no amino acid, $X_7$ is selected from the group consisting of L, T, and no amino acid, $X_8$ is selected from the group consisting of no amino acid, A, and S, $X_9$ is selected from the group consisting of no amino acid, G, A, and V, $X_{10}$ is selected from the group consisting of no amino acid, S, Y, and V, $X_{11}$ is selected from the group consisting of no amino acid and V.

In some aspects, the invention comprises an isolated antigen binding protein comprising a light chain having the amino acid sequence selected from the group consisting of: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, and some combination thereof.

In some embodiments, the antigen binding protein specifically binds to an epitope that is bound by at least one of the antigen binding proteins disclosed herein. In some embodiments, the isolated antigen binding protein further comprises a heavy chain having the amino acid sequence selected from the group consisting of: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, 60, and some combination thereof. In some embodiments, the amino acid sequence of the ABP is selected from the group consisting of SEQ ID NO: 12, 35, 23, and some combination thereof. In some embodiments, the heavy chain of the ABP comprises a CDRH3 of SEQ ID NO: 67, a CDRH2 of SEQ ID NO: 67, and a CDRH1 of SEQ ID NO: 67, and said light chain comprises a CDRL3 of SEQ ID NO: 12, a CDRL2 of SEQ ID NO: 12, and a CDRL1 of SEQ ID NO: 12. In some embodiments, the isolated antigen binding protein is a monoclonal antibody, a polyclonal antibody, a recombinant antibody, a human antibody, a humanized antibody, a chimeric antibody, a multispecific antibody, or an antibody fragment thereof. In some embodiments, the isolated antigen binding protein is a Fab fragment, a Fab' fragment, a $F(ab')_2$ fragment, a Fv fragment, a diabody, or a single chain antibody molecule. In some embodiments, the isolated antigen binding protein is a human antibody. In some embodiments, the isolated antigen binding protein is a monoclonal antibody. In some embodiments, the isolated antigen binding protein is of the IgG1-, IgG2- IgG3- or IgG4-type. In some embodiments, the isolated antigen binding protein is of the IgG4- or IgG2-type. In some embodiments, the isolated antigen binding protein is coupled to a labeling group. In some embodiments, the isolated antigen binding protein competes for binding to PCSK9 with an antigen binding protein described herein. In some embodiments, the isolated antigen binding protein is a monoclonal antibody, a polyclonal antibody, a recombinant antibody, a human antibody, a humanized antibody, a chimeric antibody, a multispecific antibody, or an antibody fragment thereof. In some embodiments, the isolated antigen binding protein is a Fab fragment, a Fab' fragment, a F(ab')$_2$ fragment, a Fv fragment, a diabody, or a single chain antibody molecule. In some embodiments, the isolated antigen binding protein is coupled to a labeling group. In some embodiments, the isolated antigen binding protein reduces binding of PCSK9 to LDLR. In some embodiments, the isolated antigen binding protein the antigen binding protein decreases an amount of LDL present in a subject when administered to the subject. In some embodiments, the isolated antigen binding protein decreases an amount of serum cholesterol present in a subject when administered to the subject. In some embodiments, the isolated antigen binding protein increases an amount of LDLR present in a subject when administered to the subject.

In some aspects, the invention comprises a vector comprising a nucleic acid molecule as described herein. In some embodiments, the invention comprises a host cell comprising a nucleic acid molecule as described herein.

In some aspects, the invention comprises an isolated antigen binding protein that competes for binding to PCSK9 with an antigen binding protein disclosed herein.

In some aspects, the invention comprises a nucleic acid molecule encoding the antigen binding protein according disclosed herein.

In some aspects, the invention comprises a pharmaceutical composition comprising at least one antigen binding protein described herein.

In some aspects, the invention comprises a method for treating or preventing a condition associated with elevated serum cholesterol levels in a patient, comprising administering to a patient in need thereof an effective amount of at least one isolated antigen binding protein disclosed herein.

In some aspects, the invention comprises a method of inhibiting binding of PCSK9 to LDLR in a subject comprising administering an effective amount of at least one antigen binding protein disclosed herein.

In some aspects, the invention comprises an antigen binding protein that selectively binds to PCSK9, wherein the antigen binding protein binds to PCSK9 with a $K_d$ that is smaller than 100 pM.

In some aspects, the invention comprises a method for treating or preventing a condition associated with elevated serum cholesterol levels in a subject, the method comprising administering to a subject in need thereof an effective amount of at least one isolated antigen binding protein disclosed herein simultaneously or sequentially with an agent that elevates the availability of LDLR protein.

In some aspects, the invention comprises a method of lowering serum cholesterol level in a subject, the method comprising administering to a subject an effective amount of at least one isolated antigen binding protein as disclosed herein.

In some aspects, the invention comprises a method of lowering serum cholesterol level in a subject, the method comprising administering to a subject an effective amount of at least one isolated antigen binding protein as disclosed herein, simultaneously or sequentially with an agent that elevates the availability of LDLR protein.

In some aspects, the invention comprises a method of increasing LDLR protein level in a subject, the method comprising administering to a subject an effective amount of at least one isolated antigen binding protein as disclosed herein.

In some aspects, the invention comprises a method of increasing LDLR protein levels in a subject, the method comprising administering to a subject an effective amount of at least one isolated antigen binding protein as disclosed herein simultaneously or sequentially with an agent that elevates the availability of LDLR protein.

In some aspects, the invention comprises a pharmaceutical composition comprising an ABP as disclosed herein and an agent that elevates the availability of LDLR protein levels. In some embodiments, the agent that elevates the availability of LDLR protein comprises a statin. In some embodiments, the statin is selected from the group consisting of atorvastatin, cerivastatin, fluvastatin, lovastatin, mevastatin, pitavastatin, pravastatin, rosuvastatin, simvastatin, and some combination thereof.

In some aspect, the invention comprises a method of making the antigen binding protein as described herein, comprising the step of preparing said antigen binding protein from a host cell that secretes said antigen binding protein.

In some aspect, the invention comprises a pharmaceutical composition comprising at least one antigen binding protein as described herein and a pharmaceutically acceptable excipient. In some embodiments, the pharmaceutical composition further comprises an additional active agent. In some embodiments, said additional active agent is selected from the group consisting of a radioisotope, radionuclide, a toxin, or a therapeutic and a chemotherapeutic group.

In some aspects, the invention comprises a method for treating or preventing a condition associated with an elevated serum cholesterol level in a patient. The method comprises administering to a patient in need thereof an effective amount of at least one isolated antigen binding protein as disclosed herein. In some embodiments, the condition is hypercholesterolemia.

In some aspects, the invention comprises a method of inhibiting binding of PCSK9 to LDLR in a patient comprising administering an effective amount of at least one antigen binding protein according as described herein.

In some aspect, the invention comprises an antigen binding protein that binds to PCSK9 with a $K_d$ that is smaller than 100 pM. In some embodiments, the antigen binding protein binds with a $K_d$ that is smaller than 10 pM. In some embodiments, the antigen binding protein binds with a $K_d$ that is less than 5 pM.

In some aspects, the invention comprises a method for treating or preventing a condition associated with elevated serum cholesterol levels in a subject, said method comprising administering to a subject in need thereof an effective amount of at least one isolated antigen binding protein described herein simultaneously or sequentially with an agent that elevates the availability of LDLR protein. In some embodiments, the agent that elevates the availability of LDLR protein comprises a statin. In some embodiments, the statin is selected from the group consisting of atorvastatin, cerivastatin, fluvastatin, lovastatin, mevastatin, pitavastatin, pravastatin, rosuvastatin, simvastatin, and some combination thereof.

In some aspects, the invention comprises a method of lowering the serum cholesterol level in a subject. The method comprises administering to a subject an effective amount of at least one isolated antigen binding protein as described herein.

In some aspects, the invention comprises a method of lowering serum cholesterol levels in a subject comprising administering to a subject an effective amount of at least one isolated antigen binding protein, as described herein, simultaneously or sequentially with an agent that elevates the availability of LDLR protein. In some embodiments, the agent that elevates the availability of LDLR protein comprises a statin. In some embodiments, the statin is selected from the group consisting of atorvastatin, cerivastatin, fluvastatin, lovastatin, mevastatin, pitavastatin, pravastatin, rosuvastatin, simvastatin, and some combination thereof.

In some aspects, the invention comprises a method of increasing LDLR protein levels in a subject by administering to a subject an effective amount of at least one isolated antigen binding protein as provided herein.

In some aspects, the invention comprises a method of increasing LDLR protein levels in a subject by administering to a subject an effective amount of at least one isolated antigen binding protein, as described herein, simultaneously or sequentially with an agent that elevates the availability of LDLR protein. In some embodiments, the agent that elevates the availability of LDLR protein levels comprises a statin. In some embodiments, the statin is selected from the group consisting of atorvastatin, cerivastatin, fluvastatin, lovastatin, mevastatin, pitavastatin, pravastatin, rosuvastatin, simvastatin, and some combination thereof.

In some aspects, the invention comprises a neutralizing antibody that binds to PCSK9 and reduces a low density lipoprotein receptor (LDLR) lowering effect of PCSK9 on LDLR. In some embodiments, the antibody specifically binds to PCSK9. In some embodiments, the antibody binds to the catalytic domain of PCSK9. In some embodiments, the antibody binds to an epitope within residues 31-447 of SEQ ID NO: 3. In some embodiments, the antibody binds to PCSK9 having an amino acid sequence that is at least 90% identical to SEQ ID NO: 3.

In some aspects, the invention comprises a neutralizing antigen binding protein that binds to PCSK9, wherein the antigen binding protein binds to PCSK9 at a location within residues 31-447 of SEQ ID NO: 3. In some embodiments, when the antigen binding protein is bound to PCSK9, the antibody is positioned 8 angstroms or less from at least one of the following residues of PCSK9: S153, I154, P155, R194, D238, A239, I369, S372, D374, C375, T377, C378, F379, V380, S381, W156, N157, L158, E159, H193, E195, H229, R237, G240, K243, D367, I368, G370, A371, S373, S376, Q382, W72, F150, A151, Q152, T214, R215, F216, H217, A220, 5221, K222, S225, H226, C255, Q256, G257, K258, N317, F318, T347, L348, G349, T350, L351, E366, D367, D374, V380, S381, Q382, S383, G384, K69, D70, P71, S148, V149, D186, T187, E211, D212, G213, R218, Q219, C223, D224, G227, H229, L253, N254, G259, P288, A290, G291, G316, R319, Y325, V346, G352, T353, G365, I368, I369, S372, S373, C378, F379, T385, S386, Q387, S153, S188, I189, Q190, S191, D192, R194, E197, G198, R199, V200, D224, R237, D238, K243, S373, D374, S376, T377, F379, I154, T187, H193, E195, I196, M201, V202, C223, T228, S235, G236, A239, G244, M247, I369, S372, C375, or C378. In some embodiments, the antibody is positioned 8 angstroms or less from at least one of the following residues of PCSK9: S153, I154, P155, R194, D238, A239, I369, S372, D374, C375, T377, C378, F379, V380, S381, W156, N157, L158, E159, H193, E195, H229, R237, G240, K243, D367, I368, G370, A371, S373, S376, or Q382. In some embodiments, the antibody is positioned 5 angstroms or less from at least one of the following residues of PCSK9: S153, I154, P155, R194, D238, A239, I369, S372, D374, C375, T377, C378, F379, V380, or S381. In some embodiments, the antibody is positioned 5 angstroms or less from at least two of the following residues of PCSK9: S153, I154, P155, 8194, D238, A239, I369, S372, D374, C375, T377, C378, F379, V380, or S381. In some embodiments, the antibody is 5 angstroms or less from at least four of the following residues of PCSK9: S153, I154, P155, R194, D238, A239, I369, S372, D374, C375, T377, C378, F379, V380, or S381. In some embodiments, the antibody is positioned 8 angstroms or less from at least one of the following residues of PCSK9: W72, F150, A151, Q152, T214, R215, F216, H217, A220, S221, K222, S225, H226, C255, Q256, G257, K258, N317, F318, T347, L348, G349, T350, L351, E366, D367, D374, V380, S381, Q382, S383, G384, K69, D70, P71, S148, V149, D186, T187, E211, D212, G213, R218, Q219, C223, D224, G227, H229, L253, N254, G259, P288, A290, G291, G316, R319, Y325, V346, G352, T353, G365, I368, I369, S372, S373, C378, F379, T385, S386, or Q387. In some embodiments, the antibody is positioned 5 angstroms or less from at least one of the following residues of PCSK9: W72, F150, A151, Q152, T214, R215, F216, H217, A220, S221, K222, S225, H226, C255, Q256, G257, K258, N317, F318, T347, L348, G349, T350, L351, E366, D367, D374, V380, S381, Q382, S383, or G384. In some embodiments, the antibody is positioned 5 angstroms or less from at least two of the following residues of PCSK9: W72, F150, A151, Q152, T214, R215, F216, H217, A220, S221, K222, S225, H226, C255, Q256, G257, K258, N317, F318, T347, L348, G349, T350, L351, E366, D367, D374, V380, S381, Q382, S383, or G384. In some embodiments, the antibody is positioned 5 angstroms or less from at least four of the following residues of PCSK9: W72, F150, A151, Q152, T214, R215, F216, H217, A220, S221, K222, S225, H226, C255, Q256, G257, K258, N317, F318, T347, L348, G349, T350, L351, E366, D367, D374, V380, S381, Q382, S383, or G384. In some embodiments, the antibody is positioned 8 angstroms or less from at least one of the following residues of PCSK9: S153, S188, I189, Q190, S191, D192, R194, E197, G198, R199, V200, D224, R237, D238, K243, S373, D374, S376, T377, F379, I154, T187, H193, E195, I196, M201, V202, C223, T228, S235, G236, A239, G244, M247, I369, 5372, C375, or C378. In some embodiments, the antibody is positioned 5 angstroms or less from at least one of the following residues of PCSK9: S153, S188, I189, Q190, S191, D192, R194, E197, G198, R199, V200, D224, R237, D238, K243, S373, D374, S376, T377, or F379. In some embodiments, the antibody is positioned 5 angstroms or less from at least two of the following residues of PCSK9: S153, S188, I189, Q190, S191, D192, R194, E197, G198, R199, V200, D224, R237, D238, K243, S373, D374, 5376, T377, or F379. In some embodiments, the antibody is positioned 5 angstroms or less from at least four of the following residues of PCSK9: S153, S188, I189, Q190, S191, D192, R194, E197, G198, R199, V200, D224, R237, D238, K243, S373, D374, S376, T377, or F379.

In some aspects, the invention comprises a neutralizing antibody that binds to PCSK9, wherein the antibody binds to PCSK9 and reduces the likelihood that PCSK9 binds to LDLR.

In some embodiments, an antibody or antigen binding molecule that binds to PCSK9 is contemplated. The antibody binds to PCSK9 at a location within residues 31-447 of SEQ ID NO: 3. In some embodiments, the antibody or antigen binding molecule, when bound to PCSK9, is positioned 8 angstroms or less from at least one of the following residues of PCSK9: S153, I154, P155, R194, D238, A239, I369, S372, D374, C375, T377, C378, F379, V380, S381, W156, N157, L158, E159, H193, E195, H229, R237, G240, K243, D367, I368, G370, A371, S373, S376, Q382, W72, F150, A151, Q152, T214, R215, F216, H217, A220, 5221, K222, S225, H226, C255, Q256, G257, K258, N317, F318, T347, L348, G349, T350, L351, E366, D367, D374, V380, S381, Q382, S383, G384, K69, D70, P71, S148, V149, D186, T187, E211, D212, G213, R218, Q219, C223, D224, G227, H229, L253, N254, G259, P288, A290, G291, G316, R319, Y325, V346, G352, T353, G365, I368, I369, 5372, S373, C378, F379, T385, S386, Q387, S153, S188, I189, Q190, S191, D192, R194, E197, G198, R199, V200, D224, R237, D238, K243, S373, D374, S376, T377, F379, I154, T187, H193, E195, I196, M201, V202, C223, T228, S235, G236, A239, G244, M247, I369, S372, C375, or C378.

In some embodiments, an isolated antibody or antigen binding molecule that blocks an antibody to PCSK9 from binding within 8 angstroms of a residue of PCSK9 is provided. In some embodiments the residue of PCSK9 is selected from at least one of the following PCSK9 residues: S153, I154, P155, R194, D238, A239, I369, S372, D374, C375, T377, C378, F379, V380, S381, W156, N157, L158, E159, H193, E195, H229, R237, G240, K243, D367, I368, G370, A371, S373, S376, Q382, W72, F150, A151, Q152, T214, R215, F216, H217, A220, S221, K222, S225, H226, C255, Q256, G257, K258, N317, F318, T347, L348, G349, T350, L351, E366, D367, D374, V380, S381, Q382, S383, G384, K69, D70, P71, S148, V149, D186, T187, E211, D212, G213, R218, Q219, C223, D224, G227, H229, L253, N254, G259, P288, A290, G291, G316, R319, Y325, V346, G352, T353, G365, I368, I369, S372, S373, C378, F379, T385, S386, Q387, S153, S188, I189, Q190, S191, D192, R194, E197, G198, R199, V200, D224, R237, D238, K243, S373, D374, S376, T377, F379, I154, T187, H193, E195, I196, M201, V202, C223, T228, S235, G236, A239, G244, M247, I369, S372, C375, or C378.

In some embodiments, an isolated antibody or antigen binding molecule that binds to PCSK9 at a location that overlaps with a location that LDLR binds to PCSK9 is provided. In some embodiments, the location that LDLR binds to PCSK9 includes at least one amino acid residue selected from the group consisting of: S153, I154, P155, R194, D238, A239, I369, S372, D374, C375, T377, C378, F379, V380, and S381.

In some embodiments, an isolated antibody or antigen binding molecule that binds to PCSK9 is provided. In some embodiments, the antibody or antigen binding molecule reduces the likelihood that EGFa will bind to PCSK9 within 8 angstroms of at least one of the following residues on PCSK9: S153, I154, P155, R194, D238, A239, I369, S372, D374, C375, T377, C378, F379, V380, S381, W156, N157, L158, E159, H193, E195, H229, R237, G240, K243, D367, I368, G370, A371, S373, S376, or Q382.

In some embodiments, an antibody, antigen binding protein, or antigen binding molecule that binds to a surface of PCSK9 that overlaps with a surface that EGFa binds, Ab 21B12 binds, and/or 31H4 binds is provided. In some embodiments, an antibody, antigen binding protein, or antigen binding molecule that binds to PCSK9 in a manner that is similar to that depicted in the figures is provided.

In some embodiments, the above embodiments are neutralizing antibodies or antigen binding proteins. In some embodiments, the antigen binding protein is not LDLR or a fragment thereof (such as EGFa).

In some aspects, the invention comprises an isolated neutralizing antibody, wherein when the antibody is bound to PCSK9, the antibody is positioned 8 angstroms or less from at least one of the following residues of PCSK9: T468, R469, M470, A471, T472, R496, R499, E501, A502, Q503, R510, H512, F515, P540, P541, A542, E543, H565, W566, E567, V568, E569, R592, E593, 5465, G466, P467, A473, I474, R476, G497, E498, M500, G504, K506, L507, V508, A511, N513, A514, G516, V536, T538, A539, A544, T548, D570, L571, H591, A594, 5595, and H597 of SEQ ID NO: 3. In some embodiments, the antibody is positioned 5 angstroms or less from at least one of the following residues of PCSK9: T468, R469, M470, A471, T472, R496, R499, E501, A502, Q503, R510, H512, F515, P540, P541, A542, E543, H565, W566, E567, V568, E569, R592, and E593 of SEQ ID NO: 3.

In some aspects, the invention comprises an isolated antigen binding protein. The antigen binding protein comprises: A) a CDRH1 of the CDRH1 sequence in SEQ ID NO: 89, a CDRH2 of the CDRH2 sequence in SEQ ID NO: 89, and a CDRH3 of the CDRH3 sequence in SEQ ID NO: 89, and B) a CDRL1 of the CDRL1 sequence in SEQ ID NO:32, a CDRL2 of the CDRL2 sequence in SEQ ID NO:32, and a CDRL3 of the CDRL3 sequence in SEQ ID NO:32.

In some aspects, the invention comprises an isolated antigen binding protein that binds to a PCSK9 protein of SEQ ID NO: 1 where the binding between said isolated antigen binding protein and a variant PCSK9 protein is less than 50% of the binding between the isolated antigen binding protein and the PCSK9 protein of SEQ ID NO: 1 and/or SEQ ID NO: 303. In some embodiments, the variant PCSK9 protein comprises at least one mutation of a residue at a position selected from the group consisting or comprising 207, 208, 185, 181, 439, 513, 538, 539, 132, 351, 390, 413, 582, 162, 164, 167, 123, 129, 311, 313, 337, 519, 521, and 554, as shown in SEQ ID NO: 1. In some embodiments, the at least one mutation selected from the group comprising or consisting of R207E, D208R, E181R, R185E, R439E, E513R, V538R, E539R, T132R, S351R, A390R, A413R, and E582R. In some embodiments, the at least one mutation is selected from the group consisting of D162R, R164E, E167R, S123R, E129R, A311R, D313R, D337R, R519E, H521R, and Q554R.

In some aspects, the invention comprises an antigen binding protein that binds to a PCSK-9 protein of SEQ ID NO: 303 in a first manner and binds to a variant of PCSK9 in a second manner. The PCSK9 variant has at least one point mutation at a position selected from the group comprising or consisting of 207, 208, 185, 181, 439, 513, 538, 539, 132, 351, 390, 413, 582, 162, 164, 167, 123, 129, 311, 313, 337, 519, 521, and 554 of SEQ ID NO: 303 and/or SEQ ID NO: 1. In some embodiments, the first Manner comprises a first EC50, a first Bmax, or a first EC50 and a first Bmax. In some embodiments, the second manner comprises a second EC50, a second Bmax, or a second EC50 and a second Bmax. The value for the first manner is different from the value for the second manner. In some embodiments, the first manner comprises a first EC50, wherein the second manner involves a second EC50, and wherein the point mutation is selected from the group consisting or comprising: R207E, D208R, E181R, R185E, R439E, E513R, V538R, E539R, T132R, S351R, A390R, A413R, and E582R. In some embodiments, the first EC50 is at least 20% different from the second EC50. In some embodiments, the first EC50 is at least 50% different from the second EC50. In some embodiments, the second EC50 is a larger numerical value than the first EC50. In some embodiments, the first EC50 is determined by a multiplex bead binding assay. In some embodiments, the second EC50 is greater than 1 um. In some embodiments, the antigen binding protein is a neutralizing antigen binding protein. In some embodiments, the neutralizing antigen binding protein is a competitive neutralizing antigen binding protein. In some embodiments, the neutralizing antigen binding protein is a non-competitive neutralizing antigen binding protein. In some embodiments, the first manner comprises a first Bmax and the second manner comprises a second Bmax that is different from the first Bmax. The PCSK9 variant has at least one point mutation selected from the group consisting or comprising: D162R, R164E, E167R, S123R, E129R, A311R, D313R, D337R, R519E, H521R, and Q554R. In some embodiments, the second Bmax is about 10% of the first Bmax. In some embodiments, the first Bmax is at least 20% different from the second Bmax. In some embodiments, the first Bmax is at least 50% different from the second Bmax.

In some aspects, the invention comprises an isolated antigen binding protein that binds to a PCSK9 protein of SEQ ID NO: 3, wherein the epitope of the antigen binding protein includes at least one of the following amino acids of SEQ ID NO: 1: 207, 208, 181, 185, 439, 513, 538, 539, 132, 351, 390, 413, 582, 162, 164, 167, 123, 129, 311, 313, 337, 519, 521, and 554.

In some aspects, the invention comprises an isolated neutralizing antigen binding protein that binds to a PCSK9 protein comprising the amino acid sequence of SEQ ID NO: 1, wherein the neutralizing antigen binding protein decreases the LDLR lowering effect of PCSK9 on LDLR. In some embodiments, the antigen binding protein is a LDLR non-competitive neutralizing antigen binding protein. In some embodiments, the antigen binding protein is a LDLR competitive neutralizing antigen binding protein.

In some aspects, the invention comprises an isolated antigen binding protein, wherein said antigen binding protein comprises: A) a CDRH1 of the CDRH1 sequence in SEQ ID NO: 49, a CDRH2 of the CDRH2 sequence in SEQ ID NO: 49, and a CDRH3 of the CDRH3 sequence in SEQ ID NO: 49, and B) a CDRL1 of the CDRL1 sequence in SEQ ID NO:23, a CDRL2 of the CDRL2 sequence in SEQ ID NO:23, and a CDRL3 of the CDRL3 sequence in SEQ ID NO:23.

In some aspects, the invention comprises a composition comprising a crystallized PCSK9 protein and an antigen binding protein that binds to PCSK9. The composition comprises the crystallized PCSK9 protein is such that the three dimensional structure of the PCSK9 protein can be determined to a resolution of about 2.2 angstroms or better. In some embodiments, the antigen binding protein is an antibody or a fragment thereof.

In some aspects, the invention comprises a crystallized PCSK9 protein and at least an EGFa section of a LDLR protein, wherein the EGFa section of the LDLR protein is bound by a PCSK9 protein, wherein said crystallized PCSK9 protein is such that the three dimensional structure of the PCSK9 protein can be determined to a resolution of about 2.2 angstroms or better. In some embodiments, the molecular model is on a computer readable medium.

In some aspects, the invention comprises the use of an antigen binding protein as described herein, in the preparation of a medicament for the lowering of serum cholesterol.

In some aspects, the invention comprises the use of an antigen binding protein as described herein, in the preparation of a medicament for treating or preventing a condition associated with elevated serum cholesterol levels in a subject.

In some aspects, the invention comprises an isolated antigen binding protein that binds PCSK9, the antigen binding protein comprising: A) a heavy chain complementary determining region (CDRH) selected from at least one of the group consisting of: (i) a CDRH1 selected from the CDRH1 within the sequences selected from the group consisting of SEQ ID NOs: 67, 79, 89, and 49, (ii) a CDRH1 that differs in amino acid sequence from the CDRH1 of (i) by an amino acid addition, deletion or substitution of not more than two amino acids; and (iii) a CDRH1 amino acid sequence selected from the group consisting of $X_1X_2X_3X_4X_5X_6X_7X_8X_9X_{10}$ (SEQ ID NO: 406), wherein $X_1$ is selected from the group consisting of G, $X_2$ is selected from the group consisting of Y, F, and G, $X_3$ is selected from the group consisting of T and S, $X_4$ is selected from the group consisting of L and F, $X_5$ is selected from the group consisting of T, S, and N, $X_6$ is selected from the group consisting of S and A, $X_7$ is selected from the group consisting of Y and F, $X_8$ is selected from the group consisting of G, S, and Y, $X_9$ is selected from the group consisting of I, M, and W, $X_{10}$ is selected from the group consisting of S, N and H, B) a light chain complementary determining region (CDRL) selected from at least one of the group consisting of: (i) a CDRL1 selected from the CDRL1 within the sequences selected from the group consisting of SEQ ID NOs: 12, 32, 35, and 23, (ii) a CDRL1 that differs in amino acid sequence from the CDRL3 of (i) by an amino acid addition, deletion or substitution of not more than two amino acids; and (iii) a CDRL1 amino acid sequence selected from the group consisting of $X_1X_2X_3X_4X_5X_6X_7X_8X_9X_{10}X_{11}X_{12}X_{13}X_{14}$ (SEQ ID NO: 407), wherein $X_1$ is selected from the group consisting of T and no amino acid, $X_2$ is selected from the group consisting of G and S, $X_3$ is selected from the group consisting of S, T, and G, $X_4$ is selected from the group consisting of S, $X_5$ is selected from the group consisting of S, $X_6$ is selected from the group consisting of N, D, and S, $X_7$ is selected from the group consisting of I, V, and N, $X_8$ is selected from the group consisting of G and I, $X_9$ is selected from the group consisting of A and G, $X_{10}$ is selected from the group consisting of G, Y, S, and N, $X_{11}$ is selected from the group consisting of Y and N, $X_{12}$ is selected from the group consisting of D, S, T, and F, $X_{13}$ is selected from the group consisting of V, $X_{14}$ is selected from the group consisting of S, N, and H. One of skill in the art will appreciate that a single ABP or antibody can meet one or more of the above options and still fall within the described invention for this embodiment.

In some aspects, the invention comprises an isolated antigen binding protein that binds PCSK9, the antigen binding protein comprising: A) a heavy chain complementary determining region (CDRH) selected from at least one of the group consisting of the following: (i) a CDRH2 selected from the CDRH2 within the sequences selected from the group consisting of SEQ ID NOs: 67, 79, 89, and 49, (ii) a CDRH2 that differs in amino acid sequence from the CDRH2 of (i) by an amino acid addition, deletion or substitution of not more than two amino acids; and (iii) a CDRH2 amino acid sequence selected from the group consisting of $X_1X_2X_3X_4X_5X_6X_7X_8X_9X_{10}X_{11}X_{12}X_{13}X_{14}X_{15}X_{16}X_{17}$ (SEQ ID NO: 408), wherein $X_1$ is selected from the group consisting of W, S, L and no amino acid, $X_2$ is selected from the group consisting of V, I, and E, $X_3$ is selected from the group consisting of S, W, and I, $X_4$ is selected from the group consisting of F, S, and N, $X_5$ is selected from the group consisting of Y, S, D, and H, $X_6$ is selected from the group consisting of N, S, and G, $X_7$ is selected from the group consisting of S and G, $X_8$ is selected from the group consisting of N, Y, D, and R, $X_9$ is selected from the group consisting of T, I, and E, $X_{10}$ is selected from the group consisting of N, S, Y, and D, $X_{11}$ is selected from the group consisting of Y, $X_{12}$ is selected from the group consisting of A and N, $X_{13}$ is selected from the group consisting of Q, D, and P, $X_{14}$ is selected from the group consisting of K and S, $X_{15}$ is selected from the group consisting of L, and V, $X_{16}$ is selected from the group consisting of Q and K, $X_{17}$ is selected from the group consisting of G and S, B) a light chain complementary determining region (CDRL) selected from at least one of the group consisting of the following: (i) a CDRL2 selected from the CDRL3 within the sequences selected from the group consisting of SEQ ID NOs: 12, 32, 35, and 23, (ii) a CDRL2 that differs in amino acid sequence from the CDRL3 of (i) by an amino acid addition, deletion or substitution of not more than two amino acids; and (iii) a CDRL2 amino acid sequence selected from the group consisting of $X_1X_2X_3X_4X_5X_6X_7$ (SEQ ID NO: 409), wherein $X_1$ is selected from the group consisting of G, E, S, and D, $X_2$ is selected from the group consisting of N, V, and Y, $X_3$ is selected from the group consisting of S and N, $X_4$ is selected from the group consisting of N, Q, and K, $X_5$ is selected from the group consisting of R, $X_6$ is selected from the group consisting of P, $X_7$ is selected from the group consisting of S.

In some aspects, the invention comprises An isolated antigen binding protein that binds PCSK9, the antigen binding protein comprising: A) a heavy chain complementary determining region (CDRH) selected from at least one of the group consisting of the following: (i) a CDRH3 selected from the CDRH3 within the sequences selected from the group consisting of SEQ ID NOs: 67, 79, 89, and 49, (ii) a CDRH3 that differs in amino acid sequence from the CDRH3 of (i) by an amino acid addition, deletion or substitution of not more than two amino acids; and (iii) a CDRH3 amino acid sequence selected from the group consisting of $X_1X_2X_3X_4X_5X_6X_7X_8X_9X_{10}X_{11}X_{12}X_{13}X_{14}$ (SEQ ID NO: 410), wherein $X_1$ is selected from the group consisting of D, and no amino acid, $X_2$ is selected from the group consisting of Y, A, and no amino acid, $X_3$ is selected from the group consisting of D, I, and no amino acid, $X_4$ is selected from the group consisting of F, A, and no amino acid, $X_5$ is selected from the group consisting of W, A, and no amino acid, $X_6$ is selected from the group consisting of S, L, and no amino acid, $X_7$ is selected from the group consisting of A, Y, G, and no amino acid, $X_8$ is selected from the group consisting of Y, Q, and no amino acid, $X_9$ is selected from the group consisting of G, Y, and L, $X_{10}$ is selected from the group consisting of Y, D, and V, $X_{11}$ is selected from the group consisting of G, A, and P, $X_{12}$ is selected from the group consisting of M and F, $X_{13}$ is selected from the group consisting of D, $X_{14}$ is selected from the group consisting of V and Y, and B) a light chain complementary determining region (CDRL) selected from at least one of the group consisting of the following: (i) a CDRL3 selected from the CDRL3 within the sequences selected from the group consisting of SEQ ID NOs: 12, 32, 35, and 23, (ii) a CDRL3 that differs in amino acid sequence from the CDRL3 of (i) by an amino acid addition, deletion or substitution of not more than two amino acids; and (iii) a CDRL3 amino acid sequence selected from the group consisting of $X_1X_2X_3X_4X_5X_6X_7X_8X_9X_{10}X_{11}$ (SEQ ID NO: 411), wherein $X_1$ is selected from the group consisting of Q, A, G, and no amino acid, $X_2$ is selected from the group consisting of S, V, T, and no amino acid, $X_3$ is selected from the group consisting of Y, N, and W, $X_4$ is selected from the group consisting of S and D, $X_5$ is selected from the group consisting of S, Y, and D, $X_6$ is selected from the group consisting of S and T, $X_7$ is selected from the group consisting of L and S, $X_8$ is selected from the group consisting of S, T, and N, $X_9$ is selected from the group consisting of G, S, and A, $X_{10}$ is selected from the group consisting of S, M, W, and Y, and $X_{11}$ is selected from the group consisting of V. In some embodiments, any of the above amino acids can be replaced by a conservative amino acid substitution.

In some aspects, the invention comprises an isolated antigen binding protein that binds PCSK9, the antigen binding protein comprises A) a heavy chain complementary determining region (CDRH) selected from at least one of the group consisting of (i) a CDRH1 selected from the CDRH1 within the sequences selected from the group consisting of SEQ ID NOs: 47, 48, 49, 50, 51, 52, 53, 54, 55, 56, 57, and 58, (ii) a CDRH1 that differs in amino acid sequence from the CDRH1 of (i) by an amino acid addition, deletion or substitution of not more than two amino acids; and (iii) a CDRH1 amino acid sequence selected from the group consisting of $X_1X_2X_3X_4X_5X_6X_7X_8X_9X_{10}$ (SEQ ID NO: 412), wherein $X_1$ is selected from the group consisting of G, P, and A, $X_2$ is selected from the group consisting of Y, W, F, T, and S, $X_3$ is selected from the group consisting of T, P, S and A, C, V, L, and I, $X_4$ is selected from the group consisting of L, F, I, V, M, A, and Y, $X_5$ is selected from the group consisting of T, P, S, and A, $X_6$ is selected from the group consisting of S, T, A, and C, $X_7$ is selected from the group consisting of Y, W, F, T, and S, $X_8$ is selected from the group consisting of G, P, and A, $X_9$ is selected from the group consisting of I, L, V, M, A, and F, $X_{10}$ is selected from the group consisting of S, T, A, and C, B) a light chain complementary determining region (CDRL) selected from at least one of the group consisting of: (i) a CDRL1 selected from the CDRL1 within the sequences selected from the group consisting of SEQ ID NOs: 14, 15, 16, 17, 18, 19, 20, 21, 22, 23, and 24, (ii) a CDRL1 that differs in amino acid sequence from the CDRL3 of (i) by an amino acid addition, deletion or substitution of not more than two amino acids; and (iii) a CDRL1 amino acid sequence selected from the group consisting of $X_1X_2X_3X_4X_5X_6X_7X_8X_9X_{10}X_{11}X_{12}X_{13}X_{14}$ (SEQ ID NO: 413), wherein $X_1$ is selected from the group consisting of T and S, $X_2$ is selected from the group consisting of G, P, and A, $X_3$ is selected from the group consisting of T, and S, $X_4$ is selected from the group consisting of S N, T, A, C, and Q, $X_5$ is selected from the group consisting of S, T, A, and C, $X_6$ is selected from the group consisting of D, and E, $X_7$ is selected from the group consisting of V, I, M, L, F, and A, $X_8$ is selected from the group consisting of G, P, and A, $X_9$ is selected from the group consisting of G, A, R, P, V, L, I, K, Q, and N, $X_{10}$ is selected from the group consisting of Y, W, F, T, and S, $X_{11}$ is selected from the group consisting of N, and Q, $X_{12}$ is selected from the group consisting of Y, S, W, F, T, A, and C, $X_{13}$ is selected from the group consisting of V, I, M, L, F, and A, $X_{14}$ is selected from the group consisting of S, T, A, and C.

In some aspects, the invention comprises an isolated antigen binding protein that binds PCSK9, the antigen binding protein comprising: A) a heavy chain complementary determining region (CDRH) selected from at least one of the group consisting of: (i) a CDRH2 selected from the CDRH2 within the sequences selected from the group consisting of SEQ ID NOs: 47, 48, 49, 50, 51, 52, 53, 54, 55, 56, 57, and 58, (ii) a CDRH2 that differs in amino acid sequence from the CDRH2 of (i) by an amino acid addition, deletion or substitution of not more than two amino acids; and (iii) a CDRH2 amino acid sequence selected from the group consisting of $X_1X_2X_3X_4X_5X_6X_7X_8X_9X_{10}X_{11}X_{12}X_{13}X_{14}$ $X_{15}X_{16}X_{17}$, (SEQ ID NO: 414), wherein $X_1$ is selected from the group consisting of W, Y, and F, $X_2$ is selected from the group consisting of V, I, M, L, F, and A, $X_3$ is selected from the group consisting of S, T, A, and C, $X_4$ is selected from the group consisting of A, F, V, L, I, Y, and M, $X_5$ is selected from the group consisting of Y, W, F, T, and S, $X_6$ is selected from the group consisting of N and Q, $X_7$ is selected from the group consisting of G, P, and A, $X_8$ is selected from the group consisting of N, and Q, $X_9$ is selected from the group consisting of T, and S, $X_{10}$ is selected from the group consisting of N, and Q, $X_{11}$ is selected from the group consisting of Y, W, F, T, and S, $X_{12}$ is selected from the group consisting of A, V, L, and I, $X_{13}$ is selected from the group consisting of Q, E, N, and D, $X_{14}$ is selected from the group consisting of K, R, Q, and N, $X_{15}$ is selected from the group consisting of L, F, V, I, M, A, and Y, $X_{16}$ is selected from the group consisting of Q, and N, $X_{17}$ is selected from the group consisting of G, P, and A, B) a light chain complementary determining region (CDRL) selected from at least one of the group consisting of: (i) a CDRL2 selected from the CDRL3 within the sequences selected from the group consisting of SEQ ID NOs: 14, 15, 16, 17, 18, 19, 20, 21, 22, 23, and 24, (ii) a CDRL2 that differs in amino acid sequence from the CDRL3 of (i) by an amino acid addition, deletion or substitution of not more than two amino acids; and (iii) a CDRL2 amino acid sequence selected from the group consisting of $X_1X_2X_3X_4X_5X_6X_7$ (SEQ ID NO: 415), wherein $X_1$ is selected from the group consisting of E, and D, $X_2$ is selected from the group consisting of V, I, M, L, F, and A, $X_3$ is selected from the group consisting of S, T, A, and C, $X_4$ is selected from the group consisting of N, and Q, $X_5$ is selected from the group consisting of R, K, Q, and N, $X_6$ is selected from the group consisting of P, and A, $X_7$ is selected from the group consisting of S, T, A, and C.

In some aspects, the invention comprises an isolated antigen binding protein that binds PCSK9, the antigen binding protein comprising: A) a heavy chain complementary determining region (CDRH) selected from at least one of the group consisting of (i) a CDRH3 selected from the CDRH3 within the sequences selected from the group consisting of SEQ ID NOs: 47, 48, 49, 50, 51, 52, 53, 54, 55, 56, 57, and 58, (ii) a CDRH3 that differs in amino acid sequence from the CDRH3 of (i) by an amino acid addition, deletion or substitution of not more than two amino acids; and (iii) a CDRH3 amino acid sequence selected from the group consisting of $X_1X_2X_3X_4X_5X_6$ (SEQ ID NO: 416), wherein $X_1$ is selected from the group consisting of G, P, A and no amino acid, $X_2$ is selected from the group consisting of Y, W, F, T, and S, $X_3$ is selected from the group consisting of G, V, P, A, I, M, L, and F, $X_4$ is selected from the group consisting of M, L, F, and I, $X_5$ is selected from the group consisting of D, and E, $X_6$ is selected from the group consisting of V, I, M, L, F, and A, B) a light chain complementary determining region (CDRL) selected from at least one of the group consisting of (i) a CDRL3 selected from the CDRL3 within the sequences selected from the group consisting of SEQ ID NOs: 14, 15, 16, 17, 18, 19, 20, 21, 22, 23, and 24, (ii) a CDRL3 that differs in amino acid sequence from the CDRL3 of (i) by an amino acid addition, deletion or substitution of not more than two amino acids; and (iii) a CDRL3 amino acid sequence selected from the group consisting of $X_1X_2X_3X_4X_5X_6X_7X_8X_9$ (SEQ ID NO: 417), wherein $X_1$ is selected from the group consisting of S, N, T, A, C, and Q, $X_2$ is selected from the group consisting of S, T, A, and C, $X_3$ is selected from the group consisting of Y, W, F, T, and S, $X_4$ is selected from the group consisting of T, and S, $X_5$ is selected from the group consisting of S, T, A, and C, $X_6$ is selected from the group consisting of S, T, A, and C, $X_7$ is selected from the group consisting of N, S, Q, T, A, and C, $X_8$ is selected from the group consisting of M, V, L, F, I, and A, $X_9$ is selected from the group consisting of V, I, M, L, F, and A.

BRIEF DESCRIPTION OF THE FIGURES

FIG. 1A depicts an amino acid sequence of the mature form of the PCSK9 with the pro-domain underlined.

FIGS. $1B_1$-$1B_4$ depict amino acid and nucleic acid sequences of PCSK9 with the pro-domain underlined and the signal sequence in bold.

FIGS. 2A-2D are sequence comparison tables of various light chains of various antigen binding proteins. FIG. 2C continues the sequence started in FIG. 2A. FIG. 2D continues the sequence started on FIG. 2B.

FIGS. 3A-3D are sequence comparison tables of various heavy chains of various antigen binding proteins. FIG. 3C continues the sequence started in FIG. 3A. FIG. 3D continues the sequence started on FIG. 3B.

FIGS. 3E-3JJ depict the amino acid and nucleic acid sequences for the variable domains of some embodiments of the antigen binding proteins.

FIG. 3KK depicts the amino acid sequences for various constant domains.

FIGS. 3LL-3BBB depict the amino acid and nucleic acid sequences for the variable domains of some embodiments of the antigen binding proteins.

FIGS. 3CCC-3JJJ are sequence comparison tables of various heavy and light chains of some embodiments of the antigen binding proteins.

Figure 4A:
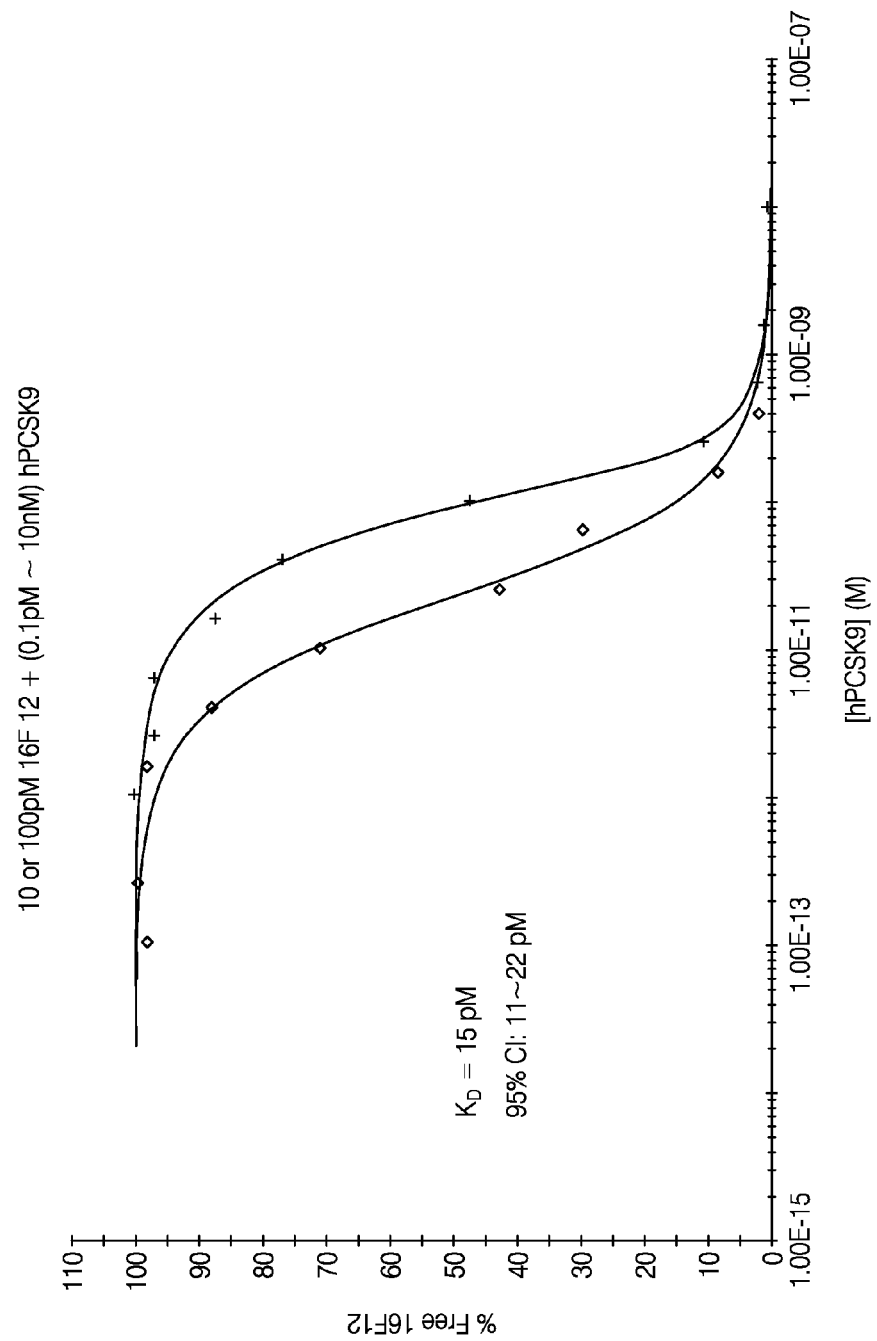

FIG. 4A is a binding curve of an antigen binding protein to human PCSK9.

Figure 4B:
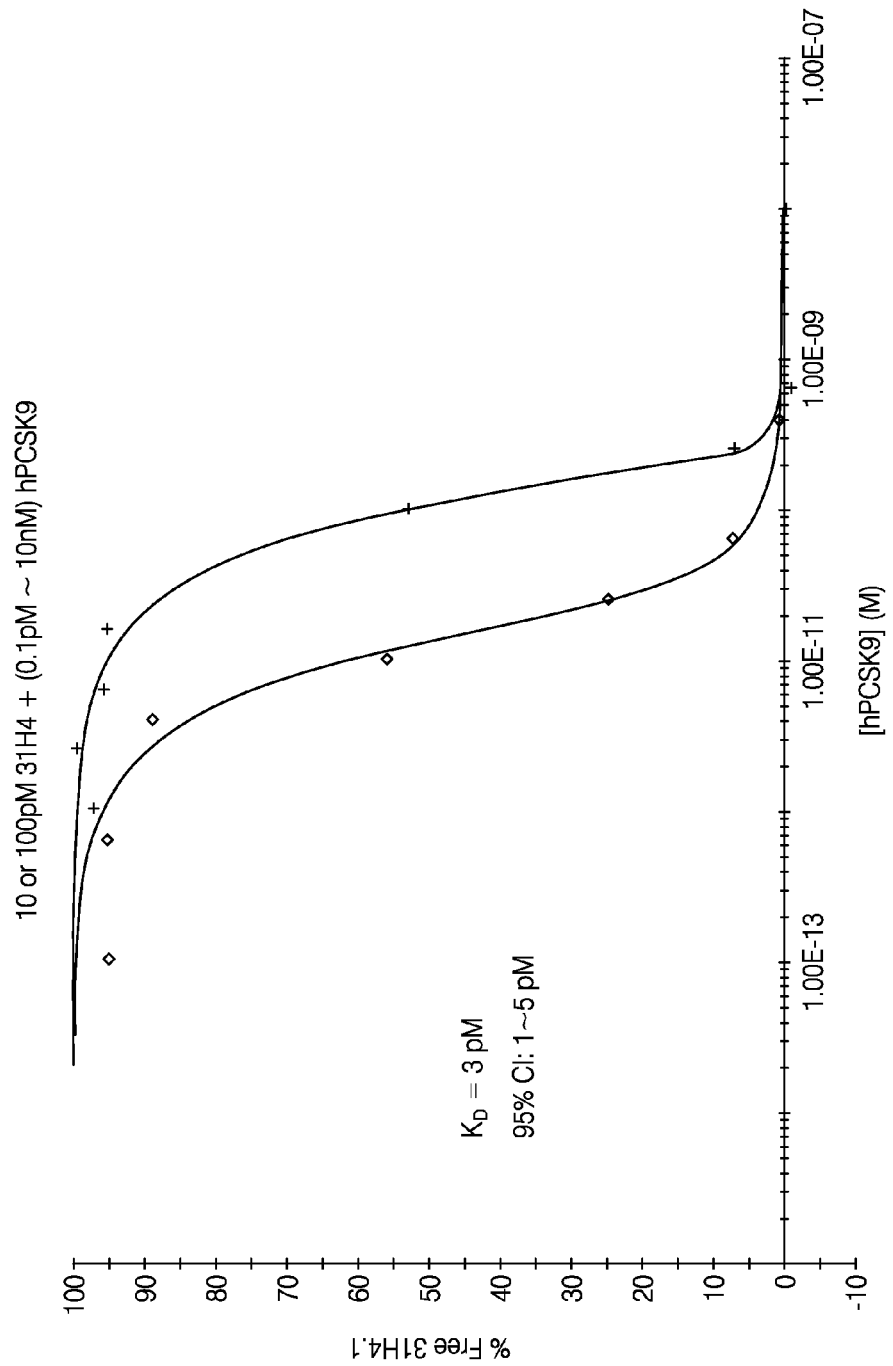

FIG. 4B is a binding curve of an antigen binding protein to human PCSK9.

Figure 4C:
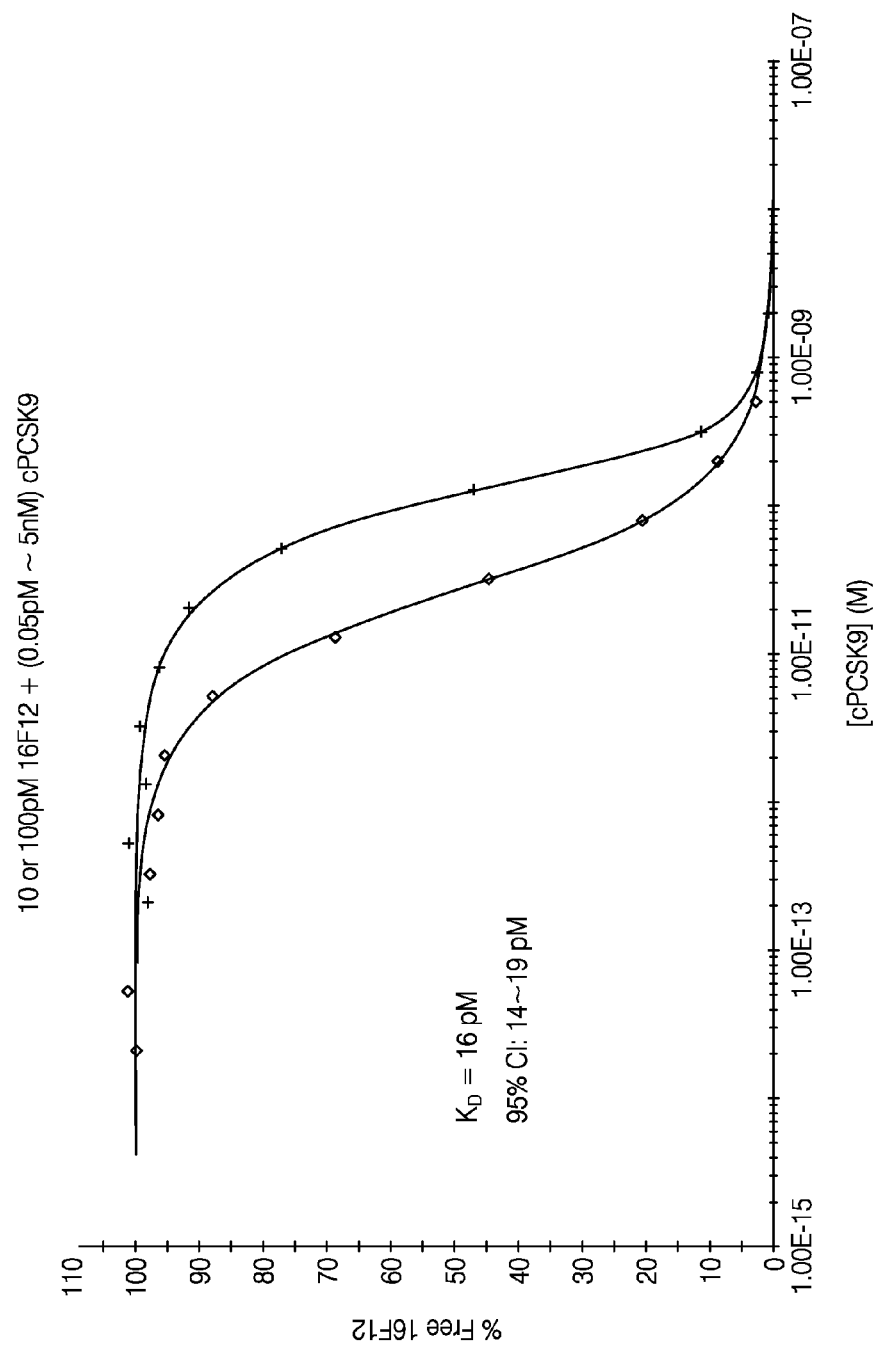

FIG. 4C is a binding curve of an antigen binding protein to cynomolgus PCSK9.

Figure 4D:
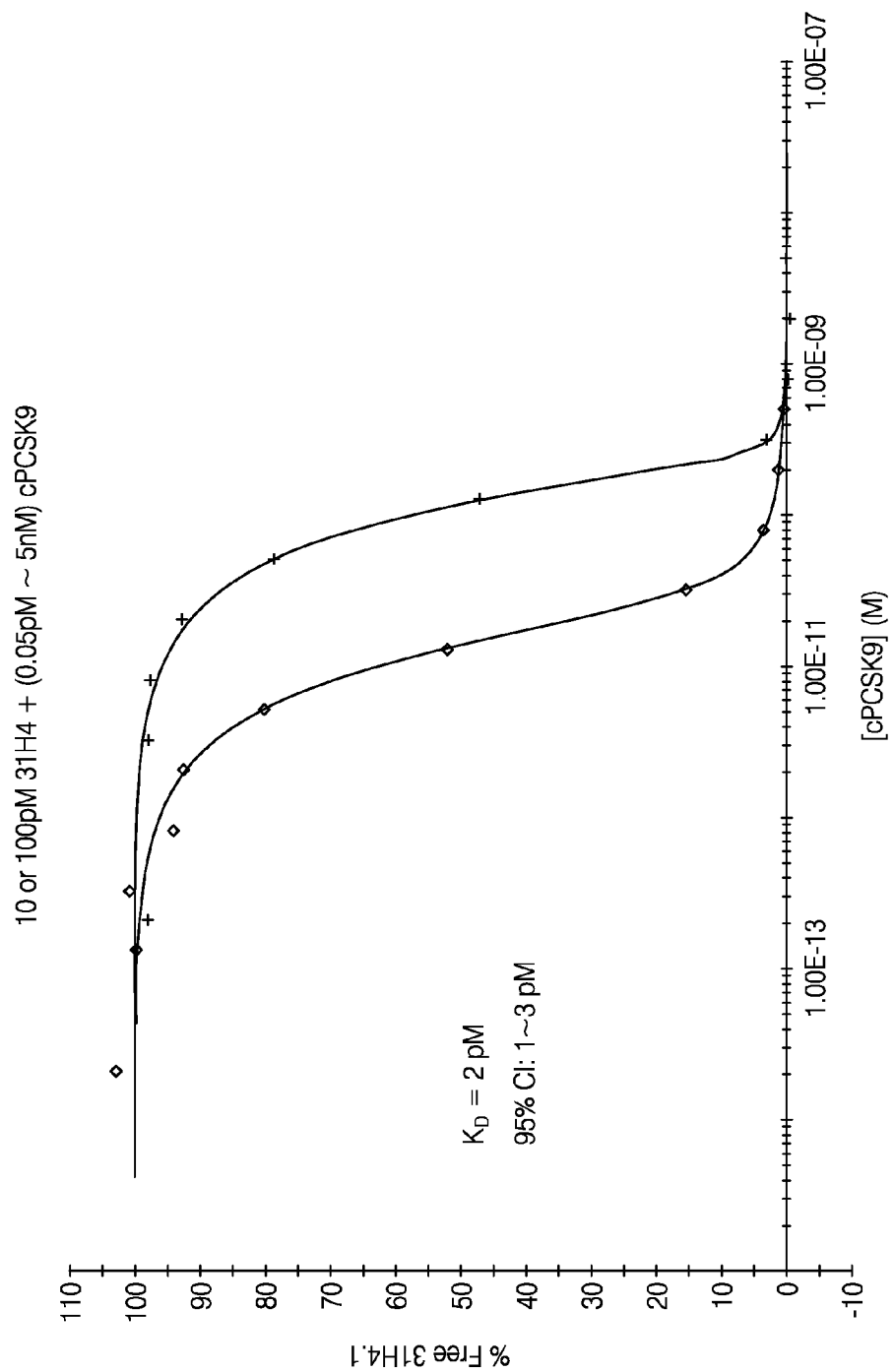

FIG. 4D is a binding curve of an antigen binding protein to cynomolgus PCSK9.

Figure 4E:
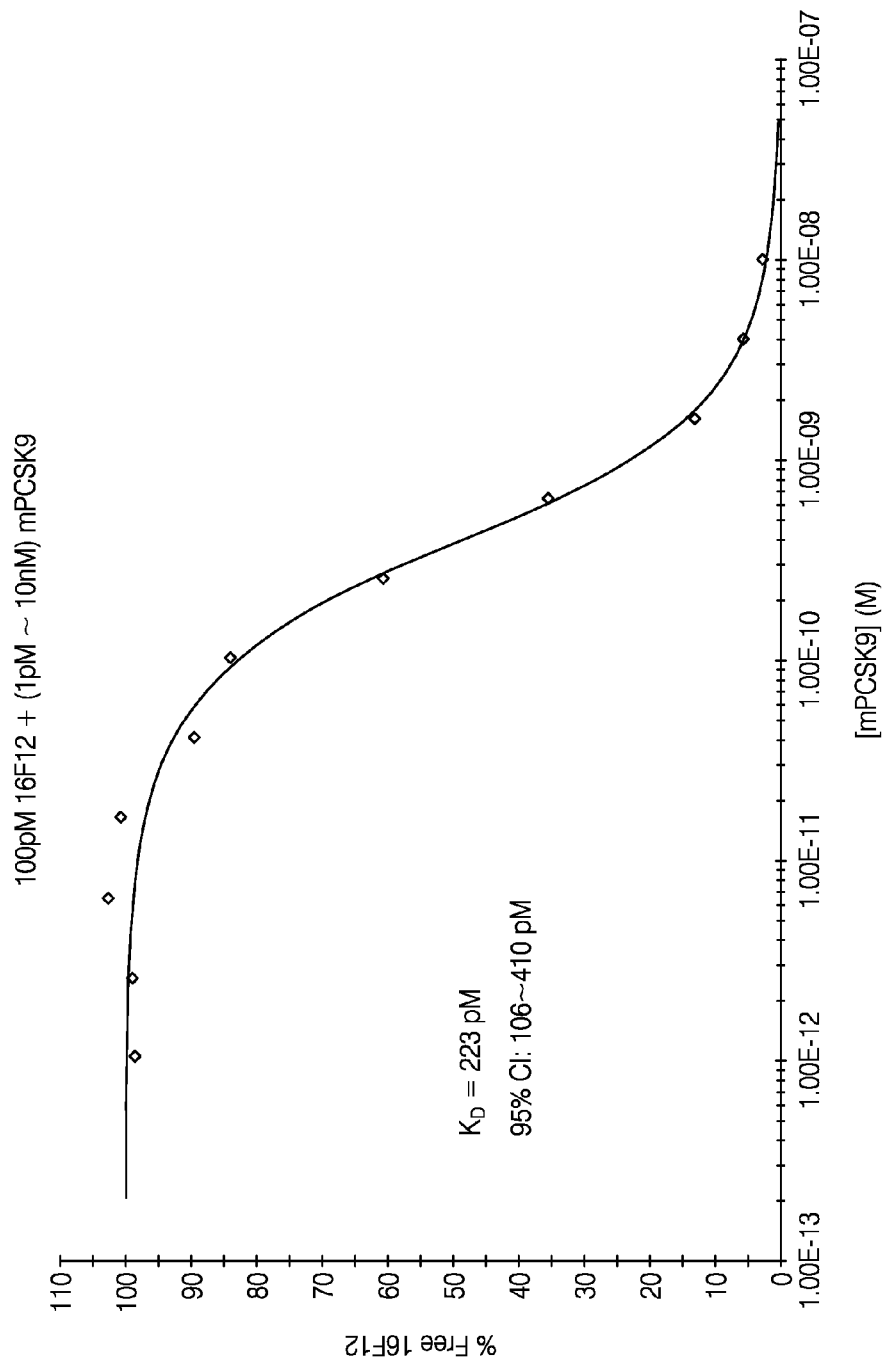

FIG. 4E is a binding curve of an antigen binding protein to mouse PCSK9.

Figure 4F:
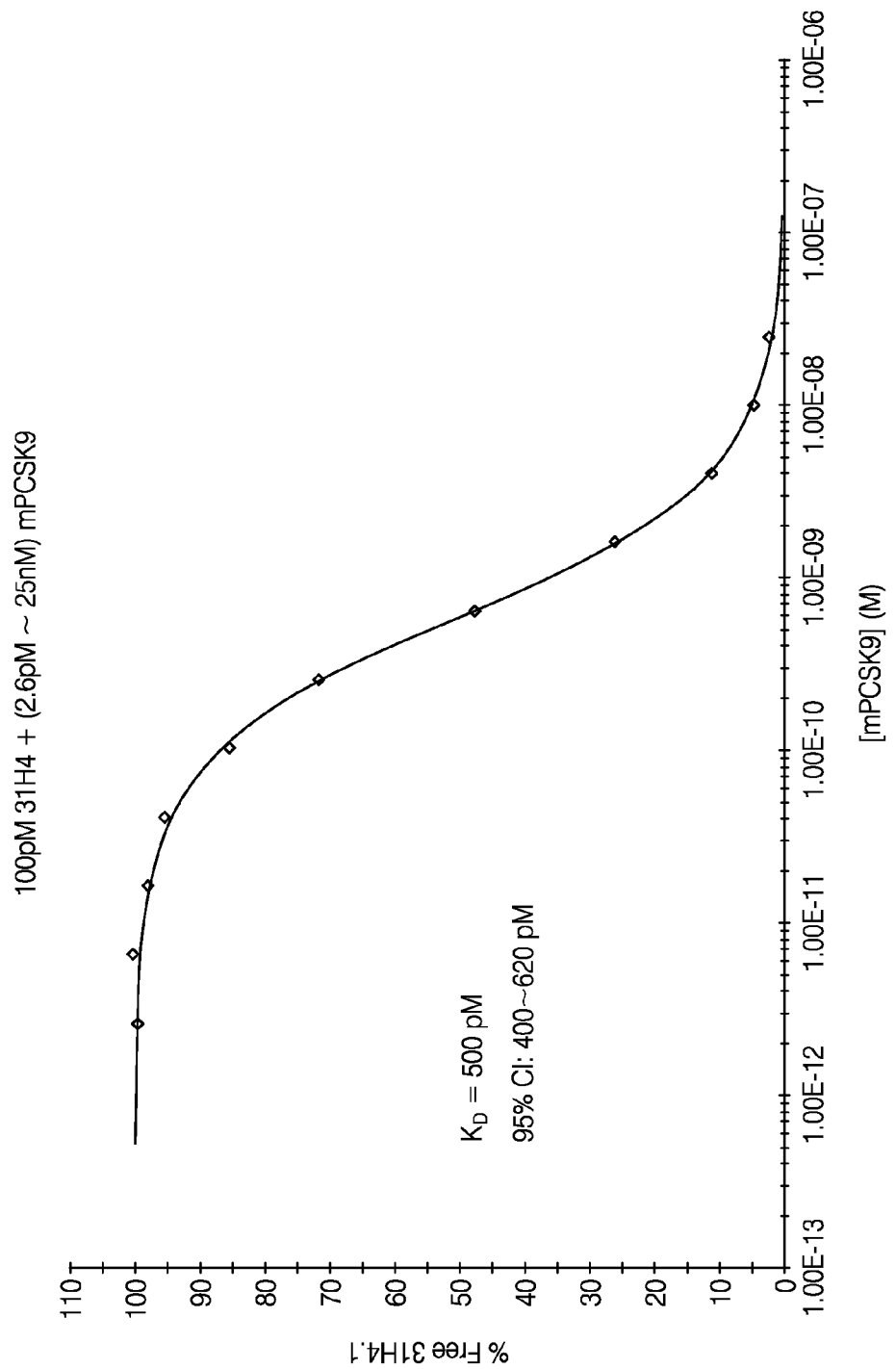

FIG. 4F is a binding curve of an antigen binding protein to mouse PCSK9.

Figure 5A:
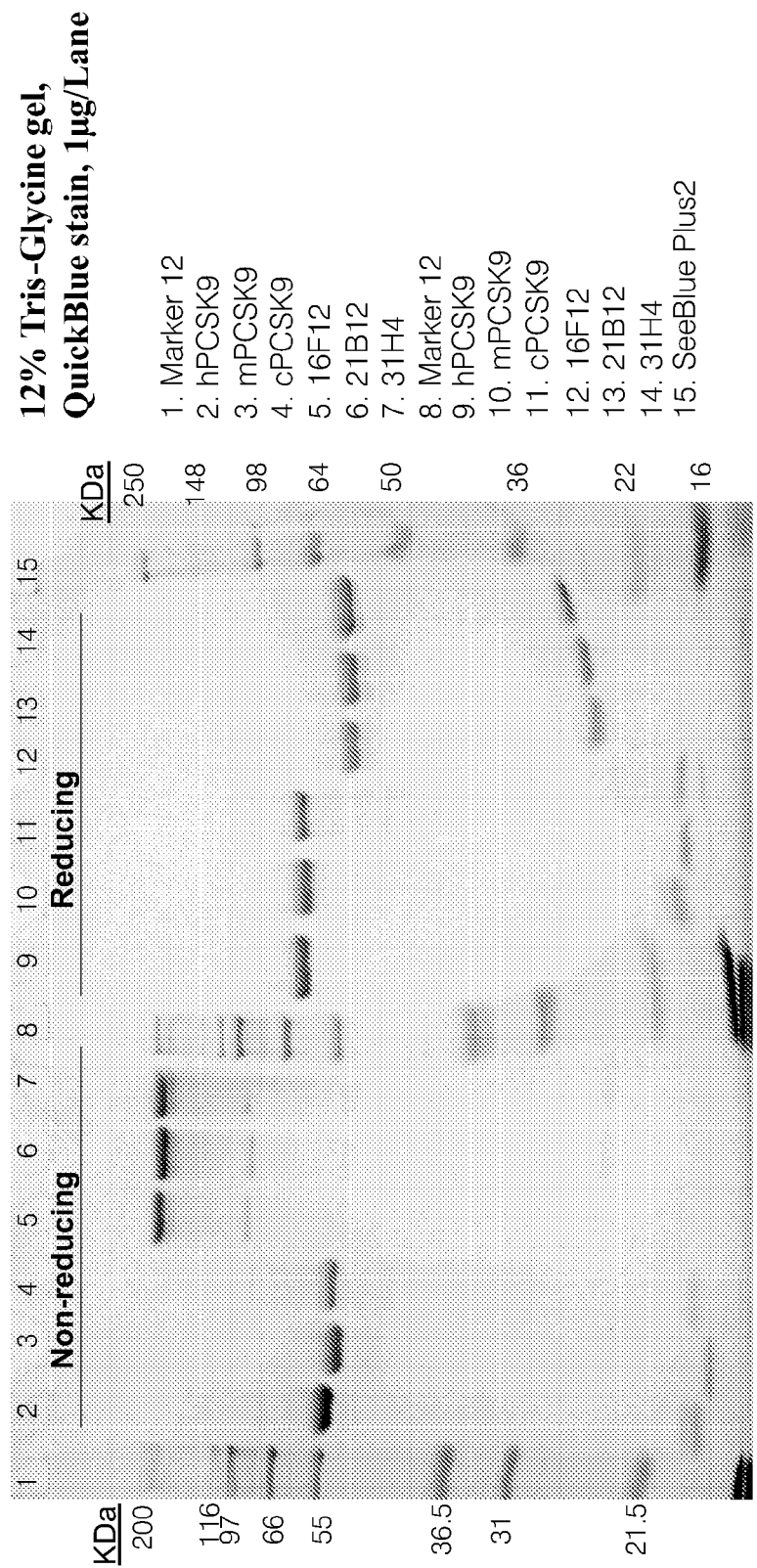

FIG. 5A depicts the results of an SDS PAGE experiment involving PCSK9 and various antigen binding proteins demonstrating the relative purity and concentration of the proteins.

Figure 5B:
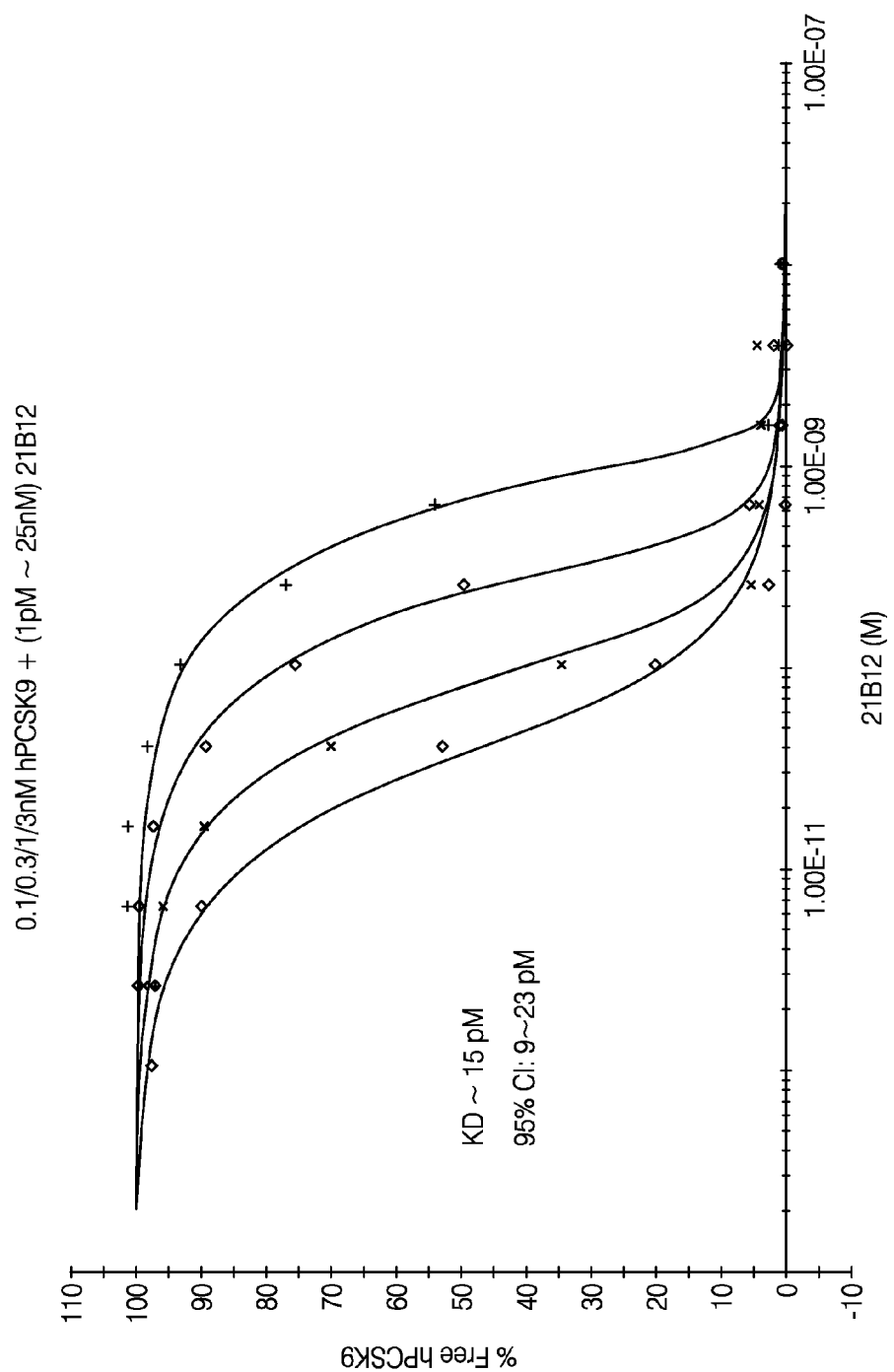
Figure 5C:
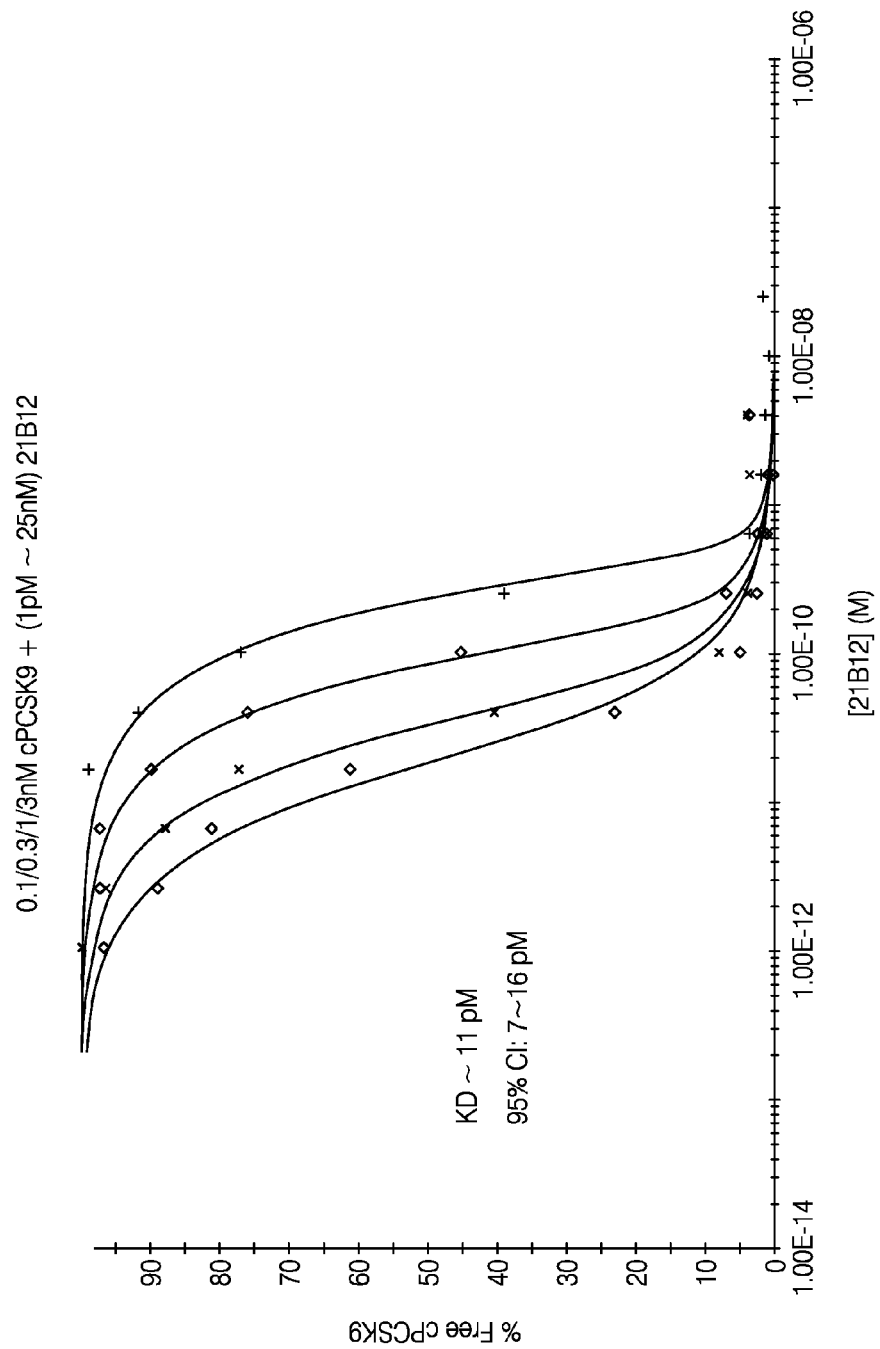

FIGS. 5B and 5C depict graphs from biacore solution equilibrium assays for 21B12.

Figure 5D:
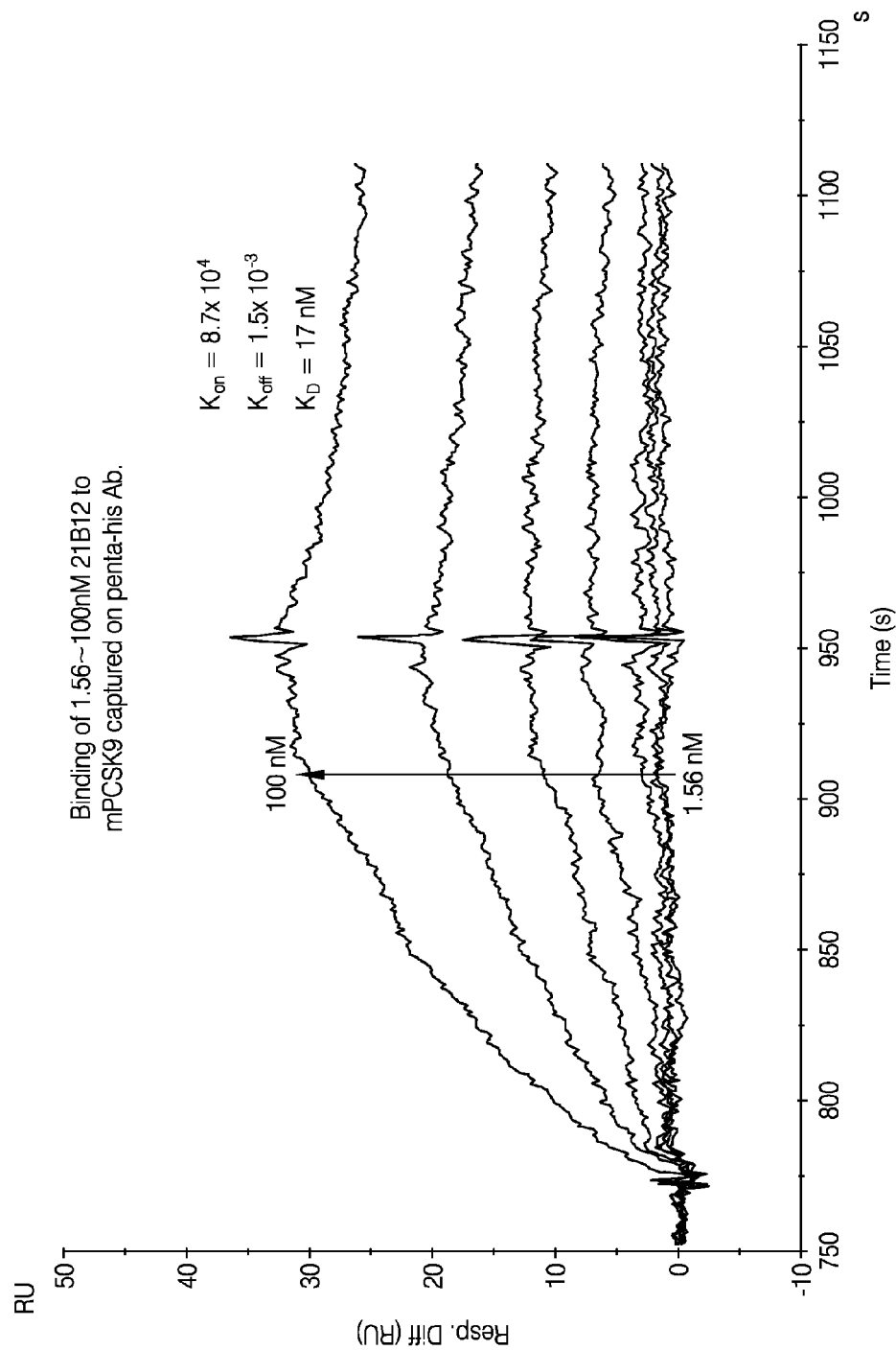

FIG. 5D depicts the graph of the kinetics from a biacore capture assay.

Figure 5E:
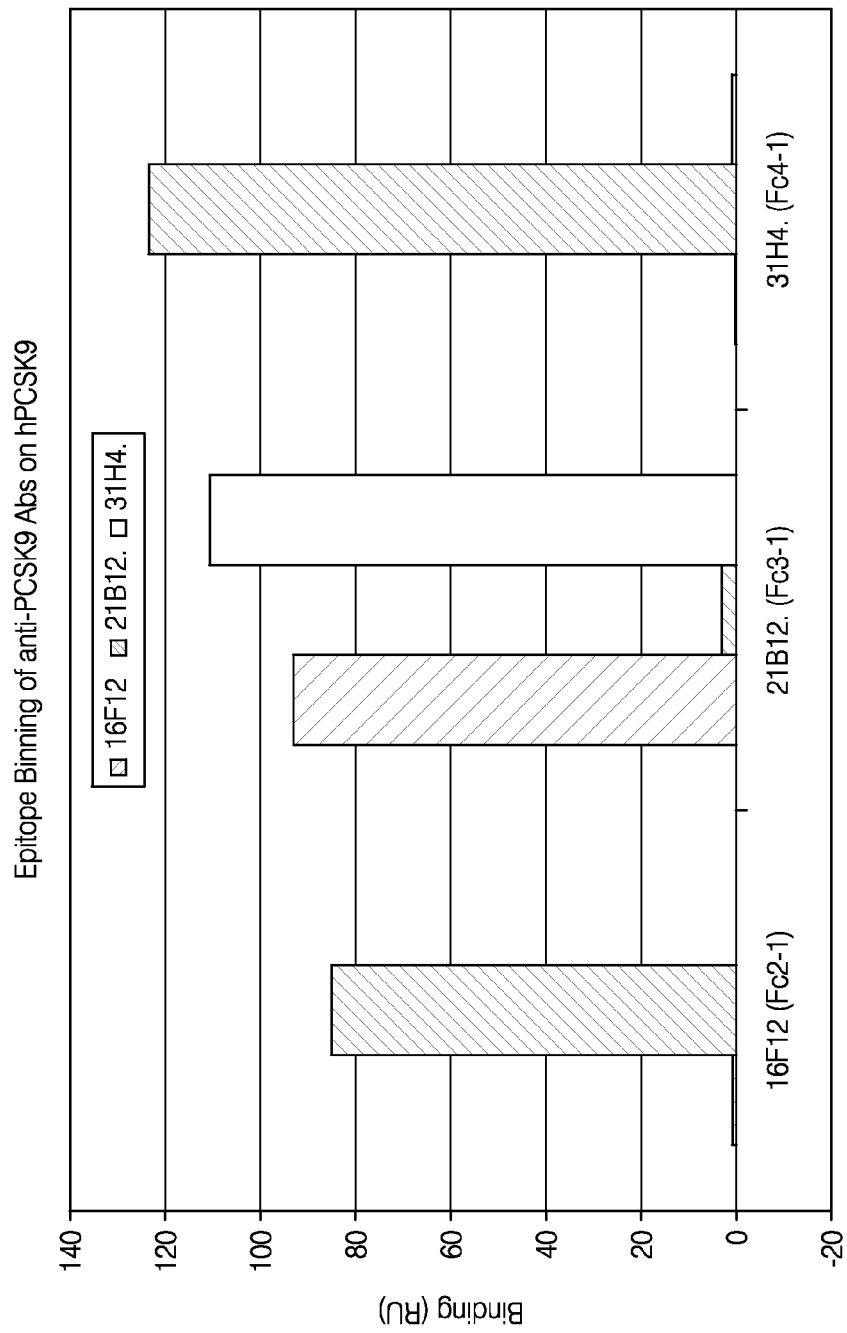

FIG. 5E depicts a bar graph depicting binning results for three ABPs.

Figure 6A:
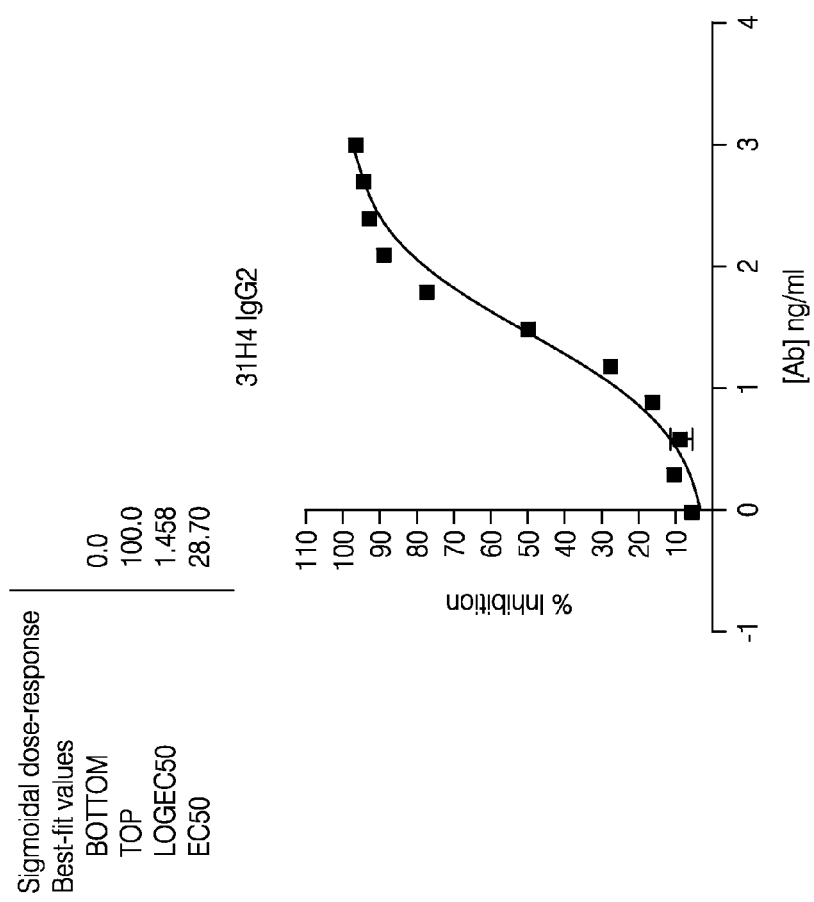
Figure 6B:
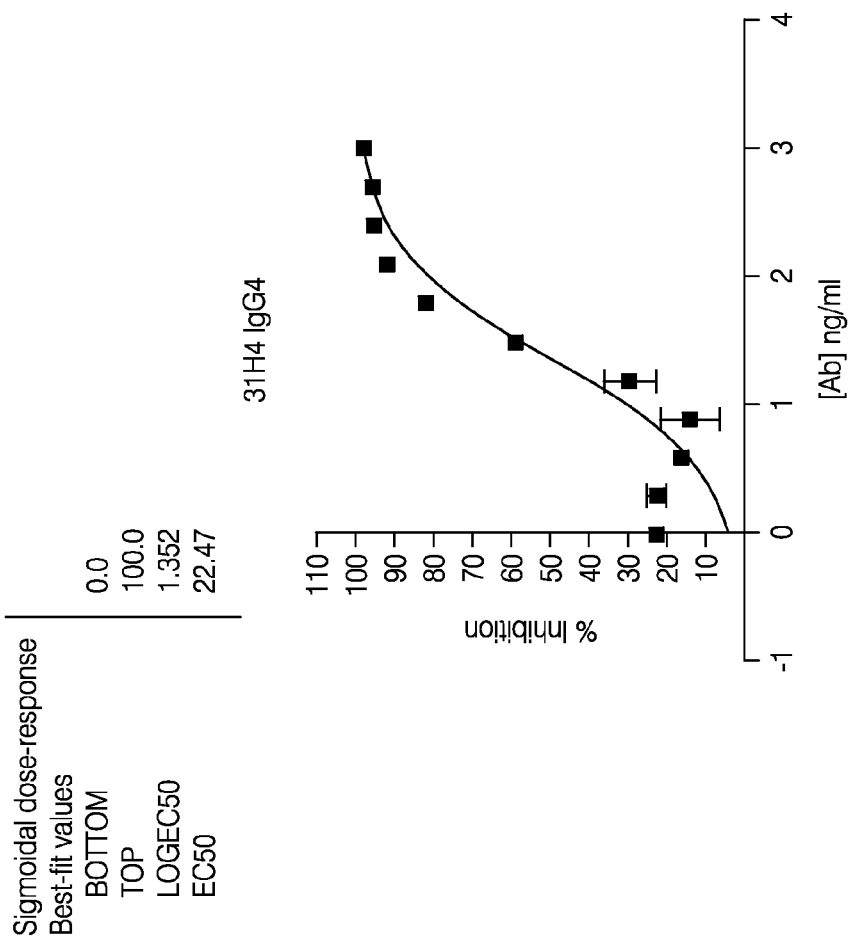

FIG. 6A is an inhibition curve of antigen binding protein 31H4 IgG2 to PCSK9 in an in vitro PCSK9:LDLR binding assay FIG. 6B is an inhibition curve of antigen binding protein 31H4 IgG4 to PCSK9 in an in vitro PCSK9:LDLR binding assay.

FIG. 6C is an inhibition curve of antigen binding protein 21B12 IgG2 to PCSK9 in an in vitro PCSK9:LDLR binding assay.

Figure 6D:
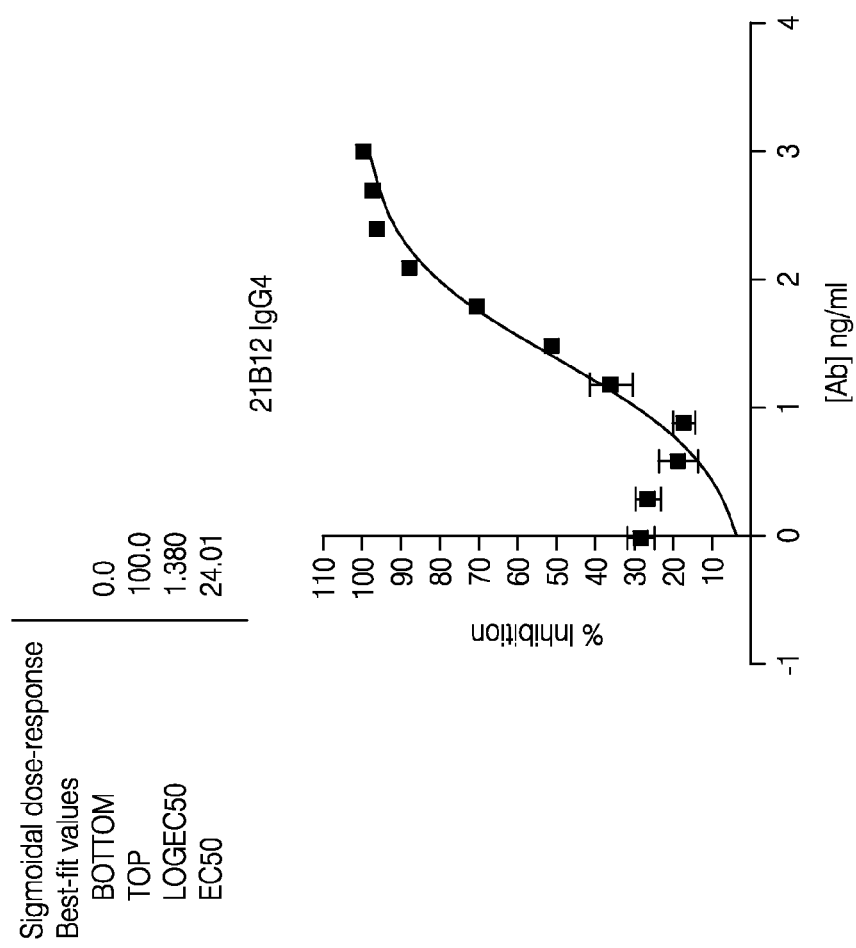

FIG. 6D is an inhibition curve of antigen binding protein 21B12 IgG4 to PCSK9 in an in vitro PCSK9:LDLR binding assay.

Figure 7A:
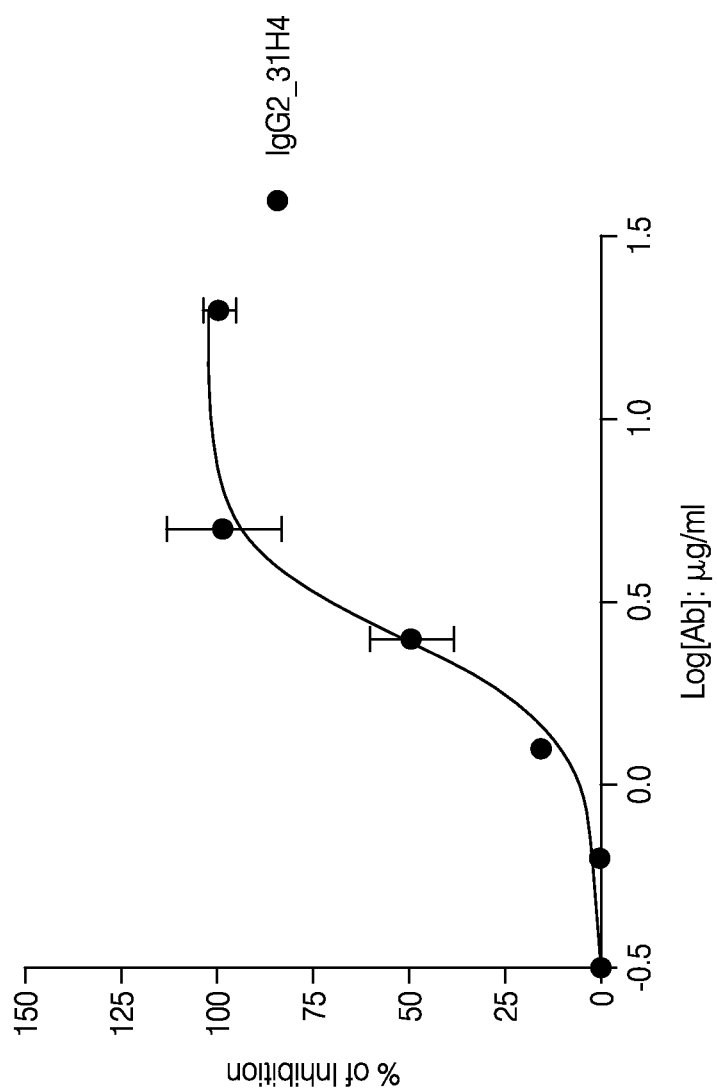

FIG. 7A is an inhibition curve of antigen binding protein 31H4 IgG2 in the cell LDL uptake assay showing the effect of the ABP to reduce the LDL uptake blocking effects of PCSK9

Figure 7B:
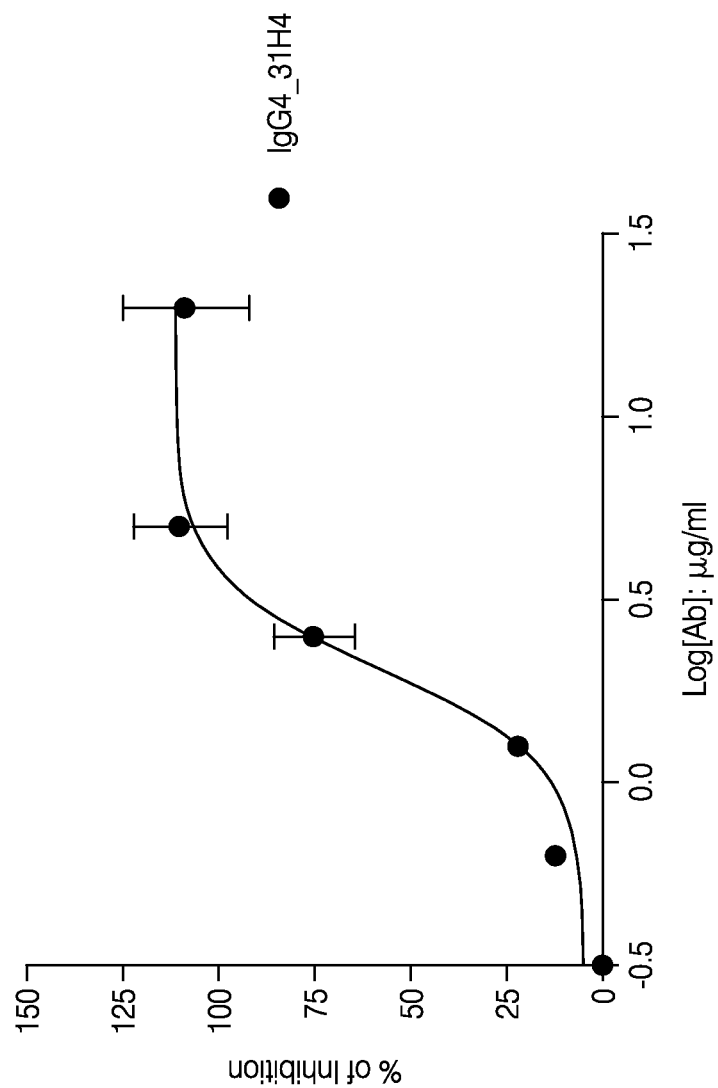

FIG. 7B is an inhibition curve of antigen binding protein 31H4 IgG4 in the cell LDL uptake assay showing the effect of the ABP to reduce the LDL uptake blocking effects of PCSK9

Figure 7C:
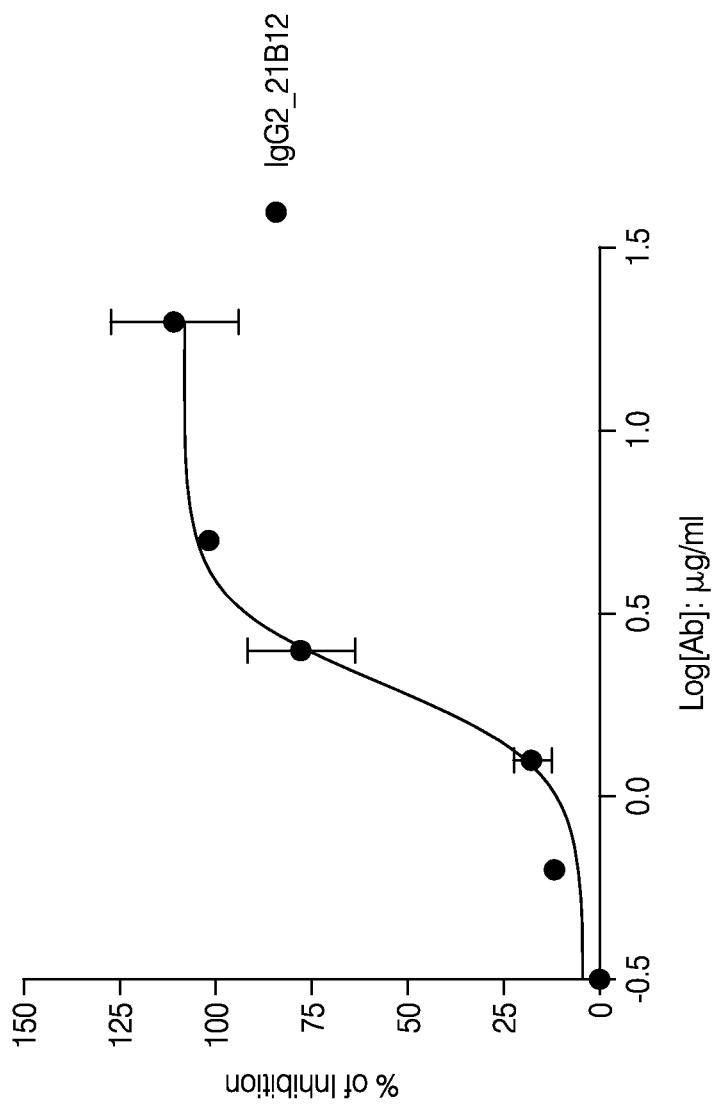

FIG. 7C is an inhibition curve of antigen binding protein 21B12 IgG2 in the cell LDL uptake assay showing the effect of the ABP to reduce the LDL uptake blocking effects of PCSK9

Figure 7D:
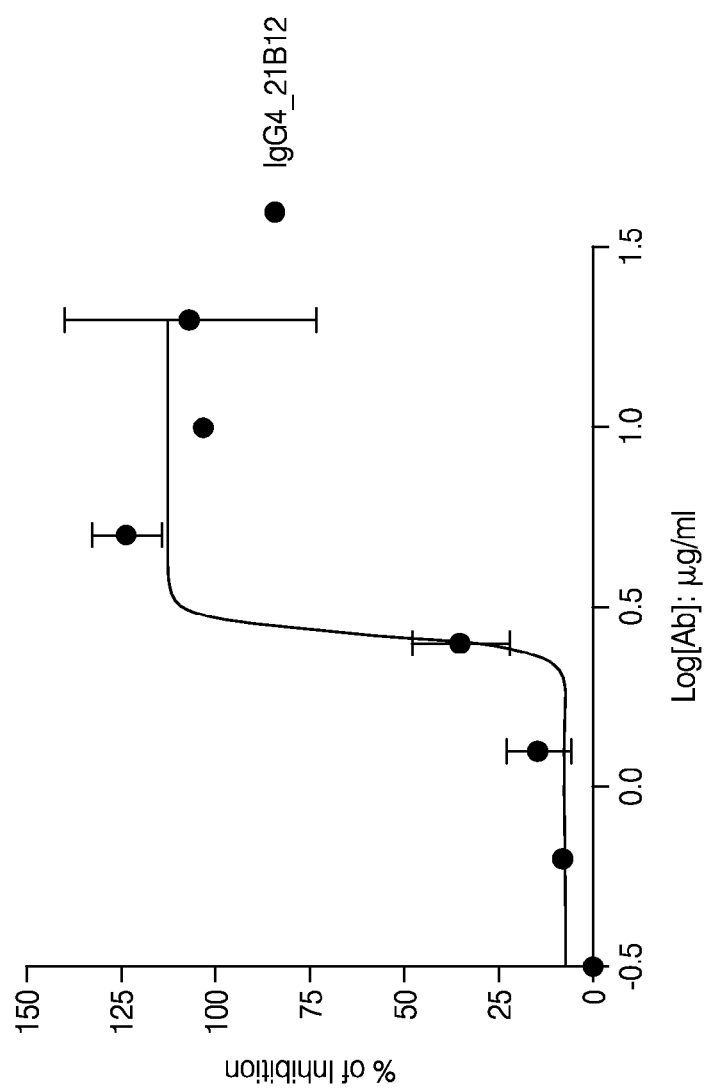

FIG. 7D is an inhibition curve of antigen binding protein 21B12 IgG4 in the cell LDL uptake assay showing the effect of the ABP to reduce the LDL uptake blocking effects of PCSK9

FIG. 8A is a graph depicting the serum cholesterol lowering ability in mice of ABP 31H4, changes relative to the IgG control treated mice (* $p<0.01$).

FIG. 8B is a graph depicting the serum cholesterol lowering ability in mice of ABP 31H4, changes relative to time=zero hours (# p, 0.05).

Figure 8D:
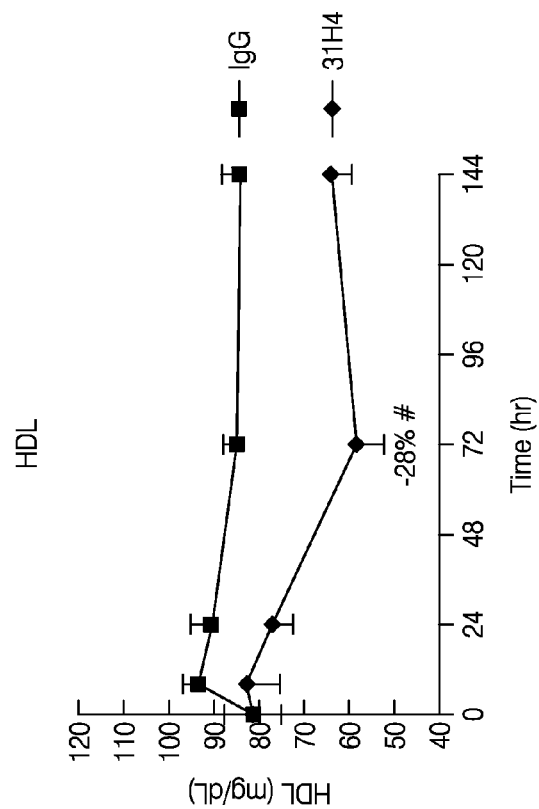
Figure 8C:
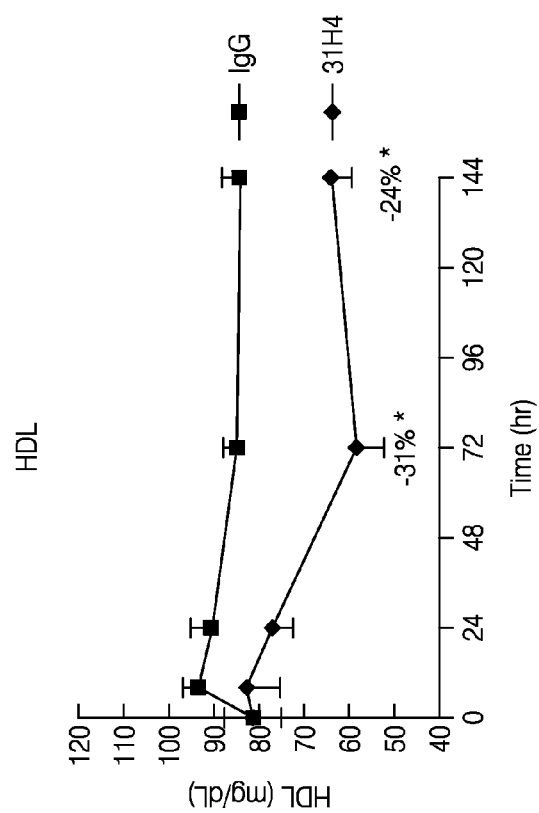

FIG. 8C is a graph depicting the effect of ABP 31H4 on HDL cholesterol levels in C57Bl/6 mice (* $p<0.01$).

FIG. 8D is a graph depicting the effect of ABP 31H4 on HDL cholesterol levels in C57Bl/6 mice (# p<0.05).

Figure 9:
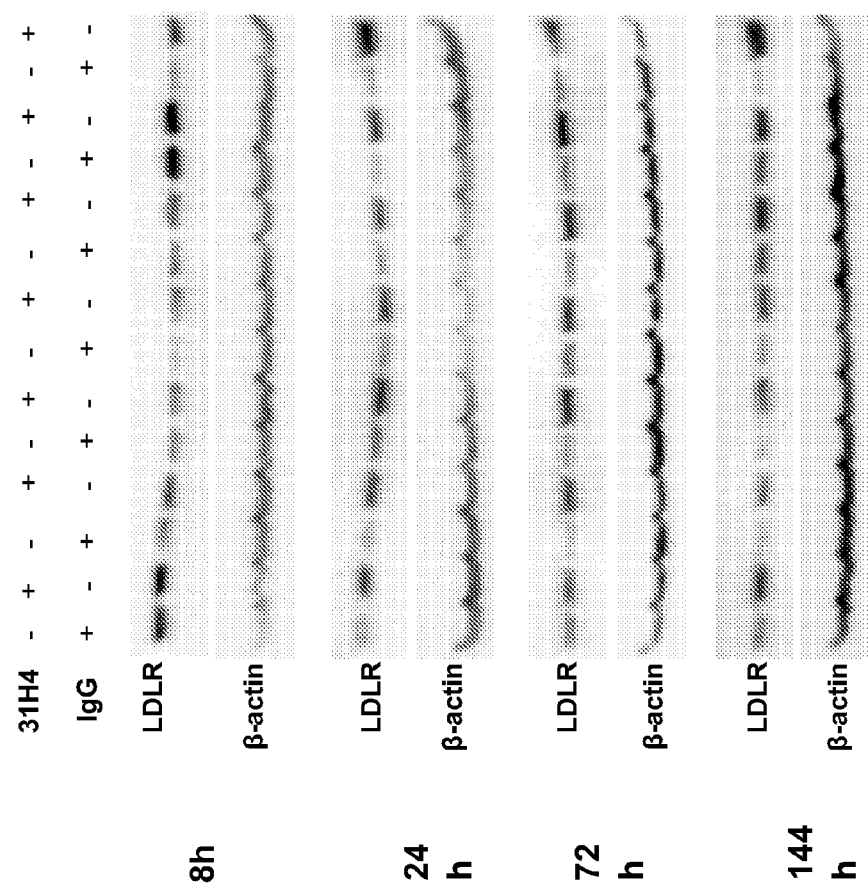

FIG. 9 depicts a western blot analysis of the ability of ABP 31H4 to enhance the amount of liver LDLR protein present after various time points.

Figure 10A:
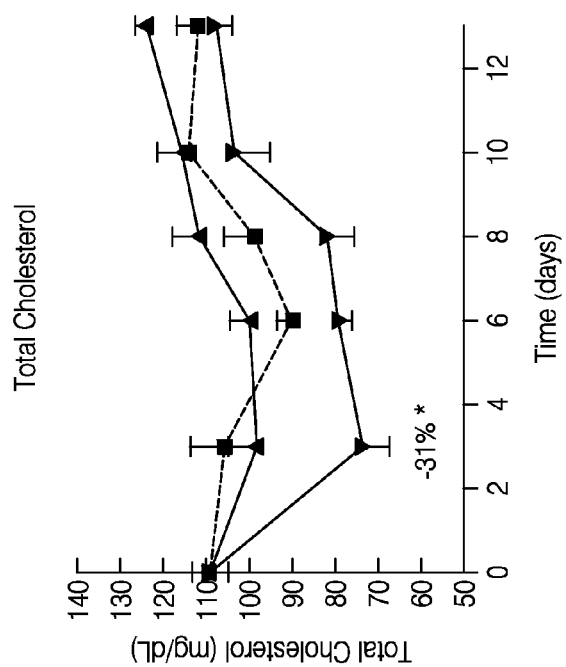

FIG. 10A is a graph depicting the ability of an antigen binding protein 31H4 to lower total serum cholesterol in wild type mice, relative.

Figure 10B:
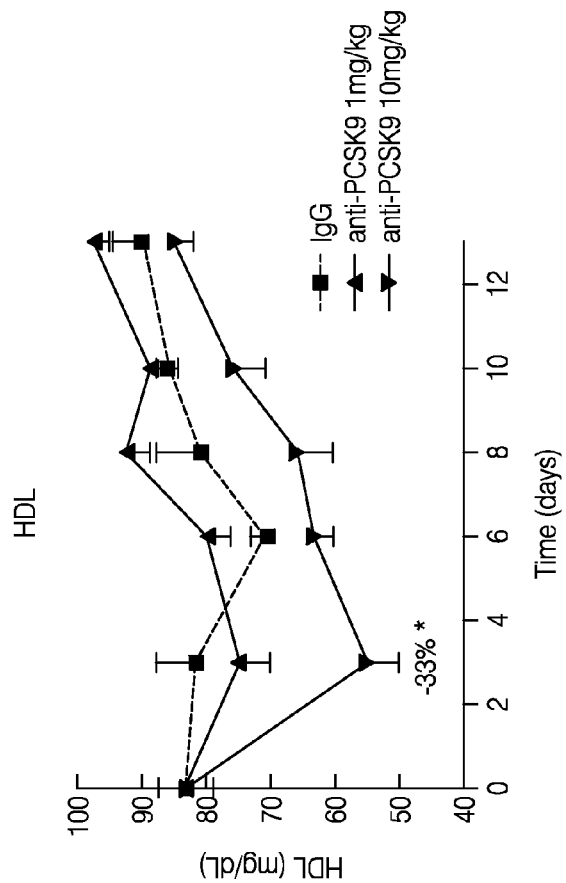

FIG. 10B is a graph depicting the ability of an antigen binding protein 31H4 to lower HDL in wild type mice.

Figure 10C:
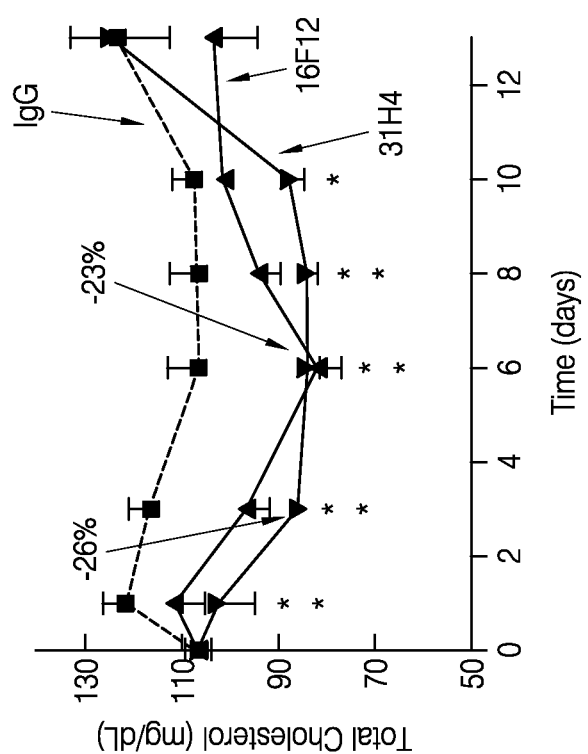

FIG. 10C is a graph depicting the serum cholesterol lowering ability of various antigen binding proteins 31H4 and 16F12.

Figure 11A:
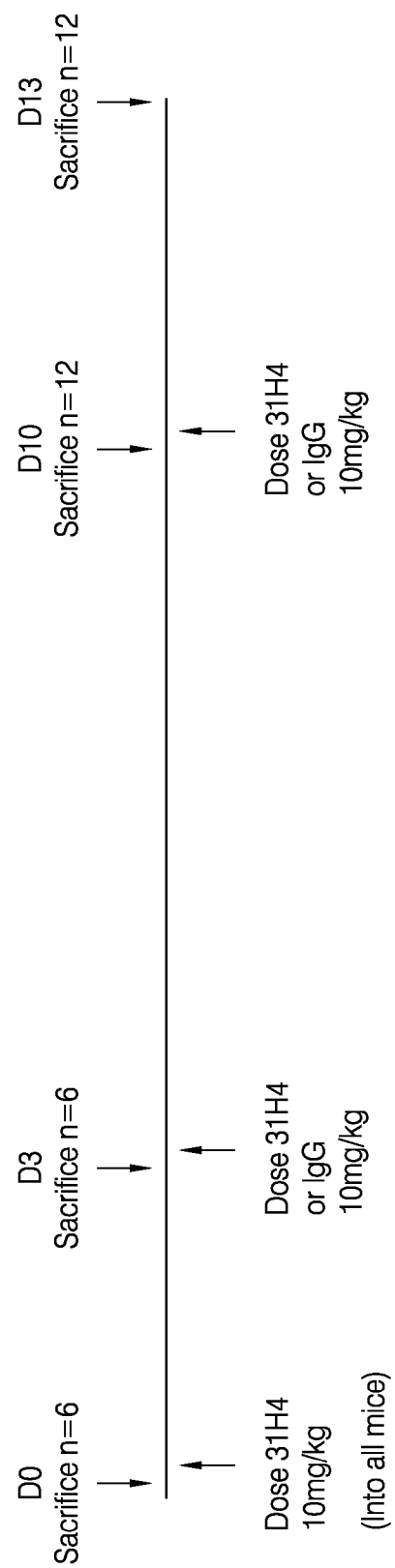

FIG. 11A depicts an injection protocol for testing the duration and ability of antigen binding proteins to lower serum cholesterol.

Figure 11B:
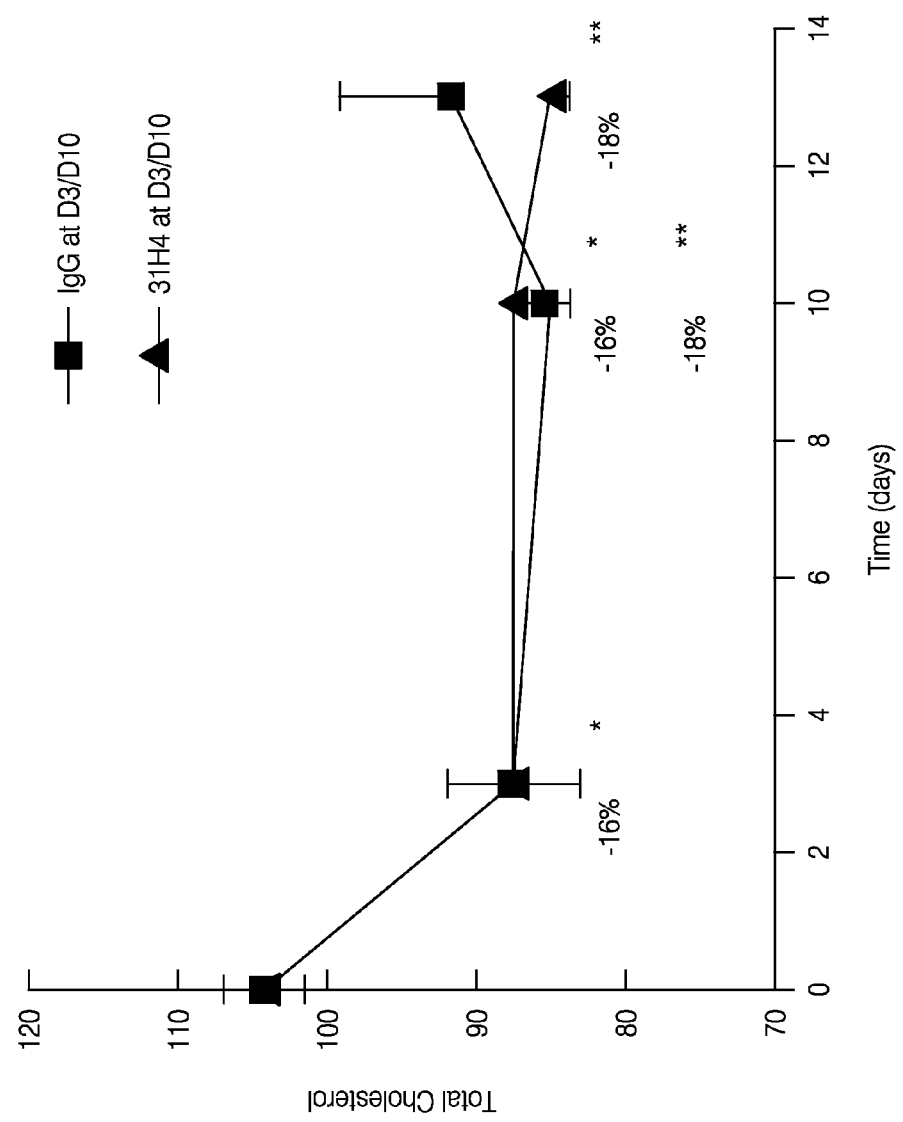

FIG. 11B is a graph depicting the results of the protocol in FIG. 11A.

Figure 12A:
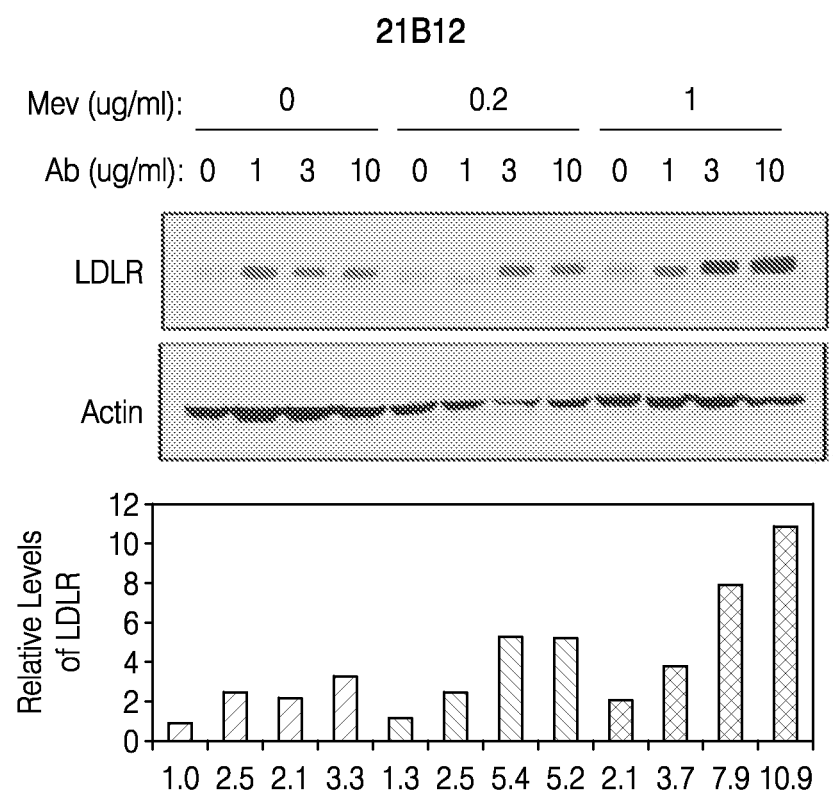

FIG. 12A depicts LDLR levels in response to the combination of a statin and ABP 21B12 in HepG2 cells.

Figure 12B:
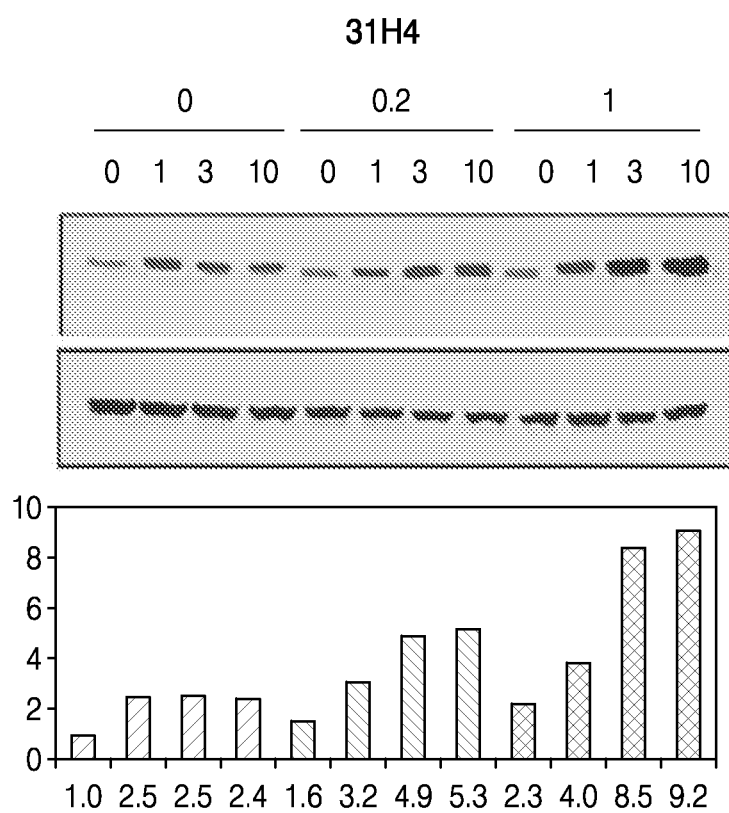

FIG. 12B depicts LDLR levels in response to the combination of a statin and ABP 31H4 in HepG2 cells.

Figure 12C:
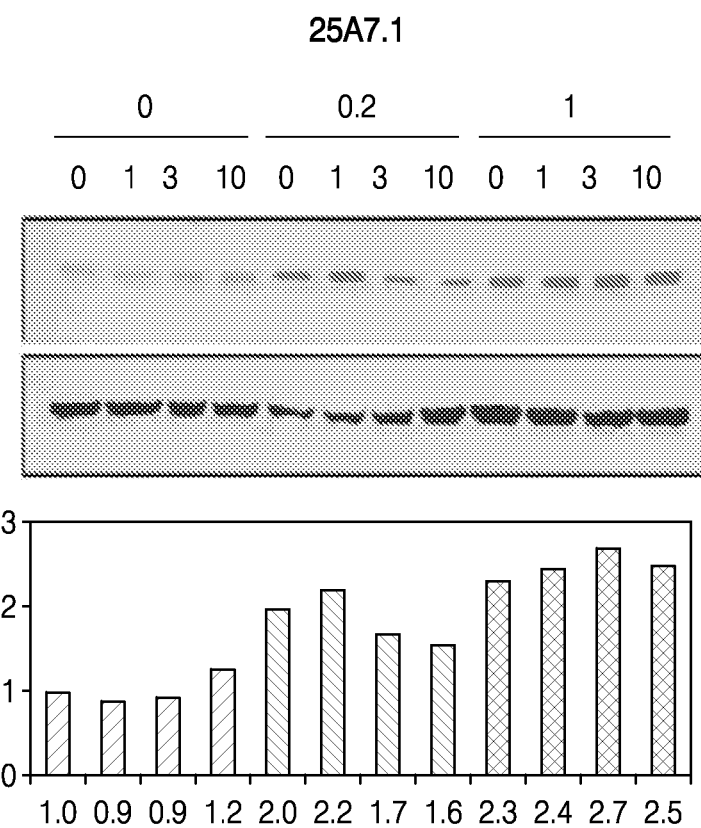

FIG. 12C depicts LDLR levels in response to the combination of a statin and ABP 25A7.1, a normeutralizing antibody, (in contrast the "25A7" a neutralizing antibody) in HepG2 cells.

Figure 12D:
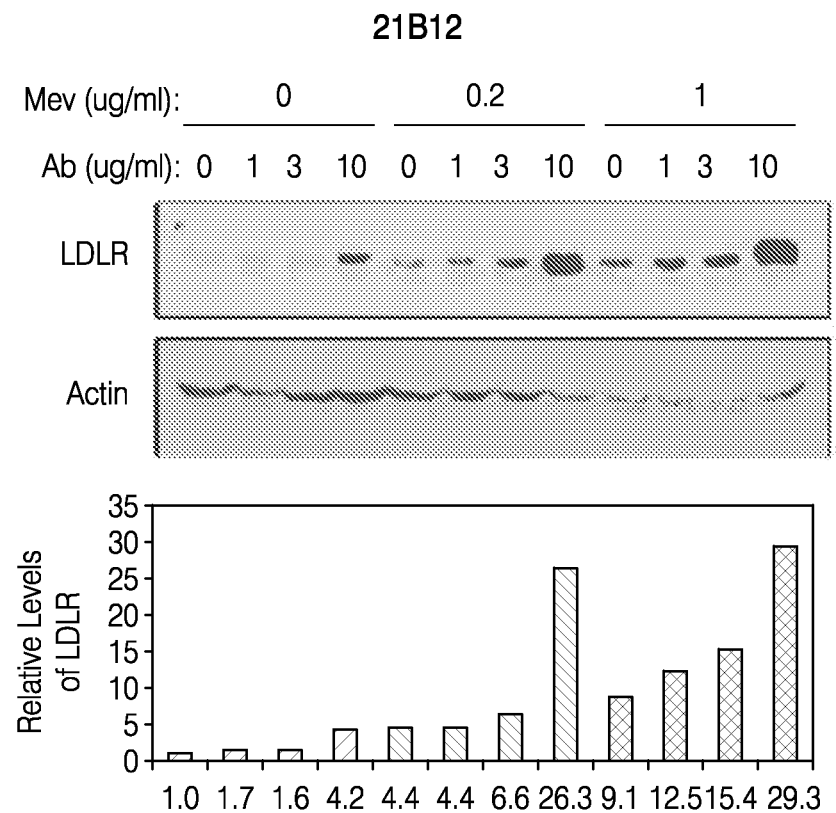

FIG. 12D depicts LDLR levels in response to the combination of a statin and ABP 21B12 in HepG2 cells overexpressing PCSK9.

Figure 12E:
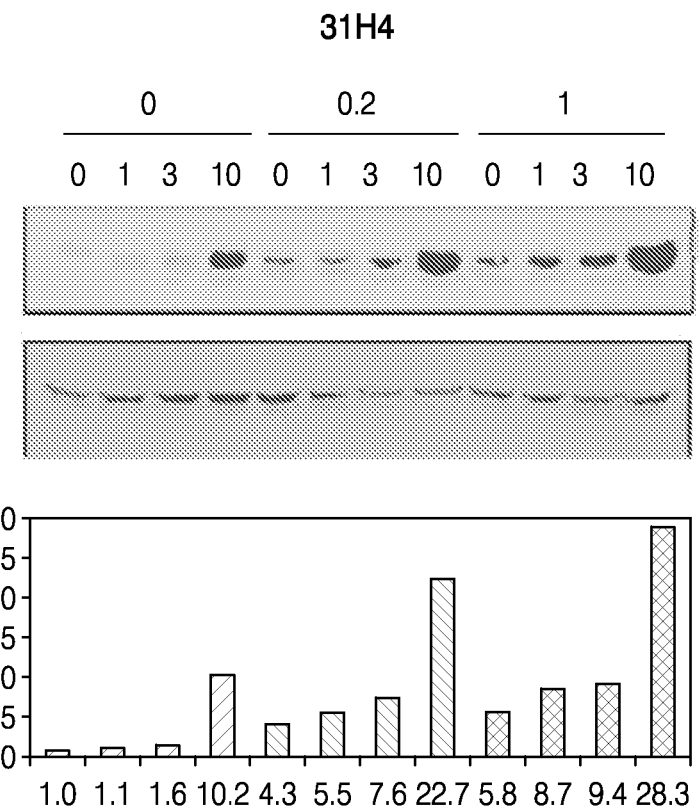

FIG. 12E depicts LDLR levels in response to the combination of a statin and ABP 31H4 in HepG2 cells overexpressing PCSK9.

Figure 12F:
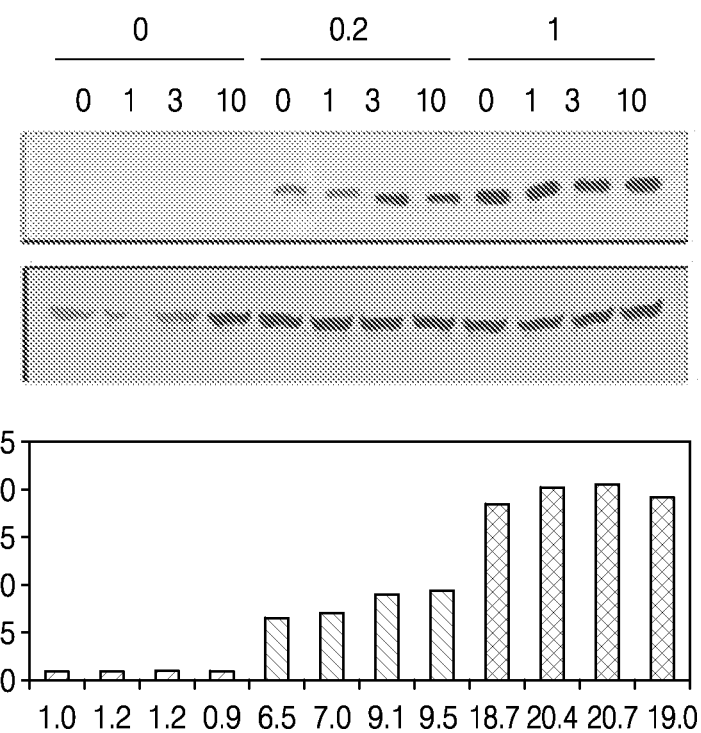

FIG. 12F depicts LDLR levels in response to the combination of a statin and ABP 25A7.1, a normeutralizing antibody, (in contrast the "25A7" a neutralizing antibody) in HepG2 cells overexpressing PCSK9.

FIG. 13A depicts the various light chain amino acid sequences of various ABPs to PCSK9. The dots (.) indicate no amino acid.

Figure 13B:
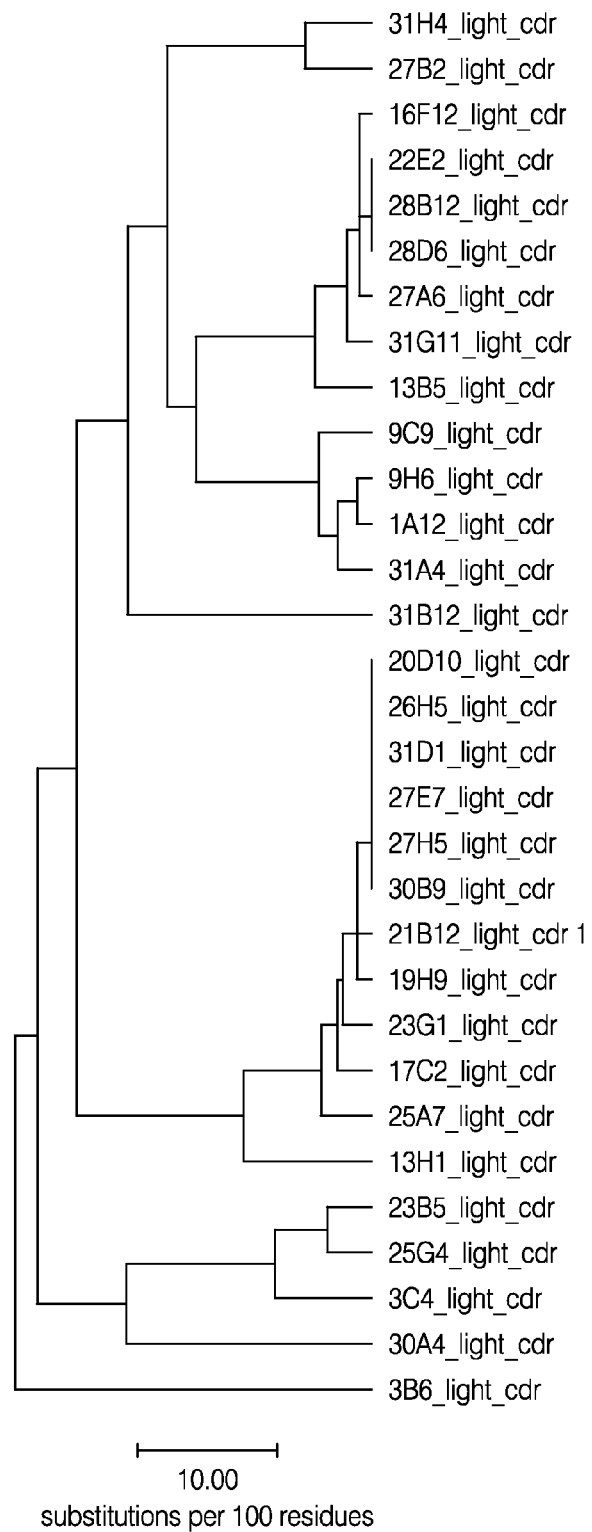

FIG. 13B depicts a light chain cladogram for various ABPs to PCSK9.

FIG. 13C depicts the various heavy chain amino acid sequences of various ABPs to PCSK9. The dots (.) indicate no amino acid.

Figure 13D:
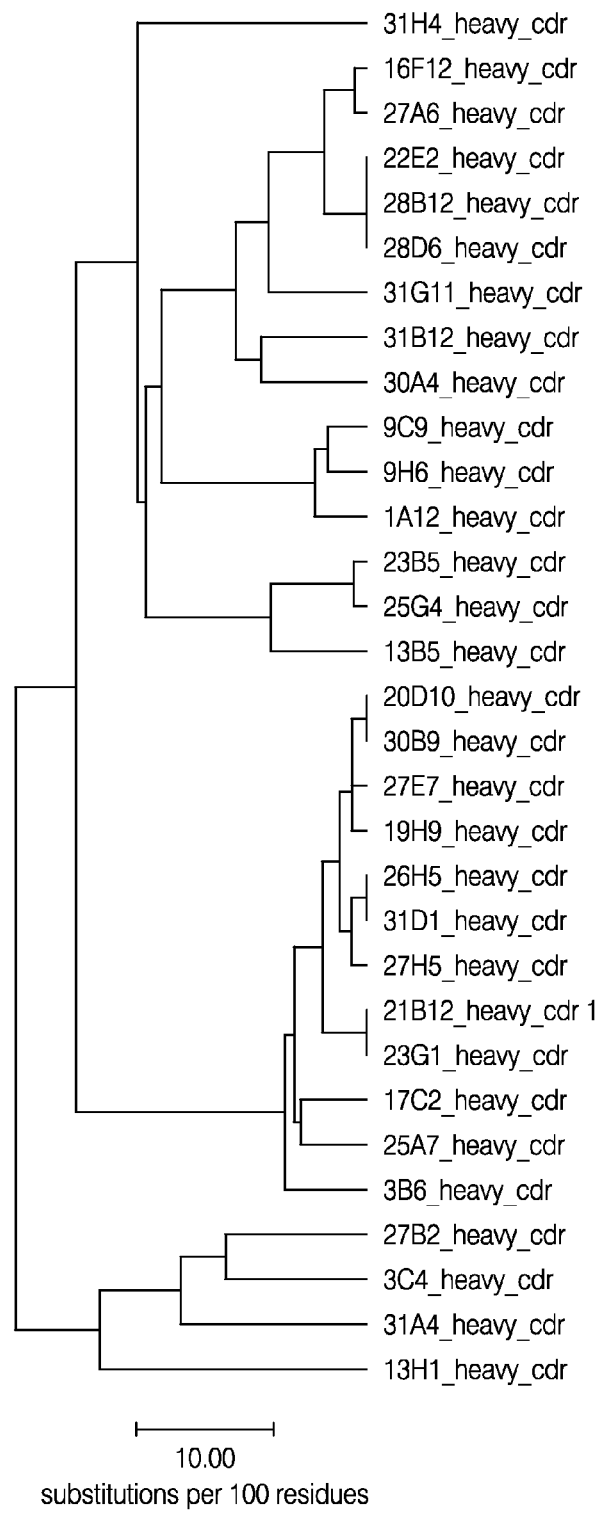

FIG. 13D depicts a heavy chain dendrogram for various ABPs to PCSK9.

Figure 13E:
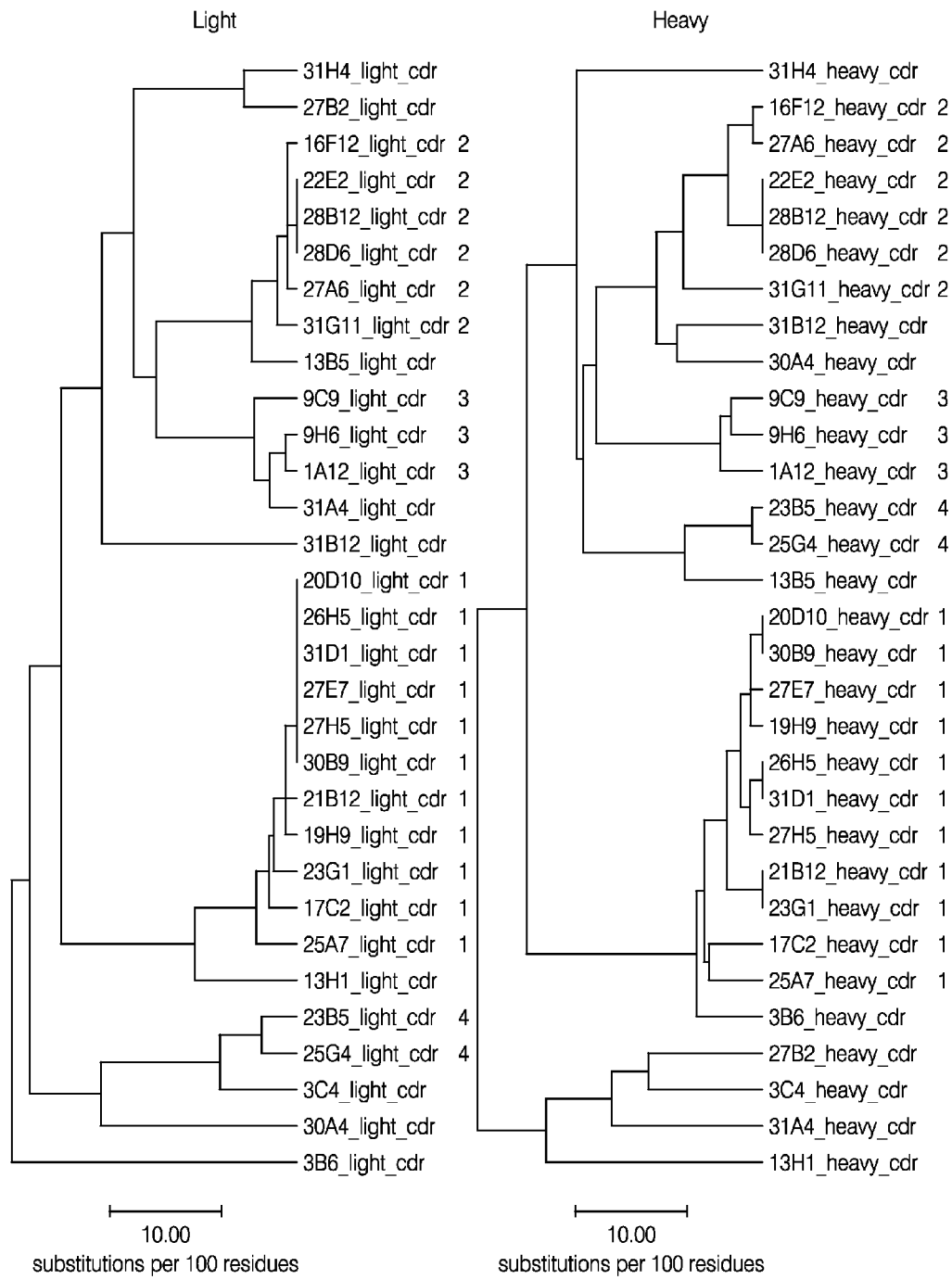

FIG. 13E depicts a comparison of light and heavy CDRs and designation of groups from which to derive consensus.

FIG. 13F depicts the consensus sequences for Groups 1 and 2.

FIG. 13G depicts the consensus sequences for Groups 3 and 4.

FIG. 13H depicts the consensus sequences for Groups 1 and 2. The dots (.) indicated identical residues.

FIG. 13I depicts the consensus sequences for Group 2. The dots (.) indicated identical residues.

FIG. 13J depicts the consensus sequences for Groups 3 and 4. The dots (.) indicated identical residues.

Figure 14A:
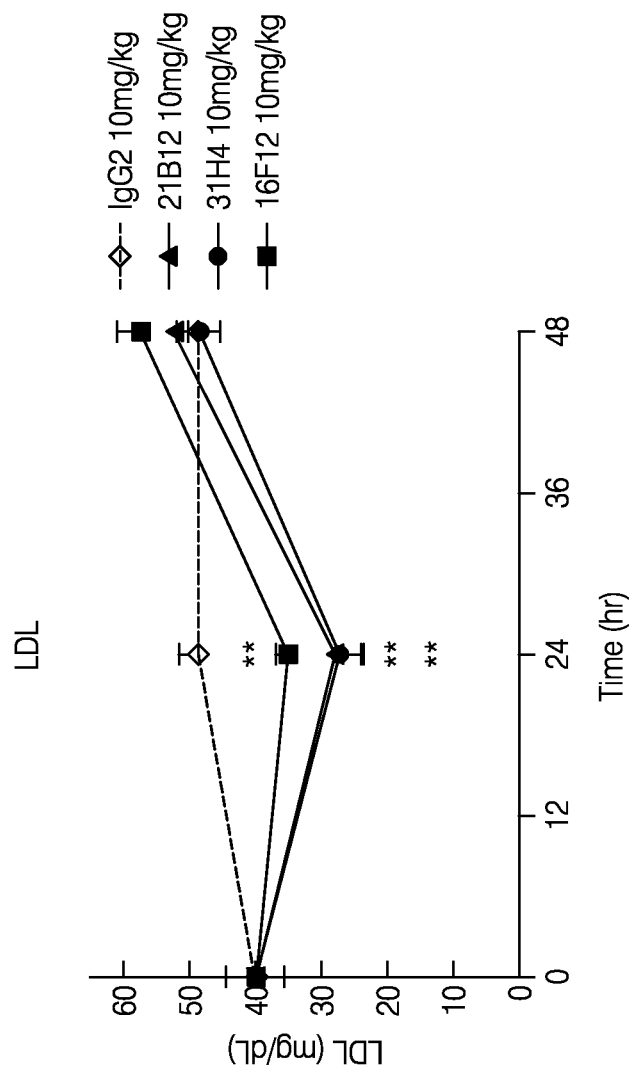

FIG. 14A is a graph depicting in vivo LDL lowering ability of various ABPs (at 10 mg/kg).

Figure 14B:
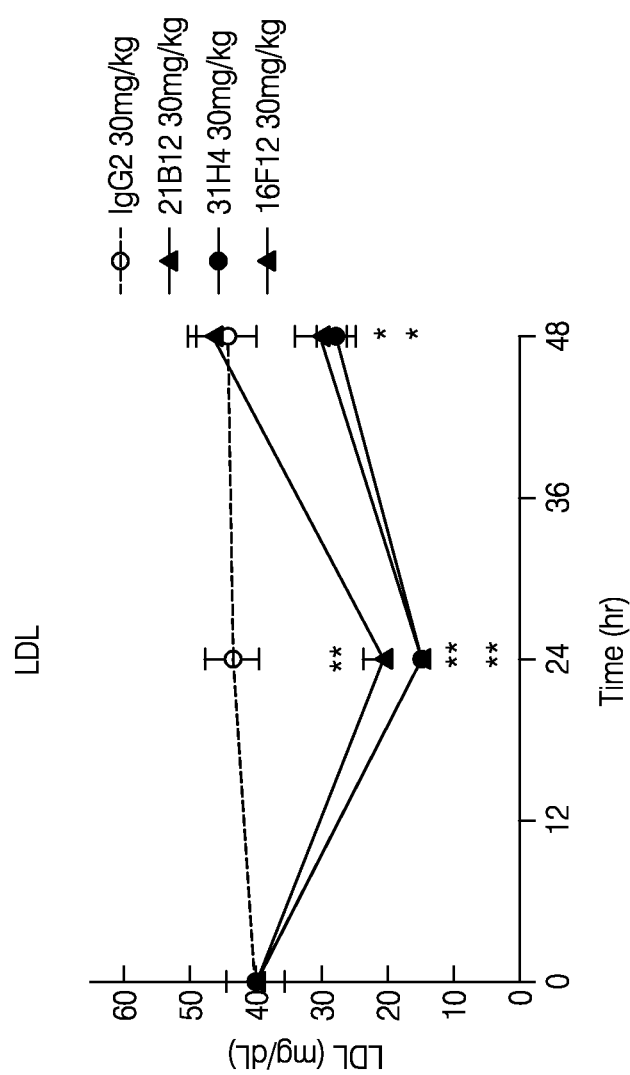

FIG. 14B is a graph depicting in vivo LDL lowering ability of various ABPs (at 30 mg/kg).

FIG. 15A and FIG. 15B are sequence comparison tables of various light chains of various embodiments of antigen binding proteins. FIG. 15B continues the sequence started in FIG. 15A.

FIG. 15C and FIG. 15D are sequence comparison tables of various light chains of various embodiments of antigen binding proteins. FIG. 15D continues the sequence started in FIG. 15C.

Figure 16B:
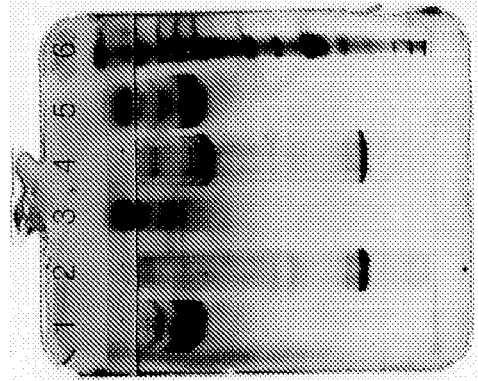
Figure 16A:
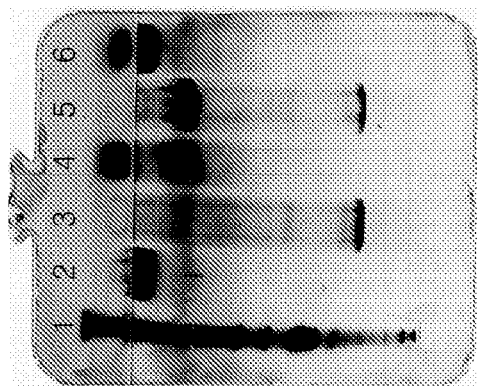

FIG. 16A is a depiction of a gel used to test the ability of Ab 21B12 to bind to the ProCat or VD sections of PCSK9.

FIG. 16B is a depiction of a gel used to test the ability of Ab 31H4 to bind to the ProCat or VD sections of PCSK9.

Figure 17:
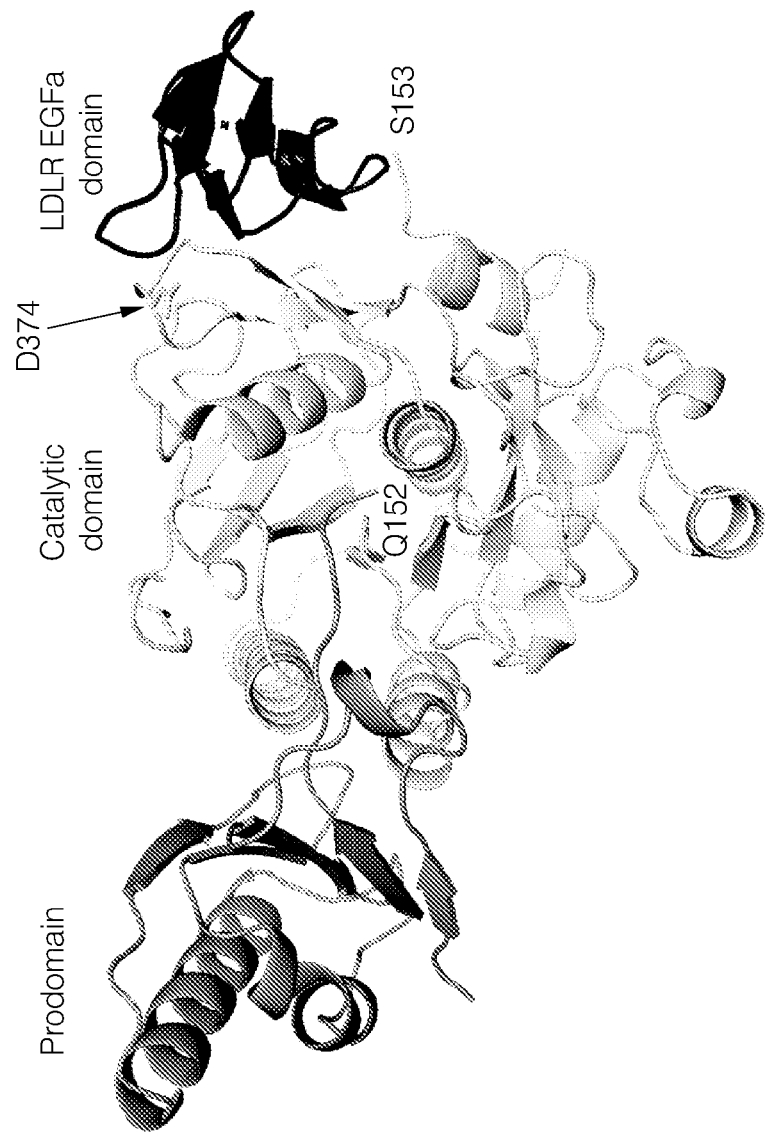

FIG. 17 is a depiction of the structure of PCSK9 and the EGFa section of LDLR.

Figure 18A:
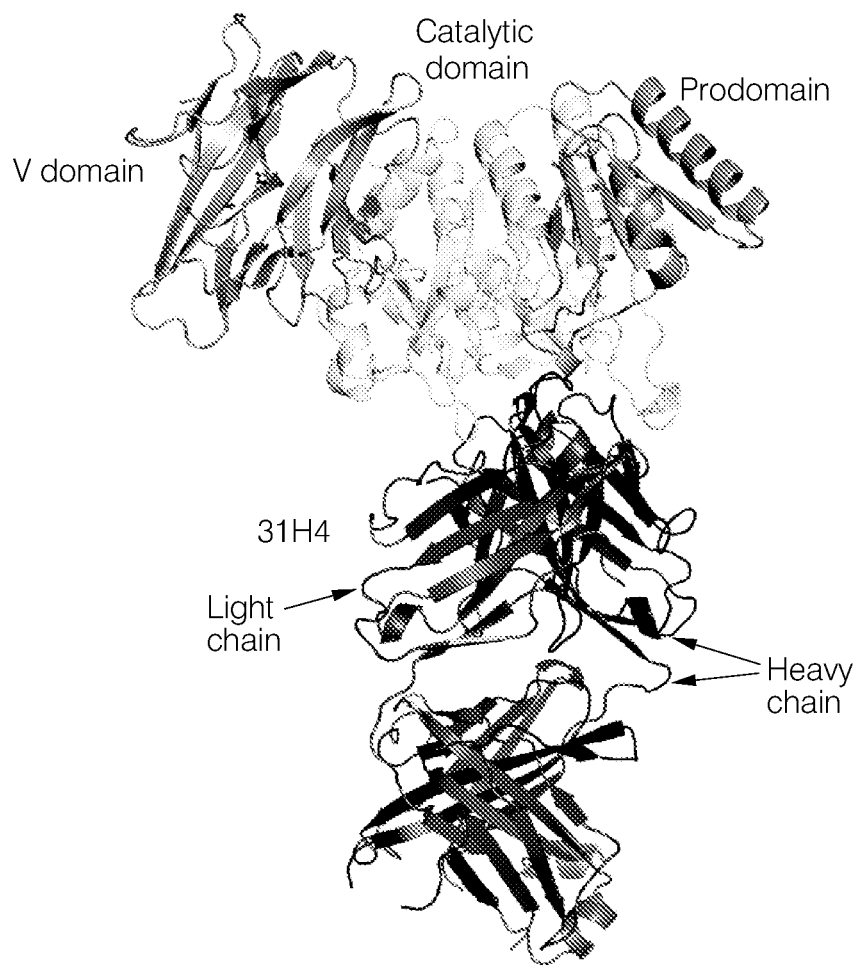

FIG. 18A is a depiction of the structure of PCSK9 and the 31H4 Ab.

Figure 18B:

FIG. 18B is a depiction of the structure of PCSK9 and the 31H4 Ab.

Figure 19A:
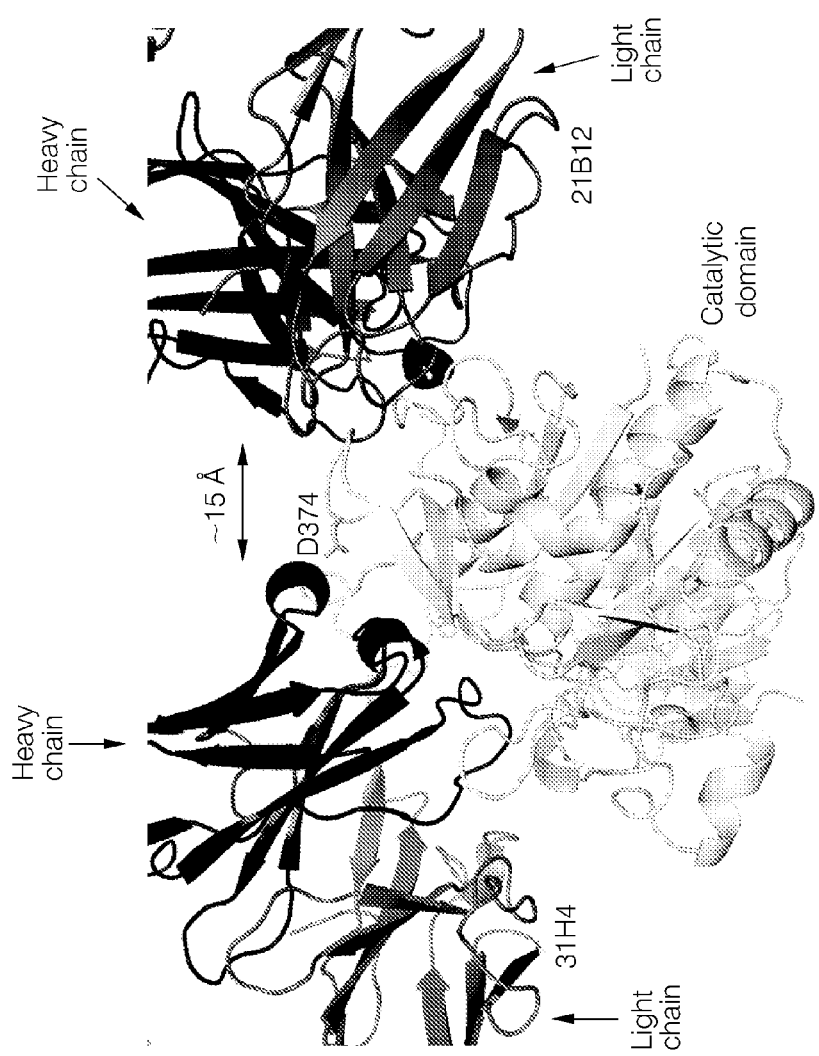

FIG. 19A is a depiction of the structure of PCSK9, the 31H4 Ab, and the 21B12 Ab.

Figure 19B:
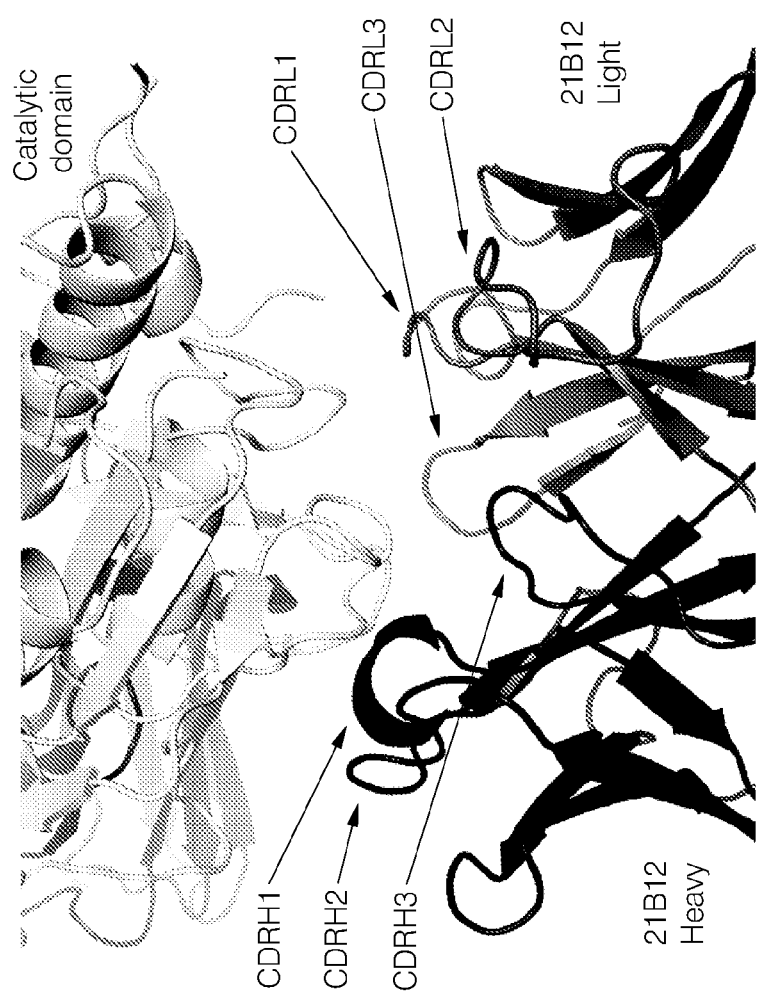

FIG. 19B is a depiction of the structure of PCSK9 and the 21B12 Ab.

Figure 20A:
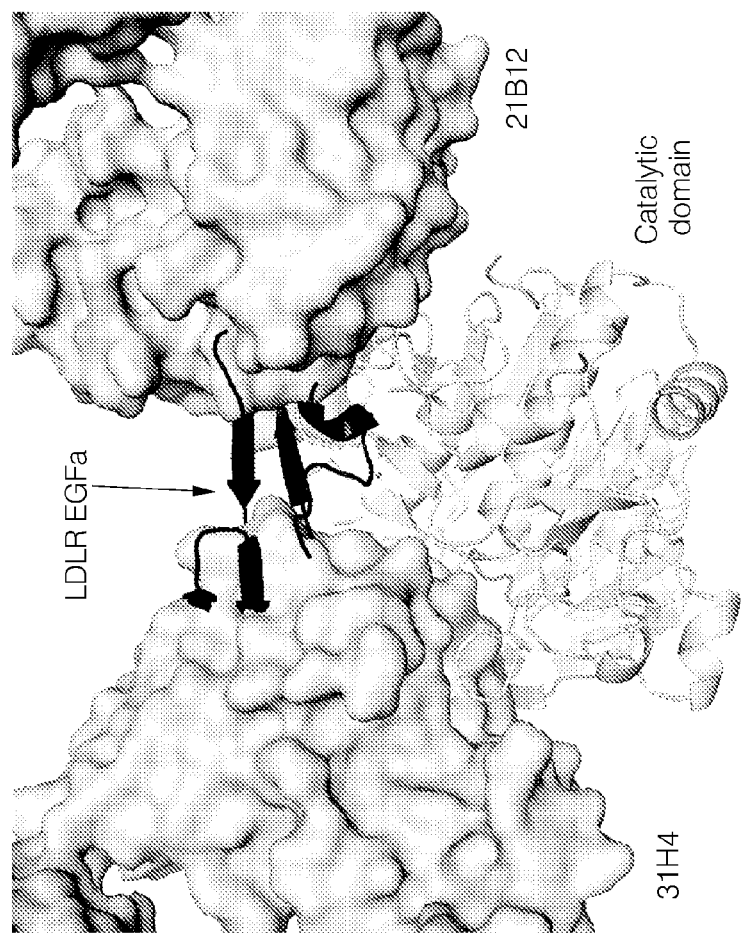

FIG. 20A is a depiction of the structure of PCSK9 and EGFa from the LDLR superimposed with the structure of antibodies 31H4 and 21B12 bound to PCSK9.

Figure 20B:
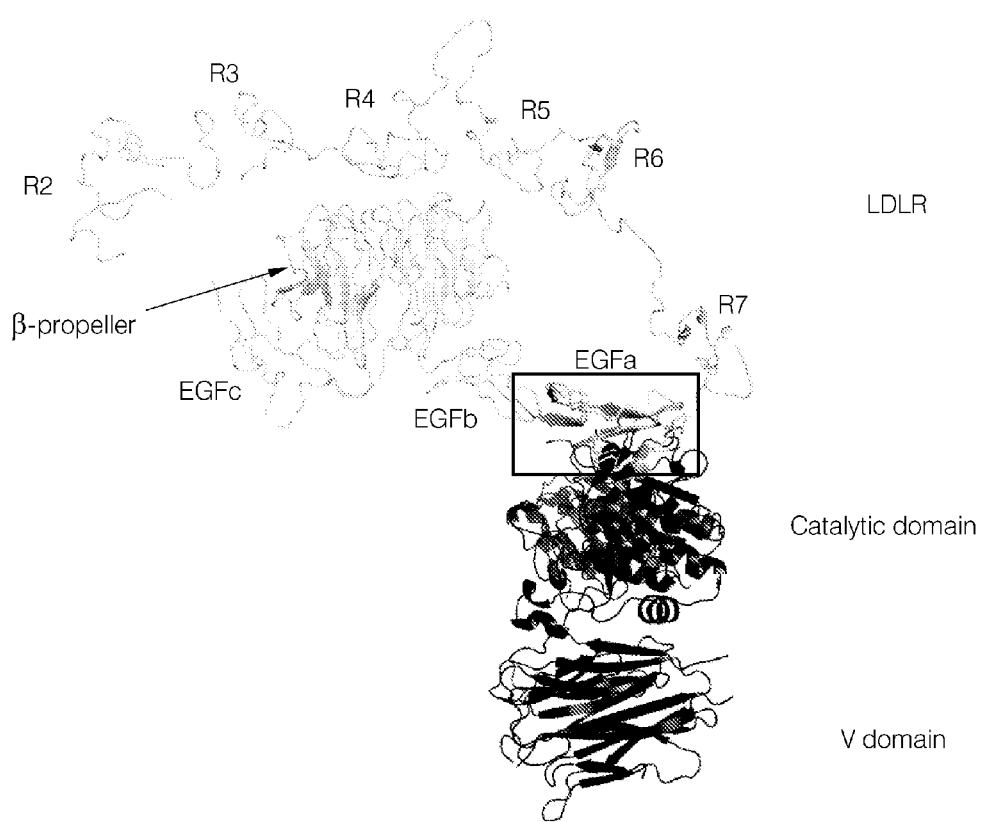

FIG. 20B is a depiction of the structural model of PCSK9 and LDLR.

Figure 20C:
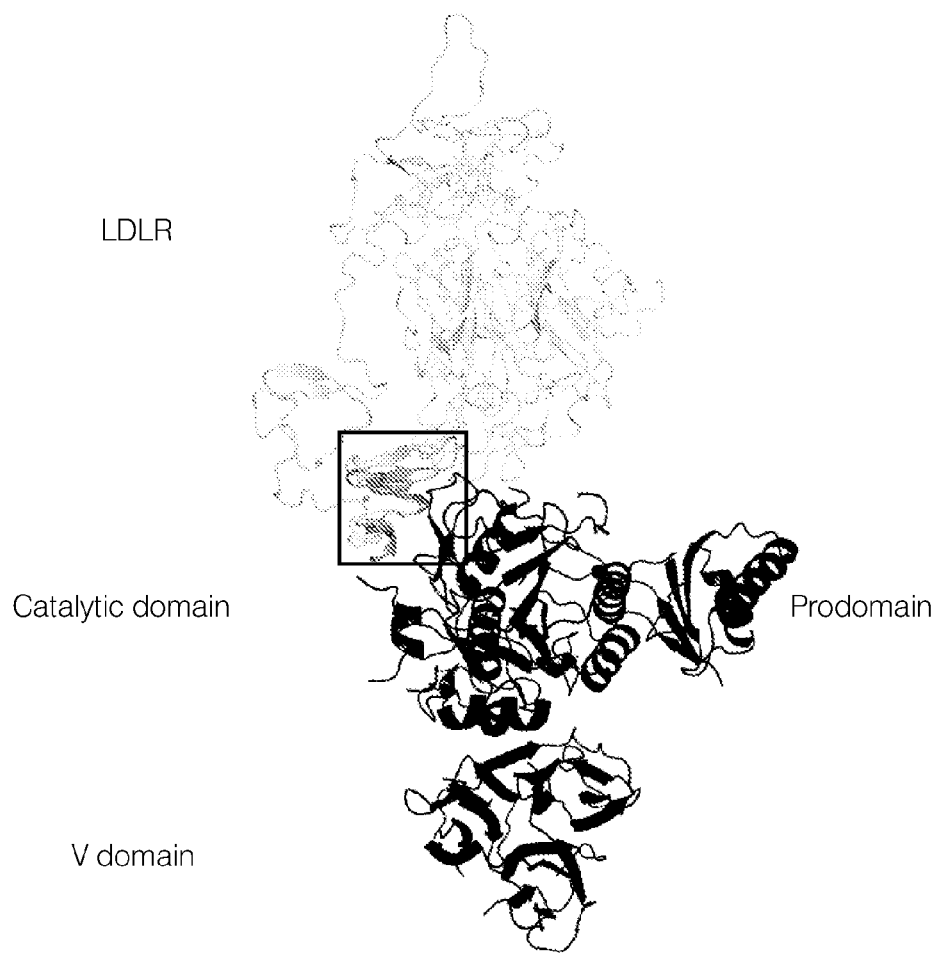

FIG. 20C is a depiction of the structural model of PCSK9 and LDLR from an alternative perspective.

Figure 20D:
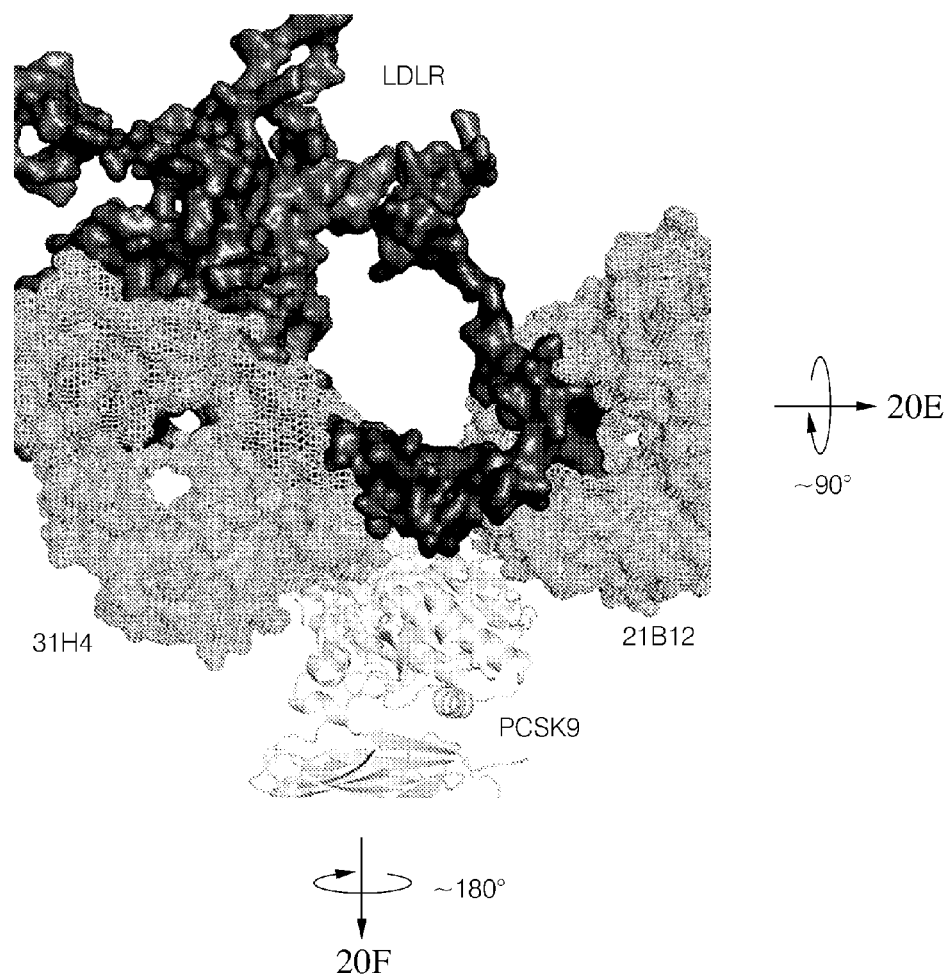

FIG. 20D is a depiction of the structural model of PCSK9 and LDLR with structural representations of 31H4 and 21B12 included.

Figure 20E:
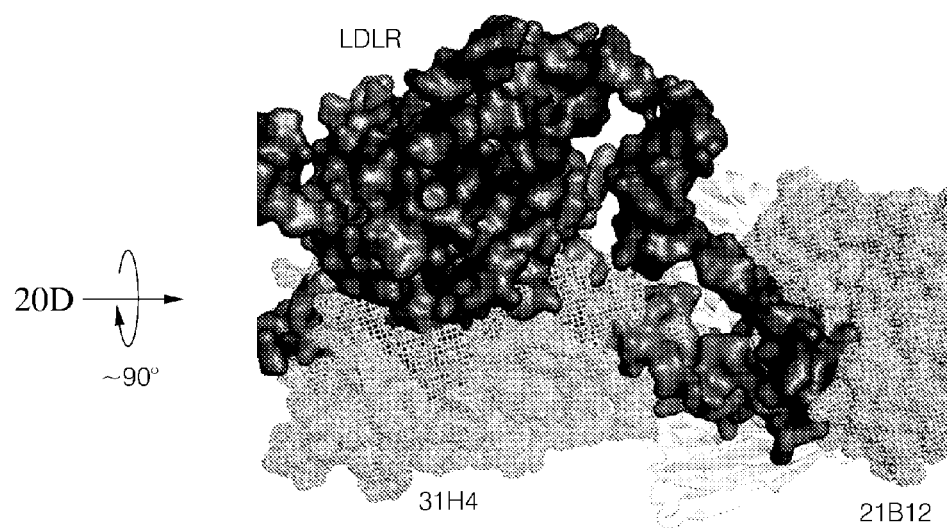

FIG. 20E is a depiction of the structural model in FIG. 20D, rotated 90 degrees about the noted axis.

Figure 20F:
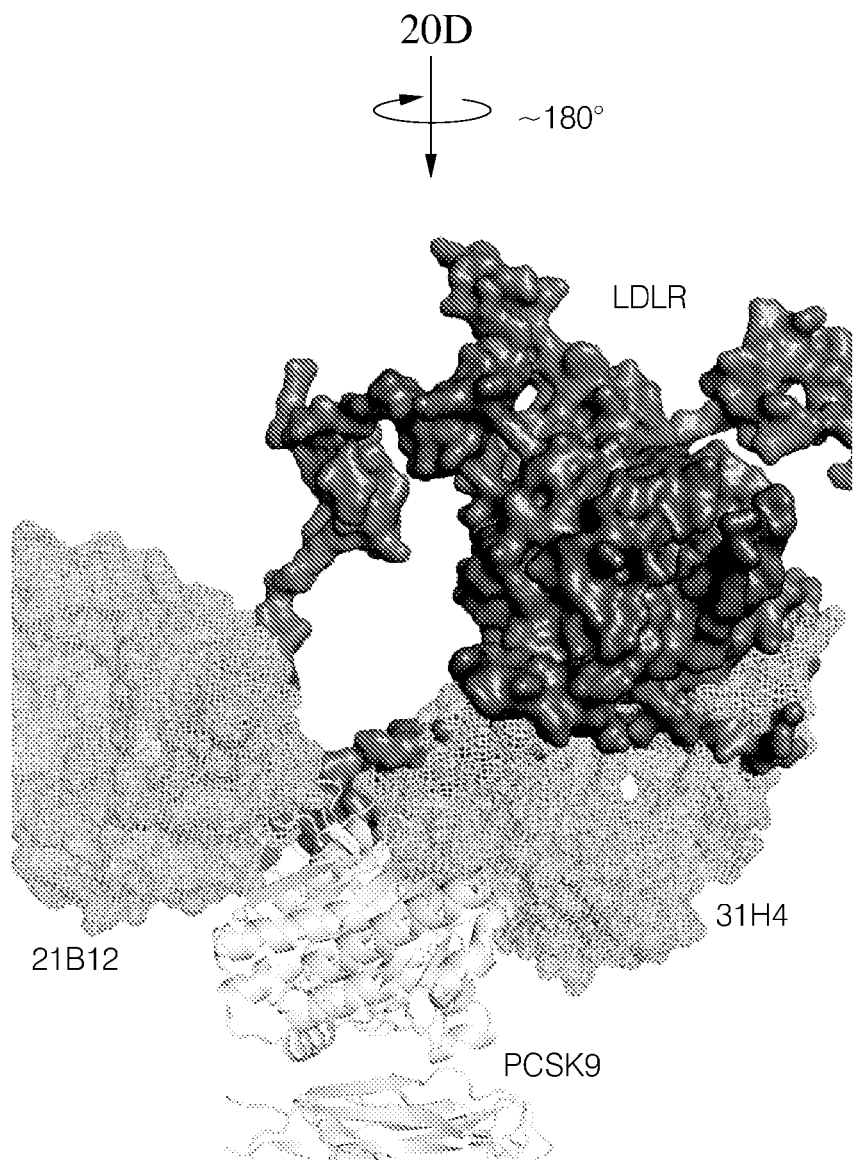

FIG. 20F is a depiction of the structural model in FIG. 20D rotated 180 degrees about the noted axis.

Figure 21A:
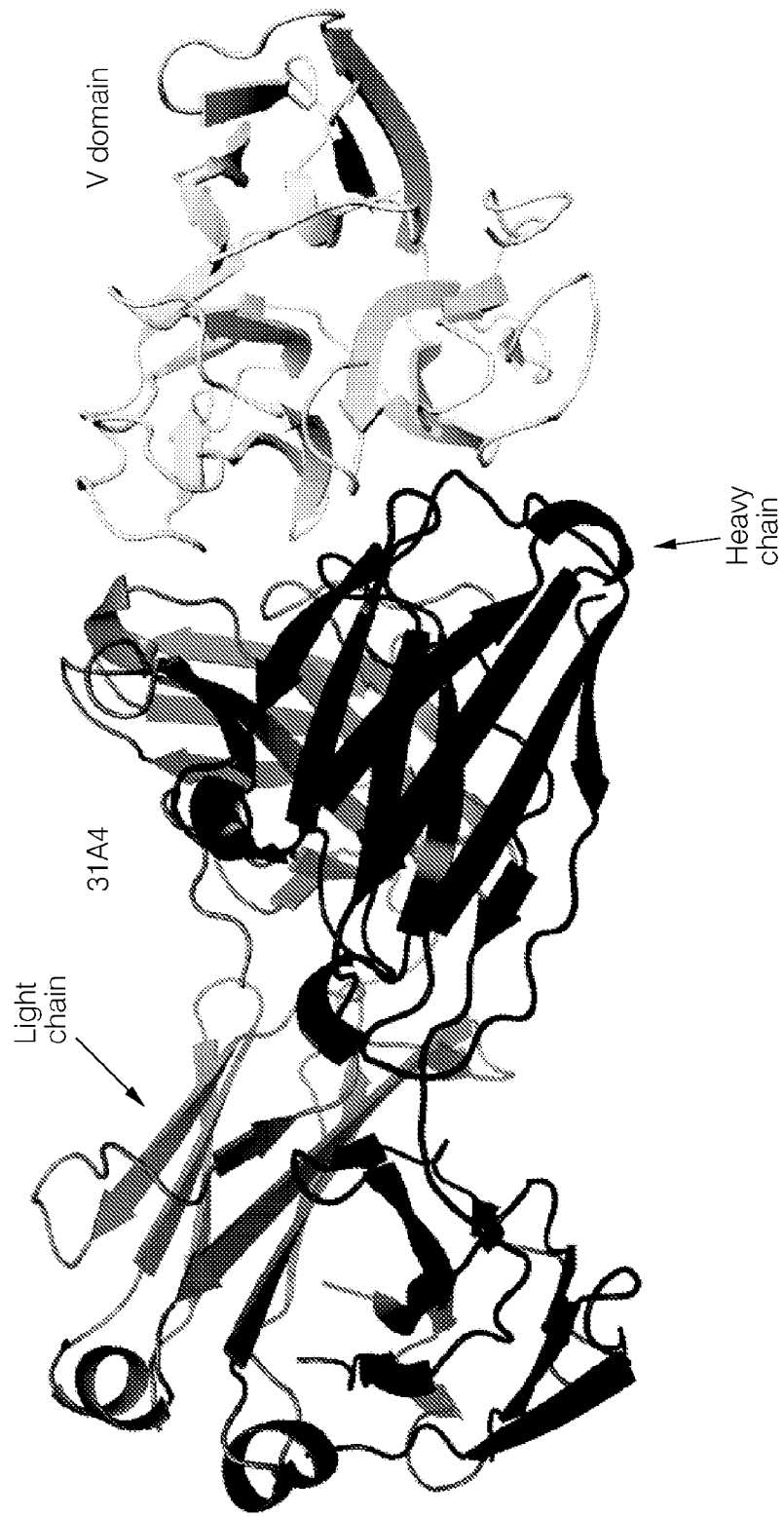

FIG. 21A is a depiction of the structure of PCSK9 and 31A4.

Figure 21B:
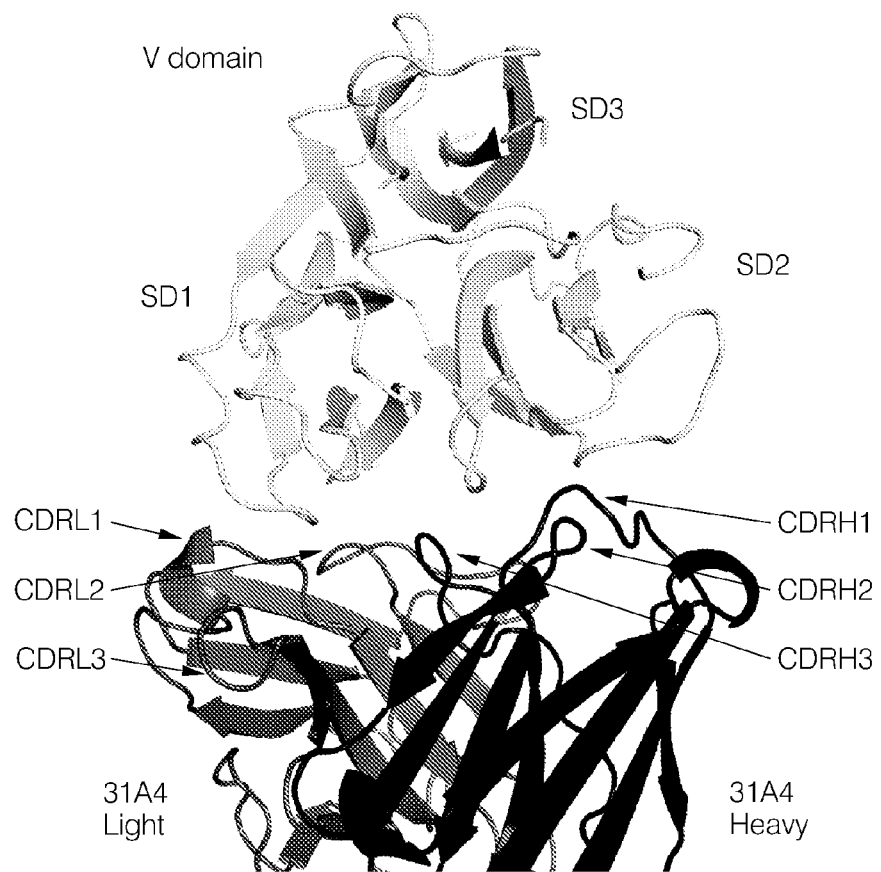

FIG. 21B is a depiction of the structure of PCSK9 and 31A4.

Figure 21C:
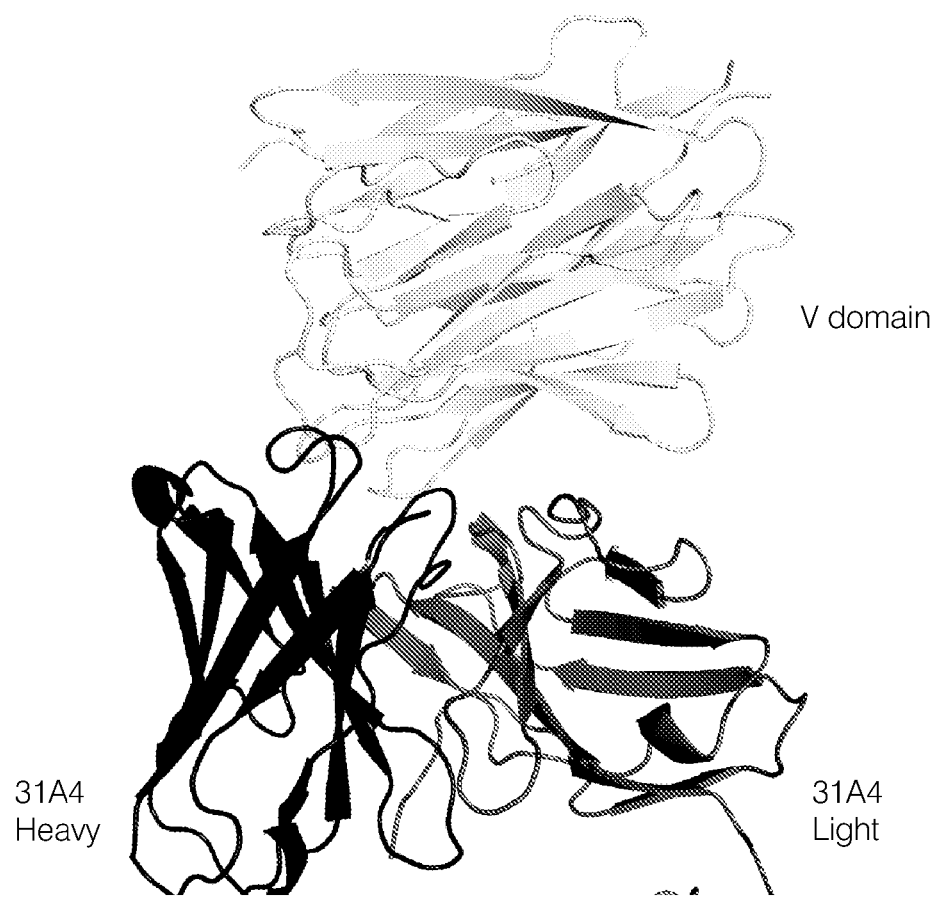

FIG. 21C is a depiction of the structure of PCSK9 and 31A4.

Figure 21D:
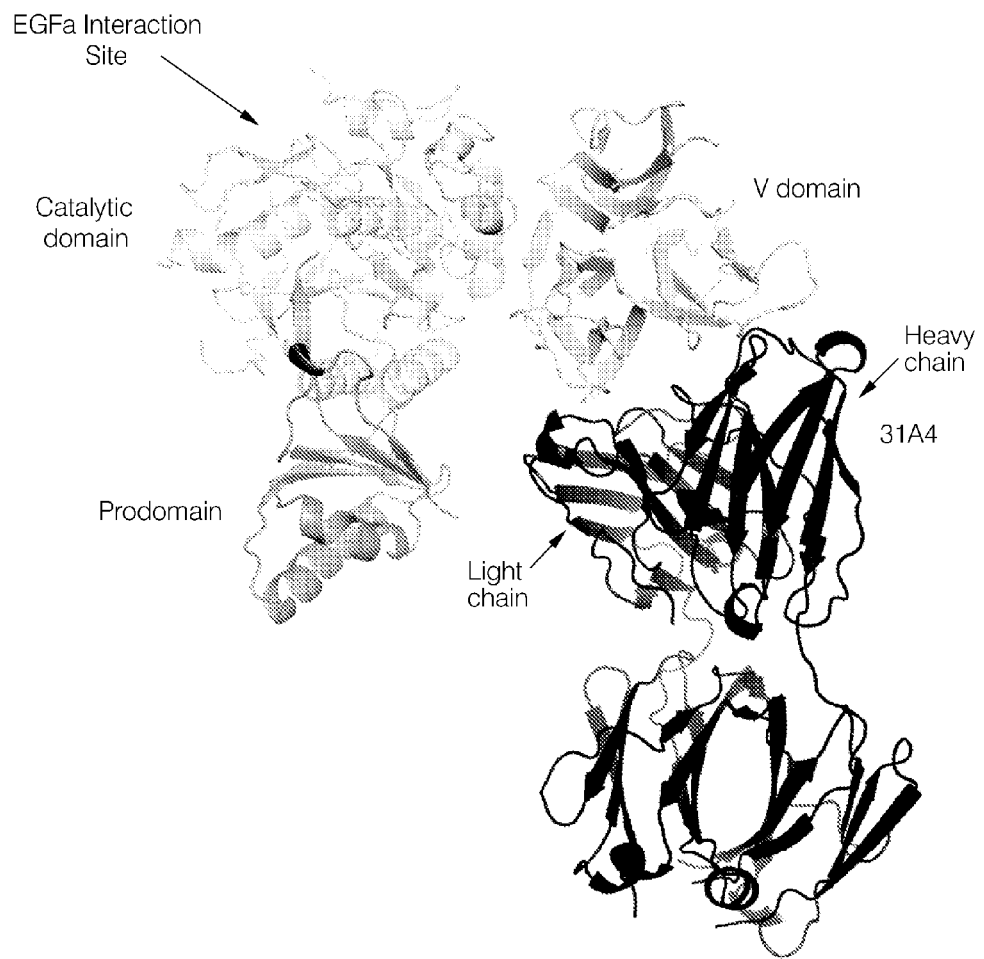

FIG. 21D is a depiction of the structural model of full length PCSK9 and 31A4.

FIG. 22 is a set of ABP sequences identifying various differences between the human ABP sequences and the ABP sequences that were raised in E. coli and used for the crystal structures.

Figure 23B:
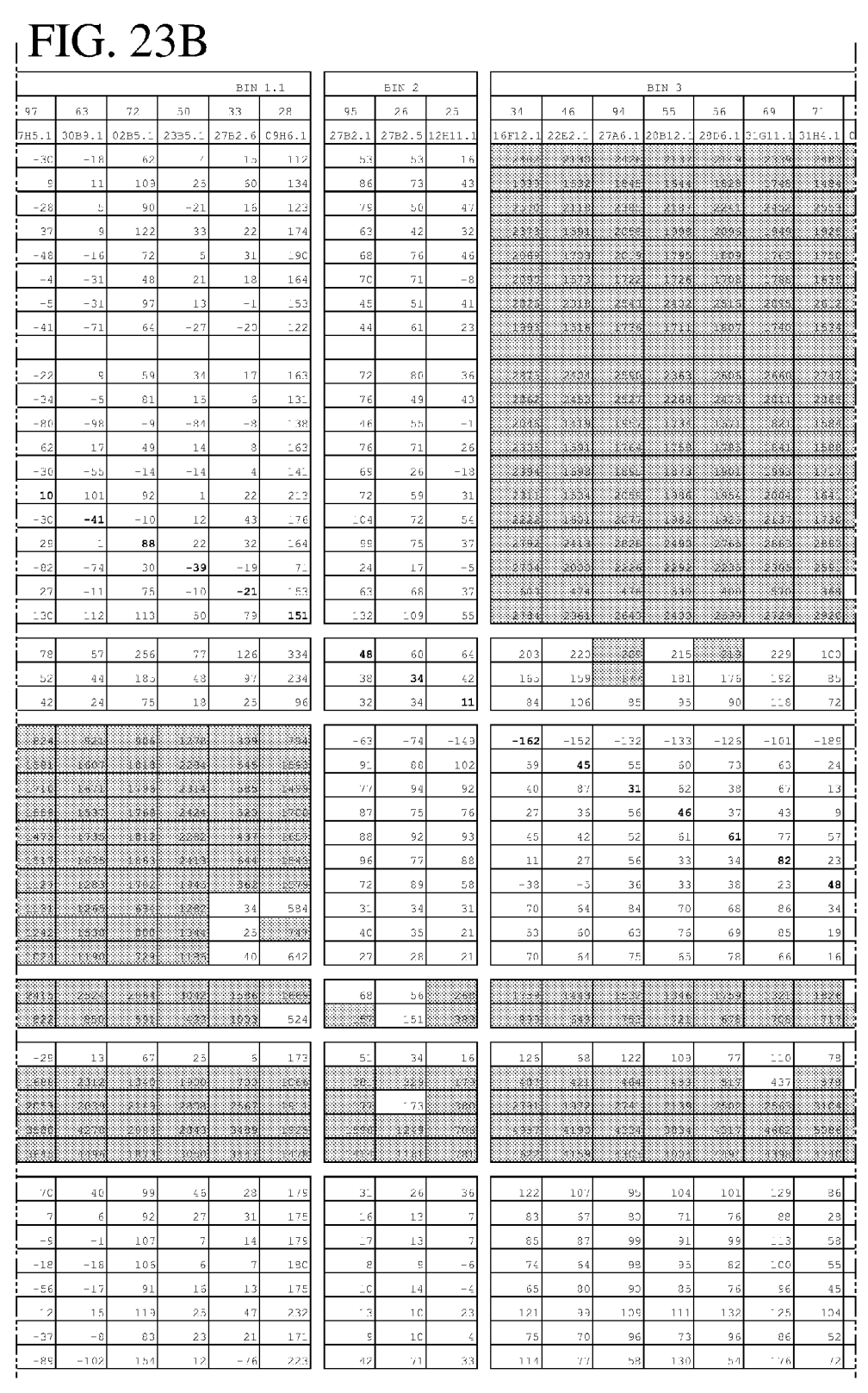
Figure 23C:
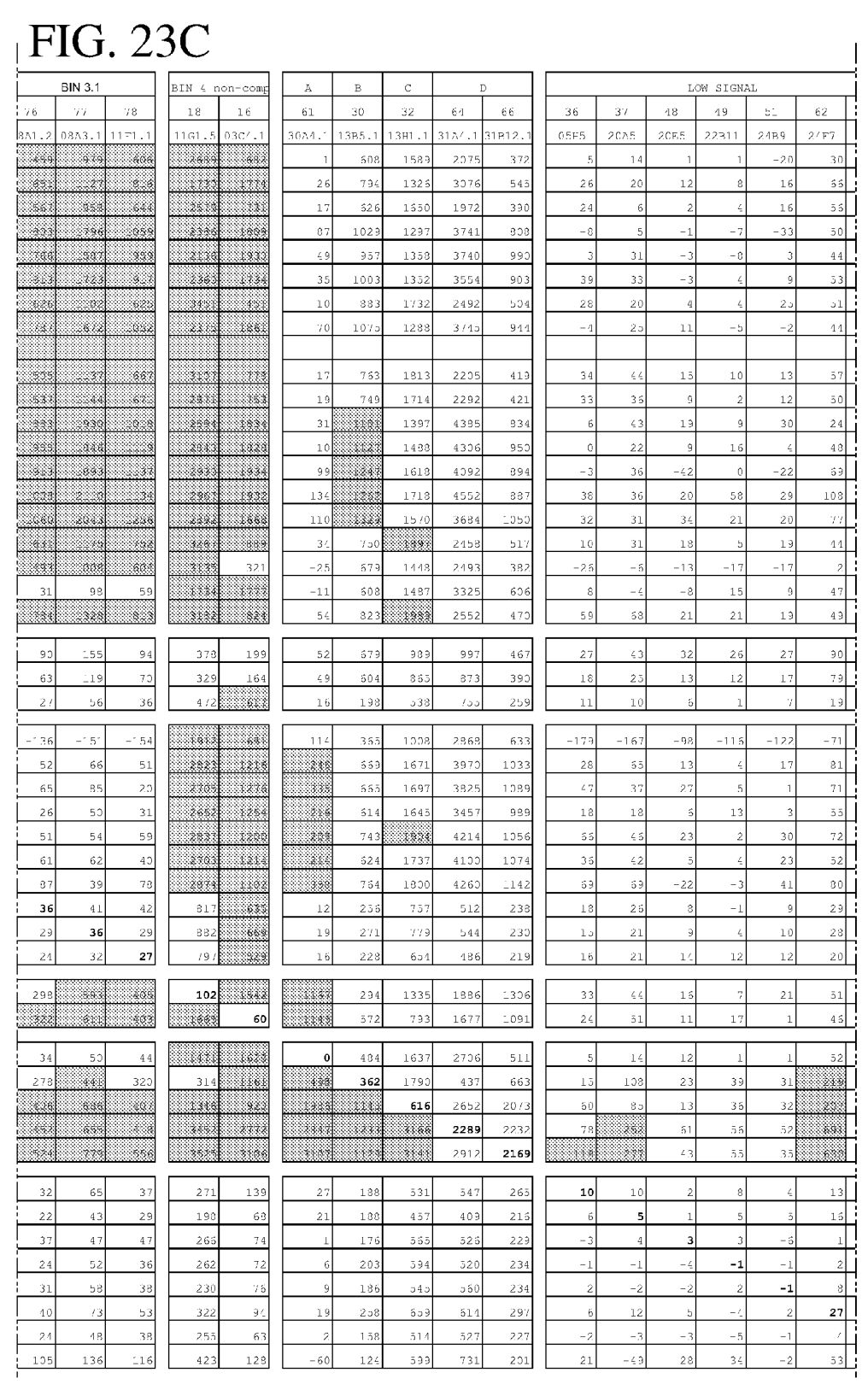
Figures 23, 23D:
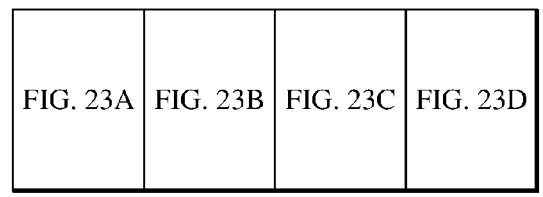

FIG. 23 is a table depicting the various binning results.

FIG. 23A is a first part of a table depicting the various binning results.

FIG. 23B is a second part of a table depicting the various binning results.

FIG. 23C is a third part of a table depicting the various binning results.

FIG. 23D is a fourth part of a table depicting the various binning results.

Figures 24A, 24B:
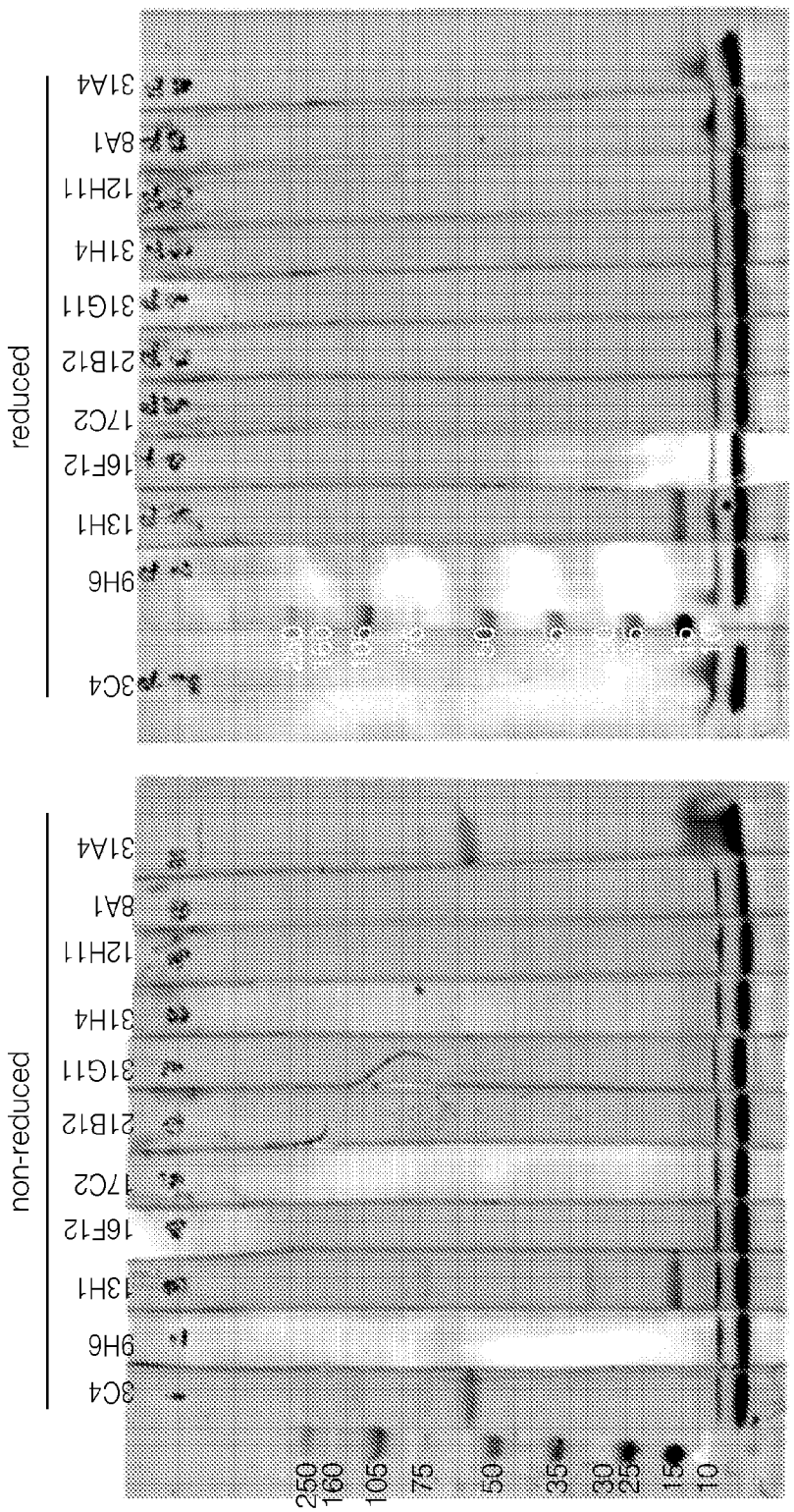

FIG. 24A is a depiction of a western blot under non-reduced conditions.

FIG. 24B is a depiction of a western blot under reduced conditions.

FIG. 25A is a depiction of the surface coverage of PCSK9.
FIG. 25B is a depiction of the surface coverage of PCSK9.
FIG. 25C is a depiction of the surface coverage of PCSK9.
FIG. 25D is a depiction of the surface coverage of PCSK9.
FIG. 25E is a depiction of the surface coverage of PCSK9.
FIG. 25F is a depiction of the surface coverage of PCSK9.

FIG. 26 is a sequence comparison of the PCSK9 amino acid sequence and all of the residues that were mutated in PCSK9 variants to examine the epitopes of the various antibodies.

FIG. 27A depicts the 21B12 epitope hits, as mapped onto a crystal structure of PCSK9 with the 21B12.

Figure 27B:
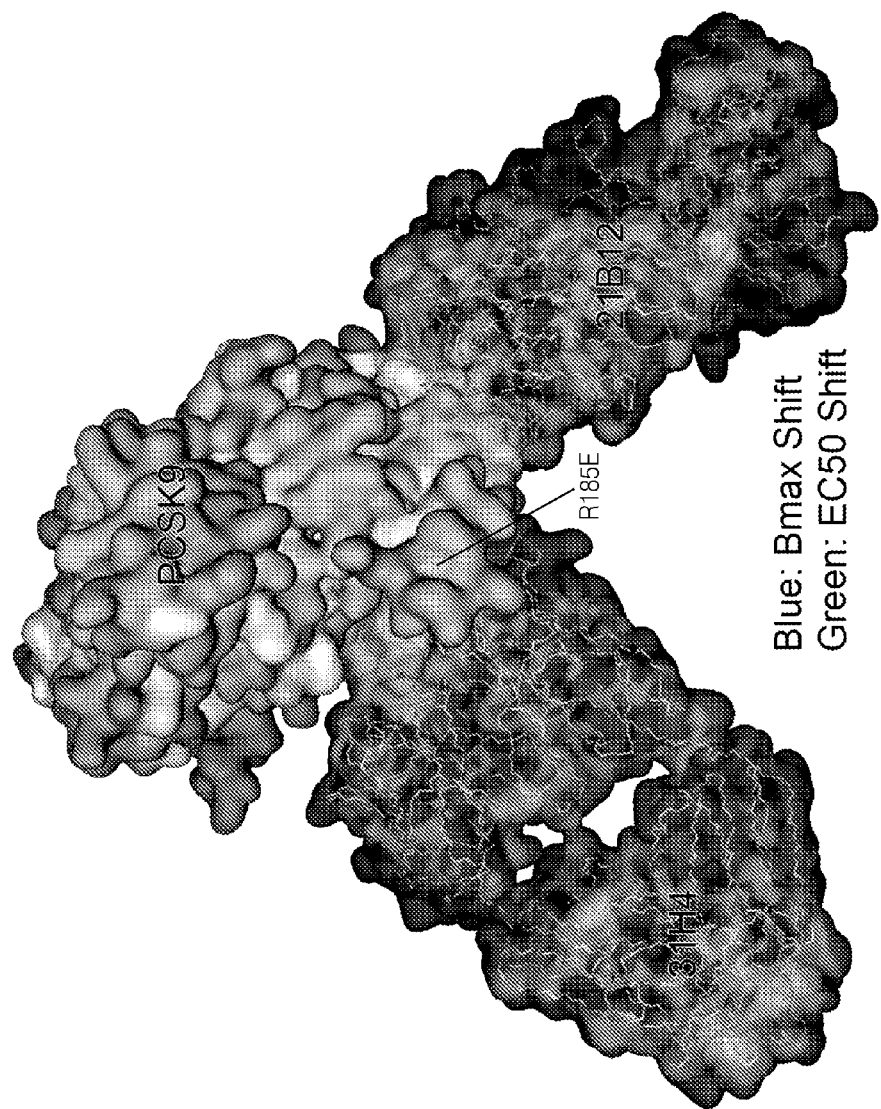

FIG. 27B depicts the 31H4 epitope hits, as mapped onto a crystal structure of PCSK9 with 31H4 and 21B1.

Figure 27C:
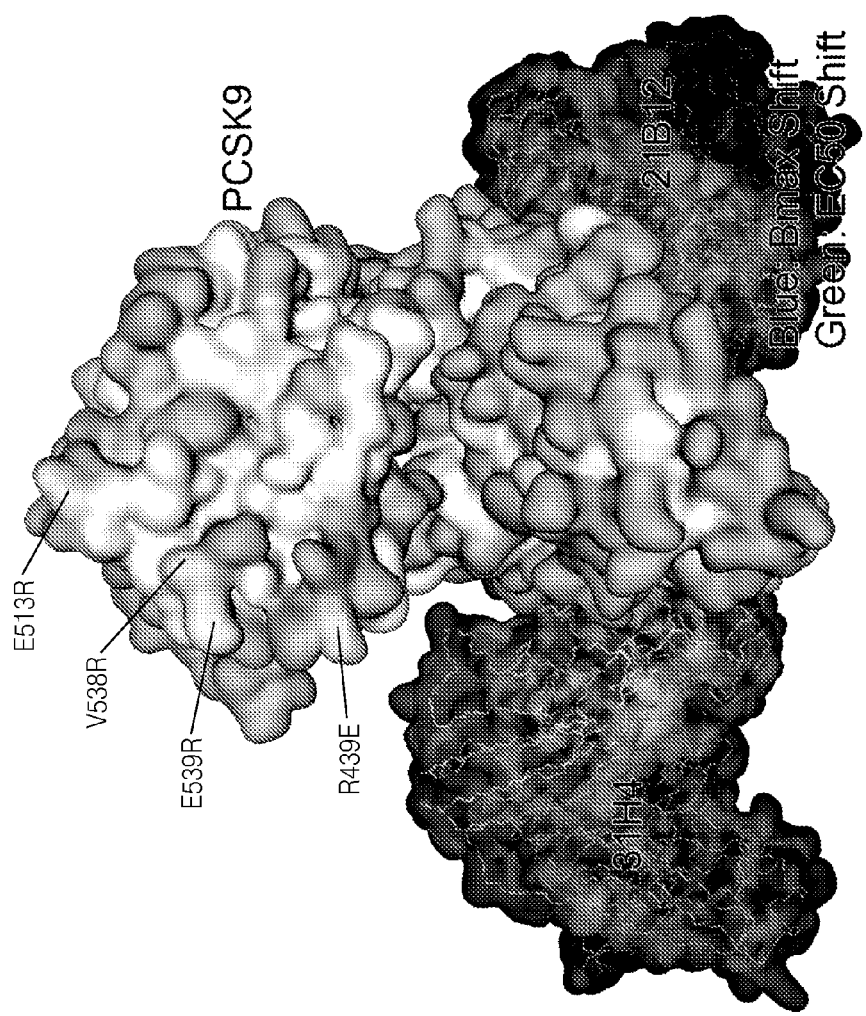

FIG. 27C depicts the 31A4 epitope hits, as mapped onto a crystal structure of PCSK9 with 31H4 and 21B12.

Figure 27D:
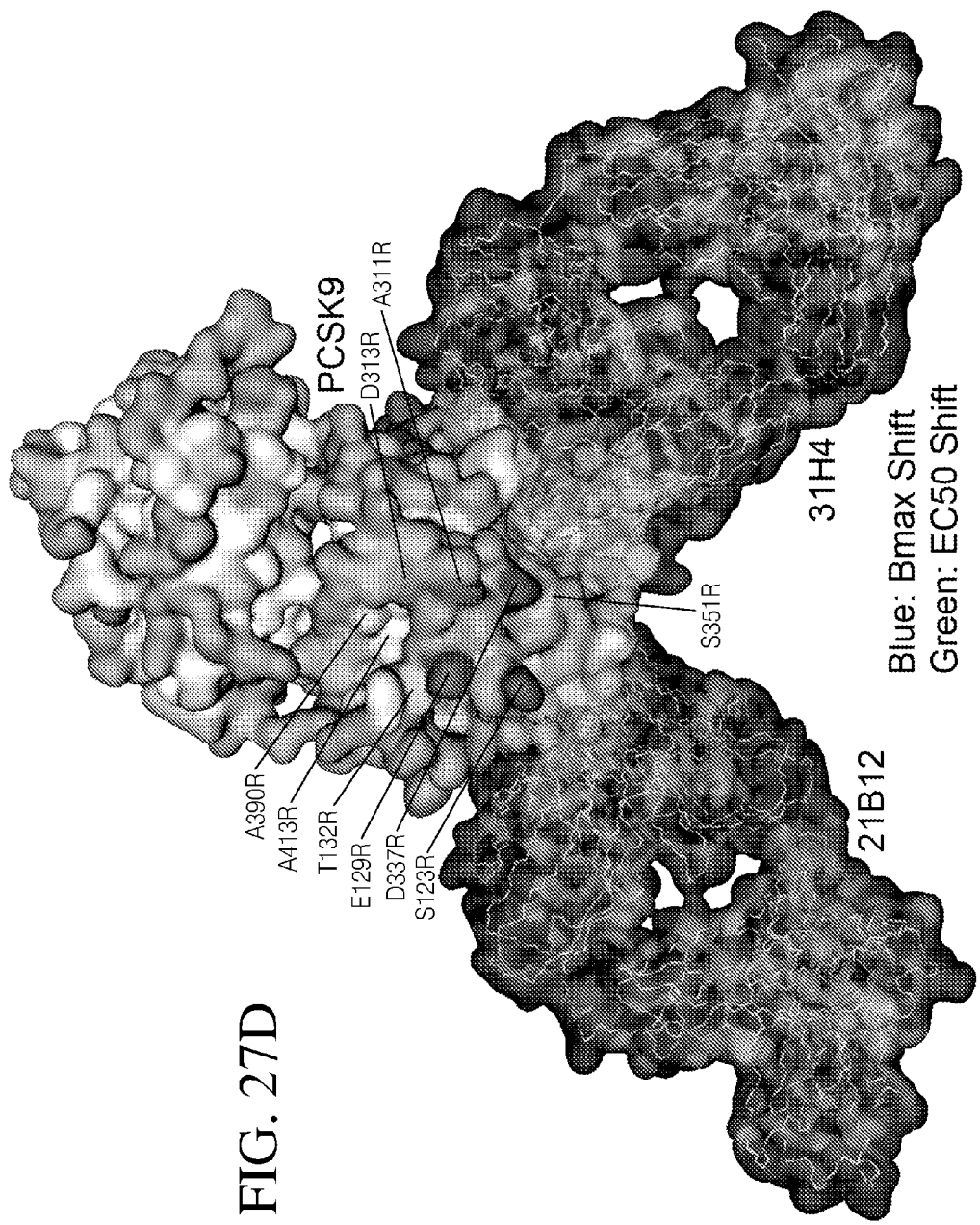

FIG. 27D depicts the 12H11 epitope hits, as mapped onto the crystal structure of PCSK9 with 31H4 and 21B12.

Figure 27E:
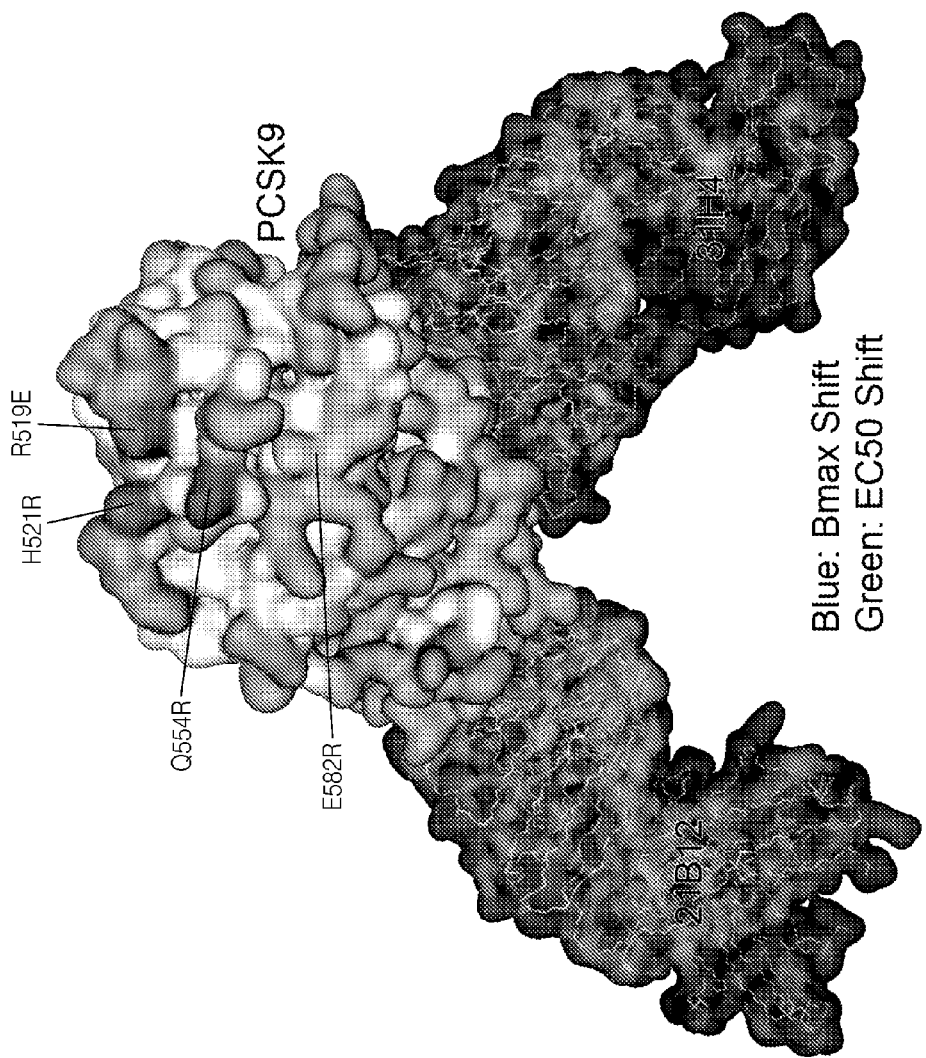

FIG. 27E depicts the 3C4 epitope hits, as mapped onto the crystal structure of PCSK9 with 31H4 and 21B12.

Figure 28A:
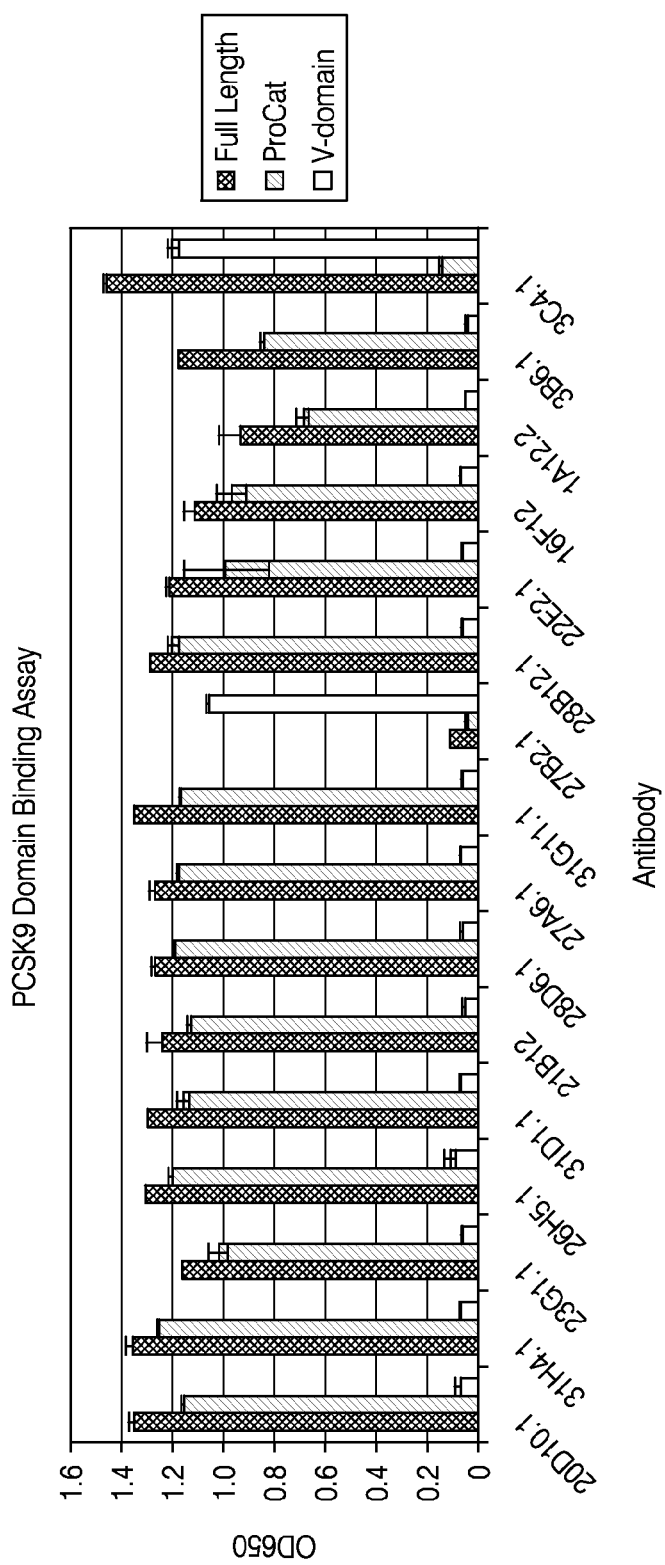

FIG. 28A is a graph demonstrating the binding ability of the various ABPs to various parts of PCSK9.

Figure 28B:
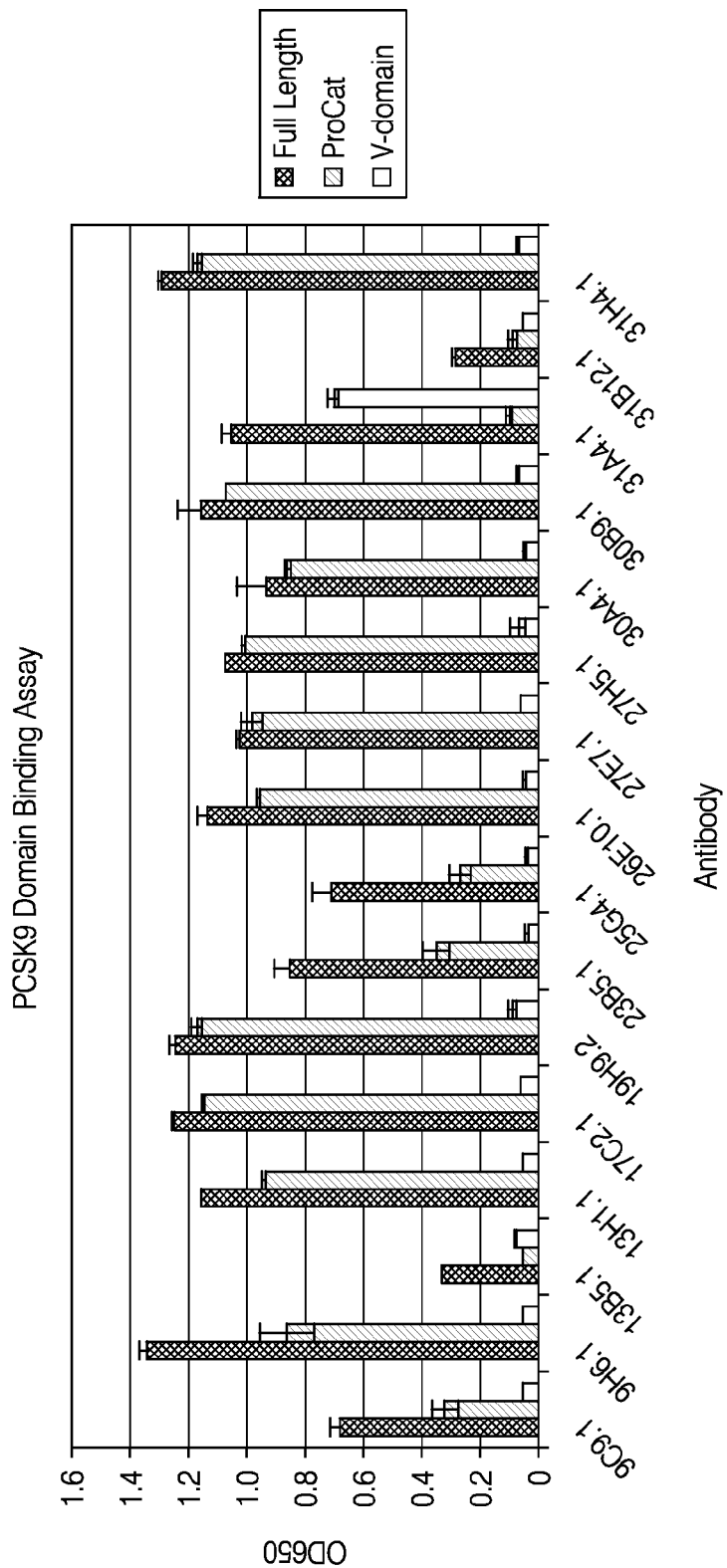

FIG. 28B is a graph demonstrating the binding ability of the various ABPs to various parts of PCSK9.

Figure 28C:
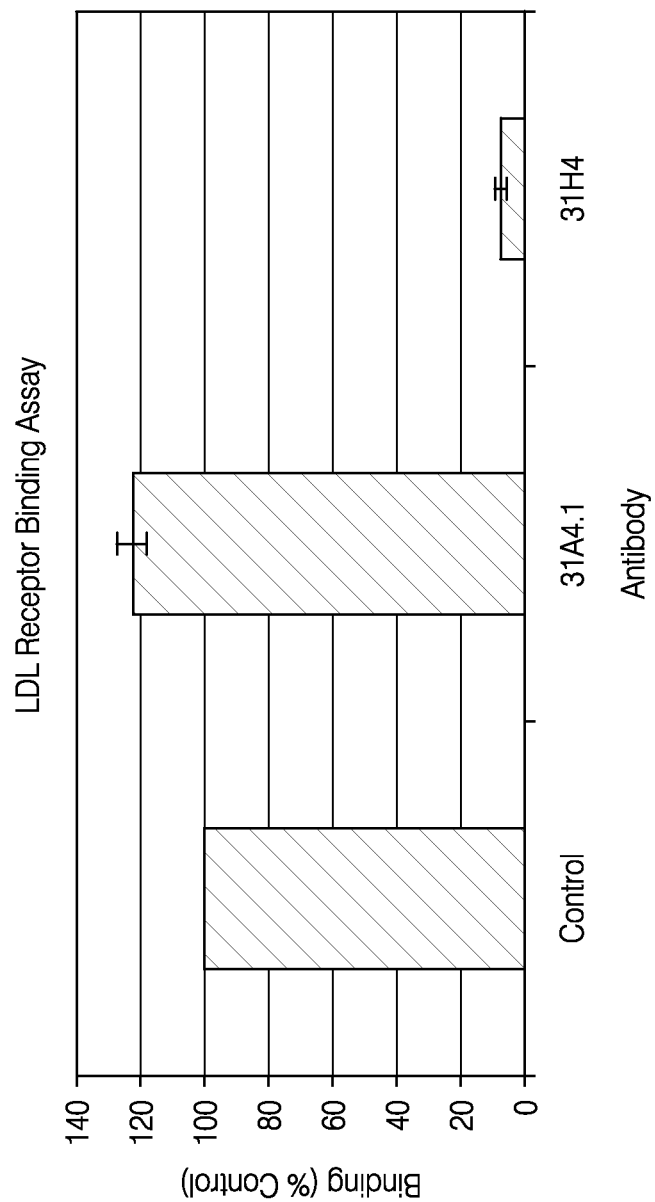

FIG. 28C is a graph comparing the LDLR binding ability of two ABPs.

Figure 28D:
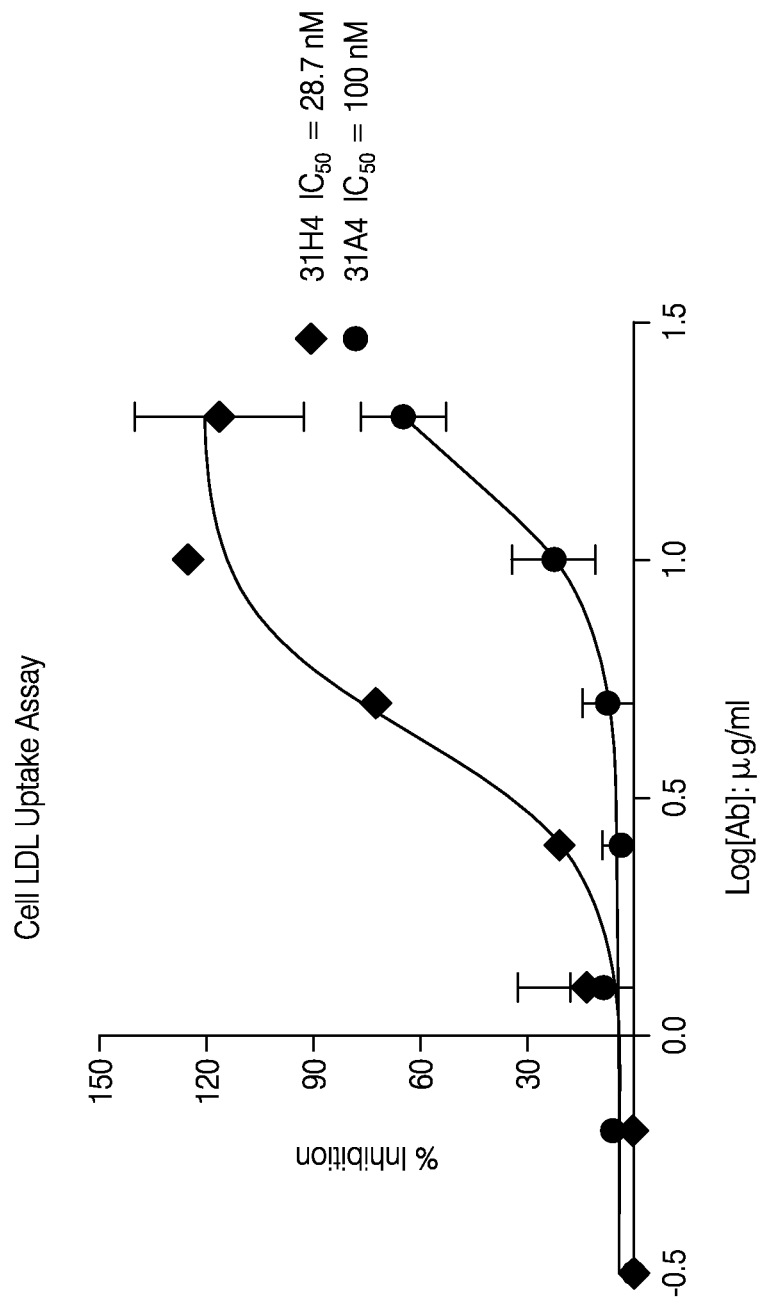

FIG. 28D is a graph comparing the cell LDL uptake activity of two ABPs.

DETAILED DESCRIPTION OF CERTAIN EXEMPLARY EMBODIMENTS

Antigen binding proteins (such as antibodies and functional binding fragments thereof) that bind to PCSK9 are disclosed herein. In some embodiments, the antigen binding proteins bind to PCSK9 and prevent PCSK9 from functioning in various ways. In some embodiments, the antigen binding proteins block or reduce the ability of PCSK9 to interact with other substances. For example, in some embodiments, the antigen binding protein binds to PCSK9 in a manner that prevents or reduces the likelihood that PCSK9 will bind to LDLR. In other embodiments, antigen binding proteins bind to PCSK9 but do not block PCSK9's ability to interact with LDLR. In some embodiments, the antigen binding proteins are human monoclonal antibodies.

As will be appreciated by one of skill in the art, in light of the present disclosure, altering the interactions between PCSK9 and LDLR can increase the amount of LDLR available for binding to LDL, which in turn decreases the amount of serum LDL in a subject, resulting in a reduction in the subject's serum cholesterol level. As such, antigen binding proteins to PCSK9 can be used in various methods and compositions for treating subjects with elevated serum cholesterol levels, at risk of elevated serum cholesterol levels, or which could benefit from a reduction in their serum cholesterol levels. Thus, various methods and techniques for lowering, maintaining, or preventing an increase in serum cholesterol are also described herein. In some embodiments, the antigen binding protein allows for binding between PCSK9 and LDLR, but the antigen binding protein prevents or reduces the adverse activity of PCSK9 on LDLR. In some embodiments, the antigen binding protein prevents or reduces the binding of PCSK9 to LDLR.

For convenience, the following sections generally outline the various meanings of the terms used herein. Following this discussion, general aspects regarding antigen binding proteins are discussed, followed by specific examples demonstrating the properties of various embodiments of the antigen binding proteins and how they can be employed.

Definitions and Embodiments

It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. As utilized in accordance with the present disclosure, the following terms, unless otherwise indicated, shall be understood to have the following meanings:

The term "proprotein convertase subtilisin kexin type 9" or "PCSK9" refers to a polypeptide as set forth in SEQ ID NO: 1 and/or 3 or fragments thereof, as well as related polypeptides, which include, but are not limited to, allelic variants, splice variants, derivative variants, substitution variants, deletion variants, and/or insertion variants including the addition of an N-terminal methionine, fusion polypeptides, and interspecies homologs. In certain embodiments, a PCSK9 polypeptide includes terminal residues, such as, but not limited to, leader sequence residues, targeting residues, amino terminal methionine residues, lysine residues, tag residues and/or fusion protein residues. "PCSK9" has also been referred to as FH3, NARC1, HCHOLA3, proprotein convertase subtilisin/kexin type 9, and neural apoptosis regulated convertase 1. The PCSK9 gene encodes a proprotein convertase protein that belongs to the proteinase K subfamily of the secretory subtilase family. The term "PCSK9" denotes both the proprotein and the product generated following autocatalysis of the proprotein. When only the autocatalyzed product is being referred to (such as for an antigen binding protein that selectively binds to the cleaved PCSK9), the protein can be referred to as the "mature," "cleaved", "processed" or "active" PCSK9. When only the inactive form is being referred to, the protein can be referred to as the "inactive", "pro-form", or "unprocessed" form of PCSK9. The term PCSK9 as used herein also includes naturally occurring alleles, such as the mutations D374Y, S127R and F216L. The term PCSK9 also encompasses PCSK9 molecules incorporating post-translational modifications of the PCSK9 amino acid sequence, such as PCSK9 sequences that have been glycosylated, PEGylated, PCSK9 sequences from which its signal sequence has been cleaved, PCSK9 sequence from which its pro domain has been cleaved from the catalytic domain but not separated from the catalytic domain (e.g., FIGS. 1A and 1B).

The term "PCSK9 activity" includes any biological effect of PCSK9. In certain embodiments, PCSK9 activity includes the ability of PCSK9 to interact or bind to a substrate or receptor. In some embodiments, PCSK9 activity is represented by the ability of PCSK9 to bind to a LDL receptor (LDLR). In some embodiments, PCSK9 binds to and catalyzes a reaction involving LDLR. In some embodiments, PCSK9 activity includes the ability of PCSK9 to alter (e.g., reduce) the availability of LDLR. In some embodiments, PCSK9 activity includes the ability of PCSK9 to increase the amount of LDL in a subject. In some embodiments, PCSK9 activity includes the ability of PCSK9 to decrease the amount of LDLR that is available to bind to LDL. In some embodiments, "PCSK9 activity" includes any biological activity resulting from PCSK9 signaling. Exemplary activities include, but are not limited to, PCSK9 binding to LDLR, PCSK9 enzyme activity that cleaves LDLR or other proteins, PCSK9 binding to proteins other than LDLR that facilitate PCSK9 action, PCSK9 altering APOB secretion (Sun X-M et al, "Evidence for effect of mutant PCSK9 on apoliprotein B secretion as the cause of unusually severe dominant hypercholesterolemia, Human Molecular Genetics 14: 1161-1169, 2005 and Ouguerram K et al, "Apolipoprotein B100 metabolism in autosomal-dominant hypercholesterolemia related to mutations in PCSK9, Arterioscler thromb Vasc Biol. 24: 1448-1453, 2004), PCSK9's role in liver regeneration and neuronal cell differentiation (Seidah N G et al, "The secretory proprotein convertase neural apoptosis-regulated convertase 1 (NARC-1): Liver regeneration and neuronal differentiation" PNAS 100: 928-933, 2003), and PCSK9s role in hepatic glucose metabolism (Costet et al., "Hepatic PCSK9 expression is regulated by nutritional status via insulin and sterol regulatory element-binding protein 1c" *J. Biol. Chem.* 281 (10):6211-18, 2006).

The term "hypercholesterolemia," as used herein, refers to a condition in which cholesterol levels are elevated above a desired level. In some embodiments, this denotes that serum cholesterol levels are elevated. In some embodiments, the desired level takes into account various "risk factors" that are known to one of skill in the art (and are described or referenced herein).

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The term "oligonucleotide" means a polynucleotide comprising 200 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides can be single stranded or double stranded, e.g., for use in the construction of a mutant gene. Oligonucleotides can be sense or antisense oligonucleotides. An oligonucleotide can include a label, including a radiolabel, a fluorescent label, a hapten or an antigenic label, for detection assays. Oligonucleotides can be used, for example, as PCR primers, cloning primers or hybridization probes.

An "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences can include, in addition to the specified sequences, coding sequences for up to ten or even up to twenty other proteins or portions thereof, or can include operably linked regulatory sequences that control expression of the coding region of the recited nucleic acid sequences, and/or can include vector sequences.

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The term "control sequence" refers to a polynucleotide sequence that can affect the expression and processing of coding sequences to which it is ligated. The nature of such control sequences can depend upon the host organism. In particular embodiments, control sequences for prokaryotes can include a promoter, a ribosomal binding site, and a transcription termination sequence. For example, control sequences for eukaryotes can include promoters comprising one or a plurality of recognition sites for transcription factors, transcription enhancer sequences, and transcription termination sequence. "Control sequences" can include leader sequences and/or fusion partner sequences.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct can include, but is not limited to, sequences that affect or control transcription, translation, and, if introns are present, affect RNA splicing of a coding region operably linked thereto.

As used herein, "operably linked" means that the components to which the term is applied are in a relationship that allows them to carry out their inherent functions under suitable conditions. For example, a control sequence in a vector that is "operably linked" to a protein coding sequence is ligated thereto so that expression of the protein coding sequence is achieved under conditions compatible with the transcriptional activity of the control sequences.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al, 1973, *Virology* 52:456; Sambrook et al., 2001, Molecular Cloning: A Laboratory Manual, supra; Davis et al, 1986, *Basic Methods in Molecular Biology*, Elsevier; Chu et al, 1981, *Gene* 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA can recombine with that of the cell by physically integrating into a chromosome of the cell, or can be maintained transiently as an episomal element without being replicated, or can replicate independently as a plasmid. A cell is considered to have been "stably transformed" when the transforming DNA is replicated with the division of the cell.

The terms "polypeptide" or "protein" means a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally-occurring amino acid and polymers. The terms "polypeptide" and "protein" specifically encompass PCSK9 antigen binding proteins, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. In certain embodiments, fragments are about five to 500 amino acids long. For example, fragments can be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a PCSK9-binding antibody, useful fragments include but are not limited to a CDR region, a variable domain of a heavy and/or light chain, a portion of an antibody chain or just its variable region including two CDRs, and the like.

The term "isolated protein" referred means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Typically, an "isolated protein" constitutes at least about 5%, at least about 10%, at least about 25%, or at least about 50% of a given sample. Genomic DNA, cDNA, mRNA or other RNA, of synthetic origin, or any combination thereof can encode such an isolated protein. Preferably, the isolated protein is substantially free from proteins or polypeptides or other contaminants that are found in its natural environment that would interfere with its therapeutic, diagnostic, prophylactic, research or other use.

The term "amino acid" includes its normal meaning in the art.

A "variant" of a polypeptide (e.g., an antigen binding protein, or an antibody) comprises an amino acid sequence wherein one or more amino acid residues are inserted into, deleted from and/or substituted into the amino acid sequence relative to another polypeptide sequence. Variants include fusion proteins.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in *Computational Molecular Biology*, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, *SIAM J. Applied Math.* 48:1073.

In calculating percent identity, the sequences being compared are typically aligned in a way that gives the largest match between the sequences. One example of a computer program that can be used to determine percent identity is the GCG program package, which includes GAP (Devereux et al., 1984, *Nucl. Acid Res.* 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually ⅒ times the gap opening penalty), as well as a comparison matrix such as PAM 250 or BLOSUM 62 are used in conjunction with the algorithm. In certain embodiments, a standard comparison matrix (see, Dayhoff et al., 1978, *Atlas of Protein Sequence and Structure* 5:345-352 for the PAM 250 comparison matrix; Henikoff et al., 1992, *Proc. Natl. Acad. Sci. U.S.A.* 89:10915-10919 for the BLOSUM 62 comparison matrix) is also used by the algorithm.

Examples of parameters that can be employed in determining percent identity for polypeptides or nucleotide sequences using the GAP program are the following:

Algorithm: Needleman et al., 1970, *J. Mol. Biol.* 48:443-453

Comparison matrix: BLOSUM 62 from Henikoff et al., 1992, supra

Gap Penalty: 12 (but with no penalty for end gaps)

Gap Length Penalty: 4

Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 or other number of contiguous amino acids of the target polypeptide.

As used herein, the twenty conventional (e.g., naturally occurring) amino acids and their abbreviations follow conventional usage. See *Immunology—A Synthesis* (2nd Edition, E. S. Golub and D. R. Gren, Eds., Sinauer Associates, Sunderland, Mass. (1991)), which is incorporated herein by reference for any purpose. Stereoisomers (e.g., D-amino acids) of the twenty conventional amino acids, unnatural amino acids such as α-, α-disubstituted amino acids, N-alkyl amino acids, lactic acid, and other unconventional amino acids can also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetyl serine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences."

Conservative amino acid substitutions can encompass non-naturally occurring amino acid residues, which are typically incorporated by chemical peptide synthesis rather than by synthesis in biological systems. These include peptidomimetics and other reversed or inverted forms of amino acid moieties.

Naturally occurring residues can be divided into classes based on common side chain properties:

1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions can involve the exchange of a member of one of these classes for a member from another class. Such substituted residues can be introduced, for example, into regions of a human antibody that are homologous with non-human antibodies, or into the non-homologous regions of the molecule.

In making changes to the antigen binding protein or the PCSK9 protein, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., J. Mol. Biol., 157:105-131 (1982). It is known that certain amino acids can be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One can also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding protein can have a greater circulating half-life than an antigen binding protein that is not chemically modified. In certain embodiments, a chemically modified antigen binding protein can have improved targeting capacity for desired cells, tissues, and/or organs. In some embodiments, a derivative antigen binding protein is covalently modified to include one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative antigen binding protein comprises one or more polymer, including, but not limited to, monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers.

In certain embodiments, a derivative is covalently modified with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity for an antigen binding protein. In certain embodiments, PEG is used to improve the therapeutic capacity for a humanized antibody. Certain such methods are discussed, for example, in U.S. Pat. No. 6,133,426, which is hereby incorporated by reference for any purpose.

Peptide analogs are commonly used in the pharmaceutical industry as non-peptide drugs with properties analogous to those of the template peptide. These types of non-peptide compound are termed "peptide mimetics" or "peptidomimetics." Fauchere, J., Adv. Drug Res., 15:29 (1986); Veber & Freidinger, TINS, p. 392 (1985); and Evans et al., J. Med. Chem., 30:1229 (1987), which are incorporated herein by reference for any purpose. Such compounds are often developed with the aid of computerized molecular modeling. Peptide mimetics that are structurally similar to therapeutically useful peptides can be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —$CH_2$ NH—, —$CH_2$ S—, —$CH_2$—$CH_2$—, —CH=CH-(cis and trans), —$COCH_2$—$CH(OH)CH_2$—, and —$CH_2$ SO—, by methods well known in the art. Systematic substitution of one or more amino acids of a consensus sequence with a D-amino acid of the same type (e.g., D-lysine in place of L-lysine) can be used in certain embodiments to generate more stable peptides. In addition, constrained peptides comprising a consensus sequence or a substantially identical consensus sequence variation can be generated by methods known in the art (Rizo and Gierasch, Ann. Rev. Biochem., 61:387 (1992), incorporated herein by reference for any purpose); for example, by adding internal cysteine residues capable of forming intramolecular disulfide bridges which cyclize the peptide.

The term "naturally occurring" as used throughout the specification in connection with biological materials such as polypeptides, nucleic acids, host cells, and the like, refers to materials which are found in nature or a form of the materials that is found in nature.

An "antigen binding protein" ("ABP") as used herein means any protein that binds a specified target antigen. In the instant application, the specified target antigen is the PCSK9 protein or fragment thereof "Antigen binding protein" includes but is not limited to antibodies and binding parts thereof, such as immunologically functional fragments. Peptibodies are another example of antigen binding proteins. The term "immunologically functional fragment" (or simply "fragment") of an antibody or immunoglobulin chain (heavy or light chain) antigen binding protein, as used herein, is a species of antigen binding protein comprising a portion (regardless of how that portion is obtained or synthesized) of an antibody that lacks at least some of the amino acids present in a full-length chain but which is still capable of specifically binding to an antigen. Such fragments are biologically active in that they bind to the target antigen and can compete with other antigen binding proteins, including intact antibodies, for binding to a given epitope. In some embodiments, the fragments are neutralizing fragments. In some embodiments, the fragments can block or reduce the likelihood of the interaction between LDLR and PCSK9. In one aspect, such a fragment will retain at least one CDR present in the full-length light or heavy chain, and in some embodiments will comprise a single heavy chain and/or light chain or portion thereof. These biologically active fragments can be produced by recombinant DNA techniques, or can be produced by enzymatic or chemical cleavage of antigen binding proteins, including intact antibodies. Immunologically functional immunoglobulin fragments include, but are not limited to, Fab, a diabody (heavy chain variable domain on the same polypeptide as a light chain variable domain, connected via a short peptide linker that is too short to permit pairing between the two domains on the same chain), Fab', F(ab)$_2$, Fv, domain antibodies and single-chain antibodies, and can be derived from any mammalian source, including but not limited to human, mouse, rat, camelid or rabbit. It is further contemplated that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life. As will be appreciated by one of skill in the art, an antigen binding protein can include nonprotein components. In some sections of the present disclosure, examples of ABPs are described herein in terms of "number/letter/number" (e.g., 25A7). In these cases, the exact name denotes a specific antibody. That is, an ABP named 25A7 is not necessarily the same as an antibody named 25A7.1, (unless they are explicitly taught as the same in the specification, e.g., 25A7 and 25A7.3). As will be appreciated by one of skill in the art, in some embodiments LDLR is not an antigen binding protein. In some embodiments, binding subsections of LDLR are not antigen binding proteins, e.g., EGFa. In some embodiments, other molecules through which PCSK9 signals in vivo are not antigen binding proteins. Such embodiments will be explicitly identified as such.

Certain antigen binding proteins described herein are antibodies or are derived from antibodies. In certain embodiments, the polypeptide structure of the antigen binding proteins is based on antibodies, including, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the ABP comprises or consists of avimers (tightly binding peptide). These various antigen binding proteins are further described herein.

An "Fc" region comprises two heavy chain fragments comprising the $C_H1$ and $C_H2$ domains of an antibody. The two heavy chain fragments are held together by two or more disulfide bonds and by hydrophobic interactions of the $C_H3$ domains.

A "Fab fragment" comprises one light chain and the $C_H1$ and variable regions of one heavy chain. The heavy chain of a Fab molecule cannot form a disulfide bond with another heavy chain molecule.

A "Fab' fragment" comprises one light chain and a portion of one heavy chain that contains the VH domain and the $C_H1$ domain and also the region between the $C_H1$ and $C_H2$ domains, such that an interchain disulfide bond can be formed between the two heavy chains of two Fab' fragments to form an F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen binding region. Single chain antibodies are discussed in detail in International Patent Application Publication No. WO 88/01649 and U.S. Pat. No. 4,946,778 and U.S. Pat. No. 5,260,203, the disclosures of which are incorporated by reference.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody can target the same or different antigens.

A "bivalent antigen binding protein" or "bivalent antibody" comprises two antigen binding sites. In some instances, the two binding sites have the same antigen specificities. Bivalent antigen binding proteins and bivalent antibodies can be bispecific, see, infra. A bivalent antibody other than a "multispecific" or "multifunctional" antibody, in certain embodiments, typically is understood to have each of its binding sites identical.

A "multispecific antigen binding protein" or "multispecific antibody" is one that targets more than one antigen or epitope.

A "bispecific," "dual-specific" or "bifunctional" antigen binding protein or antibody is a hybrid antigen binding protein or antibody, respectively, having two different antigen binding sites. Bispecific antigen binding proteins and antibodies are a species of multispecific antigen binding protein antibody and can be produced by a variety of methods including, but not limited to, fusion of hybridomas or linking of Fab' fragments. See, e.g., Songsivilai and Lachmann, 1990, *Clin. Exp. Immunol.* 79:315-321; Kostelny et al., 1992, *J. Immunol.* 148:1547-1553. The two binding sites of a bispecific antigen binding protein or antibody will bind to two different epitopes, which can reside on the same or different protein targets.

An antigen binding protein is said to "specifically bind" its target antigen when the dissociation constant ($K_d$) is $\leq 10^{-7}$ M. The ABP specifically binds antigen with "high affinity" when the $K_d$ is $\leq 5 \times 10^{-9}$ M, and with "very high affinity" when the $K_d$ is $\leq 5 \times 10^{-10}$ M. In one embodiment, the ABP has a $K_d$ of $\leq 10^{-9}$ M. In one embodiment, the off-rate is $<1 \times 10^{-5}$. In other embodiments, the ABPs will bind to human PCSK9 with a $K_d$ of between about $10^{-9}$ M and $10^{-13}$ M, and in yet another embodiment the ABPs will bind with a $K_d \leq 5 \times 10^{-10}$. As will be appreciated by one of skill in the art, in some embodiments, any or all of the antigen binding fragments can specifically bind to PCSK9.

An antigen binding protein is "selective" when it binds to one target more tightly than it binds to a second target.

"Antigen binding region" means a protein, or a portion of a protein, that specifically binds a specified antigen (e.g., a paratope). For example, that portion of an antigen binding protein that contains the amino acid residues that interact with an antigen and confer on the antigen binding protein its specificity and affinity for the antigen is referred to as "antigen binding region." An antigen binding region typically includes one or more "complementary binding regions" ("CDRs"). Certain antigen binding regions also include one or more "framework" regions. A "CDR" is an amino acid sequence that contributes to antigen binding specificity and affinity. "Framework" regions can aid in maintaining the proper conformation of the CDRs to promote binding between the antigen binding region and an antigen. Structurally, framework regions can be located in antibodies between CDRs. Examples of framework and CDR regions are shown in FIGS. 2A-3D, 3CCC-3JJJ, and 15A-15D. In some embodiments, the sequences for CDRs for the light chain of antibody 3B6 are as follows: CDR1 TLSSGYSSYEVD (SEQ ID NO: 279); CDR2 VDTGGIVGSKGE (SEQ ID NO: 280); CDR3 GADHGSGTNFVVV (SEQ ID NO: 281), and the FRs are as follows: FR1 QPVLTQPLFASASLGASVTLTC (SEQ ID NO: 282); FR2 WYQQRPGKGPRFVMR (SEQ ID NO: 283); FR3 GIPDRFSVLGSGLNRYLTIKNIQEEDESDYHC (SEQ ID NO: 284); and FR4 FGGGTKLTVL (SEQ ID NO: 285).

In certain aspects, recombinant antigen binding proteins that bind PCSK9, for example human PCSK9, are provided. In this context, a "recombinant antigen binding protein" is a protein made using recombinant techniques, i.e., through the expression of a recombinant nucleic acid as described herein. Methods and techniques for the production of recombinant proteins are well known in the art.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen binding protein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies as described further below. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

Naturally occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that can be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., *Fundamental Immunology*, Ch. 7 (Paul, W., ed., 2nd ed. Raven Press, N.Y. (1989)) (incorporated by reference in its entirety for all purposes). The variable regions of each light/heavy chain pair typically form the antigen binding site.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk, J. Mol. Biol., 196:901-917 (1987); Chothia et al., Nature, 342:878-883 (1989).

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition and the contact definition.

The Kabat definition is a standard for numbering the residues in an antibody and is typically used to identify CDR regions. See, e.g., Johnson & Wu, Nucleic Acids Res., 28: 214-8 (2000). The Chothia definition is similar to the Kabat definition, but the Chothia definition takes into account positions of certain structural loop regions. See, e.g., Chothia et al., J. Mol. Biol., 196: 901-17 (1986); Chothia et al., Nature, 342: 877-83 (1989). The AbM definition uses an integrated suite of computer programs produced by Oxford Molecular Group that model antibody structure. See, e.g., Martin et al., Proc Natl Acad Sci (USA), 86:9268-9272 (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999). The contact definition is based on an analysis of the available complex crystal structures. See, e.g., MacCallum et al, J. Mol. Biol., 5:732-45 (1996).

By convention, the CDR regions in the heavy chain are typically referred to as H1, H2, and H3 and are numbered sequentially in the direction from the amino terminus to the carboxy terminus. The CDR regions in the light chain are typically referred to as L1, L2, and L3 and are numbered sequentially in the direction from the amino terminus to the carboxy terminus.

The term "light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, $V_H$, and three constant region domains, $C_H1$, $C_H2$, and $C_H3$. The $V_H$ domain is at the amino-terminus of the polypeptide, and the $C_H$ domains are at the carboxyl-terminus, with the $C_H3$ being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

A bispecific or bifunctional antibody typically is an artificial hybrid antibody having two different heavy/light chain pairs and two different binding sites. Bispecific antibodies can be produced by a variety of methods including, but not limited to, fusion of hybridomas or linking of Fab' fragments. See, e.g., Songsivilai et al., Clin. Exp. Immunol., 79: 315-321 (1990); Kostelny et al., J. Immunol., 148:1547-1553 (1992).

Some species of mammals also produce antibodies having only a single heavy chain.

Each individual immunoglobulin chain is typically composed of several "immunoglobulin domains," each consisting of roughly 90 to 110 amino acids and having a characteristic folding pattern. These domains are the basic units of which antibody polypeptides are composed. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that can be responsible for effector function. The number of heavy chain constant region domains will depend on the isotype. IgG heavy chains, for example, contain three C region domains known as $C_H1$, $C_H2$ and $C_H3$. The antibodies that are provided can have any of these isotypes and subtypes. In certain embodiments of the present invention, an anti-PCSK9 antibody is of the IgG2 or IgG4 subtype.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target The term "neutralizing antigen binding protein" or "neutralizing antibody" refers to an antigen binding protein or antibody, respectively, that binds to a ligand and prevents or reduces the biological effect of that ligand. This can be done, for example, by directly blocking a binding site on the ligand or by binding to the ligand and altering the ligand's ability to bind through indirect means (such as structural or energetic alterations in the ligand). In some embodiments, the term can also denote an antigen binding protein that prevents the protein to which it is bound from performing a biological function. In assessing the binding and/or specificity of an antigen binding protein, e.g., an antibody or immunologically functional fragment thereof, an antibody or fragment can substantially inhibit binding of a ligand to its binding partner when an excess of antibody reduces the quantity of binding partner bound to the ligand by at least about 1-20, 20-30%, 30-40%, 40-50%, 50-60%, 60-70%, 70-80%, 80-85%, 85-90%, 90-95%, 95-97%, 97-98%, 98-99% or more (as measured in an in vitro competitive binding assay). In some embodiments, in the case of PCSK9 antigen binding proteins, such a neutralizing molecule can diminish the ability of PCSK9 to bind the LDLR. In some embodiments, the neutralizing ability is characterized and/or described via a competition assay. In some embodiments, the neutralizing ability is described in terms of an $IC_{50}$ or $EC_{50}$ value. In some embodiments, ABPs 27B2, 13H1, 13B5 and 3C4 are non-neutralizing ABPs, 3B6, 9C9 and 31A4 are weak neutralizers, and the remaining ABPs in Table 2 are strong neutralizers. In some embodiments, the antibodies or antigen binding proteins neutralize by binding to PCSK9 and preventing PCSK9 from binding to LDLR (or reducing the ability of PCSK9 to bind to LDLR). In some embodiments, the antibodies or ABPs neutralize by binding to PCSK9, and while still allowing PCSK9 to bind to LDLR, preventing or reducing the PCSK9 mediated degradation of LDLR. Thus, in some embodiments, a neutralizing ABP or antibody can still permit PCSK9/LDLR binding, but will prevent (or reduce) subsequent PCSK9 involved degradation of LDLR.

The term "target" refers to a molecule or a portion of a molecule capable of being bound by an antigen binding protein. In certain embodiments, a target can have one or more epitopes. In certain embodiments, a target is an antigen. The use of "antigen" in the phrase "antigen binding protein" simply denotes that the protein sequence that comprises the antigen can be bound by an antibody. In this context, it does not require that the protein be foreign or that it be capable of inducing an immune response.

The term "compete" when used in the context of antigen binding proteins (e.g., neutralizing antigen binding proteins or neutralizing antibodies) that compete for the same epitope means competition between antigen binding proteins as determined by an assay in which the antigen binding protein (e.g., antibody or immunologically functional fragment thereof) being tested prevents or inhibits (e.g., reduces) specific binding of a reference antigen binding protein (e.g., a ligand, or a reference antibody) to a common antigen (e.g., PCSK9 or a fragment thereof). Numerous types of competitive binding assays can be used to determine if one antigen binding protein competes with another, for example: solid phase direct or indirect radioimmunoassay (RIA), solid phase direct or indirect enzyme immunoassay (EIA), sandwich competition assay (see, e.g., Stahli et al., 1983, *Methods in Enzymology* 9:242-253); solid phase direct biotin-avidin EIA (see, e.g., Kirkland et al., 1986, *J. Immunol.* 137:3614-3619) solid phase direct labeled assay, solid phase direct labeled sandwich assay (see, e.g., Harlow and Lane, 1988, *Antibodies, A Laboratory Manual*, Cold Spring Harbor Press); solid phase direct label RIA using I-125 label (see, e.g., Morel et al., 1988, *Molec. Immunol.* 25:7-15); solid phase direct biotin-avidin EIA (see, e.g., Cheung, et al., 1990, *Virology* 176:546-552); and direct labeled RIA (Moldenhauer et al., 1990, *Scand. Immunol.* 32:77-82). Typically, such an assay involves the use of purified antigen bound to a solid surface or cells bearing either of these, an unlabelled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more.

The term "antigen" refers to a molecule or a portion of a molecule capable of being bound by a selective binding agent, such as an antigen binding protein (including, e.g., an antibody or immunological functional fragment thereof). In some embodiments, the antigen is capable of being used in an animal to produce antibodies capable of binding to that antigen. An antigen can possess one or more epitopes that are capable of interacting with different antigen binding proteins, e.g., antibodies.

The term "epitope" includes any determinant capable being bound by an antigen binding protein, such as an antibody or to a T-cell receptor. An epitope is a region of an antigen that is bound by an antigen binding protein that targets that antigen, and when the antigen is a protein, includes specific amino acids that directly contact the antigen binding protein. Most often, epitopes reside on proteins, but in some instances can reside on other kinds of molecules, such as nucleic acids. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of proteins and/or macromolecules.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, or 99% of all macromolecular species present in the composition. In other embodiments, the object species is purified to essential homogeneity wherein contaminating species cannot be detected in the composition by conventional detection methods and thus the composition consists of a single detectable macromolecular species.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotin moieties that can be detected by marked avidin (e.g., streptavidin containing a fluorescent marker or enzymatic activity that can be detected by optical or colorimetric methods). In certain embodiments, the label or marker can also be therapeutic. Various methods of labeling polypeptides and glycoproteins are known in the art and can be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$) fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce potential steric hindrance.

The term "biological sample", as used herein, includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

The term "pharmaceutical agent composition" (or agent or drug) as used herein refers to a chemical compound, composition, agent or drug capable of inducing a desired therapeutic effect when properly administered to a patient. It does not necessarily require more than one type of ingredient.

The term "therapeutically effective amount" refers to the amount of a PCSK9 antigen binding protein determined to produce a therapeutic response in a mammal. Such therapeutically effective amounts are readily ascertained by one of ordinary skill in the art.

The term "modulator," as used herein, is a compound that changes or alters the activity or function of a molecule. For example, a modulator can cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Certain exemplary activities and functions of a molecule include, but are not limited to, binding affinity, enzymatic activity, and signal transduction. Certain exemplary inhibitors include, but are not limited to, proteins, peptides, antibodies, peptibodies, carbohydrates or small organic molecules. Peptibodies are described in, e.g., U.S. Pat. No. 6,660,843 (corresponding to PCT Application No. WO 01/83525).

The terms "patient" and "subject" are used interchangeably and include human and non-human animal subjects as well as those with formally diagnosed disorders, those without formally recognized disorders, those receiving medical attention, those at risk of developing the disorders, etc.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors.

The term "prevent" does not require the 100% elimination of the possibility of an event. Rather, it denotes that the likelihood of the occurrence of the event has been reduced in the presence of the compound or method.

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See, e.g., Sambrook et al., *Molecular Cloning: A Laboratory Manual* (2d ed., Cold Spring Harbor Laboratory Press, Cold Spring Harbor, N.Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

Antigen Binding Proteins to PCSK9

Proprotein convertase subtilisin kexin type 9 (PCSK9) is a serine protease involved in regulating the levels of the low density lipoprotein receptor (LDLR) protein (Horton et al., 2007; Seidah and Prat, 2007). PCSK9 is a prohormone-proprotein convertase in the subtilisin (S8) family of serine proteases (Seidah et al., 2003). An exemplary human PCSK9 amino acid sequence is presented as SEQ ID NOs: 1 and 3. in FIG. 1A (depicting the "pro" domain of the protein as underlined) and FIG. 1B (depicting the signal sequence in bold and the pro domain underlined). An exemplary human PCSK9 coding sequence is presented as SEQ ID NO: 2 (FIG. 1B). As described herein, PCSK9 proteins can also include fragments of the full length PCSK9 protein. The structure of the PCSK9 protein has recently been solved by two groups (Cunningham et al., Nature Structural & Molecular Biology, 2007, and Piper et al., Structure, 15:1-8, 2007), the entireties of both of which are herein incorporated by reference. PCSK9 includes a signal sequence, a N-terminal prodomain, a subtilisin-like catalytic domain and a C-terminal domain.

Antigen binding proteins (ABPs) that bind PCSK9, including human PCSK9, are provided herein. In some embodiments, the antigen binding proteins provided are polypeptides which comprise one or more complementary determining regions (CDRs), as described herein. In some antigen binding proteins, the CDRs are embedded into a "framework" region, which orients the CDR(s) such that the proper antigen binding properties of the CDR(s) is achieved. In some embodiments, antigen binding proteins provided herein can interfere with, block, reduce or modulate the interaction between PCSK9 and LDLR. Such antigen binding proteins are denoted as "neutralizing." In some embodiments, binding between PCSK9 and LDLR can still occur, even though the antigen binding protein is neutralizing and bound to PCSK9. For example, in some embodiments, the ABP prevents or reduces the adverse influence of PCSK9 on LDLR without blocking the LDLR binding site on PCSK9. Thus, in some embodiments, the ABP modulates or alters PCSK9's ability to result in the degradation of LDLR, without having to prevent the binding interaction between PCSK9 and LDLR. Such ABPs can be specifically described as "non-competitively neutralizing" ABPs. In some embodiments, the neutralizing ABP binds to PCSK9 in a location and/or manner that prevents PCSK9 from binding to LDLR. Such ABPs can be specifically described as "competitively neutralizing" ABPs. Both of the above neutralizers can result in a greater amount of free LDLR being present in a subject, which results in more LDLR binding to LDL (thereby reducing the amount of LDL in the subject). In turn, this results in a reduction in the amount of serum cholesterol present in a subject.

In some embodiments, the antigen binding proteins provided herein are capable of inhibiting PCSK9-mediated activity (including binding). In some embodiments, antigen binding proteins binding to these epitopes inhibit, inter alia, interactions between PCSK9 and LDLR and other physiological effects mediated by PCSK9. In some embodiments, the antigen binding proteins are human, such as fully human antibodies to PCSK9.

In some embodiments, the ABP binds to the catalytic domain of PCSK9. In some embodiments, the ABP binds to the mature form of PCSK9. In some embodiments the ABP binds in the prodomain of PCSK9. In some embodiments, the ABP selectively binds to the mature form of PCSK9. In some embodiments, the ABP binds to the catalytic domain in a manner such that PCSK9 cannot bind or bind as efficiently to LDLR. In some embodiments, the antigen binding protein does not bind to the c-terminus of the cataylytic domain. In some embodiments, the antigen binding protein does not bind to the n-terminus of the catalytic domain. In some embodiments, the ABP does not bind to the n- or c-terminus of the PCSK9 protein. In some embodiments, the ABP binds to any one of the epitopes bound by the antibodies discussed herein. In some embodiments, this can be determined by competition assays between the antibodies disclosed herein and other antibodies. In some embodiments, the ABP binds to an epitope bound by one of the antibodies described in Table 2. In some embodiments, the antigen binding proteins bind to a specific conformational state of PCSK9 so as to prevent PCSK9 from interacting with LDLR. In some embodiments, the ABP binds to the V domain of PCSK9. In some embodiments, the ABP binds to the V domain of PCSK9 and prevents (or reduces) PCSK9 from binding to LDLR. In some embodiments, the ABP binds to the V domain of PCSK9, and while it does not prevent (or reduce) the binding of PCSK9 to LDLR, the ABP prevents or reduces the adverse activities mediated through PCSK9 on LDLR.

The antigen binding proteins that are disclosed herein have a variety of utilities. Some of the antigen binding proteins, for instance, are useful in specific binding assays, affinity purification of PCSK9, in particular human PCSK9 or its ligands and in screening assays to identify other antagonists of PCSK9 activity. Some of the antigen binding proteins are useful for inhibiting binding of PCSK9 to LDLR, or inhibiting PCSK9-mediated activities.

The antigen binding proteins can be used in a variety of therapeutic applications, as explained herein. For example, in some embodiments the PCSK9 antigen binding proteins are useful for treating conditions associated with PCSK9, such as cholesterol related disorders (or "serum cholesterol related disorders") such as hypercholesterolemia, as further described herein. Other uses for the antigen binding proteins include, for example, diagnosis of PCSK9-associated diseases or conditions and screening assays to determine the presence or absence of PCSK9. Some of the antigen binding proteins described herein are useful in treating consequences, symptoms, and/or the pathology associated with PCSK9 activity.

In some embodiments, the antigen binding proteins that are provided comprise one or more CDRs (e.g., 1, 2, 3, 4, 5 or 6 CDRs). In some embodiments, the antigen binding protein comprises (a) a polypeptide structure and (b) one or more CDRs that are inserted into and/or joined to the polypeptide structure. The polypeptide structure can take a variety of different forms. For example, it can be, or comprise, the framework of a naturally occurring antibody, or fragment or variant thereof, or can be completely synthetic in nature. Examples of various polypeptide structures are further described below.

In certain embodiments, the polypeptide structure of the antigen binding proteins is an antibody or is derived from an antibody, including, but not limited to, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and portions or fragments of each, respectively. In some instances, the antigen binding protein is an immunological fragment of an antibody (e.g., a Fab, a Fab', a F(ab')$_2$, or a scFv). The various structures are further described and defined herein.

Certain of the antigen binding proteins as provided herein specifically and/or selectively bind to human PCSK9. In some embodiments, the antigen binding protein specifically and/or selectively binds to human PCSK9 protein having and/or consisting of residues 153-692 of SEQ ID NO: 3. In some embodiments the ABP specifically and/or selectively binds to human PCSK9 having and/or consisting of residues 31-152 of SEQ ID NO: 3. In some embodiments, the ABP selectively binds to a human PCSK9 protein as depicted in FIG. 1A (SEQ ID NO: 1). In some embodiments, the antigen binding protein specifically binds to at least a fragment of the PCSK9 protein and/or a full length PCSK9 protein, with or without a signal sequence.

In embodiments where the antigen binding protein is used for therapeutic applications, an antigen binding protein can inhibit, interfere with or modulate one or more biological activities of PCSK9. In one embodiment, an antigen binding protein binds specifically to human PCSK9 and/or substantially inhibits binding of human PCSK9 to LDLR by at least about 20%-40%, 40-60%, 60-80%, 80-85%, or more (for example, by measuring binding in an in vitro competitive binding assay). Some of the antigen binding proteins that are provided herein are antibodies. In some embodiments, the ABP has a $K_d$ of less (binding more tightly) than $10^{-7}$, $10^{-8}$, $10^{-9}$, $10^{-10}$, $10^{-11}$, $10^{-12}$, $10^{-13}$ M. In some embodiments, the ABP has an $IC_{50}$ for blocking the binding of LDLR to PCSK9 (D374Y, high affinity variant) of less than 1 microM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM.

One example of an IgG2 heavy chain constant domain of an anti-PCSK9 antibody of the present invention has the amino acid sequence as shown in SEQ ID NO: 154, FIG. 3KK.

One example of an IgG4 heavy chain constant domain of an anti-PCSK9 antibody of the present invention has the amino acid sequence as shown in SEQ ID NO: 155, FIG. 3KK.

One example of a kappa light chain constant domain of an anti-PCSK9 antibody has the amino acid sequence as shown in SEQ ID NO: 157, FIG. 3KK.

One example of a lambda light chain constant domain of an anti-PCSK9 antibody has the amino acid sequence as shown in SEQ ID NO: 156, FIG. 3KK.

Variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain/light chain pair mentioned above typically are aligned by the framework regions to form a structure that binds specifically with a specific epitope on the target protein (e.g., PCSK9). From N-terminal to C-terminal, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, Md.), or Chothia & Lesk, 1987, *J. Mol. Biol.* 196:901-917; Chothia et al., 1989, *Nature* 342:878-883.

Various heavy chain and light chain variable regions are provided herein and are depicted in FIGS. 2A-3JJ and 3LL-3BBB. In some embodiments, each of these variable regions can be attached to the above heavy and light chain constant regions to form a complete antibody heavy and light chain, respectively. Further, each of the so generated heavy and light chain sequences can be combined to form a complete antibody structure.

Specific examples of some of the variable regions of the light and heavy chains of the antibodies that are provided and their corresponding amino acid sequences are summarized in TABLE 2.

TABLE 2

Exemplary Heavy and Light Chain Variable Regions

| Antibody | Light/Heavy SEQ ID NO |
|---|---|
| 30A4 | 5/74 |
| 3C4 | 7/85 |
| 23B5 | 9/71 |
| 25G4 | 10/72 |
| 31H4 | 12/67 |
| 27B2 | 13/87 |
| 25A7 | 15/58 |
| 27H5 | 16/52 |
| 26H5 | 17/51 |
| 31D1 | 18/53 |
| 20D10 | 19/48 |
| 27E7 | 20/54 |
| 30B9 | 21/55 |
| 19H9 | 22/56 |
| 26E10 | 23/49 |
| 21B12 | 23/49 |
| 17C2 | 24/57 |
| 23G1 | 26/50 |
| 13H1 | 28/91 |
| 9C9 | 30/64 |
| 9H6 | 31/62 |
| 31A4 | 32/89 |
| 1A12 | 33/65 |
| 16F12 | 35/79 |
| 22E2 | 36/80 |
| 27A6 | 37/76 |
| 28B12 | 38/77 |
| 28D6 | 39/78 |
| 31G11 | 40/83 |
| 13B5 | 42/69 |
| 31B12 | 44/81 |
| 3B6 | 46/60 |

Again, each of the exemplary variable heavy chains listed in Table 2 can be combined with any of the exemplary variable light chains shown in Table 2 to form an antibody. Table 2 shows exemplary light and heavy chain pairings found in several of the antibodies disclosed herein. In some instances, the antibodies include at least one variable heavy chain and one variable light chain from those listed in Table 2. In other instances, the antibodies contain two identical light chains and two identical heavy chains. As an example, an antibody or antigen binding protein can include a heavy chain and a light chain, two heavy chains, or two light chains. In some embodiments the antigen binding protein comprises (and/or consists) of 1, 2, and/or 3 heavy and/or light CDRs from at least one of the sequences listed in Table 2 (CDRs for the sequences are outlined in FIGS. 2A-3D, and other embodiments in FIGS. 3CCC-3JJJ and 15A-15D). In some embodiments, all 6 CDRs (CDR1-3 from the light (CDRL1, CDRL2, CDRL3) and CDR1-3 from the heavy (CDRH1, CDRH2, and CDRH3)) are part of the ABP. In some embodiments, 1, 2, 3, 4, 5, or more CDRs are included in the ABP. In some embodiments, one heavy and one light CDR from the CDRs in the sequences in Table 2 is included in the ABP (CDRs for the sequences in table 2 are outlined in FIGS. 2A-3D). In some embodiments, additional sections (e.g., as depicted in FIG. 2A-2D, 3A-3D, and other embodiments in 3CCC-3JJJ and 15A-15D) are also included in the ABP. Examples of CDRs and FRs for the heavy and light chains noted in Table 2 are outlined in FIGS. 2A-3D (and other embodiments in FIGS. 3CCC-3JJJ and 15A-15D). Optional light chain variable sequences (including CDR1, CDR2, CDR3, FR1, FR2, FR3, and FR4) can be selected from the following: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46. Optional heavy chain variable sequences (including CDR1, CDR2, CDR3, FR1, FR2, FR3, and FR4) can be selected from the following: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60. In some of the entries in FIG. 2A-3D, variations of the sequences or alternative boundaries of the CDRs and FRs are identified. These alternatives are identified with a "v1" following the ABP name. As most of these alternatives are minor in nature, only sections with differences are displayed in the table. It is understood that the remaining section of the light or heavy chain is the same as shown for the base ABP in the other panels. Thus, for example, 19H9v1 in FIG. 2C has the same FR1, CDR1, and FR2 as 19H9 in FIG. 2A as the only difference is noted in FIG. 2C. For three of the nucleic acid sequences (ABPs 26E10, 30B9, and 31B12), additional alternative nucleic acid sequences are provided in the figures. As will be appreciated by one of skill in the art, no more than one such sequence need actually be used in the creation of an antibody or ABP. Indeed, in some embodiments, only one or neither of the specific heavy or light chain nucleic acids need be present.

In some embodiments, the ABP is encoded by a nucleic acid sequence that can encode any of the protein sequences in Table 2.

In some embodiments, the ABP binds selectively to the form of PCSK9 that binds to LDLR (e.g., the autocatalyzed form of the molecule). In some embodiments, the antigen binding protein does not bind to the c-terminus of the cataylytic domain (e.g., the 5. 5-10, 10-15, 15-20, 20-25, 25-30, 30-40 most amino acids in the c-terminus). In some embodiments, the antigen binding protein does not bind to the n-terminus of the catalytic domain (e.g., the 5. 5-10, 10-15, 15-20, 20-25, 25-30, 30-40 most amino acids in the n-terminus). In some embodiments, the ABP binds to amino acids within amino acids 1-100 of the mature form of PCSK9. In some embodiments, the ABP binds to amino acids within (and/or amino acid sequences consisting of) amino acids 31-100, 100-200, 31-152, 153-692, 200-300, 300-400, 452-683, 400-500, 500-600, 31-692, 31-449, and/or 600-692. In some embodiments, the ABP binds to the catalytic domain. In some embodiments, the neutralizing and/or non-neutralizing ABP binds to the prodomain. In some embodiments, the ABP binds to both the catalytic and pro domains. In some embodiments, the ABP binds to the catalytic domain so as to obstruct an area on the catalytic domain that interacts with the pro domain. In some embodiments, the ABP binds to the catalytic domain at a location or surface that the pro-domain interacts with as outlined in Piper et al. (Structure 15:1-8 (2007), the entirety of which is hereby incorporated by reference, including the structural representations therein). In some embodiments, the ABP binds to the catalytic domain and restricts the mobility of the prodomain. In some embodiments, the ABP binds to the catalytic domain without binding to the pro-domain. In some embodiments, the ABP binds to the catalytic domain, without binding to the pro-domain, while preventing the pro-domain from reorienting to allow PCSK9 to bind to LDLR. In some embodiments, the ABP binds in the same epitope as those surrounding residues 149-152 of the pro-domain in Piper et al. In some embodiments, the ABPs bind to the groove (as outlined in Piper et al.) on the V domain. In some embodiments, the ABPs bind to the histidine-rich patch proximal to the groove on the V domain. In some embodiments, such antibodies (that bind to the V domain) are not neutralizing. In some embodiments, antibodies that bind to the V domain are neutralizing. In some embodiments, the neutralizing ABPs prevent the binding of PCSK9 to LDLR. In some embodiments, the neturalizing ABPs, while preventing the PCSK9 degradation of LDLR, do not prevent the binding of PCSK9 to LDLR (for example ABP 31A4). In some embodiments, the ABP binds to or blocks at least one of the histidines depicted in FIG. 4 of the Piper et al. paper. In some embodiments, the ABP blocks the catalytic triad in PCSK9.

In some embodiments, the antibody binds selectively to variant PCSK9 proteins, e.g., D374Y over wild type PCSK9. In some embodiments, these antibodies bind to the variant at least twice as strongly as the wild type, and preferably 2-5, 5-10, 10-100, 100-1000, 1000-10,000 fold or more to the mutant than the wild type (as measured via a $K_a$). In some embodiments, the antibody selectively inhibits variant D374Y PCSK9 from interacting with LDLR over wild type PCSK9's ability to interact with LDLR. In some embodiments, these antibodies block the variant's ability to bind to LDLR more strongly than the wild type's ability, e.g., at least twice as strongly as the wild type, and preferably 2-5, 5-10, 10-100, 100-1000 fold or more to the mutant than the wild type (as measured via an $IC_{50}$). In some embodiments, the antibody binds to and neutralizes both wild type PCSK9 and variant forms of PCSK9, such as D374Y at similar levels. In some embodiments, the antibody binds to PCSK9 to prevent variants of LDLR from binding to PCSK9. In some embodiments, the variants of LDLR are at least 50% identical to human LDLR. It is noted that variants of LDLR are known to those of skill in the art (e.g., Brown M S et al, "Calcium cages, acid baths and recycling receptors" Nature 388: 629-630, 1997). In some embodiments, the ABP can raise the level of effective LDLR in heterozygote familial hypercholesterolemia (where a loss-of function variant of LDLR is present).

In some embodiments, the ABP binds to (but does not block) variants of PCSK9 that are at least 50%, 50-60, 60-70, 70-80, 80-90, 90-95, 95-99, or greater percent identity to the form of PCSK9 depicted in FIG. 1A and/or FIG. 1B. In some embodiments, the ABP binds to (but does not block) variants of PCSK9 that are at least 50%, 50-60, 60-70, 70-80, 80-90, 90-95, 95-99, or greater percent identity to the mature form of PCSK9 depicted in FIG. 1A and/or FIG. 1B. In some embodiments, the ABP binds to and prevents variants of PCSK9 that are at least 50%, 50-60, 60-70, 70-80, 80-90, 90-95, 95-99, or greater percent identity to the form of PCSK9 depicted in FIG. 1A and/or FIG. 1B from interacting with LDLR. In some embodiments, the ABP binds to and prevents variants of PCSK9 that are at least 50, 50-60, 60-70, 70-80, 80-90, 90-95, 95-99, or greater percent identity to the mature form of PCSK9 depicted in FIG. 1B from interacting with LDLR. In some embodiments, the variant of PCSK9 is a human variant, such as variants at position 474, E620G, and/or E670G. In some embodiments, the amino acid at position 474 is valine (as in other humans) or threonine (as in cyno and mouse). Given the cross-reactivity data presented herein, it is believed that the present antibodies will readily bind to the above variants.

In some embodiments, the ABP binds to an epitope bound by one of the antibodies described in Table 2. In some embodiments, the antigen binding proteins bind to a specific conformational state of PCSK9 so as to prevent PCSK9 from interacting with LDLR.

Humanized Antigen Binding Proteins (e.g., Antibodies)

As described herein, an antigen binding protein to PCSK9 can comprise a humanized antibody and/or part thereof. An important practical application of such a strategy is the "humanization" of the mouse humoral immune system.

In certain embodiments, a humanized antibody is substantially non-immunogenic in humans. In certain embodiments, a humanized antibody has substantially the same affinity for a target as an antibody from another species from which the humanized antibody is derived. See, e.g., U.S. Pat. No. 5,530, 101, U.S. Pat. No. 5,693,761; U.S. Pat. No. 5,693,762; U.S. Pat. No. 5,585,089.

In certain embodiments, amino acids of an antibody variable domain that can be modified without diminishing the native affinity of the antigen binding domain while reducing its immunogenicity are identified. See, e.g., U.S. Pat. Nos. 5,766,886 and 5,869,619.

In certain embodiments, modification of an antibody by methods known in the art is typically designed to achieve increased binding affinity for a target and/or to reduce immunogenicity of the antibody in the recipient. In certain embodiments, humanized antibodies are modified to eliminate glycosylation sites in order to increase affinity of the antibody for its cognate antigen. See, e.g., Co et al., Mol. Immunol., 30:1361-1367 (1993). In certain embodiments, techniques such as "reshaping," "hyperchimerization," or "veneering/resurfacing" are used to produce humanized antibodies. See, e.g., Vaswami et al., Annals of Allergy, Asthma, & Immunol. 81:105 (1998); Roguska et al., Prot. Engineer., 9:895-904 (1996); and U.S. Pat. No. 6,072,035. In certain such embodiments, such techniques typically reduce antibody immunogenicity by reducing the number of foreign residues, but do not prevent anti-idiotypic and anti-allotypic responses following repeated administration of the antibodies. Certain other methods for reducing immunogenicity are described, e.g., in Gilliland et al., J. Immunol., 62(6): 3663-71 (1999).

In certain instances, humanizing antibodies results in a loss of antigen binding capacity. In certain embodiments, humanized antibodies are "back mutated." In certain such embodiments, the humanized antibody is mutated to include one or more of the amino acid residues found in the donor antibody. See, e.g., Saldanha et al., *Mol Immunol* 36:709-19 (1999).

In certain embodiments the complementarity determining regions (CDRs) of the light and heavy chain variable regions of an antibody to PCSK9 can be grafted to framework regions (FRs) from the same, or another, species. In certain embodiments, the CDRs of the light and heavy chain variable regions of an antibody to PCSK9 can be grafted to consensus human FRs. To create consensus human FRs, in certain embodiments, FRs from several human heavy chain or light chain amino acid sequences are aligned to identify a consensus amino acid sequence. In certain embodiments, the FRs of an antibody to PCSK9 heavy chain or light chain are replaced with the FRs from a different heavy chain or light chain. In certain embodiments, rare amino acids in the FRs of the heavy and light chains of an antibody to PCSK9 are not replaced, while the rest of the FR amino acids are replaced. Rare amino acids are specific amino acids that are in positions in which they are not usually found in FRs. In certain embodiments, the grafted variable regions from an antibody to PCSK9 can be used with a constant region that is different from the constant region of an antibody to PCSK9. In certain embodiments, the grafted variable regions are part of a single chain Fv antibody. CDR grafting is described, e.g., in U.S. Pat. Nos. 6,180,370, 6,054,297, 5,693,762, 5,859,205, 5,693,761, 5,565,332, 5,585,089, and 5,530,101, and in Jones et al., Nature, 321: 522-525 (1986); Riechmann et al., Nature, 332: 323-327 (1988); Verhoeyen et al., Science, 239:1534-1536 (1988), Winter, FEBS Letts., 430:92-94 (1998), which are hereby incorporated by reference for any purpose.

Human Antigen Binding Proteins (e.g., Antibodies)

As described herein, an antigen binding protein that binds to PCSK9 can comprise a human (i.e., fully human) antibody and/or part thereof. In certain embodiments, nucleotide sequences encoding, and amino acid sequences comprising, heavy and light chain immunoglobulin molecules, particularly sequences corresponding to the variable regions are provided. In certain embodiments, sequences corresponding to complementarity determining regions (CDR's), specifically from CDR1 through CDR3, are provided. According to certain embodiments, a hybridoma cell line expressing such an immunoglobulin molecule is provided. According to certain embodiments, a hybridoma cell line expressing such a monoclonal antibody is provided. In certain embodiments a hybridoma cell line is selected from at least one of the cell lines described in Table 2, e.g., 21B12, 16F12 and 31H4. In certain embodiments, a purified human monoclonal antibody to human PCSK9 is provided.

One can engineer mouse strains deficient in mouse antibody production with large fragments of the human Ig loci in anticipation that such mice would produce human antibodies in the absence of mouse antibodies. Large human Ig fragments can preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains can yield high affinity fully human antibodies against any antigen of interest, including human antigens. Using the hybridoma technology, antigen-specific human MAbs with the desired specificity can be produced and selected. Certain exemplary methods are described in WO 98/24893, U.S. Pat. No. 5,545,807, EP 546073, and EP 546073.

In certain embodiments, one can use constant regions from species other than human along with the human variable region(s).

The ability to clone and reconstruct megabase sized human loci in yeast artificial chromosomes (YACs) and to introduce them into the mouse germline provides an approach to elucidating the functional components of very large or crudely mapped loci as well as generating useful models of human disease. Furthermore, the utilization of such technology for substitution of mouse loci with their human equivalents could provide insights into the expression and regulation of human gene products during development, their communication with other systems, and their involvement in disease induction and progression.

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of functional human antibody loci into a rodent, other mammal or animal so that the rodent, other mammal or animal produces fully human antibodies.

Humanized antibodies are those antibodies that, while initially starting off containing antibody amino acid sequences that are not human, have had at least some of these nonhuman antibody amino acid sequences replaced with human antibody sequences. This is in contrast with human antibodies, in which the antibody is encoded (or capable of being encoded) by genes possessed a human.

Antigen Binding Protein Variants

Other antibodies that are provided are variants of the ABPs listed above formed by combination or subparts of the variable heavy and variable light chains shown in Table 2 and comprise variable light and/or variable heavy chains that each have at least 50%, 50-60, 60-70, 70-80%, 80-85%, 85-90%, 90-95%, 95-97%, 97-99%, or above 99% identity to the amino acid sequences of the sequences in Table 2 (either the entire sequence or a subpart of the sequence, e.g., one or more CDR). In some instances, such antibodies include at least one heavy chain and one light chain, whereas in other instances the variant forms contain two identical light chains and two identical heavy chains (or subparts thereof). In some embodiments, the sequence comparison in FIG. 2A-3D (and 13A-13J and other embodiments in 15A-15D) can be used in order to identify sections of the antibodies that can be modified by observing those variations that impact binding and those variations that do not appear to impact binding. For example, by comparing similar sequences, one can identify those sections (e.g., particular amino acids) that can be modified and how they can be modified while still retaining (or improving) the functionality of the ABP. In some embodiments, variants of ABPs include those consensus groups and sequences depicted in FIGS. 13A, 13C, 13F, 13G, 13H, 13I and/or 13J and variations are allowed in the positions identified as variable in the figures. The CDRs shown in FIGS. 13A, 13C, 13F, and 13G were defined based upon a hybrid combination of the Chothia method (based on the location of the structural loop regions, see, e.g., "Standard conformations for the canonical structures of immunoglobulins," Bissan Al-Lazikani, Arthur M. Lesk and Cyrus Chothia, *Journal of Molecular Biology*, 273(4): 927-948, 7 November (1997)) and the Kabat method (based on sequence variability, see, e.g., *Sequences of Proteins of Immunological Interest*, Fifth Edition. NIH Publication No. 91-3242, Kabat et al., (1991)). Each residue determined by either method, was included in the final list of CDR residues (and is presented in FIGS. 13A, 13C, 13F, and 13G). The CDRs in FIGS. 13H, 13I, and 13J were obtained by the Kabat method alone. Unless specified otherwise, the defined consensus sequences, CDRs, and FRs in FIGS. 13H-13J will define and control the noted CDRs and FRs for the referenced ABPs in FIG. 13.

In certain embodiments, an antigen binding protein comprises a heavy chain comprising a variable region comprising an amino acid sequence at least 90% identical to an amino acid sequence selected from at least one of the sequences of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60. In certain embodiments, an antigen binding protein comprises a heavy chain comprising a variable region comprising an amino acid sequence at least 95% identical to an amino acid sequence selected from at least one of the sequences of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60. In certain embodiments, an antigen binding protein comprises a heavy chain comprising a variable region comprising an amino acid sequence at least 99% identical to an amino acid sequence selected from at least one of the sequences of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60.

In some embodiments, the antigen binding protein comprises a sequence that is at least 90%, 90-95%, and/or 95-99% identical to one or more CDRs from the CDRs in at least one of sequences of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60. In some embodiments, 1, 2, 3, 4, 5, or 6 CDR (each being at least 90%, 90-95%, and/or 95-99% identical to the above sequences) is present.

In some embodiments, the antigen binding protein comprises a sequence that is at least 90%, 90-95%, and/or 95-99% identical to one or more FRs from the FRs in at least one of sequences of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60. In some embodiments, 1, 2, 3, or 4 FR (each being at least 90%, 90-95%, and/or 95-99% identical to the above sequences) is present.

In certain embodiments, an antigen binding protein comprises a light chain comprising a variable region comprising an amino acid sequence at least 90% identical to an amino acid sequence selected from at least one of the sequences of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46. In certain embodiments, an antigen binding protein comprises a light chain comprising a variable region comprising an amino acid sequence at least 95% identical to an amino acid sequence selected from at least one of the sequences of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46. In certain embodiments, an antigen binding protein comprises a light chain comprising a variable region comprising an amino acid sequence at least 99% identical to an amino acid sequence selected from at least one of the sequences of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46.

In some embodiments, the antigen binding protein comprises a sequence that is at least 90%, 90-95%, and/or 95-99% identical to one or more CDRs from the CDRs in at least one of sequences of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46. In some embodiments, 1, 2, 3, 4, 5, or 6 CDR (each being at least 90%, 90-95%, and/or 95-99% identical to the above sequences) is present.

In some embodiments, the antigen binding protein comprises a sequence that is at least 90%, 90-95%, and/or 95-99% identical to one or more FRs from the FRs in at least one of sequences of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46. In some embodiments, 1, 2, 3, or 4 FR (each being at least 90%, 90-95%, and/or 95-99% identical to the above sequences) is present.

In light of the present disclosure, a skilled artisan will be able to determine suitable variants of the ABPs as set forth herein using well-known techniques. In certain embodiments, one skilled in the art can identify suitable areas of the molecule that may be changed without destroying activity by targeting regions not believed to be important for activity. In certain embodiments, one can identify residues and portions of the molecules that are conserved among similar polypeptides. In certain embodiments, even areas that can be important for biological activity or for structure can be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art can opt for chemically similar amino acid substitutions for such predicted important amino acid residues.

One skilled in the art can also analyze the three-dimensional structure and amino acid sequence in relation to that structure in similar ABPs. In view of such information, one skilled in the art can predict the alignment of amino acid residues of an antibody with respect to its three dimensional structure. In certain embodiments, one skilled in the art can choose not to make radical changes to amino acid residues predicted to be on the surface of the protein, since such residues can be involved in important interactions with other molecules. Moreover, one skilled in the art can generate test variants containing a single amino acid substitution at each desired amino acid residue. The variants can then be screened using activity assays known to those skilled in the art. Such variants can be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2): 211-222 (1974); Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., Nucl. Acid. Res., 27(1):244-247

(1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., Curr. Opin. Struct. Biol., 7(3): 377-87 (1997); Sippl et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci. USA, 84(13):4355-4358 (1987)), and "evolutionary linkage" (See Holm, supra (1999), and Brenner, supra (1997)).

In certain embodiments, antigen binding protein variants include glycosylation variants wherein the number and/or type of glycosylation site has been altered compared to the amino acid sequences of a parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X can be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants can be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiocochemical or functional properties on such polypeptides. According to certain embodiments, single or multiple amino acid substitutions (in certain embodiments, conservative amino acid substitutions) can be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden & J. Tooze, eds., Garland Publishing, New York, N.Y. (1991)); and Thornton et al., Nature, 354:105 (1991), which are each incorporated herein by reference.

In some embodiments, the variants are variants of the nucleic acid sequences of the ABPs disclosed herein. One of skill in the art will appreciate that the above discussion can be used for identifying, evaluating, and/creating ABP protein variants and also for nucleic acid sequences that can encode for those protein variants. Thus, nucleic acid sequences encoding for those protein variants (as well as nucleic acid sequences that encode for the ABPs in Table 2, but are different from those explicitly disclosed herein) are contemplated. For example, an ABP variant can have at least 80, 80-85, 85-90, 90-95, 95-97, 97-99 or greater identity to at least one nucleic acid sequence described in SEQ ID NOs: 152, 153, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151 or at least one to six (and various combinations thereof) of the CDR(s) encoded by the nucleic acid sequences in SEQ ID NOs: 152, 153, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, and 151.

In some embodiments, the antibody (or nucleic acid sequence encoding it) is a variant if the nucleic acid sequence that encodes the particular ABP (or the nucleic acid sequence itself) can selectively hybridize to any of the nucleic acid sequences that encode the proteins in Table 2 (such as, but not limited to SEQ ID NO: 152, 153, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, and 151) under stringent conditions. In one embodiment, suitable moderately stringent conditions include prewashing in a solution of 5×SSC; 0.5% SDS, 1.0 mM EDTA (pH 8:0); hybridizing at 50° C., −65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS. Such hybridizing DNA sequences are also within the scope of this invention, as are nucleotide sequences that, due to code degeneracy, encode an antibody polypeptide that is encoded by a hybridizing DNA sequence and the amino acid sequences that are encoded by these nucleic acid sequences. In some embodiments, variants of CDRs include nucleic acid sequences and the amino acid sequences encoded by those sequences, that hybridize to one or more of the CDRs within the sequences noted above (individual CDRs can readily be determined in light of FIGS. 2A-3D, and other embodiments in FIGS. 3CCC-3JJJ and 15A-15D). The phrase "selectively hybridize" referred to in this context means to detectably and selectively bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

Preparation of Antigen Binding Proteins (e.g., Antibodies)

In certain embodiments, antigen binding proteins (such as antibodies) are produced by immunization with an antigen (e.g., PCSK9). In certain embodiments, antibodies can be produced by immunization with full-length PCSK9, a soluble form of PCSK9, the catalytic domain alone, the mature form of PCSK9 shown in FIG. 1A, a splice variant form of PCSK9, or a fragment thereof. In certain embodiments, the antibodies of the invention can be polyclonal or monoclonal, and/or can be recombinant antibodies. In certain embodiments, antibodies of the invention are human antibodies prepared, for example, by immunization of transgenic animals capable of producing human antibodies (see, for example, PCT Published Application No. WO 93/12227).

In certain embodiments, certain strategies can be employed to manipulate inherent properties of an antibody, such as the affinity of an antibody for its target. Such strategies include, but are not limited to, the use of site-specific or random mutagenesis of the polynucleotide molecule encoding an antibody to generate an antibody variant. In certain embodiments, such generation is followed by screening for antibody variants that exhibit the desired change, e.g. increased or decreased affinity.

In certain embodiments, the amino acid residues targeted in mutagenic strategies are those in the CDRs. In certain embodiments, amino acids in the framework regions of the variable domains are targeted. In certain embodiments, such framework regions have been shown to contribute to the target binding properties of certain antibodies. See, e.g., Hudson, Curr. Opin. Biotech., 9:395-402 (1999) and references therein.

In certain embodiments, smaller and more effectively screened libraries of antibody variants are produced by restricting random or site-directed mutagenesis to hyper-mutation sites in the CDRs, which are sites that correspond to areas prone to mutation during the somatic affinity maturation process. See, e.g., Chowdhury & Pastan, Nature Biotech., 17: 568-572 (1999) and references therein. In certain embodiments, certain types of DNA elements can be used to identify hyper-mutation sites including, but not limited to, certain direct and inverted repeats, certain consensus sequences, certain secondary structures, and certain palindromes. For example, such DNA elements that can be used to identify hyper-mutation sites include, but are not limited to, a tetra-base sequence comprising a purine (A or G), followed by guainine (G), followed by a pyrimidine (C or T), followed by either adenosine or thymidine (A or T) (i.e., A/G-G-C/T-A/T). Another example of a DNA element that can be used to identify hyper-mutation sites is the serine codon, A-G-C/T.

Preparation of Fully Human ABPs (e.g., Antibodies)

In certain embodiments, a phage display technique is used to generate monoclonal antibodies. In certain embodiments, such techniques produce fully human monoclonal antibodies. In certain embodiments, a polynucleotide encoding a single Fab or Fv antibody fragment is expressed on the surface of a phage particle. See, e.g., Hoogenboom et al., J. Mol. Biol., 227: 381 (1991); Marks et al., *J Mol Biol* 222: 581 (1991); U.S. Pat. No. 5,885,793. In certain embodiments, phage are "screened" to identify those antibody fragments having affinity for target. Thus, certain such processes mimic immune selection through the display of antibody fragment repertoires on the surface of filamentous bacteriophage, and subsequent selection of phage by their binding to target. In certain such procedures, high affinity functional neutralizing antibody fragments are isolated. In certain such embodiments (discussed in more detail below), a complete repertoire of human antibody genes is created by cloning naturally rearranged human V genes from peripheral blood lymphocytes. See, e.g., Mullinax et al., Proc Natl Acad Sci (USA), 87: 8095-8099 (1990).

According to certain embodiments, antibodies of the invention are prepared through the utilization of a transgenic mouse that has a substantial portion of the human antibody producing genome inserted but that is rendered deficient in the production of endogenous, murine antibodies. Such mice, then, are capable of producing human immunoglobulin molecules and antibodies and are deficient in the production of murine immunoglobulin molecules and antibodies. Technologies utilized for achieving this result are disclosed in the patents, applications and references disclosed in the specification, herein. In certain embodiments, one can employ methods such as those disclosed in PCT Published Application No. WO 98/24893 or in Mendez et al., Nature Genetics, 15:146-156 (1997), which are hereby incorporated by reference for any purpose.

Generally, fully human monoclonal ABPs (e.g., antibodies) specific for PCSK9 can be produced as follows. Transgenic mice containing human immunoglobulin genes are immunized with the antigen of interest, e.g. PCSK9, lymphatic cells (such as B-cells) from the mice that express antibodies are obtained. Such recovered cells are fused with a myeloid-type cell line to prepare immortal hybridoma cell lines, and such hybridoma cell lines are screened and selected to identify hybridoma cell lines that produce antibodies specific to the antigen of interest. In certain embodiments, the production of a hybridoma cell line that produces antibodies specific to PCSK9 is provided.

In certain embodiments, fully human antibodies are produced by exposing human splenocytes (B or T cells) to an antigen in vitro, and then reconstituting the exposed cells in an immunocompromised mouse, e.g. SCID or nod/SCID. See, e.g., Brams et al., J. Immol. 160: 2051-2058 (1998); Carballido et al., Nat. Med., 6: 103-106 (2000). In certain such approaches, engraftment of human fetal tissue into SCID mice (SCID-hu) results in long-term hematopoiesis and human T-cell development. See, e.g., McCune et al., Science, 241:1532-1639 (1988); Ifversen et al., Sem. Immunol., 8:243-248 (1996). In certain instances, humoral immune response in such chimeric mice is dependent on co-development of human T-cells in the animals. See, e.g., Martensson et al., Immunol., 83:1271-179 (1994). In certain approaches, human peripheral blood lymphocytes are transplanted into SCID mice. See, e.g., Mosier et al., Nature, 335:256-259 (1988). In certain such embodiments, when such transplanted cells are treated either with a priming agent, such as Staphylococcal Enterotoxin A (SEA), or with anti-human CD40 monoclonal antibodies, higher levels of B cell production is detected. See, e.g., Martensson et al., Immunol., 84: 224-230 (1995); Murphy et al., Blood, 86:1946-1953 (1995).

Thus, in certain embodiments, fully human antibodies can be produced by the expression of recombinant DNA in host cells or by expression in hybridoma cells. In other embodiments, antibodies can be produced using the phage display techniques described herein.

The antibodies described herein were prepared through the utilization of the XenoMouse® technology, as described herein. Such mice, then, are capable of producing human immunoglobulin molecules and antibodies and are deficient in the production of murine immunoglobulin molecules and antibodies. Technologies utilized for achieving the same are disclosed in the patents, applications, and references disclosed in the background section herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et at, Nature Genetics, 15:146-156 (1997), the disclosure of which is hereby incorporated by reference.

Through the use of such technology, fully human monoclonal antibodies to a variety of antigens have been produced. Essentially, XenoMouse® lines of mice are immunized with an antigen of interest (e.g. PCSK9), lymphatic cells (such as B-cells) are recovered from the hyper-immunized mice, and the recovered lymphocytes are fused with a myeloid-type cell line to prepare immortal hybridoma cell lines. These hybridoma cell lines are screened and selected to identify hybridoma cell lines that produced antibodies specific to the antigen of interest. Provided herein are methods for the production of multiple hybridoma cell lines that produce antibodies specific to PCSK9 Further, provided herein are characterization of the antibodies produced by such cell lines, including nucleotide and amino acid sequence analyses of the heavy and light chains of such antibodies.

The production of the XenoMouse® strains of mice is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430, 938, filed Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, Ser. No. 08/759,620, filed Dec. 3, 1996, U.S. Publication 2003/0093820, filed Nov. 30, 2001 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and usually a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg & Kay, U.S. Pat. Nos. 5,591,669 and 6,023,010 to Krimpenfort & Berns, U.S. Pat. Nos. 5,612,205, 5,721,367, and 5,789,215 to Berns et al., and U.S. Pat. No. 5,643,763 to Choi & Dunn, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al, 1993, Tuaillon et al., 1993, Choi et al., 1993, Lonberg et al., (1994), Taylor et al., (1994), and Tuaillon et al., (1995), Fishwild et al, (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference. Additionally, KM™ mice, which are the result of cross-breeding of Kirin's Tc mice with Medarex's minilocus (Humab) mice have been generated. These mice possess the human IgH transchromosome of the Kirin mice and the kappa chain transgene of the Genpharm mice (Ishida et al., Cloning Stem Cells, (2002) 4:91-102).

Human antibodies can also be derived by in vitro methods. Suitable examples include but are not limited to phage display (CAT, Morphosys, Dyax, Biosite/Medarex, Xoma, Symphogen, Alexion (formerly Proliferon), Affimed) ribosome display (CAT), yeast display, and the like.

In some embodiments, the antibodies described herein possess human IgG4 heavy chains as well as IgG2 heavy chains. Antibodies can also be of other human isotypes, including IgG1. The antibodies possessed high affinities, typically possessing a Kd of from about $10^{-6}$ through about $10^{-13}$ M or below, when measured by various techniques.

As will be appreciated, antibodies can be expressed in cell lines other than hybridoma cell lines. Sequences encoding particular antibodies can be used to transform a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Cell lines of particular preference are selected through determining which cell lines have high expression levels and produce antibodies with constitutive PCSK9 binding properties.

In certain embodiments, antibodies and/or ABP are produced by at least one of the following hybridomas: 21B12, 31H4, 16F12, any the other hybridomas listed in Table 2 or disclosed in the examples. In certain embodiments, antigen binding proteins bind to PCSK9 with a dissociation constant ($K_D$) of less than approximately 1 nM, e.g., 1000 pM to 100 pM, 100 pM to 10 pM, 10 pM to 1 pM, and/or 1 pM to 0.1 pM or less.

In certain embodiments, antigen binding proteins comprise an immunoglobulin molecule of at least one of the IgG1, IgG2, IgG3, IgG4, Ig E, IgA, IgD, and IgM isotype. In certain embodiments, antigen binding proteins comprise a human kappa light chain and/or a human heavy chain. In certain embodiments, the heavy chain is of the IgG1, IgG2, IgG3, IgG4, IgE, IgA, IgD, or IgM isotype. In certain embodiments, antigen binding proteins have been cloned for expression in mammalian cells. In certain embodiments, antigen binding proteins comprise a constant region other than any of the constant regions of the IgG1, IgG2, IgG3, IgG4, IgE, IgA, IgD, and IgM isotype.

In certain embodiments, antigen binding proteins comprise a human lambda light chain and a human IgG2 heavy chain. In certain embodiments, antigen binding proteins comprise a human lambda light chain and a human IgG4 heavy chain. In certain embodiments, antigen binding proteins comprise a human lambda light chain and a human IgG1, IgG3, IgE, IgA, IgD or IgM heavy chain. In other embodiments, antigen binding proteins comprise a human kappa light chain and a human IgG2 heavy chain. In certain embodiments, antigen binding proteins comprise a human kappa light chain and a human IgG4 heavy chain. In certain embodiments, antigen binding proteins comprise a human kappa light chain and a human IgG1, IgG3, IgE, IgA, IgD or IgM heavy chain. In certain embodiments, antigen binding proteins comprise variable regions of antibodies ligated to a constant region that is neither the constant region for the IgG2 isotype, nor the constant region for the IgG4 isotype. In certain embodiments, antigen binding proteins have been cloned for expression in mammalian cells.

In certain embodiments, conservative modifications to the heavy and light chains of antibodies from at least one of the hybridoma lines: 21B12, 31H4 and 16F12 (and corresponding modifications to the encoding nucleotides) will produce antibodies to PCSK9 having functional and chemical characteristics similar to those of the antibodies from the hybridoma lines: 21B12, 31H4 and 16F12. In contrast, in certain embodiments, substantial modifications in the functional and/or chemical characteristics of antibodies to PCSK9 can be accomplished by selecting substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" can involve a substitution of a native amino acid residue with a normative residue such that there is little or no effect on the polarity or charge of the amino acid residue at that position. Furthermore, any native residue in the polypeptide can also be substituted with alanine, as has been previously described for "alanine scanning mutagenesis."

Desired amino acid substitutions (whether conservative or non-conservative) can be determined by those skilled in the art at the time such substitutions are desired. In certain embodiments, amino acid substitutions can be used to identify important residues of antibodies to PCSK9, or to increase or decrease the affinity of the antibodies to PCSK9 as described herein.

In certain embodiments, antibodies of the present invention can be expressed in cell lines other than hybridoma cell lines. In certain embodiments, sequences encoding particular antibodies can be used for transformation of a suitable mammalian host cell. According to certain embodiments, transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference for any purpose). In certain embodiments, the transformation procedure used can depend upon the host to be transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include, but are not limited to, many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines can be selected through determining which cell lines have high expression levels and produce antibodies with constitutive HGF binding properties. Appropriate expression vectors for mammalian host cells are well known.

In certain embodiments, antigen binding proteins comprise one or more polypeptides. In certain embodiments, any of a variety of expression vector/host systems can be utilized to express polynucleotide molecules encoding polypeptides comprising one or more ABP components or the ABP itself. Such systems include, but are not limited to, microorganisms, such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV, tobacco mosaic virus, TMV) or transformed with bacterial expression vectors (e.g., Ti or pBR322 plasmid); or animal cell systems.

In certain embodiments, a polypeptide comprising one or more ABP components or the ABP itself is recombinantly expressed in yeast. Certain such embodiments use commercially available expression systems, e.g., the *Pichia* Expression System (Invitrogen, San Diego, Calif.), following the manufacturer's instructions. In certain embodiments, such a system relies on the pre-pro-alpha sequence to direct secretion. In certain embodiments, transcription of the insert is driven by the alcohol oxidase (AOX1) promoter upon induction by methanol.

In certain embodiments, a secreted polypeptide comprising one or more ABP components or the ABP itself is purified from yeast growth medium. In certain embodiments, the methods used to purify a polypeptide from yeast growth medium is the same as those used to purify the polypeptide from bacterial and mammalian cell supernatants.

In certain embodiments, a nucleic acid encoding a polypeptide comprising one or more ABP components or the ABP itself is cloned into a baculovirus expression vector, such as pVL1393 (PharMingen, San Diego, Calif.). In certain embodiments, such a vector can be used according to the manufacturer's directions (PharMingen) to infect *Spodoptera frugiperda* cells in sF9 protein-free media and to produce recombinant polypeptide. In certain embodiments, a polypeptide is purified and concentrated from such media using a heparin-Sepharose column (Pharmacia).

In certain embodiments, a polypeptide comprising one or more ABP components or the ABP itself is expressed in an insect system. Certain insect systems for polypeptide expression are well known to those of skill in the art. In one such system, *Autographa californica* nuclear polyhedrosis virus (AcNPV) is used as a vector to express foreign genes in *Spodoptera frugiperda* cells or in *Trichoplusia larvae*. In certain embodiments, a nucleic acid molecule encoding a polypeptide can be inserted into a nonessential gene of the virus, for example, within the polyhedrin gene, and placed under control of the promoter for that gene. In certain embodiments, successful insertion of a nucleic acid molecule will render the nonessential gene inactive. In certain embodiments, that inactivation results in a detectable characteristic. For example, inactivation of the polyhedrin gene results in the production of virus lacking coat protein.

In certain embodiments, recombinant viruses can be used to infect *S. frugiperda* cells or *Trichoplusia larvae*. See, e.g., Smith et al., J. Virol., 46: 584 (1983); Engelhard et al., Proc. Nat. Acad. Sci. (USA), 91: 3224-7 (1994).

In certain embodiments, polypeptides comprising one or more ABP components or the ABP itself made in bacterial cells are produced as insoluble inclusion bodies in the bacteria. In certain embodiments, host cells comprising such inclusion bodies are collected by centrifugation; washed in 0.15 M NaCl, 10 mM Tris, pH 8, 1 mM EDTA; and treated with 0.1 mg/ml lysozyme (Sigma, St. Louis, Mo.) for 15 minutes at room temperature. In certain embodiments, the lysate is cleared by sonication, and cell debris is pelleted by centrifugation for 10 minutes at 12,000×g. In certain embodiments, the polypeptide-containing pellet is resuspended in 50 mM Tris, pH 8, and 10 mM EDTA; layered over 50% glycerol; and centrifuged for 30 minutes at 6000×g. In certain embodiments, that pellet can be resuspended in standard phosphate buffered saline solution (PBS) free of $Mg^{++}$ and $Ca^{++}$. In certain embodiments, the polypeptide is further purified by fractionating the resuspended pellet in a denaturing SDS polyacrylamide gel (See, e.g., Sambrook et al., supra). In certain embodiments, such a gel can be soaked in 0.4 M KCl to visualize the protein, which can be excised and electro-eluted in gel-running buffer lacking SDS. According to certain embodiments, a Glutathione-S-Transferase (GST) fusion protein is produced in bacteria as a soluble protein. In certain embodiments, such GST fusion protein is purified using a GST Purification Module (Pharmacia).

In certain embodiments, it is desirable to "refold" certain polypeptides, e.g., polypeptides comprising one or more ABP components or the ABP itself. In certain embodiments, such polypeptides are produced using certain recombinant systems discussed herein. In certain embodiments, polypeptides are "refolded" and/or oxidized to form desired tertiary structure and/or to generate disulfide linkages. In certain embodiments, such structure and/or linkages are related to certain biological activity of a polypeptide. In certain embodiments, refolding is accomplished using any of a number of procedures known in the art. Exemplary methods include, but are not limited to, exposing the solubilized polypeptide agent to a pH typically above 7 in the presence of a chaotropic agent. An exemplary chaotropic agent is guanidine. In certain embodiments, the refolding/oxidation solution also contains a reducing agent and the oxidized form of that reducing agent. In certain embodiments, the reducing agent and its oxidized form are present in a ratio that will generate a particular redox potential that allows disulfide shuffling to occur. In certain embodiments, such shuffling allows the formation of cysteine bridges. Exemplary redox couples include, but are not limited to, cysteine/cystamine, glutathione/dithiobisGSH, cupric chloride, dithiothreitol DTT/dithiane DTT, and 2-mercaptoethanol (bME)/dithio-bME. In certain embodiments, a co-solvent is used to increase the efficiency of refolding. Exemplary cosolvents include, but are not limited to, glycerol, polyethylene glycol of various molecular weights, and arginine.

In certain embodiments, one substantially purifies a polypeptide comprising one or more ABP components or the ABP itself. Certain protein purification techniques are known to those of skill in the art. In certain embodiments, protein purification involves crude fractionation of polypeptide fractionations from non-polypeptide fractions. In certain embodiments, polypeptides are purified using chromatographic and/or electrophoretic techniques. Exemplary purification methods include, but are not limited to, precipitation with ammonium sulphate; precipitation with PEG; immunoprecipitation; heat denaturation followed by centrifugation; chromatography, including, but not limited to, affinity chromatography (e.g., Protein-A-Sepharose), ion exchange chromatography, exclusion chromatography, and reverse phase chromatography; gel filtration; hydroxyapatite chromatography; isoelectric focusing; polyacrylamide gel electrophoresis; and combinations of such and other techniques. In certain embodiments, a polypeptide is purified by fast protein liquid chromatography or by high pressure liquid chromotography (HPLC). In certain embodiments, purification steps can be changed or certain steps can be omitted, and still result in a suitable method for the preparation of a substantially purified polypeptide.

In certain embodiments, one quantitates the degree of purification of a polypeptide preparation. Certain methods for quantifying the degree of purification are known to those of skill in the art. Certain exemplary methods include, but are not limited to, determining the specific binding activity of the preparation and assessing the amount of a polypeptide within a preparation by SDS/PAGE analysis. Certain exemplary methods for assessing the amount of purification of a polypeptide preparation comprise calculating the binding activity of a preparation and comparing it to the binding activity of an initial extract. In certain embodiments, the results of such a calculation are expressed as "fold purification." The units used to represent the amount of binding activity depend upon the particular assay performed.

In certain embodiments, a polypeptide comprising one or more ABP components or the ABP itself is partially purified. In certain embodiments, partial purification can be accomplished by using fewer purification steps or by utilizing different forms of the same general purification scheme. For example, in certain embodiments, cation-exchange column chromatography performed utilizing an HPLC apparatus will generally result in a greater "fold purification" than the same technique utilizing a low-pressure chromatography system. In certain embodiments, methods resulting in a lower degree of purification can have advantages in total recovery of polypeptide, or in maintaining binding activity of a polypeptide.

In certain instances, the electrophoretic migration of a polypeptide can vary, sometimes significantly, with different conditions of SDS/PAGE. See, e.g., Capaldi et al., Biochem. Biophys. Res. Comm., 76: 425 (1977). It will be appreciated that under different electrophoresis conditions, the apparent molecular weights of purified or partially purified polypeptide can be different.

Exemplary Epitopes

Epitopes to which anti-PCSK9 antibodies bind are provided. In some embodiments, epitopes that are bound by the presently disclosed antibodies are particularly useful. In some embodiments, antigen binding proteins that bind to any of the epitopes that are bound by the antibodies described herein are useful. In some embodiments, the epitopes bound by any of the antibodies listed in Table 2 and FIGS. 2 and 3 are especially useful. In some embodiments, the epitope is on the catalytic domain PCSK9.

In certain embodiments, a PCSK9 epitope can be utilized to prevent (e.g., reduce) binding of an anti-PCSK9 antibody or antigen binding protein to PCSK9. In certain embodiments, a PCSK9 epitope can be utilized to decrease binding of an anti-PCSK9 antibody or antigen binding protein to PCSK9. In certain embodiments, a PCSK9 epitope can be utilized to substantially inhibit binding of an anti-PCSK9 antibody or antigen binding protein to PCSK9.

In certain embodiments, a PCSK9 epitope can be utilized to isolate antibodies or antigen binding proteins that bind to PCSK9. In certain embodiments, a PCSK9 epitope can be utilized to generate antibodies or antigen binding proteins which bind to PCSK9. In certain embodiments, a PCSK9 epitope or a sequence comprising a PCSK9 epitope can be utilized as an immunogen to generate antibodies or antigen binding proteins that bind to PCSK9. In certain embodiments, a PCSK9 epitope can be administered to an animal, and antibodies that bind to PCSK9 can subsequently be obtained from the animal. In certain embodiments, a PCSK9 epitope or a sequence comprising a PCSK9 epitope can be utilized to interfere with normal PCSK9-mediated activity, such as association of PCSK9 with the LDLR.

In some embodiments, antigen binding proteins disclosed herein bind specifically to N-terminal prodomain, a subtilisin-like catalytic domain and/or a C-terminal domain. In some embodiments, the antigen binding protein binds to the substrate-binding groove of PCSK-9 (described in Cunningham et al., incorporated herein in its entirety by reference).

In some embodiments, the domain(s)/region(s) containing residues that are in contact with or are buried by an antibody can be identified by mutating specific residues in PCSK9 (e.g., a wild-type antigen) and determining whether the antigen binding protein can bind the mutated or variant PCSK9 protein. By making a number of individual mutations, residues that play a direct role in binding or that are in sufficiently close proximity to the antibody such that a mutation can affect binding between the antigen binding protein and antigen can be identified. From a knowledge of these amino acids, the domain(s) or region(s) of the antigen that contain residues in contact with the antigen binding protein or covered by the antibody can be elucidated. Such a domain can include the binding epitope of an antigen binding protein. One specific example of this general approach utilizes an arginine/glutamic acid scanning protocol (see, e.g., Nanevicz, T., et al., 1995, *J. Biol. Chem.*, 270:37, 21619-21625 and Zupnick, A., et al., 2006, *J. Biol. Chem.*, 281:29, 20464-20473). In general, arginine and glutamic acids are substituted (typically individually) for an amino acid in the wild-type polypeptide because these amino acids are charged and bulky and thus have the potential to disrupt binding between an antigen binding protein and an antigen in the region of the antigen where the mutation is introduced. Arginines that exist in the wild-type antigen are replaced with glutamic acid. A variety of such individual mutants are obtained and the collected binding results analyzed to determine what residues affect binding.

Example 39 describes one such arginine/glutamic acid scanning of PCSK9 for PCSK9 antigen binding proteins provided herein. A series of mutant PCSK9 antigens were created, with each mutant antigen having a single mutation. Binding of each mutant PCSK9 antigen with various PCSK9 ABPs was measured and compared to the ability of the selected ABPs to bind wild-type PCSK9 (SEQ ID NO: 303).

An alteration (for example a reduction or increase) in binding between an antigen binding protein and a variant PCSK9 as used herein means that there is a change in binding affinity (e.g., as measured by known methods such as Biacore testing or the bead based assay described below in the examples), $EC_{50}$, and/or a change (for example a reduction) in the total binding capacity of the antigen binding protein (for example, as evidenced by a decrease in Bmax in a plot of antigen binding protein concentration versus antigen concentration). A significant alteration in binding indicates that the mutated residue is directly involved in binding to the antigen binding protein or is in close proximity to the binding protein when the binding protein is bound to antigen.

In some embodiments, a significant reduction in binding means that the binding affinity, EC50, and/or capacity between an antigen binding protein and a mutant PCSK9 antigen is reduced by greater than 10%, greater than 20%, greater than 40%, greater than 50%, greater than 55%, greater than 60%, greater than 65%, greater than 70%, greater than 75%, greater than 80%, greater than 85%, greater than 90% or greater than 95% relative to binding between the antigen binding protein and a wild type PCSK9 (e.g., shown in SEQ ID NO: 1 and/or SEQ ID NO: (303). In certain embodiments, binding is reduced below detectable limits. In some embodiments, a significant reduction in binding is evidenced when binding of an antigen binding protein to a variant PCSK9 protein is less than 50% (for example, less than 40%, 35%, 30%, 25%, 20%, 15% or 10%) of the binding observed between the antigen binding protein and a wild-type PCSK9 protein (for example, the protein of SEQ ID NO: 1 and/or SEQ ID NO: (303). Such binding measurements can be made using a variety of binding assays known in the art. A specific example of one such assay is described in Example 39.

In some embodiments, antigen binding proteins are provided that exhibit significantly lower binding for a variant PCSK9 protein in which a residue in a wild-type PCSK9 protein (e.g., SEQ ID NO: 1 or SEQ ID NO: 303 is substituted with arginine or glutamic acid. In some embodiments, binding of an antigen binding protein is significantly reduced or increased for a variant PCSK9 protein having any one or more (e.g., 1, 2, 3, 4, 5, 6, 7, 8, 9, 10, or 244) of the following mutations: R207E, D208R, R185E, R439E, E513R, V538R, E539R, T132R, S351R, A390R, A413R, E582R, D162R, R164E, E167R, S123R, E129R, A311R, D313R, D337R, R519E, H521R, and Q554R as compared to a wild-type PCSK9 protein (e.g., SEQ ID NO: 1 or SEQ ID NO: 303. In the shorthand notation used here, the format is: Wild type residue: Position in polypeptide: Mutant residue, with the numbering of the residues as indicated in SEQ ID NO: 1 or SEQ ID NO: 303.

In some embodiments, binding of an antigen binding protein is significantly reduced or increased for a mutant PCSK9 protein having one or more (e.g., 1, 2, 3, 4, 5, or more) mutations at the following positions: 207, 208, 185, 181, 439, 513, 538, 539, 132, 351, 390, 413, 582, 162, 164, 167, 123, 129, 311, 313, 337, 519, 521, and 554, as shown in SEQ ID NO: 1 as compared to a wild-type PCSK9 protein (e.g., SEQ ID NO: 1 or SEQ ID NO: 303. In some embodiments, binding of an antigen binding protein is reduced or increased for a mutant PCSK9 protein having one or more (e.g., 1, 2, 3, 4, 5, or more) mutations at the following positions: 207, 208, 185, 181, 439, 513, 538, 539, 132, 351, 390, 413, 582, 162, 164, 167, 123, 129, 311, 313, 337, 519, 521, and 554, as shown in SEQ ID NO: 1 as compared to a wild-type PCSK9 protein (e.g., SEQ ID NO: 1 or SEQ ID NO: 303. In some embodiments, binding of an antigen binding protein is substantially reduced or increased for a mutant PCSK9 protein having one or more (e.g., 1, 2, 3, 4, 5, or more) mutations at the following positions: 207, 208, 185, 181, 439, 513, 538, 539, 132, 351, 390, 413, 582, 162, 164, 167, 123, 129, 311, 313, 337, 519, 521, and 554, within SEQ ID NO: 1 as compared to a wild-type PCSK9 protein (e.g., SEQ ID NO: 1 or SEQ ID NO: 303.

In some embodiments, binding of an ABP is significantly reduced or increased for a mutant PCSK9 protein having one or more (e.g., 1, 2, 3, 4, 5, etc.) of the following mutations: R207E, D208R, R185E, R439E, E513R, V538R, E539R, T132R, S351R, A390R, A413R, E582R, D162R, R164E, E167R, S123R, E129R, A311R, D313R, D337R, R519E, H521R, and Q554R within SEQ ID NO: 1 or SEQ ID NO: 303, as compared to a wild-type PCSK9 protein (e.g., SEQ ID NO: 1 or SEQ ID NO: 303).

In some embodiments, binding of an ABP is significantly reduced or increased for a mutant PCSK9 protein having one or more (e.g., 1, 2, 3, 4, 5, etc.) of the following mutations: R207E, D208R, R185E, R439E, E513R, V538R, E539R, T132R, S351R, A390R, A413R, and E582R within SEQ ID NO: 1 or SEQ ID NO: 303, as compared to a wild-type PCSK9 protein (e.g., SEQ ID NO: 1 or SEQ ID NO: 303). In some embodiments, the binding is reduced. In some embodiments, the reduction in binding is observed as a change in EC50. In some embodiments, the change in EC50 is an increase in the numerical value of the EC50 (and thus is a decrease in binding).

In some embodiments, binding of an ABP is significantly reduced or increased for a mutant PCSK9 protein having one or more (e.g., 1, 2, 3, 4, 5, etc.) of the following mutations: D162R, R164E, E167R, S123R, E129R, A311R, D313R, D337R, R519E, H521R, and Q554R within SEQ ID NO: 1, as compared to a wild-type PCSK9 protein (e.g., SEQ ID NO: 1 or SEQ ID NO: 303). In some embodiments, the binding is reduced. In some embodiments, the reduction in binding is observed as a change in Bmax. In some embodiments, the shift in Bmax is a reduction of the maximum signal generated by the ABP. In some embodiments, for an amino acid to be part of an epitope, the Bmax is reduced by at least 10%, for example, reductions of at least any of the following amounts: 20, 30, 40, 50, 60, 70, 80, 90, 95, 98, 99, or 100 percent can, in some embodiments, indicate that the residue is part of the epitope.

Although the variant forms just listed are referenced with respect to the wild-type sequence shown in SEQ ID NO: 1 or SEQ ID NO: 303, it will be appreciated that in an allelic variant of PCSK9 the amino acid at the indicated position could differ. Antigen binding proteins showing significantly lower binding for such allelic forms of PCSK9 are also contemplated. Accordingly, in some embodiments, any of the above embodiments can be compared to an allelic sequence, rather than purely the wild-type sequence shown in FIG. 1A In some embodiments, binding of an antigen binding protein is significantly reduced for a variant PCSK9 protein in which the residue at a selected position in the wild-type PCSK9 protein is mutated to any other residue. In some embodiments, the herein described arginine/glutamic acid replacements are used for the identified positions. In some embodiments, alanine is used for the identified positions.

As noted above, residues directly involved in binding or covered by an antigen binding protein can be identified from scanning results. These residues can thus provide an indication of the domains or regions of SEQ ID NO: 1 (or SEQ ID NO: 303 or SEQ ID NO: 3) that contain the binding region(s) to which antigen binding proteins bind. As can be seen from the results summarized in Example 39, in some embodiments an antigen binding protein binds to a domain containing at least one of amino acids: 207, 208, 185, 181, 439, 513, 538, 539, 132, 351, 390, 413, 582, 162, 164, 167, 123, 129, 311, 313, 337, 519, 521, and 554 of SEQ ID NO: 1 or SEQ ID NO: 303. In some embodiments, the antigen binding protein binds to a region containing at least one of amino acids 207, 208, 185, 181, 439, 513, 538, 539, 132, 351, 390, 413, 582, 162, 164, 167, 123, 129, 311, 313, 337, 519, 521, and 554 of SEQ ID NO: 1 or SEQ ID NO: 303.

In some embodiments, the antigen binding protein binds to a region containing at least one of amino acids 162, 164, 167, 207 and/or 208 of SEQ ID NO: 1 or SEQ ID NO: 303. In some embodiments, more than one (e.g., 2, 3, 4, or 5) of the identified residues are part of the region that is bound by the ABP. In some embodiments, the ABP competes with ABP 21B12.

In some embodiments, the antigen binding protein binds to a region containing at least one of amino acid 185 of SEQ ID NO: 1 or SEQ ID NO: 303. In some embodiments, the ABP competes with ABP 31H4.

In some embodiments, the antigen binding protein binds to a region containing at least one of amino acids 439, 513, 538, and/or 539 of SEQ ID NO: 1 or SEQ ID NO: 303. In some embodiments, more than one (e.g., 2, 3, or 4) of the identified residues are part of the region that is bound by the ABP. In some embodiments, the ABP competes with ABP 31A4.

In some embodiments, the antigen binding protein binds to a region containing at least one of amino acids 123, 129, 311, 313, 337, 132, 351, 390, and/or 413 of SEQ ID NO: 1 or SEQ ID NO: 303. In some embodiments, more than one (e.g., 2, 3, 4, 5, 6, 7, 8, or 9) of the identified residues are part of the region that is bound by the ABP. In some embodiments, the ABP competes with ABP 12H11.

In some embodiments, the antigen binding protein binds to a region containing at least one of amino acid 582, 519, 521, and/or 554 of SEQ ID NO: 1 or SEQ ID NO: 303. In some embodiments, more than one (e.g., 2, 3, or 4) of the identified residues are part of the region that is bound by the ABP. In some embodiments, the ABP competes with ABP 3C4.

In some embodiments, the antigen binding proteins binds to the foregoing regions within a fragment or the full length sequence of SEQ ID NO: 1 or SEQ ID NO: 303. In other embodiments, antigen binding proteins bind to polypeptides consisting of these regions. The reference to "SEQ ID NO: 1 or SEQ ID NO: 303" denotes that one or both of these sequences can be employed or relevant. The phrase does not denote that only one should be employed.

As noted above, the above description references specific amino acid positions with reference to SEQ ID NO: 1. However, throughout the specification generally, reference is made to a Pro/Cat domain that commences at position 31, which is provided in SEQ ID NO: 3. As noted below, SEQ ID NO: 1 and SEQ ID NO: 303 lack the signal sequence of PCSK9. As such, any comparison between these various disclosures should take this difference in numbering into account. In particular, any amino acid position in SEQ ID NO: 1, will correspond to an amino acid position 30 amino acids further into the protein in SEQ ID NO: 3. For example, position 207 of SEQ ID NO: 1, corresponds to position 237 of SEQ ID NO: 3 (the full length sequence, and the numbering system used in the present specification generally). Table 39.6 outlines how the above noted positions, which reference SEQ ID NO: 1 (and/or SEQ ID NO: 303) correspond to SEQ ID NO: 3 (which includes the signal sequence). Thus, any of the above noted embodiments that are described in regard to SEQ ID NO: 1 (and/or SEQ ID NO: 303), are described in reference to SEQ ID NO: 3, by the noted corresponding positions.

In some embodiments, ABP 21B12 binds to an epitope including residues 162-167 (e.g., residues D162-E167 of SEQ ID NO: 1). In some embodiments, ABP 12H11 binds to an epitope that includes residues 123-132 (e.g., S123-T132 of SEQ ID NO: 1). In some embodiments, ABP 12H11 binds to an epitope that includes residues 311-313 (e.g., A311-D313 of SEQ ID NO: 1). In some embodiments, ABPs can bind to an epitope that includes any one of these strands of sequences.

Competing Antigen Binding Proteins

In another aspect, antigen binding proteins are provided that compete with one of the exemplified antibodies or functional fragments binding to the epitope described herein for specific binding to PCSK9. Such antigen binding proteins can also bind to the same epitope as one of the herein exemplified antigen binding proteins, or an overlapping epitope. Antigen binding proteins and fragments that compete with or bind to the same epitope as the exemplified antigen binding proteins are expected to show similar functional properties. The exemplified antigen binding proteins and fragments include those described above, including those with the heavy and light chains, variable region domains and CDRs included in TABLE 2 And/or FIGS. 2-3 and 15. Thus, as a specific example, the antigen binding proteins that are provided include those that compete with an antibody or antigen binding protein having:

(a) all 6 of the CDRs listed for an antibody listed in FIGS. 2-3 and 15;

(b) a VH and a VL listed for an antibody listed in Table 2; or (c) two light chains and two heavy chains as specified for an antibody listed in Table 2.

Certain Therapeutic Uses and Pharmaceutical Compositions

In certain instances, PCSK9 activity correlates with a number of human disease states. For example, in certain instances, too much or too little PCSK9 activity correlates with certain conditions, such as hypercholesterolemia. Therefore, in certain instances, modulating PCSK9 activity can be therapeutically useful. In certain embodiments, a neutralizing antigen binding protein to PCSK9 is used to modulate at least one PCSK9 activity (e.g., binding to LDLR). Such methods can treat and/or prevent and/or reduce the risk of disorders that relate to elevated serum cholesterol levels or in which elevated cholesterol levels are relevant.

As will be appreciated by one of skill in the art, in light of the present disclosure, disorders that relate to, involve, or can be influenced by varied cholesterol, LDL, or LDLR levels can be addressed by various embodiments of the antigen binding proteins. In some embodiments, a "cholesterol related disorder" (which includes "serum cholesterol related disorders") includes any one or more of the following: hypercholesterolemia, heart disease, metabolic syndrome, diabetes, coronary heart disease, stroke, cardiovascular diseases, Alzheimers disease and generally dyslipidemias, which can be manifested, for example, by an elevated total serum cholesterol, elevated LDL, elevated triglycerides, elevated VLDL, and/or low HDL. Some non-limiting examples of primary and secondary dyslipidemias that can be treated using an ABP, either alone, or in combination with one or more other agents include the metabolic syndrome, diabetes mellitus, familial combined hyperlipidemia, familial hypertriglyceridemia, familial hypercholesterolemias, including heterozygous hypercholesterolemia, homozygous hypercholesterolemia, familial defective apolipoprotein B-100; polygenic hypercholesterolemia; remnant removal disease, hepatic lipase deficiency; dyslipidemia secondary to any of the following: dietary indiscretion, hypothyroidism, drugs including estrogen and progestin therapy, beta-blockers, and thiazide diuretics; nephrotic syndrome, chronic renal failure, Cushing's syndrome, primary biliary cirrhosis, glycogen storage diseases, hepatoma, cholestasis, acromegaly, insulinoma, isolated growth hormone deficiency, and alcohol-induced hypertriglyceridemia. ABP can also be useful in preventing or treating atherosclerotic diseases, such as, for example, coronary heart disease, coronary artery disease, peripheral arterial disease, stroke (ischaemic and hemorrhagic), angina pectoris, or cerebrovascular disease and acute coronary syndrome, myocardial infarction. In some embodiments, the ABP is useful in reducing the risk of: nonfatal heart attacks, fatal and non-fatal strokes, certain types of heart surgery, hospitalization for heart failure, chest pain in patients with heart disease, and/or cardiovascular events because of established heart disease such as prior heart attack, prior heart surgery, and/or chest pain with evidence of clogged arteries. In some embodiments, the ABP and methods can be used to reduce the risk of recurrent cardiovascular events.

As will be appreciated by one of skill in the art, diseases or disorders that are generally addressable (either treatable or preventable) through the use of statins can also benefit from the application of the instant antigen binding proteins. In addition, in some embodiments, disorders or disease that can benefit from the prevention of cholesterol synthesis or increased LDLR expression can also be treated by various embodiments of the antigen binding proteins. In addition, as will be appreciated by one of skill in the art, the use of the anti-PCSK9 antibodies can be especially useful in the treatment of Diabetes. Not only is Diabetes a risk factor for coronary heart disease, but insulin increases the expression of PCSK9. That is, people with Diabetes have elevated plasma lipid levels (which can be related to high PCSK9 levels) and can benefit from lowering those levels. This is generally discussed in more detail in Costet et al. ("Hepatic PCSK9 Expression is Regulated by Nutirtional Status via Insulin and Sterol Regulatiory Element-binding Protein 1C", J. Biol. Chem., 281: 6211-6218, 2006), the entirety of which is incorporated herein by reference.

In some embodiments, the antigen binding protein is administered to those who have diabetes mellitus, abdominal aortic aneurysm, atherosclerosis and/or peripheral vascular disease in order to decrease their serum cholesterol levels to a safer range. In some embodiments, the antigen binding protein is administered to patients at risk of developing any of the herein described disorders. In some embodiments, the ABPs are administered to subjects that smoke, have hypertension or a familial history of early heart attacks.

In some embodiments, a subject is administered an ABP if they are at a moderate risk or higher on the 2004 NCEP treatment goals. In some embodiments, the ABP is admininstered to a subject if the subject's LDL cholesterol level is greater than 160 mg/dl. In some embodiments, the ABP is administered if the subjects LDL cholesterol level is greater than 130 (and they have a moderate or moderately high risk according to the 2004 NCEP treatment goals). In some embodiments, the ABP is administered if the subjects LDL cholesterol level is greater than 100 (and they have a high or very high risk according to the 2004 NCEP treatment goals).

A physician will be able to select an appropriate treatment indications and target lipid levels depending on the individual profile of a particular patient. One well-accepted standard for guiding treatment of hyperlipidemia is the Third Report of the National Cholesterol Education Program (NCEP) Expert Panel on Detection, Evaluation, and Treatment of the High Blood Cholesterol in Adults (Adult Treatment Panel III) Final Report, National Institutes of Health, NIH Publication No. 02-5215 (2002), the printed publication of which is hereby incorporated by reference in its entirety.

In some embodiments, antigen binding proteins to PCSK9 are used to decrease the amount of PCSK9 activity from an abnormally high level or even a normal level. In some embodiments, antigen binding proteins to PCSK9 are used to treat or prevent hypercholesterolemia and/or in the preparation of medicaments therefore and/or for other cholesterol related disorders (such as those noted herein). In certain embodiments, an antigen binding protein to PCSK9 is used to treat or prevent conditions such as hypercholesterolemia in which PCSK9 activity is normal. In such conditions, for example, reduction of PCSK9 activity to below normal can provide a therapeutic effect.

In some embodiments, more than one antigen binding protein to PCSK9 is used to modulate PCSK9 activity.

In certain embodiments, methods are provided of treating a cholesterol related disorder, such as hypercholesterolemia comprising administering a therapeutically effective amount of one or more antigen binding proteins to PCSK9 and another therapeutic agent.

In certain embodiments, an antigen binding protein to PCSK9 is administered alone. In certain embodiments, an antigen binding protein to PCSK9 is administered prior to the administration of at least one other therapeutic agent. In certain embodiments, an antigen binding protein to PCSK9 is administered concurrent with the administration of at least one other therapeutic agent. In certain embodiments, an antigen binding protein to PCSK9 is administered subsequent to the administration of at least one other therapeutic agent. In other embodiments, an antigen binding protein to PCSK9 is administered prior to the administration of at least one other therapeutic agent. Therapeutic agents (apart from the antigen binding protein), include, but are not limited to, at least one other cholesterol-lowering (serum and/or total body cholesterol) agent or an agent. In some embodiments, the agent increases the expression of LDLR, have been observed to increase serum HDL levels, lower LDL levels or lower triglyceride levels. Exemplary agents include, but are not limited to, statins (atorvastatin, cerivastatin, fluvastatin, lovastatin, mevastatin, pitavastatin, pravastatin, rosuvastatin, simvastatin), Nicotinic acid (Niacin) (NIACOR, NIASPAN (slow release niacin), SLO-NIACIN (slow release niacin)), Fibric acid (LOPID (Gemfibrozil), TRICOR (fenofibrate), Bile acid sequestrants (QUESTRAN (cholestyramine), colesevelam (WELCHOL), COLESTID (colestipol)), Cholesterol absorption inhibitors (ZETIA (ezetimibe)), Combining nicotinic acid with statin (ADVICOR (LOVASTATIN and NIASPAN), Combining a statin with an absorption inhibitor (VYTORIN (ZOCOR and ZETIA) and/or lipid modifying agents. In some embodiments, the ABP is combined with PPAR gamma agonsits, PPAR alpha/gamma agonists, squalene synthase inhibitors, CETP inhibitors, anti-hypertensives, anti-diabetic agents (such as sulphonyl ureas, insulin, GLP-1 analogs, DDPIV inhibitors), ApoB modulators, MTP inhibitoris and/or arteriosclerosis obliterans treatments. In some embodiments, the ABP is combined with an agent that increases the level of LDLR protein in a subject, such as statins, certain cytokines like oncostatin M, estrogen, and/or certain herbal ingredients such as berberine. In some embodiments, the ABP is combined with an agent that increases serum cholesterol levels in a subject (such as certain anti-psycotic agents, certain HIV protease inhibitors, dietary factors such as high fructose, sucrose, cholesterol or certain fatty acids and certain nuclear receptor agonists and antagonists for RXR, RAR, LXR, FXR). In some embodiments, the ABP is combined with an agent that increases the level of PCSK9 in a subject, such as statins and/or insulin. The combination of the two can allow for the undesirable side-effects of other agents to be mitigated by the ABP. As will be appreciated by one of skill in the art, in some embodiments, the ABP is combined with the other agent/compound. In some embodiments, the ABP and other agent are administered concurrently. In some embodiments, the ABP and other agent are not administered simultaneously, with the ABP being administered before or after the agent is administered. In some embodiments, the subject receives both the ABP and the other agent (that increases the level of LDLR) during a same period of prevention, occurrence of a disorder, and/or period of treatment.

Pharmaceutical compositions of the invention can be administered in combination therapy, i.e., combined with other agents. In certain embodiments, the combination therapy comprises an antigen binding protein capable of binding PCSK9, in combination with at least one anti-cholesterol agent. Agents include, but are not limited to, in vitro synthetically prepared chemical compositions, antibodies, antigen binding regions, and combinations and conjugates thereof. In certain embodiments, an agent can act as an agonist, antagonist, alllosteric modulator, or toxin. In certain embodiments, an agent can act to inhibit or stimulate its target (e.g., receptor or enzyme activation or inhibition), and thereby promote increased expression of LDLR or decrease serum cholesterol levels.

In certain embodiments, an antigen binding protein to PCSK9 can be administered prior to, concurrent with, and subsequent to treatment with a cholesterol-lowering (serum and/or total cholesterol) agent. In certain embodiments, an antigen binding protein to PCSK9 can be administered prophylactically to prevent or mitigate the onset of hypercholesterolemia, heart disease, diabetes, and/or any of the cholesterol related disorder. In certain embodiments, an antigen binding protein to PCSK9 can be administered for the treatment of an existing hypercholesterolemia condition. In some embodiments, the ABP delays the onset of the disorder and/or symptoms associated with the disorder. In some embodiments, the ABP is provided to a subject lacking any symptomtoms of any one of the cholesterol related disorders or a subset thereof.

In certain embodiments, an antigen binding protein to PCSK9 is used with particular therapeutic agents to treat various cholesterol related disorders, such as hypercholesterolemia. In certain embodiments, in view of the condition and the desired level of treatment, two, three, or more agents can be administered. In certain embodiments, such agents can be provided together by inclusion in the same formulation. In certain embodiments, such agent(s) and an antigen binding protein to PCSK9 can be provided together by inclusion in the same formulation. In certain embodiments, such agents can be formulated separately and provided together by inclusion in a treatment kit. In certain embodiments, such agents and an antigen binding protein to PCSK9 can be formulated separately and provided together by inclusion in a treatment kit. In certain embodiments, such agents can be provided separately. In certain embodiments, when administered by gene therapy, the genes encoding protein agents and/or an antigen binding protein to PCSK9 can be included in the same vector. In certain embodiments, the genes encoding protein agents and/or an antigen binding protein to PCSK9 can be under the control of the same promoter region. In certain embodiments, the genes encoding protein agents and/or an antigen binding protein to PCSK9 can be in separate vectors.

In certain embodiments, the invention provides for pharmaceutical compositions comprising an antigen binding protein to PCSK9 together with a pharmaceutically acceptable diluent, carrier, solubilizer, emulsifier, preservative and/or adjuvant.

In certain embodiments, the invention provides for pharmaceutical compositions comprising an antigen binding protein to PCSK9 and a therapeutically effective amount of at least one additional therapeutic agent, together with a pharmaceutically acceptable diluent, carrier, solubilizer, emulsifier, preservative and/or adjuvant.

In certain embodiments, an antigen binding protein to PCSK9 can be used with at least one therapeutic agent for inflammation. In certain embodiments, an antigen binding protein to PCSK9 can be used with at least one therapeutic agent for an immune disorder. Exemplary therapeutic agents for inflammation and immune disorders include, but are not limited to cyclooxygenase type 1 (COX-1) and cyclooxygenase type 2 (COX-2) inhibitors small molecule modulators of 38 kDa mitogen-activated protein kinase (p38-MAPK); small molecule modulators of intracellular molecules involved in inflammation pathways, wherein such intracellular molecules include, but are not limited to, jnk, IKK, NF-κB, ZAP70, and 1ck. Certain exemplary therapeutic agents for inflammation are described, e.g., in C. A. Dinarello & L. L. Moldawer *Proinflammatory and Anti-Inflammatory Cytokines in Rheumatoid Arthritis: A Primer for Clinicians Third Edition* (2001) Amgen Inc. Thousand Oaks, Calif.

In certain embodiments, pharmaceutical compositions will include more than one different antigen binding protein to PCSK9. In certain embodiments, pharmaceutical compositions will include more than one antigen binding protein to PCSK9 wherein the antigen binding proteins to PCSK9 bind more than one epitope. In some embodiments, the various antigen binding proteins will not compete with one another for binding to PCSK9. In some embodiments, any of the antigen binding proteins depicted in Table 2 and FIGS. 2 and/or 3 can be combined together in a pharmaceutical composition.

In certain embodiments, acceptable formulation materials preferably are nontoxic to recipients at the dosages and concentrations employed. In some embodiments, the formulation material(s) are for s.c. and/or I.V. administration. In certain embodiments, the pharmaceutical composition can contain formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (*Remington's Pharmaceutical Sciences*, 18$^{th}$ Edition, A. R. Gennaro, ed., Mack Publishing Company (1995). In some embodiments, the formulation comprises PBS; 20 mM NaOAC, pH 5.2, 50 mM NaCl; and/or 10 mM NAOAC, pH 5.2, 9% Sucrose.

In certain embodiments, an antigen binding protein to PCSK9 and/or a therapeutic molecule is linked to a half-life extending vehicle known in the art. Such vehicles include, but are not limited to, polyethylene glycol, glycogen (e.g., glycosylation of the ABP), and dextran. Such vehicles are described, e.g., in U.S. application Ser. No. 09/428,082, now U.S. Pat. No. 6,660,843 and published PCT Application No. WO 99/25044, which are hereby incorporated by reference for any purpose.

In certain embodiments, the optimal pharmaceutical composition will be determined by one skilled in the art depending upon, for example, the intended route of administration, delivery format and desired dosage. See, for example, *Remington's Pharmaceutical Sciences*, supra. In certain embodiments, such compositions may influence the physical state, stability, rate of in vivo release and rate of in vivo clearance of the antibodies of the invention.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In some embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising an antigen binding protein to PCSK9, with or without at least one additional therapeutic agents, can be prepared for storage by mixing the selected composition having the desired degree of purity with optional formulation agents (*Remington's Pharmaceutical Sciences*, supra) in the form of a lyophilized cake or an aqueous solution. Further, in certain embodiments, a composition comprising an antigen binding protein to PCSK9, with or without at least one additional therapeutic agents, can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising a desired antigen binding protein to PCSK9, with or without additional therapeutic agents, in a pharmaceutically acceptable vehicle. In certain embodiments, a vehicle for parenteral injection is sterile distilled water in which an antigen binding protein to PCSK9, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, an antigen binding protein to PCSK9, with or without at least one additional therapeutic agent, can be formulated as a dry powder for inhalation. In certain embodiments, an inhalation solution comprising an antigen binding protein to PCSK9, with or without at least one additional therapeutic agent, can be formulated with a propellant for aerosol delivery. In certain embodiments, solutions can be nebulized. Pulmonary administration is further described in PCT application no. PCT/US94/001875, which describes pulmonary delivery of chemically modified proteins.

In certain embodiments, it is contemplated that formulations can be administered orally. In certain embodiments, an antigen binding protein to PCSK9, with or without at least one additional therapeutic agents, that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of an antigen binding protein to PCSK9 and/or any additional therapeutic agents. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of an antigen binding protein to PCSK9, with or without at least one additional therapeutic agents, in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving antigen binding proteins to PCSK9, with or without at least one additional therapeutic agent(s), in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15:167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions can also include liposomes, which can be prepared by any of several methods known in the art. See, e.g., Eppstein et al., Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising an antigen binding protein to PCSK9, with or without at least one additional therapeutic agent, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which an antigen binding protein to PCSK9, with or without at least one additional therapeutic agent, is being used, the route of administration, and the size (body weight, body surface or organ size) and/or condition (the age and general health) of the patient. In certain embodiments, the clinician can titer the dosage and modify the route of administration to obtain the optimal therapeutic effect. In certain embodiments, a typical dosage can range from about 0.1 µg/kg to up to about 100 mg/kg or more, depending on the factors mentioned above. In certain embodiments, the dosage can range from 0.1 µg/kg up to about 100 mg/kg; or 1 µg/kg up to about 100 mg/kg; or 5 µg/kg up to about 100 mg/kg.

In certain embodiments, the frequency of dosing will take into account the pharmacokinetic parameters of an antigen binding protein to PCSK9 and/or any additional therapeutic agents in the formulation used. In certain embodiments, a clinician will administer the composition until a dosage is reached that achieves the desired effect. In certain embodiments, the composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data. In some embodiments, the amount and frequency of administration can take into account the desired cholesterol level (serum and/or total) to be obtained and the subject's present cholesterol level, LDL level, and/or LDLR levels, all of which can be obtained by methods that are well known to those of skill in the art.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration.

In certain embodiments, it can be desirable to use a pharmaceutical composition comprising an antigen binding protein to PCSK9, with or without at least one additional therapeutic agent, in an ex vivo manner. In such instances, cells, tissues and/or organs that have been removed from the patient are exposed to a pharmaceutical composition comprising an antigen binding protein to PCSK9, with or without at least one additional therapeutic agent, after which the cells, tissues and/or organs are subsequently implanted back into the patient.

In certain embodiments, an antigen binding protein to PCSK9 and/or any additional therapeutic agents can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

Based on the ability of ABPs to significantly neutralize PCSK9 activity (as demonstrated in the Examples below), these ABPs will have therapeutic effects in treating and preventing symptoms and conditions resulting from PCSK9-mediated activity, such as hypercholesterolemia.

Diagnostic Applications

In some embodiments, the ABP is used as a diagnostic tool. The ABP can be used to assay the amount of PCSK9 present in a sample and/or subject. As will be appreciated by one of skill in the art, such ABPs need not be neutralizing ABPs. In some embodiments, the diagnostic ABP is not a neutralizing ABP. In some embodiments, the diagnostic ABP binds to a different epitope than the neutralizing ABP binds to. In some embodiments, the two ABPs do not compete with one another.

In some embodiments, the ABPs disclosed herein are used or provided in an assay kit and/or method for the detection of PCSK9 in mammalian tissues or cells in order to screen/diagnose for a disease or disorder associated with changes in levels of PCSK9. The kit comprises an ABP that binds PCSK9 and means for indicating the binding of the ABP with PCSK9, if present, and optionally PCSK9 protein levels. Various means for indicating the presence of an ABP can be used. For example, fluorophores, other molecular probes, or enzymes can be linked to the ABP and the presence of the ABP can be observed in a variety of ways. The method for screening for such disorders can involve the use of the kit, or simply the use of one of the disclosed ABPs and the determination of whether the ABP binds to PCSK9 in a sample. As will be appreciated by one of skill in the art, high or elevated levels of PCSK9 will result in larger amounts of the ABP binding to PCSK9 in the sample. Thus, degree of ABP binding can be used to determine how much PCSK9 is in a sample. Subjects or samples with an amount of PCSK9 that is greater than a predetermined amount (e.g., an amount or range that a person without a PCSK9 related disorder would have) can be characterized as having a PCSK9 mediated disorder. In some embodiments, the ABP is administered to a subject taking a statin, in order to determine if the statin has increased the amount of PCSK9 in the subject.

In some embodiments, the ABP is a non-neutralizing ABP and is used to determine the amount of PCSK9 in a subject receiving an ABP and/or statin treatment.

EXAMPLES

The following examples, including the experiments conducted and results achieved, are provided for illustrative purposes only and are not to be construed as limiting the present invention.

Example 1

Immunization and Titering

Generation of Anti-PCSK9 Antibodies and Hybridomas

Antibodies to the mature form of PCSK9 (depicted as the sequence in FIG. 1A, with the pro-domain underlined), were raised in XenoMouse® mice (Abgenix, Fremont, Calif.), which are mice containing human immunoglobulin genes. Two groups of XenoMouse® mice, group 1 and 2, were used to produce antibodies to PCSK9. Group 1 included mice of the XenoMouse® strain XMG2-KL, which produces fully human IgG2$_\kappa$ and IgG2λ antibodies. Group 1 mice were immunized with human PCSK9. PCSK9 was prepared using standard recombinant techniques using the GenBank sequence as reference (NM__174936). Group 2 involved mice of the XenoMouse® strain XMG4-KL, which produce fully human IgG4$_\kappa$ and IgG4λ antibodies. Group 2 mice were also immunized with human PCSK9.

The mice of both groups were injected with antigen eleven times, according to the schedule in Table 3. In the initial immunizations, each mouse was injected with a total of 10 μg of antigen delivered intraperitoneally into the abdomen. Subsequent boosts are 5 ug doses and injection method is staggered between intraperitoneal injections into the abdomen and sub-cutaneous injections at the base of the tail. For intraperitoneal injections antigen is prepared as an emulsion with TiterMax® Gold (Sigma, Cat # T2684) and for subcutaneous injections antigen is mixed with Alum (aluminum phosphate) and CpG oligos. In injections 2 through 8 and 10, each mouse was injected with a total of 5 μg of antigen in the adjuvant alum gel. A final injection of 5 μg of antigen per mouse is delivered in Phospho buffered saline and delivered into 2 sites 50% IP into the abdomen and 50% SQ at the base of tail. The immunization programs are summarized in Table 3, shown below.

TABLE 3

| mouse strain | XMG2/kl | XMG4/kl |
|---|---|---|
| # of animals | 10 | 10 |
| immunogen | PCSK9-V5/His | PCSK9-V5/His |
| 1st boost | IP injection | IP injection |
| | 10 ug each | 10 ug each |
| | Titermax Gold | Titermax Gold |
| 2nd boost | tail injection | tail injection |
| | 5 ug each | 5 ug each |
| | Alum/CpG ODN | Alum/CpG ODN |
| 3rd boost | IP injection | IP injection |
| | 5 ug each | 5 ug each |
| | Titermax Gold | Titermax Gold |
| 4th boost | tail injection | tail injection |
| | 5 ug each | 5 ug each |
| | Alum/CpG ODN | Alum/CpG ODN |

TABLE 3-continued

| 5th boost | IP injection | IP injection |
|---|---|---|
| | 5 ug each | 5 ug each |
| | Titermax Gold | Titermax Gold |
| 6th boost | tail injection | tail injection |
| | 5 ug each | 5 ug each |
| | Alum/CpG ODN | Alum/CpG ODN |
| 7th boost | IP injection | IP injection |
| | 5 ug each | 5 ug each |
| | Titermax Gold | Titermax Gold |
| 8th boost | tail injection | tail injection |
| | 5 ug each | 5 ug each |
| | Alum/CpG ODN | Alum/CpG ODN |
| bleed | | |
| 9th boost | IP injection | IP injection |
| | 5 ug each | 5 ug each |
| | Titermax Gold | Titermax Gold |
| 10th boost | tail injection | tail injection |
| | 5 ug each | 5 ug each |
| | Alum/CpG ODN | Alum/CpG ODN |
| 11th boost | BIP | BIP |
| | 5 ug each | 5 ug each |
| | PBS | PBS |
| harvest | | |

The protocol used to titer the XenoMouse animals was as follows: Costar 3368 medium binding plates were coated with neutravadin @ 8 ug/ml (50 ul/well) and incubated at 4° C. in 1×PBS/0.05% azide overnight. They were washed using TiterTek 3-cycle wash with RO water. Plates were blocked using 250 ul of 1×PBS/1% milk and incubated for at least 30 minutes at RT. Block was washed off using TiterTek 3-cycle wash with RO water. One then captured b-human PCSK9 @ 2 ug/ml in 1×PBS/1% milk/10 mM $Ca^{2+}$ (assay diluent) 50 ul/well and incubated for 1 hr at RT. One then washed using TiterTek 3-cycle wash with RO water. For the primary antibody, sera was titrated 1:3 in duplicate from 1:100. This was done in assay diluent 50 ul/well and incubated for 1 hr at RT. One then washed using TiterTek 3-cycle wash with RO water. The secondary antibody was goat anti Human IgG Fc HRP @ 400 ng/ml in assay diluent at 50 ul/well. This was incubated for 1 hr at RT. This was then washed using TiterTek 3-cycle wash with RO water and patted dry on paper towels. For the substrate, one-step TMB solution (Neogen, Lexington, Ky.) was used (50 ul/well) and it was allowed to develop for 30 min at RT.

The protocols followed in the ELISA assays was as follows: For samples comprising b-PCSK9 with no V5H is tag the following protocol was employed: Costar 3368 medium binding plates (Corning Life Sciences) were employed. The plates were coated with neutravadin at 8 μg/ml in 1×PBS/0.05% Azide, (50 μl/well). The plates were incubated at 4° C. overnight. The plates were then washed using a Titertek M384 plate washer (Titertek, Huntsville, Ala.). A 3-cycle wash was performed. The plates were blocked with 250 μl of 1×PBS/1% milk and incubated approximately 30 minutes at room temperature. The plates were then washed using the M384 plate washer. A 3-cycle wash was performed. The capture was b-hu PCSK9, without a V5 tag, and was added at 2 μg/ml in 1×PBS/1% milk/10 mM $Ca^{2+}$ (40 μl/well). The plates were then incubated for 1 hour at room temperature. A 3-cycle wash was performed. Sera were titrated 1:3 in duplicate from 1:100, and row H was blank for sera. The titration was done in assay diluent, at a volume of 50 μl/well. The plates were incubated for 1 hour at room temperature. Next, a 3-cycle wash was performed. Goat anti Human IgG Fc HRP at 100 ng/ml (1:4000) in 1×PBS/1% milk/10 mM $Ca^{2+}$ (50 μl/well) was added to the plate and was incubated 1 hour at room temperature. The plates were washed once again, using a 3-cycle wash. The plates were then patted dry with paper towel. Finally, 1 step TMB (Neogen, Lexington, Ky.) (50

μl/well) was added to the plate and was quenched with 1N hydrochloric acid (50 μl/well) after 30 minutes at room temperature. OD's were read immediately at 450 nm using a Titertek plate reader.

Positive controls to detect plate bound PCSK9 were soluble LDL receptor (R&D Systems, Cat #2148LD/CF) and a polyclonal rabbit anti-PCSK9 antibody (Caymen Chemical #10007185) titrated 1:3 in duplicate from 3 μg/ml in assay diluent. LDLR was detected with goat anti LDLR(R&D Systems, Cat #AF2148) and rabbit anti goat IgGFc HRP at a concentration of 400 ng/ml; the rabbit polyclonal was detected with goat anti-rabbit IgG Fc at a concentration of 400 ng/ml in assay diluent. Negative control was naive XMG2-KL and XMG4-KL sera titrated 1:3 in duplicate from 1:100 in assay diluent.

For samples comprising b-PCSK9 with a V5H is tag the following protocol was employed: Costar 3368 medium binding plates (Corning Life Sciences) were employed. The plates were coated with neutravadin at 8 μg/ml in 1×PBS/0.05% Azide, (50 μl/well). The plates were incubated at 4° C. overnight. The plates were then washed using a Titertek M384 plate washer (Titertek, Huntsville, Ala.). A 3-cycle wash was performed. The plates were blocked with 250 μl of 1×PBS/1% milk and incubated approximately 30 minutes at room temperature. The plates were then washed using the M384 plate washer. A 3-cycle wash was performed. The capture was b-hu PCSK9, with a V5 tag, and was added at 2 μg/ml in 1×PBS/1% milk/10 mM $Ca^{2+}$ (40 μl/well). The plates were then incubated for 1 hour at room temperature. A 3-cycle wash was performed. Sera were titrated 1:3 in duplicate from 1:100, and row H was blank for sera. The titration was done in assay diluent, at a volume of 50 μl/well. The plates were incubated for 1 hour at room temperature. Next, the plates were washed using the M384 plate washer operated using a 3-cycle wash. Goat anti Human IgG Fc HRP at 400 ng/ml in 1×PBS/1% milk/10 mM $Ca^{2+}$ was added at 50 μl/well to the plate and the plate was incubated 1 hour at room temperature. The plates were washed once again, using a 3-cycle wash. The plates were then patted dry with paper towel. Finally, 1 step TMB (Neogen, Lexington, Ky.) (50 μl/well) was added to the plate and the plate was quenched with 1N hydrochloric acid (50 Owen) after 30 minutes at room temperature. OD's were read immediately at 450 nm using a Titertek plate reader.

Positive control was LDLR, rabbit anti-PCSK9 titrated 1:3 in duplicate from 3 μg/ml in assay diluent. LDLR detect with goat anti-LDLR(R&D Systems, Cat #AF2148) and rabbit anti-goat IgG Fc HRP at a concentration of 400 ng/ml; rabbit poly detected with goat anti-rabbit IgG Fc at a concentration of 400 ng/ml in assay diluent. Human anti-His 1.2,3 and anti-V5 1.7.1 titrated 1:3 in duplicate from 1 μg/ml in assay diluent; both detected with goat anti-human IgG Fc HRP at a concentration of 400 ng/ml in assay diluent. Negative control was naive XMG2-KL and XMG4-KL sera titrated 1:3 in duplicate from 1:100 in assay diluent.

Titers of the antibody against human PCSK9 were tested by ELISA assay for mice immunized with soluble antigen as described. Table 4 summarizes the ELISA data and indicates that there were some mice which appeared to be specific for PCSK9. See, e.g., Table 4. Therefore, at the end of the immunization program, 10 mice (ID in bold in Table 4) were selected for harvest, and splenocytes and lymphocytes were isolated from the spleens and lymph nodes respectively, as described herein.

TABLE 4

Summary of ELISA Results

| | Animal ID | Titer b-hu PCSK9 (V5His) @ 2 ug/ml | Titer b-hu PCSK9 @ 2 ug/ml |
|---|---|---|---|
| Group 1 - IgG2k/l | P175807 | >72900 @ OD 2.2 | 68359 |
| | P175808 | >72900 @ OD 2.3 | >72900 @ OD 2.5 |
| | P175818 | >72900 @ OD 3.2 | >72900 @ OD 3.0 |
| | P175819 | >72900 @ OD 3.4 | >72900 @ OD 3.2 |
| | P175820 | >72900 @ OD 2.4 | >72900 @ OD 2.5 |
| | P175821 | >72900 @ OD 3.4 | >72900 @ OD 3.0 |
| | P175830 | >72900 @ OD 2.6 | >72900 @ OD 2.5 |
| | P175831 | >72900 @ OD 3.1 | >72900 @ OD 3.1 |
| | P175832 | >72900 @ OD 3.8 | >72900 @ OD 3.6 |
| | P175833 | >72900 @ OD 2.6 | >72900 @ OD 2.3 |
| | P174501 | 19369 | 17109 |
| | P174503 | 31616 | 23548 |
| | P174508 | 48472 | 30996 |
| | P174509 | 23380 | 21628 |
| Group 2 - IgG4k/l | P174510 | 15120 | 9673 |
| | P175773 | 19407 | 15973 |
| | P175774 | 54580 | 44424 |
| | P175775 | 60713 | 55667 |
| | P175776 | 30871 | 22899 |
| | P175777 | 16068 | 12532 |
| | Naive G2 | <100 @ OD 0.54 | <100 @ OD 0.48 |
| | Naive G4 | <100 @ OD 1.57 | <100 @ OD 1.32 |

Example 2

Recovery of Lymphocytes, B-Cell Isolations, Fusions and Generation of Hybridomas This example outlines how the immune cells were recovered and the hybridomas were generated. Selected immunized mice were sacrificed by cervical dislocation and the draining lymph nodes were harvested and pooled from each cohort. The B cells were dissociated from lymphoid tissue by grinding in DMEM to release the cells from the tissues, and the cells were suspended in DMEM. The cells were counted, and 0.9 ml DMEM per 100 million lymphocytes was added to the cell pellet to resuspend the cells gently but completely.

Lymphocytes were mixed with nonsecretory myeloma P3X63Ag8.653 cells purchased from ATCC, cat.# CRL 1580 (Kearney et al., (1979) *J. Immunol.* 123, 1548-1550) at a ratio of 1:4. The cell mixture was gently pelleted by centrifugation at 400×g 4 min. After decanting of the supernatant, the cells were gently mixed using a 1 ml pipette. Preheated PEG/DMSO solution from Sigma (cat# P7306) (1 ml per million of B-cells) was slowly added with gentle agitation over 1 min followed by 1 min of mixing. Preheated IDMEM (2 ml per million of B cells) (DMEM without glutamine, L-glutamine, pen/strep, MEM non-essential amino acids (all from Invitrogen), was then added over 2 minutes with gentle agitation. Finally preheated IDMEM (8 ml per $10^6$ B-cells) was added over 3 minutes.

The fused cells were spun down 400×g 6 min and resuspended in 20 ml selection media (DMEM (Invitrogen), 15 FBS (Hyclone), supplemented with L-glutamine, pen/strep, MEM Non-essential amino acids, Sodium Pyruvate, 2-Mercaptoethanol (all from Invitrogen), HA-Azaserine Hypoxanthine and OPI (oxaloacetate, pyruvate, bovine insulin) (both from Sigma) and IL-6 (Boehringer Mannheim)) per million B-cells. Cells were incubated for 20-30 min at 37 C and then resuspended in 200 ml selection media and cultured for 3-4 days in T175 flask prior to 96 well plating. Thus, hybridomas that produced antigen binding proteins to PCSK9 were produced.

Example 3

Selection of PCSK9 Antibodies

The present example outlines how the various PCSK9 antigen binding proteins were characterized and selected. The binding of secreted antibodies (produced from the hybridomas produced in Examples 1 and 2) to PCSK9 was assessed. Selection of antibodies was based on binding data and inhibition of PCSK9 binding to LDLR and affinity. Binding to soluble PCSK9 was analyzed by ELISA, as described below. BIAcore® (surface plasmon resonance) was used to quantify binding affinity.

Primary Screen

A primary screen for antibodies which bind to wild-type PCSK9 was performed. The primary screen was performed on two harvests. The primary screen comprised an ELISA assay and was performed using the following protocol:

Costar 3702 medium binding 384 well plates (Corning Life Sciences) were employed. The plates were coated with neutravadin at a concentration of 4 µg/ml in 1×PBS/0.05% Azide, at a volume of 40 µl/well. The plates were incubated at 4° C. overnight. The plates were then washed using a Titertek plate washer (Titertek, Huntsville, Ala.). A 3-cycle wash was performed. The plates were blocked with 90 µl of 1×PBS/1% milk and incubated approximately 30 minutes at room temperature. The plates were then washed. Again, a 3-cycle wash was performed. The capture sample was biotinylated-PCSK9, without a V5 tag, and was added at 0.9 µg/ml in 1×PBS/1% milk/10 mM $Ca^{2+}$ at a volume of 40 µl/well. The plates were then incubated for 1 hour at room temperature. Next, the plates were washed using the Titertek plate washer operated using a 3-cycle wash. 10 µl of supernatant was transferred into 40 µl of 1×PBS/1% milk/10 mM $Ca^{2+}$ and incubated 1.5 hours at room temperature. Again the plates were washed using the Titertek plate washer operated using a 3-cycle wash. 40 µl/well of Goat anti-Human IgG Fc POD at a concentration of 100 ng/ml (1:4000) in 1×PBS/1% milk/10 mM $Ca^{2+}$ was added to the plate and was incubated 1 hour at room temperature. The plates were washed once again, using a 3-cycle wash. Finally, 40 µl/well of One-step TMB (Neogen, Lexington, Ky.) was added to the plate and quenching with 40 µl/well of 1N hydrochloric acid was performed after 30 minutes at room temperature. OD's were read immediately at 450 nm using a Titertek plate reader.

The primary screen resulted in a total of 3104 antigen specific hybridomas being identified from the two harvests. Based on highest ELISA OD, 1500 hybridomas per harvest were advanced for a total of 3000 positives.

Confirmatory Screen

The 3000 positives were then rescreened for binding to wild-type PCSK9 to confirm stable hybridomas were established. The screen was performed as follows: Costar 3702 medium binding 384 well plates (Corning Life Sciences) were employed. The plates were coated with neutravadin at 3 µg/ml in 1×PBS/0.05% Azide at a volume of 40 Owen. The plates were incubated at 4° C. overnight. The plates were then washed using a Titertek plate washer (Titertek, Huntsville, Ala.). A 3-cycle wash was performed. The plates were blocked with 90 µl of 1×PBS/1% milk and incubated approximately 30 minutes at room temperature. The plates were then washed using the M384 plate washer. A 3-cycle wash was performed. The capture sample was b-PCSK9, without a V5 tag, and was added at 0.9 µg/ml in 1×PBS/1% milk/10 mM $Ca^{2+}$ at a volume of 40 µl/well. The plates were then incubated for 1 hour at room temperature. Next, the plates were washed using a 3-cycle wash. 10 µl of supernatant was transferred into 40 µl of 1×PBS/1% milk/10 mM $Ca^{2+}$ and incubated 1.5 hours at room temperature. Again the plates were washed using the Titertek plate washer operated using a 3-cycle wash. 40 µl/well of Goat anti-Human IgG Fc POD at a concentration of 100 ng/ml (1:4000) in 1×PBS/1% milk/10 mM $Ca^{2+}$ was added to the plate, and the plate was incubated 1 hour at room temperature. The plates were washed once again, using the Titertek plate washer operated using a 3-cycle wash. Finally, 40 µl/well of One-step TMB (Neogen, Lexington, Ky.) was added to the plate and was quenched with 40 µl/well of 1N hydrochloric acid after 30 minutes at room temperature. OD's were read immediately at 450 nm using a Titertek plate reader. A total of 2441 positives repeated in the second screen. These antibodies were then used in the subsequent screenings.

Mouse Cross-reactivity Screen

The panel of hybridomas was then screened for cross-reactivity to mouse PCSK9 to make certain that the antibodies could bind to both human and mouse PCSK9. The following protocol was employed in the cross-reactivity screen: Costar 3702 medium binding 384 well plates (Corning Life Sciences) were employed. The plates were coated with neutravadin at 3 µg/ml in 1×PBS/0.05% Azide at a volume of 40 µl/well. The plates were incubated at 4° C. overnight. The plates were then washed using a Titertek plate washer (Titertek, Huntsville, Ala.). A 3-cycle wash was performed. The plates were blocked with 90 µl of 1×PBS/1% milk and incubated approximately 30 minutes at room temperature. The plates were then washed using the Titertek plate washer. A 3-cycle wash was performed. The capture sample was biotinylated-mouse PCSK9, and was added at 1 µg/ml in 1×PBS/1% milk/10 mM $Ca^{2+}$ at a volume of 40 µl/well. The plates were then incubated for 1 hour at room temperature. Next, the plates were washed using the Titertek plate washer operated using a 3-cycle wash. 50 µl of supernatant was transferred to the plates and incubated 1 hour at room temperature. Again the plates were washed using a 3-cycle wash. 40 µl/well of Goat anti-Human IgG Fc POD at a concentration of 100 ng/ml (1:4000) in 1×PBS/1% milk/10 mM $Ca^{2+}$ was added to the plate and the plate was incubated 1 hour at room temperature. The plates were washed once again, using a 3-cycle wash. Finally, 40 µl/well One-step TMB (Neogen, Lexington, Ky.) was added to the plate and was quenched with 40 µl/well of 1N hydrochloric acid after 30 minutes at room temperature. OD's were read immediately at 450 nm using a Titertek plate reader. 579 antibodies were observed to cross-react with mouse PCSK9. These antibodies were then used in the subsequent screenings.

D374Y Mutant Binding Screen

The D374Y mutation in PCSK9 has been documented in the human population (e.g., Timms K M et al, "A mutation in PCSK9 causing autosomal-dominant hypercholesterolemia in a Utah pedigree", Hum. Genet. 114: 349-353, 2004). In order to determine if the antibodies were specific for the wild type or also bound to the D374Y form of PCSK9, the samples were then screened for binding to the mutant PCSK9 sequence comprising the mutation D374Y. The protocol for the screen was as follows: Costar 3702 medium binding 384 well plates (Corning Life Sciences) were employed in the screen. The plates were coated with neutravadin at 4 µg/ml in 1×PBS/0.05% Azide at a volume of 40 µl/well. The plates were incubated at 4° C. overnight. The plates were then washed using a Titertek plate washer (Titertek, Huntsville, Ala.). A 3-cycle wash was performed. The plates were blocked with 90 µl of 1×PBS/1% milk and incubated approximately 30 minutes at room temperature. The plates were then washed using the Titertek plate washer. A 3-cycle wash was performed. The plates were coated with biotinylated human PCSK9 D374Y at a concentration of 1 µg/ml in 1×PBS/1% milk/10 mMCa$^{2+}$ and incubated for 1 hour at room temperature. The plates were then washed using a Titertek plate washer. A 3-cycle wash was performed. Late exhaust hybridoma culture supernatant was diluted 1:5 in PBS/milk/Ca$^{2+}$ (10 ml plus 40 ml) and incubated for 1 hour at room temperature. Next, 40 µl/well of rabbit anti-human PCSK9 (Cayman Chemical) and human anti-His 1.2.3 1:2 at 1 ug/ml in 1×PBS/1% milk/10 mMCa$^{2+}$ was titrated onto the plates, which were then incubated for 1 hour at room temperature. The plates were then washed using a Titertek plate washer. A 3-cycle wash was performed. 40 µl/well of Goat anti-Human IgG Fc HRP at a concentration of 100 ng/ml (1:4000) in 1×PBS/1% milk/10 mM Ca$^{2+}$ was added to the plate and the plate was incubated 1 hour at room temperature. 40 µl/well of Goat anti-rabbit IgG Fc HRP at a concentration of 100 ng/ml (1:4000) in 1×PBS/1% milk/10 mM Ca$^{2+}$ was added to the plate and the plate was incubated 1 hour at room temperature. The plates were then washed using a Titertek plate washer. A 3-cycle wash was performed. Finally, 40 µl/well of One-step TMB (Neogen, Lexington, Ky.) was added to the plate and was quenched with 40 µl/well of 1N hydrochloric acid after 30 minutes at room temperature. OD's were read immediately at 450 nm using a Titertek plate reader. Over 96% of the positive hits on the wild-type PCSK9 also bound mutant PCSK9.

Large Scale Receptor Ligand Blocking Screen

To screen for the antibodies that block PCSK9 binding to LDLR an assay was developed using the D374Y PCSK9 mutant. The mutant was used for this assay because it has a higher binding affinity to LDLR allowing a more sensitive receptor ligand blocking assay to be developed. The following protocol was employed in the receptor ligand blocking screen: Costar 3702 medium binding 384 well plates (Corning Life Sciences) were employed in the screen. The plates were coated with goat anti-LDLR(R&D Cat #AF2148) at 2 µg/ml in 1×PBS/0.05% Azide at a volume of 40 µl/well. The plates were incubated at 4° C. overnight. The plates were then washed using a Titertek plate washer (Titertek, Huntsville, Ala.). A 3-cycle wash was performed. The plates were blocked with 90 µl of 1×PBS/1% milk and incubated approximately 30 minutes at room temperature. The plates were then washed using the Titertek plate washer. A 3-cycle wash was performed. The capture sample was LDLR(R&D, Cat #2148LD/CF), and was added at 0.4 µg/ml in 1×PBS/1% milk/10 mM Ca$^{2+}$ at a volume of 40 µl/well. The plates were then incubated for 1 hour and 10 minutes at room temperature. Contemporaneously, 20 ng/ml of biotinylated human D374Y PCSK9 was incubated with 15 microliters of hybridoma exhaust supernatant in Nunc polypropylene plates and the exhaust supernatant concentration was diluted 1:5. The plates were then pre-incubated for about 1 hour and 30 minutes at room temperature. Next, the plates were washed using the Titertek plate washer operated using a 3-cycle wash. 50 µl/well of the pre-incubated mixture was transferred onto the LDLR coated ELISA plates and incubated for 1 hour at room temperature. To detect LDLR-bound b-PCSK9, 40 µl/well streptavidin HRP at 500 ng/ml in assay diluent was added to the plates. The plates were incubated for 1 hour at room temperature. The plates were again washed using a Titertek plate washer. A 3-cycle wash was performed. Finally, 40 µl/well of One-step TMB (Neogen, Lexington, Ky.) was added to the plate and was quenched with 40 µl/well of 1N hydrochloric acid after 30 minutes at room temperature. OD's were read immediately at 450 nm using a Titertek plate reader. The screen identified 384 antibodies that blocked the interaction between PCSK9 and the LDLR well, 100 antibodies blocked the interaction strongly (OD<0.3). These antibodies inhibited the binding interaction of PCSK9 and LDLR greater than 90% (greater than 90% inhibition).

Receptor Ligand Binding Assay on Blocker Subset

The receptor ligand assay was then repeated using the mutant enzyme on the 384 member subset of neutralizers identified in the first large scale receptor ligand inhibition assay. The same protocol was employed in the screen of the 384 member blocker subset assay as was done in the large scale receptor ligand blocking screen. This repeat screen confirmed the initial screening data.

This screen of the 384 member subset identified 85 antibodies that blocked interaction between the PCSK9 mutant enzyme and the LDLR greater than 90%.

Receptor Ligand Binding Assay of Blockers that Bind the Wild Type PCSK9 but not the D374Y Mutant In the initial panel of 3000 sups there were 86 antibodies shown to specifically bind to the wild-type PCSK9 and not to the huPCSK9(D374Y) mutant. These 86 sups were tested for the ability to block wild-type PCSK9 binding to the LDLR receptor. The following protocol was employed: Costar 3702 medium binding 384 well plates (Corning Life Sciences) were employed in the screen. The plates were coated with anti-His 1.2.3 at 10 µg/ml in 1×PBS/0.05% Azide at a volume of 40 µl/well. The plates were incubated at 4° C. overnight. The plates were then washed using a Titertek plate washer (Titertek, Huntsville, Ala.). A 3-cycle wash was performed. The plates were blocked with 90 µl of 1×PBS/1% milk and incubated approximately 30 minutes at room temperature. The plates were then washed using the Titertek plate washer. A 3-cycle wash was performed. LDLR(R&D Systems, #2148LD/CF or R&D Systems, #2148LD) was added at 5 µg/ml in 1×PBS/1% milk/10 mM Ca$^{2+}$ at a volume of 40 µl/well. The plates were then incubated for 1 hour at room temperature. Next, the plates were washed using the Titertek plate washer operated using a 3-cycle wash. Contemporaneously, biotinylated human wild-type PCSK9 was pre-incubated with hybridoma exhaust supernatant in Nunc polypropylene plates. 22 µl of hybridoma sup was transferred into 33 ul of b-PCSK9 at a concentration of 583 ng/ml in 1×PBS/1% milk/10 mMCa2+, giving a final b-PCSK9 concentration=350 ng/ml and the exhaust supernatant at a final dilution of 1:2.5. The plates were pre-incubated for approximately 1 hour and 30 minutes at room temperature. 50 µl/well of the preincubated mixture was transferred onto LDLR captured ELISA plates and incubated for 1 hour at room temperature. The plates were then washed using the Titertek plate washer. A 3-cycle wash was performed. 40 µl/well streptavidin HRP at 500 ng/ml in assay diluent was added to the plates. The plates were incubated for 1 hour at room temperature. The plates were then washed using a Titertek plate washer. A 3-cycle wash was performed. Finally, 40 µl/well of One-step TMB (Neogen, Lexington, Ky.) was added to the plate and was quenched with 40 µl of 1N hydrochloric acid after 30 minutes at room temperature. OD's were read immediately at 450 nm using a Titertek plate reader.

Screening Results

Based on the results of the assays described, several hybridoma lines were identified as producing antibodies with desired interactions with PCSK9. Limiting dilution was used to isolate a manageable number of clones from each line. The clones were designated by hybridoma line number (e.g.

21B12) and clone number (e.g. 21B12.1). In general, no difference among the different clones of a particular line were detected by the functional assays described herein. In a few cases, clones were identified from a particular line that behaved differently in the functional assays, for example, 25A7.1 was found not to block PCSK9/LDLR but 25A7.3 (referred to herein as 25A7) was neutralizing. The isolated clones were each expanded in 50-100 ml of hybridoma media and allowed to grow to exhaustion, (i.e., less than about 10% cell viability). The concentration and potency of the antibodies to PCSK9 in the supernatants of those cultures were determined by ELISA and by in vitro functional testing, as described herein. As a result of the screening described herein, the hybridomas with the highest titer of antibodies to PCSK9 were identified. The selected hybridomas are shown in FIGS. 2A-3D and Table 2.

Example 4.1

Production of Human 31H4 IgG4 Antibodies from Hybridomas

This example generally describes how one of the antigen binding proteins was produced from a hybridoma line. The production work used 50 ml exhaust supernatant generation followed by protein A purification. Integra production was for scale up and was performed later. Hybridoma line 31H4 was grown in T75 flasks in 20 ml of media (Integra Media, Table 5). When the hybridoma was nearly confluent in the T75 flasks, it was transferred to an Integra flask (Integra Biosciences, Integra CL1000, cat#90 005).

The Integra flask is a cell culture flask that is divided by a membrane into two chambers, a small chamber and a large chamber. A volume of 20-30 ml hybridoma cells at a minimum cell density of $1\times10^6$ cells per ml from the 31H4 hybridoma line was placed into the small chamber of an Integra flask in Integra media (see Table 5 for components of Integra media). Integra media alone (1 L) was placed in the large chambers of the Integra flasks. The membrane separating the two chambers is permeable to small molecular weight nutrients but is impermeable to hybridoma cells and to antibodies produced by those cells. Thus, the hybridoma cells and the antibodies produced by those hybridoma cells were retained in the small chamber.

After one week, media was removed from both chambers of the Integra flask and was replaced with fresh Integra media. The collected media from the small chambers was separately retained. After a second week of growth, the media from the small chamber was again collected. The collected media from week 1 from the hybridoma line was combined with the collected media from week 2 from the hybridoma line. The resulting collected media sample from the hybridoma line was spun to remove cells and debris (15 minutes at 3000 rpm) and the resulting supernatant was filtered (0.22 um). Clarified conditioned media was loaded onto a Protein A-Sepharose column. Optionally, the media can be first concentrated and then loaded onto a Protein A Sepharose column. Non-specific bindings were removed by an extensive PBS wash. Bound antibody proteins on the Protein A column were recovered by standard acidic antibody elution from Protein A columns (such as 50 mM Citrate, pH 3.0). Aggregated antibody proteins in the Protein A Sepharose pool were removed by size exclusion chromatography or binding ion exchange chromatography on anion exchanger resin such as Q Sepharose resin. The specific IEX conditions for the 31H4 proteins are Q-Sepharose HP at pH 7.8-8.0. Antibody was eluted with a NaCl gradient of 10 mM-500 mM in 25 column volumes.

TABLE 5

Composition of Media
INTEGRA MEDIA

HSFM
10% Ultra Low IgG serum
2 mmol/L L-glutamine
1% NEAA
4 g/L glucose

Example 4.2

Production of Recombinant 31H4 Human IgG2 Antibodies From Transfected Cells

The present example outlines how 31H4 IgG2 antibodies were produced from transfected cells. 293 cells for transient expression and CHO cells for stable expression were transfected with plasmids that encode 31H4 heavy and light chains. Conditioned media from transfected cells was recovered by removing cells and cell debris. Clarified conditioned media was loaded onto a Protein A-Sepharose column. Optionally, the media can first be concentrated and then loaded onto a Protein A Sepharose column. Non-specific bindings were removed by extensive PBS wash. Bound antibody proteins on the Protein A column were recovered by standard acidic antibody elution from Protein A columns (such as 50 mM citrate, pH 3.0). Aggregated antibody proteins in the Protein A Sepharose pool were removed by size exclusion chromatography or binding ion exchange chromatography on anion exchanger resin such as Q Sepharose resin. The specific IEX conditions for the 31H4 proteins are Q-Sepharose HP at pH 7.8-8.0. The antibody was eluted with a NaCl gradient of 10 mM-500 mM in 25 column volumes.

Example 5

Production of Human 21B12 IgG4 Antibodies from Hybridomas

The present example outlines how antibody 21B12 IgG4 was produced from hybridomas. Hybridoma line 21B12 was grown in T75 flasks in media (Integra Media, Table 5). When the hybridomas were nearly confluent in the T75 flasks, they were transferred to Integra flasks (Integra Biosciences, Integra CL1000, cat#90 005).

The Integra flask is a cell culture flask that is divided by a membrane into two chambers, a small chamber and a large chamber. A volume of 20-30 ml hybridoma cells at a minimum cell density of $1\times10^6$ cells per ml from the 31H4 hybridoma line was placed into the small chamber of an Integra flask in Integra media (see Table 5 for components of Integra media). Integra media alone (1 L) was placed in the large chambers of the Integra flasks. The membrane separating the two chambers is permeable to small molecular weight nutrients but is impermeable to hybridoma cells and to antibodies produced by those cells. Thus, the hybridoma cells and the antibodies produced by those hybridoma cells were retained in the small chamber. After one week, media was removed from both chambers of the Integra flask and was replaced with fresh Integra media. The collected media from the small chambers was separately retained. After a second week of growth, the media from the small chamber was again collected. The collected media from week 1 from the hybridoma line was combined with the collected media from week 2 from the hybridoma line. The resulting collected media sample from the hybridoma line was spun to remove cells and debris (15 minutes at 3000 rpm) and the resulting supernatant was filtered (0.22 µm). Clarified conditioned media were loaded onto a Protein A Sepharose column. Optionally, the media are first concentrated and then loaded onto a Protein A Sepharose column. Non-specific bindings were removed by an extensive PBS wash. Bound antibody proteins on the Protein A column were recovered by standard acidic antibody elution from Protein A columns (such as 50 mM Citrate, pH 3.0). Aggregated antibody proteins in the Protein A Sepharose pool were removed by size exclusion chromatography or binding ion exchange chromatography on anion exchanger resin such as Q Sepharose resin. The specific IEX conditions for the 21B12 proteins are Q-Sepharose HP at pH 7.8-8.0. The antibody was eluted with a NaCl gradient of 10 mM-500 mM in 25 column volumes.

Example 6

Production of Human 21B12 IgG2 Antibodies From Transfected Cells

The present example outlines how 21B12 IgG2 antibodies were produced from transfected cells. Cells (293 cells for transient expression and CHO cells for stable expression) were transfected with plasmids that encode 21B12 heavy and light chains. Conditioned media from hybridoma cells were recovered by removing cells and cell debris. Clarified conditioned media were loaded onto a Protein A-Sepharose column. Optionally, the media can first be concentrated and then loaded onto a Protein A Sepharose column. Non-specific bindings were removed by extensive PBS wash. Bound antibody proteins on the Protein A column were recovered by standard acidic antibody elution from Protein A columns (50 mM Citrate, pH 3.0). Aggregated antibody proteins in the Protein A Sepharose pool were removed by size exclusion chromatography or binding ion exchange chromatography on cation exchanger resin such as SP-Sepharose resin. The specific IEX conditions for the 21B12 proteins were SP-Sepharose HP at pH 5.2. Antibodies were eluted with 25 column volumes of buffer that contains a NaCl gradient of 10 mM-500 mM in 20 mM sodium acetate buffer.

Example 7

Production of Human 16F12 IgG4 Antibodies from Hybridomas

The present example outlines how antibody 16F12 IgG4 was produced from hybridomas. Hybridoma line 16F12 was grown in T75 flasks in media (see Table 5). When the hybridomas were nearly confluent in the T75 flasks, they were transferred to Integra flasks (Integra Biosciences, Integra CL1000, cat#90 005).

The Integra flask is a cell culture flask that is divided by a membrane into two chambers, a small chamber and a large chamber. A volume of 20-30 ml Hybridoma cells at a minimum cell density of 1×10$^6$ cells per ml from the 31H4 hybridoma line was placed into the small chamber of an Integra flask in Integra media (see Table 5 for components of Integra media). Integra media alone (1 L) was placed in the large chambers of the Integra flasks. The membrane separating the two chambers is permeable to small molecular weight nutrients but is impermeable to hybridoma cells and to antibodies produced by those cells. Thus, the hybridoma cells and the antibodies produced by those hybridoma cells were retained in the small chamber.

After one week, media was removed from both chambers of the Integra flask and was replaced with fresh Integra media. The collected media from the small chambers was separately retained. After a second week of growth, the media from the small chamber was again collected. The collected media from week 1 from the hybridoma line was combined with the collected media from week 2 from the hybridoma line. The resulting collected media sample from the hybridoma line were spun to remove cells and debris (15 minutes at 3000 rpm) and the resulting supernatants were filtered (0.22 µm). Clarified conditioned media were loaded onto a Protein A Sepharose column. Optionally, the media can be first concentrated and then loaded onto a Protein A Sepharose column. Non-specific bindings were removed by extensive PBS wash. Bound antibody proteins on the Protein A column were recovered by standard acidic antibody elution from Protein A columns (50 mM Citrate, pH 3.0). Aggregated antibody proteins in the Protein A Sepharose pool were removed by size exclusion chromatography or binding ion exchange chromatography on anion exchanger resin such as Q Sepharose resin. The specific IEX conditions for the 16F12 proteins are Q Sepharose HP at pH 7.8-8.0. Antibody was eluted with a NaCl gradient of 10 mM-500 mM in 25 column volumes.

Example 8

Production of Human 16F12 IgG2 Antibodies From Transfected Cells

The present example outlines how 16F12 IgG2 antibodies were produced from transfected cells. Cells (293 cells for transient expression and CHO cells for stable expression) were transfected with plasmids that encode 16F12 heavy and light chains. Conditioned media from hybridoma cells were recovered by removing cells and cell debris. Clarified conditioned media were loaded onto a Protein A-Sepharose. Optionally, the media can be first concentrated and then loaded onto a Protein A Sepharose column. Non-specific bindings were removed by extensive PBS wash. Bound antibody proteins on the Protein A column were recovered by standard acidic antibody elution from Protein A columns (50 mM Citrate, pH 3.0). Aggregated antibody proteins in the Protein A Sepharose pool were removed by size exclusion chromatography or binding ion exchange chromatography on cation exchanger resin such as SP Sepharose resin. The specific IEX conditions for the 16F12 proteins are SP Sepharose HP at pH 5.2. Antibody is eluted with 25 column volumes of buffer that contains a NaCl gradient of 10 mM-500 mM in 20 mM sodium acetate buffer.

Example 9

Sequence Analysis of Antibody Heavy and Light Chains

The nucleic acid and amino acid sequences for the light and heavy chains of the above antibodies were then determined by Sanger (dideoxy) nucleotide sequencing. Amino acid sequences were then deduced for the nucleic acid sequences. The nucleic acid sequences for the variable domains are depicted in FIGS. 3E-3B.

The cDNA sequences for the lambda light chain variable regions of 31H4, 21B12, and 16F12 were determined and are disclosed as SEQ ID NOs: 153, 95, and 105 respectively.

The cDNA sequences for the heavy chain variable regions of 31H4, 21B12, and 16F12 were determined and are disclosed as SEQ ID NOs: 152, 94, and 104 respectively.

The lambda light chain constant region (SEQ ID NO: 156), and the IgG2 and IgG4 heavy chain constant regions (SEQ ID NOs: 154 and 155) are shown in FIG. 3KK.

The polypeptide sequences predicted from each of those cDNA sequences were determined. The predicted polypeptide sequences for the lambda light chain variable regions of 31H4, 21B12, and 16F12 were predicted and are disclosed as SEQ ID NOs: 12, 23, and 35 respectively, the lambda light chain constant region (SEQ ID NO: 156), the heavy chain variable regions of 31H4, 21B12, and 16F12 were predicted and are disclosed as (SEQ. ID NOs. 67, 49, and 79 respectively. The IgG2 and IgG4 heavy chain constant regions (SEQ ID NOs: 154 and 155).

The FR1, CDR1, FR2, CDR2, FR3, CDR3, FR4 divisions are shown in FIG. 2A-3D.

Based on the sequence data, the germline genes from which each heavy chain or light chain variable region was derived was determined. The identity of the germline genes are indicated next to the corresponding hybridoma line in FIGS. 2A-3D and each is represented by a unique SEQ ID NO. FIGS. 2A-3D also depict the determined amino acid sequences for additional antibodies that were characterized.

Example 8

Determination of Isoelectric Points of Three Antibodies

The theoretical pIs of the antibodies based on amino acid sequence were determined to be 7.36 for 16F12; 8.47 for 21B12; and 6.84 for 31H4.

Example 9

Characterization of Binding of Antibodies to PCSK9

Having identified a number of antibodies that bind to PCSK9, several approaches were employed to quantify and further characterize the nature of the binding. In one aspect of the study, a Biacore affinity analysis was performed. In another aspect of the study a KinExA® affinity analysis was performed. The samples and buffers employed in these studies are presented in Table 6 below.

TABLE 6

| sample | [sample] mg/ml | Buffer | [sample] uM |
|---|---|---|---|
| hPCSK9 | 1.26 | PBS | 16.6 |
| mPCSK9-8xHIS | 1.44 | PBS | 18.9 |
| cPCSK9-V5-6xHIS | 0.22 | PBS | 2.9 |
| 16F12, anti-PCSK9 huIgG4 | 4.6 | 20 mM NAOAC, pH 5.2, 50 mM NaCl | 31.9 |
| 21B12, anti-PCSK9 huIgG4 | 3.84 | 10 mM NAOAC, pH 5.2, 9% Sucrose | 27.0 |
| 31H4, anti-PCSK9 huIgG4 | 3.3 | 10 mM NAOAC, pH 5.2, 9% Sucrose | 22.9 |

BIAcore® Affinity Measurements

A BIAcore® (surface plasmon resonance device, Biacore, Inc., Piscataway, N.J.) affinity analysis of the 21B12 antibodies to PCSK9 described in this Example was performed according to the manufacturer's instructions.

Briefly, the surface plasmon resonance experiments were performed using Biacore 2000 optical biosensors (Biacore, GE Healthcare, Piscataway, N.J.). Each individual anti-PCSK9 antibody was immobilized to a research-grade CM5 biosensor chip by amine-coupling at levels that gave a maximum analyte binding response (Rmax) of no more than 200 resonance units (RU). The concentration of PCSK9 protein was varied at 2 fold intervals (the analyte) and was injected over the immobilized antibody surface (at a flow rate of 100 µl/min for 1.5 minutes). Fresh BBS-P buffer (pH 7.4, 0.01 M Hepes, 0.15 M NaCl, 0.005% surfactant P-20, Biacore) supplemented with 0.01% BSA was used as binding buffer. Binding affinities of each anti-PCSK9 antibody were measured in separate experiments against each of the human, mouse, and cynomolgus monkey PCSK9 proteins at pH 7.4 (the concentrations used were 100, 50, 25, 12.5, 6.25, 3.125, and 0 nM).

In addition, the binding affinities of antibody to human PCSK9 were also measured at pH 6.0 with the pH 6.0 BBS-P buffer (pH 6.0, 0.01 M Hepes, 0.15 M NaCl, 0.005% surfactant P-20, Biacore) supplemented with 0.01% BSA. The binding signal obtained was proportional to the free PCSK9 in solution. The dissociation equilibrium constant ($K_D$) was obtained from nonlinear regression analysis of the competition curves using a dual-curve one-site homogeneous binding model (KinExA® software, Sapidyne Instruments Inc., Boise, Id.) (n=1 for the 6.0 pH runs). Interestingly, the antibodies appeared to display a tighter binding affinity at the lower pH (where the Kd was 12.5, 7.3, and 29 pM for 31H4, 21B12, and 16F12 respectively).

Antibody binding kinetic parameters including $k_a$ (association rate constant), $k_d$ (dissociation rate constant), and $K_D$ (dissociation equilibrium constant) were determined using the BIA evaluation 3.1 computer program (BIAcore, Inc. Piscataway, N.J.). Lower dissociation equilibrium constants indicate greater affinity of the antibody for PCSK9. The $K_D$ values determined by the BIAcore® affinity analysis are presented in Table 7.1, shown below.

TABLE 7.1

| Antibody | hPCSK9 | CynoPCSK9 | mPCSK9 |
|---|---|---|---|
| 31H4 | 210 pM | 190 pM | 6 nM |
| 21B12 | 190 pM | 360 pM | 460 nM |
| 16F12 | 470 pM | 870 pM | 6.4 nM |

Table 7.2 depicts the $k_{on}$ and $k_{off}$ rates.

TABLE 7.2

| — | $K_{on}$ (M − 1 s − 1) | $K_{off}$ (s − 1) | $K_D$ |
|---|---|---|---|
| 31H4.1, pH 7.4 | 2.45e+5 | 5.348e−5 | 210 pM |
| 31H4.1, pH 6 | 5.536e+6 | 6.936e−5 | 12.5 pM |
| 21B12.1, pH 7.4 | 3.4918e+4 | 6.634e−6 | 190 pM |
| 21B12.1, pH 6 | 2.291e+6 | 1.676e−5 | 7.3 pM |
| 16F12.1, pH 7.4 | 1.064e+5 | 4.983e−5 | 470 pM |
| 16F12.1, pH 6 | 2.392e+6 | 7.007e−5 | 29 pM |

KinExA® Affinity Measurements

A KinExA® (Sapidyne Instruments, Inc., Boise, Id.) affinity analysis of 16F12 and 31H4 was performed according to the manufacturer's instructions. Briefly, Reacti-Gel™ (6×) (Pierce) was pre-coated with one of human, V5-tagged cyno or His-tagged mouse PCSK9 proteins and blocked with BSA. 10 or 100 pM of either antibody 16F12 or antibody 31H4 and one of the PCSK9 proteins was then incubated with various concentrations (0.1 pM-25 nM) of PCSK9 proteins at room temperature for 8 hours before being passed through the PCSK9-coated beads. The amount of the bead-bound 16F12 or 31H4 was quantified by fluorescently (Cy5) labeled goat anti-human IgG (H+L) antibody (Jackson Immuno Research). The binding signal is proportional to the concentration of free 16F12 or 31H4 at binding equilibrium. Equilibrium dissociation constant ($K_D$) were obtained from non-linear regression of the two sets of competition curves using a one-site homogeneous binding model. The KinExA® Pro software was employed in the analysis. Binding curves generated in this analysis are presented as FIGS. 4A-4F.

Both the 16F12 and 31H4 antibodies showed similar affinity to human and cyno PCSK9, but approximately 10-250 fold lower affinity to mouse PCSK9. Of the two antibodies tested using the KinExA® system, antibody 31H4 showed higher affinity to both human and cyno PCSK9 with 3 and 2 pM $K_D$, respectively. 16F12 showed slightly weaker affinity at 15 pM $K_D$ to human PCSK9 and 16 pM $K_D$ to cyno PCSK9.

The results of the KinExA® affinity analysis are summarized in Table 8.1, shown below.

TABLE 8.1

|  | hPCSK9 | | cPCSK | | mPCSK | |
|---|---|---|---|---|---|---|
| Sample | $K_D$ (pM) | 95% CI | $K_D$ (pM) | 95% CI | $K_D$ (pM) | 95% CI |
| 16F12 | 15 | 11~22 | 16 | 14~19 | 223 | 106~410 |
| 31H4.1 | 3 | 1~5 | 2 | 1~3 | 500 | 400~620 |

In addition, a SDS PAGE was run to check the quality and quantity of the samples and is shown in FIG. 5A. cPCSK9 showed around 50% less on the gel and also from the active binding concentration calculated from KinExA® assay. Therefore, the $K_D$ of the mAbs to cPCSK9 was adjusted as 50% of the active cPCSK9 in the present.

A BIAcore solution equilibrium binding assay was used to measure the Kd values for ABP 21B12. 21B12.1 showed little signal using KinExA assay, therefore, biacore solution equilibrium assay was applied. Since no significant binding was observed on binding of antibodies to immobilized PCSK9 surface, 21B12 antibody was immobilized on the flow cell 4 of a CM5 chip using amine coupling with density around 7000 RU. Flow cell 3 was used as a background control. 0.3, 1, and 3 nM of human PCSK9 or cyno PCSK9 were mixed with a serial dilutions of 21B12.1 antibody samples (ranged from 0.001~25 nM) in PBS plus 0.1 mg/ml BSA, 0.005% P20. Binding of the free PCSK9 in the mixed solutions were measured by injecting over the 21B12.1 antibody surface. 100% PCSK9 binding signal on 21B12.1 surface was determined in the absence of mAb in the solution. A decreased PCSK9 binding response with increasing concentrations of mAb indicated that PCSK9 binding to mAb in solution, which blocked PCSK9 from binding to the immobilized peptibody surface. Plotting the PCSK9 binding signal versus mAb concentrations, $K_D$ was calculated from three sets of curves (0.3, 1 and 3 nM fixed PCSK9 concentration) using a one-site homogeneous binding model in KinExA Pro™ software. Although cPCSK9 has lower protein concentration observed from KinExA assay and SDS-gel, its concentration was not adjusted here since the concentration of cPCSK9 was not used for calculation of $K_D$. The results are displayed in Table 8.2 below and in FIGS. 5B-5D. FIG. 5B depicts the results from the solution equilibrium assay at three different hPCSK9 concentrations for hPCSK9. FIG. 5C depicts a similar set of results for mPCSK9. FIG. 5D depicts the results from the above biacore capture assay.

TABLE 8.2

|  | hPCSK9 | | cPCSK | | mPCSK | |
|---|---|---|---|---|---|---|
| Sample | $K_D$ (pM) | 95% CI | $K_D$ (pM) | 95% CI | $K_D$ (pM) | 95% CI |
| 21B12.1 | 15 | 9-23 | 11 | 7~16 | 17000 | — |

Example 10

Epitope Binning

Competition ELISA was used for anti-PCSK9 antibody binning. Briefly, to determine if two antibodies belong to the same epitope bin, one of the antibodies (mAb1) was first coated onto an ELISA plate (NUNC) at 2 µg/ml by overnight incubation. The plate was then washed and blocked with 3% BSA. Meanwhile, 30 ng/ml of biotinylated hPCSK9 was incubated with the second antibody (mAb2) for 2 hours at room temperature. The mixture was applied to coated mAb1 and incubated for 1 hour at room temperature. The ELISA plate was then washed and incubated with Neutravidin-HRP (Pierce) at 1:5000 dilutions for 1 hour. After another wash, the plate was incubated with TMB substrate and signal was detected at 650 nm using a Titertek plate reader. Antibodies with the same binding profiles were grouped together into the same epitope bin. The results of the antibody binning studies are presented in Table 8.3.

TABLE 8.3

| Clone | Bin |
|---|---|
| 21B12.2 | 1 |
| 31H4 | 3 |
| 20D10 | 1 |
| 25A7.1 | 2 |
| 25A7.3 | 1 |
| 23G1 | 1 |
| 26H5 | 1 |
| 31D1 | 1 |
| 16F12 | 3 |
| 28D6 | 3 |
| 27A6 | 3 |
| 31G1 | 1 |
| 27B2 | ND |
| 28B12 | 3 |
| 22E2 | 3 |
| 1A12.2 | 1 |
| 3B6 | 1 |
| 3C4 | 4 |
| 9C9 | 1 |
| 9H6 | 1 |
| 13B5 | 6 |
| 13H1 | 7 |
| 17C2 | 1 |
| 19H9.2 | 1 |
| 23B5 | 1 |
| 25G4 | 1 |
| 26E10 | 1 |
| 27E7 | 1 |
| 27H5 | 1 |
| 30A4 | 1 |
| 30B9 | 1 |
| 31A4 | 5 |
| 31B12 | 5 |

Additional examination of the epitope binning was performed using BIAcore. Three mAbs, 16F12, 21B12 and 31H4, were immobilized on flow cells 2, 3 and 4 with density around 8000 RU. 5 nM PCSK9 from human, mouse and cyno were injected over the mAb surfaces to reach around 100 to 500 RU. 10 nM mAbs were then injected over the PCSK9 surface. Binding of three mAbs to three different PCSK9 proteins over the three mAbs were then recorded.

If the two mAbs had a similar epitope on the antigen, mAb 1 will not show the binding to the antigen already bound to the mAb 2. If the two mAbs have the different epitope on the antigen, mAb 1 will show the binding to the antigen bound to the mAb2. FIG. 5E depicts these epitope binning results in graph form for three mAbs on human PCSk9. A similar pattern was observed for mPCSK9 and cPCSK9. As shown in the graph, 16F12 and 31H4 appear to share a similar epitope, while 21B12 appears to have a different epitope.

Example 11

Efficacy of 31H4 and 21B12 for Blocking D374Y PCSK9/LDLR Binding

This example provides the IC50 values for two of the antibodies in blocking PCSK9 D374Y's ability to bind to LDLR. Clear 384 well plates (Costar) were coated with 2 micrograms/ml of goat anti-LDL receptor antibody (R&D Systems) diluted in buffer A (100 mM sodium cacodylate, pH 7.4). Plates were washed thoroughly with buffer A and then blocked for 2 hours with buffer B (1% milk in buffer A). After washing, plates were incubated for 1.5 hours with 0.4 micrograms/ml of LDL receptor (R&D Systems) diluted in buffer C (buffer B supplemented with 10 mM CaCl2). Concurrent with this incubation, 20 ng/ml of biotinylated D374Y PCSK9 was incubated with various concentrations of the 31H4 IgG2, 31H4 IgG4, 21B12 IgG2 or 21B12 IgG4 antibody, which was diluted in buffer A, or buffer A alone (control). The LDL receptor containing plates were washed and the biotinylated D374Y PCSK9/antibody mixture was transferred to them and incubated for 1 hour at room temperature. Binding of the biotinylated D374Y to the LDL receptor was detected by incubation with streptavidin-HRP (Biosource) at 500 ng/ml in buffer C followed by TMB substrate (KPL). The signal was quenched with 1N HCl and the absorbance read at 450 nm.

The results of this binding study are shown in FIGS. 6A-6D. Summarily, $IC_{50}$ values were determined for each antibody and found to be 199 pM for 31H4 IgG2 (FIG. 6A), 156 pM for 31H4 IgG4 (FIG. 6B), 170 pM for 21B12 IgG2 (FIG. 6C), and 169 pM for 21B12 IgG4 (FIG. 6D).

The antibodies also blocked the binding of wild-type PCSK9 to the LDLR in this assay.

Example 12

Cell LDL Uptake Assay

This example demonstrates the ability of various antigen binding proteins to reduce LDL uptake by cells. Human HepG2 cells were seeded in black, clear bottom 96-well plates (Costar) at a concentration of $5\times10^5$ cells per well in DMEM medium (Mediatech, Inc) supplemented with 10% FBS and incubated at 37° C. (5% CO2) overnight. To form the PCSK9 and antibody complex, 2 µg/ml of D374Y human PCSK9 was incubated with various concentrations of antibody diluted in uptake buffer (DMEM with 1% FBS) or uptake buffer alone (control) for 1 hour at room temperature. After washing the cells with PBS, the D374Y PCSK9/antibody mixture was transferred to the cells, followed by LDL-BODIPY (Invitrogen) diluted in uptake buffer at a final concentration of 6 µg/ml. After incubation for 3 hours at 37° C. (5% CO2), cells were washed thoroughly with PBS and the cell fluorescence signal was detected by Safire™ (TECAN) at 480-520 nm (excitation) and 520-600 nm (emission).

The results of the cellular uptake assay are shown in FIGS. 7A-7D. Summarily, $IC_{50}$ values were determined for each antibody and found to be 16.7 nM for 31H4 IgG2 (FIG. 7A), 13.3 nM for 31H4 IgG4 (FIG. 7B), 13.3 nM for 21B12 IgG2 (FIG. 7C), and 18 nM for 21B12 IgG4 (FIG. 7D). These results demonstrate that the applied antigen binding proteins can reduce the effect of PCSK9 (D374Y) to block LDL updtake by cells The antibodies also blocked the effect of wild-type PCSK9 in this assay.

Example 13

Serum Cholesterol Lowering Effect of the 31H4 Antibody in 6 Day Study

In order to assess total serum cholesterol (TC) lowering in wild type (WT) mice via antibody therapy against PCSK9 protein, the following procedure was performed.

Male WT mice (C57BL/6 strain, aged 9-10 weeks, 17-27 g) obtained from Jackson Laboratory (Bar Harbor, Me.) were fed a normal chow (Harland-Teklad, Diet 2918) through out the duration of the experiment. Mice were administered either anti-PCSK9 antibody 31H4 (2 mg/ml in PBS) or control IgG (2 mg/ml in PBS) at a level of 10 mg/kg through the mouse's tail vein at T=0. Naïve mice were also set aside as a naïve control group. Dosing groups and time of sacrifice are shown in Table 9.

TABLE 9

| Group | Treatment | Time point after dosing | Number |
|-------|-----------|-------------------------|--------|
| 1 | IgG | 8 hr | 7 |
| 2 | 31H4 | 8 hr | 7 |
| 3 | IgG | 24 hr | 7 |
| 4 | 31H4 | 24 hr | 7 |
| 5 | IgG | 72 hr | 7 |
| 6 | 31H4 | 72 hr | 7 |
| 7 | IgG | 144 hr | 7 |
| 8 | 31H4 | 144 hr | 7 |
| 9 | Naïve | n/a | 7 |

Mice were sacrificed with CO2 asphyxiation at the predetermined time points shown in Table 9. Blood was collected via vena cava into eppendorf tubes and was allowed to clot at room temperature for 30 minutes. The samples were then spun down in a table top centrifuge at 12,000×g for 10 minutes to separate the serum. Serum total cholesterol and HDL-C were measured using Hitachi 912 clinical analyzer and Roche/Hitachi TC and HDL-C kits.

The results of the experiment are shown in FIGS. 8A-8D. Summarily, mice to which antibody 31H4 was administered showed decreased serum cholesterol levels over the course of the experiment (FIG. 8A and FIG. 8B). In addition, it is noted that the mice also showed decreased HDL levels (FIG. 8C and FIG. 8D). For FIG. 8A and FIG. 8C, the percentage change is in relation to the control IgG at the same time point (*P<0.01, # P<0.05). For FIG. 8B and FIG. 8D, the percentage change is in relation to total serum cholesterol and HDL levels measured in naïve animals at t=0 hrs (*P<0.01, # P<0.05).

In respect to the lowered HDL levels, it is noted that one of skill in the art will appreciate that the decrease in HDL in mice is not indicative that an HDL decrease will occur in humans and merely further reflects that the serum cholesterol level in the organism has decreased. It is noted that mice transport the majority of serum cholesterol in high density lipoprotein (HDL) particles which is different to humans who carry most serum cholesterol on LDL particles. In mice the measurement of total serum cholesterol most closely resembles the level of serum HDL-C. Mouse HDL contains apolipoprotein E (apoE) which is a ligand for the LDL receptor (LDLR) and allows it to be cleared by the LDLR. Thus, examining HDL is an appropriate indicator for the present example, in mice (with the understanding that a decrease in HDL is not expected for humans). For example, human HDL, in contrast, does not contain apoE and is not a ligand for the LDLR. As PCSK9 antibodies increase LDLR expression in mouse, the liver can clear more HDL and therefore lowers serum HDL-C levels.

Example 14

Effect of Antibody 31H4 on LDLR Levels in a 6 Day Study

The present example demonstrates that an antigen binding protein alters the level of LDLR in a subject, as predicted, over time. A Western blot analysis was performed in order to ascertain the effect of antibody 31H4 on LDLR levels. 50-100 mg of liver tissue obtained from the scarified mice described in Example 13 was homogenized in 0.3 ml of RIPA buffer (Santa Cruz Biotechnology Inc.) containing complete protease inhibitor (Roche). The homogenate was incubated on ice for 30 minutes and centrifuged to pellet cellular debris. Protein concentration in the supernatant was measured using BioRad protein assay reagents (BioRad laboratories). 100 µg of protein was denatured at 70° C. for 10 minutes and separated on 4-12% Bis-Tris SDS gradient gel (Invitrogen). Proteins were transferred to a 0.45 µm PVDF membrane (Invitrogen) and blocked in washing buffer (50 mM Tris PH7.5, 150 mM NaCL, 2 mM $CaCl_2$ and 0.05% Tween 20) containing 5% non-fat milk for 1 hour at room temperature. The blot was then probed with goat anti-mouse LDLR antibody (R&D system) 1:2000 or anti-B actin (sigma) 1:2000 for 1 hour at room temperature. The blot was washed briefly and incubated with bovine anti-goat IgG-HRP (Santa Cruz Biotechnology Inc.) 1:2000 or goat anti-mouse IgG-HRP (Upstate) 1:2000. After a 1 hour incubation at room temperature, the blot was washed thoroughly and immunoreactive bands were detected using ECL plus kit (Amersham biosciences). The Western blot showed an increase in LDLR protein levels in the presence of antibody 31H4, as depicted in FIG. 9.

Example 15

Serum Cholesterol Lowering Effect of Antibody 31 H4 in a 13 Day Study

In order to assess total serum cholesterol (TC) lowering in wild type (WT) mice via antibody therapy against PCSK9 protein in a 13 day study, the following procedure was performed.

Male WT mice (C57BL/6 strain, aged 9-10 weeks, 17-27 g) obtained from Jackson Laboratory (Bar Harbor, Me.) were fed a normal chow (Harland-Teklad, Diet 2918) through out the duration of the experiment. Mice were administered either anti-PCSK9 antibody 31H4 (2 mg/ml in PBS) or control IgG (2 mg/ml in PBS) at a level of 10 mg/kg through the mouse's tail vein at T=0. Naive mice were also set aside as naive control group.

Dosing groups and time of sacrifice are shown in Table 10. Animals were sacrificed and livers were extracted and prepared as in Example 13.

TABLE 10

| Group | Treatment | Time point after dosing | Number | Dose |
|---|---|---|---|---|
| 1 | IgG | 72 hr | 6 | 10 mg/kg |
| 2 | 31H4 | 72 hr | 6 | 10 mg/kg |
| 3 | 31H4 | 72 hr | 6 | 1 mg/kg |
| 4 | IgG | 144 hr | 6 | 10 mg/kg |
| 5 | 31H4 | 144 hr | 6 | 10 mg/kg |
| 6 | 31H4 | 144 hr | 6 | 1 mg/kg |
| 7 | IgG | 192 hr | 6 | 10 mg/kg |
| 8 | 31H4 | 192 hr | 6 | 10 mg/kg |
| 9 | 31H4 | 192 hr | 6 | 1 mg/kg |
| 10 | IgG | 240 hr | 6 | 10 mg/kg |
| 11 | 31H4 | 240 hr | 6 | 10 mg/kg |
| 12 | 31H4 | 240 hr | 6 | 1 mg/kg |
| 13 | IgG | 312 hr | 6 | 10 mg/kg |
| 14 | 31H4 | 312 hr | 6 | 10 mg/kg |
| 15 | 31H4 | 312 hr | 6 | 1 mg/kg |
| 16 | Naive | n/a | 6 | n/a |

When the 6 day experiment was extended to a 13 day study, the same serum cholesterol lowering effect observed in the 6 day study was also observed in the 13 day study. More specifically, animals dosed at 10 mg/kg demonstrated a 31% decrease in serum cholesterol on day 3, which gradually returned to pre-dosing levels by day 13. FIG. 10A depicts the results of this experiment. FIG. 10C depicts the results of repeating the above procedure with the 10 mg/kg dose of 31H4, and with another antibody, 16F12, also at 10 mg/kg. Dosing groups and time of sacrifice are shown in Table 11.

TABLE 11

| Group | Treatment | Time point after dosing | Number | Dose |
|---|---|---|---|---|
| 1 | IgG | 24 hr | 6 | 10 mg/kg |
| 2 | 16F12 | 24 hr | 6 | 10 mg/kg |
| 3 | 31H4 | 24 hr | 6 | 10 mg/kg |
| 4 | IgG | 72 hr | 6 | 10 mg/kg |
| 5 | 16F12 | 72 hr | 6 | 10 mg/kg |
| 6 | 31H4 | 72 hr | 6 | 10 mg/kg |
| 7 | IgG | 144 hr | 6 | 10 mg/kg |
| 8 | 16F12 | 144 hr | 6 | 10 mg/kg |
| 9 | 31H4 | 144 hr | 6 | 10 mg/kg |
| 10 | IgG | 192 hr | 6 | 10 mg/kg |
| 11 | 16F12 | 192 hr | 6 | 10 mg/kg |
| 12 | 31H4 | 192 hr | 6 | 10 mg/kg |
| 13 | IgG2 | 240 hr | 6 | 10 mg/kg |
| 14 | 16F12 | 240 hr | 6 | 10 mg/kg |
| 15 | 31H4 | 240 hr | 6 | 10 mg/kg |
| 16 | IgG2 | 312 hr | 6 | 10 mg/kg |
| 17 | 16F12 | 312 hr | 6 | 10 mg/kg |
| 18 | 31H4 | 312 hr | 6 | 10 mg/kg |
| 19 | Naive | n/a | 6 | 10 mg/kg |

As shown in FIG. 10C both 16F12 and 31H4 resulted in significant and substantial decreases in total serum cholesterol after just a single dose and provided benefits for over a week (10 days or more). The results of the repeated 13 day study were consistent with the results of the first 13 day study, with a decrease in serum cholesterol levels of 26% on day 3 being observed. For FIG. 10A and FIG. 10B, the percentage change is in relation to the control IgG at the same time point (*P<0.01). For FIG. 10C, the percentage change is in relation to the control IgG at the same time point (*P<0.05).

Example 16

Effect of Antibody 31H4 on HDL Levels in a 13 Day Study

The HDL levels for the animals in Example 15 were also examined. HDL levels decreased in the mice. More specifically, animals dosed at 10 mg/kg demonstrated a 33% decrease in HDL levels on day 3, which gradually returned to pre-dosing levels by day 13. FIG. 10B depicts the results of the experiment. There was a decrease in HDL levels of 34% on day 3. FIG. 10B depicts the results of the repeated 13 day experiment.

As will be appreciated by one of skill in the art, while the antibodies will lower mouse HDL, this is not expected to occur in humans because of the differences in HDL in humans and other organisms (such as mice). Thus, the decrease in mouse HDL is not indicative of a decrease in human HDL.

Example 17

Repeated Administration of Antibodies Produce Continued Benefits of Antigen Binding Peptides In order to verify that the results obtained in the Examples above can be prolonged for further benefits with additional doses, the Experiments in Examples 15 and 16 were repeated with the dosing schedule depicted in FIG. 11A. The results are displayed in FIG. 11B. As can be seen in the graph in FIG. 11B, while both sets of mice displayed a significant decrease in total serum cholesterol because all of the mice received an initial injection of the 31H4 antigen binding protein, the mice that received additional injections of the 31H4 ABP displayed a continued reduction in total serum cholesterol, while those mice that only received the control injection eventually displayed an increase in their total serum cholesterol. For FIG. 11, the percentage change is in relation to the naive animals at t=0 hours (*P<0.01, **P<0.001).

The results from this example demonstrate that, unlike other cholesterol treatment methods, in which repeated applications lead to a reduction in efficacy because of biological adjustments in the subject, the present approach does not seem to suffer from this issue over the time period examined. Moreover, this suggests that the return of total serum cholesterol or HDL cholesterol levels to baseline, observed in the previous examples is not due to some resistance to the treatment being developed by the subject, but rather the depletion of the antibody availability in the subject.

Example 18

Epitope Mapping of Human Anti PCSK9 Antibodies

This example outlines methods for determining which residues in PCSK9 are involved in forming or part of the epitope for the antigen binding proteins disclosed herein to PCSK9.

In order to determine the epitopes to which certain of the ABPs of the present invention bind, the epitopes of the ABPs can be mapped using synthetic peptides derived from the specific PCSK9 peptide sequence.

A SPOTs peptide array (Sigma Genosys) can be used to study the molecular interaction of the human anti-PCSK9 antibodies with their peptide epitope. SPOTs technology is based on the solid-phase synthesis of peptides in a format suitable for the systematic analysis of antibody epitopes. Synthesis of custom arrayed oligopeptides is commerically available from Sigma-Genosys. A peptide array of overlapping oligopeptides derived from the amino-acid sequence of the PCSK9 peptide can be obtained. The array can comprise a series of 12-mer peptides as spots on a polypropylene membrane sheets. The peptide array can span the entire length of the PCSK9 mature sequence. Each consecutive peptide can be offset by 1 residue from the previous one, yielding a nested, overlapping library of arrayed oligopeptides. The membrane carrying the peptides can be reacted with different anti-PCSK9 antibodies (1 micrograms/ml). The binding of the mAbs to the membrane-bound peptides can be assessed by an enzyme-linked immunosorbent assay using HRP-conjugated secondary antibody followed by enhanced chemiluminescence (ECL).

In addition, functional epitopes can be mapped by combinatorial alanine scanning. In this process, a combinatorial alanine-scanning strategy can be used to identify amino acids in the PCSK9 protein that are necessary for interaction with anti-PCSK9 ABPs. To accomplish this, a second set of SPOTs arrays can be used for alanine scanning. A panel of variant peptides with alanine substitutions in each of the 12 residues can be scanned as above. This will allow for the epitopes for the ABPs to the human PCSK9 to be mapped and identified.

In the alternative, given that it is possible that the epitope is conformational, a combination of alanine scanning and/or arginine scanning, antibody FAB/PCSK9 co-crystallization, and limited proteolysis/LC-MS (liquid chromatography mass spec.) can be employed to identify the epitopes.

Example 19

Uses of PCSK9 Antibodies for the Treatment of Cholesterol Related Disorders

A human patient exhibiting a Cholesterol Related Disorder (in which a reduction in cholesterol (such as serum cholesterol) can be beneficial) is administered a therapeutically effective amount of PCSK9 antibody, 31H4 (or, for example, 21B12 or 16F12). At periodic times during the treatment, the patient is monitored to determine whether the symptoms of the disorder has subsided. Following treatment, it is found that patients undergoing treatment with the PCSK9 antibody have reduced serum cholesterol levels, in comparison to patients that are not treated.

Example 20

Uses of PCSK9 Antibodies for the Treatment of Hypercholesterolemia

A human patient exhibiting symptoms of hypercholesterolemia is administered a therapeutically effective amount of PCSK9 antibody, such as 31H4 (or, for example, 21B12 or 16F12). At periodic times during the treatment, the human patient is monitored to determine whether the serum cholesterol level has declined. Following treatment, it is found that the patient receiving the treatment with the PCSK9 antibodies has reduced serum cholesterol levels in comparison to arthritis patients not receiving the treatment.

Example 21

Uses of PCSK9 Antibodies for the Prevention of Coronary Heart Disease and/or Recurrent Cardiovascular Events A human patient at risk of developing coronary heart disease is identified. The patient is administered a therapeutically effective amount of PCSK9 antibody, such as 31H4 (or, for example, 21B12 or 16F12), either alone, concurrently or sequentially with a statin, e.g., simvastatin. At periodic times during the treatment, the human patient is monitored to determine whether the patient's total serum cholesterol level changes. Throughout the preventative treatment, it is found that the patient receiving the treatment with the PCSK9 antibodies has reduced serum cholesterol thereby reducing their risk to coronary heart disases or recurrent cardiovascular events in comparison to patients not receiving the treatment.

Example 22

Use of PCSK9 Antibodies as a Diagnostic Agent

An Enzyme-Linked Immunosorbent Assay (ELISA) for the detection of PCSK9 antigen in a sample can used to diagnose patients exhibiting high levels of PCSK9 production. In the assay, wells of a microtiter plate, such as a 96-well microtiter plate or a 384-well microtiter plate, are adsorbed for several hours with a first fully human monoclonal antibody directed against PCSK9. The immobilized antibody serves as a capture antibody for any of the PCSK9 that may be present in a test sample. The wells are rinsed and treated with a blocking agent such as milk protein or albumin to prevent nonspecific adsorption of the analyte.

Subsequently the wells are treated with a test sample suspected of containing the PCSK9, or with a solution containing a standard amount of the antigen. Such a sample may be, for example, a serum sample from a subject suspected of having levels of circulating antigen considered to be diagnostic of a pathology.

After rinsing away the test sample or standard, the wells are treated with a second fully human monoclonal PCSK9 antibody that is labeled by conjugation with biotin. A monoclonal or mouse or other species origin can also be used. The labeled PCSK9 antibody serves as a detecting antibody. After rinsing away excess second antibody, the wells are treated with avidin-conjugated horseradish peroxidase (HRP) and a suitable chromogenic substrate. The concentration of the antigen in the test samples is determined by comparison with a standard curve developed from the standard samples.

This ELISA assay provides a highly specific and very sensitive assay for the detection of the PCSK9 antigen in a test sample.

Determination of PCSK9 Protein Concentration in Subjects

A sandwich ELISA can quantify PCSK9 levels in human serum. Two fully human monoclonal PCSK9 antibodies from the sandwich ELISA, recognize different epitopes on the PCSK9 molecule. Alternatively, monoclonal antibodies of mouse or other species origin may be used. The ELISA is performed as follows: 50 µL of capture PCSK9 antibody in coating buffer (0.1 M $NaHCO_3$, pH 9.6) at a concentration of 2 µg/mL is coated on ELISA plates (Fisher). After incubation at 4° C. overnight, the plates are treated with 200 µL of blocking buffer (0.5% BSA, 0.1% Tween 20, 0.01% Thimerosal in PBS) for 1 hour at 25° C. The plates are washed (3×) using 0.05% Tween 20 in PBS (washing buffer, WB). Normal or patient sera (Clinomics, Bioreclaimation) are diluted in blocking buffer containing 50% human serum. The plates are incubated with serum samples overnight at 4° C., washed with WB, and then incubated with 100 µL/well of biotinylated detection PCSK9 antibody for 1 hour at 25° C. After washing, the plates are incubated with HRP-Streptavidin for 15 minutes, washed as before, and then treated with 100 µL/well of o-phenylenediamine in $H_2O_2$ (Sigma developing solution) for color generation. The reaction is stopped with 50 µL/well of $H_2SO_4$ (2M) and analyzed using an ELISA plate reader at 492 nm. Concentration of PCSK9 antigen in serum samples is calculated by comparison to dilutions of purified PCSK9 antigen using a four parameter curve fitting program.

Determination of PCSK9 Variant Protein Concentration in Subjects

The steps outlined above can be performed using antibodies noted herein that bind to both the wild type PCSK9 and the variant PCSK9 (D374Y). Next, antibodies that bind to the wild type but not the mutant can be used (again using a similar protocol as outlined above) to determine if the PCSK9 present in the subject is wild type or the D374Y variant. As will be appreciatedy by one of skill in the art, results that are positive for both rounds will be wild-type, while those that are positive for the first round, but not the second round of antibodies, will include the D374Y mutation. There are high frequency mutations in the population that are known and the could benefit particularly from an agent such as the ABPs disclosed herein.

Example 23

Use of PCSK9 Antigen Binding Protein for the Prevention of Hypercholesterolemia

A human patient exhibiting a risk of developing hypercholesterolemia is identified via family history analysis and/or lifestyle, and/or current cholesterol levels. The subject is regularly administered (e.g., one time weekly) a therapeutically effective amount of PCSK9 antibody, 31H4 (or, for example, 21B12 or 16F12). At periodic times during the treatment, the patient is monitored to determine whether serum cholesterol levels have decreased. Following treatment, it is found that subjects undergoing preventative treatment with the PCSK9 antibody have lowered serum cholesterol levels, in comparison to subjects that are not treated.

Example 24

PCSK9 ABPs Further Upregulated LDLR in the Presence of Statins

This example demonstrates that ABPs to PCSK9 produced further increases in LDLR availability when used in the presence of statins, demonstrating that further benefits can be achieved by the combined use of the two.

HepG2 cells were seeded in DMEM with 10% fetal bovine serum (FBS) and grown to ~90% confluence. The cells were treated with indicated amounts of mevinolin (a statin, Sigma) and PCSK9 ABPs (FIGS. 12A-12C) in DMEM with 3% FBS for 48 hours. Total cell lysates were prepared. 50 mg of total proteins were separated by gel electrophoresis and transferred to PVDF membrane. Immunoblots were performed using rabbit anti-human LDL receptor antibody (Fitzgerald) or rabbit anti-human b-actin antibody. The enhanced chemiluminescent results are shown in the top panels of FIGS. 12A-12C. The intensity of the bands were quantified by ImageJ software and normalized by b-actin. The relative levels of LDLR are shown in the lower panels of FIGS. 12A-12C. ABPs 21B12 and 31H4 are PCSK9 neutralizing antibodies, while 25A7.1 is a non-neutralizing antibody.

HepG2-PCSK9 cells were also created. These were stable HepG2 cell line transfected with human PCSK9. The cells were seeded in DMEM with 10% fetal bovine serum (FBS) and grew to ~90% confluence. The cells were treated with indicated amounts of mevinolin (Sigma) and PCSK9 ABPs (FIGS. 12D-12F) in DMEM with 3% FBS for 48 hours. Total cell lysates were prepared. 50 mg of total proteins were separated by gel electrophoresis and transferred to PVDF membrane. Immunoblots were performed using rabbit anti-human LDL receptor antibody (Fitzgerald) or rabbit anti-human b-actin antibody. The enhanced chemiluminescent results are shown in the top panels. The intensity of the bands were quantified by ImageJ software and normalized by b-actin.

As can be seen in the results depicted in FIGS. 12A-12F, increasing amounts of the neutralizing antibody and increasing amounts of the statin generally resulted in increases in the level of LDLR. This increase in effectiveness for increasing levels of the ABP is especially evident in FIGS. 12D-12F, in which the cells were also transfected with PCSK9, allowing the ABPs to demonstrate their effectiveness to a greater extent.

Interestingly, as demonstrated by the results in the comparison of FIGS. 12D-12F to 12A-12C, the influence of the ABP concentrations on LDLR levels increased dramatically when PCSK9 was being produced by the cells. In addition, it is clear that the neutralizing ABPs (21B12 and 31H4) resulted in a greater increase in LDLR levels, even in the presence of statins, than the 25A7.1 ABP (a non-neutralizer), demonstrating that additional benefits can be achieved by the use of both statins and ABPs to PCSK9.

Example 25

Consensus Sequences

Consensus sequences were determined using standard phylogenic analyses of the CDRs corresponding to the $V_H$ and $V_L$ of anti-PCSK9 ABPs. The consensus sequences were determined by keeping the CDRs contiguous within the same sequence corresponding to a $V_H$ or $V_L$. Briefly, amino acid sequences corresponding to the entire variable domains of either $V_H$ or $V_L$ were converted to FASTA formatting for ease in processing comparative alignments and inferring phylogenies. Next, framework regions of these sequences were replaced with an artificial linker sequence ("bbbbbbbbbb" placeholders, non-specific nucleic acid construct) so that examination of the CDRs alone could be performed without introducing any amino acid position weighting bias due to coincident events (e.g., such as unrelated antibodies that serendipitously share a common germline framework heritage) while still keeping CDRs contiguous within the same sequence corresponding to a $V_H$ or $V_L$. $V_H$ or $V_L$ sequences of this format were then subjected to sequence similarity alignment interrogation using a program that employs a standard ClutalW-like algorithm (see, Thompson et al., 1994, *Nucleic Acids Res.* 22:4673-4680). A gap creation penalty of 8.0 was employed along with a gap extension penalty of 2.0. This program likewise generated phylograms (phylogenic tree illustrations) based on sequence similarity alignments using either UPGMA (unweighted pair group method using arithmetic averages) or Neighbor-Joining methods (see, Saitou and Nei, 1987, *Molecular Biology and Evolution* 4:406-425) to construct and illustrate similarity and distinction of sequence groups via branch length comparison and grouping. Both methods produced similar results but UPGMA-derived trees were ultimately used as the method employs a simpler and more conservative set of assumptions. UPGMA-derived trees were generated where similar groups of sequences were defined as having fewer than 15 substitutions per 100 residues (see, legend in tree illustrations for scale) amongst individual sequences within the group and were used to define consensus sequence collections. The results of the comparisons are depicted in FIGS. 13A-13J. In FIG. 13E, the groups were chosen so that sequences in the light chain that Glade are also a Glade in the heavy chain and have fewer than 15 substitutions.

As will be appreciated by one of skill in the art, the results presented in FIGS. 13A-13J present a large amount of guidance as to the importance of particular amino acids (for example, those amino acids that are conserved) and which amino acid positions can likely be altered (for example, those positions that have different amino acids for different ABPs).

Example 26

Mouse Model for PCSK9 and ABP Ability to Lower LDL In Vivo

To generate mice which over-expressed human PCSK9, three week old WT C57Bl/6 mice were injected via tail vein administration with various concentrations of adenoassociated virus (AAV), recombinantly modified to express human PCSK9, to determine the correct titer which would provide a measurable increase of LDL-cholesterol in the mice. Using this particular virus that expressed human PCSK9, it was determined that 4.5×10E12 pfu of virus would result in an LDL-cholesterol level of approximately 40 mg/dL in circulating blood (normal levels of LDL in a WT mice are approximately 10 mg/dL). The human PCSK9 levels in these animals was found to be approximately 13 ug/mL. A colony of mice were generated using this injection criteria.

One week after injection, mice were assessed for LDL-cholesterol levels, and randomized into different treatment groups. Animals were then administered, via tail vein injection, a single bolus injection of either 10 mg/kg or 30 mg/kg of 16F12, 21B12, or 31H4 antigen binding proteins. IgG2 ABP was administered in a separate group of animals as a dosing control. Subgroups of animals (n=6-7) were then euthanized at 24 and 48 hours after ABP administration. There were no effects on LDL-cholesterol levels following IgG2 administration at either dose. Both 31H4 and 21B12 demonstrated significant LDL-cholesterol lowering up to and including 48 hours post-administration, as compared to IgG2 control (shown in FIGS. 14A and 14B at two different doses). 16F12 shows an intermediary LDL-cholesterol lowering response, with levels returning to baseline of approximately 40 mg/dL by the 48 hour time point. This data is consistent with in vitro binding data (Biacore and Kinexa), which shows near equivalent binding affinity between 31H4 and 21B12, and a lesser affinity of 16F12 to human PCSK9.

As can be seen in the results, total cholesterol and HDL-cholesterol were reduced by the PCSK9 ABPs in the model (both total and HDL-C are elevated above WT mice due to the overexpression of PCSK9). While cholesterol lowering in this model appears to occur over a relatively short period of time, this is believed to be due to the levels of human PCSK9 that are present, which are supraphysiologically high in this model. In addition, given that the expression is governed by AAV, there is no regulation of PCSK9 expression. In these figures, (\*) denotes a $P<0.05$, and (\*\*) denotes a $P<0.005$ as compared to LDL-cholesterol levels observed in IgG2 control injected animals at the same time point. The 13 microgram/ml level of serum human PCSK9 in the mice corresponds to an approximately 520-fold increase above the endogenous mouse PCSK9 levels (~25 ng/ml), and an approximately 75-fold increase above average human serum levels (~175 ng/ml). Thus, the antigen binding proteins should be even more effective in humans.

As will be appreciated by one of skill in the art, the above results demonstrate that appropriateness of the mouse model for testing the antigen binding protein's ability to alter serum cholesterol in a subject. One of skill in the art will also recognize that the use of mouse HDL to monitor serum cholesterol levels in a mouse, while useful for monitoring mouse serum cholesterol levels, is not indicative of the ABPs impact on human HDL in humans. For example, Cohen et al. ("Sequence variations in PCSK9, low LDL, and protection against coronary heart disease", N Engl J Med, 354:1264-1272, 2006) demonstrated the lack of any effect of the PCSK9 loss-of-function mutations on human HDL levels (the entirety of which is incorporated by reference). Thus, one of skill in the art will appreciate that the ability of the ABP to lower mouse HDL (which lack LDL) is not indicative of the ABP's ability to lower human HDL. Indeed, as shown by Cohen, this is unlikely to occur for neutralizing antibodies in humans.

Example 27

31H4 and 21B12 Bind to the ProCat Region of PCSK9

The present example describes one method for determining where various antibodies bind to PCSK9.

The ProCat (31-449 of SEQ ID NO: 3) or V domain (450-692 of SEQ ID NO: 3) of the PCSK9 protein was combined with either antibody 31H4 or 21B12. The samples were analyzed by Native PAGE for complex formation. As can be seen in FIG. 16A and FIG. 16B, gel shifts were present for the ProCat/31H4 and ProCat/21B12 samples, demonstrating that the antibodies bound to the ProCat domain.

Example 28

The LDLR EGFa Domain Binds to the Catalytic Domain of PCSK9

The present example presents the solved crystal structure of PCSK9 ProCat (31-454 of SEQ ID NO: 3) bound to the LDLR EGFa domain (293-334) at 2.9 Å resolution (the conditions for which are described in the below Examples).

A representation of the structure of PCSK9 bound to EGFa is shown in FIG. 17. The crystal structure (and its depiction in FIG. 17) reveals that the EGFa domain of LDLR binds to the catalytic domain of PCSK9. In addition, the interaction of PCSK9 and EGFa appears to occur across a surface of PCSK9 that is between residues D374 and S153 in the structure depicted in FIG. 17.

Specific core PCSK9 amino acid residues of the interaction interface with the LDLR EGFa domain were defined as PCSK9 residues that are within 5 Å of the EGFa domain. The core residues are as follows: S153, I154, P155, R194, D238, A239, I369, S372, D374, C375, T377, C378, F379, V380, and S381.

Boundary PCSK9 amino acid residues of the interaction interface with the LDLR EGFa domain were defined as PCSK9 residues that are 5-8 Å from the EGFa domain. The boundary residues are as follows: W156, N157, L158, E159, H193, E195, H229, R237, G240, K243, D367, I368, G370, A371, S373, S376, and Q382. Residues that are underlined are nearly or completely buried within PCSK9.

As will be appreciated by one of skill in the art, the results from this example demonstrate where PCSK9 and EGFa interact. Thus, antibodies that interact with or block any of these residues can be useful as antibodies that inhibit the interaction between PCSK9 and the EGFa domain of LDLR (and/or LDLR generally). In some embodiments, antibodies that, when bound to PCSK9, interact with or block any of the above residues or are within 15-8, 8, 8-5, or 5 angstroms of the above residues are contemplated to provide useful inhibition of PCSK9 binding to LDLR.

Example 29

31H4 Interacts with Amino Acid Residues from Both the Pro- and Catalytic Domains of PCSK9

The present example presents the crystal structure of full length PCSK9 (N533A mutant of SEQ ID NO: 3) bound to the Fab fragment of 31H4, determined to 2.3 Å resolution (the conditions for which are described in the below Examples). This structure, depicted in FIGS. 18A and 18B, shows that 31H4 binds to PCSK9 in the region of the catalytic site and makes contacts with amino acid residues from both the pro-domain and catalytic domain.

The depicted structure also allows one to identify specific core PCSK9 amino acid residues for the interaction interface of 31H4 with PCSK9. This was defined as residues that are within 5 Å of the 31H4 protein. The core residues are as follows: W72, F150, A151, Q152, T214, R215, F216, H217, A220, S221, K222, S225, H226, C255, Q256, G257, K258, N317, F318, T347, L348, G349, T350, L351, E366, D367, D374, V380, S381, Q382, S383, and G384.

The structures were also used to identify boundary PCSK9 amino acid residues for the interaction interface with 31H4. These residues were PCSK9 residues that were 5-8 Å from the 31H4 protein. The boundary residues are as follows: K69, D70, P71, S148, V149, D186, T187, E211, D212, G213, R218, Q219, C223, D224, G227, H229, L253, N254, G259, P288, A290, G291, G316, R319, Y325, V346, G352, T353, G365, I368, I369, S372, S373, C378, F379, T385, S386, and Q387. Amino acid residues completely buried within the PCSK9 protein are underlined.

As will be appreciated by one of skill in the art, FIG. 18B depicts the interaction between the CDRs on the antigen binding protein and PCSK9. As such, the model allows one of skill in the art to identify the residues and/or CDRs that are especially important in the paratope, and which residues are less critical to the paratope. As can be seen in FIG. 18B, the heavy chain CDR1, CDR2, and CDR3 are most directly involved in the antigen binding protein's binding to the epitope, with the CDRs from the light chain being relatively far away from the epitope. As such, it is probable that larger variations in the light chain CDRs are possible, without unduly interfering with the binding of the antigen binding protein to PCSK9. In some embodiments, residues in the structures that directly interact are conserved (or alternatively conservatively replaced) while residues that are not directly interacting with one another can be altered to a greater extent. As such, one of skill in the art, given the present teachings, can predict which residues and areas of the antigen binding proteins can be varied without unduly interfering with the antigen binding protein's ability to bind to PCSK9. For example, those residues that are located closest to PCSK9 when the antigen binding protein is bound to PCSK9 are those that likely play a more important role in the binding of the antigen binding protein to PCSK9. As above, these residues can be divided into those that are within 5 angstroms of PCSK9 and those that are between 5 and 8 angstroms. Specific core 31H4 amino acid residues of the interaction interface with PCSK9 were defined as 31H4 residues that are within 5 Å of the PCSK9 protein. For the heavy chain, the residues that are within 5 angstroms include the following: T28, S30, S31, Y32, S54, S55, S56, Y57, I58, S59, Y60, N74, A75, R98, Y100, F102, W103, S104, A105, Y106, Y107, D108, A109, and D111. For the light chain, those residues that are within 5 angstroms include the following: L48, S51, Y93, and S98. For the heavy chain, those residues that are 5-8 Å from the PCSK9 protein include the following: G26, F27, F29, W47, S50, I51, S52, S53, K65, F68, T69, I70, S71, R72, D73, K76, N77, D99, D101, F110, and V112. For the light chain, those residues that are within 5-8 angstroms of PCSK9 include A31, G32, Y33, D34, H36, Y38, I50, G52, N55, R56, P57, S58, D94, S95, 596, L97, G99, and S100.

As will be appreciated by one of skill in the art, the results from Example 29 demonstrate where antibodies to PCSK9 can interact on PCSK9 and still block PCSK9 from interacting with EGFa (and thus LDLR). Thus, antigen binding proteins that interact with any of these PCSK9 residues, or that block any of these residues (e.g., from other antigen binding proteins that bind to these residues), can be useful as antibodies that inhibit the interaction of PCSK9 and EGFa (and LDLR accordingly). Thus, in some embodiments, antigen binding proteins that interact with any of the above residues or interact with residues that are within 5 Å of the above residues are contemplated to provide useful inhibition PCSK9 binding to LDLR. Similarly, antigen binding proteins that block any of the above residues (which can be determined, for example, via a competition assay) can also be useful for inhibition of the PC SK9/LDLR interaction.

Example 30

21B12 Binds to the Catalytic Domain of PCSK9, has a Distinct Binding Site from 31H4 and can Bind to PCSK9 Simultaneously with 31H4

The present example presents the crystal structure of PCSK9 ProCat (31-449 of SEQ ID NO: 3) bound to the Fab fragments of 31H4 and 21B12, determined at 2.8 Å resolution (the conditions for which are described in the below Examples). This crystal structure, depicted in FIG. 19A and FIG. 19B, shows that 31H4 and 21B12 have distinct binding sites on PCSK9 and that both antigen binding proteins can bind to PCSK9 simultaneously. The structure shows that 21B12 interacts with amino acid residues from PCSK9's catalytic domain. In this structure, the interaction between PCSK9 and 31H4 is similar to what was observed above.

Specific core PCSK9 amino acid residues of the interaction interface with 21B12 were defined as PCSK9 residues that are within 5 Å of the 21B12 protein. The core residues are as follows: S153, S188, I189, Q190, S191, D192, R194, E197, G198, R199, V200, D224, R237, D238, K243, S373, D374, S376, T377, and F379.

Boundary PCSK9 amino acid residues of the interaction interface with 21B12 were defined as PCSK9 residues that were 5-8 Å from the 21B12 protein. The boundary residues are as follows: I154, T187, H193, E195, <u>I196</u>, M201, V202, C223, <u>T228</u>, <u>S235</u>, <u>G236</u>, A239, G244, M247, I369, S372, C375, and C378. Amino acid residues nearly or completely buried within the PCSK9 protein are underlined.

As will be appreciated by one of skill in the art, FIG. 19B depicts the interaction between the CDRs on the antigen binding protein and PCSK9. As such, the model allows one of skill in the art to identify the residues and/or CDRs which are especially important for the paratope and which residues are less critical to the paratope. As can be seen in the structure, heavy chain CDR2 and light chain CDR1 appear to closely interact with the epitope. Next, heavy chain CDR1, heavy chain CDR3 and light chain CDR3, appear to be close to the epitope, but not as close as the first set of CDRs. Finally, light chain CDR2 appears to be some distance from the epitope. As such, it is probable that larger variations in the more distant CDRs are possible without unduly interfering with the binding of the antigen binding protein to PCSK9. In some embodiments, residues in the structures that directly interact are conserved (or alternatively conservatively replaced) while residues that are not directly interacting with one another can be altered to a greater extent. As such, one of skill in the art, given the present teachings, can predict which residues and areas of the antigen binding proteins can be varied without unduly interfering with the antigen binding protein's ability to bind to PCSK9. For example, those residues that are located closest to PCSK9 when the antigen binding protein is bound to PCSK9 are those that likely play a more important role in the binding of the antigen binding protein to PCSK9. As above, these residues can be divided into those that are within 5 angstroms of PCSK9 and those that are between 5 and 8 angstroms. Specific core 21B12 amino acid residues of the interaction interface with PCSK9 were defined as 21B12 residues that are within 5 Å of the PCSK9 protein. For the heavy chain, the residues that are within 5 angstroms include the following: T30, S31, Y32, G33, W50, S52, F53, Y54, N55, N57, N59, R98, G99, Y100, and G101. For the light chain, those residues that are within 5 angstroms include the following: G30, G31, Y32, N33, S34, E52, Y93, T94, S95, T96, and S97. For the heavy chain, those residues that are 5-8 Å from the PCSK9 protein include the following: T28, L29, I34, S35, W47, V51, G56, T58, Y60, T72, M102, and D103. For the light chain, those residues that are within 5-8 angstroms of PCSK9 include the following: S26, V29, V35, Y51, N55, S92, M98, and V99.

As will be appreciated by one of skill in the art, the results from Example 30 demonstrate where antigen binding proteins to PCSK9 can interact on PCSK9 and still block PCSK9 from interacting with EGFa (and thus LDLR). Thus, antigen binding proteins that interact with any of these PCSK9 residues or that block any of these residues can be useful as antibodies that inhibit the interaction of PCSK9 and EGFa (and LDLR accordingly). Thus, in some embodiments, antibodies that interact with any of the above residues or interact with residues that are within 5 Å of the above residues are contemplated to provide useful inhibition PCSK9 binding to LDLR. Similarly, antigen binding proteins that block any of the above residues (which can be determined, for example, via a competition assay) can also be useful for inhibition of PCSK9/LDLR interaction.

Example 31

Interaction Between EGFa, PCSK9, and the Antibodies

The structure of the ternary complex (PCSK9/31H4/21B12) from the above example was overlaid on the PCSK9/EGFa structure (determined as described in Example 28) and the result of this combination is depicted in FIG. 20A. This figure demonstrates areas on PCSK9 which can be usefully targeted to inhibit PCSK9 interaction with EGFa. The figure shows that both 31H4 and 21B12 partially overlap with the position of the EGFa domain of LDLR and sterically interfere with its binding to PCSK9. In addition, as can be seen in the structures, 21B12 directly interacts with a subset of amino acid residues that are specifically involved in binding to the LDLR EGFa domain.

As noted above, analysis of the crystal structures identified specific amino acids involved in the interaction between PCSK9 and the partner proteins (the core and boundary regions of the interface on the PCSK9 surface) and the spatial requirements of these partner proteins to interact with PCSK9. The structures suggest ways to inhibit the interaction between PCSK9 and the LDLR. First, as noted above, binding an agent to PCSK9 where it shares residues in common with the binding site of the EGFa domain of the LDLR would inhibit the interaction between PCSK9 and the LDLR. Second, an agent that binds outside of the residues in common can sterically interfere with the EGFa domain or regions of the LDLR that are either N- or C-terminal to the EGFa domain to prevent the interaction between PCSK9 and the LDLR.

In some embodiments, the residues that are involved in both EGFa binding and are close to the areas where the above noted antigen binding proteins bind are especially useful for manipulating PCSK9 binding to LDLR. For example, amino acid residues from interfaces in common in both the core region and boundary region for the different binding partners are listed in Table 12 below. Amino acid residues completely buried within the PCSK9 protein are underlined.

TABLE 12

| Parameters | Amino acid position(s) |
| --- | --- |
| 31H4/EGFa both under 5 Å | D374, V380, S381 |
| 31H4 under 5 Å/EGFa 5-8 Å | D367, Q382 |
| 31H4 at 5-8 Å/EGFa under 5 Å | I369, S372, C378, F379 |
| 31H4/EGFa both at 5-8 Å | H229, S373 |
| 21B12/EGFa both under 5 Å | S153, R194, D238, D374, T377, F379 |
| 21B12 under 5 Å/EGFa 5-8 Å | R237, K243, S373, S376 |
| 21B12 at 5-8 Å/EGFa under 5 Å | I154, A239, I369, S372, C375, C378 |
| 21B12/EGFa both at 5-8 Å | H193, E195 |

As will be appreciated by one of skill in the art, in some embodiments, the antigen binding proteins bind to and/or block at least one of the above noted residues.

Example 32

Structural Interaction of LDLR and PCSK9

A model of full length PCSK9 bound to a full length representation of the LDLR was made using the PCSK9 ProCat (31-454 of SEQ ID NO: 3)/EGFa complex structure. The structure of full length PCSK9[1] (Piper, D. E. et al. The crystal structure of PCSK9: a regulator of plasma LDL-cholesterol. *Structure* 15, 545-52 (2007)) was overlaid onto the PCSK9 ProCat 31-454 from the complex and the structure of the LDLR in its low pH conformation (Rudenko, G. et al. Structure of the LDL receptor extracellular domain at endosomal pH. *Science* 298, 2353-8 (2002)) was overlaid onto the EGFa domain from the complex. Depictions of the model are shown in FIGS. 20B and 20C. The EGFa domain is indicated by the box in the figure. The figures show regions of the LDLR outside of the immediate EGFa binding domain that lie in close proximity to PCSK9. FIGS. 20D-20F show the above interaction, along with mesh surface representations of antibody 31H4 and 21B12 from three different angles. As is clear from the depictions, not only can the antibody interact and/or interfere with LDLR's interaction with PCSK9 at the actual binding site, but other steric interactions appear to occur as well.

In light of the above results, it is clear that antigen binding proteins that bind to PCSK9 can also inhibit the interaction between PCSK9 and the LDLR by clashing with various regions of the LDLR (not just the site at which LDLR and PCSK9 interact). For example, it can clash with repeat 7 (R7), the EGFb domain, and/or the β-propeller domain.

Embodiments of Antigen Binding Molecules that Bind to or Block EGFa Interaction with PCSK9

As will be appreciated by one of skill in the art, Examples 28-32, and their accompanying figures, provide a detailed description of how and where EGFa interacts with PCSK9 and how two representative neutralizing antigen binding proteins, 21B12 and 31H4 interact with PCSK9 and produce their neutralizing effect. As such, one of skill in the art will readily be able to identify antigen binding molecules that can similarly reduce the binding between EGFa (including LDLR) and PCSK9 by identifying other antigen binding molecules that bind at or near at least one of the same locations on PCSK9. While the relevant locations (or epitopes) on PCSK9 are identified in the figures and the present description, it can also be advantageous to describe these sites as being within a set distance from residues that have been identified as close to the EGFa binding site. In some embodiments, an antigen binding molecule will bind to or within 30 angstroms of one or more of the following residues (numbering in reference to SEQ ID NO: 3): S153, I154, P155, R194, D238, A239, I369, S372, D374, C375, T377, C378, F379, V380, S381, W156, N157, L158, E159, H193, E195, H229, R237, G240, K243, D367, I368, G370, A371, S373, S376, Q382, W72, F150, A151, Q152, T214, R215, F216, H217, A220, S221, K222, S225, H226, C255, Q256, G257, K258, N317, F318, T347, L348, G349, T350, L351, E366, D367, D374, V380, S381, Q382, S383, G384, K69, D70, P71, S148, V149, D186, T187, E211, D212, G213, R218, Q219, C223, D224, G227, H229, L253, N254, G259, P288, A290, G291, G316, R319, Y325, V346, G352, T353, G365, I368, I369, S372, S373, C378, F379, T385, S386, Q387, S153, S188, I189, Q190, S191, D192, R194, E197, G198, R199, V200, D224, R237, D238, K243, S373, D374, S376, T377, F379, I154, T187, H193, E195, I196, M201, V202, C223, T228, S235, G236, A239, G244, M247, I369, S372, C375, or C378. In some embodiments, the antigen binding molecule binds within 30 angstroms of one or more of the following residues (numbering in reference to SEQ ID NO: 3): S153, I154, P155, R194, D238, A239, I369, S372, D374, C375, T377, C378, F379, V380, S381, W156, N157, L158, E159, H193, E195, H229, R237, G240, K243, D367, I368, G370, A371, S373, S376, or Q382. In some embodiments, the antigen binding molecule binds within 30 angstroms of one or more of the following residues (numbering in reference to SEQ ID NO: 3): W72, F150, A151, Q152, T214, R215, F216, H217, A220, S221, K222, S225, H226, C255, Q256, G257, K258, N317, F318, T347, L348, G349, T350, L351, E366, D367, D374, V380, S381, Q382, S383, G384, K69, D70, P71, S148, V149, D186, T187, E211, D212, G213, R218, Q219, C223, D224, G227, H229, L253, N254, G259, P288, A290, G291, G316, R319, Y325, V346, G352, T353, G365, I368, I369, S372, S373, C378, F379, T385, S386, or Q387. In some embodiments, the antigen binding molecule binds within 30 angstroms of one or more of the following residues (numbering in reference to SEQ ID NO: 3): S153, S188, I189, Q190, S191, D192, R194, E197, G198, R199, V200, D224, R237, D238, K243, S373, D374, S376, T377, F379, I154, T187, H193, E195, I196, M201, V202, C223, T228, S235, G236, A239, G244, M247, I369, S372, C375, or C378.

In some embodiments, the antigen binding molecule binds within 30, 30-25, 25-20, 20-15, 15-8,8,8-5, 5, 5-4, 4 or less angstroms from one or more of the above residues. In some embodiments, the antigen binding molecule, when bound to PCSK9, is within at least one of the above distances, for more than one of the above noted residues. For example, in some embodiments, the antigen binding molecule is within one of the recited distances (e.g., 30, 30-25, 25-20, 20-15, 15-8,8,8-

5, 5, 5-4, 4 or less) for at least 2, 3, 4, 5, 6, 7, 8, 9, 10, 11, 12, 13, 14, 15, 16, 17, 18, 19, 20, 20-25, 25-30, 30-35, 35-40, 40-45, 45-50, 50-55, 55-60, 60-65, 65-70, 70-75 or more of the above residues. In some embodiments, the antigen binding molecule is within one of the recited distances for at least 1-10, 10-20, 20-30, 30-40, 40-50, 50-60, 60-70, 70-80, 80-90, 90-95, 95-99, 99-100% of the residues identified in each group of subgroup thereof (such as only those surface residues in the group). Unless specifically stated otherwise, the distance between the antigen binding molecule and PCSK9 is the shortest distance between the covalently bonded atom on PCSK9 and the covalently bonded atom of the antigen binding molecule that are the closest atoms of PCSK9 and the antigen binding molecule. Similarly, unless specifically stated otherwise, the distance between a residue (on the antigen binding molecule or PCSK9) and another protein (either PCSK9 or the antigen binding molecule respectively), is the distance from the closest point on the identified residue to the closest covalently bonded part of the other protein. In some embodiments, the distance can be measured from the backbone of the amino acid chains. In some embodiments, the distance can be measured between an edge of the paratope and an edge (closest to one another) of the epitope. In some embodiments, the distance can be measured between the center of the surface of the paratope and the center of the surface of the epitope. As will be appreciated by one of skill in the art, the present description is applicable for each of the individual sets of residues listed herein. For example, the above ranges are contemplated generally and specifically for the 8 angstrom residues listed in Examples 28-32 and the 5 angstrom residues listed in Examples 28-32.

In some embodiments, the antigen binding molecule binds to a surface on PCSK9 that is bound by at least one of EGFa, 21B12, or 31H4. In some embodiments, the antigen binding molecule binds to PCSK9 at a location that overlaps with the interaction locations between PCSK9 and EFGa, Ab 31H4, and/or Ab 21B12 (as described in the above examples and figures). In some embodiments, the antigen binding molecule binds to PCSK9 at a position that is further away from one of the above recited residues. In some embodiments, such an antigen binding molecule can still be an effective neutralizing antigen binding molecule.

In some embodiments, the structure of the catalytic domain of PCSK9 can be described as generally being triangular (as shown in FIG. 19A). The first side of the triangle is shown as being bound by 31H4. The second side of the triangle is shown as being bound by 21B12, and the third side of the triangle is positioned toward the bottom of the page, immediately above the "FIG. 19A" label. In some embodiments, antigen binding molecules that bind to the first and/or second sides of the catalytic domain of PCSK9 can be useful as neutralizing antibodies as they can either directly or sterically interfere with EGFa's binding to PCSK9. As will be appreciated by one of skill in the art, when the antigen binding molecules are large enough, such as a full antibody, the antigen binding molecule need not directly bind to the EGFa binding site in order to interfere with the binding of EGFa to PCSK9.

As will be appreciated by one of skill in the art, while the EGFa domain of the LDLR has been used in many of the examples, the models and structures are still applicable to how the full length LDLR protein will interact with PCSK9. Indeed, the additional structure present on the full length LDLR protein presents additional protein space that can further be blocked by one of the antigen binding molecules. As such, if the antigen binding molecule blocks or inhibits binding of EGFa to PCSK9, it will likely be at least as, if not more, effective with the full length LDLR protein. Similarly, antigen binding molecules that are within a set distance or block various residues that are relevant for inhibiting EGFa binding, will likely be as effective, if not more effective, for the full length LDLR.

As will be appreciated by one of skill in the art, any molecule that blocks or binds to the above noted PCSK9 residues (or within the recited distances), or that inhibits one or more of the interactions noted in the above examples and figures, can be used to inhibit the interaction of EGFa (or LDLR generally) and PCSK9. As such, the molecule need not be limited to an antigen binding "protein," as any antigen binding molecule can also serve the required purpose. Examples of antigen binding molecules include aptamers, which can be either oligonucleic acid or peptide molecules. Other examples of antigen binding molecules include avimers, peptibodies, small molecules and polymers, and modified versions of EGFa that can increase its affinity to PCSK9 and/or half-life, such as mutation of amino acids, glycosylation, pegylation, Fc fusions, and avimer fusions. As will be appreciated by one of skill in the art, in some embodiments LDLR is not an antigen binding molecule. In some embodiments, binding subsections of LDLR are not antigen binding molecules, e.g., EGFa. In some embodiments, other molecules through which PCSK9 signals in vivo are not antigen binding molecules. Such embodiments will be explicitly identified as such.

Example 33

Expression and Purification of Protein Samples

The present example describes some embodiments for how the various embodiments of the PCSK9 proteins/variants were made and purified (including the LDLR EGFa domain). PCSK9 proteins/variants (e.g., PSCK9 31-692 N533A, PCSK9 449TEV and PCSK9 ProCat 31-454) were expressed in baculovirus infected Hi-5 insect cells with an N-terminal honeybee melittin signal peptide followed by a $His_6$ tag. The PCSK9 proteins were purified by nickel affinity chromatography, ion exchange chromatography and size exclusion chromatography. The melittin-$His_6$ tag was removed during purification by cleavage with TEV protease. The construct PCSK9 449TEV was used to generate PCSK9 ProCat (31-449) and V domain (450-692) samples. This construct had a TEV protease cleavage site inserted between PCSK9 residues 449 and 450. For the full length N555A variant for crystallography, the PCSK9 31-454 fragment, and the PCSK9 449TEV variant for crystalography, the post rTEV protein product also included an initial GAMG sequence. Thus, post rTEV cleavage, these proteins were GAMG-PCSK9. Furthermore, the PCSK9 449TEV protein included the sequence "ENLYFQ" (SEQ ID NO: 403) inserted between positions H449 and G450 of SEQ ID NO: 3. After cleavage with rTEV, the PCSK9 ProCat protein generated from this construct was GAMG-PCSK9 (31-449)-ENLYFQ and the V domain generated from this construct was PCSK9 (450-692) of SEQ ID NO: 3.

The 21B12 and 31H4Fab fragments were expressed in *E. coli*. These proteins were purified by nickel affinity chromatography, size exclusion chromatography and ion exchange chromatography.

The LDLR EGFa domain (293-334) was expressed as a GST fusion protein in *E. coli*. The EGFa domain was purified by ion exchange chromatography, glutathione sepharose affinity chromatography and size exclusion chromatography.

The GST protein was removed during the purification by cleavage with PreScission protease.

Example 34

Complex Formation and Crystallization

The present example describes how complexes and crystals used in the above structure examination Examples were made.

The PCSK9 31-692 N533A/31H4 complex was made by mixing a 1.5 molar excess of the 31H4Fab with PCSK9. The complex was purified by size exclusion chromatography to remove excess 31H4Fab. The PCSK9 31-692 N533A/31H4 complex crystallizes in 0.1 M Tris pH 8.3, 0.2 M sodium acetate, 15% PEG 4000, 6% dextran sulfate sodium salt (Mr 5000).

The PCSK9 ProCat 31-449/31H4/21B12 complex was made by first mixing a 1.5 molar excess of 31H4Fab with PCSK9 31-449. The complex was separated from excess 31H4 by purification on a size exclusion chromatography column. A 1.5 molar excess of 21B12 Fab was then added to the PCSK9 31-449/31H4 complex. The ternary complex was separated from excess 21B12 by purification on a size exclusion chromatography column. The PCSK9 ProCat 31-449/31H4/21B12 complex crystallizes in 0.1 M Tris pH 8.5, 0.2 M ammonium phosphate monobasic, 50% MPD.

The PCSK9 ProCat 31-454/EGFa complex was made by mixing a 1.2 molar excess of EGFa domain with PCSK9 31-454. The PCSK9 ProCat 31-454/EGFa domain complex crystallizes in 0.2 M potassium formate, 20% PEG 3350.

Example 35

Data Collection and Structure Determination

The present example describes how the datasets were collected and the structures determined for the above structure examination Examples.

Initial datasets for the PCSK9 31-692 N533A/31H4 and PCSK9 ProCat 31-449/31H4/21B12 crystals were collected on a Rigaku FR-E X-ray source. The PCSK9 ProCat 31-454/EGFa dataset and higher resolution datasets for the PCSK9 31-692 N533A/31H4 and PCSK9 ProCat 31-449/31H4/21B12 crystals were collected at the Berkeley Advanced Light Source beamline 5.0.2. All datasets were processed with denzo/scalepack or HKL2000 (Otwinowski, Z., Borek, D., Majewski, W. & Minor, W. Multiparametric scaling of diffraction intensities. *Acta Crystallogr A* 59, 228-34 (2003)).

PCSK9/31H4 crystals grew in the C2 space group with unit cell dimensions a=264.9, b=137.4, c=69.9 Å, β=102.8° and diffract to 2.3 Å resolution. The PCSK9/31H4 structure was solved by molecular replacement with the program MOLREP (The CCP4 suite: programs for protein crystallography. *Acta Crystallogr D Biol Crystallogr* 50, 760-3 (1994) using the PCSK9 structure (Piper, D. E. et al. The crystal structure of PCSK9: a regulator of plasma LDL-cholesterol. *Structure* 15, 545-52 (2007)) as the starting search model. Keeping the PCSK9 31-692 solution fixed, an antibody variable domain was used as a search model. Keeping the PCSK9 31-692/antibody variable domain solution fixed, an antibody constant domain was used as a search model. The complete structure was improved with multiple rounds of model building with Quanta and refinement with cnx. (Brunger, A. T. et al. Crystallography & NMR system: A new software suite for macromolecular structure determination. *Acta Crystallogr D Biol Crystallogr* 54, 905-21 (1998)).

PCSK9/31H4/21B12 crystals grew in the $P2_12_12$ space group with unit cell dimensions a=138.7, b=246.2, c=51.3 Å and diffract to 2.8 Å resolution. The PCSK9/31H4/21B12 structure was solved by molecular replacement with the program MOLREP using the PCSK9 ProCat/31H4 variable domain as the starting search model. Keeping the PCSK9 ProCat/31H4 variable domain fixed, a search for antibody constant domain was performed. Keeping the PCSK9 ProCat/31H4/21B12 constant domain fixed, an antibody variable domain was used as a search model. The complete structure was improved with multiple rounds of model building with Quanta and refinement with cnx.

PCSK9/EGFa domain crystals grew in the space group $P6_522$ with unit cell dimensions a=b=70.6, c=321.8 Å and diffract to 2.9 Å resolution. The PCSK9/EGFa domain structure was solved by molecular replacement with the program MOLREP using the PCSK9 ProCat as the starting search model. Analysis of the electron density maps showed clear electron density for the EGFa domain. The LDLR EGFa domain was fit by hand and the model was improved with multiple rounds of model building with Quanta and refinement with cnx.

Core interaction interface amino acids were determined as being all amino acid residues with at least one atom less than or equal to 5 Å from the PCSK9 partner protein. 5 Å was chosen as the core region cutoff distance to allow for atoms within a van der Waals radius plus a possible water-mediated hydrogen bond. Boundary interaction interface amino acids were determined as all amino acid residues with at least one atom less than or equal to 8 Å from the PCSK9 partner protein but not included in the core interaction list. Less than or equal to 8 Å was chosen as the boundary region cutoff distance to allow for the length of an extended arginine amino acid. Amino acids that met these distance criteria were calculated with the program PyMOL. (DeLano, W. L. The PyMOL Molecular Graphics System. (Palo Alto, 2002)).

Example 36

Crystal Structure of PCSK9 and 31A4

The crystal structure of the 31A4/PCSK9 complex was deteremined.

Expression and Purification of Protein Samples

PCSK9 449TEV (a PCSK9 construct with a TEV protease cleavage site inserted between residue 449 and 450, numbering according to SEQ ID NO: 3) was expressed in baculovirus infected Hi-5 insect cells with an N-terminal honeybee melittin signal peptide followed by a $His_6$ tag. The PCSK9 protein was purified by first by nickel affinity chromatography. TEV protease was used to remove the melittin-$His_6$ tag and cleave the PCSK9 protein between the catalytic domain and V domain. The V domain was further purified by ion exchange chromatography and size exclusion chromatography. The 31A4 Fab fragment was expressed in *E. coli*. This protein was purified by nickel affinity chromatography, size exclusion chromatography and ion exchange chromatography.

Complex Formation and Crystallization

The PCSK9 V domain/31A4 complex was made by mixing a 1.5 molar excess of PCSK9 V domain with 31A4 Fab. The complex was separated from excess PCSK9 V domain by purification on a size exclusion chromatography column. The PCSK9 V domain/31A4 complex crystallized in 1.1 M Succinic acid pH 7, 2% PEG MME 2000.

Data Collection and Structure Determination

The dataset for the PCSK9 V domain/31A4 crystal was collected on a Rigaku FR-E x-ray source and processed with denzo/scalepack (Otwinowski, Z., Borek, D., Majewski, W. & Minor, W. Multiparametric scaling of diffraction intensities. *Acta Cgstallogr A* 59, 228-34 (2003)).

PCSK9 V domain/31A4 crystals grow in the $P2_12_12_1$ space group with unit cell dimensions a=74.6, b=131.1, c=197.9 Å with two complex molecules per asymmetric unit, and diffract to 2.2 Å resolution. The PCSK9 V domain/31A4 structure was solved by molecular replacement with the program MOLREP (CCP4. The CCP4 suite: programs for protein crystallography. *Acta Crystallogr D Biol Crystallogr* 50, 760-3 (1994)) using the V domain of the PCSK9 structure (Piper, D. E. et al. The crystal structure of PCSK9: a regulator of plasma LDL-cholesterol. *Structure* 15, 545-52 (2007)) as the starting search model. Keeping the PCSK9 450-692 solution fixed, an antibody variable domain was used as a search model. After initial refinement, the antibody constant domains were fit by hand. The complete structure was improved with multiple rounds of model building with Quanta and refinement with cnx (Brunger, A. T. et al. Crystallography & NMR system: A new software suite for macromolecular structure determination. *Acta Crystallogr D Biol Crystallogr* 54, 905-21 (1998)).

Core interaction interface amino acids were determined as being all amino acid residues with at least one atom less than or equal to 5 Å from the PCSK9 partner protein. 5 Å was chosen as the core region cutoff distance to allow for atoms within a van der Waals radius plus a possible water-mediated hydrogen bond. Boundary interaction interface amino acids were determined as all amino acid residues with at least one atom less than or equal to 8 Å from the PCSK9 partner protein but not included in the core interaction list. Less than or equal to 8 Å was chosen as the boundary region cutoff distance to allow for the length of an extended arginine amino acid. Amino acids that met these distance criteria were calculated with the program PyMOL (DeLano, W. L. The PyMOL Molecular Graphics System. (Palo Alto, 2002)). Distances were calculated using the V domain "A" and 31A4 "L1,H1" complex.

The crystal structure of the PCSK9 V domain bound to the Fab fragment of 31A4 was determined at 2.2 Å resolution. The depictions of the crystal structure are provided in FIGS. 21A-21D. FIGS. 21A-21C shows that the 31A4 Fab binds to the PCSK9 V domain in the region of subdomains 1 and 2.

A model of full length PCSK9 bound the 31A4 Fab was made. The structure of full length PCSK9 was overlaid onto the PCSK9 V domain from the complex. A figure of this model is shown in FIG. 21D. The site of the interaction between the EGFa domain of the LDLR and PCSK9 is highlighted.

Analysis of the structure shows where this antibody interacts with PCSK9 and demonstrated that antibodies that do not bind to the LDLR binding surface of PCSK9 can still inhibit the degradation of LDLR that is mediated through PCSK9 (when the results are viewed in combination with Example 40 and 41 below). In addition, analysis of the crystal structure allows for identification of specific amino acids involved in the interaction between PCSK9 and the 31A4 antibody. Furthermore, the core and boundary regions of the interface on the PCSK9 surface were also determined. Specific core PCSK9 amino acid residues of the interaction interface with 31A4 were defined as PCSK9 residues that are within 5 Å of the 31A4 protein. The core residues are T468, R469, M470, A471, T472, R496, R499, E501, A502, Q503, R510, H512, F515, P540, P541, A542, E543, H565, W566, E567, V568, E569, R592, and E593. Boundary PCSK9 amino acid residues of the interaction interface with 31A4 were defined as PCSK9 residues that are 5-8 Å from the 31A4 protein. The boundary residues are as follows: S465, G466, P467, A473, I474, R476, <u>G497</u>, <u>E498</u>, M500, G504, K506, L507, V508, <u>A511</u>, <u>N513</u>, A514, G516, V536, T538, A539, A544, T548, D570, L571, H591, A594, 5595, and H597. Amino acid residues nearly or completely buried within the PCSK9 protein are highlighted by underline. As noted herein, the numbering references the amino acid positions of SEQ ID NO: 3 (adjusted as noted herein).

Specific core 31A4 amino acid residues of the interaction interface with PCSK9 were defined as 31A4 residues that are within 5 Å of the PCSK9 protein. The core residues for the 31A4 antibody are as follows: Heavy Chain: G27, S28, F29, S30, A31, Y32, Y33, E50, N52, H53, R56, D58, K76, G98, Q99, L100, and V101; Light Chain: S31, N32, T33, Y50, S51, N52, N53, Q54, W92, and D94. Boundary 31A4 amino acid residues of the interaction interface with PCSK9 were defined as 31A4 residues that are 5-8 Å from the PCSK9 protein. The boundary residues for 31A4 are as follows: Heavy Chain: V2, G26, W34, N35, W47, I151, S54, T57, Y59, A96, R97, P102, F103, and D104; Light Chain: S26, S27, N28, G30, V34, N35, R55, P56, K67, V91, D93, S95, N97, G98, and W99.

The crystal structure also displayed the spatial requirements of this ABP in its interaction with PCSK9. As shown in this structure, surprisingly, antibodies that bind to PCSK9 without directly preventing PCSK9's interaction with the LDLR can still inhibit PCSK9's function.

In some embodiments, any antigen binding protein that binds to, covers, or prevents 31A4 from interacting with any of the above residues can be employed to bind to or neutralize PCSK9. In some embodiments, the ABP binds to or interacts with at least one of the following PCSK9 (SEQ ID NO: 3) residues: T468, R469, M470, A471, T472, R496, R499, E501, A502, Q503, R510, H512, F515, P540, P541, A542, E543, H565, W566, E567, V568, E569, R592, and E593. In some embodiments, the ABP is within 5 angstroms of one or more of the above residues. In some embodiments, the ABP binds to or interacts with at least one of the following PCSK9 (SEQ ID NO: 3) residues: 5465, G466, P467, A473, I474, R476, <u>G497</u>, <u>E498</u>, M500, G504, K506, L507, V508, <u>A511</u>, <u>N513</u>, A514, G516, V536, T538, A539, A544, T548, D570, L571, H591, A594, 5595, and H597. In some embodiments, the ABP is 5 to 8 angstroms from one or more of the above residues. In some embodiments, the ABP interacts, blocks, or is within 8 angstroms of 1, 2, 3, 4, 5, 6, 7, 8, 9, 10, 11, 12, 13, 14, 15, 20, 25, 30, 35, 40, 45, or 50 of the above residues.

The coordinates for the crystal structures discussed in the above Examples are are presented in Table 35.1 (full length PCSK9 and 31H4), Table 35.2 (PCSK9 and EGFa), Table 35.3 (PCSK9, 31H4, and 21B12), and Table 35.4 (PCSK9 and 31A4). Antigen binding proteins and molecules that interact with the relevant areas or residues of the structure of PCSK9 (including those areas or residues within 15, 15-8,8,8-5, 5, or fewer angstroms from where EGFa, or the antibodies, interact with PCSK9) depicted in the figures and/or their corresponding positions on the structures from the coordinates are also contemplated.

The antibodies that are described in the coordinates were raised in *E. coli* and thus possess some minor amino acid differences from the fully human antibodies. The first residue in the variable region was a glutamic acid instead of a glutamine for the heavy and light chains of 21B12 and for the light chain for 31H4. In addition to the differences in the sequence of variable region, there were also some differences in the constant region of the antibodies described by the coordinates (again due to the fact that the antibody was raised in *E. coli*). FIG. 22 highlights (via underlining shading, or bold) the differences between the constant regions of the 21B12, 31H4, and 31A4 Fabs (raised in *E. coli*) when compared to SEQ ID NOs: 156, and 155. For 21B12 31H4, and 31A4, the light chain constant sequence is similar to human lambda (SEQ ID NO: 156). The underlined glycine residue is an insertion between where the 21B12 and 31H4 variable sequences stop and the lambda sequence starts.

For both 21B12 and 31H4, the heavy chain constant is similar to human IgG4 (SEQ ID NO: 155). The highlighted differences in FIG. 22 are shown in Table 36.1:

TABLE 36.1

Crystal SEQ ID NO: 155

| | |
|---|---|
| S | C |
| K | R |
| G | E |
| G | S |
| Q | K |
| I | T |
| N | D |
| K | R |
| P | S |

In regard to 31A4, while it also has the same distinctions noted above, there are three additional differences. As shown in FIG. 22, there are two additional amino acids at the start, which comes from incomplete processing of the signal peptide in *E. coli* expression. In addition, there is one additional substitution in the 31A4 heavy chain constant region when compared to SEQ ID NO: 155, which is the adjustment of a L (in SEQ ID NO: 155) to a H. Finally, 31A4 does have a glutamine as the initial amino acid of the Fab, rather than the adjustment to glutamic acid noted above for 21B12 and 31H4.

For all three antibodies, the end of the heavy chain (boxed in dark grey) differs as well, but the amino acids are not ordered in the structure so they do not appear in the coordinates. As will be appreciated by one of skill in the art, his-tags are not a required part of the ABP and should not be considered as part of the ABP's sequence, unless explicitly called out by reference to a specific SEQ ID NO that includes a histidine tag and a statement that the ABP sequence "includes the Histidine tag."

Example 37

Epitope Mapping—Binning

An alternative set of binning experiments was conducted in addition to the set in Example 10. As in Example 10, ABPs that compete with each other can be thought of as binding to the same site on the target and in common parlance are said to "bin" together.

A modification of the Multiplexed Binning method described by Jia, et al (J. Immunological Methods, 288 (2004) 91-98) was used. Individual bead codes of streptavidin-coated Luminex beads was incubated in 100 ul 0.5 ug/ml biotinylated monovalent mouse-anti-human IgG capture antibody (BD Pharmingen, #555785) for 1 hour at room temperature in the dark, then washed 3× with PBSA, phosphate buffered saline (PBS) plus 1% bovine serum albumin (BSA). Each bead code was separately incubated with 100 ul 2 ug/ml anti-PCSK9 antibody (Coating Antibody) for 1 hour then washed 3× with PBSA. The beads were pooled then dispensed to a 96-well filter plate (Millipore, #MSBVN1250). 100 ul of 2 ug/ml purified PCSK9 protein was added to half the wells. Buffer was added to the other half as control. The reaction was incubated for 1 hour then washed. 100 ul of a 2 ug/ml anti-PCSK9 antibody (Detection Ab) was added to all the wells, incubated for 1 hour then washed. An irrelevant human-IgG (Jackson, #009-000-003) was run as another control. 20 ul PE-conjugated monovalent mouse-anti-human IgG (BD Pharmingen, #555787) was added to each well and incubated for 1 hour then washed. Beads were resuspended in 100 ul PBSA and a minimum of 100 events/bead code were collected on the BioPlex instrument (BioRad).

Median Fluorescent Intensity (MFI) of the antibody pair without PCSK9 was subtracted from signal of the corresponding reaction containing PCSK9. For the antibody pair to be considered bound simultaneously, and therefore in different bins, the subtracted signal had to be greater than 3 times the signal of the antibody competing with itself and the 3 times the signal of the antibody competing with the irrelevant antibody.

The data from the above is depicted in FIGS. 23A-23D. The ABPs fell into five bins. The shaded boxes indicate ABPs that can bind simultaneously to PCSK9. The nonshaded boxes indicate those ABPs that compete with each other for binding. A summary of the results is shown in Table 37.1.

TABLE 37.1

| BIN 1 | BIN 2 | BIN 3 | BIN 4 | BIN 5 |
|---|---|---|---|---|
| 01A12.2 | 27B2.1 | 16F12.1 | 11G1.5 | 30A4.1 |
| 03B6.1 | 27B2.5 | 22E2.1 | 03C4.1 | 13B5.1 |
| 09C9.1 | 12H11.1 | 27A6.1 | | 13H1.1 |
| 17C2.1 | | 28B12.1 | | 31A4.1 |
| 21B12.2 | | 28D6.1 | | 31B12.1 |
| 23G1.1 | | 31G11.1 | | |
| 25G4.1 | | 31H4.1 | | |
| 26E10.1 | | 08A1.2 | | |
| 11H4.1 | | 08A3.1 | | |
| 11H8.1 | | 11F1.1 | | |
| 19H9.2 | | | | |
| 26H5.1 | | | | |
| 27E7.1 | | | | |
| 27H5.1 | | | | |
| 30B9.1 | | | | |
| 02B5.1 | | | | |
| 23B5.1 | | | | |
| 27B2.6 | | | | |
| 09H6.1 | | | | |

Bins 1 (competes with ABP 21B12) and 3 (competes with 31H4) are exclusive of each other; bin 2 competes with bins 1 and 3; and Bin 4 does not compete with bins 1 and 3. Bin 5, in this example, is presented as a "catch all" bin to describe those ABPs that do not fit into the other bins. Thus, the above identified ABPs in each of the binds are representative of different types of epitope locations on PCSK9, some of which overlap with each other.

As will be appreciated by one of skill in the art, if the reference ABP prevents the binding of the probe ABP then the antibodies are said to be in the same bin. The order in which the ABPs are employed can be important. If ABP A is employed as the reference ABP and blocks the binding of ABP B the converse is not always true: ABP B used as the reference ABP will not necessarily block ABP A. There are a number of factors in play here: the binding of an ABP can cause conformational changes in the target which prevent the binding of the second ABP, or epitopes which overlap but do not completely occlude each other may allow for the second ABP to still have enough high-affinity interactions with the target to allow binding. ABPs with a much higher affinity may have a greater ability to bump a blocking ABP out of the way. In general, if competition is observed in either order the ABPs are said to bin together, and if both ABPs can block each other then it is likely that the epitopes overlap more completely.

Example 38

Epitope Mapping—Western Blot

The present example demonstrates whether or not the epitopes for the examined ABPs were linear or conformational. Denaturing reducing and denaturing non-reducing western blots were run to determine which antibodies have a conformational epitope. Antibodies that bind to a denaturing reducing western blot have a linear epitope and are not conformational. The results are presented in FIG. 24A and FIG. 24B. For the blot, 0.5 ug/lane of purified full-length human PCSK9 was run on a 4-12% NuPAGE Bis-Tris gel and MES SDS Running Buffer. 1 ug/ml anti-PCSK9 antibodies, except 0.5 ug/ml 31G11, were used to probe the blot. 1:5000 donkey-anti-human-IR700 secondary was used and read on a LiCOR instrument. Antibody 13H1 bound to a linear epitope on the pro-domain of PCSK9. All other antibodies displayed results that were consistent with conformational epitopes. These gels split apart the pro-domain from the rest of the protein, and the pro domain ran at about 15 kDa. In addition, 3C4 and 31A4 appeared to bind to conformational epitopes which were preserved by disulfide bonds, as these antibodies bound to PCSK-9 under denaturing conditions where the disulfide bonds had been preserved (left) but reducing the samples (right) eliminated binding.

Example 39

Epitope Mapping—Arginine/Glutamic Acid Scanning

Representative ABPs from each bin (from Example 37) were selected for further epitope analysis. An arginine/glutamic acid-scanning strategy was performed for mapping ABP binding to PCSK9. By way of background, this method determines if a residue is part of the structural epitope, meaning those residues in the antigen which contact or are buried by the antibody. Arginine and glutamic acid sidechains are charged and bulky and can disrupt antibody binding even if the mutated residue is not directly involved in antibody binding.

Residue Selection

The crystal structure of PCSK9 was used to select the residues to be mutated for epitope mapping. The method used to choose residues to mutate involved both computational mechanisms and interactive structure analysis. The PCSK9 structure contained gaps of missing residues and was missing 30 amino acids in the N- (i.e., the signal sequence) and 10 amino acids in the C-termini. The internal missing residues were modeled onto the structure, but the N- and C-terminal missing residues were not. The solvent exposure ratio for each residue was calculated: the surface area of each residue in the context of the protein (SA1) was divided by the surface area of the residue in a trimer with flanking glycines (SA2) with a conserved backbone structure. Residues with solvent exposure ratio greater than 10% (R10) were selected as well as the 40 missing terminal residues. From these, prolines and glycines with positive Φ angles were excluded to reduce the possibility of misfolding. The number of residues to be mutated in the V domain was reduced by using a solvent exposure ratio of 37% along with visual inspection of the entire protein to bring the total number of mutations to 285. Various orientations of the surface of PCSK9 with these various classes identifies are shown in FIG. 25A-25F. In these figures, lightest gray denotes areas that were not selected or were deselected darker gray denotes those residues selected).

Cloning and Expression

Once the residues to be altered were identified, the various residues were altered. Human PCSK9 was cloned into the pTT5 vector with a C-terminal Flag-His tag. Mutants were made from this original construct by site-directed mutagenesis using a QuikChange II kit from Stratagene. Sense and anti-sense oligonucleotides used for mutagenesis were designed using Amgen's MutaGenie software. All PCSK9 constructs were expressed in transiently-transfected 293-6E cells in 24-well plates and re-racked into three 96-well plates with a non-mutated PCSK9 control (wild-type, WT) in each plate. Expression levels and integrity of the recombinant proteins in conditioned media were checked by Western blot. Of the 285 mutants originally selected, 41 failed in cloning or expression. 244 mutants were used for epitope mapping. An alignment of the PCSK9 parent sequence and a representative PCSK9 sequence with the 244 mutated residues is shown in FIG. 26. Separate constructs were made containing a single mutation. For the purposes of the epitope sequences and the epitope based inventions involving changes in binding, the sequences are provided in reference to SEQ ID NO: 1 and/or SEQ ID NO: 303. The sequences in FIG. 26 were the sequences used for the present binding epitope studies. One of skill in the art will appreciate that the present results apply to other PCSK9 variants disclosed herein as well (e.g., SEQ ID NO: 1 and 3, as well as the other allelic variants).

Five antibodies, a representative of each bin, were chosen for fine epitope mapping. They were 21B12, 31H4, 12H11, 31A4, 3C4. All conformational epitope antibodies. Three, 21B12, 31H4, and 31A4 were also crystallized with PCSK9, as described above.

Structural and Functional Epitopes

Epitopes can be further defined as structural or functional. Functional epitopes are generally a subset of the structural epitopes and have those residues that directly contribute to the affinity of the interaction (e.g. hydrogen bonds, ionic interactions). Structural epitopes can be thought of as the patch of the target which is covered by the antibody.

The scanning mutagenesis employed was an arginine and glutamic acid scan. These two sidechains were chosen due to their large steric bulk and their charge, which allows mutations that occur in the structural epitope to have a greater effect on antibody binding. Arginine was generally employed except when the WT reside was arginine, and in these cases the residue was mutated to glutamic acid to switch the charge.

For the purpose of epitope mapping, a bead-based multiplexed assay was used to measure antibody binding to PCSK9 and PCSK9 mutants simultaneously. Antibody binding to mutants was then compared to its binding to the wild-type in the same well. The variants were split into three groups: Group 1: 81 variants+2 wt controls+1 negative control+1 other PCSK9 supernatant; Group 2: 81 variants+2 wt controls+2 negative controls; and Group 3: 82 variants+2 wt control+1 negative control.

The assay was run as follows: 85 sets of color-coded strepavidin-coated LumAvidin beads (Luminex) were bound with biotinylated anti-pentaHis antibody (Qiagen, #1019225) for 1 hour at room temperature (RT) then washed three times in PBS, 1% BSA, 0.1% Tween 20. Each color-coded bead set was then allowed to bind to a PCSK9 mutant, wild-type, or negative control in 150 ul supernatant overnight at 4° C.

The color-coded bead sets, each associated to a specific protein, were washed and pooled. At this point, there were 3 pools of 85 bead sets, one pool for each group of mutants and controls. The beads from each pool were aliquoted to 24 wells (3 columns) of a 96-well filter plate (Millipore, #MSBVN1250). 100 ul of anti-PCSK9 antibodies in 4-fold dilutions were added to nine columns for triplicate points and incubated for 1 hour at RT and washed. 100 ul of 1:200 dilution phycoerythrin (PE)-conjugated anti-human IgG Fc (Jackson Immunoresearch, #109-116-170) was added to each well and incubated for 1 hour at RT and washed.

Beads were resuspended in 1% BSA in PBS, shaken for 10 mins and read on the BioPlex instrument (Bio-Rad). The instrument identifies each bead by its color-code thereby identifying the specific protein associated with the color code. At the same time, it measures the amount of antibody bound to the beads by fluorescence intensity of the PE dye. Antibody binding to each mutant can then be compared directly its binding to the wild type in the same pool. IL-17R chimera E was used as a negative control. A summary of all of the mutants examined is shown in Table 39.1 (with reference to the sequence numbering used in FIGS. 1A and 26).

A four-parameter logistic model was fitted to the binding data for each bead region. The resulting file, containing curve quality control (QC) results and parameter estimates for top (max), bottom (min), Hillslope (slope), and natural log of EC50 (xmid) of the curves, was used as the raw data for the analysis. B-B variability for each parameter was then estimated by fitting mixed effect model using SAS PROC MIXED procedure. Only curves with "good" QC status were included in the analysis. The final mixed effect model included only residual (i.e. individual bead regions) as random effect. Least squares means (LS-mean) for each parameter were estimated by the mixed effect model as well. B-B SD was calculated by taking square root of B-B variance. Fold change between LS-mean+2SD and LS-mean−2SD, which represent approximately upper and lower 97.5 percentile of the population, was also calculated. The results are displayed in Table 39.2

TABLE 39.1

| | 1 | 2 | 3 | 4 | 5 | 6 | 7 | 8 | 9 | 10 | 11 | 12 |
|---|---|---|---|---|---|---|---|---|---|---|---|---|
| A | WT PCSK9 | Y8R | E18R | P26R | A38R | T56R | A70R | H83R | E102R | L128R | D145R | |
| B | Q1R | E9R | E19R | E27R | K39R | H57R | Q71R | V84R | L105R | E129R | S148R | |
| C | E2R | E10R | D20R | G29R | D40R | L58R | A73R | H86R | K106R | R130E | pcsk9 supe test | |
| D | D3R | L11R | G21R | T30R | L44R | Q60R | R74E | K95R | H109R | T132R | IL17R chimera E | |
| E | E4R | V12R | L22R | T31R | T47R | E62R | R75E | S97R | D111R | D139R | WT PCSK9 | |
| F | D5R | A14R | A23R | A32R | K53R | R63E | Y77R | G98R | A121R | E140R | | |
| G | G6R | L15R | E24R | T33R | E54R | R66E | L78R | D99R | S123R | Y141R | | |
| H | D7R | S17R | A25R | H35R | E55R | R67E | L82R | L101R | W126R | Q142R | | |

| | 1 | 2 | 3 | 4 | 5 | 6 | 7 | 8 | 9 | 10 | 11 | 12 |
|---|---|---|---|---|---|---|---|---|---|---|---|---|
| A | WT PCSK9 | M171R | E181R | Q189R | K213R | R242E | G251R | L294R | L321R | Q352R | E380R | |
| B | L149R | V172R | D182R | A190R | G214R | K243R | G262R | A311R | E336R | M368R | R384E | |
| C | S158R | T173R | G183R | S191R | S216R | S244R | R265E | Q312R | D336R | S371R | IL17R chimera E | |
| D | Q160R | D174R | T184R | K192R | R221E | Q245R | A269R | D313R | D344R | A372R | IL17R chimera E | |
| E | S161R | E176R | R185E | S195R | Q226R | L246R | Q272R | Q314R | T347R | E373R | WT PCSK9 | |
| F | D162R | N177R | F186R | H196R | K228R | V247R | R276E | T317R | F349R | E375R | | |
| G | R164E | V178R | H187R | R207E | T230R | Q248R | A277R | L318R | V350R | T377R | | |
| H | E167R | E180R | R188E | D208R | F240R | V250R | R289E | T320R | S351R | L378R | | |

| | 1 | 2 | 3 | 4 | 5 | 6 | 7 | 8 | 9 | 10 | 11 | 12 |
|---|---|---|---|---|---|---|---|---|---|---|---|---|
| A | WT PCSK9 | N395R | V405R | W423R | R446E | E513R | Q525R | Q554R | Q589R | S632R | A641R | |
| B | I386R | E396R | N409R | Q424R | D450R | A514R | E537R | N556R | Q591R | T633R | R650E | |
| C | H387R | A397R | A413R | A433R | A472R | S515R | V538R | K579R | A595R | T634R | R652E | |
| D | F388R | W398R | S417R | H434R | F485R | M516R | E539R | V580R | E597R | G635R | IL17R chimera E | |
| E | A390R | E401R | T418R | T438R | G486R | R519E | L541R | K581R | E598R | S636R | WT PCSK9 | |
| F | K391R | D402R | H419R | R439E | E488R | H521R | H544R | E582R | V620R | T637R | | |
| G | D392R | Q403R | G420R | M440R | N503R | H523R | V548R | H583R | R629E | S638R | | |
| H | V393R | R404E | A421R | T442R | T508R | Q524R | R552E | G584R | V631R | E639R | | |

Bead Variability Study

Before running the epitope mapping binding assay, a validation experiment was conducted to assess the "bead region" to "bead region" (B-B) variability. In the validation experiment, all beads were conjugated with the same wild type control protein. Therefore, the difference between beads regions was due to purely B-B variance and was not confounded by difference between wild type and mutant proteins. The titration of antibody was run with twelve replications in different wells.

The objective of this statistical analysis was to estimate the B-B variability of the estimated EC50 of binding curves. The estimated B-B standard deviation (SD) was then used to build the EC50 confidence intervals of wild type and mutant proteins during curve comparison experiments.

TABLE 39.2

Least square mean and bead-to-bead variance estimations

| Assay ID | parname | Ls Mean | B-B Variance | −2SD | +2SD | Fold Change* |
|---|---|---|---|---|---|---|
| PCSK9 | max | 15000 | 997719 | 13002.3 | 16997.7 | 1.3 |
| PCSK9 | min | 162.09 | 1919.66 | 74.5 | 249.7 | 3.4 |
| PCSK9 | slope | 0.8549 | 0.000599 | 0.8 | 0.9 | 1.1 |
| PCSK9 | xmid | 3.1715 | 0.002098 | 3.1 | 3.3 | 1.2 |

*xmid is natural log of the EC50. Fold change for mind was converted back to original scale.

Identifying Residues in the Structural Epitope

A residue was considered part of the structural epitope (a "hit") when mutating it to arginine or glutamic acid alters antibody binding. This is seen as a shift in the EC50 or a reduction of maximum signal compared to antibody binding to wild type. Statistical analyses of antibody binding curves to wild type and mutants were used to identify statistically significant EC50 shifts. The analysis takes into consideration variation in the assay and curve fitting.

Hit Identification Based on EC50 Comparison

The EC50 and Bmax values were generated from a Weighted 4-Parameter Logistical model fitted to the binding data using S-PLUS with VarPower software (Insightful Corporation, Seattle Wash.). The EC50s of the mutant binding curves and wild type binding curves were compared. Statistically significant differences were identified as hits for further consideration. The curves with "nofit" or "badfit" flags were excluded from the analysis.

The Variations in EC50 Estimates

Two sources of variations were considered in the comparison of EC50 estimates, variation from the curve fit and the bead-bead variation. Wild types and mutants were linked to different beads, hence their difference are confounded with the bead-bead difference (described above). The curve fit variation was estimated by the standard error of the log EC50 estimates. Bead-bead variation was experimentally determined using an experiment where wild type controls were linked to each one of the beads (described above). The bead variation in EC50 estimates of wild type binding curve from this experiment was used to estimate the bead-bead variation in the actual epitope mapping experiment.

Testing for EC50 Shift Between Mutants and Wild Type

The comparisons of two EC50s (in log scale) was conducted using Student's t-test. The t-statistic was calculated as the ratio between delta (the absolute differences between EC50 estimates) and the standard deviation of delta. The variance of delta was estimated by the sum, of the three components, variance estimate of EC50 for mutant and wild type curves in the nonlinear regression and two times the bead-bead variance estimated from a separate experiment. The multiple of two for the bead-bead variance was due to the assumption that both mutant and wild type beads had the same variance. The degree of freedom of the standard deviation of delta was calculated using the Satterthwaite's (1946) approximation. Individual p-values and confidence intervals (95% and 99%) were derived based on Student's t distribution for each comparison. In the case of multiple wild type controls, a conservative approach was taken by picking the wild type control that was most similar to the mutant, i.e., picking the ones with the largest p-values.

Multiplicity adjustments were important to control the false positive(s) while conducting a large number of tests simultaneously. Two forms of multiplicity adjustment were implemented for this analysis: family wise error (FWE) control and false discovery rate (FDR) control. The FWE approach controls the probability that one or more hits are not real; FDR approach controls the expected proportion of false positive among the selected hits. The former approach is more conservative and less powerful than the latter one. There are many methods available for both approaches, for this analysis, the Hochberg's (1988) method for FWE analysis and Benjamini-Hochberg's (1995) FDR method for FDR analysis were selected. Adjusted p-values for both approaches were calculated.

Results

EC50 Shift

Mutations whose EC50 is significantly different from wild type, e.g., having a False Discovery Rate adjusted p-value for the whole assay of 0.01 or less, were considered part of the structural epitope. All the hits also had a Familywise type I error rate adjusted p-value for each antibody of less than 0.01 except residue R185E for antibody 31H4 which had an FWE adjusted p-value per antibody of 0.0109. The residues in the structural epitope of the various antibodies determined by EC50 shift are shown in Table 39.3 (point mutations are with reference to SEQ ID NO: 1 and 303)

TABLE 39.3

| Antibody | Mutation | FDR Adjusted Pval | FWE Adjusted By Pval | Low99 | Low95 | FoldChange | High95 | High99 | RawPval |
|---|---|---|---|---|---|---|---|---|---|
| 21B12 | D208R | 0.0000 | 0.0000 | 0.3628 | 0.3844 | 0.4602 | 0.5509 | 0.5837 | 0.0000 |
| 21B12 | R207E | 0.0000 | 0.0000 | 1.7148 | 1.8488 | 2.3191 | 2.9090 | 3.1364 | 0.0000 |
| 31H4 | R185E | 0.0024 | 0.0109 | 1.2444 | 1.3525 | 1.7421 | 2.2439 | 2.4388 | 0.0000 |
| 31A4 | E513R | 0.0001 | 0.0003 | 1.4764 | 1.6219 | 2.1560 | 2.8660 | 3.1485 | 0.0000 |
| 31A4 | E539R | 0.0000 | 0.0000 | 1.6014 | 1.7461 | 2.2726 | 2.9578 | 3.2252 | 0.0000 |
| 31A4 | R439E | 0.0000 | 0.0000 | 3.1565 | 3.6501 | 5.5738 | 8.5113 | 9.8420 | 0.0000 |
| 31A4 | V538R | 0.0004 | 0.0013 | 1.4225 | 1.5700 | 2.1142 | 2.8471 | 3.1423 | 0.0000 |
| 12H11 | A390R | 0.0000 | 0.0001 | 1.4140 | 1.5286 | 1.9389 | 2.4594 | 2.6588 | 0.0000 |
| 12H11 | A413R | 0.0009 | 0.0028 | 1.2840 | 1.3891 | 1.7653 | 2.2434 | 2.4269 | 0.0000 |
| 12H11 | S351R | 0.0009 | 0.0028 | 1.2513 | 1.3444 | 1.6761 | 2.0896 | 2.2452 | 0.0000 |
| 12H11 | T132R | 0.0000 | 0.0001 | 1.3476 | 1.4392 | 1.7631 | 2.1599 | 2.3068 | 0.0000 |
| 3C4 | E582R | 0.0016 | 0.0069 | 1.3523 | 1.5025 | 2.0642 | 2.8359 | 3.1509 | 0.0000 |

Maximum Signal Reduction

The percent maximum signal was calculated using the maximum signal from the curve fitting (BmaxPerWT) and raw data point (RawMaxPerWT). Mutations that reduced the antibody binding maximum signal by ≥70% as compared to to wild type signal or that reduced the signal of one antibody compared to other antibodies by >50% when all other antibodies are at least 40% of wild type were considered hits and part of the epitope. Table 39.4 displays the residues that are in the structural epitope (italics) as determined by reduction of maximum signal.

TABLE 39.4

| antibody | Mutants | BmaxPerWT | RawMaxPerWT |
|---|---|---|---|
| 21B12 | A311 R | 141.6388 | 139.7010 |
| 31H4 | A311 R | 145.2189 | 147.8244 |
| 31A4 | A311R | 103.4377 | 96.2214 |
| *12H11* | *A311R* | | *14.9600* |
| 3C4 | A311R | 129.0460 | 131.2060 |
| *21B12* | *D162R* | | *7.0520* |
| 31H4 | D162R | 108.8308 | 112.4904 |
| 31A4 | D162R | 98.8873 | 95.9268 |
| 12H11 | D162R | 94.6280 | 97.4928 |
| 3C4 | D162R | 101.4281 | 100.1586 |
| 21B12 | D313R | 45.8356 | 45.0011 |

TABLE 39.4-continued

| antibody | Mutants | BmaxPerWT | RawMaxPerWT |
|---|---|---|---|
| 31H4 | D313R | 45.6242 | 44.9706 |
| 31A4 | D313R | 47.9728 | 44.7741 |
| *12H11* | *D313R* | *16.1811* | *18.4262* |
| 3C4 | D313R | 58.5269 | 57.6032 |
| 21B12 | D337R | 61.9070 | 62.2852 |
| 31H4 | D337R | 63.1604 | 64.1029 |
| 31A4 | D337R | 62.9124 | 59.4852 |
| *12H11* | *D337R* |  | *10.8443* |
| 3C4 | D337R | 73.0326 | 73.9961 |
| *21B12* | *E129R* | *139.9772* | *138.9671* |
| 31H4 | E129R | 141.6792 | 139.1764 |
| 31A4 | E129R | 77.3005 | 74.8946 |
| *12H11* | *E129R* | *28.6398* | *29.3751* |
| 3C4 | E129R | 85.7701 | 85.7802 |
| *21B12* | *E167R* |  | *15.1082* |
| 31H4 | E167R | 127.4479 | 128.2698 |
| 31A4 | E167R | 115.3403 | 112.6951 |
| 12H11 | E167R | 111.0979 | 109.6813 |
| 3C4 | E167R | 109.3223 | 108.7864 |
| 21B12 | H521R | 133.8480 | 133.9791 |
| 31H4 | H521R | 130.2068 | 128.4879 |
| 31A4 | H521R | 124.5091 | 129.3218 |
| 12H11 | H521R | 130.7979 | 134.4355 |
| *3C4* | *H521R* |  | *22.1077* |
| 21B12 | Q554R | 125.9594 | 125.2103 |
| 31H4 | Q554R | 122.2045 | 128.7304 |
| 31A4 | Q554R | 113.6769 | 121.3369 |
| 12H11 | Q554R | 116.1789 | 118.4170 |
| 3C4 | Q554R |  | 31.8416 |
| *21B12* | *R164E* | *17.3807* | *19.8505* |
| 31 H4 | R164E | 97.8218 | 99.6673 |
| 31A4 | R164E | 98.2595 | 96.3352 |
| 12H11 | R164E | 88.0067 | 89.8807 |
| 3C4 | R164E | 105.0589 | 105.7286 |
| 31B12 | R519E | 139.4598 | 141.2949 |
| 31H4 | R519E | 135.5609 | 140.0000 |
| 31A4 | R519E | 134.2303 | 137.1110 |
| 12H11 | R519E | 135.4755 | 137.0824 |
| *3C4* | *R519E* |  | *44.0091* |
| 21 B12 | S123R | 87.6431 | 88.1356 |
| 31H4 | S123R | 85.5312 | 84.7668 |
| 31A4 | S123R | 68.4371 | 66.6131 |
| *12H11* | *S123R* | *20.8560* | *20.6910* |
| 3C4 | S123R | 73.6475 | 71.5959 |

(Point mutations are with reference to SEQ ID NO: 1 and FIG. 26).

Table 39.5 displays a summary of all of the hits for the various antibodies.

TABLE 39.5

| EC50 shift hits | | | | | Bmax shift hits | | | | |
|---|---|---|---|---|---|---|---|---|---|
| 21B12 | 31H4 | 31A4 | 12H11 | 3C4 | 21B12 | 31H4 | 31A4 | 12H11 | 3C4 |
| R207E | R185E | R439E | T132R | E582R | D162R |  |  | S123R | R519E |
| D208R* |  | E513R | S351R |  | R164E |  |  | E129R | H521R |
|  |  | V538R | A390R |  | E167R |  |  | A311R | Q554R |
|  |  | E539R | A413R |  |  |  |  | D313R |  |
|  |  |  |  |  |  |  |  | D337R |  |

*decreases EC50

To further examine how these residues form part of or all of the relevant epitopes, the above noted positions were mapped onto various crystal structure models, the results are shown in FIG. 27A through 27E. FIG. 27A depicts the 21B12 epitope hits, as mapped onto a crystal structure of PCSK9 with the 21B12 antibody. The structure identifies PCSK9 residues as follows: light gray indicates those residues that were not mutated (with the exception of those residues that are explicitly indicated on the structure) and darker gray indicates those residues mutated (a minority of which failed to express). Residues that are explicitly indicated were tested (regardless of the shading indicated on the figure) and resulted in a significant change in EC50 and/or Bmax The epitope hits were based on Bmax shift. In this figure, 31H4 is behind 21 B12.

FIG. 27B depicts the 31H4 epitope hits, as mapped onto a crystal structure of PCSK9 with 31H4 and 21B12 antibodies. The structure identifies PCSK9 residues as follows: light gray indicates those residues that were not mutated (with the exception of those residues that are explicitly indicated on the structure) and darker gray indicates those residues mutated (a minority of which failed to express). Residues that are explicitly indicated were tested (regardless of the shading indicated on the figure) and resulted in a significant change in EC50 and/or Bmax. The epitope hits were based on the EC50 shift.

FIG. 27C depicts the 31A4 epitope hits, as mapped onto a crystal structure of PCSK9 with 31H4 and 21B12 antibodies. The structure identifies PCSK9 residues as follows: light gray indicates those residues that were not mutated (with the exception of those residues that are explicitly indicated on the structure) and darker gray indicates those residues mutated (a minority of which failed to express). Residues that are explicitly indicated were tested (regardless of the shading indicated on the figure) and resulted in a significant change in EC50 and/or Bmax. The epitope hits were based on the EC50 shift. 31A4 antibody is known to bind to the V-domain of PCSK9, which appears consistent with the results presented in FIG. 27C.

FIG. 27D depicts the 12H11 epitope hits, as mapped onto the crystal structure of PCSK9 with 31H4 and 21B12 antibodies. The structure identifies PCSK9 residues as follows: light gray indicates those residues that were not mutated (with the exception of those residues that are explicitly indicated on the structure) and darker gray indicates those residues mutated (a minority of which failed to express). Residues that are explicitly indicated were tested (regardless of the shading indicated on the figure) and resulted in a significant change in EC50 and/or Bmax. 12H11 competes with 21B12 and 31H4 in the binning assay described above.

FIG. 27E depicts the 3C4 epitope hits, as mapped onto the crystal structure of PCSK9 with 31H4 and 21B12 antibodies. The structure identifies PCSK9 residues as follows: light gray indicates those residues that were not mutated (with the exception of those residues that are explicitly indicated on the structure) and darker gray indicates those residues mutated (a minority of which failed to express). Residues that are explicitly indicated were tested (regardless of the shading indicated on the figure) and resulted in a significant change in EC50 and/or Bmax.

3C4 does not compete with 21B12 and 31H4 in the binning assay. 3C4 binds to the V-domain in the domain binding assay (see results from Example 40, FIGS. 28A and 28B).

While there were approximately a dozen mutants that could have been expected to have an effect on binding (based upon the crystal structure), the present experiment demonstrated that, surprisingly, they did not. As will be appreciated by one of skill in the art, the results presented above are in good agreement with the crystal structures and PCSK-9's binding of these antibodies. This demonstrates that the provided structural and corresponding functional data adequately identifies the key residues and areas of interaction of the neutralizing ABPs and PCSK9. Thus, variants of the ABPs that possess the ability to bind to the above noted areas are adequately provided by the present description.

As will be appreciated by one of skill in the art, while the B-max drop and EC50 shift hits can be considered manifestations of the same phenomenon, strictly speaking, a B-max drop alone does not reflect a loss of affinity per se but, rather, the destruction of some percentage of the epitope of an antibody. Although there is no overlap in the hits determined by B-max and EC50, mutations with a strong affect on binding may not allow for the generation of a useful binding curve and hence, no EC50 can be determined for such variants.

As will be appreciated by one of skill in the art, ABPs in the same bin (with the exception of bin 5, which as noted above, is a general catch all bin) likely bind to overlapping sites on the target protein. As such, the above epitopes and relevant residues can generally be extended to all such ABPs in the same bin.

To further examine the above results in regard to ABP 31H4, position E1 81R, which, according to the above crystal structure, was predicted to interact with R185 to form part of the surface that interacts with the ABP, was also altered (E1 81R). The results, while not statistically significant on their own, were, when combined with the crystal structure, demonstrative of 31H4 interacting with E1 81R (data not shown). Thus, position 181 also appears to form part of the epitope for the 31H4 ABP.

As noted above, the above binding data and epitope characterization references a PCSK9 sequence (SEQ ID NO: 1) that does not include the first 30 amino acids of PCSK9. Thus, the numbering system of this protein fragment, and the SEQ ID NO:s that refer to this fragment, are shifted by 30 amino acids compared to the data and experiments that used a full length PCSK9 numbering system (such as that used in the crystal study data described above). Thus, to compare these results, an extra 30 amino acids should be added to the positions in each of the above epitope mapping results. For example, position 207 of SEQ ID NO: 1 (or SEQ ID NO: 303), correlates to position 237 of SEQ ID NO: 3 (the full length sequence, and the numbering system used throughout the rest of the specification). Table 39.6 outlines how the above noted positions, which reference SEQ ID NO: 1 (and/or SEQ ID NO: 303) correlate with SEQ ID NO: 3 (which includes the signal sequence).

TABLE 39.6

| AMINO ACID POSITION IN SEQ ID NO: 1 (EPITOPE DATA) | AMINO ACID POSITION IN SEQ ID NO: 3 (EPITOPE DATA) |
|---|---|
| 207 | 237 |
| 208 | 238 |
| 185 | 215 |
| 181 | 211 |
| 439 | 469 |
| 513 | 543 |
| 538 | 568 |
| 539 | 569 |
| 132 | 162 |
| 351 | 381 |
| 390 | 420 |

TABLE 39.6-continued

| AMINO ACID POSITION IN SEQ ID NO: 1 (EPITOPE DATA) | AMINO ACID POSITION IN SEQ ID NO: 3 (EPITOPE DATA) |
|---|---|
| 413 | 443 |
| 582 | 612 |
| 162 | 192 |
| 164 | 194 |
| 167 | 197 |
| 123 | 153 |
| 129 | 159 |
| 311 | 341 |
| 313 | 343 |
| 337 | 367 |
| 519 | 549 |
| 521 | 551 |
| 554 | 584 |

Thus, those embodiments described herein with reference to SEQ ID NO: 1 can also be described, by their above noted corresponding position with reference to SEQ ID NO: 3.

Example 40

PCSK9 Domain Binding Assay

The present example examined where on PCSK9 the various ABPs bound.

Clear, 96 well maxisorp plates (Nunc) were coated overnight with 2 ug/ml of various anti-PCSK9 antibodies diluted in PBS. Plates were washed thoroughly with PBS/0.05% Tween-20 and then blocked for two hours with 3% BSA/PBS. After washing, plates were incubated for two hours with either full length PCSK9 (aa 31-692 SEQ ID NO: 3), procat PCSK9 (aa 31-449 SEQ ID NO: 3) or v-domain PCSK9 (aa 450-692 of SEQ ID NO: 3) diluted in general assay diluent (Immunochemistry Technologies, LLC). Plates were washed and a rabbit polyclonal biotinylated anti-PCSK9 antibody (D8774), which recognizes the procat and v-domain as well as full-length PCSK9, was added at 1 ug/ml (in 1% BSA/PBS). Bound full-length, procat or v-domain PCSK9 was detected by incubation with neutravidin-HRP (Thermo Scientific) at 200 ng/ml (in 1% BSA/PBS) followed by TMB substrate (KPL) and absorbance measurement at 650 nm. The results, presented in FIGS. 28A and 28B, demonstrate the ability of the various ABS to bind to various parts of PCSK9. As shown in FIG. 28B, ABP 31A4 binds to the V domain of PCSK9.

Example 41

Neutralizing, Non-Competitive Antigen Binding Proteins

The present example demonstrates how to identify and characterize an antigen binding protein that is non-competitive with LDLR for binding with PCSK9, but is still neutralizing towards PCSK9 activity. In other words, such an antigen binding protein will not block PCSK9 from binding to LDLR, but will prevent or reduce PCSK9 mediated LDLR degradation.

Clear, 384 well plates (Costar) were coated with 2 ug/ml of goat anti-LDL receptor antibody (R&D Systems) diluted in buffer A (100 mM sodium cacodylate, pH 7.4). Plates were washed thoroughly with buffer A and then blocked for 2 hours with buffer B (1% milk in buffer A). After washing, plates were incubated for 1.5 hours with 0.4 ug/ml of LDL receptor (R&D Systems) diluted in buffer C (buffer B supplemented with 10 mM CaCl₂). Concurrent with this incubation, 20 ng/ml of biotinylated D374Y PCSK9 was incubated with 100 ng/ml of antibody diluted in buffer A or buffer A alone (control). The LDL receptor containing plates were washed and the biotinylated D374Y PCSK9/antibody mixture was transferred to them and incubated for 1 hour at room temperature. Binding of the biotinylated D374Y to the LDL receptor was detected by incubation with streptavidin-HRP (Biosource) at 500 ng/ml in buffer C followed by TMB substrate (KPL). The signal was quenched with 1N HCl and the absorbance read at 450 nm. The results are presented in FIG. 28C, which shows that while ABP 31H4 inhibits LDLR binding, ABP 31A4 does not inhibit LDLR binding to PCSK9. In combination with the results from Example 40 and shown in FIGS. 28A and 28B, it is clear that 31A4 ABP binds to the V domain of PCSK9 and does not block the interaction of PCSK9 with LDLR.

Next, the Ability of ABP 31A4 to serve as a neutralizing ABP was further confirmed via a cell LDL uptake assay (as described in the examples above). The results of this LDL uptake assay are presented in FIG. 28D. As shown in FIG. 28D, ABP 31A4 displays significant PCSK9 neutralizing ability. Thus, in light of Example 40 and the present results, it is clear that ABPs can bind to PCSK9 without blocking the PCSK9 and LDLR binding interaction, while still being useful as neutralizing PCSK9 ABPs.

Incorporation by Reference

All references cited herein, including patents, patent applications, papers, text books, and the like, and the references cited therein, to the extent that they are not already, are hereby incorporated herein by reference in their entirety. To the extent that any of the definitions or terms provided in the references incorporated by reference differ from the terms and discussion provided herein, the present terms and definitions control.

Equivalents

The foregoing written specification is considered to be sufficient to enable one skilled in the art to practice the invention. The foregoing description and examples detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. An isolated monoclonal antibody that binds an epitope on hPCSK9 comprising one or more of residues 207, 208, 162, 164, 167, 132, 351, 390, 413, 123, 129, 311, 313, or 337 of SEQ ID NO:1, and wherein the monoclonal antibody blocks binding of PCSK9 to LDLR.

2. The isolated monoclonal antibody of claim 1, wherein the isolated monoclonal antibody is a neutralizing antibody.

3. The isolated monoclonal antibody of claim 2, wherein the isolated monoclonal antibody is a human antibody.

4. The isolated monoclonal antibody of claim 2, wherein the epitope comprises a structural epitope.

5. The isolated monoclonal antibody of claim 4, wherein the epitope comprises residue R207.

6. The isolated monoclonal antibody of claim 4, wherein the epitope comprises residue D208.

7. The isolated monoclonal antibody of claim 4, wherein the epitope comprises residue D162.

8. The isolated monoclonal antibody of claim 4, wherein the epitope comprises residue R164.

9. The isolated monoclonal antibody of claim 4, wherein the epitope comprises residue E167.

10. The isolated monoclonal antibody of claim 4, wherein the epitope comprises residue T132.

11. The isolated monoclonal antibody of claim 4, wherein the epitope comprises residue S351.

12. The isolated monoclonal antibody of claim 4, wherein the epitope comprises residue A390.

13. The isolated monoclonal antibody of claim 4, wherein the epitope comprises residue A413.

14. The isolated monoclonal antibody of claim 4, wherein the epitope comprises residue S123.

15. The isolated monoclonal antibody of claim 4, wherein the epitope comprises residue E129.

16. The isolated monoclonal antibody of claim 4, wherein the epitope comprises residue A311.

17. The isolated monoclonal antibody of claim 4, wherein the epitope comprises residue D313.

18. The isolated monoclonal antibody of claim 4, wherein the epitope comprises residue D337.

19. The isolated monoclonal antibody of claim 1, wherein the epitope comprises at least two of residues 207, 208, 162, 164, 167, 132, 351, 390, 413, 123, 129, 311, 313, or 337 of SEQ ID NO:1.

20. The isolated monoclonal antibody of claim 1, wherein the epitope comprises at least three of residues 207, 208, 162, 164, 167, 132, 351, 390, 413, 123, 129, 311, 313, or 337 of SEQ ID NO:1.

21. The isolated monoclonal antibody of claim 1, wherein the epitope comprises at least four of residues 207, 208, 162, 164, 167, 132, 351, 390, 413, 123, 129, 311, 313, or 337 of SEQ ID NO:1.

22. The isolated human monoclonal antibody of claim 1, wherein the isolated antibody was produced by a CHO cell.

23. The isolated human monoclonal antibody of claim 1, wherein the isolated monoclonal antibody binds to PCSK9 with a $K_D$ of less than or equal to $5 \times 10^{-9}$ M.

24. The isolated human monoclonal antibody of claim 1, wherein the isolated monoclonal antibody comprises a light chain region that comprises an amino acid sequence of SEQ ID NO: 157.

25. An isolated monoclonal neutralizing antibody specific for PCSK9 that binds at least one of amino acid residues 207, 208, 162, 164, 167, 132, 351, 390, 413, 123, 129, 311, 313, or 337 of SEQ ID NO:1, and wherein the monoclonal antibody blocks binding of PCSK9 to LDLR.

26. The isolated monoclonal neutralizing antibody of claim 25, wherein the isolated monoclonal neutralizing antibody is human, and wherein the isolated monoclonal neutralizing antibody comprises a light chain that comprises the amino acid sequence of SEQ ID NO: 157.

27. The isolated monoclonal neutralizing antibody of claim 25, wherein the isolated monoclonal antibody binds to at least two of amino acid residues 207, 208, 162, 164, 167, 132, 351, 390, 413, 123, 129, 311, 313, or 337 of SEQ ID NO:1.

28. The isolated monoclonal neutralizing antibody of claim 25, wherein the isolated monoclonal antibody binds to at least three of amino acid residues 207, 208, 162, 164, 167, 132, 351, 390, 413, 123, 129, 311, 313, or 337 of SEQ ID NO:1.

29. The isolated monoclonal neutralizing antibody of claim 25, wherein the isolated monoclonal antibody binds to at least four of amino acid residues 207, 208, 162, 164, 167, 132, 351, 390, 413, 123, 129, 311, 313, or 337 of SEQ ID NO:1.

30. The isolated monoclonal neutralizing antibody of claim 25, wherein the isolated monoclonal antibody competes for binding to PCSK9 with an antibody comprising a heavy chain variable region having an amino acid sequence of SEQ ID NO: 49 and a light chain variable region having an amino acid sequence of SEQ ID NO: 23.

* * * * *

UNITED STATES PATENT AND TRADEMARK OFFICE
CERTIFICATE OF CORRECTION

PATENT NO. : 8,883,983 B2
APPLICATION NO. : 14/261065
DATED : November 11, 2014
INVENTOR(S) : Simon Mark Jackson et al.

It is certified that error appears in the above-identified patent and that said Letters Patent is hereby corrected as shown below:

In the Specification,

On column 29, line 40, please change "—$COCH_2$—$CH(OH)CH_2$" to ----$COCH_2$--, --$CH(OH)CH_2$----.

On column 57, line 40, please change "*larvae*" to --larvae--.

On column 57, line 51, please change "*larvae*" to --larvae--.

On column 99, lines 54-55, please change "W156, N157, L158, E159, H193, E195, H229, R237, G240, K243, D367, I368, G370" to --W156, N157, L158, E159, H193, E195, H229, R237, G240, K243, D367, I368, G370--.

On column 119, approximately line 27, on Table 39.4, please change:

"3C4   Q554R   31.8416" to --*3C4   Q554R   31.8416*--, therefor.

Signed and Sealed this
Twentieth Day of January, 2015

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,883,983 B2 | |
| APPLICATION NO. | : 14/261065 | |
| DATED | : November 11, 2014 | |
| INVENTOR(S) | : Simon Mark Jackson et al. | |

It is certified that error appears in the above-identified patent and that said Letters Patent is hereby corrected as shown below:

On the Title Page,

In column 2 (page 3, item 56) at line 25, Under Other Publications, change "Aterioscler" to --Arterioscler--.

In column 2 (page 4, item 56) at line 13, Under Other Publications, change "Xlllth" to --XIIIth--.

In column 2 (page 4, item 56) at line 27, Under Other Publications, change "Vase." to --Vasc.--.

In column 2 (page 5, item 56) at line 53, Under Other Publications, change "extracelluarly" to --extracellularly--.

In column 1 (page 6, item 56) at line 49, Under Other Publications, change "hypercholersterolemia" to --hypercholesterolemia--.

In column 2 (page 6, item 56) at line 11, Under Other Publications, change "PSK9" to --PCSK9--.

In column 1 (page 8, item 56) at line 70, Under Other Publications, change "a the" to --of the--.

In column 1 (page 9, item 56) at line 59, Under Other Publications, change "apoliprotein" to --apolipoprotein--.

In column 2 (page 9, item 56) at line 24, Under Other Publications, change "Hypercholesterolema" to --Hypercholesterolemia--.

In the Specification,

In column 1 at line 12, Change "Ser" to --Ser.--.

In column 2 at line 3, Change "al," to --al.,--.

Signed and Sealed this
Twenty-fifth Day of August, 2015

Michelle K. Lee
*Director of the United States Patent and Trademark Office*

CERTIFICATE OF CORRECTION (continued)
U.S. Pat. No. 8,883,983 B2

In column 2 at line 24, Change "S8A" to --S8A.--.

In column 5 at line 5, Change "of" to --of:--. (Second Occurrence)

In column 6 at line 65, Change "IgG2-" to --IgG2-,--.

In column 9 at line 43, Change "5221," to --S221,--.

In column 9 at line 65, Change "8194," to --R194,--.

In column 10 at line 36, Change "5372," to --S372,--.

In column 10 at line 44, Change "5376," to --S376,--.

In column 10 at line 64, Change "5221," to --S221,--.

In column 11 at line 3, Change "5372," to --S372,--.

In column 11 at line 64, Change "5465," to --S465,--.

In column 11 at line 67, Change "5595," to --S595,--.

In column 12 at line 36, Change "of" to --of:--.

In column 12 at line 40, Change "Manner" to --manner--.

In column 14 at line 42, Change "$X_{14}$  $X_{15}$" to --$X_{14}X_{15}$--.

In column 15 at line 61, Change "of" to --of:--.

In column 16 at line 47, Change "$X_{14}$  $X_{15}$" to --$X_{14}X_{15}$--.

In column 17 at line 19 (approx.), Change "of" to --of:--.

In column 17 at line 34, Change "of" to --of:--.

In column 18 at line 36, Change "assay" to --assay.--.

In column 18 at line 48, Change "PCSK9" to --PCSK9.--.

In column 18 at line 51, Change "PCSK9" to --PCSK9.--.

In column 18 at line 55, Change "PCSK9" to --PCSK9.--.

In column 18 at line 59, Change "PCSK9" to --PCSK9.--.

In column 19 at line 25, Change "normeutralizing" to --nonneutralizing--.

In column 19 at line 35, Change "normeutralizing" to --nonneutralizing--.

In column 23 at line 6, Change "al," to --al.,--.

In column 23 at line 6, Change "apoliprotein" to --apolipoprotein--.

In column 23 at line 9, Change "al," to --al.,--.

In column 23 at line 13, Change "al," to --al.,--.

In column 23 at lines 37-38, Change "phosphoroamidate." to --phosphoramidate.--.

In column 24 at line 55, Change "al," to --al.,--.

In column 24 at line 56, Change "al," to --al.,--.

In column 24 at line 57, Change "al," to --al.,--.

In column 27 at line 6, Change "N-acetyl serine," to --N-acetylserine,--.

In column 28 at line 67, Change "Nos." to --Nos:--.

CERTIFICATE OF CORRECTION (continued)
U.S. Pat. No. 8,883,983 B2

In column 29 at line 38, Change "—CH$_2$ NH—," to -- —CH$_2$NH—,--.

In column 29 at line 39, Change "—CH$_2$ S—," to -- —CH$_2$S—,--.

In column 29 at line 40, Change "—CH$_2$ SO—," to -- —CH$_2$SO—,--.

In column 30 at line 22, Change "F(ab)$_2$," to --F(ab')$_2$,--.

In column 31 at line 59, Change "<1×10$^{-5}$" to --≤1×10$^{-5}$--.

In column 32 at line 20, Change "CDR2VDTGGIVGSKGE" to --CDR2 VDTGGIVGSKGE--.

In column 32 at line 23, Change "FR2WYQQRPGKGPRFVMR" to --FR2 WYQQRPGKGPRFVMR--.

In column 32 at line 24, Change "FR3GIPDRFSVLGSGLNRYLTIKNIQEEDESDYHC" to --FR3 GIPDRFSVLGSGLNRYLTIKNIQEEDESDYHC--.

In column 32 at line 25, Change "FR4FGGGTKLTVL" to --FR4 FGGGTKLTVL--.

In column 34 at line 11, Change "al," to -- al.,--.

In column 35 at line 5, Change "target" to --target.--.

In column 36 at line 10, After "Scand." insert --J.--.

In column 37 at line 18, Change "$^{131}$I)" to --$^{131}$I),--.

In column 38 at line 36, Change "3." to --3--.

In column 39 at line 29 (approx.), Change "cataylytic" to --catalytic--.

In column 42 at lines 61-62, Change "cataylytic" to --catalytic--.

In column 42 at line 62, Change "5. 5-10" to --"5, 5-10"--.

In column 42 at line 65, Change "5. 5-10" to --"5, 5-10"--.

In column 43 at line 33, Change "neturalizing" to --neutralizing--.

In column 43 at line 44, Change "K$_a$)." to --K$_d$).--.

In column 43 at line 59, Change "al," to --al.,--.

In column 52 at line 4, Change "guainine" to --guanine--.

In column 52 at line 60, Change "Immol." to --Immunol.--.

In column 53 at line 30, Change "al," to --al.,--.

In column 54 at line 37, Change "al," to --al.,--.

In column 54 at line 39, Change "al," to --al.,--.

In column 56 at line 16, Change "normative" to --nonnative--.

In column 58 at line 33, Change "dithiobisGSH," to --dithiobis GSH,--.

In column 58 at line 58, Change "chromotography" to --chromatography--.

In column 64 at line 31, Change "apoplipoprotein" to --apolipoprotein--.

In column 65 at line 3, Change "Nutirtional" to --Nutritional--.

In column 65 at line 4, Change "Regulatiory" to --Regulatory--.

CERTIFICATE OF CORRECTION (continued)

U.S. Pat. No. 8,883,983 B2

In column 65 at lines 18-19, Change "admininstered" to --administered--.

In column 66 at lines 18-19, Change "agonsits," to --agonists,--.

In column 66 at line 21, Change "sulphonyl ureas," to --sulphonylureas,--.

In column 66 at line 22, Change "inhibitoris" to --inhibitors--.

In column 66 at line 29, Change "anti-psycotic" to --anti-psychotic--.

In column 66 at line 56, Change "alllosteric" to --allosteric--.

In column 67 at lines 6-7, Change "sympotoms" to --symptoms--.

In column 68 at line 37, Change "tyloxapal);" to --tyloxapol);--.

In column 74 at line 24 (approx.), Change "neutravadin" to --neutravidin--.

In column 74 at line 44, Change "V5H is" to --V5His--.

In column 74 at line 47, Change "neutravadin" to --neutravidin--.

In column 75 at line 8, Change "Caymen" to --Cayman--.

In column 75 at line 10 (approx.), Change "LDLR(R&D" to --LDLR (R&D--.

In column 75 at line 17, Change "V5H is" to --V5His--.

In column 75 at line 20 (approx.), Change "neutravadin" to --neutravidin--.

In column 75 at line 45 (approx.), Change "(50 Owen)" to --(50 μl/well)--.

In column 75 at line 49, Change "LDLR(R&D" to --LDLR (R&D--.

In column 75 at line 52, Change "1.2,3" to --1.2.3--.

In column 76 at line 6 (approx., TABLE 4), Change "ml" to --ml--. (Second Occurrence)

In column 76 at line 60 (approx.), Change "15" to --15%--.

In column 76 at line 66, Change "37C" to --37° C--.

In column 77 at lines 24-25, Change "neutravadin" to --neutravidin--.

In column 77 at line 59, Change "neutravadin" to --neutravidin--.

In column 77 at line 60, Change "40 Owen." to --40 μl/well.--.

In column 78 at lines 26-27, Change "neutravadin" to --neutravidin--.

In column 78 at line 55, Change "al," to --al.,--.

In column 78 at line 64, Change "neutravadin" to --neutravidin--.

In column 79 at line 41, Change "LDLR(R&D" to --LDLR (R&D--.

In column 79 at line 49, Change "LDLR(R&D" to --LDLR (R&D--.

In column 80 at line 36, Change "LDLR(R&D" to --LDLR (R&D--.

In column 80 at line 59, Change "40 μl" to --40 μl/well--.

In column 84 at line 61, Change "3B." to --3JJ.--.

In column 86 at line 5, Change "BBS-P" to --HBS-P--.

In column 86 at line 14, Change "BBS-P" to --HBS-P--.

In column 88 at line 6 (approx., TABLE 8.2), Change "9-23" to --9~23--.

CERTIFICATE OF CORRECTION (continued)
U.S. Pat. No. 8,883,983 B2

In column 90 at lines 7-8, Change "updtake" to --uptake--.

In column 90 at line 21, Change "Harland-Teklad," to --Harlan-Teklad,--.

In column 90 at line 21, Change "through out" to --throughout--.

In column 91 at line 23, Change "scarified" to --sacrificed--.

In column 91 at line 37 (approx.), Change "anti-B" to --anti-β--.

In column 91 at line 50, Change "31 H4" to --31H4--.

In column 91 at line 58 (approx.), Change "Harland-Teklad," to --Harlan-Teklad,--.

In column 91 at line 58 (approx.), Change "through out" to --throughout--.

In column 93 at line 39, Change "exampless" to --examples--.

In column 93 at line 59, Change "commerically" to --commercially--.

In column 95 at line 2, Change "disases" to --diseases--.

In column 95 at line 54 (approx.), Change "Bioreclaimation" to --Bioreclamation--.

In column 96 at line 9, Change "appreciatedy" to --appreciated--.

In column 96 at line 14, Change "the" to --that--.

In column 97 at line 26, Change "phylogenic" to --phylogenetic--.

In column 97 at line 44, Change "ClutalW-like" to --ClustalW-like--.

In column 97 at line 47, Change "phylogenic" to --phylogenetic--.

In column 97 at line 63, Change "Glade" to --clade--.

In column 97 at line 64, Change "Glade" to --clade--.

In column 98 at lines 13-14, Change "adenoassociated" to --adeno-associated--.

In column 100 at line 29, Change "5372," to --S372,--.

In column 101 at line 5, Change "596," to --S96,--.

In column 101 at line 21, Change "PC SK9" to --PCSK9--.

In column 104 at line 24, Change "5221," to --S221,--.

In column 104 at line 45, Change "5221," to --S221,--.

In column 104 at line 57, Change "5376," to --S376,--.

In column 104 at line 61, Change "15-8,8,8-5," to --15-8, 8, 8-5,--.

In columns 104-105 at line 67 (Col. 104) at line 1 (Col. 105), Change "15-8,8,8-5," to --15-8, 8, 8-5,--.

In column 106 at line 50, Change "crystalography," to --crystallography,--.

In column 106 at line 60, Change "31H4Fab" to --31H4 Fab--.

In column 107 at line 12, Change "31H4Fab" to --31H4 Fab--.

In column 107 at line 14, Change "31H4Fab" to --31H4 Fab--.

In column 107 at line 19, Change "31H4Fab" to --31H4 Fab--.

In column 108 at line 43, Change "deteremined." to --determined.--.

In column 109 at line 3, Change "Cgstallogr" to --Crystallogr--.

In column 110 at line 4, Change "5595," to --S595,--.

In column 110 at lines 5-8, Delete "H597. ... herein)." and insert the same on Col. 110, Line 4, after "and" as the continuation of the same paragraph.

In column 110 at line 38, Change "5465," to --S465,--.

In column 110 at line 41, Change "5595," to --S595,--.

In column 110 at line 47, Change "are are" to --are--.

In column 110 at line 52, Change "15-8,8,8-5," to --15-8, 8, 8-5,--.

In column 111 at line 2, Change "21B12" to --21B12,--.

In column 114 at lines 61-62, Change "strepavidin" to --streptavidin--.

In columns 115-116 at line 5 (TABLE 39.1), Change "chimers" to --chimera--.

In columns 115-116 at line 12 (TABLE 39.1), Change "D336R" to --D337R--.

In column 116 at line 22 (approx.), Change "39.2" to --39.2.--.

In column 116 at line 65 (approx., below TABLE 39.2), Change "mind" to --xmid--.

In column 117 at line 52 (approx.), Change "sum," to --sum--.

In column 118 at line 25, Change "303)" to --303).--.

In column 118 at lines 47-48, Change "to to" to --to--.

In column 118 at line 57 (approx., TABLE 39.4), Change "A311 R" to --A311R--.

In column 118 at line 58 (approx., TABLE 39.4), Change "A311 R" to --A311R--.

In column 119 at line 27 (approx., TABLE 39.4), Change "31 H4" to --31H4--.

In column 119 at line 32 (approx., TABLE 39.4), Change "31B12" to --21B12--.

In column 119 at line 35 (approx., TABLE 39.4), Change "21 B12" to --21B12--.

In column 120 at line 2, Change "Bmax" to --Bmax.--.

In column 121 at line 27, Change "E1 81R," to --E181R,--.

In column 121 at lines 29-30, Change "(E1 81R)." to --(E181R).--.

In column 121 at line 32, Change "E1 81R" to --E181R--.

In column 121 at line 39, Change "NO:s" to --NOs:--.